(12) United States Patent
Chen et al.

(10) Patent No.: US 11,708,344 B2
(45) Date of Patent: *Jul. 25, 2023

(54) FLAVONE DERIVATIVES FOR THE TREATMENT AND PROPHYLAXIS OF HEPATITIS B VIRUS DISEASE

(71) Applicant: Hoffmann-La Roche Inc., Little Falls, NJ (US)

(72) Inventors: Dongdong Chen, Shanghai (CN); Song Feng, Shanghai (CN); Min Jiang, Shanghai (CN); Yongfu Liu, Shanghai (CN); Jiamin Zheng, Shanghai (CN)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/282,369

(22) PCT Filed: Oct. 1, 2019

(86) PCT No.: PCT/EP2019/076502
§ 371 (c)(1),
(2) Date: Apr. 1, 2021

(87) PCT Pub. No.: WO2020/070088
PCT Pub. Date: Apr. 9, 2020

(65) Prior Publication Data
US 2023/0074887 A1     Mar. 9, 2023

(30) Foreign Application Priority Data

Oct. 3, 2018  (WO) ................ PCT/CN2018/109241

(51) Int. Cl.
| | | |
|---|---|---|
| *C07D 311/32* | (2006.01) | |
| *C07D 405/04* | (2006.01) | |
| *C07D 407/10* | (2006.01) | |
| *C07D 413/10* | (2006.01) | |
| *C07D 417/10* | (2006.01) | |
| *C07D 405/10* | (2006.01) | |

(52) U.S. Cl.
CPC .......... *C07D 311/32* (2013.01); *C07D 405/04* (2013.01); *C07D 405/10* (2013.01); *C07D 407/10* (2013.01); *C07D 413/10* (2013.01); *C07D 417/10* (2013.01)

(58) Field of Classification Search
CPC ............................ C07D 311/32; C07D 405/04
See application file for complete search history.

(56) References Cited

U.S. PATENT DOCUMENTS

2015/0320702 A1   12/2015   Chou et al.
2021/0387996 A1   12/2021   Feng et al.

FOREIGN PATENT DOCUMENTS

| CN | 1796381 A      | 5/2006  |
| WO | 2007/135592 A1 | 11/2007 |
| WO | 2013/127361 A1 | 6/2013  |
| WO | 2004/007475 A1 | 7/2013  |
| WO | 2015/061294 A2 | 4/2015  |
| WO | 2015/161309 A1 | 4/2015  |

OTHER PUBLICATIONS

Daskiewicz, J et al., "Effects of Flavonoids on Cell Proliferation and Caspase Activation in a Human Colonic Cell Line HT29: An SAR Study" J Med Chem 48(8):2790-2804 (Mar. 30, 2005).
"International Preliminary Report on Patentability—PCT/EP2019/076502" (Report dated Mar. 23, 2021, Chapter I), :pp. 1-7 (dated Apr. 15, 2021).
"International Search Report—PCT/EP2019/076502" (w/Written Opinion), :pp. 1-12 (dated Nov. 18, 2019).
Shih, T. L. et al., "Copper-mediated trimethylsilyl azide in amination of bromoflavonoids to synthesize unique aminoflavonoids" Tetrahedron 70(23):3657-3664 (Jun. 10, 2014).
Wang, W., et al., "Effect of Oenanthe javanica flavone on human and duck hepatitis B virus infection" Acta Pharmacol Sin 26(5):587-592 (May 1, 2005).
Zhang, F., et al., "A review of non-nucleoside anti-hepatitis B virus agents" Eur J Med Chem 75(30):267-281 (Mar. 21, 2014).

*Primary Examiner* — Golam M Shameem
(74) *Attorney, Agent, or Firm* — Genentech, Inc.; Richard G.A. Bone

(57) ABSTRACT

The present invention provides novel compounds having the general formula (Formula I): wherein $R^1$ to $R^6$, $G_1$, $G_2$, $A_1$ to $A_4$ and m are as described herein, compositions including the compounds and methods of using the compounds.

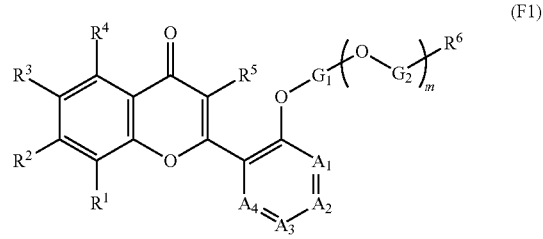

(F1)

29 Claims, 1 Drawing Sheet
Specification includes a Sequence Listing.

SEQUENCE LISTING

<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
aagaaaaacc ccgcctgtaa                                                  20

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cctgttctga ctactgcctc tcc                                              23

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
cctgatgtga tgttctccat gttcagc                                          27

Flavone derivatives for the treatment and prophylaxis of Hepatitis B Virus disease
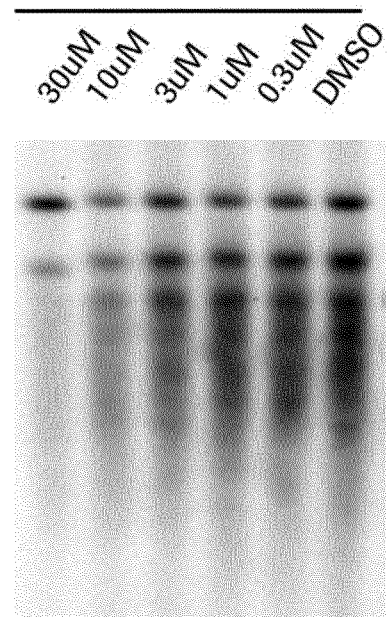

FLAVONE DERIVATIVES FOR THE TREATMENT AND PROPHYLAXIS OF HEPATITIS B VIRUS DISEASE

The present invention relates to organic compounds useful for therapy and/or prophylaxis of HBV infection in a mammal, and in particular to cccDNA (covalently closed circular DNA) inhibitors useful for treating HBV infection.

FIELD OF THE INVENTION

The present invention relates to flavone derivatives having pharmaceutical activity, their manufacture, pharmaceutical compositions containing them and their potential use as medicaments.

The present invention relates to compounds of formula (I)

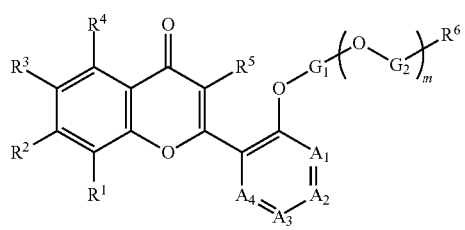

wherein $R^1$ to $R^6$, $G_1$, $G_2$, $A_1$ to $A_4$ and m are as described below, or pharmaceutically acceptable salts thereof.

Hepatitis B virus (HBV) infection is one of the most prevalent viral infections and is a leading cause of chronic hepatitis. It is estimated that worldwide, around 2 billion people have evidence of past or present infection with HBV. Over 250 million individuals are currently chronically infected with HBV and are therefore at high risk to develop liver fibrosis, cirrhosis and hepatocellular carcinoma (HCC). There are data to indicate ~800,000 deaths per year are directly linked to HBV infection (Lozano, R. et al., Lancet (2012), 380 (9859), 2095-2128; Goldstein, S. T. et al., Int J Epidemiol (2005), 34 (6), 1329-1339).

Many countries in the world administer hepatitis B vaccine starting at birth or in early childhood, which has greatly reduced the incidence and prevalence of hepatitis B in most endemic regions over the past few decades. However the vaccine has no impact on people who were infected before the widely use of the vaccine in developing end-stage liver disease or HCC (Chen, D. S., J Hepatol (2009), 50 (4), 805-816). Vaccination at birth of infants born to HBV positive mothers is usually not sufficient for protecting vertical transmission and combination with hepatitis B immune globulin is needed (Li, X. M. et al., World J Gastroenterol (2003), 9 (7), 1501-1503).

Currently FDA-approved treatments for chronic hepatitis B include two type 1 interferons (IFN) which are IFNalfa-2b and pegylated IFN alfa-2a and six nucleos(t)ide analogues (NAs) which are lamivudine (3TC), tenofovir disoproxil fumarate (TDF), adefovir (ADV), telbivudine (LdT), entecavir (ETV), and vemlidy (tenofovir alafenamide (TAF)). IFN treatment is finite, but it is known to have severe side effects, and only a small percentage of patients showed a sustained virological response, measured as loss of hepatitis B surface antigen (HBsAg). NAs are inhibitors of the HBV reverse transcriptase, profoundly reduce the viral load in vast majority of treated patients, and lead to improvement of liver function and reduced incidence of liver failure and hepatocellular carcinoma. However, the treatment of NAs is infinite (Ahmed, M. et al., Drug Discov Today (2015), 20 (5), 548-561; Zoulim, F. and Locarnini, S., Gastroenterology (2009), 137 (5), 1593-1608 e1591-1592).

HBV chronic infection is caused by persistence of covalently closed circular (ccc)DNA, which exists as an episomal form in hepatocyte nuclei. cccDNA serves as the template for viral RNA transcription and subsequent viral DNA generation. Only a few copies of cccDNA per liver cell can establish or re-initiate viral replication. Therefore, a complete cure of chronic hepatitis B will require elimination of cccDNA or permanently silencing of cccDNA. However, cccDNA is intrinsically very stable and currently available therapeutics could not eliminate cccDNA or permanently silence cccDNA (Nassal, M., Gut (2015), 64 (12), 1972-1984; Gish, R. G. et al., Antiviral Res (2015), 121, 47-58; Levrero, M. et al., J Hepatol (2009), 51 (3), 581-592.). The current SoC could not eliminate the cccDNA which are already present in the infected cells. There is an urgent need to discover and develop new anti-HBV reagents to eliminate or permanently silence cccDNA, the source of chronicity (Ahmed, M. et al., Drug Discov Today (2015), 20 (5), 548-561; Nassal, M., Gut (2015), 64 (12), 1972-1984).

SUMMARY OF THE INVENTION

Objects of the present invention are novel compounds of formula (I), their manufacture, medicaments based on a compound in accordance with the invention and their production as well as the use of compounds of formula (I) as cccDNA inhibitors and for the treatment or prophylaxis of HBV infection. The compounds of formula (I) show superior anti-HBV activity. In addition, the compounds of formula (I) also show good PK profiles and good liver micro some stability.

The present invention relates to a compound of formula (I)

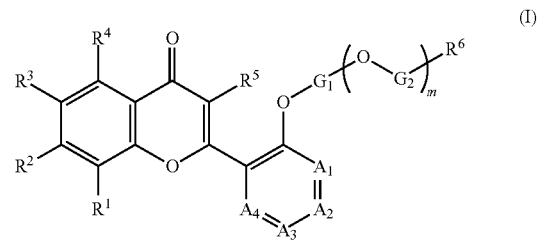

wherein
$R^1$ is selected from halogen and haloC$_{1-6}$alkyl;
$R^2$ is selected from H, halogen, C$_{1-6}$alkyl, C$_{1-6}$alkoxy, C$_{3-7}$cycloalkyl and haloC$_{1-6}$alkyl;
$R^3$ is selected from H, halogen and C$_{1-6}$alkoxy;
$R^4$ is selected from H, hydroxy and haloC$_{1-6}$alkyl;
$R^5$ is selected from H, halogen, C$_{1-6}$alkyl, C$_{1-6}$alkoxy and hydroxy;
$R^6$ is selected from carboxy, C$_{1-6}$alkoxycarbonyl, carboxyC$_{1-6}$alkoxycarbonyl, carboxyC$_{3-7}$cycloalkylaminocarbonyl, carboxyheterocyclylcarbonyl, C$_{3-7}$cycloalkylsulfonylaminocarbonyl, hydroxyC$_{1-6}$alkylaminocarbonyl, C$_{1-6}$alkylsulfonylheterocyclylcarbonyl, heterocyclylcarbonyl, hydroxyheterocyclylcarbonyl, (hydroxy)$_2$heterocyclylcarbonyl, C$_{1-6}$alkylsulfonylaminocarbonylheterocyclylcarbonyl, C$_{4-6}$alkylsulfonylaminocarbonyl, cyano, ($C_{1-6}$alkyl)$_2$aminosulfonyl, aminocarbonyl, aminosulfonyl, $C_{3-7}$cycloalkylaminocarbonylcarbonyl and $C_{3-7}$cycloalkylaminocarbonyl;

$A_1$ is selected from N and $CR^7$; wherein $R^7$ is selected from H, halogen and halo$C_{1-6}$alkyl;

$A_2$ is selected from N and $CR^8$; wherein $R^8$ is selected from H, halogen, hydroxy, $C_{1-6}$alkyl, $C_{1-6}$alkoxy, $C_{3-7}$cycloalkyl, halo$C_{1-6}$alkyl, halo$C_{1-6}$alkoxy, halo$C_{1-6}$alkyl$C_{1-6}$alkoxy, $C_{4-6}$alkylsulfanyl, $C_{1-6}$alkylsulfonyl, $C_{3-7}$cycloalkyl$C_{1-6}$alkoxy and heterocyclyl; wherein heterocyclyl is unsubstituted or substituted one or two or three times independently by oxo;

$A_3$ is selected from N and $CR^9$; wherein $R^9$ is selected from H, amino, halogen, hydroxy, $C_{1-6}$alkyl, $C_{1-6}$alkoxy, halo$C_{1-6}$alkyl, halo$C_{1-6}$alkoxy, halo$C_{1-6}$alkyl$C_{1-6}$alkoxy and $C_{3-7}$cycloalkyl$C_{1-6}$alkoxy;

or $R^8$ and $R^9$, together with the atoms to which they are attached, form a heterocyclyl ring; wherein heterocyclyl ring is unsubstituted or substituted by one or two or three or four substituents independently selected from halogen, $C_{1-6}$alkyl and oxo;

$A_4$ is selected from N and $CR^{10}$; wherein $R^{10}$ is selected from H and halogen;

$G_1$ is selected from $C_{1-6}$alkyl, $C_{3-7}$cycloalkyl, $C_{3-7}$cycloalkyl$C_{1-6}$alkyl, phenyl$C_{1-6}$alkyl, $C_{1-6}$alkyl$C_{3-7}$cycloalkyl$C_{1-6}$alkyl and heterocyclyl; wherein $C_{1-6}$alkyl, $C_{3-7}$cycloalkyl, $C_{3-7}$cycloalkyl$C_{1-6}$alkyl, phenyl$C_{1-6}$alkyl, $C_{1-6}$alkyl$C_{3-7}$cycloalkyl$C_{1-6}$alkyl and heterocyclyl are unsubstituted or substituted by one or two or three substituents independently selected from hydroxy, amino, $C_{3-7}$cycloalkylsulfonylamino, $C_{1-6}$alkylphenylsulfonylamino, phenylsulfonyl, $C_{3-7}$cycloalkylsulfonyl, $C_{1-6}$alkoxyphenylsulfonyl, phenylcarbonyl, phenylcarbonylamino, $C_{1-6}$alkylcarbonylamino, $C_{1-6}$alkylaminosulfonylamino, aminocarbonyamino, ($C_{1-6}$alkoxy)$_2$phenylaminosulfonylamino, $C_{4-6}$alkoxycarbonylcarbonylamino, ($C_{1-6}$alkyl)$_2$aminosulfonylamino, $C_{4-6}$alkylaminocarbonylamino, $C_{1-6}$alkylaminosulfonyl, aminosulfonylamino, $C_{3-7}$cycloalkylaminosulfonylamino and phenyl$C_{1-6}$alkylaminosulfonylamino;

$G_2$ is selected from $C_{1-6}$alkyl, $C_{3-7}$cycloalkyl and phenyl;

m is selected from 0 and 1;

or a pharmaceutically acceptable salt thereof.

DETAILED DESCRIPTION OF THE INVENTION

Definitions

As used herein, the term "$C_{1-6}$alkyl" alone or in combination signifies a saturated, linear- or branched chain alkyl group containing 1 to 6, particularly 1 to 4 carbon atoms, for example methyl, ethyl, propyl, isopropyl, 1-butyl, 2-butyl, tert-butyl, neopentyl, hexyl, isohexyl and the like. Particular "$C_{1-6}$alkyl" groups are methyl, ethyl, propyl, isopropyl and tert-butyl. More particularly, "$C_{1-6}$alkyl" groups are methyl, ethyl and propyl.

The term "$C_{1-6}$alkoxy" alone or in combination signifies a group $C_{1-6}$alkyl-O—, wherein the "$C_{1-6}$alkyl" is as defined above; for example methoxy, ethoxy, propoxy, iso-propoxy, n-butoxy, iso-butoxy, 2-butoxy, tert-butoxy, pentoxy, hexyloxy and the like. Particular "$C_{1-6}$alkoxy" groups are methoxy, ethoxy and propoxy. More particularly, "$C_{1-6}$alkoxy" group is methoxy.

The term "halogen" and "halo" are used interchangeably herein and denote fluoro, chloro, bromo, or iodo.

The term "halo$C_{1-6}$alkyl" denotes an alkyl group wherein at least one of the hydrogen atoms of the alkyl group is replaced by same or different halogen atoms, particularly fluoro atoms. Examples of halo$C_{1-6}$alkyl include monochloro-, difluoro- or trifluoro-methyl, -ethyl or -propyl, for example difluoromethyl and trifluoromethyl.

The term "halo$C_{1-6}$alkoxy" denotes a $C_{1-6}$alkoxy group wherein at least one of the hydrogen atoms of the $C_{1-6}$alkoxy group is replaced by same or different halogen atoms, particularly fluoro atoms. Examples of halo$C_{1-6}$alkoxy include mono fluoro-, difluoro- or trifluoro-methoxy, -ethoxy or -propoxy, for example difluoromethoxy and trifluoromethoxy.

The term "$C_{3-7}$cycloalkyl" denotes to a saturated carbon ring containing from 3 to 7 carbon atoms, particularly from 3 to 6 carbon atoms, for example, cyclopropyl, cyclobutyl, cyclopentyl, cyclohexyl, cycloheptyl and the like. Particular "$C_{3-7}$cycloalkyl" group is cyclopropyl, cyclobutyl or cyclopentyl.

The term "$C_{3-7}$cycloalkoxy" denotes a group $C_{3-7}$cycloalkyl-O—, wherein the "$C_{3-7}$cycloalkyl" is as defined above; for example cyclopropoxy, cyclobutoxy, cyclopentoxy. Particular "$C_{3-7}$cycloalkoxy" group is cyclobutoxy.

"heterocyclyl" refers to any mono-, bi-, tricyclic or spiro, saturated or unsaturated, aromatic (heteroaryl) or non-aromatic (e.g., heterocycloalkyl), ring system, having 3 to 20 ring atoms, where the ring atoms are carbon, and at least one atom in the ring or ring system is a heteroatom selected from nitrogen, sulfur or oxygen. If any ring atom of a cyclic system is a heteroatom, that system is a heterocyclyl, regardless of the point of attachment of the cyclic system to the rest of the molecule. In one example, heterocyclyl includes 3-11 ring atoms ("members") and includes monocycles, bicycles, tricycles and spiro ring systems, wherein the ring atoms are carbon, where at least one atom in the ring or ring system is a heteroatom selected from nitrogen, sulfur or oxygen. In one example, heterocyclyl includes 3- to 7-membered monocycles having 1, 2, 3 or 4 heteroatoms selected from nitrogen, sulfur or oxygen. In another example, heterocyclyl includes 4-, 5- or 6-membered monocycles having 1, 2, 3 or 4 heteroatoms selected from nitrogen, sulfur or oxygen. In one example, heterocyclyl includes 8- to 12-membered bicycles having 1, 2, 3, 4, 5 or 6 heteroatoms selected from nitrogen, sulfur or oxygen. In another example, heterocyclyl includes 9- or 10-membered bicycles having 1, 2, 3, 4, or 6 heteroatoms selected from nitrogen, sulfur or oxygen. Exemplary heterocyclyls are pyrrolidinyl, morpholinyl, thiazolyl, oxazolidinyl, 1,3-dioxole, 2,3-dihydrofuran, 2,3-dihydro-1,4-dioxine or 2,3-dihydro-1H-pyrrole. Heterocyclyl may be optionally substituted by halogen, OH, SH, cyano, $NH_2$, $NHCH_3$, $N(CH_3)_2$, $NO_2$, $N_3$, $C(O)CH_3$, COOH, $CO_2CH_3$, $C_{1-6}$alkyl, $C_{1-6}$alkoxy, oxo, halo$C_{1-6}$alkyl, phenyl or heterocyclyl.

The term "cyano" as used herein means a substituent having a carbon atom joined to a nitrogen atom by a triple bond.

The term "oxo" means an =O group and may be attached to a carbon atom or a sulfur atom.

The term "enantiomer" denotes two stereoisomers of a compound which are non-superimposable mirror images of one another.

The term "diastereomer" denotes a stereoisomer with two or more centers of chirality and whose molecules are not mirror images of one another. Diastereomers have different physical properties, e.g. melting points, boiling points, spectral properties, and reactivities.

The term "PG" denotes a protecting group, which is introduced into a molecule by chemical modification of a functional group to obtain chemoselectivity in a subsequent chemical reaction. Typical protecting groups are Boc, Cbz and Bn.

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of formula (I) and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethyl ammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Bastin R. J., et al., Organic Process Research & Development 2000, 4, 427-435. Particular are the sodium salts of the compounds of formula (I).

Compounds of the general formula (I) which contain one or several chiral centers can either be present as racemates, diastereomeric mixtures, or optically active single isomers. The racemates can be separated according to known methods into the enantiomers. Particularly, diastereomeric salts which can be separated by crystallization are formed from the racemic mixtures by reaction with an optically active acid such as e.g. D- or L-tartaric acid, mandelic acid, malic acid, lactic acid or camphorsulfonic acid.

Cccdna Inhibitors

The present invention provides (i) a compound having the general formula (I):

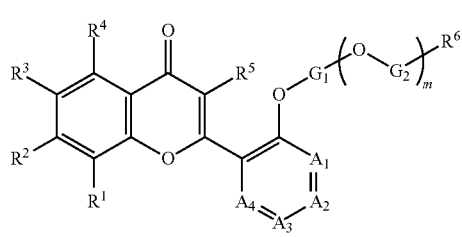

(I)

wherein
$R^1$ is selected from halogen and haloC$_{1-6}$alkyl;
$R^2$ is selected from H, halogen, C$_{1-6}$alkyl, C$_{1-6}$alkoxy, C$_{3-7}$cycloalkyl and haloC$_{1-6}$alkyl;
$R^3$ is selected from H, halogen and C$_{1-6}$alkoxy;
$R^4$ is selected from H, hydroxy and haloC$_{1-6}$alkyl;
$R^5$ is selected from H, halogen, C$_{1-6}$alkyl, C$_{1-6}$alkoxy and hydroxy;
$R^6$ is selected from carboxy, C$_{1-6}$alkoxycarbonyl, carboxyC$_{1-6}$alkoxycarbonyl, carboxyC$_{3-7}$cycloalkylaminocarbonyl, carboxyheterocyclylcarbonyl, C$_{3-7}$cycloalkylsulfonylaminocarbonyl, hydroxyC$_{1-6}$alkylaminocarbonyl, C$_{4-6}$alkylsulfonylheterocyclylcarbonyl, heterocyclylcarbonyl, hydroxyheterocyclylcarbonyl, (hydroxy)$_2$heterocyclylcarbonyl, C$_{1-6}$alkylsulfonylaminocarbonylheterocyclylcarbonyl, C$_{4-6}$alkylsulfonylaminocarbonyl, cyano, (C$_{1-6}$alkyl)$_2$aminosulfonyl, aminocarbonyl, aminosulfonyl, C$_{3-7}$cycloalkylaminocarbonylcarbonyl and C$_{3-7}$cycloalkylaminocarbonyl;
$A_1$ is selected from N and CR$^7$; wherein R$^7$ is selected from H, halogen and haloC$_{1-6}$alkyl;
$A_2$ is selected from N and CR$^8$; wherein R$^8$ is selected from H, halogen, hydroxy, C$_{1-6}$alkyl, C$_{1-6}$alkoxy, C$_{3-7}$cycloalkyl, haloC$_{1-6}$alkyl, haloC$_{1-6}$alkoxy, haloC$_{1-6}$alkylC$_{1-6}$alkoxy, C$_{1-6}$alkylsulfanyl, C$_{1-6}$alkylsulfonyl, C$_{3-7}$cycloalkylC$_{1-6}$alkoxy and heterocyclyl; wherein heterocyclyl is unsubstituted or substituted one or two or three times independently by oxo;
$A_3$ is selected from N and CR$^9$; wherein R$^9$ is selected from H, amino, halogen, hydroxy, C$_{4-6}$alkyl, C$_{1-6}$alkoxy, haloC$_{1-6}$alkyl, haloC$_{1-6}$alkoxy, haloC$_{1-6}$alkylC$_{1-6}$alkoxy and C$_{3-7}$cycloalkylC$_{4-6}$alkoxy;
or R$^8$ and R$^9$, together with the atoms to which they are attached, form a heterocyclyl ring; wherein heterocyclyl ring is unsubstituted or substituted by one or two or three or four substituents independently selected from halogen, C$_{1-6}$alkyl and oxo;
$A_4$ is selected from N and CR$^{10}$; wherein R$^{10}$ is selected from H and halogen;
$G_1$ is selected from C$_{1-6}$alkyl, C$_{3-7}$cycloalkyl, C$_{3-7}$cycloalkylC$_{1-6}$alkyl, phenylC$_{1-6}$alkyl, C$_{4-6}$alkylC$_{3-7}$cycloalkylC$_{1-6}$alkyl and heterocyclyl; wherein C$_{1-6}$alkyl, C$_{3-7}$cycloalkyl, C$_{3-7}$cycloalkylC$_{1-6}$alkyl, phenylC$_{1-6}$alkyl, C$_{1-6}$alkylC$_{3-7}$cycloalkylC$_{1-6}$alkyl and heterocyclyl are unsubstituted or substituted by one or two or three substituents independently selected from hydroxy, amino, C$_{3-7}$cycloalkylsulfonylamino, C$_{1-6}$alkylphenylsulfonylamino, phenylsulfonyl, C$_{3-7}$cycloalkylsulfonyl, C$_{1-6}$alkoxyphenylsulfonyl, phenylcarbonyl, phenylcarbonylamino, C$_{1-6}$alkylcarbonylamino, C$_{1-6}$alkylaminosulfonylamino, aminocarbonyamino, (C$_{1-6}$alkoxy)$_2$phenylaminosulfonylamino, C$_{1-6}$alkoxycarbonylcarbonylamino, (C$_{1-6}$alkyl)$_2$aminosulfonylamino, C$_{1-6}$alkylaminocarbonylamino, C$_{1-6}$alkylaminosulfonyl, aminosulfonylamino, C$_{3-7}$cycloalkylaminosulfonylamino and phenylC$_{1-6}$alkylaminosulfonylamino;
$G_2$ is selected from C$_{1-6}$alkyl, C$_{3-7}$cycloalkyl and phenyl;
m is selected from 0 and 1;
or a pharmaceutically acceptable salt thereof.

A further embodiment of the present invention is (ii) a compound of formula (I) according to embodiment (i) or a pharmaceutically acceptable salt thereof, wherein
$R^1$ is selected from halogen and haloC$_{1-6}$alkyl;
$R^2$ is selected from H, halogen, C$_{1-6}$alkyl, C$_{1-6}$alkoxy, C$_{3-7}$cycloalkyl and haloC$_{1-6}$alkyl;
$R^3$ is selected from H, halogen and C$_{1-6}$alkoxy;
$R^4$ is selected from H, hydroxy and haloC$_{1-6}$alkyl;
$R^5$ is selected from H, halogen, C$_{1-6}$alkyl, C$_{1-6}$alkoxy and hydroxy;
$R^6$ is selected from carboxy, C$_{1-6}$alkoxycarbonyl, carboxyC$_{1-6}$alkoxycarbonyl, carboxyC$_{3-7}$cycloalkylaminocarbonyl, carboxypyrrolidinylcarbonyl, C$_{3-7}$cycloalkylsulfonylaminocarbonyl, hydroxyC$_{1-6}$alkylaminocarbonyl, C$_{4-6}$alkylsulfonylpyrrolidinylcarbonyl, morpholinylcarbonyl, hydroxypyrrolidinylcarbonyl, (hydroxy)$_2$pyrrolidinylcarbonyl, C$_{1-6}$alkylsulfonylaminocarbonylpyrrolidinylcarbonyl, C$_{1-6}$ alkylsulfonylaminocarbonyl, cyano, ($C_{1-6}$alkyl)$_2$aminosulfonyl, aminocarbonyl, aminosulfonyl, $C_{3-7}$cycloalkylaminocarbonylcarbonyl and $C_{3-7}$cycloalkylaminocarbonyl;

$A_1$ is selected from N and $CR^7$; wherein $R^7$ is selected from H, halogen and halo$C_{1-6}$alkyl;

$A_2$ is selected from N and $CR^8$; wherein $R^8$ is selected from H, halogen, hydroxy, $C_{1-6}$alkyl, $C_{1-6}$alkoxy, $C_{3-7}$cycloalkyl, halo$C_{1-6}$alkyl, halo$C_{1-6}$alkoxy, halo$C_{1-6}$alkyl$C_{1-6}$alkoxy, $C_{1-6}$alkylsulfanyl, $C_{1-6}$alkylsulfonyl, $C_{3-7}$cycloalkyl$C_{1-6}$alkoxy, thiazolyl, morpholinyl, pyrrolidinyl and oxazolidinyl; wherein pyrrolidinyl and oxazolidinyl are unsubstituted or substituted by one or two or three substituents independently selected from oxo;

$A_3$ is selected from N and $CR^9$; wherein $R^9$ is selected from H, amino, halogen, hydroxy, $C_{4-6}$alkyl, $C_{1-6}$alkoxy, halo$C_{1-6}$alkyl, halo$C_{1-6}$alkoxy, halo$C_{1-6}$alkyl$C_{1-6}$alkoxy and $C_{3-7}$cycloalkyl$C_{1-6}$alkoxy;

or $R^8$ and $R^9$, together with the atoms to which they are attached, form a 5- or 6-membered heterocyclyl ring; wherein 5- or 6-membered heterocyclyl ring is unsubstituted or substituted by one or two or three or four substituents independently selected from halogen, $C_{1-6}$alkyl and oxo;

$A_4$ is selected from N and $CR^{10}$; wherein $R^{10}$ is selected from H and halogen;

$G_1$ is selected from $C_{1-6}$alkyl, $C_{3-7}$cycloalkyl, $C_{3-7}$cycloalkyl$C_{1-6}$alkyl, phenyl$C_{1-6}$alkyl, $C_{1-6}$alkyl$C_{3-7}$cycloalkyl$C_{1-6}$alkyl and pyrrolidinyl; wherein $C_{1-6}$alkyl, $C_{3-7}$cycloalkyl, $C_{3-7}$cycloalkyl$C_{1-6}$alkyl, phenyl$C_{1-6}$alkyl, $C_{1-6}$alkyl$C_{3-7}$cycloalkyl$C_{1-6}$alkyl and pyrrolidinyl are unsubstituted or substituted by one or two or three substituents independently selected from hydroxy, amino, $C_{3-7}$cycloalkylsulfonylamino, $C_{1-6}$alkylphenylsulfonylamino, phenylsulfonyl, $C_{3-7}$cycloalkylsulfonyl, $C_{1-6}$alkoxyphenylsulfonyl, phenylcarbonyl, phenylcarbonylamino, $C_{1-6}$alkylcarbonylamino, $C_{1-6}$alkylaminosulfonylamino, aminocarbonyamino, ($C_{1-6}$alkoxy)$_2$phenylaminosulfonylamino, $C_{4-6}$alkoxycarbonylcarbonylamino, ($C_{1-6}$alkyl)$_2$aminosulfonylamino, $C_{1-6}$alkylaminocarbonylamino, $C_{1-6}$alkylaminosulfonyl, aminosulfonylamino, $C_{3-7}$cycloalkylaminosulfonylamino and phenyl$C_{1-6}$alkylaminosulfonylamino;

$G_2$ is selected from $C_{1-6}$alkyl, $C_{3-7}$cycloalkyl and phenyl;

m is selected from 0 and 1.

A further embodiment of the present invention is (iii) a compound of formula (I) according to embodiment (i) or a pharmaceutically acceptable salt thereof, wherein $R^1$ is selected from F, Cl, Br and $CF_3$;

$R^2$ is selected from H, F, Cl, Br, methyl, methoxy, $CF_3$ and cyclopropyl;

$R^3$ is selected from H, F and methoxy;

$R^4$ is selected from H, hydroxy and $CF_3$;

$R^5$ is selected from H, hydroxy, methyl and methoxy;

$R^6$ is selected from carboxy, methoxycarbonyl, carboxyisopropoxycarbonyl, carboxycyclobutylaminocarbonyl, carboxypyrrolidinylcarbonyl, cyclopropylsulfonylaminocarbonyl, hydroxyethylaminocarbonyl, methylsulfonylpyrrolidinylcarbonyl, hydroxypyrrolidinylcarbonyl, (hydroxy)$_2$pyrrolidinylcarbonyl, morpholinylcarbonyl, methylsulfonylaminocarbonylpyrrolidinylcarbonyl, methylsulfonylaminocarbonyl, cyano, (methyl)$_2$aminosulfonyl, aminocarbonyl, aminosulfonyl, cyclopropylaminocarbonylcarbonyl and cyclopropylaminocarbonyl;

$A_1$ is selected from N and $CR^7$; wherein $R^7$ is selected from H, F, Cl, Br and $CF_3$;

$A_2$ is selected from N and $CR^8$; wherein $R^8$ is selected from H, F, Cl, Br, $CF_3$, hydroxy, methyl, ethyl, isopropyl, methoxy, ethoxy, propoxy, cyclopropyl, trifluoromethoxy, difluoromethoxy, trifluoromethylmethoxy, methylsulfonyl, methylsulfanyl, cyclopropylmethoxy, thiazolyl, morpholinyl, pyrrolidinyl and oxazolidinyl; wherein pyrrolidinyl and oxazolidinyl are unsubstituted or substituted one or two or three times independently by oxo;

$A_3$ is selected from N and $CR^9$; wherein $R^9$ is selected from H, amino, hydroxy, F, Cl, Br, $CF_3$, methyl, methoxy, ethoxy, difluoromethoxy, trifluoromethoxy, trifluoromethylmethoxy, difluoromethyl and cyclopropylmethoxy;

or $R^8$ and $R^9$, together with the atoms to which they are attached, form a 5- or 6-membered heterocyclyl ring; wherein 5- or 6-membered heterocyclyl ring is unsubstituted or substituted by one or two or three or four substituents independently selected from F, methyl and oxo;

$A_4$ is selected from N and $CR^{10}$; wherein $R^{10}$ is selected from H and F;

$G_1$ is selected from methyl, ethyl, propyl, isopropyl, butyl, isobutyl, neopentyl, hexyl, isohexyl, cyclobutyl, cyclopentyl, cyclohexyl, cyclobutylmethyl, phenylmethyl, methylcyclopropylmethyl and pyrrolidinyl; wherein methyl, ethyl, propyl, isopropyl, butyl, isobutyl, neopentyl, hexyl, isohexyl, cyclobutyl, cyclopentyl, cyclohexyl, cyclobutylmethyl, phenylmethyl, methylcyclopropylmethyl and pyrrolidinyl are unsubstituted or substituted by one or two or three substituents independently selected from hydroxy, amino, cyclopropylsulfonylamino, methylphenylsulfonylamino, phenylsulfonyl, cyclopropylsulfonyl, methoxyphenylsulfonyl, phenylcarbonyl, phenylcarbonylamino, methylcarbonylamino, ethylaminosulfonylamino, aminocarbonylamino, (methoxy)$_2$phenylcarbamoylamino, ethyoxycarbonylcarbonylamino, dimethylaminosulfonylamino, ethylaminocarbonylamino, ethylaminosulfonyl, aminosulfonylamino, methylaminosulfonylamino, isopropylaminosulfonylamino, cyclopropylaminosulfonylamino and phenylmethylaminosulfonylamino;

$G_2$ is selected from methyl, isopropyl, cyclobutyl, cyclopentyl and phenyl;

m is selected from 0 and 1.

A further embodiment of the present invention is (iv) a compound of formula (I) according to embodiment (i) or a pharmaceutically acceptable salt thereof, wherein $R^1$ is halogen;

$R^2$ is selected from H, halogen, $C_{1-6}$alkoxy and $C_{3-7}$cycloalkyl;

$R^3$ is selected from H, halogen and $C_{1-6}$alkoxy;

$R^4$ is selected from H and hydroxy;

$R^5$ is selected from H, $C_{1-6}$alkyl, $C_{1-6}$alkoxy and hydroxy;

$R^6$ is selected from carboxy, $C_{1-6}$alkoxycarbonyl, carboxy$C_{1-6}$alkoxycarbonyl, carboxy$C_{3-7}$cycloalkylaminocarbonyl, carboxypyrrolidinylcarbonyl, $C_{3-7}$cycloalkylsulfonylaminocarbonyl, hydroxy$C_{1-6}$alkylaminocarbonyl, $C_{4-6}$alkylsulfonylpyrrolidinylcarbonyl, morpholinylcarbonyl, hydroxypyrrolidinylcarbonyl, (hydroxy)$_2$pyrrolidinylcarbonyl, $C_{1-6}$alkylsulfonylaminocarbonylpyrrolidinylcarbonyl, ($C_{1-6}$alkyl)$_2$aminosulfonyl and aminosulfonyl;

$A_1$ is $CR^7$; wherein $R^7$ is selected from H and halogen;

$A_2$ is $CR^8$; wherein $R^8$ is selected from H, hydroxy, halogen, $C_{1-6}$alkyl, $C_{1-6}$alkoxy, halo$C_{1-6}$alkyl, halo$C_{1-6}$alkoxy and halo$C_{1-6}$alkyl$C_{1-6}$alkoxy;

$A_3$ is selected from N and $CR^9$; wherein $R^9$ is selected from H, halogen, hydroxy, $C_{1-6}$alkyl, $C_{1-6}$alkoxy and $haloC_{1-6}$alkoxy;
or $R^8$ and $R^9$, together with the atoms to which they are attached, form a 5- or 6-membered heterocyclyl ring;
$A_4$ is selected from N and $CR^{10}$; wherein $R^{10}$ is selected from H and halogen;
$G_1$ is selected from $C_{1-6}$alkyl and $C_{1-6}$alkyl$C_{3-7}$cycloalkyl$C_{1-6}$alkyl; wherein $C_{1-6}$alkyl is unsubstituted or substituted by one or two or three substituents independently selected from hydroxy, amino, $C_{3-7}$cycloalkylsulfonylamino, $C_{1-6}$alkylphenylsulfonylamino and $C_{1-6}$alkylaminosulfonylamino;
m is 0.

A further embodiment of the present invention is (v) a compound of formula (I) according to embodiment (i) or a pharmaceutically acceptable salt thereof, wherein
$R^1$ is selected from F, Cl and Br;
$R^2$ is selected from H, F, Cl, Br, methoxy and $CF_3$;
$R^3$ is selected from H, F and methoxy;
$R^4$ is selected from H and hydroxy;
$R^5$ is selected from H and hydroxy;
$R^6$ is carboxy, methoxycarbonyl, carboxyisopropoxycarbonyl, carboxycyclobutylaminocarbonyl, carboxypyrrolidinylcarbonyl, cyclopropylsulfonylaminocarbonyl, hydroxyethylaminocarbonyl, methylsulfonylpyrrolidinylcarbonyl, hydroxypyrrolidinylcarbonyl, (hydroxy)$_2$pyrrolidinylcarbonyl, morpholinylcarbonyl, methylsulfonylaminocarbonylpyrrolidinylcarbonyl, (methyl)$_2$aminosulfonyl or aminosulfonyl;
$A_1$ is $CR^7$; wherein $R^7$ is selected from H, F, Cl and Br;
$A_2$ is $CR^8$; wherein $R^8$ is selected from H, F, Cl, Br, $CF_3$, hydroxy, methyl, methoxy, trifluoromethoxy and trifluoromethylmethoxy;
$A_3$ is $CR^9$; wherein $R^9$ is selected from H, hydroxy, F, Cl, Br, methyl, methoxy and trifluoromethoxy;
or $R^8$ and $R^9$, together with the atoms to which they are attached, form a 5- or 6-membered heterocyclyl ring;
$A_4$ is selected from N and $CR^{10}$; wherein $R^{10}$ is selected from H and F;
$G_1$ is selected from methyl, ethyl, propyl, isopropyl, butyl, isobutyl, neopentyl, hexyl, isohexyl and methylcyclopropylmethyl; wherein ethyl is unsubstituted or substituted by one or two or three substituents independently selected from hydroxy, amino, cyclopropylsulfonylamino, methylphenylsulfonylamino and ethylaminosulfonylamino;
m is 0.

A further embodiment of the present invention is (vi) a compound of formula (I) according to embodiment (i) or a pharmaceutically acceptable salt thereof, wherein $R^1$ is halogen.

A further embodiment of the present invention is (vii) a compound of formula (I) according to embodiment (i) or a pharmaceutically acceptable salt thereof, wherein $R^1$ is selected from Cl and Br.

A further embodiment of the present invention is (viii) a compound of formula (I) according to embodiment (i) or a pharmaceutically acceptable salt, or enantiomer, or diastereomer thereof, wherein $R^6$ is selected from carboxy and $C_{1-6}$alkoxycarbonyl.

A further embodiment of the present invention is (ix) a compound of formula (I) according to embodiment (i) or a pharmaceutically acceptable salt thereof, wherein $R^6$ is selected from carboxy and methoxycarbonyl.

A further embodiment of the present invention is (x) a compound of formula (I) according to embodiment (i) or a pharmaceutically acceptable salt thereof, wherein $A_2$ is $CR^8$; wherein $R^8$ is selected from halogen, $C_{1-6}$alkoxy, $haloC_{1-6}$alkyl and $haloC_{1-6}$alkoxy.

A further embodiment of the present invention is (xi) a compound of formula (I) according to embodiment (i) or a pharmaceutically acceptable salt thereof, wherein $A_2$ is $CR^8$; wherein $R^8$ is selected from Cl, Br, $CF_3$, methoxy and trifluoromethoxy.

A further embodiment of the present invention is (xii) a compound of formula (I) according to embodiment (i) or a pharmaceutically acceptable salt thereof, wherein $A_3$ is $CR^9$; wherein $R^9$ is selected from H, $C_{1-6}$alkyl and $C_{1-6}$alkoxy.

A further embodiment of the present invention is (xiii) a compound of formula (I) according to embodiment (i) or a pharmaceutically acceptable salt thereof, wherein $A_3$ is $CR^9$; wherein $R^9$ is selected from H, methyl and methoxy.

A further embodiment of the present invention is (xiv) a compound of formula (I) according to embodiment (i) or a pharmaceutically acceptable salt thereof, wherein $G_1$ is $C_{1-6}$alkyl; wherein $C_{1-6}$alkyl is unsubstituted or substituted by one substituent independently selected from $C_{3-7}$cycloalkylsulfonylamino and $C_{1-6}$alkylaminosulfonylamino.

A further embodiment of the present invention is (xv) a compound of formula (I) according to embodiment (i) or a pharmaceutically acceptable salt thereof, wherein $G_1$ is ethyl; wherein ethyl is unsubstituted or substituted by one substituent independently selected from cyclopropylsulfonylamino and ethylaminosulfonylamino.

A further embodiment of the present invention is (xvi) a compound of formula (I) according to embodiment (i) or a pharmaceutically acceptable salt thereof, wherein
$R^1$ is halogen;
$R^2$ is H;
$R^3$ is H;
$R^4$ is H;
$R^5$ is H;
$R^6$ is selected from carboxy and $C_{1-6}$alkoxycarbonyl;
$A_1$ is CH;
$A_2$ is $CR^8$; wherein $R^8$ is selected from halogen, $C_{1-6}$alkoxy, $haloC_{1-6}$alkyl and $haloC_{1-6}$alkoxy;
$A_3$ is $CR^9$; wherein $R^9$ is selected from H, methyl and methoxy;
$A_4$ is CH;
$G_1$ is $C_{1-6}$alkyl; wherein $C_{1-6}$alkyl is unsubstituted or substituted by one substituent independently selected from $C_{3-7}$cycloalkylsulfonylamino and $C_{1-6}$alkylaminosulfonylamino;
m is 0.

A further embodiment of the present invention is (xvii) a compound of formula (I) according to embodiment (i) or a pharmaceutically acceptable salt thereof, wherein
$R^1$ is selected from Cl and Br;
$R^2$ is H;
$R^3$ is H;
$R^4$ is H;
$R^5$ is H;
$R^6$ is selected from carboxy and methoxycarbonyl;
$A_1$ is CH;
$A_2$ is $CR^8$; wherein $R^8$ is selected from Cl, Br, $CF_3$, methoxy and trifluoromethoxy;
$A_3$ is $CR^9$; wherein $R^9$ is selected from H, methyl and methoxy;
$A_4$ is CH;
$G_1$ is ethyl; wherein ethyl is unsubstituted or substituted by one substituent independently selected from cyclopropylsulfonylamino and ethylaminosulfonylamino;
m is 0.

In another embodiment (xviii) of the present invention, particular compounds of the present invention are selected from:

3-[2-(8-chloro-4-oxo-chromen-2-yl)-5-(trifluoromethyl)phenoxy]propanoic acid;
methyl 3-[2-(8-chloro-4-oxo-chromen-2-yl)-5-(trifluoromethyl)phenoxy]propanoate;
3-[2-(8-chloro-6-fluoro-4-oxo-chromen-2-yl)-5-(trifluoromethyl)phenoxy]propanoic acid;
3-[5-bromo-2-(8-chloro-4-oxo-chromen-2-yl)phenoxy]propanoic acid;
3-[5-chloro-2-(8-chloro-4-oxo-chromen-2-yl)-4-methylphenoxy]propanoic acid;
3-[5-bromo-2-(8-chloro-4-oxo-chromen-2-yl)-4-methylphenoxy]propanoic acid;
3-[5-bromo-2-(8-chloro-4-oxo-chromen-2-yl)-4-methoxyphenoxy]propanoic acid;
3-[5-chloro-2-(8-chloro-4-oxo-chromen-2-yl)-4-methoxyphenoxy]propanoic acid;
3-[2-(8-chloro-4-oxo-chromen-2-yl)-5-(trifluoromethoxy)phenoxy]propanoic acid;
3-[2-(8-chloro-4-oxo-chromen-2-yl)-4,5-dimethoxy-phenoxy]propanoic acid;
3-[[6-(8-chloro-4-oxo-chromen-2-yl)-1,3-benzodioxol-5-yl]oxy]propanoic acid;
3-[2-(8-chloro-4-oxo-chromen-2-yl)-5-methoxy-4-methyl-phenoxy]propanoic acid;
3-[2-(8-chloro-4-oxo-chromen-2-yl)-5-methyl-phenoxy]propanoic acid;
3-[5-bromo-2-(8-chloro-4-oxo-chromen-2-yl)-4-(trifluoromethoxy)phenoxy]propanoic acid;
3-[2-(8-chloro-4-oxo-chromen-2-yl)-4-methoxy-5-methyl-phenoxy]propanoic acid;
3-[4-bromo-2-(8-chloro-4-oxo-chromen-2-yl)-5-(trifluoromethoxy)phenoxy]propanoic acid;
3-[2-(8-chloro-4-oxo-chromen-2-yl)-4-methyl-5-(trifluoromethoxy)phenoxy]propanoic acid;
3-[2-bromo-6-(8-chloro-4-oxo-chromen-2-yl)-4-methyl-phenoxy]propanoic acid;
3-[2-(8-chloro-4-oxo-chromen-2-yl)-5-methyl-4-(trifluoromethoxy)phenoxy]propanoic acid;
3-[5-bromo-2-(8-chloro-4-oxo-chromen-2-yl)-3-fluoro-phenoxy]propanoic acid;
3-[2-(8-chloro-4-oxo-chromen-2-yl)-3-fluoro-5-methylphenoxy]propanoic acid;
3-[2-(8-bromo-4-oxo-chromen-2-yl)-5-(trifluoromethoxy)phenoxy]propanoic acid;
3-[2-(7-bromo-8-chloro-4-oxo-chromen-2-yl)-5-(trifluoromethoxy)phenoxy]propanoic acid;
3-[2-(8-bromo-4-oxo-chromen-2-yl)-5-methyl-phenoxy]propanoic acid;
3-[2-(8-bromo-4-oxo-chromen-2-yl)-5-chloro-4-methylphenoxy]propanoic acid;
3-[[5-bromo-2-(8-chloro-4-oxo-chromen-2-yl)-3-pyridyl]oxy]propanoic acid;
3-[2-(8-chloro-7-fluoro-4-oxo-chromen-2-yl)-5-(trifluoromethyl)phenoxy]propanoic acid;
3-[2-(8-chloro-7-methoxy-4-oxo-chromen-2-yl)-5-(trifluoromethyl)phenoxy]propanoic acid;
3-[2-(8-chloro-6-methoxy-4-oxo-chromen-2-yl)-5-(trifluoromethyl)phenoxy]propanoic acid;
3-[2-(8-chloro-3-methyl-4-oxo-chromen-2-yl)-5-(trifluoromethyl)phenoxy]propanoic acid;
methyl 3-[5-chloro-2-(8-chloro-4-oxo-chromen-2-yl)-4-methyl-phenoxy]propanoate;
3-[2-(8-chloro-4-oxo-chromen-2-yl)-5-(trifluoromethyl)phenoxy]butanoic acid;
3-[3-[2-(8-chloro-4-oxo-chromen-2-yl)-5-(trifluoromethyl)phenoxy]butanoyloxy]butanoic acid;
3-[2-(8-chloro-4-oxo-chromen-2-yl)-4-methoxy-5-(2,2,2-trifluoroethoxy)phenoxy]propanoic acid;
3-[2-[8-chloro-4-oxo-7-(trifluoromethyl)chromen-2-yl]-5-(trifluoromethoxy)phenoxy]propanoic acid;
3-[2-(8-chloro-4-oxo-chromen-2-yl)-4-methoxy-5-(trifluoromethyl)phenoxy]propanoic acid;
3-[2-(8-chloro-4-oxo-chromen-2-yl)-4-methyl-5-(trifluoromethyl)phenoxy]propanoic acid;
3-[2-(8-chloro-5-hydroxy-4-oxo-chromen-2-yl)-5-(trifluoromethyl)phenoxy]propanoic acid;
3-[2-(8-chloro-3-hydroxy-4-oxo-chromen-2-yl)-5-(trifluoromethyl)phenoxy]propanoic acid;
3-[2-(8-chloro-3-methoxy-4-oxo-chromen-2-yl)-5-(trifluoromethyl)phenoxy]propanoic acid;
2-[2-(8-chloro-4-oxo-chromen-2-yl)-5-(trifluoromethoxy)phenoxy]acetic acid;
2-[2-(8-chloro-4-oxo-chromen-2-yl)-5-methyl-phenoxy]acetic acid;
2-[2-(8-chloro-4-oxo-chromen-2-yl)-4,5-dimethoxy-phenoxy]acetic acid;
2-[2-(8-chloro-4-oxo-chromen-2-yl)-5-(trifluoromethyl)phenoxy]acetic acid;
4-[2-(8-chloro-4-oxo-chromen-2-yl)-5-(trifluoromethyl)phenoxy]butanoic acid;
4-[2-(8-chloro-4-oxo-chromen-2-yl)-5-(trifluoromethoxy)phenoxy]butanoic acid;
4-[5-bromo-2-(8-chloro-4-oxo-chromen-2-yl)-4-methylphenoxy]butanoic acid;
4-[5-bromo-2-(8-chloro-4-oxo-chromen-2-yl)phenoxy]butanoic acid;
4-[2-(8-chloro-4-oxo-chromen-2-yl)-4,5-dimethoxy-phenoxy]butanoic acid
4-[5-chloro-2-(8-chloro-4-oxo-chromen-2-yl)-4-methylphenoxy]butanoic acid
4-[5-bromo-2-(8-chloro-4-oxo-chromen-2-yl)-4-methoxyphenoxy]butanoic acid
4-[2-(8-chloro-4-oxo-chromen-2-yl)-5-methyl-phenoxy]butanoic acid
4-[2-(8-chloro-4-oxo-chromen-2-yl)-5-methoxy-4-methylphenoxy]butanoic acid;
3-[2-(8-chloro-4-oxo-chromen-2-yl)-5-(trifluoromethoxy)phenoxy]-2,2-dimethyl-propanoic acid;
3-[2-(8-chloro-4-oxo-chromen-2-yl)-5-(trifluoromethyl)phenoxy]-2,2-dimethyl-propanoic acid;
3-[2-(8-chloro-4-oxo-chromen-2-yl)-5-methyl-phenoxy]-2,2-dimethyl-propanoic acid;
3-[5-chloro-2-(8-chloro-4-oxo-chromen-2-yl)-4-methylphenoxy]-2,2-dimethyl-propanoic acid;
5-[2-(8-chloro-4-oxo-chromen-2-yl)-5-(trifluoromethyl)phenoxy]pentanoic acid;
7-[2-(8-chloro-4-oxo-chromen-2-yl)-5-(trifluoromethyl)phenoxy]heptanoic acid;
2-[1-[[2-(8-chloro-4-oxo-chromen-2-yl)-4,5-dimethoxyphenoxy]methyl]cyclopropyl]acetic acid;
2-[1-[[5-bromo-2-(8-chloro-4-oxo-chromen-2-yl)-4-methyl-phenoxy]methyl]cyclopropyl]acetic acid;
2-[1-[[5-bromo-2-(8-chloro-4-oxo-chromen-2-yl)phenoxy]methyl]cyclopropyl]acetic acid;
2-5-bromo-2-(8-chloro-4-oxo-chromen-2-yl)phenoxy]-2-methyl-propanoic acid;
5-[2-(8-chloro-4-oxo-chromen-2-yl)-5-(trifluoromethoxy)phenoxy]-2,2-dimethyl-pentanoic acid;
2-[5-bromo-2-(8-chloro-4-oxo-chromen-2-yl)-4-methylphenoxy]acetic acid;

3-[[2-[2-(8-chloro-4-oxo-chromen-2-yl)-5-(trifluoromethyl)
  phenoxy]acetyl]amino]cyclobutanecarboxylic acid;
(2R)-1-[3-[5-bromo-2-(8-chloro-4-oxo-chromen-2-yl)phe-
  noxy]propanoyl]pyrrolidine-2-carboxylic acid;
(2S)-1-[3-[5-bromo-2-(8-chloro-4-oxo-chromen-2-yl)phe-
  noxy]propanoyl]pyrrolidine-2-carboxylic acid;
(2R)-1-[2-[2-(8-chloro-4-oxo-chromen-2-yl)-5-methyl-phe-
  noxy]acetyl]pyrrolidine-2-carboxylic acid;
(2S)-1-[2-[2-(8-chloro-4-oxo-chromen-2-yl)-5-methyl-phe-
  noxy]acetyl]pyrrolidine-2-carboxylic acid;
(2R)-1-[2-[5-bromo-2-(8-chloro-4-oxo-chromen-2-yl)-4-
  methyl-phenoxy]acetyl]pyrrolidine-2-carboxylic acid;
(2S)-1-[2-[5-bromo-2-(8-chloro-4-oxo-chromen-2-yl)-4-
  methyl-phenoxy]acetyl]pyrrolidine-2-carboxylic acid;
(2R)-1-[2-[2-(8-chloro-4-oxo-chromen-2-yl)-5-(trifluorom-
  ethyl)phenoxy]acetyl]pyrrolidine-2-carboxylic acid;
(2S)-1-[2-[2-(8-chloro-4-oxo-chromen-2-yl)-5-(trifluorom-
  ethyl)phenoxy]acetyl]pyrrolidine-2-carboxylic acid;
(3S)-1-[2-[2-(8-chloro-4-oxo-chromen-2-yl)-5-(trifluorom-
  ethyl)phenoxy]acetyl]pyrrolidine-3-carboxylic acid;
3-[2-(8-chloro-4-oxo-chromen-2-yl)-5-(trifluoromethyl)
  phenoxy]-N-cyclopropylsulfonyl-propanamide;
3-[2-(8-chloro-4-oxo-chromen-2-yl)-4,5-dimethoxy-phe-
  noxy]-N-cyclopropylsulfonyl-propanamide;
2-[2-(8-chloro-4-oxo-chromen-2-yl)-5-(trifluoromethyl)
  phenoxy]-N-(2-hydroxy ethyl) acetamide;
8-chloro-2-[2-[2-(3-methylsulfonylpyrrolidin-1-yl)-2-oxo-
  ethoxy]-4-(trifluoromethyl)phenyl]chromen-4-one;
2-[4-bromo-2-[2-[(3S)-3-hydroxypyrrolidin-1-yl]-2-oxo-
  ethoxy]-5-methyl-phenyl]-8-chloro-chromen-4-one;
2-[4-bromo-2-[2-[(3R)-3-hydroxypyrrolidin-1-yl]-2-oxo-
  ethoxy]-5-methyl-phenyl]-8-chloro-chromen-4-one;
2-[4-bromo-5-methyl-2-[2-oxo-2-[rac-(3S,4R)-3,4-dihy-
  droxypyrrolidin-1-yl]ethoxy]phenyl]-8-chloro-chromen-
  4-one;
2-[2-(8-chloro-4-oxo-chromen-2-yl)-4,5-dimethoxy-phe-
  noxy]-N-cyclopropylsulfonyl-acetamide;
8-chloro-2-[2-[2-(2-morpholino-2-oxo-ethoxy]-4-(trifluorom-
  ethyl)phenyl]chromen-4-one;
(2S)-1-[2-[2-(8-chloro-4-oxo-chromen-2-yl)-5-methyl-phe-
  noxy]acetyl]-N-methylsulfonyl-pyrrolidine-2-carboxam-
  ide;
(2R)-1-[2-[2-(8-chloro-4-oxo-chromen-2-yl)-5-methyl-phe-
  noxy]acetyl]-N-methylsulfonyl-pyrrolidine-2-carboxam-
  ide;
(2S)-2-amino-3-[2-(8-chloro-4-oxo-chromen-2-yl)-5-(trif-
  luoromethyl)phenoxy]propanoic acid;
(2S)-3-[2-(8-chloro-4-oxo-chromen-2-yl)-5-(trifluorom-
  ethyl)phenoxy]-2-(cyclopropylsulfonylamino)propanoic
  acid;
(2S)-3-[2-(8-chloro-4-oxo-chromen-2-yl)-5-(trifluorom-
  ethyl)phenoxy]-2-(p-tolylsulfonylamino)propanoic acid;
methyl(2S)-3-[2-(8-chloro-4-oxo-chromen-2-yl)-5-(trifluo-
  romethyl)phenoxy]-2-(ethylsulfamoylamino)propanoate;
(2S)-3-[2-(8-chloro-4-oxo-chromen-2-yl)-5-(trifluorom-
  ethyl)phenoxy]-2-(ethylsulfamoylamino)propanoic acid;
4-[2-(8-chloro-5-hydroxy-4-oxo-chromen-2-yl)-5-(trifluo-
  romethyl)phenoxy]butanoic acid;
3-[5-bromo-2-(8-chloro-4-oxo-chromen-2-yl)phenoxy]-N,
  N-dimethyl-propane-1-sulfonamide;
3-[2-(8-chloro-4-oxo-chromen-2-yl)-5-(trifluoromethyl)
  phenoxy]propane-1-sulfonamide;
and
3-[2-(8-chloro-4-oxo-chromen-2-yl)-5-(trifluoromethyl)
  phenoxy]-2-hydroxy-propanoic acid;
or a pharmaceutically acceptable salt thereof.

In another embodiment (xix) of the present invention, particular compounds of the present invention are selected from:
3-[2-(8-chloro-4-oxo-chromen-2-yl)-5-(trifluoromethyl)
  phenoxy]propanoic acid;
methyl 3-[2-(8-chloro-4-oxo-chromen-2-yl)-5-(trifluorom-
  ethyl)phenoxy]propanoate;
3-[5-chloro-2-(8-chloro-4-oxo-chromen-2-yl)-4-methyl-
  phenoxy]propanoic acid;
3-[5-bromo-2-(8-chloro-4-oxo-chromen-2-yl)-4-methyl-
  phenoxy]propanoic acid;
3-[5-chloro-2-(8-chloro-4-oxo-chromen-2-yl)-4-methoxy-
  phenoxy]propanoic acid;
3-[2-(8-chloro-4-oxo-chromen-2-yl)-5-(trifluoromethoxy)
  phenoxy]propanoic acid;
3-[2-(8-chloro-4-oxo-chromen-2-yl)-5-methoxy-4-methyl-
  phenoxy]propanoic acid;
3-[2-(8-bromo-4-oxo-chromen-2-yl)-5-chloro-4-methyl-
  phenoxy]propanoic acid;
(2S)-3-[2-(8-chloro-4-oxo-chromen-2-yl)-5-(trifluorom-
  ethyl)phenoxy]-2-(cyclopropylsulfonylamino)propanoic
  acid; and
(2S)-3-[2-(8-chloro-4-oxo-chromen-2-yl)-5-(trifluorom-
  ethyl)phenoxy]-2-(ethylsulfamoylamino)propanoic acid;
or a pharmaceutically acceptable salt thereof.

A further embodiment of the present invention is (xx) a compound of formula (I) according to embodiment (i) or a pharmaceutically acceptable salt thereof, wherein
$R^1$ is halogen;
$R^2$ is H;
$R^3$ is H;
$R^4$ is selected from H and hydroxy;
$R^5$ is H;
$R^6$ is selected from carboxy, $C_{3-7}$cycloalkylsulfonylaminocarbonyl and $C_{4-6}$alkylsulfonylaminocarbonyl;
$A_1$ is CH;
$A_2$ is $CR^8$; wherein $R^8$ is selected from H, halogen, $C_{1-6}$alkyl, $C_{1-6}$alkoxy, $C_{3-7}$cycloalkyl, halo$C_{1-6}$alkyl and halo$C_{1-6}$alkoxy;
$A_3$ is $CR^9$; wherein $R^9$ is selected from H, halogen, $C_{1-6}$alkyl, $C_{1-6}$alkoxy and halo$C_{1-6}$alkyl; or $R^8$ and $R^9$, together with the atoms to which they are attached, form a 5-membered heterocyclyl ring;
$A_4$ is CH;
$G_1$ is selected from $C_{3-7}$cycloalkyl, $C_{3-7}$cycloalkyl$C_{1-6}$alkyl, phenyl$C_{1-6}$alkyl and pyrrolidinyl; wherein pyrrolidinyl is unsubstituted or substituted by one or two or three substituents independently selected from phenylsulfonyl, $C_{3-7}$cycloalkylsulfonyl, $C_{4-6}$alkoxyphenylsulfonyl and phenylcarbonyl;
m is 0.

A further embodiment of the present invention is (xxi) a compound of formula (I) according to embodiment (i) or a pharmaceutically acceptable salt thereof, wherein
$R^1$ is selected from F, Cl and Br;
$R^2$ is H;
$R^3$ is H;
$R^4$ is selected from Fl and hydroxy;
$R^5$ is H;
$R^6$ is selected from carboxy, cyclopropylsulfonylaminocarbonyl, methylsulfonylaminocarbonyl and cyano;
$A_1$ is CH;
$A_2$ is $CR^8$; wherein $R^8$ is selected from H, F, Cl, Br, $CF_3$, methyl, ethyl, isopropyl, methoxy, ethoxy, cyclopropyl and trifluoromethoxy;

$A_3$ is $CR^9$; wherein $R^9$ is selected from H, F, Cl, Br, methyl, methoxy and trifluoromethyl; or $R^8$ and $R^9$, together with the atoms to which they are attached, form a 5-membered heterocyclyl ring;
$A_4$ is CH;
$G_1$ is selected from phenylmethyl, cyclobutyl, cyclohexyl, cyclobutylmethyl, cyclopentyl and pyrrolidinyl; wherein pyrrolidinyl is unsubstituted or substituted by one or two or three substituents independently selected from phenylsulfonyl, cyclopropylsulfonyl, methoxyphenylsulfonyl and phenylcarbonyl;
m is 0.

A further embodiment of the present invention is (xxii) a compound of formula (I) according to embodiment (i) or a pharmaceutically acceptable salt thereof, wherein $R^1$ is halogen.

A further embodiment of the present invention is (xxiii) a compound of formula (I) according to embodiment (i) or a pharmaceutically acceptable salt thereof, wherein $R^1$ is selected from Cl and Br.

A further embodiment of the present invention is (xxiv) a compound of formula (I) according to embodiment (i) or a pharmaceutically acceptable salt thereof, wherein $R^6$ is selected from carboxy and $C_{3-7}$cycloalkylsulfonylaminocarbonyl.

A further embodiment of the present invention is (xxv) a compound of formula (I) according to embodiment (i) or a pharmaceutically acceptable salt thereof, wherein $R^6$ is selected from carboxy and cyclopropylsulfonylaminocarbonyl.

A further embodiment of the present invention is (xxvi) a compound of formula (I) according to embodiment (i) or a pharmaceutically acceptable salt, or enantiomer, or diastereomer thereof, wherein $A_2$ is $CR^8$; wherein $R^8$ is selected from halogen and halo$C_{1-6}$alkyl.

A further embodiment of the present invention is (xxvii) a compound of formula (I) according to embodiment (i) or a pharmaceutically acceptable salt thereof, wherein $A_2$ is $CR^8$; wherein $R^8$ is selected from Cl and $CF_3$.

A further embodiment of the present invention is (xxviii) a compound of formula (I) according to embodiment (i) or a pharmaceutically acceptable salt thereof, wherein $A_3$ is $CR^9$; wherein $R^9$ is selected from H and $C_{1-6}$alkyl.

A further embodiment of the present invention is (xxix) a compound of formula (I) according to embodiment (i) or a pharmaceutically acceptable salt thereof, wherein $A_3$ is $CR^9$; wherein $R^9$ is selected from H and methyl.

A further embodiment of the present invention is (xxx) a compound of formula (I) according to embodiment (i) or a pharmaceutically acceptable salt thereof, wherein wherein $G_1$ is selected from $C_{3-7}$cycloalkyl and pyrrolidinyl; wherein pyrrolidinyl is substituted one time by phenylsulfonyl.

A further embodiment of the present invention is (xxxi) a compound of formula (I) according to embodiment (i) or a pharmaceutically acceptable salt thereof, wherein $G_1$ is cyclobutyl or pyrrolidinyl; wherein pyrrolidinyl is substituted one time by phenylsulfonyl.

A further embodiment of the present invention is (xxxii) a compound of formula (I) according to embodiment (i) or a pharmaceutically acceptable salt thereof, wherein
$R^1$ is halogen;
$R^2$ is H;
$R^3$ is H;
$R^4$ is H;
$R^5$ is H;
$R^6$ is selected from carboxy and $C_{3-7}$cycloalkylsulfonylaminocarbonyl;
$A_1$ is CH;
$A_2$ is $CR^8$; wherein $R^8$ is selected from halogen and halo$C_{1-6}$alkyl;
$A_3$ is $CR^9$; wherein $R^9$ is selected from H and $C_{1-6}$alkyl;
$A_4$ is CH;
$G_4$ is selected from $C_{3-7}$cycloalkyl and pyrrolidinyl; wherein pyrrolidinyl is substituted one time by phenylsulfonyl.
m is 0.

A further embodiment of the present invention is (xxxiii) a compound of formula (I) according to embodiment (i) or a pharmaceutically acceptable salt thereof, wherein
$R^1$ is selected from Cl and Br;
$R^2$ is H;
$R^3$ is H;
$R^4$ is H;
$R^5$ is H;
$R^6$ is selected from carboxy and cyclopropylsulfonylaminocarbonyl;
$A_1$ is CH;
$A_2$ is $CR^8$; wherein $R^8$ is selected from F, Cl, Br and $CF_3$;
$A_3$ is $CR^9$; wherein $R^9$ is selected from H and methyl;
$A_4$ is CH;
$G_4$ is selected from cyclobutyl and pyrrolidinyl; wherein pyrrolidinyl is substituted one time by phenylsulfonyl;
m is 0.

In another embodiment (xxxiv) of the present invention, particular compounds of the present invention are selected from:
3-[[5-bromo-2-(8-chloro-4-oxo-chromen-2-yl)phenoxy]methyl]benzoic acid;
3-[5-bromo-2-(8-chloro-4-oxo-chromen-2-yl)phenoxy]cyclobutanecarboxylic acid;
cis-3-[2-(8-chloro-4-oxo-chromen-2-yl)phenoxy]cyclobutanecarboxylic acid;
trans-3-[2-(8-chloro-4-oxo-chromen-2-yl)phenoxy]cyclobutanecarboxylic acid;
3-[2-(8-chloro-4-oxo-chromen-2-yl)-5-(trifluoromethyl)phenoxy]cyclobutanecarboxylic acid;
3-[5-bromo-2-(8-chloro-4-oxo-chromen-2-yl)-4-methoxyphenoxy]cyclobutanecarboxylic acid;
3-[2-(8-chloro-4-oxo-chromen-2-yl)-5-(trifluoromethoxy)phenoxy]cyclobutanecarboxylic acid;
3-[2-(8-chloro-4-oxo-chromen-2-yl)-4,5-dimethoxy-phenoxy]cyclobutanecarboxylic acid;
3-[4-bromo-2-(8-chloro-4-oxo-chromen-2-yl)-5-(trifluoromethoxy)phenoxy]cyclobutanecarboxylic acid;
3-[2-bromo-6-(8-chloro-4-oxo-chromen-2-yl)-4-methylphenoxy]cyclobutanecarboxylic acid;
4-[5-bromo-2-(8-chloro-4-oxo-chromen-2-yl)phenoxy]cyclohexanecarboxylic acid;
cis-3-[2-(8-chloro-4-oxo-chromen-2-yl)-5-methoxy-phenoxy]cyclobutanecarboxylic acid;
trans-3-[2-(8-chloro-4-oxo-chromen-2-yl)-5-methoxy-phenoxy]cyclobutanecarboxylic acid;
cis-3-[5-chloro-2-(8-chloro-4-oxo-chromen-2-yl)-4-methylphenoxy]cyclobutanecarboxylic acid;
trans-3-[5-chloro-2-(8-chloro-4-oxo-chromen-2-yl)-4-methyl-phenoxy]cyclobutanecarboxylic acid;
cis-3-[5-bromo-2-(8-chloro-4-oxo-chromen-2-yl)-4-methylphenoxy]cyclobutanecarboxylic acid;
trans-3-[5-bromo-2-(8-chloro-4-oxo-chromen-2-yl)-4-methyl-phenoxy]cyclobutanecarboxylic acid;
trans-3-[4-bromo-2-(8-chloro-4-oxo-chromen-2-yl)-5-methoxy-phenoxy]cyclobutanecarboxylic acid;
cis-3-[2-(8-chloro-4-oxo-chromen-2-yl)-5-(trifluoromethoxy)phenoxy]cyclobutanecarboxylic acid;

cis-3-[2-(8-chloro-4-oxo-chromen-2-yl)-4-methyl-phenoxy]cyclobutanecarboxylic acid
trans-3-[2-(8-chloro-4-oxo-chromen-2-yl)-5-methoxy-4-methyl-phenoxy]cyclobutanecarboxylic acid;
cis-3-[2-(8-chloro-4-oxo-chromen-2-yl)-5-methyl-phenoxy]cyclobutanecarboxylic acid;
trans-3-[2-(8-chloro-4-oxo-chromen-2-yl)-5-methyl-phenoxy]cyclobutanecarboxylic acid;
cis-3-[2-(8-chloro-4-oxo-chromen-2-yl)-5-ethyl-phenoxy]cyclobutanecarboxylic acid;
trans-3-[2-(8-chloro-4-oxo-chromen-2-yl)-5-ethyl-phenoxy]cyclobutanecarboxylic acid;
cis-3-[2-(8-chloro-4-oxo-chromen-2-yl)-5-isopropyl-phenoxy]cyclobutanecarboxylic acid;
trans-3-[2-(8-chloro-4-oxo-chromen-2-yl)-5-isopropyl-phenoxy]cyclobutanecarboxylic acid;
trans-3-[2-(8-chloro-4-oxo-chromen-2-yl)-4-methoxy-phenoxy]cyclobutanecarboxylic acid;
trans-3-[2-(8-bromo-4-oxo-chromen-2-yl)phenoxy]cyclobutanecarboxylic acid;
cis-3-[2-(8-bromo-4-oxo-chromen-2-yl)phenoxy]cyclobutanecarboxylic acid;
trans-3-[[6-(8-chloro-4-oxo-chromen-2-yl)-2,3-dihydro benzofuran-5-yl]oxy]cyclobutanecarboxylic acid;
trans-3-[5-bromo-2-(8-chloro-4-oxo-chromen-2-yl)-4-(trifluoromethyl)phenoxy]cyclobutanecarboxylic acid;
cis-3-[[5-bromo-2-(8-chloro-4-oxo-chromen-2-yl)phenoxy]methyl]cyclobutanecarboxylic acid;
trans-3-[[5-bromo-2-(8-chloro-4-oxo-chromen-2-yl)phenoxy]methyl]cyclobutanecarboxylic acid;
cis-3-[[2-(8-chloro-4-oxo-chromen-2-yl)phenoxy]methyl]cyclobutanecarboxylic acid;
trans-3-[[2-(8-chloro-4-oxo-chromen-2-yl)phenoxy]methyl]cyclobutanecarboxylic acid;
cis-3-[[2-(8-chloro-4-oxo-chromen-2-yl)-4-methoxy-phenoxy]methyl]cyclobutanecarboxylic acid;
trans-3-[[2-(8-chloro-4-oxo-chromen-2-yl)-4-methoxy-phenoxy]methyl]cyclobutanecarboxylic acid;
cis-3-[5-bromo-2-(8-chloro-4-oxo-chromen-2-yl)phenoxy]cyclopentanecarboxylic acid;
trans-3-[5-bromo-2-(8-chloro-4-oxo-chromen-2-yl)phenoxy]cyclopentanecarboxylic acid;
trans-3-[[5-bromo-2-(8-chloro-4-oxo-chromen-2-yl)-3-pyridyl]oxy]cyclobutanecarboxylic acid;
cis-3-[2-(8-chloro-4-oxo-chromen-2-yl)-5-cyclopropyl-phenoxy]cyclobutanecarboxylic acid;
trans-3-[2-(8-chloro-4-oxo-chromen-2-yl)-5-cyclopropyl-phenoxy]cyclobutanecarboxylic acid;
cis-3-[5-bromo-2-(8-chloro-5-hydroxy-4-oxo-chromen-2-yl)phenoxy]cyclobutanecarboxylic acid;
cis-3-[2-(8-chloro-5-hydroxy-4-oxo-chromen-2-yl)-5-methyl-phenoxy]cyclobutanecarboxylic acid;
trans-3-[2-(8-chloro-5-hydroxy-4-oxo-chromen-2-yl)-5-methyl-phenoxy]cyclobutanecarboxylic acid;
trans-3-[5-bromo-2-(8-chloro-5-hydroxy-4-oxo-chromen-2-yl)phenoxy]cyclobutanecarboxylic acid;
cis-3-[2-(8-chloro-5-hydroxy-4-oxo-chromen-2-yl)-5-(trifluoromethyl)phenoxy]cyclobutanecarboxylic acid;
trans-3-[2-(8-chloro-5-hydroxy-4-oxo-chromen-2-yl)-5-(trifluoromethyl)phenoxy]cyclobutanecarboxylic acid;
cis-3-[2-(8-chloro-5-hydroxy-4-oxo-chromen-2-yl)-5-ethoxy-phenoxy]cyclobutanecarboxylic acid;
trans-3-[2-(8-chloro-5-hydroxy-4-oxo-chromen-2-yl)-5-ethoxy-phenoxy]cyclobutanecarboxylic acid;
cis-3-[5-bromo-2-(8-chloro-5-hydroxy-4-oxo-chromen-2-yl)-4-methyl-phenoxy]cyclobutanecarboxylic acid;
trans-3-[5-bromo-2-(8-chloro-5-hydroxy-4-oxo-chromen-2-yl)-4-methyl-phenoxy]cyclobutanecarboxylic acid;
3-[2-(8-chloro-5-hydroxy-4-oxo-chromen-2-yl)-4,5-dimethoxy-phenoxy]cyclobutanecarboxylic acid;
cis-3-[2-(8-chloro-4-oxo-chromen-2-yl)-5-(trifluoromethyl)phenoxy]-N-cyclopropylsulfonyl-cyclobutanecarboxamide;
trans-3-[2-(8-chloro-4-oxo-chromen-2-yl)-5-(trifluoromethyl)phenoxy]-N-cyclopropylsulfonyl-cyclobutanecarboxamide;
cis-3-[5-bromo-2-(8-chloro-4-oxo-chromen-2-yl)phenoxy]-N-methylsulfonyl-cyclobutanecarboxamide;
trans-3-[5-bromo-2-(8-chloro-4-oxo-chromen-2-yl)phenoxy]-N-methylsulfonyl-cyclobutanecarboxamide;
cis-3-[2-(8-chloro-4-oxo-chromen-2-yl)-5-(trifluoromethoxy)phenoxy]-N-methylsulfonyl-cyclobutanecarboxamide;
trans-3-[2-(8-chloro-4-oxo-chromen-2-yl)-5-(trifluoromethoxy)phenoxy]-N-methylsulfonyl-cyclobutanecarboxamide;
cis-3-[2-(8-chloro-4-oxo-chromen-2-yl)-5-(trifluoromethyl)phenoxy]-N-methylsulfonyl-cyclobutanecarboxamide;
trans-3-[2-(8-chloro-4-oxo-chromen-2-yl)-5-(trifluoromethyl)phenoxy]-N-methylsulfonyl-cyclobutanecarboxamide;
cis-3-[5-bromo-2-(8-chloro-4-oxo-chromen-2-yl)-4-methyl-phenoxy]-N-methylsulfonyl-cyclobutanecarboxamide;
trans-3-[5-bromo-2-(8-chloro-4-oxo-chromen-2-yl)-4-methyl-phenoxy]-N-methylsulfonyl-cyclobutanecarboxamide;
cis-3-[2-(8-chloro-4-oxo-chromen-2-yl)-5-methoxy-4-methyl-phenoxy]-N-methylsulfonyl-cyclobutanecarboxamide;
trans-3-[2-(8-chloro-4-oxo-chromen-2-yl)-5-methoxy-4-methyl-phenoxy]-N-methylsulfonyl-cyclobutanecarboxamide;
cis-3-[2-(8-chloro-4-oxo-chromen-2-yl)-5-methyl-phenoxy]-N-methylsulfonyl-cyclobutanecarboxamide;
trans-3-[2-(8-chloro-4-oxo-chromen-2-yl)-5-methyl-phenoxy]-N-methylsulfonyl-cyclobutanecarboxamide;
cis-3-[2-(8-chloro-4-oxo-chromen-2-yl)-5-methyl-phenoxy]-N-cyclopropylsulfonyl-cyclobutanecarboxamide;
trans-3-[2-(8-chloro-4-oxo-chromen-2-yl)-5-methyl-phenoxy]-N-cyclopropylsulfonyl-cyclobutanecarboxamide;
cis-3-[5-bromo-2-(8-chloro-4-oxo-chromen-2-yl)-4-methoxy-phenoxy]-N-methylsulfonyl-cyclobutanecarboxamide;
trans-3-[5-bromo-2-(8-chloro-4-oxo-chromen-2-yl)-4-methoxy-phenoxy]-N-methylsulfonyl-cyclobutanecarboxamide;
cis-3-[5-bromo-2-(8-chloro-4-oxo-chromen-2-yl)-4-methoxy-phenoxy]-N-cyclopropylsulfonyl-cyclobutanecarboxamide;
cis-3-[4-bromo-2-(8-chloro-4-oxo-chromen-2-yl)-5-methoxy-phenoxy]-N-methylsulfonyl-cyclobutanecarboxamide;
trans-3-[4-bromo-2-(8-chloro-4-oxo-chromen-2-yl)-5-methoxy-phenoxy]-N-methylsulfonyl-cyclobutanecarboxamide;
cis-3-[4-bromo-2-(8-chloro-4-oxo-chromen-2-yl)-5-methoxy-phenoxy]-N-cyclopropylsulfonyl-cyclobutanecarboxamide;
3-[2-(8-chloro-4-oxo-chromen-2-yl)-4,5-dimethoxy-phenoxy]-N-methylsulfonyl-cyclobutanecarboxamide;
3-[2-(8-chloro-4-oxo-chromen-2-yl)-5-(trifluoromethyl)phenoxy]cyclobutanecarbonitrile;

(2S,4S)-4-[5-bromo-2-(8-chloro-4-oxo-chromen-2-yl)phenoxy]pyrrolidine-2-carboxylic acid;
(2S,4R)-1-(benzenesulfonyl)-4-[2-(8-chloro-4-oxo-chromen-2-yl)-5-(trifluoromethyl)phenoxy]pyrrolidine-2-carboxylic acid;
(2S,4R)-4-[2-(8-chloro-4-oxo-chromen-2-yl)-5-(trifluoromethyl)phenoxy]-1-cyclopropylsulfonyl-pyrrolidine-2-carboxylic acid;
(2S,4S)-4-[2-(8-chloro-4-oxo-chromen-2-yl)-5-(trifluoromethyl)phenoxy]-1-cyclopropylsulfonyl-pyrrolidine-2-carboxylic acid;
(2S,4S)-4-[2-(8-chloro-4-oxo-chromen-2-yl)-5-(trifluoromethyl)phenoxy]-1-(3-methoxyphenyl)sulfonyl-pyrrolidine-2-carboxylic acid;
(2S,4S)-1-(benzenesulfonyl)-4-[2-(8-chloro-4-oxo-chromen-2-yl)-5-(trifluoromethyl)phenoxy]pyrrolidine-2-carboxylic acid;
(2S,4S)-1-(benzenesulfonyl)-4-[2-(8-chloro-4-oxo-chromen-2-yl)-4,5-dimethoxy-phenoxy]pyrrolidine-2-carboxylic acid;
(2S,4S)-1-(benzenesulfonyl)-4-[5-bromo-2-(8-chloro-4-oxo-chromen-2-yl)phenoxy]pyrrolidine-2-carboxylic acid;
(2S,4S)-4-[5-bromo-2-(8-chloro-4-oxo-chromen-2-yl)phenoxy]-1-cyclopropylsulfonyl-pyrrolidine-2-carboxylic acid;
(2S,4S)-1-(benzenesulfonyl)-4-[5-chloro-2-(8-chloro-4-oxo-chromen-2-yl)-4-methyl-phenoxy]pyrrolidine-2-carboxylic acid;
(2S,4S)-1-(benzenesulfonyl)-4-[2-(8-chloro-4-oxo-chromen-2-yl)-5-(trifluoromethoxy)phenoxy]pyrrolidine-2-carboxylic acid;
(2S,4S)-1-benzoyl-4-[5-bromo-2-(8-chloro-4-oxo-chromen-2-yl)phenoxy]pyrrolidine-2-carboxylic acid;
(2R,4S)-1-(benzenesulfonyl)-4-[2-(8-chloro-4-oxo-chromen-2-yl)-5-(trifluoromethyl)phenoxy]pyrrolidine-2-carboxylic acid; and
(2R,4R)-1-(benzenesulfonyl)-4-[2-(8-chloro-4-oxo-chromen-2-yl)-5-(trifluoromethyl)phenoxy]pyrrolidine-2-carboxylic acid;
or a pharmaceutically acceptable salt thereof.

In another embodiment (xxxv) of the present invention, particular compounds of the present invention are selected from:
3-[2-(8-chloro-4-oxo-chromen-2-yl)-5-(trifluoromethyl)phenoxy]cyclobutanecarboxylic acid;
trans-3-[5-chloro-2-(8-chloro-4-oxo-chromen-2-yl)-4-methyl-phenoxy]cyclobutanecarboxylic acid;
trans-3-[2-(8-chloro-4-oxo-chromen-2-yl)-5-(trifluoromethyl)phenoxy]-N-cyclopropylsulfonyl-cyclobutanecarboxamide;
(2S,4R)-1-(benzenesulfonyl)-4-[2-(8-chloro-4-oxo-chromen-2-yl)-5-(trifluoromethyl)phenoxy]pyrrolidine-2-carboxylic acid; and
(2R,4S)-1-(benzenesulfonyl)-4-[2-(8-chloro-4-oxo-chromen-2-yl)-5-(trifluoromethyl)phenoxy]pyrrolidine-2-carboxylic acid;
or a pharmaceutically acceptable salt thereof.

A further embodiment of the present invention is (xxxvi) a compound of formula (I) according to embodiment (i) or a pharmaceutically acceptable salt thereof, wherein
$R^1$ is selected from halogen and halo$C_{1-6}$alkyl;
$R^2$ is selected from H, halogen, $C_{1-6}$alkyl, $C_{3-7}$cycloalkyl and halo$C_{1-6}$alkyl;
$R^3$ is selected from H and halogen;
$R^4$ is selected from H, hydroxy and halo$C_{1-6}$alkyl;
$R^5$ is selected from H and $C_{1-6}$alkoxy;
$R^6$ is selected from carboxy, $C_{1-6}$alkoxycarbonyl, carboxypyrrolidinylcarbonyl, $C_{3-7}$cycloalkylsulfonylaminocarbonyl, hydroxypyrrolidinylcarbonyl, $C_{4-6}$alkylsulfonylaminocarbonyl and aminocarbonyl;
$A_1$ is $CR^7$; wherein $R^7$ is selected from H and halogen;
$A_2$ is selected from N and $CR^8$; wherein $R^8$ is selected from H, halogen, hydroxy, $C_{1-6}$alkyl, $C_{1-6}$alkoxy, $C_{3-7}$cycloalkyl, halo$C_{1-6}$alkyl, halo$C_{1-6}$alkoxy, $C_{1-6}$alkylsulfanyl, $C_{4-6}$alkylsulfonyl, $C_{3-7}$cycloalkyl$C_{1-6}$alkoxy, thiazolyl, morpholinyl, pyrrolidinyl and oxazolidinyl; wherein pyrrolidinyl and oxazolidinyl are unsubstituted or substituted one or two or three times independently by oxo;
$A_3$ is $CR^9$; wherein $R^9$ is selected from H, amino, halogen, hydroxy, $C_{1-6}$alkyl, $C_{1-6}$alkoxy, halo$C_{1-6}$alkyl, halo$C_{1-6}$alkoxy, halo$C_{1-6}$alkyl$C_{1-6}$alkoxy and $C_{3-7}$cycloalkyl$C_{1-6}$alkoxy;
or $R^8$ and $R^9$, together with the atoms to which they are attached, form a 5- or 6-membered heterocyclyl ring; wherein 5- or 6-membered heterocyclyl ring is unsubstituted or substituted by one or two or three or four substituents independently selected from halogen, $C_{1-6}$alkyl and oxo;
$A_4$ is selected from N and $CR^{10}$; wherein $R^{10}$ is selected from H and halogen;
$G_1$ is $C_{1-6}$alkyl; wherein $C_{1-6}$alkyl is unsubstituted or substituted one or two or three times by hydroxy;
$G_2$ is selected from $C_{1-6}$alkyl, $C_{3-7}$cycloalkyl and phenyl;
m is 1.

A further embodiment of the present invention is (xxxvi) a compound of formula (I) according to embodiment (i) or a pharmaceutically acceptable salt thereof, wherein
$R^1$ is selected from F, Cl, Br and $CF_3$;
$R^2$ is selected from FI, F, Cl, Br, methyl, $CF_3$ and cyclopropyl;
$R^3$ is selected from FI and F;
$R^4$ is selected from FI, hydroxy and $CF_3$;
$R^5$ is selected from FI and methoxy;
$R^6$ is selected from carboxy, methoxycarbonyl, carboxypyrrolidinylcarbonyl, cyclopropylsulfonylaminocarbonyl, hydroxypyrrolidinylcarbonyl, methylsulfonylaminocarbonyl and aminocarbonyl;
$A_1$ is $CR^7$; wherein $R^7$ is selected from FI, F, Cl and Br;
$A_2$ is selected from N and $CR^8$; wherein $R^8$ is selected from FI, F, Cl, Br, CIA hydroxy, methyl, methoxy, ethoxy, propoxy, cyclopropyl, trifluoromethoxy, difluoromethoxy, trifluoromethylmethoxy, methylsulfonyl, methylsulfanyl, cyclopropylmethoxy, thiazolyl, morpholinyl, pyrrolidinyl and oxazolidinyl; wherein pyrrolidinyl and oxazolidinyl are unsubstituted or substituted one or two or three times independently by oxo;
$A_3$ is $CR^9$; wherein $R^9$ is selected from FI, amino, hydroxy, F, Cl, Br, $CF_3$, methyl, methoxy, ethoxy, difluoromethoxy, trifluoromethoxy, trifluoromethylmethoxy, difluoromethyl and cyclopropylmethoxy;
or $R^8$ and $R^9$, together with the atoms to which they are attached, form a 5- or 6-membered heterocyclyl ring; wherein 5- or 6-membered heterocyclyl ring is unsubstituted or substituted by one or two or three or four substituents independently selected from F, methyl and oxo;
$A_4$ is selected from N and $CR^{10}$; wherein $R^{10}$ is selected from H and F;
$G_4$ is selected from ethyl, propyl, butyl and neopentyl; wherein propyl is unsubstituted or substituted one or two or three times by hydroxy;
$G_2$ is selected from methyl, isopropyl, cyclobutyl, cyclopentyl and phenyl;
m is 1.

A further embodiment of the present invention is (xxxvii) a compound of formula (I) according to embodiment (i) or a pharmaceutically acceptable salt thereof, wherein $R^1$ is halogen.

A further embodiment of the present invention is (xxxviii) a compound of formula (I) according to embodiment (i) or a pharmaceutically acceptable salt thereof, wherein $R^1$ is selected from Cl and Br.

A further embodiment of the present invention is (xxxix) a compound of formula (I) according to embodiment (i) or a pharmaceutically acceptable salt thereof, wherein $R^6$ is carboxy.

A further embodiment of the present invention is (xl) a compound of formula (I) according to embodiment (i) or a pharmaceutically acceptable salt thereof, wherein $A_2$ is $CR^8$; wherein $R^8$ is selected from halogen, $C_{1-6}$alkyl, $C_{1-6}$alkoxy and halo$C_{1-6}$alkyl.

A further embodiment of the present invention is (xli) a compound of formula (I) according to embodiment (i) or a pharmaceutically acceptable salt thereof, wherein $A_2$ is $CR^8$; wherein $R^8$ is selected from Cl, $CF_3$, methyl and methoxy.

A further embodiment of the present invention is (xlii) a compound of formula (I) according to embodiment (i) or a pharmaceutically acceptable salt thereof, wherein $A_3$ is $CR^9$; wherein $R^9$ is selected from H, $C_{1-6}$alkyl and $C_{1-6}$alkoxy.

A further embodiment of the present invention is (xliii) a compound of formula (I) according to embodiment (i) or a pharmaceutically acceptable salt thereof, wherein $A_3$ is $CR^9$; wherein $R^9$ is selected from H, methyl and methoxy.

A further embodiment of the present invention is (xliv) a compound of formula (I) according to embodiment (i) or a pharmaceutically acceptable salt thereof, wherein $G_1$ is $C_{4-6}$alkyl.

A further embodiment of the present invention is (xlv) a compound of formula (I) according to embodiment (i) or a pharmaceutically acceptable salt thereof, wherein $G_1$ is selected from ethyl and propyl.

A further embodiment of the present invention is (xlvi) a compound of formula (I) according to embodiment (i) or a pharmaceutically acceptable salt thereof, wherein $G_2$ is selected from $C_{1-6}$alkyl and $C_{3-7}$cycloalkyl.

A further embodiment of the present invention is (xlvii) a compound of formula (I) according to embodiment (i) or a pharmaceutically acceptable salt thereof, wherein $G_2$ is selected from methyl and cyclobutyl.

A further embodiment of the present invention is (il) a compound of formula (I) according to embodiment (i) or a pharmaceutically acceptable salt thereof, wherein
$R^1$ is halogen;
$R^2$ is H;
$R^3$ is H;
$R^4$ is H;
$R^5$ is H;
$R^6$ is carboxy;
$A_1$ is CH;
$A_2$ is $CR^8$; wherein $R^8$ is selected from halogen, $C_{1-6}$alkyl, $C_{1-6}$alkoxy and halo$C_{1-6}$alkyl;
$A_3$ is $CR^9$; wherein $R^9$ is selected from H, $C_{1-6}$alkyl and $C_{1-6}$alkoxy;
$A_4$ is CH;
$G_4$ is $C_{1-6}$alkyl.
$G_2$ is selected from $C_{1-6}$alkyl and $C_{3-7}$cycloalkyl.
m is 1.

A further embodiment of the present invention is (l) a compound of formula (I) according to embodiment (i) or a pharmaceutically acceptable salt thereof, wherein $R^1$ is selected from Cl and Br;
$R^2$ is H;
$R^3$ is H;
$R^4$ is H;
$R^5$ is H;
$R^6$ is carboxy;
$A_1$ is CH;
$A_2$ is $CR^8$; wherein $R^8$ is selected from Cl, $CF_3$, methyl and methoxy;
$A_3$ is $CR^9$; wherein $R^9$ is selected from H, methyl and methoxy;
$A_4$ is CH;
$G_4$ is selected from ethyl and propyl;
$G_2$ is selected from methyl and cyclobutyl;
m is 1.

In another embodiment (li) of the present invention, particular compounds of the present invention are selected from:
2-[3-[2-(8-chloro-4-oxo-chromen-2-yl)-5-(trifluoromethyl)phenoxy]propoxy]acetic acid;
2-[3-[2-(8-chloro-4-oxo-chromen-2-yl)-5-methyl-phenoxy]propoxy]acetic acid;
methyl 3-[2-[5-bromo-2-(8-chloro-4-oxo-chromen-2-yl)phenoxy]ethoxy]cyclobutanecarboxylate;
cis-3-[2-[5-bromo-2-(8-chloro-4-oxo-chromen-2-yl)phenoxy]ethoxy]cyclobutanecarboxylic acid;
trans-3-[2-[5-bromo-2-(8-chloro-4-oxo-chromen-2-yl)phenoxy]ethoxy]cyclobutanecarboxylic acid;
3-[2-[5-chloro-2-(8-chloro-4-oxo-chromen-2-yl)phenoxy]ethoxy]cyclobutanecarboxylic acid;
2-[2-[2-(8-chloro-4-oxo-chromen-2-yl)-5-(trifluoromethyl)phenoxy]ethoxy]acetic acid;
2-[2-[5-bromo-2-(8-chloro-4-oxo-chromen-2-yl)phenoxy]ethoxy]acetic acid;
2-[3-[5-chloro-2-(8-chloro-4-oxo-chromen-2-yl)phenoxy]propoxy]acetic acid;
2-[3-[5-bromo-2-(8-chloro-4-oxo-chromen-2-yl)phenoxy]propoxy]acetic acid;
2-[3-[5-bromo-2-(8-chloro-4-oxo-chromen-2-yl)-4-methyl-phenoxy]propoxy]acetic acid;
2-[3-[2-(8-chloro-4-oxo-chromen-2-yl)-4,5-dimethoxy-phenoxy]propoxy]acetic acid;
2-[3-[5-bromo-2-(8-chloro-4-oxo-chromen-2-yl)-4-methoxy-phenoxy]propoxy]acetic acid;
2-[3-[2-(8-chloro-4-oxo-chromen-2-yl)-5-(trifluoromethoxy)phenoxy]propoxy]acetic acid;
2-[3-[[6-(8-chloro-4-oxo-chromen-2-yl)-1,3-benzodioxol-5-yl]oxy]propoxy]acetic acid;
2-[3-[5-chloro-2-(8-chloro-4-oxo-chromen-2-yl)-4-methoxy-phenoxy]propoxy]acetic acid;
2-[3-[2-(8-bromo-4-oxo-chromen-2-yl)-5-methyl-phenoxy]propoxy]acetic acid;
2-[3-[2-(8-bromo-4-oxo-chromen-2-yl)-5-chloro-4-methyl-phenoxy]propoxy]acetic acid;
2-[3-[5-chloro-2-(8-chloro-4-oxo-chromen-2-yl)-4-methyl-phenoxy]propoxy]acetic acid;
2-[2-[5-bromo-2-(8-chloro-4-oxo-chromen-2-yl)-4-methoxy-phenoxy]ethoxy]acetic acid;
2-[2-[5-bromo-2-(8-chloro-4-oxo-chromen-2-yl)-4-methyl-phenoxy]ethoxy]acetic acid;
2-[2-[2-(8-chloro-4-oxo-chromen-2-yl)-4,5-dimethoxy-phenoxy]ethoxy]acetic acid;
2-[2-[2-(8-chloro-4-oxo-chromen-2-yl)-5-(trifluoromethoxy)phenoxy]ethoxy]acetic acid;
2-[3-[2-(8-chloro-4-oxo-chromen-2-yl)-5-(trifluoromethyl)phenoxy]butoxy]acetic acid;

cis-3-[2-[2-(8-chloro-4-oxo-chromen-2-yl)phenoxy]ethoxy]
    cyclobutanecarboxylic acid;
trans-3-[2-[2-(8-chloro-4-oxo-chromen-2-yl)phenoxy]
    ethoxy]cyclobutanecarboxylic acid;
cis-3-[2-[2-(8-chloro-4-oxo-chromen-2-yl)-5-(trifluorom-
    ethyl)phenoxy]ethoxy]cyclobutanecarboxylic acid;
trans-3-[2-[[5-bromo-2-(8-chloro-4-oxo-chromen-2-yl)-3-
    pyridyl]oxy]ethoxy]cyclobutanecarboxylic acid;
cis-3-[2-[5-bromo-2-(8-chloro-6-fluoro-4-oxo-chromen-2-
    yl)phenoxy]ethoxy]cyclobutanecarboxylic acid;
cis-3-[2-[2-(8-chloro-7-methyl-4-oxo-chromen-2-yl)phe-
    noxy]ethoxy]cyclobutanecarboxylic acid;
trans-3-[2-[2-(8-chloro-7-methyl-4-oxo-chromen-2-yl)phe-
    noxy]ethoxy]cyclobutanecarboxylic acid;
cis-3-[2-[5-bromo-2-(8-chloro-7-fluoro-4-oxo-chromen-2-
    yl)phenoxy]ethoxy]cyclobutanecarboxylic acid;
trans-3-[2-[5-bromo-2-(8-chloro-7-fluoro-4-oxo-chromen-
    2-yl)phenoxy]ethoxy]cyclobutanecarboxylic acid;
cis-3-[2-[5-bromo-2-(8-chloro-4-oxo-chromen-2-yl)-4-
    methyl-phenoxy]ethoxy]cyclobutanecarboxylic acid;
cis-3-[2-[4-bromo-2-(8-chloro-4-oxo-chromen-2-yl)-5-
    fluoro-phenoxy]ethoxy]cyclobutanecarboxylic acid;
cis-3-[2-[2-(8-chloro-4-oxo-chromen-2-yl)-4-fluoro-phe-
    noxy]ethoxy]cyclobutanecarboxylic acid;
trans-3-[2-[2-(8-chloro-4-oxo-chromen-2-yl)-4-fluoro-phe-
    noxy]ethoxy]cyclobutanecarboxylic acid;
cis-3-[2-[2-(8-chloro-4-oxo-chromen-2-yl)-5-fluoro-phe-
    noxy]ethoxy]cyclobutanecarboxylic acid;
trans-3-[2-[2-(8-chloro-4-oxo-chromen-2-yl)-5-fluoro-phe-
    noxy]ethoxy]cyclobutanecarboxylic acid;
cis-3-[2-[2-(8-chloro-4-oxo-chromen-2-yl)-5-ethoxy-phe-
    noxy]ethoxy]cyclobutanecarboxylic acid;
trans-3-[2-[2-(8-chloro-4-oxo-chromen-2-yl)-5-ethoxy-phe-
    noxy]ethoxy]cyclobutanecarboxylic acid;
cis-3-[2-[2-(8-chloro-6-fluoro-4-oxo-chromen-2-yl)phe-
    noxy]ethoxy]cyclobutanecarboxylic acid;
trans-3-[2-[2-(8-chloro-6-fluoro-4-oxo-chromen-2-yl)phe-
    noxy]ethoxy]cyclobutanecarboxylic acid;
cis-3-[2-[2-(8-chloro-4-oxo-chromen-2-yl)-6-fluoro-phe-
    noxy]ethoxy]cyclobutanecarboxylic acid;
trans-3-[2-[2-(8-chloro-4-oxo-chromen-2-yl)-6-fluoro-phe-
    noxy]ethoxy]cyclobutanecarboxylic acid;
cis-3-[2-[2-(8-chloro-4-oxo-chromen-2-yl)-5-methyl-phe-
    noxy]ethoxy]cyclobutanecarboxylic acid;
trans-3-[2-[2-(8-chloro-4-oxo-chromen-2-yl)-5-methyl-phe-
    noxy]ethoxy]cyclobutanecarboxylic acid;
cis-3-[2-[2-(8-chloro-4-oxo-chromen-2-yl)-5-methoxy-phe-
    noxy]ethoxy]cyclobutanecarboxylic acid;
trans-3-[2-[2-(8-chloro-4-oxo-chromen-2-yl)-5-methoxy-
    phenoxy]ethoxy]cyclobutanecarboxylic acid;
cis-3-[2-[4-bromo-2-(8-chloro-4-oxo-chromen-2-yl)-5-
    methoxy-phenoxy]ethoxy]cyclobutanecarboxylic acid;
trans-3-[2-[4-bromo-2-(8-chloro-4-oxo-chromen-2-yl)-5-
    methoxy-phenoxy]ethoxy]cyclobutanecarboxylic acid;
cis-3-[2-[2-(8-chloro-4-oxo-chromen-2-yl)-5-methoxy-4-
    methyl-phenoxy]ethoxy]cyclobutanecarboxylic acid;
trans-3-[2-[2-(8-chloro-4-oxo-chromen-2-yl)-5-methoxy-4-
    methyl-phenoxy]ethoxy]cyclobutanecarboxylic acid;
cis-3-[2-[5-bromo-2-(8-chloro-4-oxo-chromen-2-yl)-4-(trif-
    luoromethyl)phenoxy]ethoxy]cyclobutanecarboxylic
    acid;
trans-3-[2-[5-bromo-2-(8-chloro-4-oxo-chromen-2-yl)-4-
    (trifluoromethyl)phenoxy]ethoxy]cyclobutanecarboxylic
    acid;
cis-3-[2-[[6-(8-chloro-4-oxo-chromen-2-yl)-1,3-benzodi-
    oxol-5-yl]oxy]ethoxy]cyclobutanecarboxylic acid;
trans-3-[2-[[6-(8-chloro-4-oxo-chromen-2-yl)-1,3-benzodi-
    oxol-5-yl]oxy]ethoxy]cyclobutanecarboxylic acid;
cis-3-[2-[5-bromo-2-(8-chloro-4-oxo-chromen-2-yl)-4-
    fluoro-phenoxy]ethoxy]cyclobutanecarboxylic acid;
trans-3-[2-[5-bromo-2-(8-chloro-4-oxo-chromen-2-yl)-4-
    fluoro-phenoxy]ethoxy]cyclobutanecarboxylic acid;
cis-3-[2-[2-(8-chloro-6-fluoro-4-oxo-chromen-2-yl)-5-
    fluoro-phenoxy]ethoxy]cyclobutanecarboxylic acid;
trans-3-[2-[2-(8-chloro-6-fluoro-4-oxo-chromen-2-yl)-5-
    fluoro-phenoxy]ethoxy]cyclobutanecarboxylic acid;
cis-3-[2-[2-(8-bromo-4-oxo-chromen-2-yl)phenoxy]ethoxy]
    cyclobutanecarboxylic acid;
trans-3-[2-[2-(8-bromo-4-oxo-chromen-2-yl)phenoxy]
    ethoxy]cyclobutanecarboxylic acid; cis-3-[2-[2-[4-oxo-8-
    (trifluoromethyl)chromen-2-yl]phenoxy]ethoxy]cyclobu-
    tanecarboxylic acid;
trans-3-[2-[2-[4-oxo-8-(trifluoromethyl)chromen-2-yl]phe-
    noxy]ethoxy]cyclobutanecarboxylic acid;
cis-3-[2-[5-bromo-2-[8-chloro-4-oxo-7-(trifluoromethyl)
    chromen-2-yl]phenoxy]ethoxy]cyclobutanecarboxylic
    acid;
trans-3-[2-[5-bromo-2-[8-chloro-4-oxo-7-(trifluoromethyl)
    chromen-2-yl]phenoxy]ethoxy]cyclobutanecarboxylic
    acid;
cis-3-[2-[5-bromo-2-[8-chloro-4-oxo-5-(trifluoromethyl)
    chromen-2-yl]phenoxy]ethoxy]cyclobutanecarboxylic
    acid;
trans-3-[2-[5-chromo-2-[8-chloro-4-oxo-5-(trifluoromethyl)
    chromen-2-yl]phenoxy]ethoxy]cyclobutanecarboxylic
    acid;
3-[2-[2-(8-chloro-4-oxo-chromen-2-yl)-4-methyl-phenoxy]
    ethoxy]cyclobutanecarboxylic acid;
trans-3-[2-[2-(8-chloro-4-oxo-chromen-2-yl)-4-methyl-phe-
    noxy]ethoxy]cyclobutanecarboxylic acid;
cis-3-[2-[2-(8-chloro-4-oxo-chromen-2-yl)-4-ethoxy-phe-
    noxy]ethoxy]cyclobutanecarboxylic acid;
trans-3-[2-[2-(8-chloro-4-oxo-chromen-2-yl)-4-ethoxy-phe-
    noxy]ethoxy]cyclobutanecarboxylic acid;
cis-3-[2-[2-(8-chloro-4-oxo-chromen-2-yl)-5-(trifluo-
    romethoxy)phenoxy]ethoxy]cyclobutanecarboxylic acid;
trans-3-[2-[4-chromo-2-(8-chloro-6-fluoro-4-oxo-chromen-
    2-yl)phenoxy]ethoxy]cyclobutanecarboxylic acid;
cis-3-[2-[2-(8-chloro-7-fluoro-4-oxo-chromen-2-yl)phe-
    noxy]ethoxy]cyclobutanecarboxylic acid;
cis-3-[2-[5-chloro-2-(8-chloro-4-oxo-chromen-2-yl)-4-
    methyl-phenoxy]ethoxy]cyclobutanecarboxylic acid;
cis-3-[3-[5-bromo-2-(8-chloro-4-oxo-chromen-2-yl)phe-
    noxy]propoxy]cyclobutanecarboxylic acid;
trans-3-[3-[5-chromo-2-(8-chloro-4-oxo-chromen-2-yl)phe-
    noxy]propoxy]cyclobutanecarboxylic acid;
cis-3-[2-[5-bromo-4-chloro-2-(8-chloro-4-oxo-chromen-2-
    yl)phenoxy]ethoxy]cyclobutanecarboxylic acid;
cis-3-[2-[2-(8-chloro-7-cyclopropyl-4-oxo-chromen-2-yl)
    phenoxy]ethoxy]cyclobutanecarboxylic acid;
cis-3-[2-[2-(8-chloro-4-oxo-chromen-2-yl)-4-methoxy-phe-
    noxy]ethoxy]cyclobutanecarboxylic acid;
3-[2-[[4-(8-chloro-4-oxo-chromen-2-yl)-3-pyridyl]oxy]
    ethoxy]cyclobutanecarboxylic acid
3-[2-[2-(8-chloro-4-oxo-chromen-2-yl)-5-(2-oxooxazoli-
    din-3-yl)phenoxy]ethoxy]cyclobutanecarboxylic acid;
methyl 3-[2-[2-(8-chloro-4-oxo-chromen-2-yl)-5-(2-
    oxooxazolidin-3-yl)phenoxy]ethoxy]cyclobutanecar-
    boxylate;
cis-3-[2-[2-(8-chloro-4-oxo-chromen-2-yl)-5-(2-oxopyrroli-
    din-1-yl)phenoxy]ethoxy]cyclobutanecarboxylic acid;
trans-3-[2-[2-(8-chloro-4-oxo-chromen-2-yl)-5-(2-oxopyr-
    rolidin-1-yl)phenoxy]ethoxy]cyclobutanecarboxylic acid;

cis-3-[2-[2-(8-chloro-4-oxo-chromen-2-yl)-5-methylsulfanyl-phenoxy]ethoxy]cyclobutanecarboxylic acid;
trans-3-[2-[2-(8-chloro-4-oxo-chromen-2-yl)-5-methylsulfanyl-phenoxy]ethoxy]cyclobutanecarboxylic acid;
trans-methyl 3-[2-[2-(8-chloro-4-oxo-chromen-2-yl)-5-methylsulfonyl-phenoxy]ethoxy]cyclobutanecarboxylate;
cis-3-[2-[2-(8-chloro-4-oxo-chromen-2-yl)-5-thiazol-2-yl-phenoxy]ethoxy]cyclobutanecarboxylic acid;
trans-3-[2-[2-(8-chloro-4-oxo-chromen-2-yl)-5-thiazol-2-yl-phenoxy]ethoxy]cyclobutanecarboxylic acid;
trans-3-[2-[2-(8-chloro-4-oxo-chromen-2-yl)-5-morpholino-phenoxy]ethoxy]cyclobutanecarboxylic acid;
cis-3-[2-[2-(8-chloro-4-oxo-chromen-2-yl)-5-pyrrol id in-1-yl-phenoxy]ethoxy]cyclobutanecarboxylic acid;
cis-3-[2-[2-(8-chloro-4-oxo-chromen-2-yl)-5-cyclopropyl-phenoxy]ethoxy]cyclobutanecarboxylic acid;
trans-3-[2-[2-(8-chloro-4-oxo-chromen-2-yl)-5-cyclopropyl-phenoxy]ethoxy]cyclobutanecarboxylic acid;
3-[2-[2-bromo-6-(8-chloro-6-fluoro-4-oxo-chromen-2-yl)phenoxy]ethoxy]cyclobutanecarboxylic acid;
cis-3-[2-[5-bromo-2-(8-chloro-4-oxo-chromen-2-yl)-3-fluoro-phenoxy]ethoxy]cyclobutanecarboxylic acid;
cis-3-[2-[2-(8-chloro-4-oxo-chromen-2-yl)-4,5-dimethoxy-phenoxy]ethoxy]cyclobutanecarboxylic acid;
cis-3-[2-[5-bromo-2-(8-chloro-4-oxo-chromen-2-yl)-4-methoxy-phenoxy]ethoxy]cyclobutanecarboxylic acid;
3-[2-[[7-(8-chloro-4-oxo-chromen-2-yl)-2,3-dihydro-1,4-benzodioxin-6-yl]oxy]ethoxy]cyclobutanecarboxylic acid;
cis-3-[2-[2-(8-chloro-4-oxo-chromen-2-yl)-4-(difluoromethyl)-5-methyl-phenoxy]ethoxy]cyclobutanecarboxylic acid;
cis-3-[2-[2-(8-chloro-4-oxo-chromen-2-yl)-5-hydroxy-4-methoxy-phenoxy]ethoxy]cyclobutanecarboxylic acid;
cis-3-[2-[2-(8-chloro-4-oxo-chromen-2-yl)-4-methoxy-5-propoxy-phenoxy]ethoxy]cyclobutanecarboxylic acid;
cis-3-[2-[2-(8-chloro-4-oxo-chromen-2-yl)-5-ethoxy-4-methoxy-phenoxy]ethoxy]cyclobutanecarboxylic acid;
cis-3-[2-[2-(8-chloro-4-oxo-chromen-2-yl)-5-(cyclopropylmethoxy)-4-methoxy-phenoxy]ethoxy]cyclobutanecarboxylic acid;
cis-3-[2-[2-(8-chloro-4-oxo-chromen-2-yl)-4-methoxy-5-(2,2,2-trifluoroethoxy)phenoxy]ethoxy]cyclobutanecarboxylic acid;
cis-3-[2-[2-(8-chloro-4-oxo-chromen-2-yl)-5-(difluoromethoxy)-4-methoxy-phenoxy]ethoxy]cyclobutanecarboxylic acid;
cis-3-[2-[2-(8-chloro-4-oxo-chromen-2-yl)-4-(cyclopropylmethoxy)-5-methoxy-phenoxy]ethoxy]cyclobutanecarboxylic acid;
cis-3-[2-[2-(8-chloro-4-oxo-chromen-2-yl)-4-hydroxy-5-methoxy-phenoxy]ethoxy]cyclobutanecarboxylic acid;
cis-3-[2-[2-(8-chloro-4-oxo-chromen-2-yl)-4-ethoxy-5-methoxy-phenoxy]ethoxy]cyclobutanecarboxylic acid;
cis-3-[2-[2-(8-chloro-4-oxo-chromen-2-yl)-5-methoxy-4-(2,2,2-trifluoroethoxy)phenoxy]ethoxy]cyclobutanecarboxylic acid;
cis-3-[2-[2-(8-chloro-4-oxo-chromen-2-yl)-4-(difluoromethoxy)-5-methoxy-phenoxy]ethoxy]cyclobutanecarboxylic acid;
cis-3-[2-[2-(8-chloro-4-oxo-chromen-2-yl)-4,5-bis(difluoromethoxy)phenoxy]ethoxy]cyclobutanecarboxylic acid;
cis-3-[2-[2-(8-chloro-4-oxo-chromen-2-yl)-4,5-diethoxy-phenoxy]ethoxy]cyclobutanecarboxylic acid;
cis-3-[2-[2-(8-chloro-4-oxo-chromen-2-yl)-5-methoxy-4-(trifluoromethoxy)phenoxy]ethoxy]cyclobutanecarboxylic acid;
cis-3-[2-[2-(8-chloro-4-oxo-chromen-2-yl)-5-hydroxy-4-(trifluoromethoxy)phenoxy]ethoxy]cyclobutanecarboxylic acid;
cis-3-[2-[6-(8-chloro-4-oxo-chromen-2-yl)-2-oxo-indolin-5-yl]oxyethoxy]cyclobutanecarboxylic acid;
cis-3-[2-[6-(8-chloro-4-oxo-chromen-2-yl)-3,3-dimethyl-2-oxo-indolin-5-yl]oxyethoxy]cyclobutanecarboxylic acid;
cis-3-[2-[6-(8-chloro-4-oxo-chromen-2-yl)-1,3,3-tri methyl-2-oxo-indolin-5-yl]oxyethoxy]cyclobutanecarboxylic acid;
cis-3-[2-[2-[8-chloro-4-oxo-5-(trifluoromethyl)chromen-2-yl]phenoxy]ethoxy]cyclobutanecarboxylic acid;
cis-3-[2-[2-[8-chloro-4-oxo-5-(trifluoromethyl)chromen-2-yl]-5-ethoxy-phenoxy]ethoxy]cyclobutanecarboxylic acid;
cis-3-[2-[2-[8-chloro-4-oxo-5-(trifluoromethyl)chromen-2-yl]-4,5-dimethoxy-phenoxy]ethoxy]cyclobutanecarboxylic acid;
3-[2-[2-[8-chloro-4-oxo-7-(trifluoromethyl)chromen-2-yl]-5-ethoxy-phenoxy]ethoxy]cyclobutanecarboxylic acid;
cis-3-[2-[2-(8-chloro-5-hydroxy-4-oxo-chromen-2-yl)-4,5-dimethoxy-phenoxy]ethoxy]cyclobutanecarboxylic acid;
cis-3-[2-[2-(8-chloro-5-hydroxy-4-oxo-chromen-2-yl)-5-(trifluoromethyl)phenoxy]ethoxy]cyclobutanecarboxylic acid;
2-[3-[2-(8-chloro-5-hydroxy-4-oxo-chromen-2-yl)-5-(trifluoromethyl)phenoxy]propoxy]acetic acid;
cis-3-[2-[5-bromo-2-(8-chloro-3-methoxy-4-oxo-chromen-2-yl)phenoxy]ethoxy]cyclobutanecarboxylic acid;
cis-3-[2-[[6-(8-chloro-4-oxo-chromen-2-yl)-2,2-difluoro-1,3-benzodioxol-5-yl]oxy]ethoxy]cyclobutanecarboxylic acid;
3-[3-[2-(8-chloro-4-oxo-chromen-2-yl)-5-(trifluoromethyl)phenoxy]propoxy]cyclobutanecarboxylic acid;
3-[3-[2-(8-chloro-4-oxo-chromen-2-yl)-5-(trifluoromethyl)phenoxy]propoxy]cyclopentanecarboxylic acid;
3-[3-[5-bromo-2-(8-chloro-4-oxo-chromen-2-yl)phenoxy]propoxy]cyclopentanecarboxylic acid;
3-[2-[5-bromo-2-(8-chloro-4-oxo-chromen-2-yl)phenoxy]ethoxy]cyclopentanecarboxylic acid;
4-[2-[5-bromo-2-(8-chloro-4-oxo-chromen-2-yl)phenoxy]ethoxy]benzoic acid;
3-[2-[5-bromo-2-(8-chloro-4-oxo-chromen-2-yl)phenoxy]ethoxy]benzoic acid;
2-[3-[2-(8-chloro-4-oxo-chromen-2-yl)-5-(trifluoromethyl)phenoxy]propoxy]-2-methyl-propanoic acid;
cis-3-[3-[5-bromo-2-(8-chloro-4-oxo-chromen-2-yl)phenoxy]-2,2-dimethyl-propoxy]cyclobutanecarboxylic acid;
trans-3-[3-[5-bromo-2-(8-chloro-4-oxo-chromen-2-yl)phenoxy]-2,2-dimethyl-propoxy]cyclobutanecarboxylic acid;
(3R)-1-[2-[2-[5-bromo-2-(8-chloro-4-oxo-chromen-2-yl)phenoxy]ethoxy]acetyl]pyrrolidine-3-carboxylic acid;
(3S)-1-[2-[2-[5-bromo-2-(8-chloro-4-oxo-chromen-2-yl)phenoxy]ethoxy]acetyl]pyrrolidine-3-carboxylic acid;
2-[3-[5-bromo-2-(8-chloro-4-oxo-chromen-2-yl)phenoxy]-2-hydroxy-propoxy]acetic acid;
2-[3-[5-bromo-2-(8-chloro-4-oxo-chromen-2-yl)phenoxy]-2-hydroxy-propoxy]acetamide;
2-[3-[2-(8-chloro-4-oxo-chromen-2-yl)-5-(trifluoromethyl)phenoxy]-2-hydroxy-propoxy]acetic acid;
2-[2-[5-bromo-2-(8-chloro-4-oxo-chromen-2-yl)phenoxy]ethoxy]-N-cyclopropylsulfonyl-acetamide;
2-[3-[2-(8-chloro-4-oxo-chromen-2-yl)-5-(trifluoromethyl)phenoxy]propoxy]-N-cyclopropylsulfonyl-acetamide;
2-[2-[2-(8-chloro-4-oxo-chromen-2-yl)-5-(trifluoromethyl)phenoxy]ethoxy]-N-cyclopropylsulfonyl-acetamide;

cis-3-[2-[2-(8-chloro-4-oxo-chromen-2-yl)-4,5-dimethoxy-phenoxy]ethoxy]-N-cyclopropylsulfonyl-cyclobutanecarboxamide;
2-[2-[2-(8-chloro-4-oxo-chromen-2-yl)-5-(trifluoromethyl)phenoxy]ethoxy]-N-methylsulfonyl-acetamide;
cis-3-[2-[2-(8-chloro-4-oxo-chromen-2-yl)-5-(trifluoromethyl)phenoxy]ethoxy]-N-methylsulfonyl-cyclobutanecarboxamide;
cis-3-[2-[5-bromo-2-(8-chloro-4-oxo-chromen-2-yl)phenoxy]ethoxy]-N-methylsulfonyl-cyclobutanecarboxamide;
trans-3-[2-[5-bromo-2-(8-chloro-4-oxo-chromen-2-yl)phenoxy]ethoxy]-N-methylsulfonyl-cyclobutanecarboxamide;
3-[3-[2-(8-chloro-4-oxo-chromen-2-yl)-5-(trifluoromethyl)phenoxy]propoxy]-N-methylsulfonyl-cyclopentanecarboxamide;
cis-3-[2-[2-(8-chloro-4-oxo-chromen-2-yl)-4,5-dimethoxy-phenoxy]ethoxy]-N-methylsulfonyl-cyclobutanecarboxamide; and
2-[4-bromo-2-[2-[2-(3-hydroxypyrrolidin-1-yl)-2-oxo-ethoxy]ethoxy]phenyl]-8-chloro-chromen-4-one;
or a pharmaceutically acceptable salt thereof.

In another embodiment (Iii) of the present invention, particular compounds of the present invention are selected from:

2-[3-[2-(8-chloro-4-oxo-chromen-2-yl)-5-(trifluoromethyl)phenoxy]propoxy]acetic acid;
2-[3-[2-(8-chloro-4-oxo-chromen-2-yl)-5-methyl-phenoxy]propoxy]acetic acid;
2-[3-[5-chloro-2-(8-chloro-4-oxo-chromen-2-yl)phenoxy]propoxy]acetic acid;
2-[3-[2-(8-bromo-4-oxo-chromen-2-yl)-5-methyl-phenoxy]propoxy]acetic acid;
2-[3-[5-chloro-2-(8-chloro-4-oxo-chromen-2-yl)-4-methyl-phenoxy]propoxy]acetic acid; and
cis-3-[2-[2-(8-chloro-4-oxo-chromen-2-yl)-4,5-dimethoxy-phenoxy]ethoxy]cyclobutanecarboxylic acid;
or a pharmaceutically acceptable salt thereof.

Synthesis

The compounds of the present invention can be prepared by any conventional means. Suitable processes for synthesizing these compounds as well as their starting materials are provided in the schemes below and in the subsequent examples. All substituents, in particular, $R^1$ to $R^6$, $G_1$, $G_2$, $A^1$ to $A^4$ and m are defined above unless otherwise indicated. Furthermore, and unless explicitly otherwise stated, all reactions, reaction conditions, abbreviations and symbols have the meanings well known to a person of ordinary skill in the art.

Scheme 1

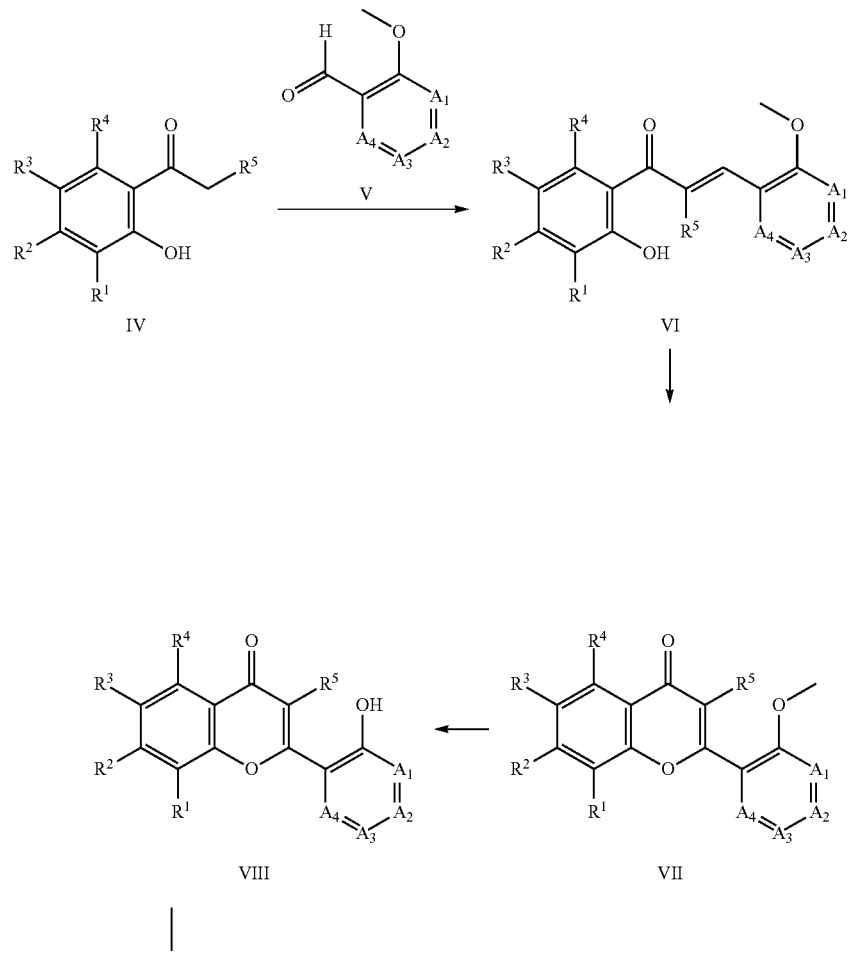

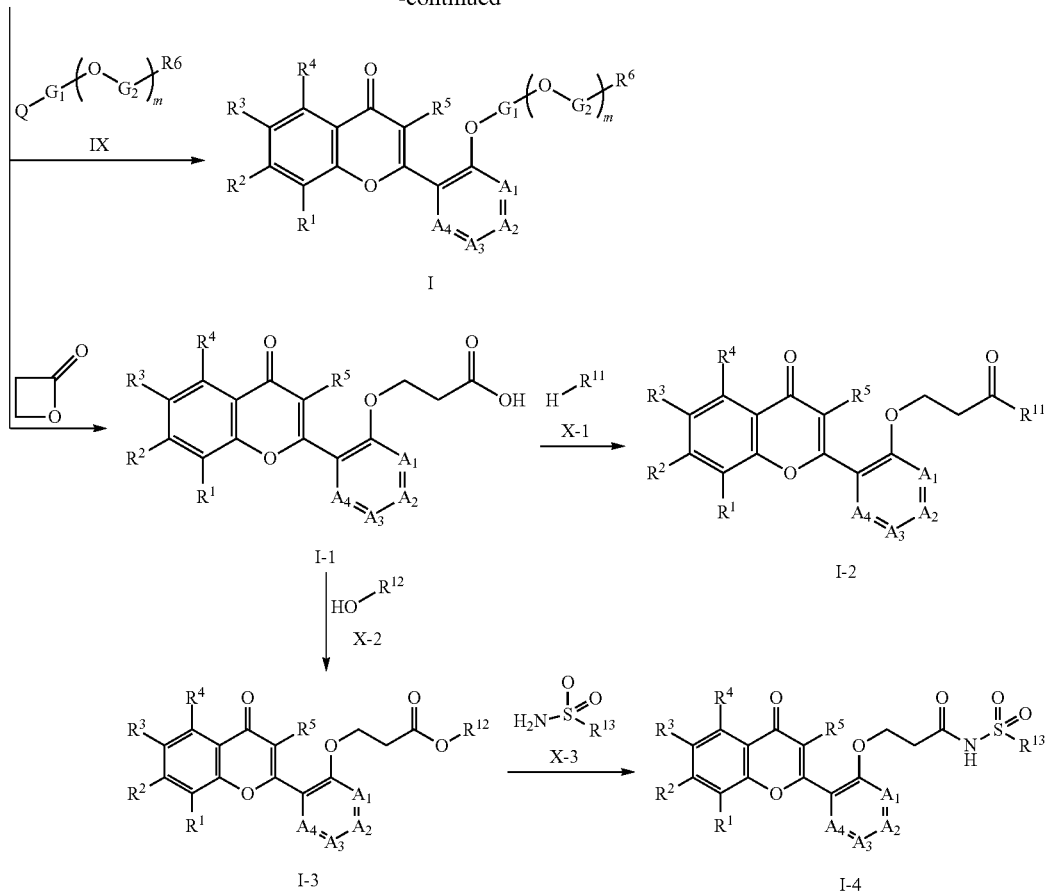

Wherein Q is halogen, OTs or OMs; $R^{11}$ is $C_{3-7}$cycloalkylamino or hydroxy$C_{1-6}$alkylamino; $R^{12}$ is $C_{1-6}$alkyl; $R^{13}$ is selected from $C_{1-6}$alkyl and $C_{3-7}$cycloalkyl.

Condensation of ketone IV with aldehyde V in the presence of a base, such as KOH, in a suitable solvent, such as ethanol, affords α,β-unsaturated carbonyl intermediate VI. Cyclization of α,β-unsaturated carbonyl intermediate VI in the presence of a suitable Lewis acid, such as $I_2$, KI or NaI, in a suitable solvent, such as DMSO, affords flavone derivative VII. Demethylation of flavone derivative VII with a suitable Lewis acid, such as $BBr_3$, in a suitable solvent, such as dichloromethane, affords compound of formula VIII. Substitution of compound of formula VIII with compound of formula IX in the presence of a suitable base, such as $K_2CO_3$, in a suitable solvent, such as DMF, affords compound of formula I. Treatment of compound of formula VIII with oxetan-2-one in the presence of a suitable base, such as t-BuOK, in a suitable solvent, such as DMF, affords propanoic acid derivative I-1. Condensation of propanoic acid derivative I-1 with compound of formula X-1 in the presence of a suitable condensation reagent, such as HATU, with a suitable base, such as TEA, in a suitable solvent, such as DCM, affords amide derivative I-2. Esterification of propanoic acid derivative I-1 with compound of formula X-2 in the presence of a suitable acid, such as HCl, affords ester derivative I-3. Substitution of ester derivative I-3 with compound of formula X-3 in the presence of a suitable acid, such as $TiCl_4$, in a suitable solvent, such as DCM, affords compound of formula I-4.

Scheme 2

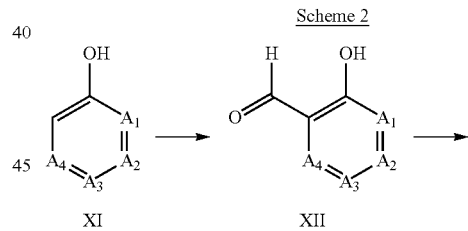

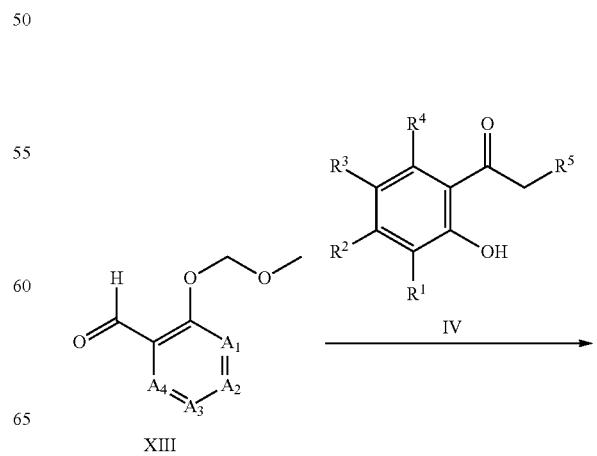

-continued

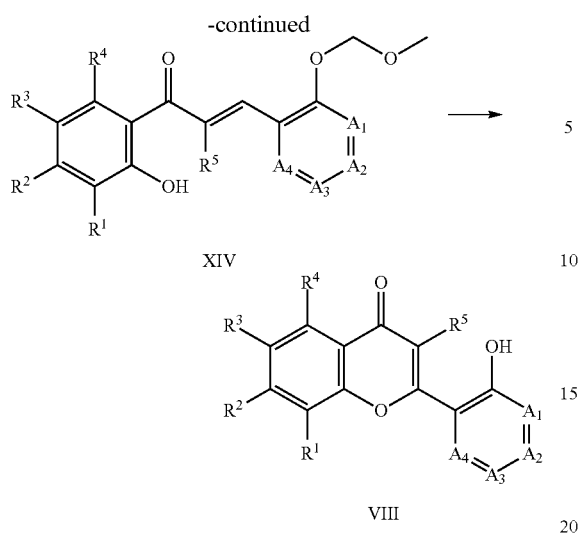

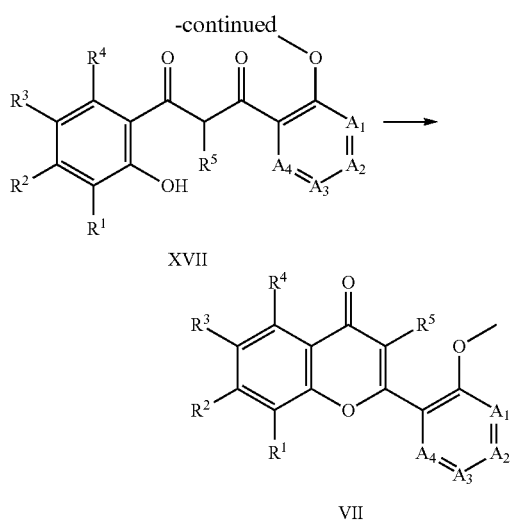

The compound of formula VIII can also be prepared according to the Scheme 2. Formylation of compound of formula XI with formaldehyde in the presence of a suitable base, such as TEA, with a suitable Lewis acid, such as $MgCl_2$, in a suitable solvent, such as ACN, affords aldehyde derivative XII. Protection hydroxy group of aldehyde derivative XII with bromo(methoxy)methane in the presence of a suitable base, such as NaH, in a suitable solvent, such as THF, affords compounds of formula XIII. Condensation of compound of formula XIII with substituted ketone IV in the presence of a base, such as KOFI, in a suitable solvent, such as ethanol, affords α,β-unsaturated carbonyl intermediate XIV. Cyclization of intermediate XIV in the presence of a suitable Lewis acid, such as $I_2$, KI or NaI, in a suitable solvent, such as DMSO, affords compound of formula VIII.

The flavone derivative VII can also be prepared according to the Scheme 3. Treatment of substituted ketone IV with substituted acyl chloride XV in the presence of a base, such as TEA, in a suitable solvent, such as DCM, affords ester derivative XVI. Treatment ester derivative XVI with a suitable base, such as KOH, in a suitable solvent, such as pyridine, affords intermediate XVII. Cyclization of intermediate XVII in the presence of a suitable acid such as $H_2SO_4$, in a suitable solvent, such as acetic acid, affords flavone derivative VII.

Scheme 3

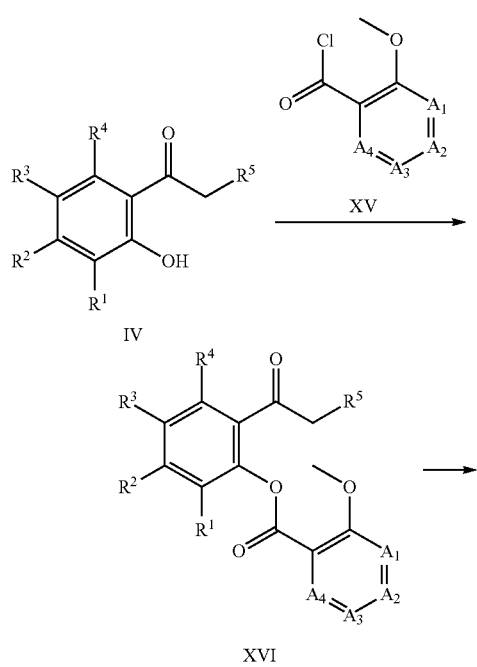

Scheme 4

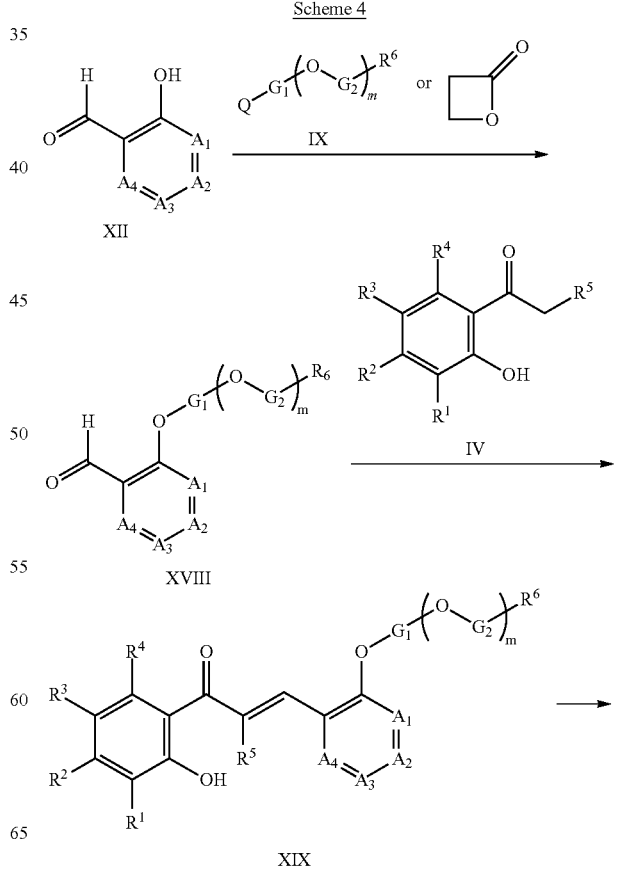

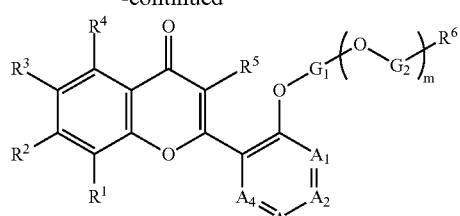

I

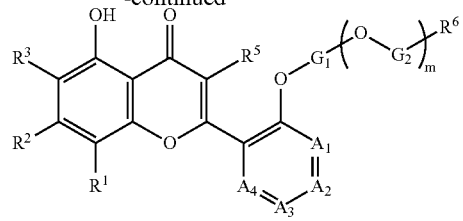

I-5

Wherein Q is halogen, OTs or OMs.

Substitution of aldehyde derivative XII with compound of formula IX or oxetan-2-one in the presence of a suitable base, such as $K_2CO_3$ or NaH, in a suitable solvent, such as DMF, affords compound of formula XVIII. Condensation of compound of formula XVIII with ketone IV in the presence of a base, such as KOH, in a suitable solvent, such as ethanol, affords α,β-unsaturated carbonyl intermediate XIX. Cyclization of α,β-unsaturated carbonyl intermediate XIX in the presence of a suitable Lewis acid, such as $I_2$, KI or NaI, in a suitable solvent, such as DMSO, affords compound of formula I.

Protection hydroxy group of compound of formula XX with bromo(methoxy)methane in the presence of a suitable base, such as NaH, in a suitable solvent, such as THF, affords compound of formula XXI. Condensation of compound of formula XXI with compound of formula XVIII in the presence of a base, such as KOH, in a suitable solvent, such as ethanol, affords α,β-unsaturated carbonyl intermediate XXII. Cyclization of α,β-unsaturated carbonyl intermediate XXII in the presence of a suitable Lewis acid, such as $I_2$, KI or NaI, in a suitable solvent, such as DMSO, affords compound of formula I-5.

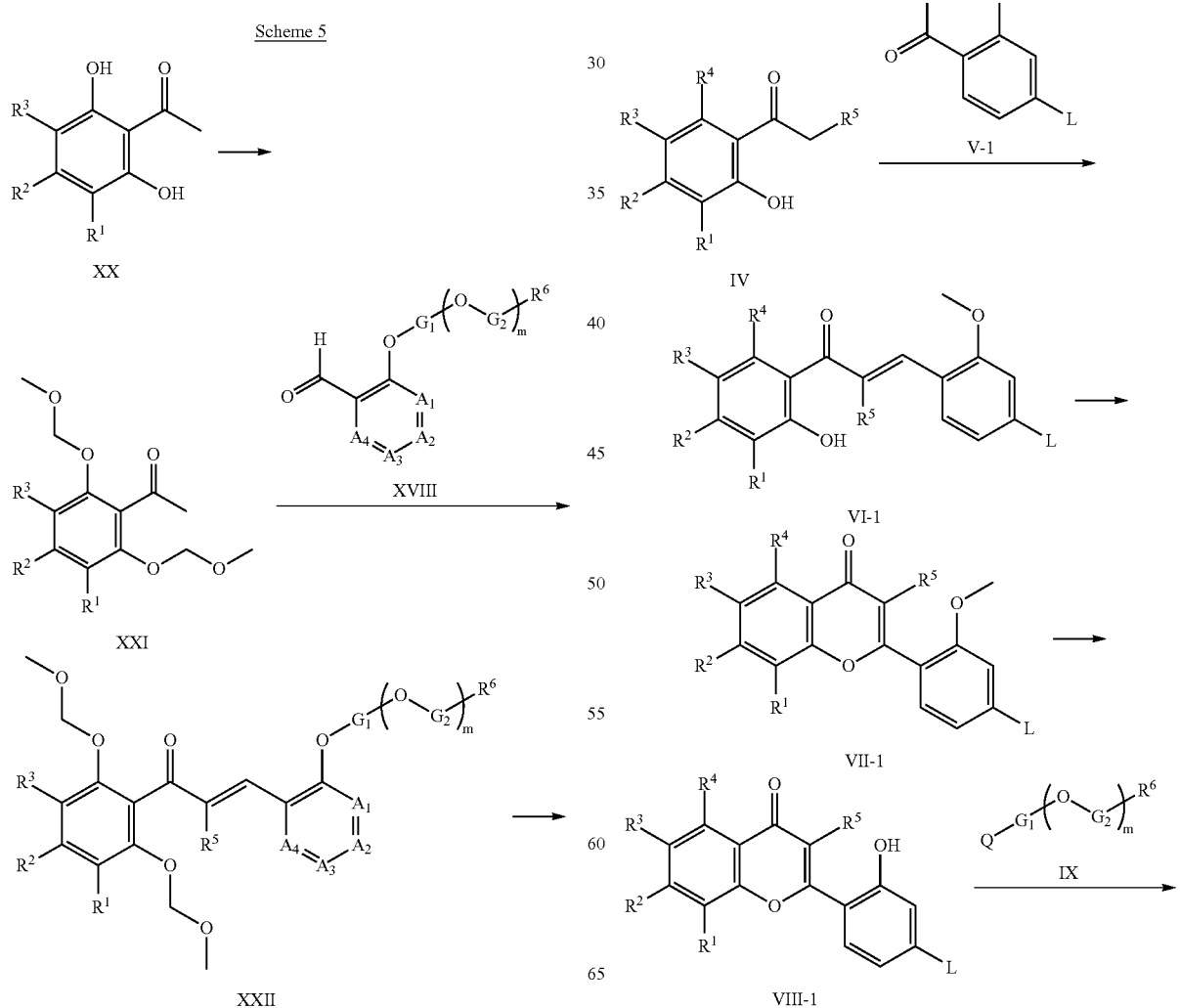

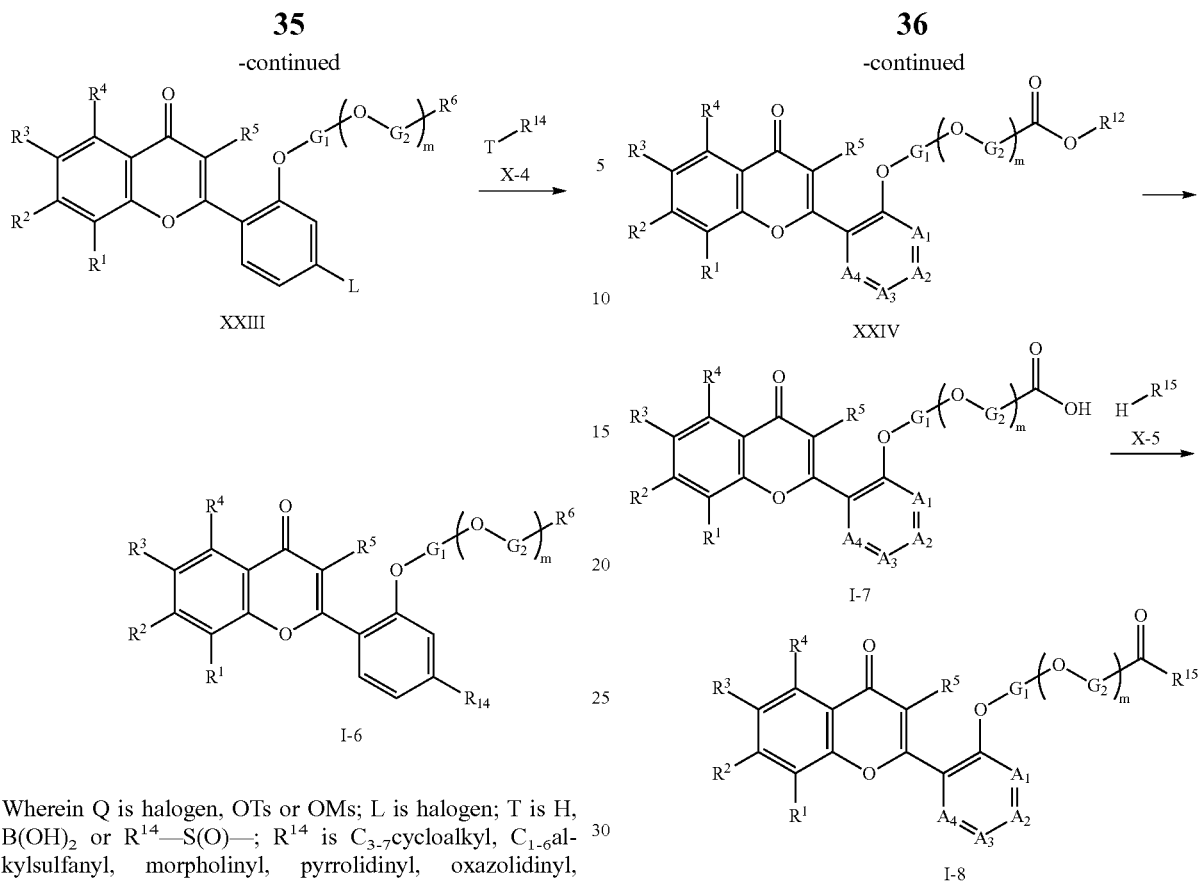

Wherein Q is halogen, OTs or OMs; L is halogen; T is H, B(OH)$_2$ or R$^{14}$—S(O)—; R$^{14}$ is C$_{3-7}$cycloalkyl, C$_{1-6}$alkylsulfanyl, morpholinyl, pyrrolidinyl, oxazolidinyl, haloC$_{1-6}$alkyl, thiazolyl; wherein pyrrolidinyl and oxazolidinyl are unsubstituted or substituted one time by oxo.

Condensation of ketone IV with aldehyde V-1 in the presence of a base, such as KOH, in a suitable solvent, such as ethanol, affords α,β-unsaturated carbonyl intermediate VI-1. Cyclization of α,β-unsaturated carbonyl intermediate VI-1 in the presence of a suitable Lewis acid, such as I$_2$, KI or NaI, in a suitable solvent, such as DMSO, affords flavone derivative VII-1. Demethylation of flavone derivative VII-1 with a suitable Lewis acid, such as BBr$_3$, in a suitable solvent, such as dichloromethane, affords compound of formula VIII-1. Substitution of compound of formula VIII-1 with compound of formula IX in the presence of a suitable base, such as K$_2$CO$_3$, in a suitable solvent, such as DMF, affords compound of formula XXIII. Treatment of compound of formula XXIII with compound of formula X-4 in the presence of a suitable catalyst, such as CuI or Pd(OAc)$_2$, in a suitable solvent, such as DMF, affords compound of formula I-6.

Wherein Q is halogen, OTs or OMs; R$^{12}$ is C$_{1-6}$alkyl; R$^{15}$ is selected from C$_{3-7}$cycloalkylamino, C$_{3-7}$cycloalkylsulfonylamino, C$_{1-6}$alkylsulfonylamino and C$_{1-6}$alkylamino.

Substitution of compound of formula VIII with compound of formula IX-1 in the presence of a suitable base, such as K$_2$CO$_3$, in a suitable solvent, such as DMF, affords compound of formula XXIV. Hydrolysis of compound of formula XXIV in the presence of a suitable base, such as LiOH, in a suitable solvent, such as THF and water, affords compound of formula I-7. Condensation of compound of formula I-7 with compound of formula X-5 in the presence of a suitable condensation reagent, such as HATU, with a suitable base, such as TEA, in a suitable solvent, such as DCM, affords amide derivative I-8.

Scheme 7

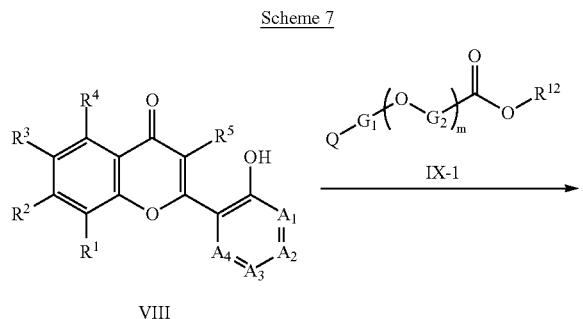

Scheme 8

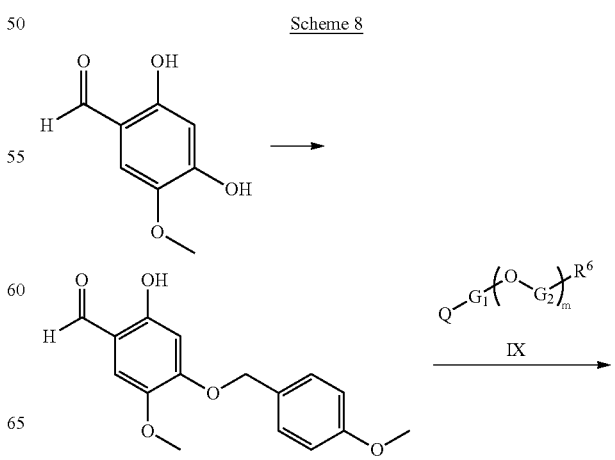

-continued

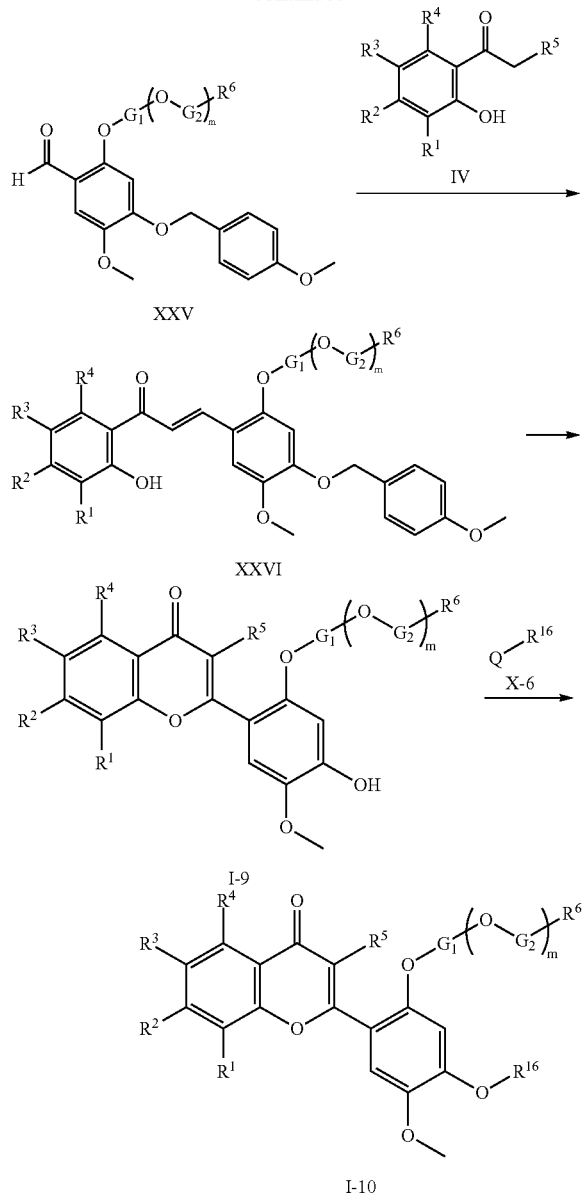

Wherein Q is halogen, OTs or OMs; $R^{16}$ is $C_{1-6}$alkyl or halo$C_{1-6}$alkyl.

Protection the hydroxy group of 2,4-dihydroxy-5-methoxy-benzaldehyde with 1-(bromomethyl)-4-methoxy-benzene in the presence of a suitable base, such as NaHCO$_3$, in a suitable solvent, such as DMF, affords 2-hydroxy-5-methoxy-4-[(4-methoxyphenyl)methoxy]benzaldehyde. Substitution of 2-hydroxy-5-methoxy-4-[(4-methoxyphenyl)methoxy]benzaldehyde with compound of formula IX in the presence of a suitable base, such as K$_2$CO$_3$, in a suitable solvent, such as DMF, affords compound of formula XXV. Condensation of compound of formula XXV with ketone IV in the presence of a base, such as KOFI, in a suitable solvent, such as ethanol, affords α,β-unsaturated carbonyl intermediate XXVI. Cyclization of intermediate XXVI in the presence of a suitable Lewis acid, such as I$_2$, KI or NaI, in a suitable solvent, such as DMSO, affords compound of formula I-9. Alkylation of compound of formula I-9 with compound of formula X-6 in the presence of a suitable base, such as K$_2$CO$_3$, in a suitable solvent, such as DMF, affords compound of formula I-10.

Scheme 9

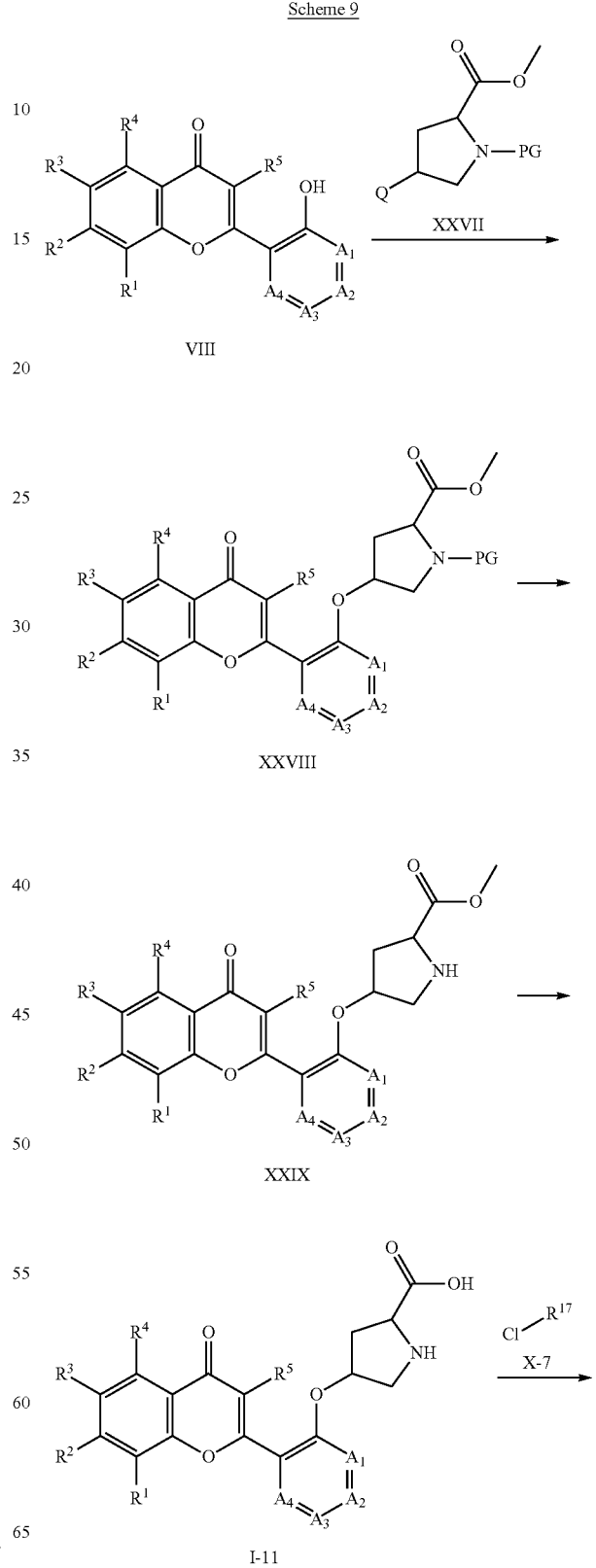

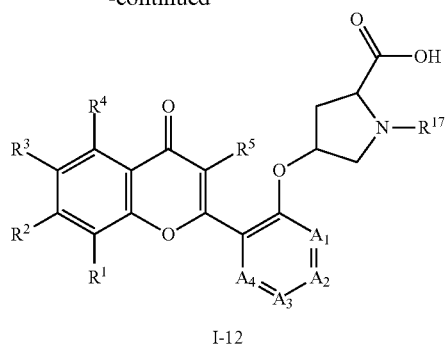

I-12

Wherein Q is halogen, OTs or OMs; PG is Boc; $R^{17}$ is $C_{3-7}$cycloalkylsulfonyl, $C_{1-6}$alkylsulfonyl, phenylsulfonyl or phenylcarbonyl;

Substitution of compound of formula VIII with compound of formula XXVII in the presence of a suitable base, such as $K_2CO_3$, in a suitable solvent, such as DMF, affords compound of formula XXVIII. Deprotection of compound of formula XXVIII with a suitable acid, such as TFA, in a suitable solvent, such as DCM, affords compound of formula XXIX. Hydrolysis of compound of formula XXIX with a suitable base, such as LiOH, in a suitable solvent, such as THF and water, affords compound of formula I-11 Treatment of compound of formula I-11 with compound of formula X-7 in the presence of a suitable base, such as LiOH, in a suitable solvent such as THF, affords compound of formula I-12.

Scheme 10

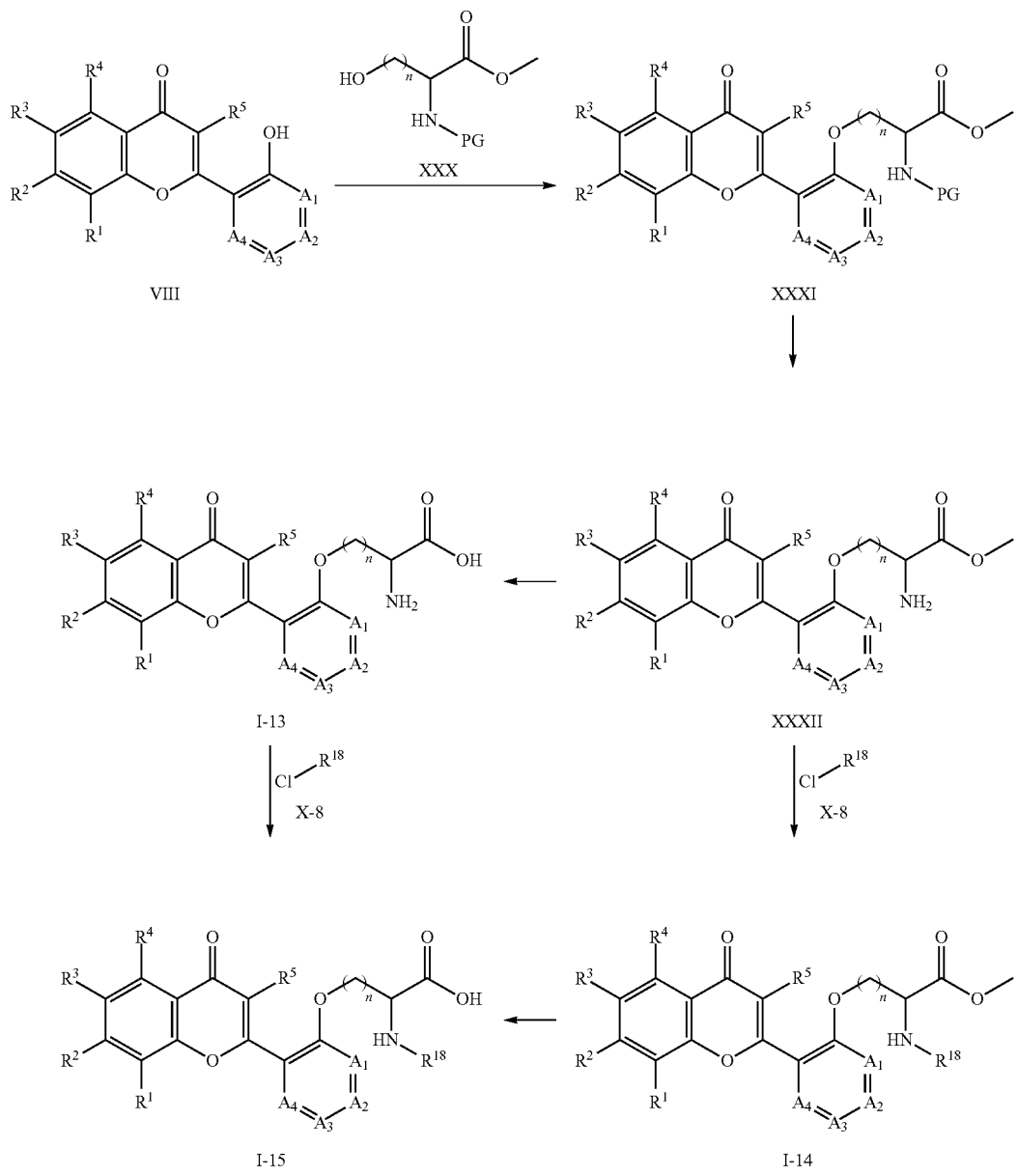

Wherein Q is halogen, OTs, OTf or OMs; PG is Boc; $R^{18}$ is $C_{3-7}$cycloalkylsulfonyl, $C_{4-6}$alkylsulfonyl, phenylsulfonyl or $C_{1-6}$alkylaminosulfonyl; n=1 or 2

Condensation of compound of formula VIII with compound of formula XXX, affords compound of formula XXXI. Deprotection of compound of formula XXXI with a suitable acid, such as TFA, in a suitable solvent, such as DCM, affords compound of formula XXXII. Hydrolysis of compound of formula XXXII with a suitable base, such as LiOH, in a suitable solvent, such as THF and water, affords compound of formula I-13. Treatment of compound of formula I-13 with compound of formula X-8 in the presence of a suitable base, such as LiOH, in a suitable solvent such as THF, affords compound of formula I-15. Treatment of compound of formula XXXII with compound of formula X-8 in the presence of a suitable base, such as TEA, in a suitable solvent such as DCM, affords compound of formula I-14. Hydrolysis of compound of formula I-14 with a suitable base, such as trimethylstannanol, in a suitable solvent, such as DCE, affords compound of formula I-15.

This invention also relates to a process for the preparation of a compound of formula (I) comprising any one of the following steps:

(a) substitution of a compound of formula (VIII),

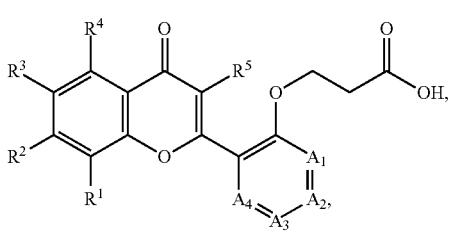

(VIII)

with a compound of formula (IX),

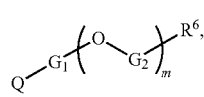

(IX)

in the presence of a base;

(b) treatment of a compound of formula (VIII), with oxetan-2-one in the presence of a base;

(c) condensation of propanoic acid derivative (I-1),

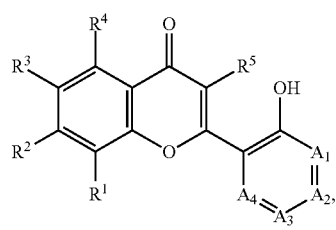

(I-1)

with a compound of formula (X-1),

(X-1)

in the presence of a condensation reagent with a base;

(d) esterification of propanoic acid derivative (I-1), with a compound of formula (X-2),

(X-2)

in the presence of an acid;

(e) substitution of ester derivative (I-3),

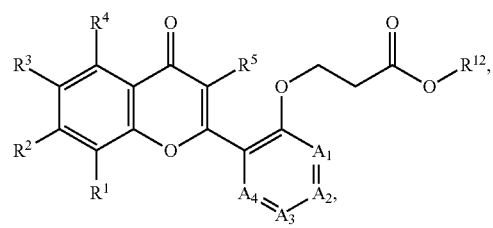

(I-3)

with a compound of formula (X-3),

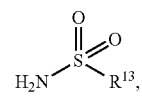

(X-3)

in the presence of an acid;

(f) cyclization of α,β-unsaturated carbonyl intermediate (XIX),

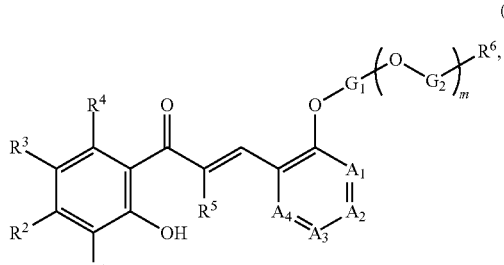

(XIX)

in the presence of a suitable Lewis acid;

(g) cyclization of α,β-unsaturated carbonyl intermediate (XXII),

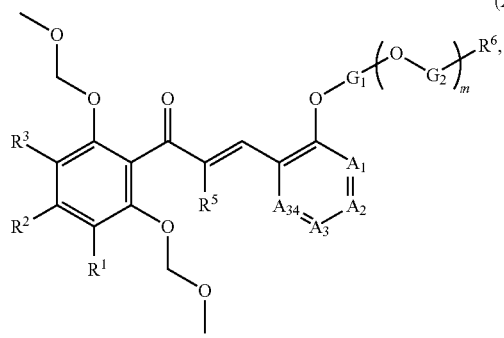
(XXII)

in the presence of a suitable Lewis acid;

(h) treatment of compound of formula (XXIII),

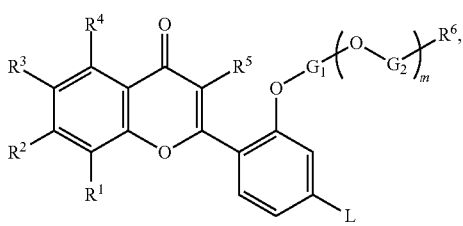
(XXIII)

with a compound of formula (X-4),

(X-4)

in the presence of a catalyst;

(i) hydrolysis of compound of formula (XXIV),

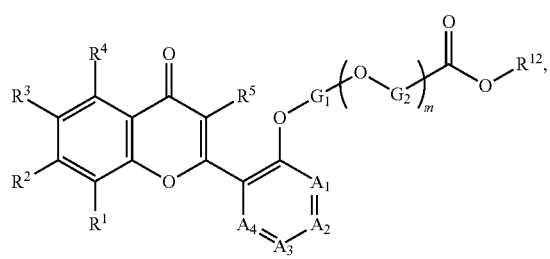
(XXIV)

in the presence of a base;

(j) condensation of compound of formula (I-7),

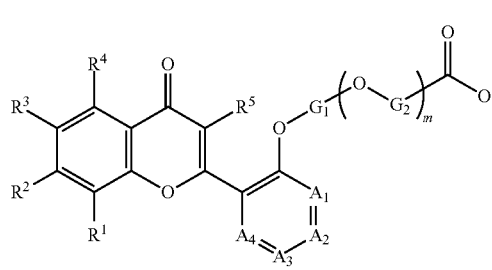
(I-7)

with a compound of formula (X-5),

(X-5)

in the presence of a condensation reagent, with a base;

(k) cyclization of intermediate (XXVI),

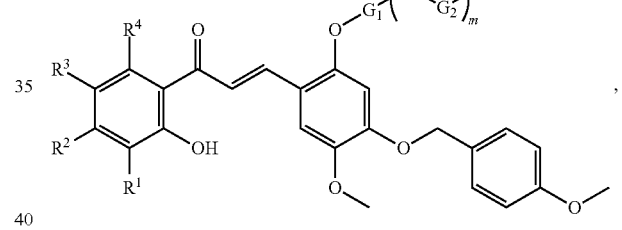
(XXVI)

in the presence of a suitable Lewis acid;

(l) alkylation of compound of formula (I-9),

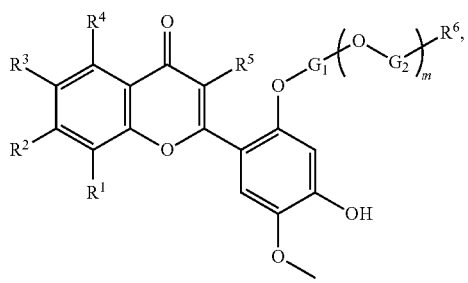
(I-9)

with a compound of formula (X-6),

(X-6)

in the presence of a base;

(m) hydrolysis of compound of formula (XXIX),

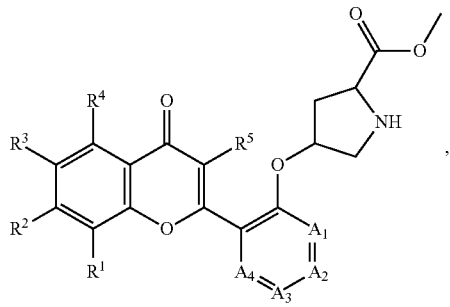
(XXIX)

in the presence of a base;
(n) hydrolysis of compound of formula (I-11),

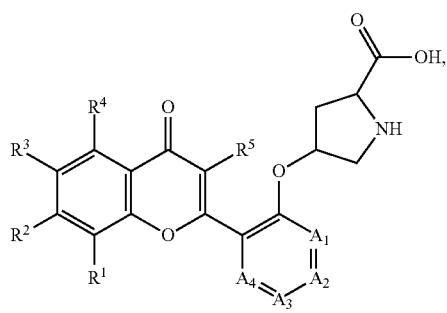
(I-11)

with a compound of formula (X-7),

(X-7)

in the presence of a base;
(o) hydrolysis of compound of formula (XXXII),

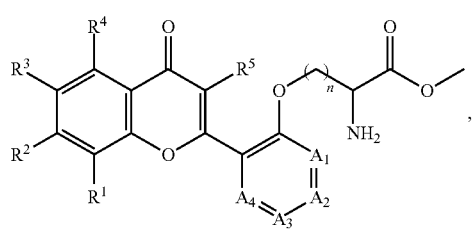
(XXXII)

in the presence of a base;

(p) treatment of compound of formula (I-13),

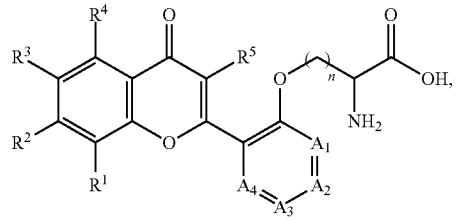
(I-13)

with a compound of formula (X-8),

(X-8)

in the presence of a base;
(q) treatment of compound of formula (XXXII), with a compound of formula (X-8) in the presence of a base;
(r) hydrolysis of compound of formula (I-14),

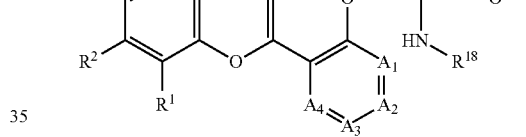
(I-14)

with a compound of formula (X-8) in the presence of a base; wherein $R^1$ to $R^{10}$, $G_1$; $G_2$, $A^1$ to $A^4$ and m are defined as any one of claims 1 to 66; Q is halogen, OTs or OMs; L is halogen; T is H, $B(OH)_2$ or $R^{14}$—S(O)—; $R^{11}$ is $C_{3-7}$cycloalkylamino or hydroxy$C_{1-6}$alkylamino; $R^{12}$ is $C_{1-6}$alkyl; $R^{13}$ is $C_{1-6}$alkyl or $C_{3-7}$cycloalkyl; $R^{14}$ is $C_{3-7}$cycloalkyl, $C_{1-6}$alkylsulfanyl, morpholinyl, pyrrolidinyl, oxazolidinyl, halo$C_{1-6}$alkyl, thiazolyl; wherein pyrrolidinyl and oxazolidinyl are unsubstituted or substituted one time by oxo; $R^{15}$ is selected from $C_{3-7}$cycloalkylamino, $C_{3-7}$cycloalkylsulfonylamino, $C_{1-6}$alkylsulfonylamino and $C_{4-6}$alkylamino; $R^{16}$ is $C_{1-6}$alkyl or halo$C_{1-6}$alkyl; PG is Boc; $R^{17}$ is $C_{3-7}$cycloalkylsulfonyl, $C_{1-6}$alkylsulfonyl, phenylsulfonyl, phenylcarbonyl; R is $C_{3-7}$cycloalkylsulfonyl, $C_{1-6}$alkylsulfonyl, phenylsulfonyl or $C_{1-6}$alkylaminosulfonyl; n=1 or 2;
the base in step (a) can be for example $K_2CO_3$;
the base in step (b) can be for example t-BuOK;
the condensation reagent in step (c) can be for example HATU; the base in step (c) can be for example TEA;
the acid in step (d) can be for example HCl;
the acid in step (e) can be for example $TiCl_4$;
the Lewis acid in step (f) can be for example $I_2$, KI or NaI;
the Lewis acid in step (g) can be for example $I_2$, KI or NaI;
the catalyst in step (h) can be for example CuI or $Pd(OAc)_2$;
the base in step (i) can be for example LiOH;
the condensation reagent in step (j) can be for example HATU; the base in step (j) can be for example TEA;
the Lewis acid in step (k) can be for example $I_2$, KI or NaI;
the base in step (l) can be for example $K_2CO_3$;
the base in step (m) can be for example LiOH;
the base in step (n) can be for example LiOH;

the base in step (o) can be for example LiOH;
the base in step (p) can be for example LiOH;
the base in step (q) can be for example TEA;
the base in step (r) can be for example trimethylstannanol.

A compound of formula (I) when manufactured according to the above process is also an object of the invention.

Pharmaceutical Compositions and Administration

The invention also relates to a compound of formula (I) for use as therapeutically active substance. Another embodiment provides pharmaceutical compositions or medicaments containing the compounds of the invention and a therapeutically inert carrier, diluent or excipient, as well as methods of using the compounds of the invention to prepare such compositions and medicaments. In one example, compounds of formula (I) may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) is formulated in an acetate buffer, at pH 5. In another embodiment, the compounds of formula (I) are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to inhibit cccDNA in HBV patients, consequently lead to the reduction of HBsAg and HBeAg (HBV e antigen) in serum. For example, such amount may be below the amount that is toxic to normal cells, or the mammal as a whole.

In one example, the pharmaceutically effective amount of the compound of the invention administered parenterally per dose will be in the range of about 0.1 to 100 mg/kg, alternatively about 0.1 to 50 mg/kg of patient body weight per day, with the typical initial range of compound used being 0.3 to 15 mg/kg/day. In another embodiment, oral unit dosage forms, such as tablets and capsules, preferably contain from about 25 to about 1000 mg of the compound of the invention.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, symps, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

An example of a suitable oral dosage form is a tablet containing about 25 to 500 mg of the compound of the invention compounded with about 90 to 30 mg anhydrous lactose, about 5 to 40 mg sodium croscarmellose, about 5 to 30 mg polyvinylpyrrolidone (PVP) K30, and about 1 to 10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 5 to 400 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

An embodiment, therefore, includes a pharmaceutical composition comprising a compound of formula (I), or a pharmaceutically acceptable salt thereof.

In a further embodiment includes a pharmaceutical composition comprising a compound of formula (I), or a pharmaceutically acceptable salt thereof, together with a pharmaceutically acceptable carrier or excipient.

Another embodiment includes a pharmaceutical composition comprising a compound of formula (I), or a pharmaceutically acceptable salt thereof for use in the treatment of HBV infection.

Indications and Methods of Treatment

The compounds of the invention can inhibit cccDNA and have anti-HBV activity. Accordingly, the compounds of the invention are useful for the treatment or prophylaxis of HBV infection.

The invention relates to the use of a compound of formula (I) for the inhibition of cccDNA.

The invention also relates to the use of a compound of formula (I) for the inhibition of HBeAg.

The invention further relates to the use of a compound of formula (I) for the inhibition of HBsAg.

The invention relates to the use of a compound of formula (I) for the inhibition of HBV DNA.

The invention relates to the use of a compound of formula (I) for the treatment or prophylaxis of HBV infection.

The use of a compound of formula (I) for the preparation of medicaments useful in the treatment or prophylaxis diseases that are related to HBV infection is an object of the invention.

The invention relates in particular to the use of a compound of formula (I) for the preparation of a medicament for the treatment or prophylaxis of HBV infection.

Another embodiment includes a method for the treatment or prophylaxis of HBV infection, which method comprises administering an effective amount of a compound of Formula (I), or pharmaceutically acceptable salts thereof.

BRIEF DESCRIPTION OF THE FIGURES(S)

FIG. 1: the result of BIO-Example 3 in cccDNA Southern Blot assay, it indicates that C003-A dose-dependently reduced cccDNA level in HepDES19 cells.

EXAMPLES

The invention will be more fully understood by reference to the following examples. They should not, however, be construed as limiting the scope of the invention.

Abbreviations used herein are as follows:
ACN: acetonitrile
$BBr_3$: boron tribromide
DMAP: 4-dimethylaminopyridine
DMF: N,N-dimethylformamide
$IC_{50}$: the molar concentration of an inhibitor, which produces 50% of the maximum possible response for that inhibitor.
FBS: fetal bovine serum
$H_2O_2$: hydrogen peroxide
HPLC: high performance liquid chromatography
MS (ESI): mass spectroscopy (electron spray ionization)
Ms: methylsulfonyl
obsd.: observed
PE: petroleum ether
EtOAc: ethyl acetate
AcOH: acetic acid
DIBAL: diisobutylaluminium hydride
THF: tetrahydrofuran
LiHMDS: lithium bis(trimethylsilyl)amide
$LiAlH_4$: lithium aluminium hydride
TFA: trifluoro acetic acid
$MnO_2$: manganese dioxide
DIPEA: N,N-Diisopropylethylamine
HATU: 1-[Bis(dimethylamino)methylene]-1H-1,2,3-triazolo[4,5-b]pyridinium 3-oxid hexafluorophosphate
DIAD: Diisopropyl azodicarboxylate
DABCO: 1,4-Diazabicyclo[2.2.2]octane
m-CPBA: 3-Chlorobenzene-1-carboperoxoic acid
DAST: Diethylaminosulfur trifluoride
RuPhos Pd G2: Chloro(2-dicyclohexylphosphino-2',6'-diisopropoxy-1,1'-biphenyl)[2-(2'-amino-1,1'-biphenyl)]palladium(II)
Ts: p-tolylsulfonyl
δ: chemical shift

GENERAL EXPERIMENTAL CONDITIONS

Intermediates and final compounds were purified by flash chromatography using one of the following instruments: i) Biotage SP1 system and the Quad 12/25 Cartridge module, ii) column chromatography on silica gel combi-flash chromatography instrument. Silica gel Brand and pore size: i) KP-SIL 60 Å, particle size: 40-60 μm; ii) CAS registry NO: Silica Gel: 63231-67-4, particle size: 47-60 micron silica gel; iii) ZCX from Qingdao Haiyang Chemical Co., Ltd, pore: 200-300 or 300-400.

Intermediates and final compounds were purified by preparative HPLC on reversed phase column using X Bridge™ Perp $C_{18}$ (5 μm, OBD™ 30×100 mm) column or SunFire™ Perp $C_{18}$ (5 μm, OBD™ 30×100 mm) column.

LC/MS spectra were obtained using a Waters UPLC-SQD Mass. Standard LC/MS conditions were as follows (running time 3 minutes):
Acidic condition: A: 0.1% formic acid and 1% acetonitrile in $H_2O$; B: 0.1% formic acid in acetonitrile;
Basic condition: A: 0.05% $NH_3$—$H_2O$ in $H_2O$; B: acetonitrile.

Mass spectra (MS): generally only ions which indicate the parent mass are reported, and unless otherwise stated the mass ion quoted is the positive mass ion $(M+H)^+$.

NMR Spectra were obtained using Bruker Avance 400 MHz.

All reactions involving air-sensitive reagents were performed under an argon atmosphere. Reagents were used as received from commercial suppliers without further purification unless otherwise noted.

PREPARATIVE EXAMPLES

Intermediate 1: 8-chloro-2-[2-hydroxy-4-(trifluoromethyl)phenyl]chromen-4-one

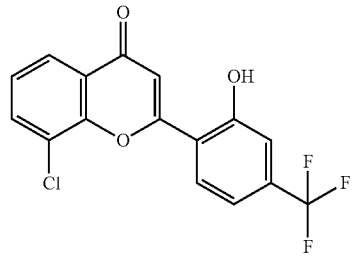

Int-1

Step 1: Preparation of (E)-1-(3-chloro-2-hydroxyphenyl)-3-[2-methoxy-4-(trifluoromethyl)phenyl]prop-2-en-1-one

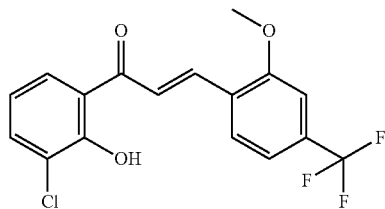

Int-1a

A mixture of 1-(3-chloro-2-hydroxy-phenyl)ethanone (CAS #: 3226-34-4, Cat. #: BD11027, from Bide Pharmatech, 2.5 g, 14.7 mmol), 2-methoxy-4-(trifluoromethyl)benzaldehyde (CAS #: 132927-09-4, Cat. #: H26797, from Alfa Aesar, 2 g, 14.7 mmol) and KOH (1.64 g, 29.3 mmol) in EtOH (25 mL) was stirred at 100° C. for 3 hours. After the reaction was completed, the mixture was then adjusted to pH ~4 by addition of 2N HCl and the resulting suspension was filtered. The solid was collected and dried in vacuo to give the crude (E)-1-(3-chloro-2-hydroxy-phenyl)-3-[2-methoxy-4-(trifluoromethyl)phenyl]prop-2-en-1-one (3.3 g, 78%) as a yellow solid, which was used in the next step directly without further purification. MS obsd. (ESI$^+$) [(M+H)$^+$]:357.2.

Step 2: Preparation of 8-chloro-2-[2-methoxy-4-(trifluoromethyl)phenyl]chromen-4-one

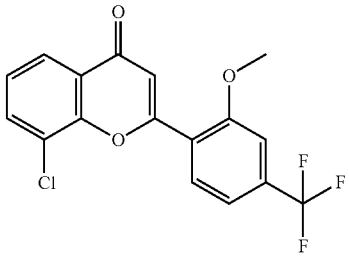
Int-1b

To a solution of (E)-1-(3-chloro-2-hydroxy-phenyl)-3-[2-methoxy-4-(trifluoromethyl)phenyl]prop-2-en-1-one (5.3 g, 18.4 mmol) in DMSO (60 mL) was added I$_2$ (466 mg, 1.84 mmol) and then the mixture was stirred at 140° C. for 3 hours. After the reaction was completed, the mixture was cooled to room temperature, quenched with saturated NaHSO$_3$ solution (10 mL). The mixture was diluted with water (100 mL) and the resulting suspension was filtered. The solid was collected and dried in vacuo to give the 8-chloro-2-[2-methoxy-4-(trifluoromethyl)phenyl]chromen-4-one (5 g, 95% yield) as a yellow solid, which was used in the next step directly without further purification. MS obsd. (ESI$^+$) [(M+H)$^+$]: 355.1.

Step 3: Preparation of 8-chloro-2-[2-hydroxy-4-(trifluoromethyl)phenyl]chromen-4-one

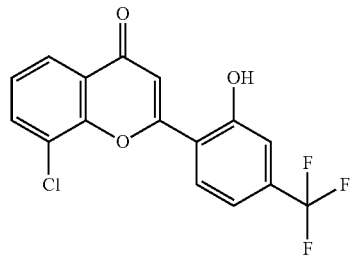
Int-1

To a solution of 8-chloro-2-[2-methoxy-4-(trifluoromethyl)phenyl]chromen-4-one (5 g, 14.0 mmol) in dichloromethane (40 mL) was added BBr$_3$ (1 M solution in dichloromethane, 69.8 mL, 69.8 mmol) at room temperature. The mixture was stirred at room temperature overnight. After the reaction was completed, the mixture was concentrated in vacuo and the residue was suspended in saturated NH$_4$Cl solution (30 mL). The solid was collected by filtration and dried in vacuo to give the crude 8-chloro-2-[2-hydroxy-4-(trifluoromethyl)phenyl]chromen-4-one (4.1 g, 85.9% yield) as a yellow solid, which was used in the next step directly without further purification. MS obsd. (ESI$^+$) [(M+H)$^+$]: 341.2.

Intermediate 2: 8-chloro-2-(2-hydroxy-4-methyl-phenyl)chromen-4-one

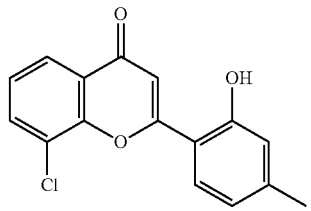
Int-2

Int-2 was prepared in analogy to the procedure described for the preparation of compound Int-1 by using 2-methoxy-4-methyl-benzaldehyde as the starting material instead of 2-methoxy-4-(trifluoromethyl)benzaldehyde in Step 1. MS obsd. (ESI$^+$) [(M+H)$^+$]: 287.1.

Intermediate 3: 8-chloro-2-(2-hydroxyphenyl)chromen-4-one

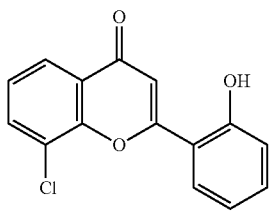
Int-3

Int-3 was prepared in analogy to the procedure described for the preparation of compound Int-1 by using 2-hydroxy-benzaldehyde as the starting material instead of 2-methoxy-4-(trifluoromethyl)benzaldehyde in Step 1. MS obsd. (ESI$^+$) [(M+H)$^+$]: 273.2.

Intermediate 4: 2-(4-bromo-2-hydroxy-phenyl)-8-chloro-chromen-4-one

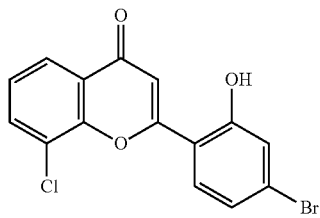
Int-4

Int-4 was prepared in analogy to the procedure described for the preparation of compound Int-1 by using 4-bromo-2-hydroxy-benzaldehyde as the starting material instead of 2-methoxy-4-(trifluoromethyl)benzaldehyde in Step 1. MS obsd. (ESI$^+$) [(M+H)$^+$]:351.2.

Intermediate 5: 8-chloro-2-(4-chloro-2-hydroxy-5-methyl-phenyl)chromen-4-one

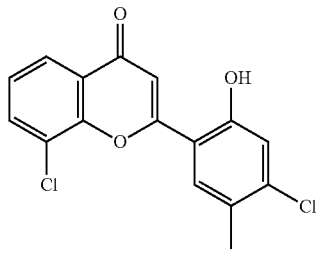

Int-5

Step 1: Preparation of 4-chloro-2-hydroxy-5-methyl-benzaldehyde

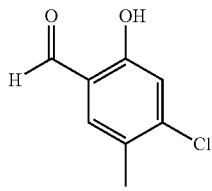

Int-5a

To a solution of 3-chloro-4-methyl-phenol (10.0 g, 70.1 mmol) in ACN (200 mL) were added formaldehyde (8.42 g, 280.54 mmol), TEA (39.1 mL, 280.5 mmol) and magnesium chloride (27.0 mL, 210.4 mmol) and the mixture was stirred at 80° C. for 16 hours. After the reaction was completed, the reaction was quenched with 1M HCl (500 mL) and extracted with EtOAc (150 mL) three times. The combined organic layer was washed with brine, dried over $Na_2SO_4$ and concentrated in vacuo to give the crude 4-chloro-2-hydroxy-5-methyl-benzaldehyde (11.3 g, 66.24 mmol, 94.45% yield) as brown oil, which was used in the next step directly without further purification.

Step 2: Preparation of 4-chloro-2-(methoxymethoxy)-5-methyl-benzaldehyde

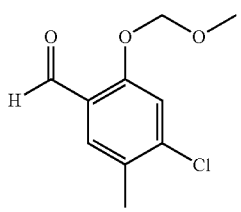

Int-5b

To a solution of 4-chloro-2-hydroxy-5-methyl-benzaldehyde (9.6 g, 56.28 mmol, in THE (100 mL) cooled at 0° C. was added sodium hydride (3.38 g, 84.41 mmol) in portions. After addition, the mixture was stirred at 0° C. for 30 minutes and then to the resulting mixture was added bromomethyl methyl ether (10.55 g, 84.41 mmol) dropwise. The reaction mixture was stirred at 0° C. for another 2 hours. After the reaction was complete, the mixture was poured into ice-water (200 ml) slowly and extracted with EtOAc (80 mL) three times. The combined organic layer was washed with brine, dried over $Na_2SO_4$ and concentrated in vacuo to give the crude 4-chloro-2-(methoxymethoxy)-5-methyl-benzaldehyde (12 g 99.34% yield) as a white solid, which was used in the next step directly without further purification. MS obsd. $(ESI^+)[(M+H)^+]$: 215.1.

Step 3: Preparation of (E)-1-(3-chloro-2-hydroxy-phenyl)-3-[4-chloro-2-(methoxymethoxy)-5-methyl-phenyl]prop-2-en-1-one

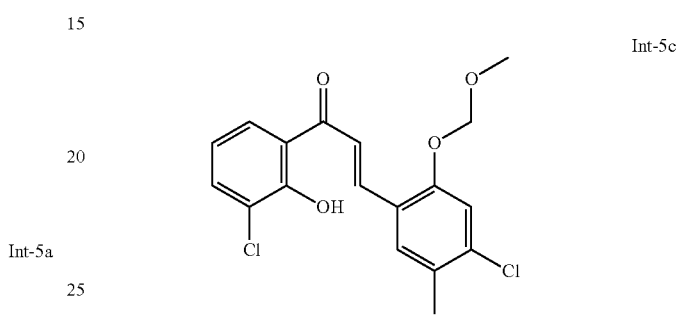

Int-5c

To a solution of 4-chloro-2-(methoxymethoxy)-5-methyl-benzaldehyde (6.0 g, 27.95 mmol), 1-(3-chloro-2-hydroxy-phenyl)ethanone (4.77 g, 27.95 mmol) in EtOH (300 mL) was added KOH (15.68 g, 279.52 mmol) and the mixture was then stirred at 35° C. for 16 hours. After the reaction was completed, the mixture was poured into 0.5 M HCl (200 mL) and the resulting suspension was then filtered. The solid was collected and then dried under vacuum to give the crude (E)-1-(3-chloro-2-hydroxy-phenyl)-3-[4-chloro-2-(methoxymethoxy)-5-methyl-phenyl]prop-2-en-1-one (10 g, 27.23 mmol, 97.42% yield) as a yellow solid, which was used in the next step directly without further purification. MS obsd. $(ESI^+)[(M+H)^+]$: 367.0.

Step 4: Preparation of 8-chloro-2-[4-chloro-2-(methoxymethoxy)-5-methyl-phenyl]chromen-4-one

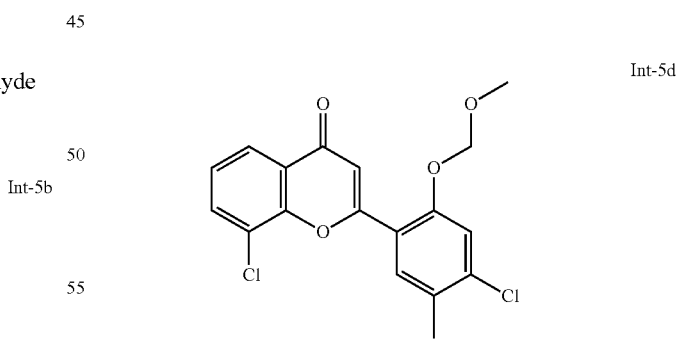

Int-5d

To a solution of (E)-1-(3-chloro-2-hydroxy-phenyl)-3-[4-chloro-2-(methoxymethoxy)-5-methyl-phenyl]prop-2-en-1-one (10.0 g, 27.23 mmol, 1 eq) in DMSO (250 mL) was added iodine (345.58 mg, 1.36 mmol, 0.050 eq) and the mixture was then stirred at 140° C. under $N_2$ for 2 hours. After the reaction was complete, the mixture was poured into ice-water and the resulting suspension was filtered. The solid was washed with water and then collected to give the crude 8-chloro-2-[4-chloro-2-(methoxymethoxy)-5-methylphenyl]chromen-4-one (8.7 g, 23.82 mmol, 87.48% yield) as a yellow solid, which was used in the next step directly without further purification. MS obsd. (ESI⁺)[(M+H)⁺]: 365.0.

Step 5: Preparation of 8-chloro-2-(4-chloro-2-hydroxy-5-methyl-phenyl)chromen-4-one

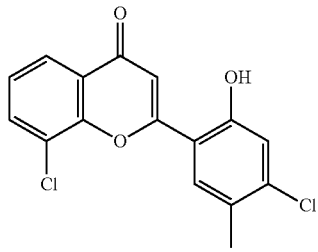

Int-5

To a solution of 8-chloro-2-[4-chloro-2-(methoxymethoxy)-5-methyl-phenyl]chromen-4-one (3.4 g, 9.31 mmol, 1 eq) in dichloromethane (10 mL) was added trifluoroacetic acid (10.0 mL, 129.8 mmol, 13.94 eq). The reaction mixture was then stirred at room temperature for 16 hours. After the reaction was completed, The reaction mixture was concentrated in vacuo to give the crude 8-chloro-2-(4-chloro-2-hydroxy-5-methyl-phenyl)chromen-4-one (2.7 g, 8.41 mmol, 90.31% yield) as a brown solid, which was used in the next step directly. MS obsd. (ESI⁺) [(M+H)⁺]: 320.9.

Intermediate 6: 2-(4-bromo-2-hydroxy-5-methyl-phenyl)-8-chloro-chromen-4-one

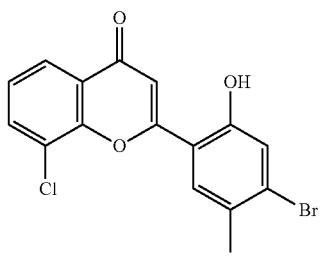

Int-6

Step 1: Preparation of 4-bromo-2-hydroxy-5-methyl-benzaldehyde

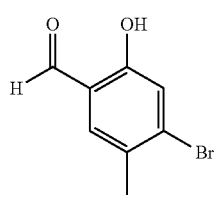

Int-6a

Int-6a was prepared in analogy to the procedure described for the preparation of compound Int-5a by using 3-bromo-4-methyl-phenol as the starting material instead of 3-chloro-4-methyl-phenol in Step 1.

Step 2: Preparation of 2-(4-bromo-2-hydroxy-5-methyl-phenyl)-8-chloro-chromen-4-one

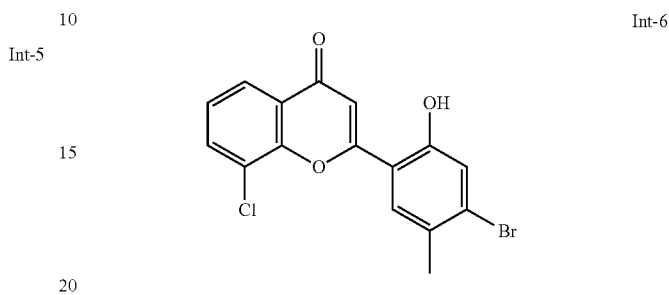

Int-6

Int-6 was prepared in analogy to the procedure described for the preparation of compound Int-5 by using 4-bromo-2-hydroxy-5-methyl-benzaldehyde as the starting material instead of 4-chloro-2-hydroxy-5-methyl-benzaldehyde in Step 2. MS obsd. (ESI⁺) [(M+H)⁺]: 341.0.

Intermediate 7: 2-(4-bromo-2-hydroxy-5-methoxy-phenyl)-8-chloro-chromen-4-one

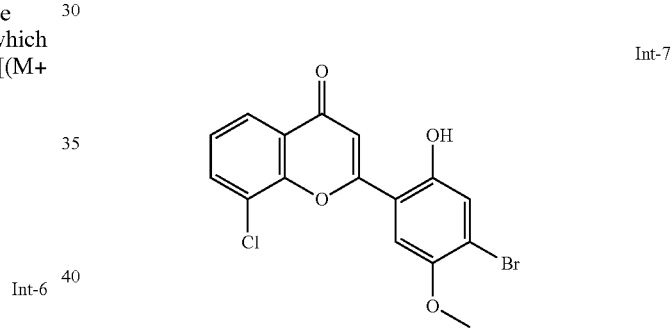

Int-7

Int-7 was prepared in analogy to the procedure described for the preparation of compound Int-5 by using 4-bromo-2-hydroxy-5-methoxy-benzaldehyde (CAS #: 63272-66-2, Cat. #: SY025557, from Accela ChemBio Inc.) as the starting material instead of 4-chloro-2-hydroxy-5-methyl-benzaldehyde in Step 2. MS obsd. (ESI⁺) [(M+H)⁺]: 381.1.

Intermediate 8: 8-chloro-2-(4-chloro-2-hydroxy-5-methoxy-phenyl)chromen-4-one

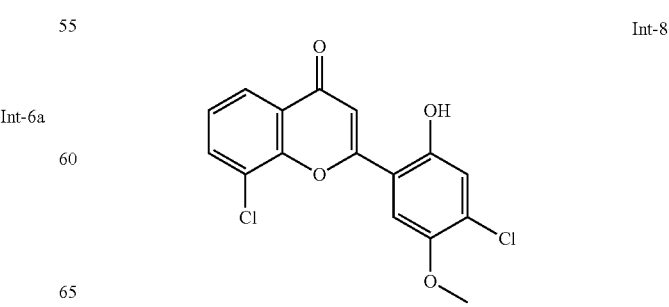

Int-8

Step 1: Preparation of 4-chloro-2-hydroxy-5-methoxy-benzaldehyde

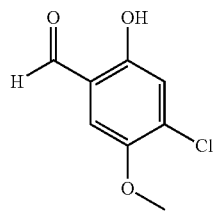

Int-8a

Int-8a was prepared in analogy to the procedure described for the preparation of compound Int-5a by using 3-chloro-4-methoxy-phenol as the starting material instead of 3-chloro-4-methyl-phenol in Step 1.

Step 2: Preparation of 8-chloro-2-(4-chloro-2-hydroxy-5-methoxy-phenyl)chromen-4-one

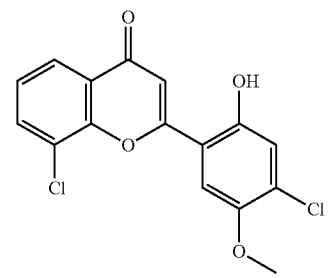

Int-8

Int-8 was prepared in analogy to the procedure described for the preparation of compound Int-5 by using 4-chloro-2-hydroxy-5-methoxy-benzaldehyde as the starting material instead of 4-chloro-2-hydroxy-5-methyl-benzaldehyde in Step 2. MS obsd. (ESI$^+$) [(M+H)$^+$]: 337.2. Intermediate 9: 8-chloro-2-[2-hydroxy-4-(trifluoromethoxy)phenyl]chromen-4-one

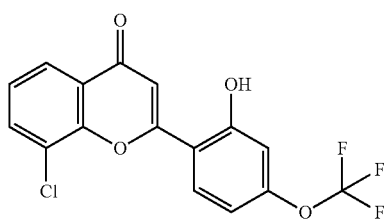

Int-9

Int-9 was prepared in analogy to the procedure described for the preparation of compound Int-1 by using 2-methoxy-4-(trifluoromethoxy)benzaldehyde (CAS #: 886500-13-6, Cat. #: BD188719, from Bepharm) as the starting material instead of 2-methoxy-4-(trifluoromethyl)benzaldehyde in Step 1. MS obsd. (ESI$^+$) [(M+H)$^+$]: 357.1.

Intermediate 10: 8-chloro-2-(2-hydroxy-4,5-dimethoxy-phenyl)chromen-4-one

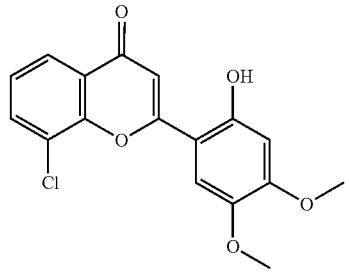

Int-10

Int-10 was prepared in analogy to the procedure described for the preparation of compound Int-5 by using 2-hydroxy-4,5-dimethoxy-benzaldehyde (CAS #: 14382-91-3, Cat. #: SY025559, from Accela ChemBio Inc.) as the starting material instead of 4-chloro-2-hydroxy-5-methyl-benzaldehyde in Step 2. MS obsd. (ESI$^+$) [(M+H)$^+$]: 333.2.

Intermediate 11: 8-chloro-2-(6-hydroxy-1,3-benzodioxol-5-yl)chromen-4-one

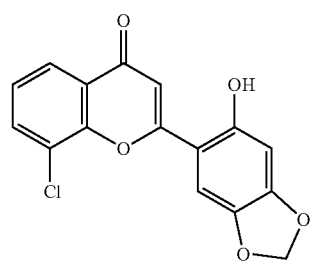

Int-11

Int-11 was prepared in analogy to the procedure described for the preparation of compound Int-5 by using 1,3-benzodioxol-5-ol (CAS #: 533-31-3, Cat. #: SY015819, from Accela ChemBio Inc.) as the starting material instead of 3-chloro-4-methyl-phenol in Step 1. MS obsd. (ESI$^+$) [(M+H)$^+$]: 317.3.

Intermediate 12: 8-chloro-2-(2-hydroxy-4-methoxy-5-methyl-phenyl)chromen-4-one

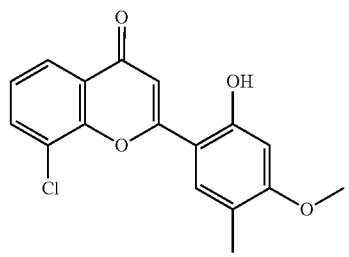

Int-12

Step 1: Preparation of
2-hydroxy-4-methoxy-5-methyl-benzaldehyde

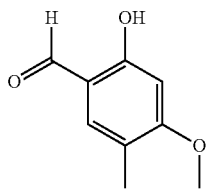

Int-12a

Int-12a was prepared in analogy to the procedure described for the preparation of compound Int-5a by using 3-methoxy-4-methyl-phenol as the starting material instead of 3-chloro-4-methyl-phenol in Step 1.

Step 2: Preparation of 8-chloro-2-(2-hydroxy-4-methoxy-5-methyl-phenyl)chromen-4-one

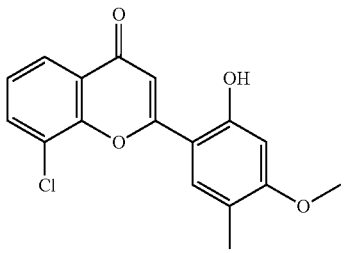

Int-12

Int-12 was prepared in analogy to the procedure described for the preparation of compound Int-5 by using 2-hydroxy-4-methoxy-5-methyl-benzaldehyde (Int-12a) as the starting material instead of 4-chloro-2-hydroxy-5-methyl-benzaldehyde in Step 2. MS obsd. (ESI$^+$) [(M+H)$^+$]: 317.1.

Intermediate 13: 8-chloro-2-(2-hydroxy-4-methoxy-phenyl)chromen-4-one

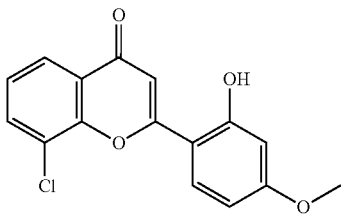

Int-13

Int-13 was prepared in analogy to the procedure described for the preparation of compound Int-5 by using 2-hydroxy-4-methoxy-benzaldehyde (CAS #: 673-22-3, Cat. #: SY012912, from Accela ChemBio Inc.) as the starting material instead of 4-chloro-2-hydroxy-5-methyl-benzaldehyde in Step 2. MS obsd. (ESI$^+$) [(M+H)$^+$]: 302.9.

Intermediate 14: 2-[4-bromo-2-hydroxy-5-(trifluoromethoxy)phenyl]-8-chloro-chromen-4-one

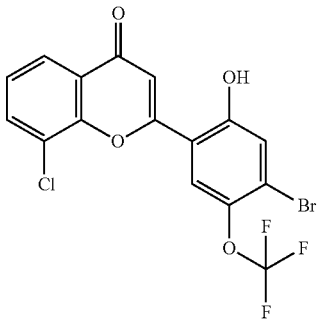

Int-14

Step 1: Preparation of
2-bromo-4-methoxy-1-(trifluoromethoxy)benzene

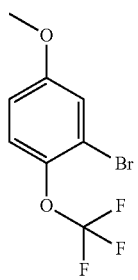

Int-14a

To a solution of 3-bromo-4-(trifluoromethoxy)phenol (CAS #: 886496-88-4, Cat. #: SY024383, from Accela ChemBio Inc., 2000.0 mg, 7.9 mmol) and K$_2$CO$_3$ (2151.0 mg, 15.8 mmol) in acetone (50 mL) were added iodomethane (2.2 g, 15.6 mmol) and the mixture was stirred at room temperature for 18 hours. After the reaction was completed, the mixture was filtered and the filtrate was concentrated in vacuo. The residue was purified by column chromatography on silica gel (eluent with PE:EtOAc=10:1 to 3:1) to give 2-bromo-4-methoxy-1-(trifluoromethoxy)benzene (1800 mg, yield 85.3%) as a yellow solid. MS obsd. (ESI$^+$) [(M+Na)]$^+$: 294.0.

Step 2: Preparation of
4-bromo-2-methoxy-5-(trifluoromethoxy)benzaldehyde

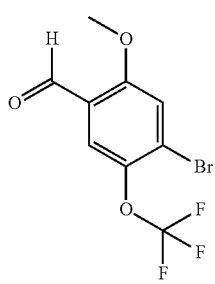

Int-14b

To a solution of 2-bromo-4-methoxy-1-(trifluoromethoxy)benzene (2000 mg, 7.4 mmol) in DCM (20 mL) cooled at 78° C. was added TiCl$_4$ (1680 mg, 8.86 mmol) and the mixture was stirred at −78° C. for 30 minutes. To the resulting solution was added 1,1-dichlorodimethyl ether (1866 mg, 16.3 mmol). The reaction was then warmed to room temperature and stirred at room temperature for 2 hours. After the reaction was completed, the reaction was quenched by NH$_4$Cl solution (30 mL) and extracted with DCM (20 mL) three times. The combined organic layer was dried over MgSO$_4$ and concentrated in vacuo. The residue was purified by column chromatography on silica gel (eluent with PE:EtOAc 100:1 to 3:1) to give 4-bromo-2-methoxy-5-(trifluoromethoxy)benzaldehyde (500 mg, 22.7% yield) as a white solid. $^1$H NMR (CDCl$_3$, 400 MHz): δ ppm 10.30 (s, 1H), 7.69 (d, J=1.3 Hz, 1H), 7.22 (s, 1H), 3.90 (s, 3H).

Step 3: Preparation of 2-[4-bromo-2-hydroxy-5-(trifluoromethoxy)phenyl]-8-chloro-chromen-4-one

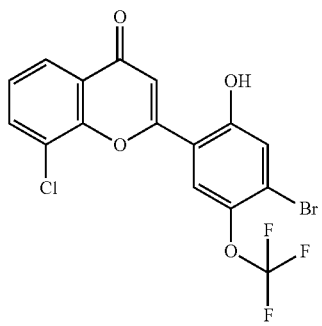

Int-14

Int-14 was prepared in analogy to the procedure described for the preparation of compound Int-1 by using 4-bromo-2-methoxy-5-(trifluoromethoxy)benzaldehyde as the starting material instead of 2-methoxy-4-(trifluoromethyl)benzaldehyde in Step 1. MS obsd. (ESI$^+$) [(M+H)]$^+$: 436.0.

Intermediate 15: 8-chloro-2-(2-hydroxy-5-methoxy-4-methyl-phenyl)chromen-4-one

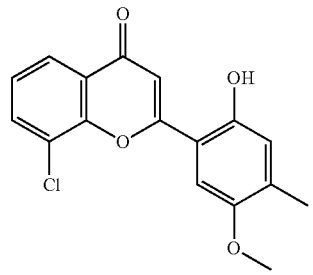

Int-15

Step 1: Preparation of 2-hydroxy-5-methoxy-4-methyl-benzaldehyde

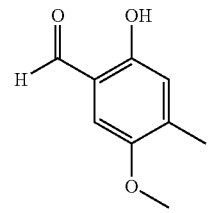

Int-15a

Int-15a was prepared in analogy to the procedure described for the preparation of compound Int-5a by using 4-methoxy-3-methyl-phenol as the starting material instead of 3-chloro-4-methyl-phenol in Step 1.

Step 2: Preparation of 8-chloro-2-(2-hydroxy-5-methoxy-4-methyl-phenyl)chromen-4-one

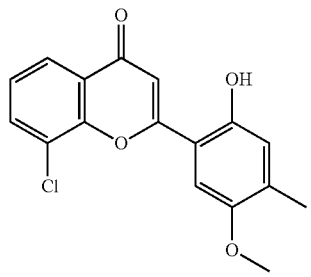

Int-15

Int-15 was prepared in analogy to the procedure described for the preparation of compound Int-5 by using 2-hydroxy-5-methoxy-4-methyl-benzaldehyde (Int-15a) as the starting material instead of 4-chloro-2-hydroxy-5-methyl-benzaldehyde in Step 2. MS obsd. (ESI$^+$) [(M+H)]$^+$: 317.2.

Intermediate 16: 2-[5-bromo-2-hydroxy-4-(trifluoromethoxy)phenyl]-8-chloro-chromen-4-one

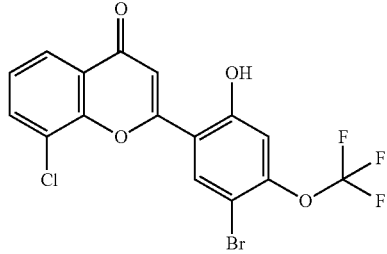

Int-16

Step 1: Preparation of 5-bromo-2-hydroxy-4-(trifluoromethoxy)benzaldehyde

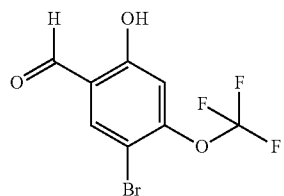

Int-16a

Int-16a was prepared in analogy to the procedure described for the preparation of compound Int-5a by using 4-bromo-3-(trifluoromethoxy)phenol (CAS #: 886499-93-0, Cat. #: BD217660, from Bide Pharmtach) as the starting material instead of 3-chloro-4-methy 1-phenol in Step 1.

Step 2: Preparation of 5-bromo-2-(methoxymethoxy)-4-(trifluoromethoxy)benzaldehyde

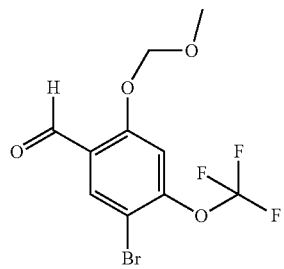

Int-16b

Int-16b was prepared in analogy to the procedure described for the preparation of compound Int-5b by using 5-bromo-2-hydroxy-4-(trifluoromethoxy)benzaldehyde as the starting material instead of 4-chloro-2-hydroxy-5-methyl-benzaldehyde in Step 2.

Step 3: Preparation of 2-[5-bromo-2-hydroxy-4-(trifluoromethoxy)phenyl]-8-chloro-chromen-4-one

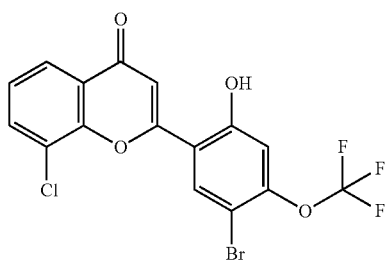

Int-16

Int-16 was prepared in analogy to the procedure described for the preparation of compound Int-5 by using 5-bromo-2-(methoxymethoxy)-4-(trifluoromethoxy)benzaldehyde as the starting material instead of 4-chloro-2-(methoxymethoxy)-5-methyl-benzaldehyde in Step 3. MS obsd. (ESI$^+$) [(M+H)]$^+$: 435.1.

Intermediate 17: 8-chloro-2-[2-hydroxy-5-methyl-4-(trifluoromethoxy)phenyl]chromen-4-one

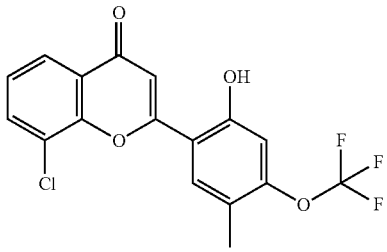

Int-17

Step 1: Preparation of 2-(methoxymethoxy)-5-methyl-4-(trifluoromethoxy)benzaldehyde

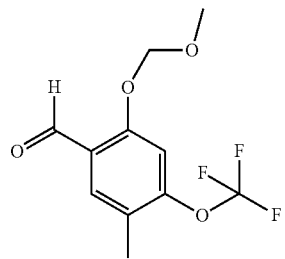

Int-17a

To a solution of 5-bromo-2-(methoxymethoxy)-4-(trifluoromethoxy)benzaldehyde (Int-16b, 500 mg, 1.52 mmol), trimethylboroxine (381 mg, 3.02 mmol), K$_2$CO$_3$ (630 mg, 4.56 mmol) in dioxane (10 mL) under N$_2$ was added Pd(dppf)$_2$C$_{1-2}$ (111.1 mg, 0.1 mmol) and the mixture was then stirred at 110° C. under N$_2$ for 1 hour. After the reaction was completed, the mixture was cooled to room temperature and concentrated in vacuo. The residue was purified by column chromatography on silica gel (eluent with PE/EtOAc=100:1 to 2:1) to give 2-(methoxymethoxy)-5-methyl-4-(trifluoromethoxy)benzaldehyde (310 mg, 77.2% yield) as an off-white solid.

Step 2: Preparation of 8-chloro-2-[2-hydroxy-5-methyl-4-(trifluoromethoxy)phenyl]chromen-4-one

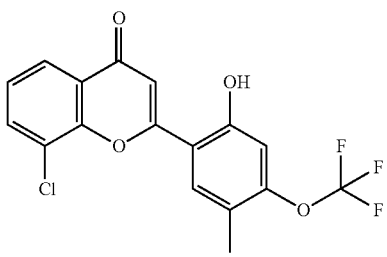

Int-17

Int-17 was prepared in analogy to the procedure described for the preparation of compound Int-5 by using 2-(methoxymethoxy)-5-methyl-4-(trifluoromethoxy)benzaldehyde as the starting material instead of 4-chloro-2-(methoxymethoxy)-5-methyl-benzaldehyde in Step 3. MS obsd. (ESI$^+$) [(M+H)]$^+$: 371.2.

Intermediate 18: 2-(3-bromo-2-hydroxy-5-methyl-phenyl)-8-chloro-chromen-4-one

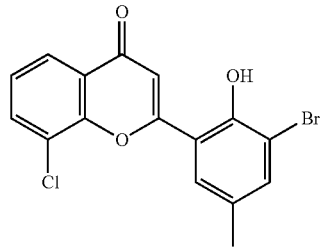

Int-18

Step 1: Preparation of 3-bromo-2-hydroxy-5-methyl-benzaldehyde

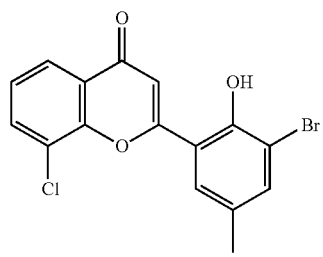

Int-18a

Int-18a was prepared in analogy to the procedure described for the preparation of compound Int-5a by using 2-bromo-4-methyl-phenol as the starting material instead of 3-chloro-4-methyl-phenol in Step 1.

Step 2: Preparation of 2-(3-bromo-2-hydroxy-5-methyl-phenyl)-8-chloro-chromen-4-one Int-18

Int-18 was prepared in analogy to the procedure described for the preparation of compound Int-5 by using 3-bromo-2-hydroxy-5-methyl-benzaldehyde as the starting material instead of 4-chloro-2-hydroxy-5-methyl-benzaldehyde in Step 2. MS obsd. (ESI$^+$) [(M+H)]$^+$: 365.1.

Intermediate 19: 8-chloro-2-[2-hydroxy-4-methyl-5-(trifluoromethoxy)phenyl]chromen-4-one

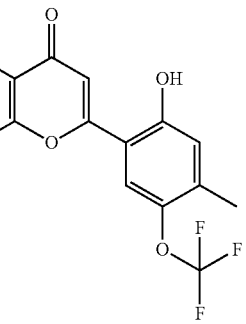

Int-19

Step 1: Preparation of 4-bromo-2-hydroxy-5-(trifluoromethoxy)benzaldehyde

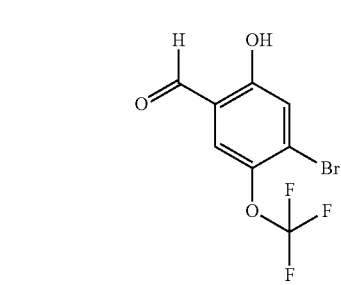

Int-19a

To a solution of 4-bromo-2-methoxy-5-(trifluoromethoxy)benzaldehyde (Int-14b, 2 g, 4.7 mmol) in DCM (30 mL) cooled at −78° C. under N$_2$ atmosphere was added BBr$_3$ (3.35 g, 13.6 mmol). After completion of addition, the solution was stirred at −78° C. for additional 30 minutes. After the reaction was completed, the solution was poured into ice-water (50 mL) and the resulting suspension was extracted with EtOAc (100 mL) three times. The combined organic layer was concentrated in vacuo and the residue was purified by column chromatography on silica gel (eluent with PE:DCM=1:1) to give the 4-bromo-2-hydroxy-5-(trifluoromethoxy)benzaldehyde (1.7 g, 75.8%) as a brown solid. MS obsd. (ESI$^+$) [(M+H)$^+$]: 285.0.

Step 2: Preparation of 4-bromo-2-(methoxymethoxy)-5-(trifluoromethoxy)benzaldehyde

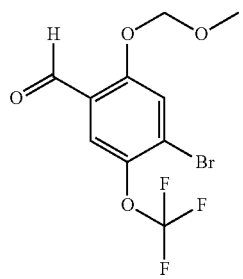
Int-19b

Int-19b was prepared in analogy to the procedure described for the preparation of compound Int-5b by using 4-bromo-2-hydroxy-5-(trifluoromethoxy)benzaldehyde as the starting material instead of 4-chloro-2-hydroxy-5-methyl-benzaldehyde in Step 2.

Step 3: Preparation of 2-(methoxymethoxy)-4-methyl-5-(trifluoromethoxy)benzaldehyde

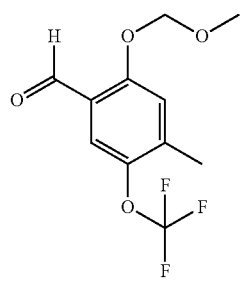
Int-19c

Int-19c was prepared in analogy to the procedure described for the preparation of compound Int-17a by using 4-bromo-2-(methoxymethoxy)-5-(trifluoromethoxy)benzaldehyde as the starting material instead of 5-bromo-2-(methoxymethoxy)-4-(trifluoromethoxy)benzaldehyde in Step 1.

Step 4: Preparation of 8-chloro-2-[2-hydroxy-4-methyl-5-(trifluoromethoxy)phenyl]chromen-4-one

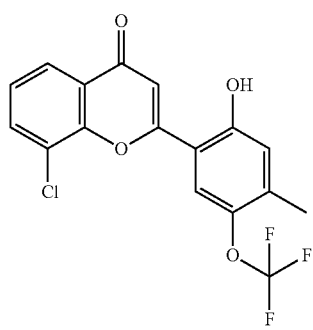
Int-19

Int-19 was prepared in analogy to the procedure described for the preparation of compound Int-5 by using 2-(methoxymethoxy)-4-methyl-5-(trifluoromethoxy)benzaldehyde as the starting material instead of 4-chloro-2-(methoxymethoxy)-5-methyl-benzaldehyde in Step 3. MS obsd. (ESI+) [(M+H)]+: 371.1.

Intermediate 20: 2-(4-bromo-2-fluoro-6-hydroxy-phenyl)-8-chloro-chromen-4-one

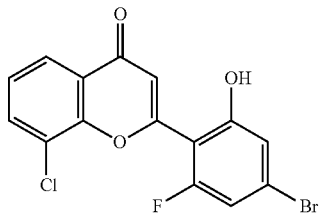
Int-20

Step 1: Preparation of 2-(4-bromo-2-fluoro-6-methoxy-phenyl)-8-chloro-chromen-4-one

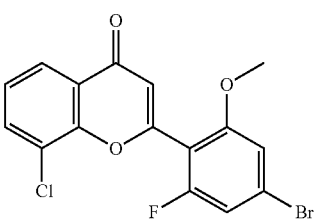
Int-20a

Int-20a was prepared in analogy to the procedure described for the preparation of compound Int-1b by using 4-bromo-2-fluoro-6-methoxybenzaldehyde (CAS #: 856767-09-4, Cat. #: BD259901, from Bide Pharmatech) as the starting material instead of 2-methoxy-4-(trifluoromethyl)benzaldehyde in Step 1.

Step 2: Preparation of 2-(4-bromo-2-fluoro-6-hydroxy-phenyl)-8-chloro-chromen-4-one

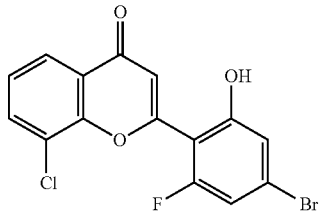
Int-20

Int-20 was prepared in analogy to the procedure described for the preparation of compound Int-1 by using 2-(4-bromo-2-fluoro-6-methoxy-phenyl)-8-chloro-chromen-4-one as the starting material instead of 8-chloro-2-[2-methoxy-4-(trifluoromethyl)phenyl]chromen-4-one in Step 3. MS obsd. (ESI+) [(M+H)]+: 369.2.

Intermediate 21: 8-chloro-2-(2-fluoro-6-hydroxy-4-methyl-phenyl)chromen-4-one

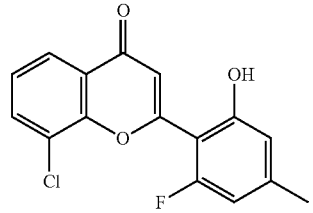

Int-21

Step 1: Preparation of 8-chloro-2-(2-fluoro-6-methoxy-4-methyl-phenyl)chromen-4-one

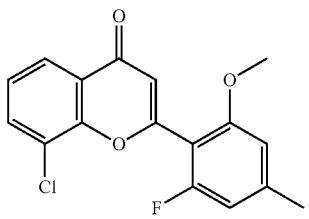

Int-21a

To a solution of 2-(4-bromo-2-fluoro-6-methoxy-phenyl)-8-chloro-chromen-4-one (Int-22a, 300.0 mg, 0.8 mmol), trimethylboroxine (196.4 mg, 1.56 mmol), $K_2CO_3$ (324.3 mg, 2.35 mmol) in dioxane (10 mL) under $N_2$ was added $Pd(dppf)_2Cl_{1-2}$ (57.8 mg, 0.08 mmol) and the mixture was then stirred at 110° C. under $N_2$ for 1 hour. After the reaction was completed, the mixture was cooled to room temperature and concentrated in vacuo, the residue was purified by column chromatography on silica gel (eluent with PE/EtOAc=100:1 to 2:1) to give 8-chloro-2-(2-fluoro-6-methoxy-4-methyl-phenyl)chromen-4-one (150 mg, 57.2% yield) as an off-white solid.

Step 2: Preparation of 8-chloro-2-(2-fluoro-6-hydroxy-4-methyl-phenyl)chromen-4-one

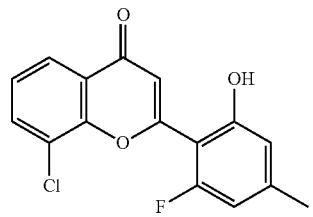

Int-21

Int-21 was prepared in analogy to the procedure described for the preparation of compound Int-1 by using 8-chloro-2-(2-fluoro-6-methoxy-4-methyl-phenyl)chromen-4-one as the starting material instead of 8-chloro-2-[2-methoxy-4-(trifluoromethyl)phenyl]chromen-4-one in Step 3. MS obsd. (ESI$^+$) [(M+H)]$^+$: 305.0.

Intermediate 22: 8-bromo-2-[2-hydroxy-4-(trifluoromethoxy)phenyl]chromen-4-one

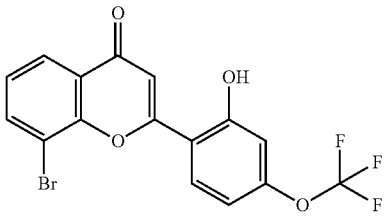

Int-22

Int-22 was prepared in analogy to the procedure described for the preparation of compound Int-1 by using 1-(3-bromo-2-hydroxy-phenyl)ethanone (CAS #: 1836-05-1, Cat. #: BD50461, from Bide Pharmatech) and 2-methoxy-4-(trifluoromethoxy)benzaldehyde as the starting materials instead of 1-(3-chloro-2-hydroxy-phenyl)ethanone and 2-methoxy-4-(trifluoromethyl)benzaldehyde in Step 1. MS obsd. (ESI$^+$) [(M+H)]$^+$: 401.2.

Intermediate 23: 7-bromo-8-chloro-2-[2-hydroxy-4-(trifluoromethoxy)phenyl]chromen-4-one

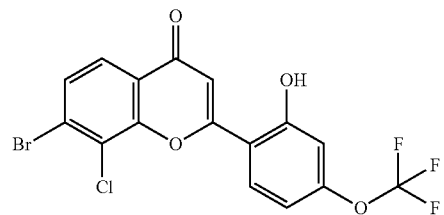

Int-23

Step 1: Preparation of (3-bromo-2-chloro-phenyl) acetate

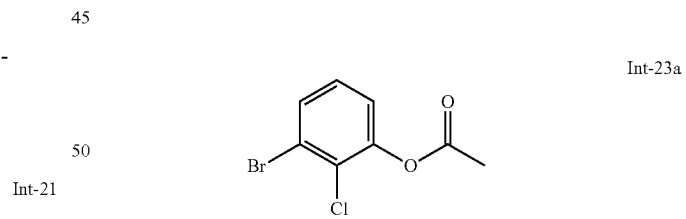

Int-23a

To a mixture of 3-bromo-2-chloro-phenol (10.0 g, 68.24 mmol) and TEA (7.6 g, 75.06 mmol) in dichloromethane (150 mL) was added acetyl chloride (5.36 g, 68.24 mmol) at 0° C. and the mixture was then stirred at room temperature for 16 hours. After the reaction was completed, the mixture was poured into water (30 mL) and extracted with dichloromethane (50 mL) three times. The combined organic layer was washed with brine, dried over anhydrous $Na_2SO_4$ and concentrated in vacuo. The residue was then purified by column chromatography on silica gel (elution with PE:EtOAc=50:1-20:1) to give (3-bromo-2-chloro-phenyl) acetate (10.0 g, 75%) as colorless oil. MS obsd. (ESI$^+$) [(M+H)]$^+$: 247.9.

Step 2: Preparation of 1-(4-bromo-3-chloro-2-hydroxy-phenyl)ethanone

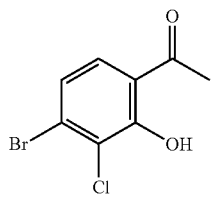
Int-23b

A mixture of (3-bromo-2-chloro-phenyl) acetate (10.0 g, 53.03 mmol) and AlCl₃ (7.07 g, 53.03 mmol) was stirred at 150° C. for 5 hours. After the reaction was completed, the mixture was poured into water (100 mL) and extracted with EtOAc (250 mL) twice. The combined organic layer was washed with brine, dried over anhydrous Na₂SO₄ and concentrated in vacuo. The residue was then purified by column chromatography on silica gel (elution with PE:EtOAc=50:1-20:1) to give 1-(4-bromo-3-chloro-2-hydroxy-phenyl)ethanone (3.0 g, 30.0%) as a white solid. MS obsd. (ESI⁺) [(M+H)⁺]: 247.9.

Step 3: Preparation of 7-bromo-8-chloro-2-[2-hydroxy-4-(trifluoromethoxy)phenyl]chromen-4-one

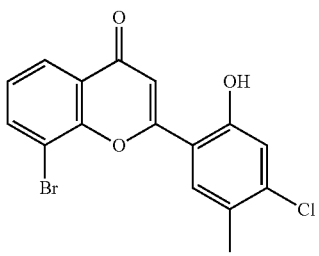
Int-23

Int-23 was prepared in analogy to the procedure described for the preparation of compound Int-1 by using 1-(4-bromo-3-chloro-2-hydroxy-phenyl)ethanone and 2-methoxy-4-(trifluoromethoxy)benzaldehyde as the starting materials instead of 1-(3-chloro-2-hydroxy-phenyl)ethanone and 2-methoxy-4-(trifluoromethyl)benzaldehyde in Step 1. MS obsd. (ESI⁺) [(M+H)⁺]: 435.1.

Intermediate 24: 8-bromo-2-(2-hydroxy-4-methyl-phenyl)chromen-4-one

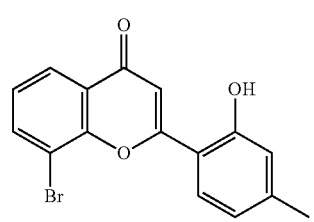
Int-24

Int-24 was prepared in analogy to the procedure described for the preparation of compound Int-1 by using 1-(3-bromo-2-hydroxy-phenyl)ethanone and 2-methoxy-4-methyl-benzaldehyde as the starting materials instead of 1-(3-chloro-2-hydroxy-phenyl)ethanone and 2-methoxy-4-(trifluoromethyl)benzaldehyde in Step 1. MS obsd. (ESI⁺) [(M+H)⁺]: 331.1.

Intermediate 25: 8-bromo-2-(4-chloro-2-hydroxy-5-methyl-phenyl)chromen-4-one

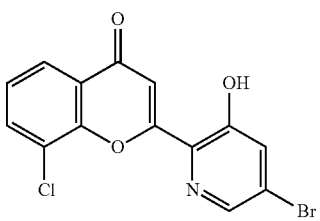
Int-25

Int-25 was prepared in analogy to the procedure described for the preparation of compound Int-5 by using 1-(3-bromo-2-hydroxy-phenyl)ethanone as the starting material instead of 1-(3-chloro-2-hydroxy-phenyl)ethanone in Step 3. MS obsd. (ESI⁺) [(M+H)⁺]: 365.0.

Intermediate 26: 2-(5-bromo-3-hydroxy-2-pyridyl)-8-chloro-chromen-4-one

Int-26

Step 1: Preparation of 5-bromo-3-methoxy-pyridine-2-carboxylic acid

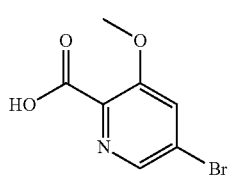
Int-26a

To a solution of 5-bromo-3-methoxy-pyridine-2-carbonitrile (CAS #: 36057-46-2, Cat. #: SY162901, from Accela ChemBio Inc, 3.2 g, 15.02 mmol) in THF (80 mL) was added 5N NaOH solution (15 mL, 75 mmol) and the mixture was stirred at 110° C. for 6 hours. The mixture was then cooled to room temperature and adjusted to pH~3 by addition of 6N HCl. The resulting mixture was diluted with EtOAc (150 mL), washed with water (30 mL) twice, brine (30 mL), dried over MgSO₄ and concentrated in vacuo to give 5-bromo-3-methoxy-pyridine-2-carboxylic acid (2.5 g, 71.73% yield) as a white solid. $^1$H NMR (400 MHz, CDCl$_3$) δ ppm: 13.27 (br s, 1H), 8.29 (d, J=1.7 Hz, 1H), 7.92 (d, J=1.7 Hz, 1H), 3.88 (s, 3H). MS obsd. (ESI$^+$)[(M+H)$^+$]: 232.0.

Step 2: Preparation of 5-bromo-3-methoxy-pyridine-2-carbonyl chloride

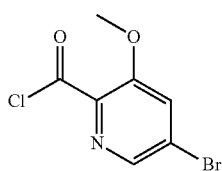

Int-26b

To a solution of 5-bromo-3-methoxy-pyridine-2-carboxylic acid (1.5 g, 6.46 mmol) in DCM (60 mL) was added oxalyl chloride (4.1 g, 32.32 mmol, 5 eq) at 0° C. and the mixture was stirred at room temperature for 2 hours. The resulting mixture was concentrated in vacuo to give 5-bromo-3-methoxy-pyridine-2-carbonyl chloride (1.61 g, 99.43% yield) as dark brown oil, which was used in the next step directly without further purification.

Step 3: Preparation of (2-acetyl-6-chloro-phenyl) 5-bromo-3-methoxy-pyridine-2-carboxylate

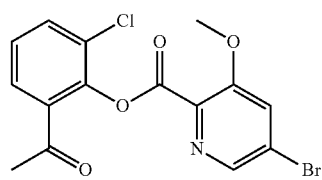

Int-26c

To a solution of 1-(3-chloro-2-hydroxy-phenyl)ethanone (1.1 g, 6.47 mmol) and TEA (4.51 mL, 32.34 mmol) in DCM (40 mL) was added 5-bromo-3-methoxy-pyridine-2-carbonyl chloride solution (1.62 g, 6.47 mmol, dissolved in DCM (15 mL)) at 0° C. The mixture was stirred at room temperature for 2 hours. The mixture was then concentrated in vacuo and the residue was redissolved in EtOAc (150 mL). The resulting solution was washed with water (30 mL) twice, brine (50 mL), dried over Na$_2$SO$_4$ and concentrated in vacuo. The residue was then purified by column chromatography (eluted with PE/EtOAc=100:1 to 2:1) to give (2-acetyl-6-chloro-phenyl) 5-bromo-3-methoxy-pyridine-2-carboxylate (1.0 g, 40.2% yield) as a red solid. MS obsd. (ESI$^+$) [(M+H)$^+$]: 383.9.

Step 4: Preparation of 2-(5-bromo-3-methoxy-2-pyridyl)-8-chloro-chromen-4-one

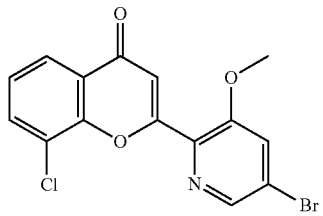

Int-26d

To a solution of (2-acetyl-6-chloro-phenyl) 5-bromo-3-methoxy-pyridine-2-carboxylate (1.0 g, 2.6 mmol) in pyridine (15 mL) was added KOH (218.8 mg, 3.9 mmol) and the mixture was stirred at 50° C. for 30 minutes. The mixture was poured into 4N HCl (50 mL) and the mixture was adjusted to pH~9 by addition of saturated Na$_2$CO$_3$ solution. The mixture was extracted with CHCl$_3$ (50 mL) four times. The combined organic layer was washed with H$_2$O (100 mL), brine, dried over MgSO$_4$, filtered and the filtrate was concentrated in vacuo. The residue was dissolved in AcOH (20 mL) and to the resulting solution was added H$_2$SO$_4$ (0.26 g, 2.6 mmol). The mixture was stirred at 100° C. for 2 hours and the mixture was concentrated in vacuo. The residue was diluted with water (30 mL) and adjusted to pH~9 by addition of saturated Na$_2$CO$_3$. The resulting mixture was extracted with CHCl$_3$ (50 mL) four times. The combined organic layer was washed with H$_2$O (100 mL), brine, dried over MgSO$_4$, filtered and the filtrate was concentrated in vacuo. The residue was purified by column chromatography on silica gel (eluent with PE/EtOAc=3:1) to give 2-(5-bromo-3-methoxy-2-pyridyl)-8-chloro-chromen-4-one (420 mg, 44.06% yield) as a red solid. MS obsd. (ESI$^+$)[(M+H)$^+$]: 366.0.

Step 5: Preparation of 2-(5-bromo-3-hydroxy-2-pyridyl)-8-chloro-chromen-4-one

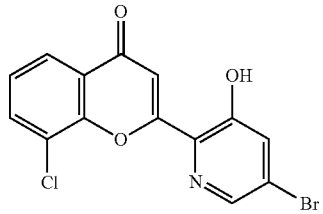

Int-26

To a solution of 2-(5-bromo-3-methoxy-2-pyridyl)-8-chloro-chromen-4-one (200.0 mg, 0.550 mmol) in chloroform (20 mL) was added BBr$_3$ (25.0 mL) at 0° C. and the mixture was stirred at 50° C. for 48 hours. Then to the resulting solution was added MeOH (10 mL) and the mixture was concentrated in vacuo. The residue was triturated with solvent (eluted with PE:EtOAc=20:1, 15 mL) and the mixture was then filtered to give 2-(5-bromo-3-hydroxy-2-pyridyl)-8-chloro-chromen-4-one (150 mg, 77.98% yield) as a brown solid. MS obsd. (ESI$^+$) [(M+H)$^+$]: 351.9.

Intermediate 27: 2-[4-bromo-2-hydroxy-5-(trifluoromethyl)phenyl]-8-chloro-chromen-4-one

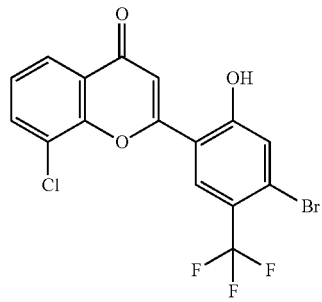

Int-27

Step 1: Preparation of methyl 4-amino-5-iodo-2-methoxy-benzoate

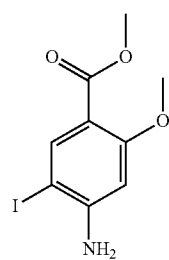

Int-27a

To a solution of methyl 4-amino-2-methoxybenzoate (CAS #: 27492-84-8, Cat. #: SY007291, from Accela ChemBio Inc, 20.0 g, 110.38 mmol) in 1,4-dioxane (80 mL) and pyridine (80 mL) was added iodine (56.0 g, 220.76 mmol) at room temperature. The resulting mixture was heated at 50° C. for 3 hours. After the reaction was completed, the mixture was cooled to room temperature and quenched by 2M Na$_2$SO$_3$ solution (200 mL). The resulting solution was extracted with EtOAc (50 mL) three times. The combined organic layer was washed with water, brine, dried over Na$_2$SO$_4$ and then concentrated in vacuo. The residue was purified by column chromatography on silica gel (eluted with PE:EtOAc=2/1) to give methyl 4-amino-5-iodo-2-methoxy-benzoate (21.0 g, 68.38 mmol, 57.62% yield, purity 93.78%) as a light yellow solid. MS obsd. (ESI$^+$) [(M+H)$^+$]: 308.0.

Step 2: Preparation of methyl 4-bromo-5-iodo-2-methoxy-benzoate

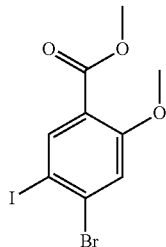

Int-27b

To a mixture of methyl 4-amino-5-iodo-2-methoxy-benzoate (2 g, 6.51 mmol) and copper (I) bromide (1.3 g, 9.12 mmol) in ACN (15 mL) cooled in an ice-water bath were added isoamyl nitrite (839.27 mg, 7.16 mmol). Then the mixture was stirred at 70° C. for 1 hour. After the reaction was completed, the reaction mixture was poured into water (40 mL) and the resulting suspension was extracted with EtOAc (30 mL) three times. The combined organic phase was washed with brine (20 mL), dried over Na$_2$SO$_4$ and concentrated in vacuo. The residue was purified by column chromatography on silica gel (eluted with PE/EtOAc=10/1) to give methyl 4-bromo-5-iodo-2-methoxy-benzoate (1.5 g, 4.04 mmol, 57.74% yield, purity 83.31%) as a light yellow solid.

Step 3: Preparation of methyl 4-bromo-2-methoxy-5-(trifluoromethyl)benzoate

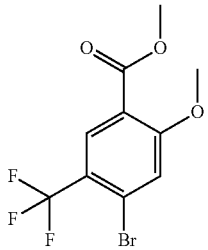

Int-27c

To a solution of methyl 4-bromo-5-iodo-2-methoxy-benzoate (1.82 g, 4.91 mmol) in DMF (20 mL) were added methyl 2,2-difluoro-2-(fluorosulfonyl)acetate (1.88 g, 9.81 mmol) and iodocopper (1.86 g, 9.81 mmol) under N$_2$ atmosphere. The mixture was then stirred at 85° C. for 6 hours. The reaction mixture was then filtered and the filtrate was diluted with water (100 mL). The resulting suspension was extracted with EtOAc (80 mL) three times. The combined organic layer was washed by brine, dried over Na$_2$SO$_4$ and concentrated in vacuo. The residue was purified by column chromatography on silica gel (eluted with PE:EtOAc=4:1) to give methyl 4-bromo-2-methoxy-5-(trifluoromethyl)benzoate (1.20 mg, 3.83 mmol, 68.75% yield) as a light yellow solid. MS obsd. (ESI$^+$)[(M+H)$^+$]: 313.0.

Step 4: Preparation of [4-bromo-2-methoxy-5-(trifluoromethyl)phenyl]methanol

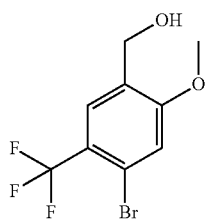

To a solution of methyl 4-bromo-2-methoxy-5-(trifluoromethyl)benzoate (1500.0 mg, 4.79 mmol) in THF (20 mL) was added DIBAL (2 mol/L in THF, 12 mL, 24 mmol) dropwise at −78° C. and the reaction was stirred at −78° C. for extra 2 hours after addition. After the reaction was completed, the reaction was quenched with NH$_4$Cl solution (4 mL) and the resulting solution was stirred at room temperature for 10 minutes. The mixture was then diluted with water (40 mL) and extracted with EtOAc (50 mL) three times. The combined organic layer was washed with brine, dried over Na$_2$SO$_4$ and concentrated in vacuo to give [4-bromo-2-methoxy-5-(trifluoromethyl)phenyl]methanol (1100 mg, 72.49% yield) as a light yellow solid.

Step 5: Preparation of 4-bromo-2-methoxy-5-(trifluoromethyl)benzaldehyde

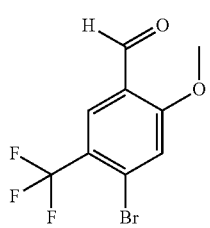

To a solution of [4-bromo-2-methoxy-5-(trifluoromethyl)phenyl]methanol (120.0 mg, 0.420 mmol) in DCM (5 mL) cooled in an ice-water bath was added Dess-Martin periodinane (214.26 mg, 0.510 mmol) and the resulting mixture was stirred at room temperature for another 0.5 hour. After the reaction was completed, the reaction mixture was quenched with water (20 mL) and then extracted with DCM (20 mL) three times, the combined organic layer was washed with brine, dried over anhydrous Na$_2$SO$_4$ and concentrated in vacuo to give 4-bromo-2-methoxy-5-(trifluoromethyl)benzaldehyde (86 mg, 64.24% yield) as a light yellow solid. MS obsd. (ESI$^+$)[(M+H)$^+$]: 283.0.

Step 6: Preparation of 2-[4-bromo-2-hydroxy-5-(trifluoromethyl)phenyl]-8-chloro-chromen-4-one

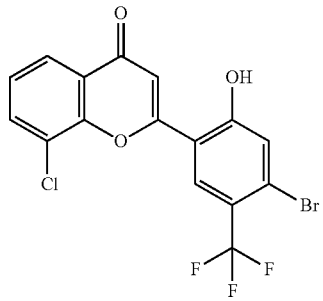

Int-27 was prepared in analogy to the procedure described for the preparation of compound Int-1 by using 4-bromo-2-hydroxy-benzaldehyde as the starting material instead of 2-methoxy-4-(trifluoromethyl)benzaldehyde in Step 1. MS obsd. (ESI$^+$)[(M+H)$^+$]: 419.2.

Intermediate 28: 8-bromo-2-(2-hydroxyphenyl)chromen-4-one

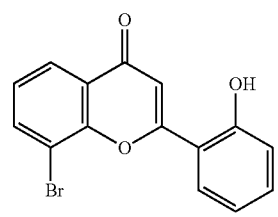

Int-28 was prepared in analogy to the procedure described for the preparation of compound Int-1 by using 1-(3-bromo-2-hydroxy-phenyl)ethanone and 2-methoxybenzaldehyde as the starting materials instead of 1-(3-chloro-2-hydroxy-phenyl)ethanone and 2-methoxy-4-(trifluoromethyl)benzaldehyde in Step 1. MS obsd. (ESI$^+$)[(M+H)$^+$]: 317.1.

Intermediate 29: 8-chloro-2-(4-ethyl-2-hydroxyphenyl)chromen-4-one

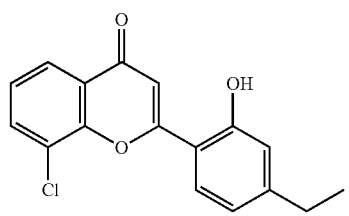

Int-29 was prepared in analogy to the procedure described for the preparation of compound Int-1 by using 4-ethyl-2-methoxy-benzaldehyde as the starting materials instead of 2-methoxy-4-(trifluoromethyl)benzaldehyde in Step 1. MS obsd. (ESI$^+$)[(M+H)$^+$]: 301.2.

Intermediate 30: 8-chloro-2-(2-hydroxy-4-isopropyl-phenyl)chromen-4-one

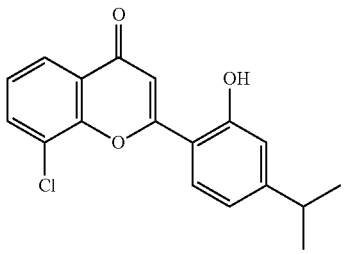

Int-30

Int-30 was prepared in analogy to the procedure described for the preparation of compound Int-1 by using 4-isopropyl-2-methoxy-benzaldehyde as the starting materials instead of 2-methoxy-4-(trifluoromethyl)benzaldehyde in Step 1. MS obsd. (ESI$^+$)[(M+H)$^+$]: 315.1.

Intermediate 31: 8-chloro-2-(2-hydroxy-5-methyl-phenyl)chromen-4-one

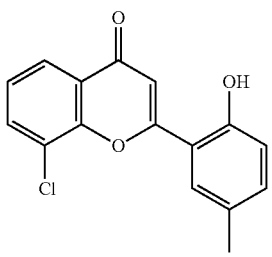

Int-31

Int-31 was prepared in analogy to the procedure described for the preparation of compound Int-1 by using 2-methoxy-5-methyl-benzaldehyde as the starting materials instead of 2-methoxy-4-(trifluoromethyl)benzaldehyde in Step 1. MS obsd. (ESI$^+$)[(M+H)$^+$]: 287.1.

Intermediate 32: 8-chloro-2-(2-hydroxy-5-methoxy-phenyl)chromen-4-one

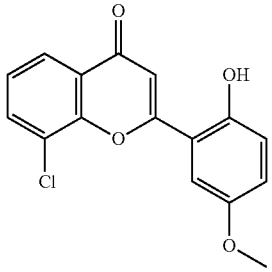

Int-32

Int-32 was prepared in analogy to the procedure described for the preparation of compound Int-5 by using 2-hydroxy-5-methoxy-benzaldehyde as the starting material instead of 4-chloro-2-hydroxy-5-methyl-benzaldehyde in Step 2. MS obsd. (ESI$^+$)[(M+H)$^+$]: 303.0.

Intermediate 33: 8-chloro-2-(5-hydroxy-2,3-dihydrobenzofuran-6-yl)chromen-4-one

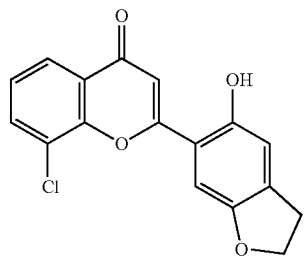

Int-33

Step 1: Preparation of 5-hydroxy-2,3-dihydrobenzofuran-6-carbaldehyde

Int-33a

Int-33a was prepared in analogy to the procedure described for the preparation of compound Int-5a by using 2,3-dihydrobenzofuran-5-ol as the starting material instead of 3-chloro-4-methyl-phenol in Step 1.

Step 2: Preparation of 8-chloro-2-(5-hydroxy-2,3-dihydrobenzofuran-6-yl)chromen-4-one

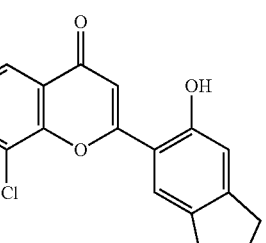

Int-33

Int-33 was prepared in analogy to the procedure described for the preparation of compound Int-5 by using 5-hydroxy-2,3-dihydrobenzofuran-6-carbaldehyde as the starting material instead of 4-chloro-2-hydroxy-5-methyl-benzaldehyde in Step 2. MS obsd. (ESI$^+$)[(M+H)$^+$]: 314.9.

Intermediate 34: 2-(5-bromo-2-hydroxy-4-methoxy-phenyl)-8-chloro-chromen-4-one

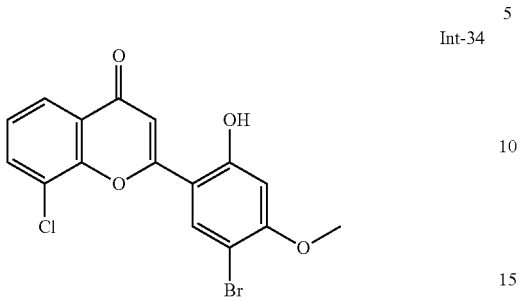

Int-34

Int-34 was prepared in analogy to the procedure described for the preparation of compound Int-5 by using 5-bromo-2-hydroxy-4-methoxybenzaldehyde as the starting material instead of 4-chloro-2-hydroxy-5-methyl-benzaldehyde in Step 2. MS obsd. (ESI$^+$)[(M+H)$^+$]: 381.1.

Intermediate 35: 8-chloro-2-(4-chloro-2-hydroxy-phenyl)chromen-4-one

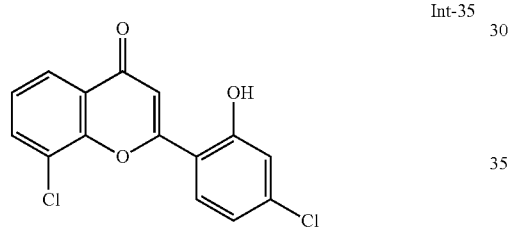

Int-35

Int-35 was prepared in analogy to the procedure described for the preparation of compound Int-5 by using 4-chloro-2-hydroxy-benzaldehyde as the starting material instead of 4-chloro-2-hydroxy-5-methyl-benzaldehyde in Step 2. MS obsd. (ESI$^+$)[(M+H)$^+$]: 307.1.

Intermediate 36: 2-(5-bromo-2-hydroxy-phenyl)-8-chloro-chromen-4-one

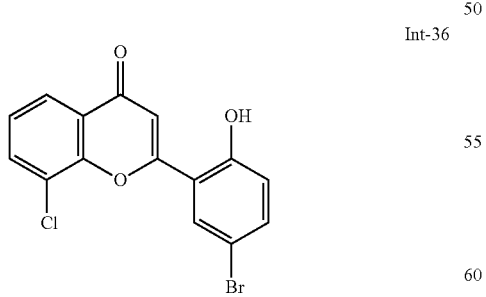

Int-36

Int-36 was prepared in analogy to the procedure described for the preparation of compound Int-5 by using 5-bromo-2-hydroxy-benzaldehyde as the starting material instead of 4-chloro-2-hydroxy-5-methyl-benzaldehyde in Step 2. MS obsd. (ESI$^+$)[(M+H)$^+$]: 351.0.

Intermediate 37: 2-(4-bromo-2-hydroxy-phenyl)-8-chloro-6-fluoro-chromen-4-one

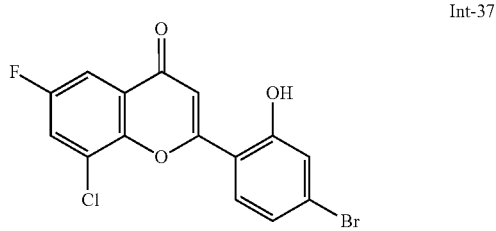 [SMILES: O=c1cc(-c2ccc(Br)cc2O)oc2c(Cl)cc(F)cc12]

Int-37

Step 1: Preparation of 1-(3-chloro-5-fluoro-2-hydroxy-phenyl)ethanone

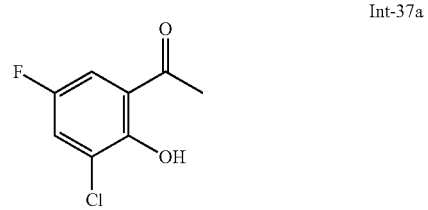

Int-37a

Compound Int-37a was prepared in analogy to the procedure described for the preparation of compound Int-23b by using 2-chloro-4-fluoro-phenol as the starting materials instead of 3-bromo-2-chloro-phenol in Step 1.

Step 2: Preparation of 2-(4-bromo-2-hydroxy-phenyl)-8-chloro-6-fluoro-chromen-4-one

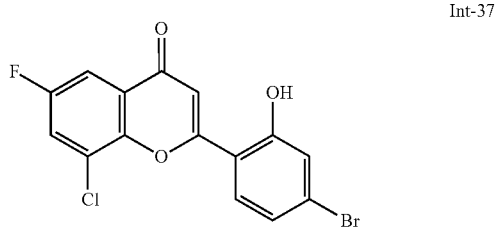 [SMILES: O=c1cc(-c2ccc(Br)cc2O)oc2c(Cl)cc(F)cc12]

Int-37

Int-37 was prepared in analogy to the procedure described for the preparation of compound Int-1 by using 1-(3-chloro-5-fluoro-2-hydroxy-phenyl)ethanone and 4-bromo-2-methoxy-benzaldehyde as the starting materials instead of 1-(3-chloro-2-hydroxy-phenyl)ethanone and 2-methoxy-4-(trifluoromethyl)benzaldehyde in Step 1. MS obsd. (ESI$^+$)[(M+H)$^+$]: 369.1.

Intermediate 38: 8-chloro-2-(2-hydroxyphenyl)-7-methyl-chromen-4-one

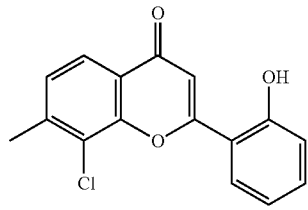
Int-38

Step 1: Preparation of 1-(3-chloro-2-hydroxy-4-methyl-phenyl)ethanone

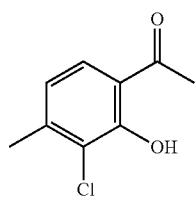
Int-38a

To a solution of 1-(4-bromo-3-chloro-2-hydroxy-phenyl)ethanone (2.4 g, 9.62 mmol), trimethylboroxine (1449.06 mg, 11.54 mmol), potassium carbonate (3323.72 mg, 24.05 mmol) in 1,4-dioxane (30 mL) and water (2 mL) was added Pd(dppf)$_2$C$_{1-2}$ (791.39 mg, 0.960 mmol) under N$_2$ atmosphere. The mixture was stirred at 110° C. for 5 hours. The mixture was filtered and the filtrate was concentrated in vacuo. The residue was purified by column chromatography on silica gel (eluent with PE:EtOAc=20:1 to 3:1) to give 1-(3-chloro-2-hydroxy-4-methyl-phenyl)ethanone (1.3 g, 69.5% yield) as an off-white solid. MS obsd. (ESI$^+$) [(M+H)$^+$]: 185.1.

Step 2: Preparation of 8-chloro-2-(2-hydroxyphenyl)-7-methyl-chromen-4-one

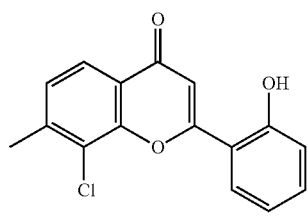
Int-38

Int-38 was prepared in analogy to the procedure described for the preparation of compound Int-1 by using 1-(3-chloro-2-hydroxy-4-methyl-phenyl)ethanone and 2-methoxybenzaldehyde as the starting materials instead of 1-(3-chloro-2-hydroxy-phenyl)ethanone and 2-methoxy-4-(trifluoromethyl)benzaldehyde in Step 1. MS obsd. (ESI$^+$) [(M+H)$^+$]: 287.2.

Intermediate 39: 2-(4-bromo-2-hydroxy-phenyl)-8-chloro-7-fluoro-chromen-4-one

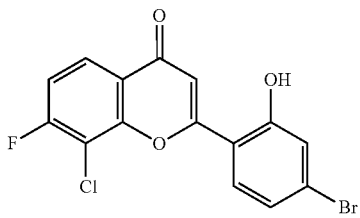
Int-39

Step 1: Preparation of 1-(3-chloro-4-fluoro-2-hydroxy-phenyl)ethanone

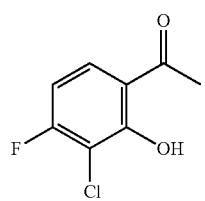
Int-39a

Compound Int-39a was prepared in analogy to the procedure described for the preparation of compound Int-23b by using 2-chloro-3-fluoro-phenol as the starting materials instead of 3-bromo-2-chloro-phenol in Step 1.

Step 2: Preparation of 2-(4-bromo-2-hydroxy-phenyl)-8-chloro-7-fluoro-chromen-4-one

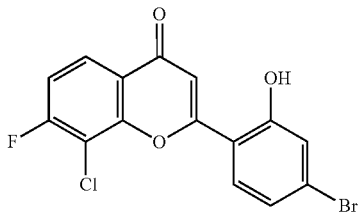
Int-39

Int-39 was prepared in analogy to the procedure described for the preparation of compound Int-1 by using 1-(3-chloro-4-fluoro-2-hydroxy-phenyl)ethanone and 4-bromo-2-methoxy-benzaldehyde as the starting materials instead of 1-(3-chloro-2-hydroxy-phenyl)ethanone and 2-methoxy-4-(trifluoromethyl)benzaldehyde in Step 1. MS obsd. (ESI$^+$) [(M+H)$^+$]: 369.2.

Intermediate 40: 2-(5-bromo-4-fluoro-2-hydroxy-phenyl)-8-chloro-chromen-4-one

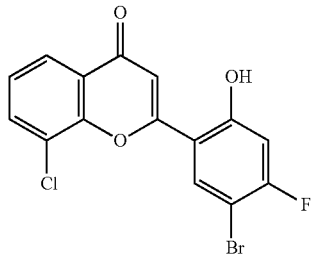

Int-40

Int-40 was prepared in analogy to the procedure described for the preparation of compound Int-5 by using 5-bromo-4-fluoro-2-hydroxybenzaldehyde as the starting material instead of 4-chloro-2-hydroxy-5-methyl-benzaldehyde in Step 2. MS obsd. (ESI$^+$)[(M+H)$^+$]: 369.2.

Intermediate 41: 8-chloro-2-(5-fluoro-2-hydroxy-phenyl)chromen-4-one

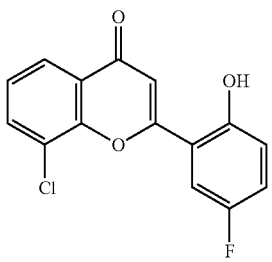

Int-41

Int-41 was prepared in analogy to the procedure described for the preparation of compound Int-5 by using 5-fluoro-2-hydroxy-benzaldehyde as the starting material instead of 4-chloro-2-hydroxy-5-methyl-benzaldehyde in Step 2. MS obsd. (ESI$^+$)[(M+H)$^+$]: 291.1.

Intermediate 42: 8-chloro-2-(4-fluoro-2-hydroxy-phenyl)chromen-4-one

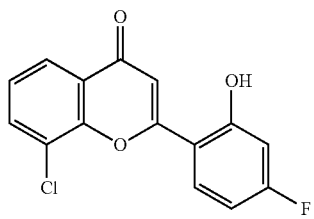

Int-42

Int-42 was prepared in analogy to the procedure described for the preparation of compound Int-5 by using 4-fluoro-2-hydroxy-benzaldehyde as the starting material instead of 4-chloro-2-hydroxy-5-methyl-benzaldehyde in Step 2. MS obsd. (ESI$^+$)[(M+H)$^+$]: 291.1.

Intermediate 43: 8-chloro-2-(4-ethoxy-2-hydroxy-phenyl)chromen-4-one

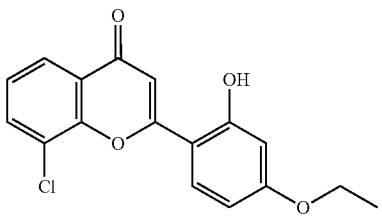

Int-43

Int-43 was prepared in analogy to the procedure described for the preparation of compound Int-5 by using 4-ethoxy-2-hydroxy-benzaldehyde as the starting material instead of 4-chloro-2-hydroxy-5-methyl-benzaldehyde in Step 2. MS obsd. (ESI$^+$)[(M+H)$^+$]: 317.2.

Intermediate 44: 8-chloro-6-fluoro-2-(2-hydroxyphenyl)chromen-4-one

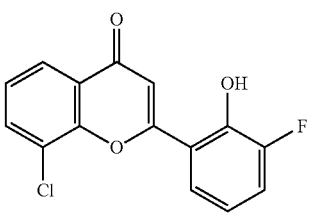

Int-44

Int-44 was prepared in analogy to the procedure described for the preparation of compound Int-1 by using 1-(3-chloro-5-fluoro-2-hydroxy-phenyl)ethanone and 2-methoxybenzaldehyde as the starting materials instead of 1-(3-chloro-2-hydroxy-phenyl)ethanone and 2-methoxy-4-(trifluoromethyl)benzaldehyde in Step 1. MS obsd. (ESI$^+$) [(M+H)$^+$]: 291.2.

Intermediate 45: 8-chloro-2-(3-fluoro-2-hydroxy-phenyl)chromen-4-one

Int-45

Int-45 was prepared in analogy to the procedure described for the preparation of compound Int-5 by using 3-fluoro-2-hydroxy-benzaldehyde as the starting material instead of 4-chloro-2-hydroxy-5-methyl-benzaldehyde in Step 2. MS obsd. (ESI$^+$)[(M+H)$^+$]: 291.1.

Intermediate 46: 2-(4-bromo-5-fluoro-2-hydroxy-phenyl)-8-chloro-chromen-4-one

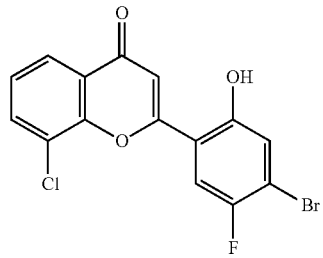
Int-46

Int-46 was prepared in analogy to the procedure described for the preparation of compound Int-5 by using 4-bromo-5-fluoro-2-hydroxy-benzaldehyde as the starting material instead of 4-chloro-2-hydroxy-5-methyl-benzaldehyde in Step 2. MS obsd. (ESI$^+$)[(M+H)$^+$]: 369.2.

Intermediate 47: 8-chloro-6-fluoro-2-(4-fluoro-2-hydroxy-phenyl)chromen-4-one

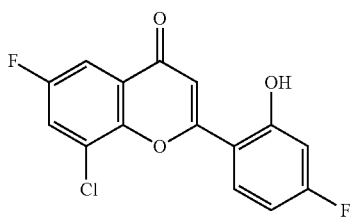
Int-47

Int-47 was prepared in analogy to the procedure described for the preparation of compound Int-5 by using 4-fluoro-2-hydroxy-benzaldehyde as the starting material instead of 4-chloro-2-hydroxy-5-methyl-benzaldehyde in Step 2 and using 1-(3-chloro-5-fluoro-2-hydroxy-phenyl)ethanone as the starting materials instead of 1-(3-chloro-2-hydroxy-phenyl)ethanone in Step 3. MS obsd. (ESI$^+$)[(M+H)$^+$]: 309.1.

Intermediate 48: 2-(2-hydroxyphenyl)-8-(trifluoromethyl)chromen-4-one

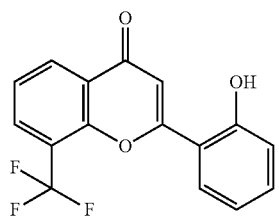
Int-48

Step 1: Preparation of 1-[2-fluoro-3-(trifluoromethyl)phenyl]-3-(2-methoxyphenyl)propane-1,3-dione

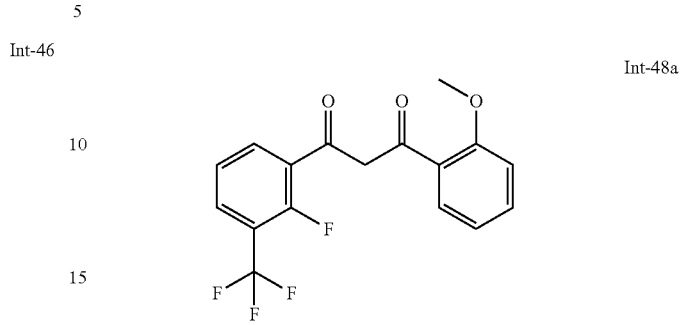
Int-48a

To a solution of 2-fluoro-3-(trifluoromethyl)benzoic acid (208 mg, 999 μmol) in DCM (15 ml) was added oxalyl chloride (254 mg, 175 μl, 2 mmol) and the mixture was then stirred at room temperature for 3 hours. The mixture was then concentrated in vacuo to give the crude 2-fluoro-3-(trifluoromethyl)benzoyl chloride, which was then dissolved in THF (2 mL).

To a solution of 1-(2-methoxyphenyl)ethan-1-one (225 mg, 1.5 mmol) in THF (15 ml) cooled at 0° C. was added LiHMDS (3 ml, 3 mmol) and the mixture was stirred at room temperature for 30 minutes. Then to the resulting solution was added 2-fluoro-3-(trifluoromethyl)benzoyl chloride solution prepared above. The mixture was then stirred at room temperature. The mixture was concentrated in vacuo to give the crude 1-[2-fluoro-3-(trifluoromethyl)phenyl]-3-(2-methoxyphenyl)propane-1,3-dione (340 mg, 100% yield), which was used in the next step directly without further purification. MS obsd. (ESI$^+$)[(M+H)$^+$]: 341.1.

Step 2: Preparation of 2-(2-methoxyphenyl)-8-(trifluoromethyl)chromen-4-one

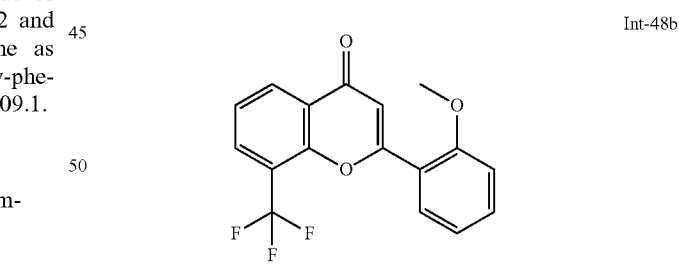
Int-48b

To a solution of 1-[2-fluoro-3-(trifluoromethyl)phenyl]-3-(2-methoxyphenyl)propane-1,3-dione (340 mg, 999 μmol) in DMF (3 mL) was added K$_2$CO$_3$ (414 mg, 3 mmol) and the mixture was then stirred at 100° C. under microwave condition for 30 minutes. The mixture was then quenched with 4N HCl (4 mL) and water (20 mL), the resulting mixture was extracted with EtOAc (30 mL) three times. The combined organic layer was concentrated in vacuo and the residue was purified by column chromatography on silica gel to give 2-(2-methoxyphenyl)-8-(trifluoromethyl)chromen-4-one (270 mg, 84.4% yield) as a yellow solid. MS obsd. (ESI$^+$)[(M+H)$^+$]: 321.2.

Step 3: Preparation of 2-(2-hydroxyphenyl)-8-(trifluoromethyl)chromen-4-one

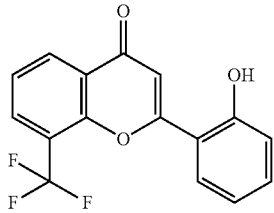

Int-48

Int-48 was prepared in analogy to the procedure described for the preparation of compound Int-1 by using 2-(2-methoxyphenyl)-8-(trifluoromethyl)chromen-4-one as the starting material instead of 8-chloro-2-[2-methoxy-4-(trifluoromethyl)phenyl]chromen-4-one in Step 3. MS obsd. (ESI$^+$)[(M+H)$^+$]: 307.1.

Intermediate 49: 2-(4-bromo-2-hydroxy-phenyl)-8-chloro-7-(trifluoromethyl)chromen-4-one

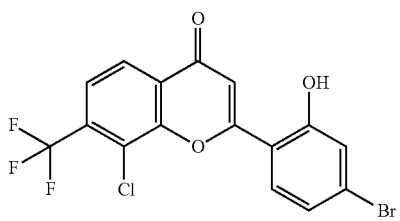

Int-49

Step 1: Preparation of 1-[4-bromo-3-chloro-2-[(4-methoxyphenyl)methoxy]phenyl]ethanone

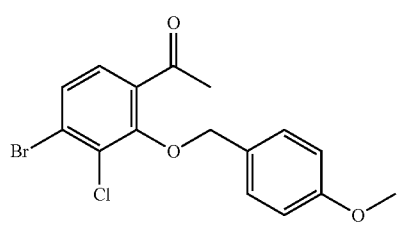

Int-49a

To a solution of 1-(4-bromo-3-chloro-2-hydroxy-phenyl)ethanone (1800.0 mg, 7.21 mmol) in DMF (15 mL) were added potassium carbonate (2.16 mL, 18.04 mmol) and 4-methoxybenzylchloride (0.98 mL, 7.21 mmol) at room temperature. The mixture was stirred at 80° C. for 2 hours. The mixture was the quenched with water (50 mL) and extracted with EtOAc (150 mL) three times. The combined organic layer was washed with brine (80 mL), dried over Na$_2$SO$_4$ and concentrated in vacuo. The residue was purified by column chromatography on silica gel (eluent with PE:EtOAc 100:1 to 10:1) to give 1-[4-bromo-3-chloro-2-[(4-methoxyphenyl)methoxy]phenyl]ethanone (1800 mg, 67.5% yield) as a light yellow solid. MS obsd. (ESI$^+$)[(M+Na)$^+$]: 391.0.

Step 2: Preparation of 1-[3-chloro-2-[(4-methoxyphenyl)methoxy]-4-(trifluoromethyl)phenyl]ethanone

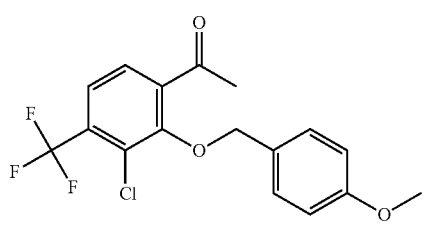

Int-49b

To a solution of 1-[4-bromo-3-chloro-2-[(4-methoxyphenyl)methoxy]phenyl]ethanone (1500.0 mg, 4.06 mmol) in DMF (8 mL) were added CuI (3864.23 mg, 20.29 mmol) and methyl 2,2-difluoro-2-fluorosulfonyl-acetate (3573.27 mg, 20.29 mmol) at room temperature. The mixture was stirred at 110° C. for 18 hours. The mixture was then quenched with water (100 mL) and extracted with EtOAc (130 mL) three times. The combined organic layer was washed with brine, dried over Na$_2$SO$_4$ and concentrated in vacuo. The residue was purified by column chromatography on silica gel (eluent with PE:EtOAc=100:1 to 15:1) to give 1-[3-chloro-2-[(4-methoxyphenyl)methoxy]-4-(trifluoromethyl)phenyl]ethanone (700 mg, 1.95 mmol) as a light yellow solid.

Step 3: Preparation of 1-[3-chloro-2-hydroxy-4-(trifluoromethyl)phenyl]ethanone

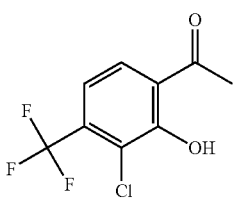

Int-49c

A solution of 1-[3-chloro-2-[(4-methoxyphenyl)methoxy]-4-(trifluoromethyl)phenyl]ethanone (700.0 mg, 1.95 mmol) in trifluoroacetic acid (2.8 mL, 36.34 mmol) was stirred at 120° C. for 1.5 hours. The mixture was then concentrated in vacuo and the residue was purified by column chromatography on silica gel (eluent with PE:EtOAc=100:1 to 4:1) to give 1-[3-chloro-2-hydroxy-4-(trifluoromethyl)phenyl]ethanone (360 mg, 75.78% yield) as colorless liquid. MS obsd. (EST)[(M−H)$^−$]: 236.9.

Step 4: Preparation of 2-(4-bromo-2-hydroxy-phenyl)-8-chloro-7-(trifluoromethyl)chromen-4-one

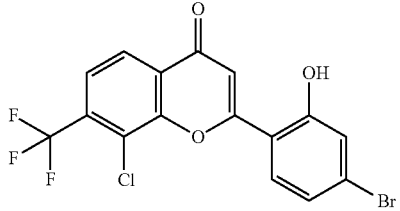
Int-49

Int-49 was prepared in analogy to the procedure described for the preparation of compound Int-5 by using 4-bromo-2-hydroxy-benzaldehyde as the starting material instead of 4-chloro-2-hydroxy-5-methyl-benzaldehyde in Step 2 and using 1-[3-chloro-2-hydroxy-4-(trifluoromethyl)phenyl]ethanone as the starting materials instead of 1-(3-chloro-2-hydroxy-phenyl)ethanone in Step 3. MS obsd. (ESI$^+$)[(M+H)$^+$]: 419.1.

Intermediate 50: 2-(4-bromo-2-hydroxy-phenyl)-8-chloro-5-(trifluoromethyl)chromen-4-one

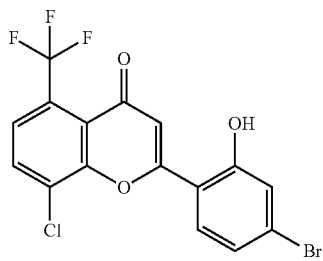
Int-50

Step 1: Preparation of 1-(6-bromo-3-chloro-2-hydroxy-phenyl)ethanone

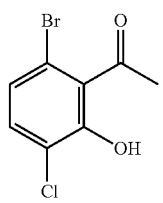
Int-50a

Compound Int-50a was prepared in analogy to the procedure described for the preparation of compound Int-23b by using 5-bromo-2-chloro-phenol as the starting materials instead of 3-bromo-2-chloro-phenol in Step 1.

Step 2: Preparation of 1-[3-chloro-2-hydroxy-6-(trifluoromethyl)phenyl]ethanone

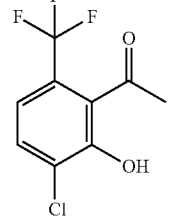
Int-50b

Compound Int-50b was prepared in analogy to the procedure described for the preparation of compound Int-49c by using 1-(6-bromo-3-chloro-2-hydroxy-phenyl)ethanone as the starting materials instead of 1-(4-bromo-3-chloro-2-hydroxy-phenyl)ethanone in Step 1.

Step 3: Preparation of 2-(4-bromo-2-hydroxy-phenyl)-8-chloro-5-(trifluoromethyl)chromen-4-one

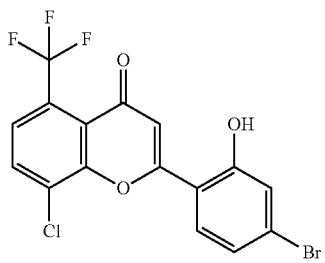
Int-50

Int-50 was prepared in analogy to the procedure described for the preparation of compound Int-5 by using 4-bromo-2-hydroxy-benzaldehyde as the starting material instead of 4-chloro-2-hydroxy-5-methyl-benzaldehyde in Step 2 and using 1-[3-chloro-2-hydroxy-6-(trifluoromethyl)phenyl]ethanone as the starting materials instead of 1-(3-chloro-2-hydroxy-phenyl)ethanone in Step 3. MS obsd. (ESI$^+$)[(M+H)$^+$]: 419.0.

Intermediate 51: 8-chloro-2-(5-ethoxy-2-hydroxy-phenyl)chromen-4-one

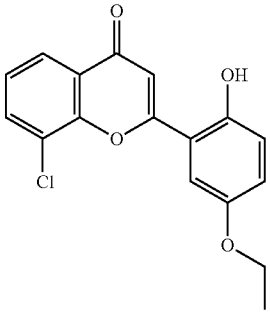
Int-51

Int-51 was prepared in analogy to the procedure described for the preparation of compound Int-5 by using 5-ethoxy-2-hydroxy-benzaldehyde as the starting material instead of 4-chloro-2-hydroxy-5-methyl-benzaldehyde in Step 2. MS obsd. (ESI⁺)[(M+H)⁺]: 317.2.

Intermediate 52: 2-(5-bromo-2-hydroxy-phenyl)-8-chloro-6-fluoro-chromen-4-one

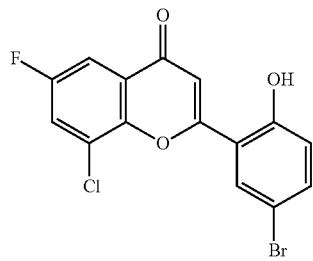

Int-52

Int-52 was prepared in analogy to the procedure described for the preparation of compound Int-5 by using 5-bromo-2-hydroxy-benzaldehyde as the starting material instead of 4-chloro-2-hydroxy-5-methyl-benzaldehyde in Step 2 and using 1-(3-chloro-5-fluoro-2-hydroxy-phenyl)ethanone as the starting materials instead of 1-(3-chloro-2-hydroxy-phenyl)ethanone in Step 3. MS obsd. (ESI⁺)[(M+H)⁺]: 369.1.

Intermediate 53: 2-(5-bromo-2-hydroxy-phenyl)-8-chloro-7-fluoro-chromen-4-one

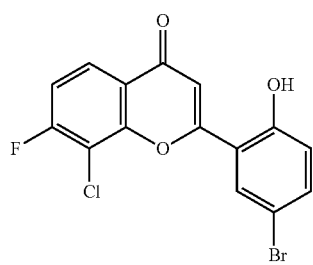

Int-53

Int-53 was prepared in analogy to the procedure described for the preparation of compound Int-5 by using 5-bromo-2-hydroxy-benzaldehyde as the starting material instead of 4-chloro-2-hydroxy-5-methyl-benzaldehyde in Step 2 and using 1-(3-chloro-4-fluoro-2-hydroxy-phenyl)ethanone as the starting materials instead of 1-(3-chloro-2-hydroxy-phenyl)ethanone in Step 3. MS obsd. (ESI⁺)[(M+H)⁺]: 369.1.

Intermediate 54: 2-(4-bromo-5-chloro-2-hydroxy-phenyl)-8-chloro-chromen-4-one

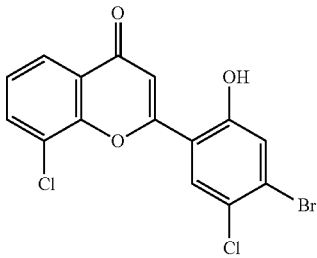

Int-54

Step 1: Preparation of methyl 4-amino-5-chloro-2-methoxy-benzoate

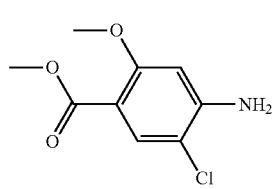

Int-54a

To a solution of 4-amino-5-chloro-2-methoxybenzoic acid (2.0 g, 9.92 mmol) in methanol (50 mL) was added SOCl₂ (23.6 g, 198.4 mmol) dropwise and the resulting solution was stirred at 60° C. for 16 hours. The mixture was then concentrated in vacuo to give the crude methyl 4-amino-5-chloro-2-methoxy-benzoate (3.5 g, 98.17% yield) as a yellow solid, which was used in the next step directly without further purification. MS obsd. (ESI⁺) [(M+H)⁺]: 216.1.

Step 2: Preparation of methyl 4-bromo-5-chloro-2-methoxy-benzoate

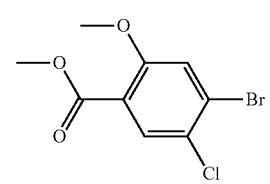

Int-54b

To a solution of methyl 4-amino-5-chloro-2-methoxy-benzoate (3.3 g, 15.3 mmol) in hydrobromic acid (74.29 g, 918.24 mmol) cooled at 0° C. was added a solution of sodium nitrite (1.16 g, 16.83 mmol) in water (20 mL) slowly. After addition, the solution was stirred at 0° C. for 1 hour. To the resulting solution was added CuBr (3.07 g, 21.43 mmol) and the mixture was stirred at 25° C. for 2 hours. The mixture was then diluted with water (100 mL) and extracted with EtOAc (100 mL) twice. The combined organic phase was concentrated in vacuo and the residue was purified by column chromatography on silica gel (eluted with PE:E- tOAc=4:1) to give methyl 4-bromo-5-chloro-2-methoxy-benzoate (1.8 g, 37.87% yield) as a yellow solid.

Step 3: Preparation of (4-bromo-5-chloro-2-methoxy-phenyl)methanol

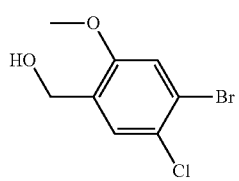
Int-54c

To a solution of methyl 4-bromo-5-chloro-2-methoxy-benzoate (1.0 g, 3.58 mmol) in THF (20 mL) cooled at −78° C. was added LiAlH$_4$ (271.89 mg, 7.16 mmol) and the mixture was stirred at −78° C. for 2 hours. After the reaction was completed, to the resulting mixture was added water (0.5 mL), 10% NaOH aqueous solution (0.5 mL) and water (1.5 mL) in sequence. The resulting mixture was filtered and the filtrate was concentrated in vacuo to give (4-bromo-5-chloro-2-methoxy-phenyl)methanol (1.5 g, 100% yield) as a yellow solid, which was used in the next step directly without further purification.

Step 4: Preparation of 4-bromo-5-chloro-2-methoxy-benzaldehyde

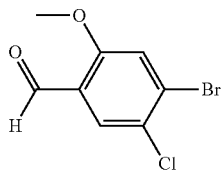
Int-54d

To a solution of (4-bromo-5-chloro-2-methoxy-phenyl)methanol (1.5 g, 5.96 mmol) in DCM (30 mL) was added MnO$_2$ (5.19 g, 59.64 mmol, 10 eq) and the mixture was stirred at 25° C. for 16 hours. The mixture was then filtered and the filtrate was concentrated in vacuo. The residue was purified by column chromatography on silica gel (eluent with PE:DCM=1:1) to give 4-bromo-5-chloro-2-methoxy-benzaldehyde (625 mg, 37.8% yield) as a white solid. MS obsd. (ESI$^+$) [(M+H)$^+$]: 249.0.

Step 5: Preparation of 2-(4-bromo-5-chloro-2-hydroxy-phenyl)-8-chloro-chromen-4-one

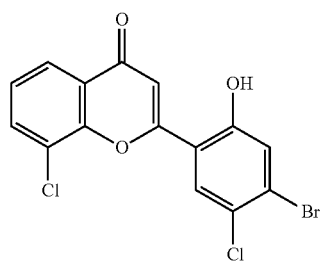
Int-54

Int-54 was prepared in analogy to the procedure described for the preparation of compound Int-1 by using 4-bromo-5-chloro-2-methoxy-benzaldehyde as the starting material instead of 2-methoxy-4-(trifluoromethyl)benzaldehyde in Step 1. MS obsd. (ESI$^+$) [(M+H)$^+$]:385.1.

Intermediate 55: 8-chloro-7-cyclopropyl-2-(2-hydroxyphenyl)chromen-4-one

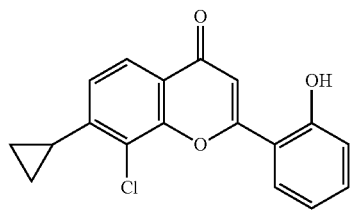
Int-55

Step 1: Preparation of 1-(3-chloro-4-cyclopropyl-2-hydroxy-phenyl)ethanone

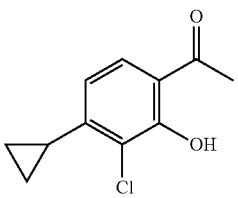
Int-55a

To a solution of 1-(4-bromo-3-chloro-2-hydroxy-phenyl)ethanone (1000.0 mg, 4.01 mmol), Cs$_2$CO$_3$ (2611.89 mg, 8.02 mmol), potassium cyclopropyltrifluoroborate (2372.52 mg, 16.03 mmol) in 1,4-dioxane (30 mL) and water (2 mL) was added Pd(dppf)$_2$C$_{1-2}$ (2932.78 mg, 4.01 mmol) under N$_2$ atmosphere. The mixture was stirred at 110° C. for 5 hours. The mixture was filtered and the filtrate was concentrated in vacuo. The residue was purified by column chromatography on silica gel (eluted with PE:EtOAc=20:1 to 3:1) to give 1-(3-chloro-4-cyclopropyl-2-hydroxy-phenyl)ethanone (560 mg, 66.32% yield). MS obsd. (ESI$^+$)[(M+H)$^+$]: 211.1.

Step 2: Preparation of 8-chloro-7-cyclopropyl-2-(2-hydroxyphenyl)chromen-4-one

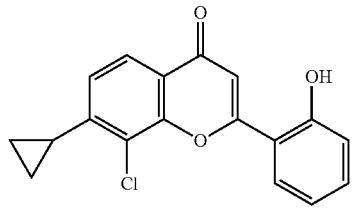
Int-55

Int-55 was prepared in analogy to the procedure described for the preparation of compound Int-1 by using 1-(3-chloro- 4-cyclopropyl-2-hydroxy-phenyl)ethanone and 2-methoxy-benzaldehyde as the starting materials instead of 1-(3-chloro-2-hydroxy-phenyl)ethanone and 2-methoxy-4-(trifluoromethyl)benzaldehyde in Step 1. MS obsd. (ESI+) [(M+H)+]:313.2.

Intermediate A1:
1-(3-chloro-2-hydroxy-4-methoxy-phenyl)ethanone

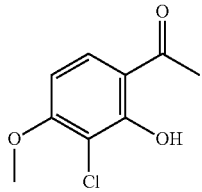
Int-A1

Compound Int-A1 was prepared in analogy to the procedure described for the preparation of compound Int-23b by using 2-chloro-3-methoxy-phenol as the starting materials instead of 3-bromo-2-chloro-phenol in Step 1.

Intermediate A2:
1-(3-chloro-2-hydroxy-5-methoxy-phenyl)ethanone

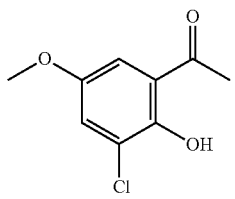
Int-A2

Compound Int-A2 was prepared in analogy to the procedure described for the preparation of compound Int-23b by using 2-chloro-4-methoxy-phenol as the starting materials instead of 3-bromo-2-chloro-phenol in Step 1.

Intermediate T1: methyl 3-[2-(p-tolylsulfonyloxy)ethoxy]cyclobutanecarboxylate

Int-T1

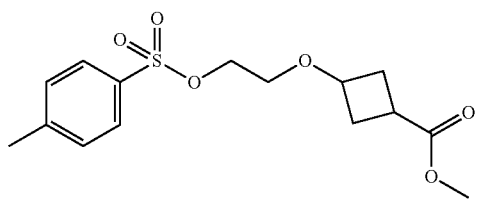

Step 1: Preparation of 2-benzyloxyethoxy(trimethyl)silane

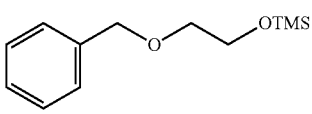
Int-T1a

To a solution of 2-benzyloxyethanol (20.0 g, 131.4 mmol) and TEA (20.0 g, 197.1 mmol) in dichloromethane (200 mL) cooled at 0° C. was added trimethylsilyl chloride (17.1 g, 157.7 mmol) and the mixture was then stirred at 25° C. for 16 hours. After the reaction was completed, the mixture was concentrated in vacuo and the residue was purified by column chromatography on silica gel (eluted with PE:EtOAc=50:1 to 10:1) to give the 2-benzyloxyethoxy(trimethyl)silane (25.0 g, 84.9%) as a colorless oil.

Step 2: Preparation of methyl 3-(2-benzyloxyethoxy)cyclobutanecarboxylate

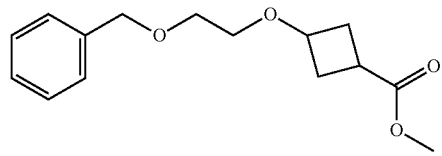
Int-T1b

To a solution of 2-benzyloxyethoxy(trimethyl)silane (25.0 g, 111.4 mmol) and methyl 3-oxocyclobutanecarboxylate (CAS #: 4934-99-0, Cat. #: PB01390, from PharmaBlock (NanJing) R&D Co. Ltd, 15.0 g, 117.0 mmol) in dichloro methane (200 mL) was added trimethylsilyl trifluoromethanesulfonate (12.4 g, 55.7 mmol) dropwise at −78° C. After addition, the mixture was stirred at −78° C. for additional 1 hour, then to the resulting mixture was added triethylsilane (14.25 g, 122.57 mmol). After addition, the resulting mixture was warmed to room temperature and stirred for additional 1 hour. After the reaction was completed, the mixture was washed with saturated NH4Cl solution, brine, dried over anhydrous sodium sulfate, and concentrated in vacuo. The residue was purified by column chromatography on silica gel (elution with PE/EtOAc=100:1~50:1) to give methyl 3-(2-benzyloxyethoxy)cyclobutanecarboxylate (28 g, 95.1%) as a colorless oil. MS obsd. (ESI+) [(M+H)+]: 265.1.

Step 3: Preparation of methyl 3-(2-hydroxyethoxy)cyclobutanecarboxylate

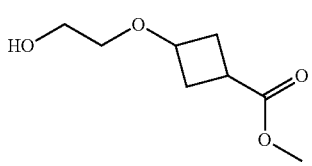
Int-T1c

To a solution of methyl 3-(2-benzyloxyethoxy)cyclobutanecarboxylate (28.0 g, 105.9 mmol) in MeOH (300.0 mL) was added Pd(OH)$_2$ (wet) (1.48 g, 10.6 mmol) at room temperature and the mixture was then hydrogenated under H$_2$ atmosphere at room temperature overnight. After the reaction was completed, the reaction was filtered through silica gel pad and the filtrate was concentrated in vacuo to give 18 g crude methyl 3-(2-hydroxyethoxy)cyclobutanecarboxylate (18 g, 97.6%) as a colorless oil.

Step 4: Preparation of methyl 3-[2-(p-tolylsulfonyloxy)ethoxy]cyclobutanecarboxylate

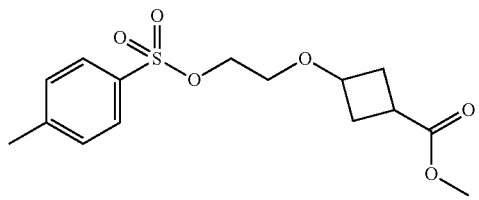

Int-T1

To a solution of methyl 3-(2-hydroxyethoxy)cyclobutanecarboxylate (5 g, 28.7 mmol) and DMAP (5.26 g, 43.1 mmol) in dichloromethane (80 mL) was added 4-methylbenzene-1-sulfonyl chloride (6.02 g, 31.6 mmol) at room temperature and the mixture was then stirred at room temperature overnight. After the reaction was completed, the mixture was washed with 1N HCl (25 mL), water (15 mL), saturated NaHCO$_3$ solution, brine and concentrated in vacuo to give the crude methyl 3-[2-(p-tolylsulfonyloxy)ethoxy]cyclobutanecarboxylate (8.1 g, 85.6%) as a colorless oil, which was used in next step directly without further purification. MS obsd. (ESI$^+$) [(M+H)$^+$]: 329.2.

Intermediate T2: methyl 3-[3-(p-tolylsulfonyloxy)propoxy]cyclobutanecarboxylate

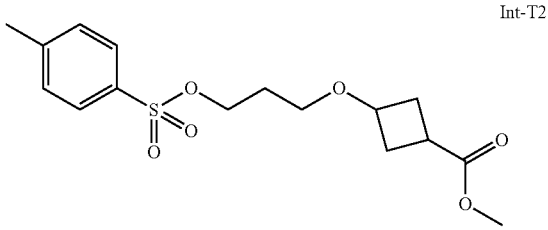

Int-T2

Int-T2 was prepared in analogy to the procedure described for the preparation of compound Int-T1 by using 3-benzyloxypropan-1-ol as the starting material instead of 2-benzyloxyethanol in Step 1. MS obsd. (ESI$^+$) [(M+H)$^+$]: 343.1.

Intermediate T3: tert-butyl 2-[3-(p-tolylsulfonyloxy)propoxy]acetate

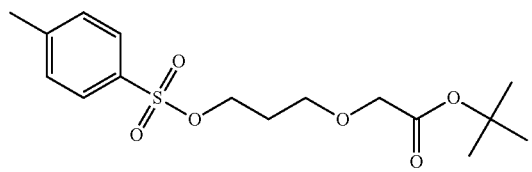

Int-T3

Step 1: Preparation of tert-butyl 2-(3-(benzyloxy)propoxy)acetate

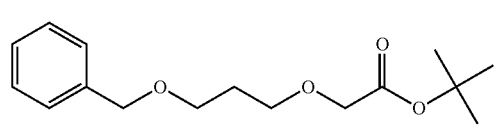

Int-T3a

To a mixture of NaOH (10M, 300.0 ml), tert-butyl 2-bromoacetate (23.5 g, 120.3 mmol) and tetrabutylammonium iodide (8.8 g, 24.06 mmol) in DCM (300 mL) was added 3-benzyloxypropan-1-ol (12.99 mL, 120.32 mmol) at 30° C. and the mixture was stirred at 30° C. for 72 hours. After the reaction was completed, the organic phase was separated out and the aquatic phase was extracted with DCM (150 mL) twice. The combined organic layer was washed with brine, dried over MgSO$_4$ and concentrated in vacuo. The residue was purified by column chromatography on silica gel (eluent with PE:EtOAc=3:1) to give tert-butyl 2-(3-(benzyloxy)propoxy)acetate (21.3 g, 63.3% yield) as a colorless liquid. MS obsd. (ESI$^+$) [(M+Na)$^+$]: 303.2.

Step 2: Preparation of tert-butyl 2-[3-(p-tolylsulfonyloxy)propoxy]acetate

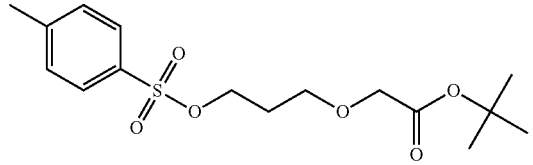

Int-T3

Int-T3 was prepared in analogy to the procedure described for the preparation of compound Int-T1 by using tert-butyl 2-(3-(benzyloxy)propoxy)acetate as the starting material instead of methyl 3-(2-benzyloxyethoxy)cyclobutanecarboxylate in Step 3. MS obsd. (ESI$^+$) [(M+H)$^+$]: 345.0.

Intermediate T4: methyl 2-[2-(p-tolylsulfonyloxy)ethoxy]acetate

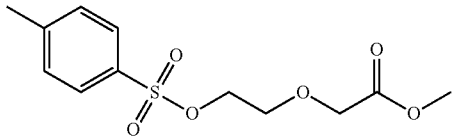

Int-T4 was prepared in analogy to the procedure described for the preparation of compound Int-T3 by using 2-benzyloxyethanol and methyl 2-bromoacetate as the starting material instead of 3-benzyloxypropan-1-ol and tert-butyl bromoacetate in Step 1. MS obsd. (ESI+) [(M+H)+]: 289.1.

Intermediate T5: methyl 3-[2-(p-tolylsulfonyloxy)ethoxy]cyclopentanecarboxylate

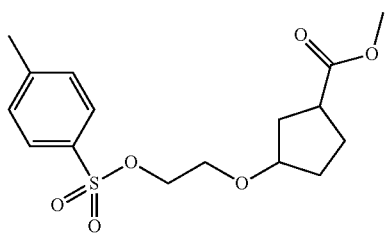

Int-T5 was prepared in analogy to the procedure described for the preparation of compound Int-T1 by using methyl 3-oxocyclobutanecarboxylate as the starting material instead of methyl 3-oxocyclopentanecarboxylate in Step 2. MS obsd. (ESI+) [(M+H)+]: 343.0.

Intermediate T6: methyl 3-[3-(p-tolylsulfonyloxy)propoxy]cyclopentanecarboxylate

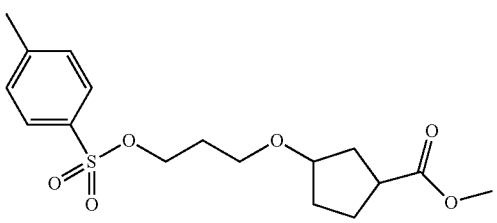

Int-T6 was prepared in analogy to the procedure described for the preparation of compound Int-T1 by using 3-benzyloxypropan-1-ol as the starting material instead of 2-benzyloxyethanol in Step 1 and using methyl 3-oxocyclobutanecarboxylate as the starting material instead of methyl 3-oxocyclopentanecarboxylate in Step 2. MS obsd. (ESI+) [(M+H)+]: 357.1.

Intermediate T7: methyl 2,2-dimethyl-3-(p-tolylsulfonyloxy)propanoate

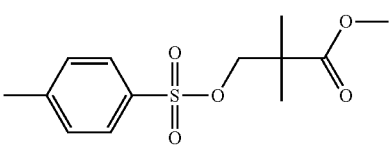

Int-T7 was prepared in analogy to the procedure described for the preparation of compound Int-T1 by using methyl 3-hydroxy-2,2-dimethyl-propanoate as the starting material instead of methyl 3-(2-hydroxyethoxy)cyclobutanecarboxylate in Step 4. MS obsd. (ESI+) [(M+H)+]: 287.1.

Intermediate T8: methyl 3-(p-tolylsulfonyloxymethyl)cyclobutanecarboxylate

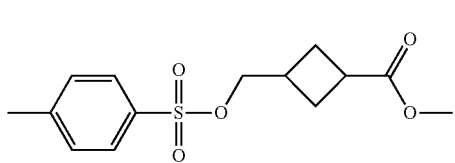

Int-T8 was prepared in analogy to the procedure described for the preparation of compound Int-T1 by using methyl 3-(hydroxymethyl)cyclobutanecarboxylate as the starting material instead of methyl 3-(2-hydroxyethoxy)cyclobutanecarboxylate in Step 4. MS obsd. (ESI+) [(M+H)+]: 299.2.

Intermediate T9: methyl 3-(p-tolylsulfonyloxy)cyclopentanecarboxylate

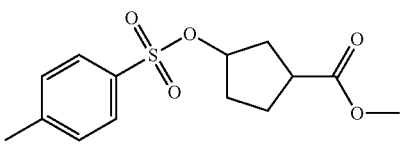

Int-T9 was prepared in analogy to the procedure described for the preparation of compound Int-T1 by using methyl 3-hydroxycyclopentanecarboxylate as the starting material instead of methyl 3-(2-hydroxyethoxy)cyclobutanecarboxylate in Step 4. MS obsd. (ESI+) [(M+H)+]: 299.2.

Intermediate T10: methyl 4-(p-tolylsulfonyloxy)cyclohexanecarboxylate

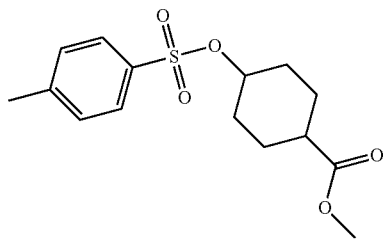

Int-T10

Int-T10 was prepared in analogy to the procedure described for the preparation of compound Int-T1 by using methyl 4-hydroxycyclohexanecarboxylate as the starting material instead of methyl 3-(2-hydroxyethoxy)cyclobutanecarboxylate in Step 4. MS obsd. (ESI$^+$) [(M+H)$^+$]: 313.1.

Intermediate T11: cis-tert-butyl 3-[2-(p-tolylsulfonyloxy)ethoxy]cyclobutanecarboxylate

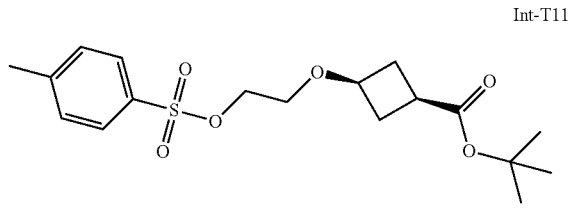 [SMILES: Cc1ccc(S(=O)(=O)OCCO[C@H]2C[C@@H](C(=O)OC(C)(C)C)C2)cc1]

Int-T11

Step 1: Preparation of cis-tert-butyl 3-(2-benzyloxyethoxy)cyclobutanecarboxylate

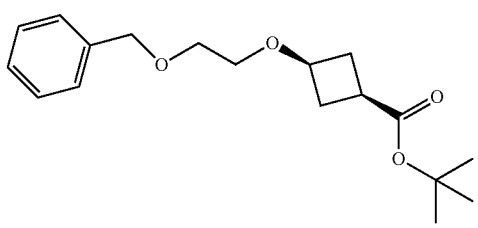

Int-T11a

To a solution of trifluoromethanesulfonic anhydride (27.8 g, 98.56 mmol) and 2,6-lutidine (11.48 mL, 98.56 mmol) in DCM (100 mL) cooled at −30° C. was added 2-(benzyloxy)ethanol (10.0 g, 65.71 mmol) and the reaction mixture was stirred at −30° C. for 1 hour. The reaction mixture was washed with brine (30 ml) twice and the organic layer was concentrated in vacuo to give the crude 2-(benzyloxy)ethyl trifluoromethanesulfonate (18.7 g) as yellow oil.

To a solution of cis-tert-butyl 3-hydroxycyclobutanecarboxylate (CAS #: 939768-64-6, Cat. #: B253665, from BePharm Ltd., 11.3 g, 65.71 mmol) in THF (150 mL) cooled at 0° C. was added NaH (3942.44 mg, 98.56 mmol) and the mixture was stirred at room temperature for 1 hour. To the resulting solution was added 2-(benzyloxy)ethyl trifluoromethanesulfonate (18.7 g, previously prepared) and the mixture was stirred at room temperature for 2 hours. The reaction was then quenched with ice water (100 mL) and the resulting reaction was extracted with EtOAc (200 mL) twice. The combined organic layer was dried over Na$_2$SO$_4$ and concentrated in vacuo. The residue was purified by column chromatography on silica gel (eluent with PE:EtOAc 100:1 to 2:1) to give cis-tert-butyl 3-(2-benzyloxyethoxy)cyclobutanecarboxylate (10.0 g, 49.67% yield) as a yellow oil. $^1$H NMR (CDCl$_3$, 400 MHz): δ ppm 1.44 (s, 9H), 2.17 (m, 2H), 2.54-2.42 (m, 3H), 3.55-3.50 (m, 2H), 3.62-3.57 (m, 2H), 3.99-3.83 (m, 1H), 4.57 (s, 2H), 7.30-7.27 (m, 1H), 7.34 (d, J=4.3 Hz, 4H). MS obsd. (ESI$^+$) [(M+Na)$^+$]: 329.1.

Step 2: Preparation of cis-tert-butyl 3-[2-(p-tolylsulfonyloxy)ethoxy]cyclobutanecarboxylate Int-T11

Int-T11 was prepared in analogy to the procedure described for the preparation of compound Int-T1 by using cis-tert-butyl 3-(2-benzyloxyethoxy)cyclobutanecarboxylate as the starting material instead of methyl 3-(2-benzyloxyethoxy)cyclobutanecarboxylate in Step 3. MS obsd. (ESI$^+$) [(M+H)$^+$]: 371.2.

Intermediate Pro1: O1-tert-butyl O2-methyl (2S, 4S)-4-(p-tolylsulfonyloxy)pyrrolidine-1,2-dicarboxylate

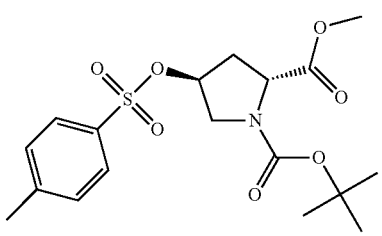

Int-Pro1

Int-Pro1 is commercially available from TCI Shanghai, CAS #: 88043-21-4, Cat. #: B5247.

Intermediate Pro2: O1-tert-butyl O2-methyl (2S, 4S)-4-(p-tolylsulfonyloxy)pyrrolidine-1,2-dicarboxylate

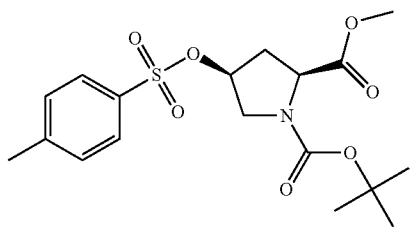

Int-Pro2

Int-Pro2 was prepared in analogy to the procedure described for the preparation of compound Int-T1 by using O1-tert-butyl O2-methyl (2S,4S)-4-hydroxypyrrolidine-1,2-dicarboxylate (CAS #: 102195-79-9, Cat. #: PB02365, from PharmaBlock (Nanjing) R&D Co. Ltd) as the starting material instead of methyl 3-(2-hydroxyethoxy)cyclobutanecarboxylate in Step 4. MS obsd. (ESI$^+$) [(M+H)$^+$]: 400.1.

Intermediate Pro3: O1-tert-butyl O2-methyl (2R, 4R)-4-(p-tolylsulfonyloxy)pyrrolidine-1,2-dicarboxylate

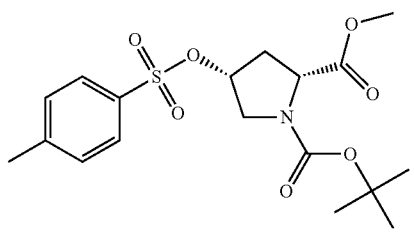

Int-Pro3

Int-Pro3 was prepared in analogy to the procedure described for the preparation of compound Int-T1 by using O1-tert-butyl O2-methyl (2R,4R)-4-hydroxypyrrolidine-1, 2-dicarboxylate (CAS #: 114676-69-6, Cat. #: PB06230, from PharmaBlock (Nanjing) R&D Co. Ltd) as the starting material instead of methyl 3-(2-hydroxyethoxy)cyclobutanecarboxylate in Step 4. MS obsd. (ESI$^+$) [(M+H)$^+$]: 400.1.

Intermediate Pro4: O1-tert-butyl O2-methyl (2S, 4S)-4-(p-tolylsulfonyloxy)pyrrolidine-1,2-dicarboxylate

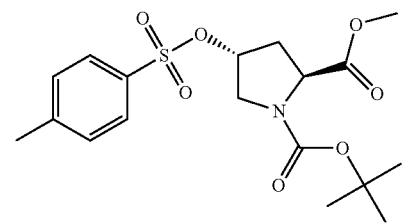

Int-Pro4

Int-Pro4 was prepared in analogy to the procedure described for the preparation of compound Int-T1 by using O1-tert-butyl O2-methyl (2S,4R)-4-hydroxypyrrolidine-1,2-dicarboxylate (CAS #: 74844-91-0, Cat. #: PB02363, from PharmaBlock (Nanjing) R&D Co. Ltd) as the starting material instead of methyl 3-(2-hydroxyethoxy)cyclobutanecarboxylate in Step 4. MS obsd. (ESI$^+$) [(M+H)$^+$]: 400.1.

Example A001: 3-[2-(8-chloro-4-oxo-chromen-2-yl)-5-(trifluoromethyl)phenoxy]propanoic acid

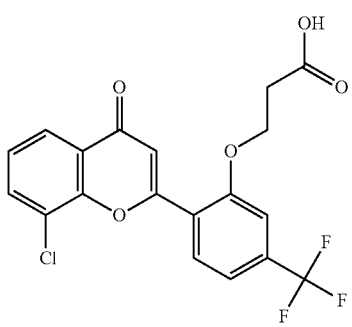

A001

Step 1: Preparation of 3-[2-(8-chloro-4-oxo-chromen-2-yl)-5-(trifluoromethyl)phenoxy]propanoic acid

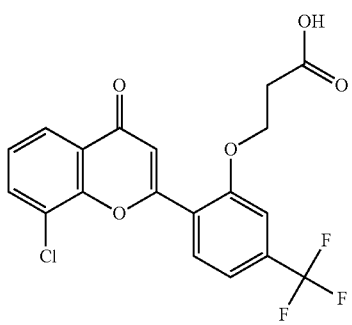

A001

To a solution of 8-chloro-2-[2-hydroxy-4-(trifluoromethyl)phenyl]chromen-4-one (Int-1, 0.37 g, 1.09 mmol, as the "CORE" in Table 1) in DMF (8 mL) was added NaH (26.1 mg, 1.09 mmol) and the mixture was stirred at 60° C. for 10 minutes. Then to the resulting suspension was added oxetan-2-one (115 mg, 100 μl, 1.6 mmol) dropwise and the reaction mixture was stirred at 60° C. for 4 hours. After the reaction was completed, the reaction was adjusted to pH~4 by addition of 4N HCl and extracted with EtOAc (30 mL) three times. The combined organic layer was washed with brine, dried over anhydrous Na$_2$SO$_4$ and concentrated in vacuo. The residue was purified by Prep-HPLC to give 3-[2-(8-chloro-4-oxo-chromen-2-yl)-5-(trifluoromethyl)phenoxy]propanoic acid (61 mg, 12.9% yield) as a yellow solid. $^1$H NMR (DMSO-d$_6$, 400 MHz): δ ppm 12.35-12.55 (m, 1H), 8.15 (d, J=7.9 Hz, 1H), 7.99-8.06 (m, 2H), 7.57-7.63 (m, 2H), 7.52 (t, J=7.9 Hz, 1H), 7.04-7.10 (m, 1H), 4.47 (t, J=5.8 Hz, 2H), 2.81 (t, J=5.8 Hz, 2H). MS obsd. (ESI$^+$) [(M+H)$^+$]: 413.1.

Example A002: methyl 3-[2-(8-chloro-4-oxo-chromen-2-yl)-5-(trifluoromethyl)phenoxy]propanoate

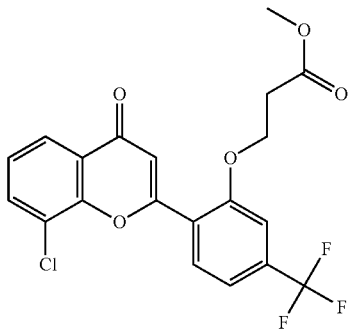

A002

To a solution of 3-[2-(8-chloro-4-oxo-chromen-2-yl)-5-(trifluoromethyl)phenoxy]propanoic acid (9.0 g, 21.81 mmol, crude prepared above) in methanol (90 mL) was added thionyl chloride (4.75 mL, 65.42 mmol). Then the mixture was stirred at 40° C. for 2 hours. After the reaction was completed, the mixture was concentrated in vacuo and the residue was diluted with water (40 mL). The resulting suspension was extracted with EtOAc (50 mL) three times. The combined organic layer was washed with brine (50 mL), dried with MgSO$_4$ and concentrated in vacuo. The residue was then purified by column chromatography on silica gel (eluted with PE:EtOAc=2:1) to give methyl 3-[2-(8-chloro-4-oxo-chromen-2-yl)-5-(trifluoromethyl)phenoxy]propanoate (5.3 g, 56.95% yield) as a yellow solid. $^1$H NMR (DMSO-d$_6$, 400 MHz): δ ppm 8.15 (d, J=8.1 Hz, 1H), 7.99-8.05 (m, 2H), 7.57-7.64 (m, 2H), 7.52 (t, J=7.9 Hz, 1H), 6.96-7.01 (m, 1H), 4.50 (t, J=5.7 Hz, 2H), 3.62 (s, 3H), 2.89 (s, 2H). MS obsd. (ESI$^+$) [(M+H)$^+$]: 427.0.

Example A003: 3-[2-(8-chloro-6-fluoro-4-oxo-chromen-2-yl)-5-(trifluoromethyl)phenoxy]propanoic acid

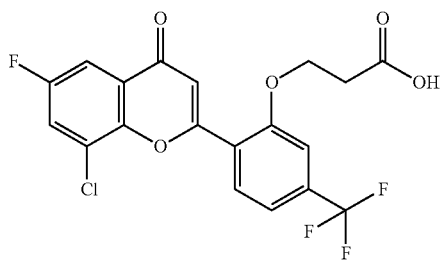

A003

Step 1: Preparation of 3-[2-formyl-5-(trifluoromethyl)phenoxy]propanoic acid

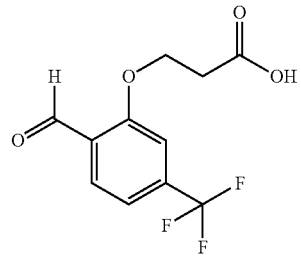

A003a

To a solution of NaOH (315 mg, 7.9 mmol) in water (10 mL) was added 3-bromopropionic acid (1.27 g, 7.9 mmol) and the mixture was stirred at r.t. for 30 minutes. The resulting mixture was added into a mixture of 2-hydroxy-4-(trifluoromethyl)benzaldehyde (1500 mg, 7.9 mmol, as the "SM1" in Table 2) and NaOH (315 mg, 7.9 mmol) in water (10 mL) at 100° C. dropwise and the mixture was stirred at 100° C. for another 30 minutes. After the reaction was completed, the mixture was diluted with water (30 mL) and adjusted to pH~2 by addition of 1N hydrochloric acid. The resulting solution was extracted with EtOAc (30 mL) three times. The combined organic layer was washed with brine (30 mL) twice, dried over Na$_2$SO$_4$ and concentrated in vacuo. The residue was purified by column chromatography on silica gel (eluent with PE:EtOAc=3:1) to give 3-[2-formyl-5-(trifluoromethyl)phenoxy]propanoic acid (600 mg, yield 29%) as a white solid. MS obsd. (ESI$^+$) [(M+H)$^+$]:263.1.

Step 2: Preparation of 3-[2-[(E)-3-(3-chloro-5-fluoro-2-hydroxy-phenyl)-3-oxo-prop-1-enyl]-5-(trifluoromethyl)phenoxy]propanoic acid

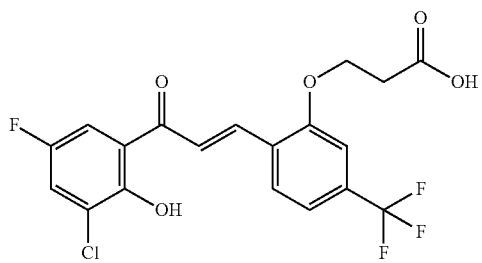

A003b

To a solution of 3-[2-formyl-5-(trifluoromethyl)phenoxy] propanoic acid (230.0 mg, 0.870 mmol) and 1-(3-chloro-5-fluoro-2-hydroxy-phenyl)ethanone (165.0 mg, 0.85 mmol, as the "SM2" in Table 2) in ethanol (10 mL) was added KOH (492.0 mg, 8.7 mmol). The mixture was stirred at 35° C. for 16 hours. After the reaction was completed, the reaction mixture was diluted with water (50 mL) and acidified to pH~1.0 by addition of 1N HCl. The resulting suspension was filtered. The solid was collected and dried in vacuo to give the crude 3-[2-[(E)-3-(3-chloro-5-fluoro-2-hydroxy-phenyl)-3-oxo-prop-1-enyl]-5-(trifluoromethyl)phenoxy]

propanoic acid (200.0 mg, 52.6% yield) as a yellow solid, which was used in the next step directly. MS obsd. (ESI⁺) [(M+H)⁺]:433.0.

Step 3: Preparation of 3-[2-(8-chloro-6-fluoro-4-oxo-chromen-2-yl)-5-(trifluoromethyl)phenoxy]propanoic acid

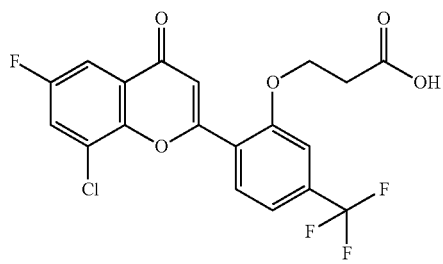

A003

To a solution of 3-[2-[(E)-3-(3-chloro-5-fluoro-2-hydroxy-phenyl)-3-oxo-prop-1-enyl]-5-(trifluoromethyl)phenoxy]propanoic acid (150.0 mg, 0.34 mmol) in DMSO (3 mL) was added iodine (4 mg, 0.05 mmol). Then the mixture was stirred at 140° C. for 3 hours. After the reaction was completed, the mixture was poured into water (50 mL). The resulting suspension was filtered and the filtered cake was washed with water (50 mL) twice. The filtered cake was then collected, triturated with EtOAc (20 mL) and the resulting suspension was then filtered to give 3-[2-(8-chloro-6-fluoro-4-oxo-chromen-2-yl)-5-(trifluoromethyl)phenoxy]propanoic acid (30.2 mg, 19.2% yield) as a yellow solid. ¹H NMR (DMSO-d₆, 400 MHz): δ ppm 12.28-12.58 (m, 1H), 8.08-8.19 (m, 2H), 7.71-7.79 (m, 1H), 7.54-7.63 (m, 2H), 7.00-7.10 (m, 1H), 4.46 (t, J=5.9 Hz, 2H), 2.80 (t, J=5.7 Hz, 2H). MS obsd. (ESI⁺) [(M+H)⁺]:431.0.

The following Example A004 to Example A026 were prepared in analogy to the procedure described for the preparation of Example A001, replacing 8-chloro-2-[2-hydroxy-4-(trifluoromethyl)phenyl]chromen-4-one (Int-1) with "CORE" by the reagent indicated in Table

TABLE 1

| | Compounds synthesis and characterization | | |
|---|---|---|---|
| Example No. | Compounds Name and Structure | Core | ¹H NMR and (ESI⁺) |
| A004 | 3-[5-bromo-2-(8-chloro-4-oxo-chromen-2-yl)phenoxy]propanoic acid | Int-4 | ¹H NMR (DMSO-d₆, 400 MHz): δ ppm 12.38-12.81 (br s, 1H), 7.95-8.06 (m, 2H), 7.84-7.93 (m, 1H), 7.36-7.57 (m, 3H), 7.04 (s, 1H), 4.25-4.48 (m, 2H), 2.69-2.79 (m, 2H). MS obsd. (ESI⁺)[(M + H)⁺]: 423.0. |
| A005 | 3-[5-chloro-2-(8-chloro-4-oxo-chromen-2-yl)-4-methyl-phenoxy]propanoic acid | Int-5 | ¹H NMR (DMSO-d₆, 400 MHz): δ ppm 7.93-8.04 (m, 2H), 7.86-7.90 (m, 1H), 7.43-7.53 (m, 1H), 7.31-7.41 (m, 1H), 6.92-7.04 (m, 1H), 4.28-4.39 (m, 2H), 2.70-2.80 (m, 2H), 2.39 (s, 3H). MS obsd. (ESI⁺) [(M + H)⁺]: 393.1. |
| A006 | 3-[5-bromo-2-(8-chloro-4-oxo-chromen-2-yl)-4-methyl-phenoxy]propanoic acid | Int-6 | ¹H NMR (DMSO-d₆, 400 MHz): δ ppm 12.35-12.58 (m, 1H), 8.00 (td, J = 7.6, 1.3 Hz, 2H), 7.88 (s, 1H), 7.54 (s, 1H), 7.49 (t, J = 7.9 Hz, 1H), 6.99 (s, 1H), 4.36 (t, J = 5.8 Hz, 2H), 2.77 (t, J = 5.7 Hz, 2H), 2.39 (s, 3H). MS obsd. (ESI⁺) [(M + H)⁺]: 437.0. |

TABLE 1-continued

Compounds synthesis and characterization

| Example No. | Compounds Name and Structure | Core | $^1$H NMR and (ESI$^+$) |
|---|---|---|---|
| A007 | 3-[5-bromo-2-(8-chloro-4-oxo-chromen-2-yl)-4-methoxy-phenoxy]propanoic acid | Int-7 | $^1$H NMR (DMSO-d$_6$, 400 MHz): δ ppm 7.91-8.03 (m, 2H), 7.60-7.68 (m, 1H), 7.45-7.56 (m, 2H), 7.07-7.14 (m, 1H), 4.25-4.35 (m, 2H), 3.92 (s, 3H), 2.58-2.62 (m, 2H). MS obsd. (ESI$^+$) [(M + H)$^+$]: 453.1. |
| A008 | 3-[5-chloro-2-(8-chloro-4-oxo-chromen-2-yl)-4-methoxy-phenoxy]propanoic acid | Int-8 | $^1$H NMR (DMSO-d$_6$, 400 MHz): δ ppm 7.93-8.05 (m, 2H), 7.68-7.73 (m, 1H), 7.49-7.55 (m, 1H), 7.42 (s, 1H), 7.18-7.23 (m, 1H), 4.27 (t, J = 6.9 Hz, 2H), 3.91 (s, 3H), 2.32 (t, J = 6.8 Hz, 2H). MS obsd. (ESI$^+$) [(M + H)$^+$]: 409.0. |
| A009 | 3-[2-(8-chloro-4-oxo-chromen-2-yl)-5-(trifluoromethoxy)phenoxy]propanoic acid | Int-9 | $^1$H NMR (DMSO-d$_6$, 400 MHz): δ ppm 12.50 (s, 1H), 8.05-8.11 (m, 1H), 7.96-8.04 (m, 2H), 7.47-7.54 (m, 1H), 7.31-7.36 (m, 1H), 7.21-7.29 (m, 1H), 6.99-7.05 (m, 1H), 4.34-4.45 (m, 2H), 2.76-2.83 (m, 2H). MS obsd. (ESI$^+$) [(M + H)$^+$]: 429.1. |
| A010 | 3-[2-(8-chloro-4-oxo-chromen-2-yl)-4,5-dimethoxy-phenoxy]propanoic acid | Int-10 | $^1$H NMR (DMSO-d$_6$, 400 MHz): δ ppm 12.16-12.44 (m, 1H), 7.89-8.06 (m, 2H), 7.55-7.62 (m, 1H), 7.47 (t, J = 7.9 Hz, 1H), 6.99-7.10 (m, 1H), 6.90 (s, 1H), 4.34-4.43 (m, 2H), 3.92 (s, 3H), 3.81 (s, 3H), 2.74-2.88 (m, 2H). MS obsd. (ESI$^+$) [(M + H)$^+$]: 405.0. |

TABLE 1-continued

Compounds synthesis and characterization

| Example No. | Compounds Name and Structure | Core | $^1$H NMR and (ESI$^+$) |
|---|---|---|---|
| A011 | 3-[[6-(8-chloro-4-oxo-chromen-2-yl)-1,3-benzodioxol-5-yl]oxy]propanoic acid | Int-11 | $^1$H NMR (DMSO-d$_6$, 400 MHz): δ ppm 7.98 (dd, J = 11.2, 6.6 Hz, 2H), 7.48 (dd, J = 16.8, 8.6 Hz, 2H), 7.10 (s, 1H), 6.98 (s, 1H), 6.14 (s, 2H), 4.32 (t, J = 5.8 Hz, 2H), 2.76 (d, J = 5.4 Hz, 2H). . MS obsd. (ESI$^+$) [(M + H)$^+$]: 389.1. |
| A012 | 3-[2-(8-chloro-4-oxo-chromen-2-yl)-5-methoxy-4-methyl-phenoxy]propanoic acid | Int-12 | $^1$H NMR (DMSO-d$_6$, 400 MHz): δ ppm 7.93-8.02 (m, 2H), 7.75-7.81 (m, 1H), 7.41-7.50 (m, 1H), 6.98-7.04 (m, 1H), 6.79-6.83 (m, 1H), 4.32-4.47 (m, 2H), −3.96 (s, 3H), 2.74-2.86 (m, 2H), 2.20 (s, 3H). MS obsd. (ESI$^+$) [(M + H)$^+$]: 389.1. |
| A013 | 3-[2-(8-chloro-4-oxo-chromen-2-yl)-5-methyl-phenoxy]propanoic | Int-13 | $^1$H NMR (DMSO-d$_6$, 400 MHz): δ ppm 7.95-8.02 (m, 2H), 7.84-7.92 (m, 1H), 7.44-7.52 (m, 1H), 7.12-7.20 (m, 1H), 7.00-7.06 (m, 2H), 4.30-4.41 (m, 2H), 2.75-2.84 (m, 2H), 2.44 (s, 3H). MS obsd. (ESI$^+$) [(M + H)$^+$]: 359.1.. |
| A014 | 3-[5-bromo-2-(8-chloro-4-oxo-chromen-2-yl)-4-(trifluoromethoxy)phenoxy] propanoic acid | Int-14 | $^1$H NMR (DMSO-d$_6$, 400 MHz): δ ppm 7.93-8.06 (m, 3H), 7.72-7.80 (m, 1H), 7.48 (t, J = 7.9 Hz, 1H), 7.07 (s, 1H), 4.37-4.48 (m, 2H), 2.79 (t, J = 5.8 Hz, 2H). MS obsd. (ESI$^+$) [(M + H)$^+$]: 506.9. |

TABLE 1-continued

Compounds synthesis and characterization

| Example No. | Compounds Name and Structure | Core | ¹H NMR and (ESI⁺) |
|---|---|---|---|
| A015 | 3-[2-(8-chloro-4-oxo-chromen-2-yl)-4-methoxy-5-methyl-phenoxy]propanoic acid 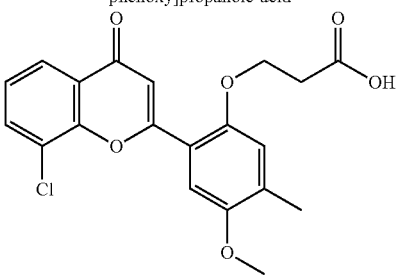 | Int-15 | ¹H NMR (DMSO-$d_6$, 400 MHz): δ ppm 12.27-12.42 (m, 1H), 7.99-8.09 (m, 2H), 7.45-7.57 (m, 2H), 7.14-7.26 (m, 1H), 7.01-7.12 (m, 1H), 4.31 (br t, J = 5.5 Hz, 2H), 3.85 (s, 3H), 2.77 (br t, J = 5.7 Hz, 2H), 2.26 (s, 3H). MS obsd. (ESI⁺) [(M + H)⁺]: 389.1. |
| A016 | 3-[4-bromo-2-(8-chloro-4-oxo-chromen-2-yl)-5-(trifluoromethoxy)phenoxy]propanoic acid 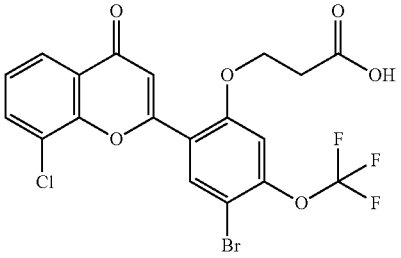 [SMILES: O=C(O)CCOc1cc(OC(F)(F)F)c(Br)cc1-c1cc(=O)c2cccc(Cl)c2o1] | Int-16 | ¹H NMR (DMSO-$d_6$, 400 MHz): δ ppm 12.28-12.57 (m, 1H), 8.27 (s, 1H), 8.01 (ddd, J = 9.9, 8.1, 1.4 Hz, 2H), 7.43-7.56 (m, 2H), 7.01 (s, 1H), 4.41 (t, J = 5.8 Hz, 2H), 2.73-2.86 (t, J = 5.8 Hz, 2H). MS obsd. (ESI⁺) [(M + H)⁺]: 507.0. |
| A017 | 3-[2-(8-chloro-4-oxo-chromen-2-yl)-4-methyl-5-(trifluoromethoxy)phenoxy]propanoic acid 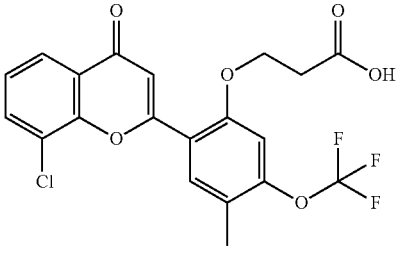 [SMILES: Cc1cc(-c2cc(=O)c3cccc(Cl)c3o2)c(OCCC(=O)O)cc1OC(F)(F)F] | Int-17 | ¹H NMR (DMSO-$d_6$, 400 MHz): δ ppm 7.95-8.05 (m, 2H), 7.90-7.93 (m, 1H), 7.50 (t, J = 7.9 Hz, 1H), 7.19 (s, 1H), 7.13 (s, 1H), 4.29 (t, J = 6.9 Hz, 2H), 2.36 (t, J = 6.8 Hz, 2H), 2.30 (s, 3H). MS obsd. (ESI⁺) [(M + H)⁺]: 443.0. |
| A018 | 3-[2-bromo-6-(8-chloro-4-oxo-chromen-2-yl)-4-methyl-phenoxy]propanoic acid 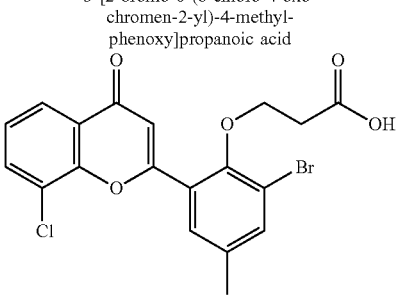 | Int-18 | ¹H NMR (DMSO-$d_6$, 400 MHz): δ ppm 12.32 (s, 1H), 7.96-8.06 (m, 2H), 7.72-7.77 (m, 1H), 7.58-7.65 (m, 1H), 7.46-7.56 (m, 1H), 6.83 (s, 1H), 4.13-4.18 (m, 2H), 2.58-2.63 (m, 2H), 2.37 (s, 3H). MS obsd. (ESI⁺) [(M + H)⁺]: 437.1. |

TABLE 1-continued

Compounds synthesis and characterization

| Example No. | Compounds Name and Structure | Core | $^1$H NMR and (ESI$^+$) |
|---|---|---|---|
| A019 | 3-[2-(8-chloro-4-oxo-chromen-2-yl)-5-methyl-4-(trifluoromethoxy)phenoxy] propanoic acid 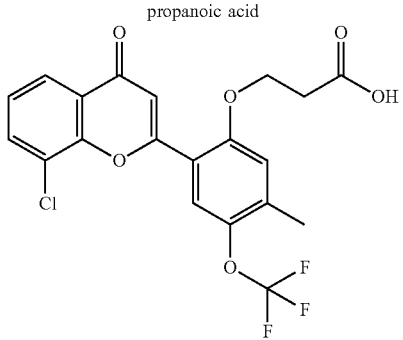 | Int-19 | $^1$H NMR (DMSO-d$_6$, 400 MHz): δ ppm 7.94-8.02 (m, 2H), 7.90 (m, 1H), 7.43-7.52 (m, 1H), 7.35 (m, 1H), 7.09 (s, 1H), 4.38 (tt, J = 5.6 Hz, 2H), 2.77 (t, J = 5.7 Hz, 2H), 2.36 (s, 3H). MS obsd. (ESI$^+$) [(M + H)$^+$]: 443.0. |
| A020 | 3-[5-bromo-2-(8-chloro-4-oxo-chromen-2-yl)-3-fluoro-phenoxy]propanoic acid 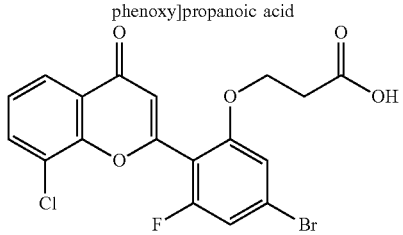 | Int-22 | $^1$H NMR (DMSO-d$_6$, 400 MHz): δ ppm 7.95-8.07 (m, 2H), 7.53 (t, J = 7.9 Hz, 1H), 7.36-7.48 (m, 2H), 6.63 (s, 1H), 4.33 (t, J = 5.9 Hz, 2H), 2.65 (t, J = 5.9 Hz, 2H). MS obsd. (ESI$^+$) [(M + H)$^+$]: 441.1. |
| A021 | 3-[2-(8-chloro-4-oxo-chromen-2-yl)-3-fluoro-5-methyl-phenoxy]propanoic acid 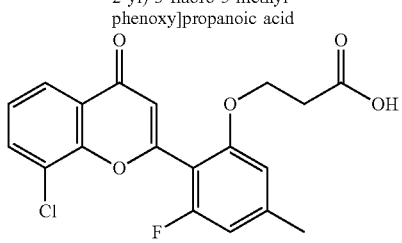 | Int-21 | $^1$H NMR (DMSO-d$_6$, 400 MHz): δ ppm 12.04-12.63 (m, 1H), 7.94-8.07 (m, 2H), 7.51 (t, J = 7.9 Hz, 1H), 6.94-7.06 (m, 1H), 6.89 (br d, J = 10.6 Hz, 1H), 6.46-6.60 (m, 1H), 4.28 (br t, J = 5.9 Hz, 2H), 2.65 (br t, J = 5.9 Hz, 2H), 2.40 (s, 3H). MS obsd. (ESI$^+$) [(M + H)$^+$]: 377.1. |
| A022 | 3-[2-(8-bromo-4-oxo-chromen-2-yl)-5-(trifluoromethoxy)phenoxy] propanoic acid 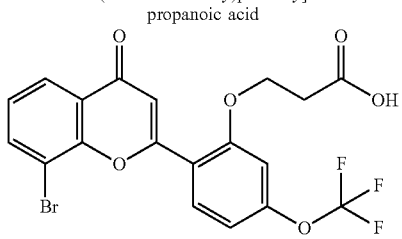 | Int-22 | $^1$H NMR (DMSO-d$_6$, 400 MHz): δ ppm 8.09-8.18 (m, 2H), 8.00-8.06 (m, 1H), 7.41-7.48 (m, 1H), 7.30-7.37 (m, 1H), 7.21-7.29 (m, 1H), 7.00-7.06 (m, 1H), 4.32-4.45 (m, 2H), 2.76-2.87 (m, 2H). MS obsd. (ESI$^+$) [(M + H)$^+$]: 473.1. |

TABLE 1-continued

Compounds synthesis and characterization

| Example No. | Compounds Name and Structure | Core | $^1$H NMR and (ESI$^+$) |
|---|---|---|---|
| A023 | 3-[2-(7-bromo-8-chloro-4-oxo-chromen-2-yl)-5-(trifluoromethoxy)phenoxy]propanoic acid | Int-23 | $^1$H NMR (DMSO-d$_6$, 400 MHz): δ ppm 8.04-8.14 (m, 1H), 7.84-7.95 (m, 2H), 7.31-7.37 (m, 1H), 7.20-7.28 (m, 1H), 6.97-7.07 (m, 1H), 4.32-4.45 (m, 2H), 2.76-2.83 (m, 2H). MS obsd. (ESI$^+$) [(M + H)$^+$]: 507.1. |
| A024 | 3-[2-(8-bromo-4-oxo-chromen-2-yl)-5-methyl-phenoxy]propanoic acid | Int-24 | $^1$H NMR (DMSO-d$_6$, 400 MHz): δ ppm 8.08-8.15 (m, 1H), 7.98-8.04 (m, 1H), 7.88-7.97 (m, 1H), 7.37-7.47 (m, 1H), 7.09-7.17 (m, 1H), 6.97-7.08 (m, 2H), 4.29-4.42 (m, 2H), 2.74-2.84 (m, 2H), 2.41 (s, 3H). MS obsd. (ESI$^+$) [(M + H)$^+$]: 403.1. |
| A025 | 3-[2-(8-bromo-4-oxo-chromen-2-yl)-5-chloro-4-methyl-phenoxy]propanoic acid | Int-25 | $^1$H NMR (DMSO-d$_6$, 400 MHz): δ ppm 8.09-8.15 (m, 1H), 7.98-8.03 (m, 1H), 7.92-7.96 (m, 1H), 7.39-7.45 (m, 1H), 7.34-7.38 (m, 1H), 7.02 (s, 1H), 4.32-4.37 (m, 2H), 2.70-2.76 (m, 2H), 2.38 (s, 3H). MS obsd. (ESI$^+$) [(M + H)$^+$]: 437.1. |
| A026 | 3-[[5-bromo-2-(8-chloro-4-oxo-chromen-2-yl)-3-pyridyl]oxy]propanoic acid | Int-26 | $^1$H NMR (DMSO-d$_6$, 400 MHz): δ ppm 12.37-12.52 (br s, 1H), 8.54 (d, J = 1.8 Hz, 1H), 8.13-8.21 (m, 1H), 7.95-8.06 (m, 2H), 7.41-7.58 (m, 1H), 6.90-6.99 (m, 1H), 4.44 (t, J = 5.9 Hz, 2H), 2.79 (t, J = 5.9 Hz, 2H). MS obsd. (ESI$^+$) [(M + H)$^+$]: 424.2. |

The following Example A031 to Example A040 were prepared in analogy to the procedure described for the preparation of Example A003, replacing 2-hydroxy-4-(trifluoromethyl)benzaldehyde with "SM1" in step 1, and replacing 1-(3-chloro-5-fluoro-2-hydroxy-phenyl)ethanone with "SM2" in step2. The "SM1" and "SM2" are the reagents indicated in Table 2.

TABLE 2

Compounds synthesis and characterization

| Example No. | Compounds Name and Structure | SM1 and SM2 | $^1$H NMR and (ESI$^+$) |
|---|---|---|---|
| A031 | 3-[2-(8-chloro-7-fluoro-4-oxo-chromen-2-yl)-5-(trifluoromethyl)phenoxy] propanoic acid | SM1: 2-hydroxy-4-(trifluoromethyl)benzaldehyde<br>SM2: 1-(3-chloro-4-fluoro-2-hydroxy-phenyl)ethanone | $^1$H NMR (DMSO-d$_6$, 400 MHz): δ ppm 12.19-12.59 (m, 1H), 8.11-8.19 (m, 1H), 8.02-8.11 (m, 1H), 7.56-7.64 (m, 3H), 7.03-7.09 (m, 1H), 4.33-4.52 (m, 2H), 2.75-2.83 (m, 2H). MS obsd. (ESI$^+$) [(M + H)$^+$]: 431.0. |
| A032 | 3-[2-(8-chloro-7-methoxy-4-oxo-chromen-2-yl)-5-(trifluoromethyl)phenoxy] propanoic acid | SM1: 2-hydroxy-4-(trifluoromethyl)benzaldehyde<br>SM2: 1-(3-chloro-2-hydroxy-4-methoxy-phenyl)ethanone (Int-A1) | $^1$H NMR (DMSO-d$_6$, 400 MHz): δ ppm 12.42 (s, 1H), 8.14 (d, J = 8.0 Hz, 1H), 8.01 (d, J = 9.0 Hz, 1H), 7.58 (d, J = 10.2 Hz, 2H), 7.40 (d, J = 9.1 Hz, 1H), 6.99 (s, 1H), 4.46 (t, J = 5.8 Hz, 2H), 4.04 (s, 3H), 2.80 (t, J = 5.8 Hz, 2H). MS obsd. (ESI$^+$) [(M + H)$^+$]: 443.0. |
| A033 | 3-[2-(8-chloro-6-methoxy-4-oxo-chromen-2-yl)-5-(trifluoromethyl)phenoxy] propanoic acid | SM1: 2-hydroxy-4-(trifluoromethyl)benzaldehyde<br>SM2: 1-(3-chloro-2-hydroxy-5-methoxy-phenyl)ethanone (Int-A2) | $^1$H NMR (DMSO-d$_6$, 400 MHz): δ ppm 12.39-12.52 (m, 1H), 8.12 (d, J = 7.8 Hz, 1H), 7.68-7.75 (m, 1H), 7.55-7.62 (m, 2H), 7.40 (d, J = 2.9 Hz, 1H), 7.03 (s, 1H), 4.39-4.50 (m, 2H), 3.90 (s, 3H), 2.80 (t, J = 5.7 Hz, 2H). MS obsd. (ESI$^+$) [(M + H)$^+$]: 443.0. |
| A034 | 3-[2-(8-chloro-3-methyl-4-oxo-chromen-2-yl)-5-(trifluoromethyl)phenoxy] propanoic acid | SM1: 2-hydroxy-4-(trifluoromethyl)benzaldehyde<br>SM2: 1-(3-chloro-2-hydroxy-phenyl)propan-1-one (CAS #: 938-67-0, Cat. #: PB94453, from PharmaBlock (Nanjing)) | $^1$H NMR (DMSO-d$_6$, 400 MHz): δ ppm. 8.06 (dd, J = 7.9, 1.6 Hz, 1H), 7.99 (dd, J = 7.8, 1.5 Hz, 1H), 7.80 (d, J = 7.8 Hz, 1H), 7.57-7.61 (m, 1H), 7.46-7.55 (m, 2H), 4.36 (br t, J = 6.2 Hz, 2H), 2.53-2.57 (m, 2H), 1.79 (s, 3H). MS obsd. (ESI$^+$) [(M + H)$^+$]: 427.0. |

Example A038: methyl 3-[5-chloro-2-(8-chloro-4-oxo-chromen-2-yl)-4-methyl-phenoxy]propanoate

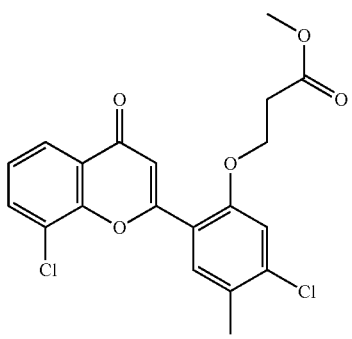

A038

Example A038 was prepared in analogy to the procedure described for the preparation of Example A002 by using 3-[5-chloro-2-(8-chloro-4-oxo-chromen-2-yl)-4-methyl-phenoxy]propanoic acid (Example A005) as the starting material instead of 3-[2-(8-chloro-4-oxo-chromen-2-yl)-5-(trifluoromethyl)phenoxy]propanoic acid (Example A001). $^1$H NMR (DMSO-$d_6$, 400 MHz): δ ppm. 7.93-8.08 (m, 2H), 7.79-7.91 (m, 1H), 7.45-7.58 (m, 1H), 7.30-7.45 (m, 1H), 6.83-6.97 (m, 1H), 4.39 (m, 2H), 3.63 (s, 3H), 2.87 (m, 2H), 2.35 (s, 3H). MS obsd. (ESI$^+$) [(M+H)$^+$]:407.0.

Example A039: 3-[2-(8-chloro-4-oxo-chromen-2-yl)-5-(trifluoromethyl)phenoxy]butanoic acid and Example A040: 3-[3-[2-(8-chloro-4-oxo-chromen-2-yl)-5-(trifluoromethyl)phenoxy]butanoyloxy]butanoic acid

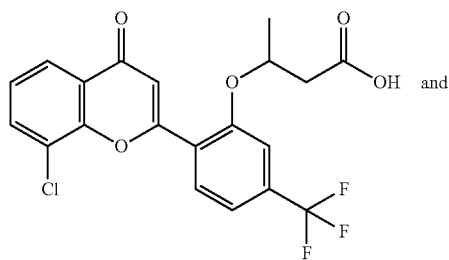

A039 and

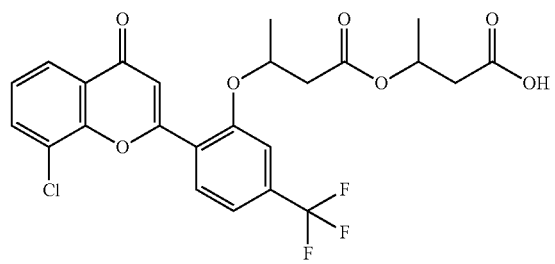

A040

To a solution of 8-chloro-2-[2-hydroxy-4-(trifluoromethyl)phenyl]chromen-4-one (Int-1, 0.37 g, 1.09 mmol) in DMF (8 mL) was added NaH (26.1 mg, 1.09 mmol) and the mixture was stirred at 60° C. for 10 minutes. Then to the resulting suspension was dropwise added 4-methyloxetan-2-one (115 mg, 100 μl, 1.6 mmol) dropwise and the reaction mixture was stirred at 60° C. for 4 hours. After the reaction was completed, the reaction was adjusted to pH~4 by addition of 4N HCl and extracted with EtOAc (30 mL) three times. The combined organic layer was washed with brine, dried over anhydrous Na$_2$SO$_4$ and concentrated in vacuo. The residue was purified by Prep-HPLC to give 3-[2-(8-chloro-4-oxo-chromen-2-yl)-5-(trifluoromethyl)phenoxy]butanoic acid (15.8 mg, 2.4% yield) and 3-[3-[2-(8-chloro-4-oxo-chromen-2-yl)-5-(trifluoromethyl)phenoxy]butanoyloxy]butanoic acid (5.5 mg, 0.7% yield) as yellow solid.

Example A039: $^1$H NMR (DMSO-$d_6$, 400 MHz): δ ppm. 8.06-8.15 (m, 1H), 7.99-8.05 (m, 2H), 7.54-7.68 (m, 3H), 7.03 (s, 1H), 5.17 (q, 1H, J=6.2 Hz), 2.71 (d, 2H, J=6.2 Hz), 1.38 (d, 3H, J=6.1 Hz). MS obsd. (ESI$^+$) [(M+H)$^+$]:427.4.

Example A040: $^1$H NMR (DMSO-$d_6$, 400 MHz): δ ppm 8.12 (d, J=7.7 Hz, 1H), 8.02 (dq, J=7.9, 1.3 Hz, 2H), 7.61-7.65 (m, 1H), 7.56 (d, J=8.2 Hz, 1H), 7.52 (t, J=7.9 Hz, 1H), 7.00 (s, 1H), 5.19 (br d, J=6.1 Hz, 1H), 5.04 (d, J=6.4 Hz, 1H), 2.75 (d, J=6.4 Hz, 2H), 2.43 (d, J=6.6 Hz, 2H), 1.38 (d, J=6.1 Hz, 3H), 1.05 (d, J=6.4 Hz, 3H). MS obsd. (ESI$^+$) [(M+H)$^+$]:513.4.

Example A041: [2-(8-chloro-4-oxo-chromen-2-yl)-4-methoxy-5-(2,2,2-trifluoroethoxy)phenoxy]propanoic acid

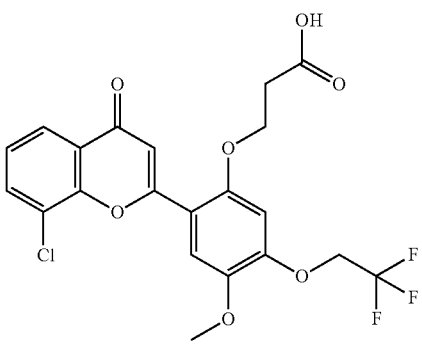

A041

Step 1: Preparation of 2,4-dihydroxy-5-methoxy-benzaldehyde

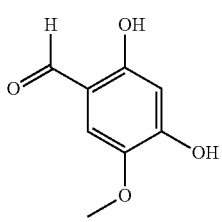

A041a

Compound A041a was prepared in analogy to the procedure described for the preparation of compound Int-5a by using 4-methoxybenzene-1,3-diol as the starting material instead of 3-chloro-4-methyl-phenol in Step 1.

Step 2: Preparation of 2-hydroxy-5-methoxy-4-(2,2,2-trifluoroethoxy)benzaldehyde

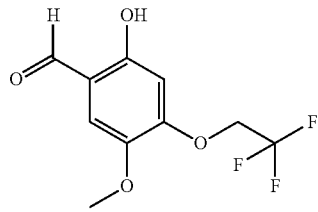

A041b

To a solution of 2,4-dihydroxy-5-methoxy-benzaldehyde (1300.0 mg, 7.73 mmol) in DMF (15 mL) was added Sodium bicarbonate (779.4 mg, 9.28 mmol) and 2,2,2-trifluoroethyl trifluoromethanesulfonate (0.92 mL, 7.73 mmol) and the mixture was stirred at 85° C. for 24 hours. After the reaction was completed, the reaction mixture was quenched with water (100 mL) and the resulting mixture was extracted with EtOAc (50 mL) three times. The combined organic layer was washed with brine (50 mL) twice, dried over MgSO4 and then concentrated in vacuo. The residue was then purified by column chromatography on silica gel (eluent with PE:EtOAc=5:1) to give 2-hydroxy-5-methoxy-4-(2,2,2-trifluoroethoxy)benzaldehyde (880 mg, 45.5% yield) as a light yellow solid. MS obsd. (ESI$^+$) [(M+H)$^+$]:251.0.

Step 3: Preparation of 3-[2-formyl-4-methoxy-5-(2,2,2-trifluoroethoxy)phenoxy]propanoic acid

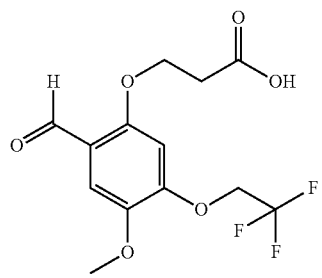

A041c

To a solution of 2-hydroxy-5-methoxy-4-(2,2,2-trifluoroethoxy)benzaldehyde (800.0 mg, 3.2 mmol) in DMF (10 mL) was added sodium hydride (84.42 mg, 3.52 mmol) and the mixture was stirred at 25° C. for 30 minutes. Then to the resulting solution was added beta-propiolactone (230.44 mg, 3.2 mmol) and the mixture was stirred at 25° C. for 16 hours. After the reaction was completed, the reaction was quenched with water (100 mL) and the resulting mixture was adjusted to pH~2 with 1N hydrochloric acid. The resulting solution was then extracted with EtOAc (50 mL) three times. The combined organic layer was washed with brine (50 mL) twice, dried over Na$_2$SO$_4$ and concentrated in vacuo. The residue was purified by Prep-HPLC to give 3-[2-formyl-4-methoxy-5-(2,2,2-trifluoroethoxy)phenoxy]propanoic acid (270 mg, 26.2% yield) as a white solid. MS obsd. (ESI$^+$) [(M+H)$^+$]:323.1.

Step 4: Preparation of 3-[2-[(E)-3-(3-chloro-2-hydroxy-phenyl)-3-oxo-prop-1-enyl]-4-methoxy-5-(2,2,2-trifluoroethoxy)phenoxy]propanoic acid

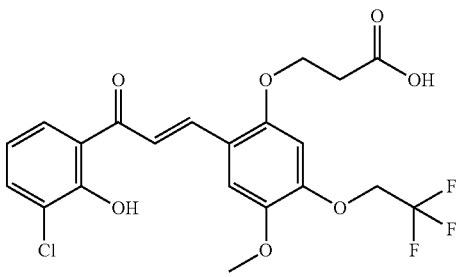

A041d

To a solution of 3-[2-formyl-4-methoxy-5-(2,2,2-trifluoroethoxy)phenoxy]propanoic acid (270.0 mg, 0.840 mmol) and 1-(3-chloro-2-hydroxy-phenyl)ethanone (142.94 mg, 0.840 mmol) in ethanol (10 mL) was added KOH (470.11 mg, 8.38 mmol) and the mixture was stirred at 35° C. for 16 hours. After the reaction was completed, the reaction mixture was diluted with water (50 mL) and acidified to pH 1.0 by addition of 1N HCl. The resulting suspension was filtered and solid was washed with water. The cake was collected and dried in vacuo to give the crude 3-[2-[(E)-3-(3-chloro-2-hydroxy-phenyl)-3-oxo-prop-1-enyl]-4-methoxy-5-(2,2,2-trifluoroethoxy)phenoxy]propanoic acid (280 mg, 70.38% yield) as an orange solid, which was used in the next step directly. MS obsd. (ESI$^+$) [(M+H)$^+$]:475.1.

Step 5: Preparation of 3-[2-(8-chloro-4-oxo-chromen-2-yl)-4-methoxy-5-(2,2,2-trifluoroethoxy)phenoxy]propanoic acid

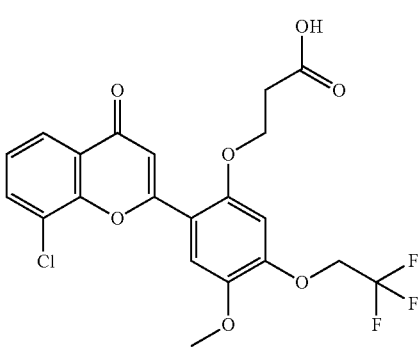

A041

To a solution of 3-[2-[(E)-3-(3-chloro-2-hydroxy-phenyl)-3-oxo-prop-1-enyl]-4-methoxy-5-(2,2,2-trifluoroethoxy)phenoxy]propanoic acid (230.0 mg, 0.480 mmol) in DMSO (3 mL) was added iodine (8.61 mg, 0.030 mmol). Then the mixture was stirred at 140° C. for 3 hours. After the reaction was completed, the mixture was poured into water (50 mL) and the resulting suspension was filtrate, the filtered cake was washed with water (50 mL) twice. The filtered cake was then collected, triturated with EtOAc (20 mL) and the resulting suspension was then filtered to give 3-[2-(8-chloro-4-oxo-chromen-2-yl)-4-methoxy-5-(2,2,2-trifluoroethoxy)phenoxy]propanoic acid (116.4 mg, 50.82% yield)

as a yellow solid. $^1$H NMR (DMSO-d$_6$, 400 MHz): δ ppm 12.38-12.53 (m, 1H), 7.92-8.04 (m, 2H), 7.58-7.70 (m, 1H), 7.40-7.53 (m, 1H), 7.06 (s, 2H), 4.88-5.03 (m, 2H), 4.38 (t, J=5.8 Hz, 2H), 3.74-3.93 (m, 3H), 2.74-2.88 (m, 2H). MS obsd. (ESI$^+$) [(M+H)$^+$]:473.0.

Example A042: 3-[2-[8-chloro-4-oxo-7-(trifluoromethyl)chromen-2-yl]-5-(trifluoromethoxy)phenoxy]propanoic acid

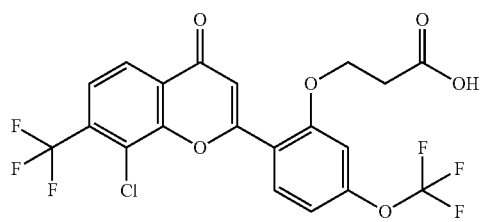

A042

Step 1: Preparation of methyl 3-[2-(7-bromo-8-chloro-4-oxo-chromen-2-yl)-5-(trifluoromethoxy)phenoxy]propanoate

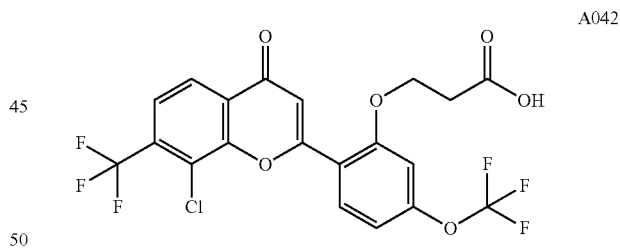

A042a

To a solution of 3-[2-(7-bromo-8-chloro-4-oxo-chromen-2-yl)-5-(trifluoromethoxy)phenoxy]propanoic acid (Example A023, 600 mg, 1.18 mmol) in methanol (8 mL) was added SOCl$_2$ (1.64 g, 1 mL, 13.8 mmol) at room temperature and the resulting mixture was stirred at 25° C. for 4 hours. After the reaction was completed, the reaction was adjusted to pH~4 by addition of 4N HCl and then extracted with EtOAc (50 mL) three times. The combined organic layer was washed with brine, dried over anhydrous Na$_2$SO$_4$ and concentrated in vacuo. The residue was purified by Prep-HPLC to give methyl 3-[2-(7-bromo-8-chloro-4-oxo-chromen-2-yl)-5-(trifluoromethoxy)phenoxy]propanoate (100 mg, 16.2% yield) as a white foam. MS obsd. (ESI$^+$) [(M+H)$^+$]: 521.1.

Step 2: Preparation of methyl 3-[2-[8-chloro-4-oxo-7-(trifluoromethyl)chromen-2-yl]-5-(trifluoromethoxy)phenoxy]propanoate

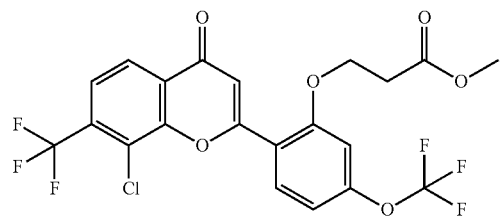

A042b

To a solution of methyl 3-[2-(7-bromo-8-chloro-4-oxo-chromen-2-yl)-5-(trifluoromethoxy)phenoxy]propanoate (100 mg, 192 μmol) and copper (I) iodide (110 mg, 575 μmol) in DMF (2 mL) was added methyl 2,2-difluoro-2-(fluorosulfonyl)acetate (368 mg, 246 μL, 1.92 mmol) at room temperature and the resulting mixture was stirred at 105° C. for 4 hours. After the reaction was completed, the reaction was adjusted to pH~4 by addition of 4N HCl and then extracted with EtOAc (50 mL) three times. The combined organic layer was washed with brine, dried over anhydrous Na$_2$SO$_4$ and concentrated in vacuo. The residue was purified by column chromatography on silica gel (eluent with PE:EtOAc=10:1 to 3:1) to give methyl 3-[2-[8-chloro-4-oxo-7-(trifluoromethyl)chromen-2-yl]-5-(trifluoromethoxy)phenoxy]propanoate (40 mg, 40.9% yield) as a white foam. MS obsd. (ESI$^+$) [(M+H)$^+$]:511.1.

Step 3: Preparation of 3-[2-[8-chloro-4-oxo-7-(trifluoromethyl)chromen-2-yl]-5-(trifluoromethoxy)phenoxy]propanoic acid

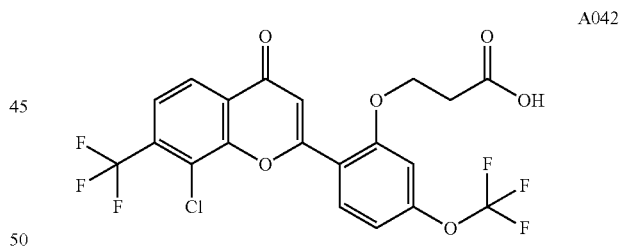

A042

To a solution of methyl 3-(2-(8-chloro-4-oxo-7-(trifluoromethyl)-4H-chromen-2-yl)-5-(trifluoromethoxy)phenoxy)propanoate (50 mg, 97.9 μmol) in the mixed solvent of THF (5 mL) and water (5 mL) was added 3.0 M HCl (261 μL, 783 μmol) at room temperature and the mixture was then stirred at 60° C. for 2 hours. After the reaction was completed, the mixture was extracted with EtOAc (10 mL) three times. The combined organic layer was washed with brine, dried over anhydrous Na$_2$SO$_4$ and concentrated in vacuo. The residue was purified by Prep-HPLC to give 3-[2-[8-chloro-4-oxo-7-(trifluoromethyl)chromen-2-yl]-5-(trifluoromethoxy)phenoxy]propanoic acid (7 mg, 113.7% yield) as a white foam. $^1$H NMR (DMSO-d$_6$, 400 MHz): δ ppm 8.09-8.20 (m, 2H), 7.83-7.98 (m, 1H), 7.31-7.41 (m, 1H), 7.22-7.30 (m, 1H), 7.10 (s, 1H), 4.34-4.45 (m, 2H), 2.74-2.85 (m, 2H). MS obsd. (ESI$^+$) [(M+H)$^+$]:497.1.

Example A043: 3-[2-(8-chloro-4-oxo-chromen-2-yl)-4-methoxy-5-(trifluoromethyl)phenoxy]propanoic acid

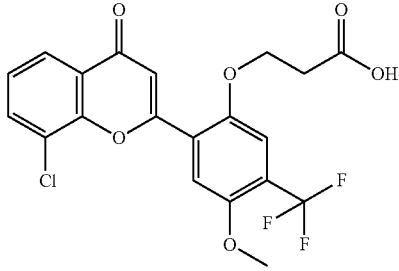

A043

Example A043 was prepared in analogy to the procedure described for the preparation of example A042 by using 3-[5-bromo-2-(8-chloro-4-oxo-chromen-2-yl)-4-methoxy-phenoxy]propanoic acid (Example A007) as the starting material instead of 3-[2-(7-bromo-8-chloro-4-oxo-chromen-2-yl)-5-(trifluoromethoxy)phenoxy]propanoic acid (Example A023) in step 1. $^1$H NMR (DMSO-$d_6$, 400 MHZ): δ ppm 7.99-8.05 (m, 3H), 7.74-7.82 (m, 1H), 7.46-7.57 (m, 2H), 7.06-7.12 (m, 1H), 4.33-4.43 (m, 2H), 3.95 (s, 3H), 2.70-2.80 (m, 2H). MS obsd. (ESI$^+$) [(M+H)$^+$]:443.1.

Example A044: 3-[2-(8-chloro-4-oxo-chromen-2-yl)-4-methyl-5-(trifluoromethyl)phenoxy]propanoic acid

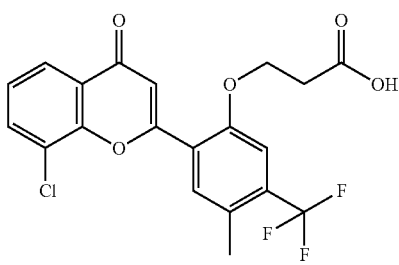

A044

Example A044 was prepared in analogy to the procedure described for the preparation of example A042 by using 3-[5-bromo-2-(8-chloro-4-oxo-chromen-2-yl)-4-methyl-phenoxy]propanoic acid (Example A006) as the starting material instead of 3-[2-(7-bromo-8-chloro-4-oxo-chromen-2-yl)-5-(trifluoromethoxy)phenoxy]propanoic acid (Example A023) in Step 1. $^1$H NMR (DMSO-$d_6$, 400 MHz): δ ppm 7.98-8.08 (m, 2H), 7.90-7.98 (m, 1H), 7.47-7.55 (m, 2H), 7.04 (s, 1H), 4.37-4.47 (m, 2H), 2.74-2.84 (m, 2H), 2.48 (s, 3H). MS obsd. (ESI$^+$) [(M+H)$^+$]:427.1.

Example A045: 3-[2-(8-chloro-5-hydroxy-4-oxo-chromen-2-yl)-5-(trifluoromethyl)phenoxy]propanoic acid

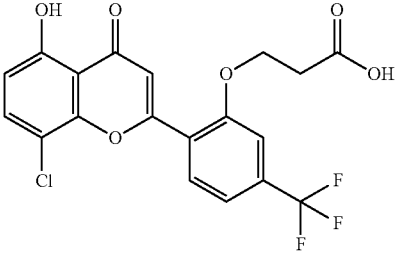

A045

Step 1: Preparation of 1-(3-chloro-2,6-dihydroxy-phenyl)ethanone

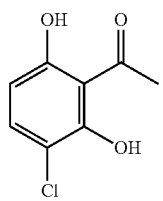

A045a

A mixture of 1-(2,6-dihydroxyphenyl)ethan-1-one (5.0 g, 32.9 mmol), 1-chloropyrrolidine-2,5-dione (5.27 g, 39.4 mmol) in acetic acid (25 mL) was stirred at 50° C. for 2 hours. After the reaction was completed, the mixture was concentrated in vacuo, the residue was triturated with EtOAc (15 mL) and the suspension was then filtered. The filtrate was concentrated in vacuo, the residue was purified by column chromatography on silica gel (eluent with PE:EtOAc=100:1 to 3:1) to give 1-(3-chloro-2,6-dihydroxy-phenyl)ethanone (5.0 g, 81.5% yield) as a yellow solid.

Step 2: Preparation of 1-[3-chloro-2,6-bis(methoxymethoxy)phenyl]ethanone

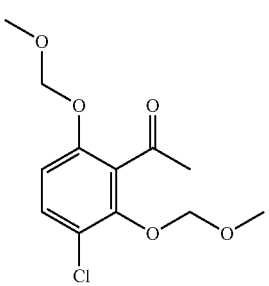

A045b

To a solution of 1-(3-chloro-2,6-dihydroxy-phenyl)ethanone (500.0 mg, 2.68 mmol) in THF (10 mL) cooled at 0° C. was added sodium hydride (321.56 mg, 8.04 mmol) and the mixture was stirred at 0° C. for 20 minutes Then to the resulting solution was added bromomethyl methyl ether (0.66 mL, 8.04 mmol) and the mixture stirred at room temperature for another 30 minutes. After the reaction was completed, the reaction was quenched with water (20 mL) and extracted with EtOAc (50 mL) twice. The combined organic layer was washed with brine, dried over Na$_2$SO$_4$ and concentrated in vacuo. The residue was purified by column chromatography on silica gel (eluted with PE:EtOAc=100:1 to 10:1) to give 1-[3-chloro-2,6-bis(methoxymethoxy)phenyl]ethanone (400 mg, 53.4% yield) as an off-white solid.

Step 3: Preparation of 3-[2-[(E)-3-[3-chloro-2,6-bis(methoxymethoxy)phenyl]-3-oxo-prop-1-enyl]-5-(trifluoromethyl)phenoxy]propanoic acid

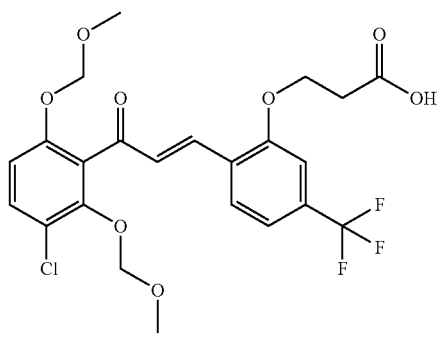

A045c

To a solution of 1-[3-chloro-2,6-bis(methoxymethoxy)phenyl]ethanone (83.1 mg, 0.3 mmol) and 3-[2-formyl-5-(trifluoromethyl)phenoxy]propanoic acid (80 mg, 0.3 mmol) in ethanol (5 mL) was added KOH (171 mg, 3.05 mmol) and the mixture was then stirred at 40° C. for 16 hours. After the reaction was completed, the mixture was diluted with water (20 mL) and adjusted to pH~6 by addition of 1N HCl. The resulting mixture was extracted with EtOAc (20 mL) three times. The combined organic layer was washed with brine (20 mL) twice, dried over Na$_2$SO$_4$ and concentrated in vacuo to give 3-[2-[(E)-3-[3-chloro-2,6-bis(methoxymethoxy)phenyl]-3-oxo-prop-1-enyl]-5-(trifluoromethyl)phenoxy]propanoic acid (150 mg, 97.4% yield) as an orange oil.

Step 4: Preparation of 3-[2-(8-chloro-5-hydroxy-4-oxo-chromen-2-yl)-5-(trifluoromethyl)phenoxy]propanoic acid

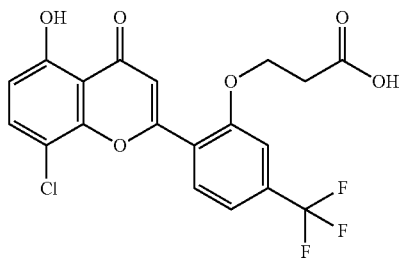

A045

To a solution of 3-[2-[(E)-3-[3-chloro-2,6-bis(methoxymethoxy)phenyl]-3-oxo-prop-1-enyl]-5-(trifluoromethyl)phenoxy]propanoic acid (150 mg, 0.29 mmol) in DMSO (8 ml) was added I$_2$ (5.1 mg, 0.02 mmol) and the mixture was stirred at 140° C. for 2 hours. After the reaction was completed, the mixture was diluted with water (30 mL) and extracted with EtOAc (30 mL) three times. The combined organic layer was washed with brine, dried over Na$_2$SO$_4$ and concentrated in vacuo. The residue was purified by Prep-HPLC to give 3-[2-(8-chloro-5-hydroxy-4-oxo-chromen-2-yl)-5-(trifluoromethyl)phenoxy]propanoic acid (39.3 mg, 37.1% yield) as a yellow solid. $^1$H NMR (DMSO-d$_6$, 400 MHz): δ ppm. 12.53 (s, 1H), 8.11-8.19 (m, 1H), 7.83-7.91 (m, 1H), 7.58-7.65 (m, 2H), 7.14 (s, 1H), 6.89 (d, J=8.8 Hz, 1H), 4.48 (t, J=5.8 Hz, 2H), 2.81 (t, J=5.8 Hz, 2H). MS obsd. (ESI$^+$) [(M+H)$^+$]:429.0.

Example A046: 3-[2-(8-chloro-3-hydroxy-4-oxo-chromen-2-yl)-5-(trifluoromethyl)phenoxy]propanoic acid

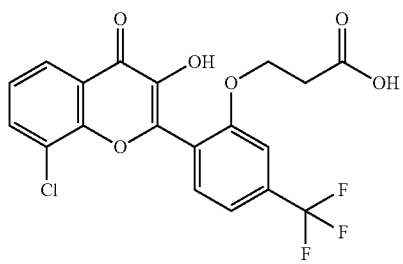 [SMILES: Cc1c(-c2ccc(C(F)(F)F)cc2OCCC(=O)O)oc2c(Cl)cccc2c1=O]

A046

Step 1: Preparation of 3-[2-[(E)-3-(3-chloro-2-hydroxy-phenyl)-3-oxo-prop-1-enyl]-5-(trifluoromethyl)phenoxy]propanoic acid

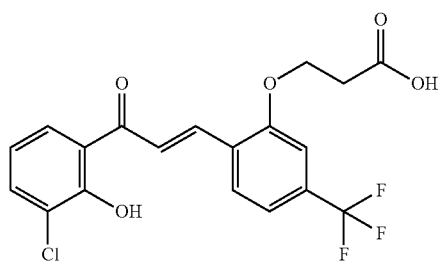

A046a

Compound A046a was prepared in analogy to the procedure described for the preparation of example A003b by using 1-(3-chloro-2-hydroxy-phenyl)ethanone as the starting material instead of 1-(3-chloro-5-fluoro-2-hydroxy-phenyl)ethanone in step 2.

Step 2: Preparation of 3-[2-(8-chloro-3-hydroxy-4-oxo-chromen-2-yl)-5-(trifluoromethyl)phenoxy]propanoic acid

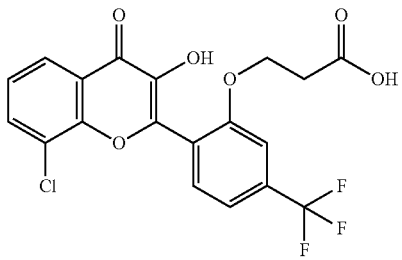

A046

To a solution of 3-[2-[(E)-3-(3-chloro-2-hydroxy-phenyl)-3-oxo-prop-1-enyl]-5-(trifluoromethyl)phenoxy]propanoic acid (100 mg, 240 μmol) in dioxane (3 mL) was added diethylamine (52.3 mg, 0.7 mmol) and H$_2$O$_2$ (0.5 mL, 30%) at room temperature and the reaction was then stirred at room temperature for 2 hours. After the reaction was completed, the mixture was concentrated in vacuo and the residue was purified by Prep-HPLC to give 3-[2-(8-chloro-3-hydroxy-4-oxo-chromen-2-yl)-5-(trifluoromethyl)phenoxy]propanoic acid (70 mg, 22.5% yield) as a white solid. $^1$H NMR (DMSO-d$_6$, 400 MHz): δ ppm 12.21-12.31 (m, 1H), 8.09 (dd, J=8.0, 1.5 Hz, 1H), 8.01 (dd, J=7.8, 1.5 Hz, 1H), 7.79 (d, J=7.6 Hz, 1H), 7.58-7.61 (m, 1H), 7.48-7.55 (m, 2H), 4.39 (t, J=6.1 Hz, 2H), 2.62 (t, J=6.1 Hz, 2H). MS obsd. (ESI$^+$) [(M+H)$^+$]:429.1.

Example A047: 3-[2-(8-chloro-3-methoxy-4-oxo-chromen-2-yl)-5-(trifluoromethyl)phenoxy]propanoic acid

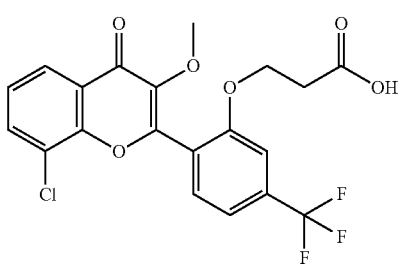

A047

Step 1: Preparation of methyl 3-[2-(8-chloro-3-methoxy-4-oxo-chromen-2-yl)-5-(trifluoromethyl)phenoxy]propanoate

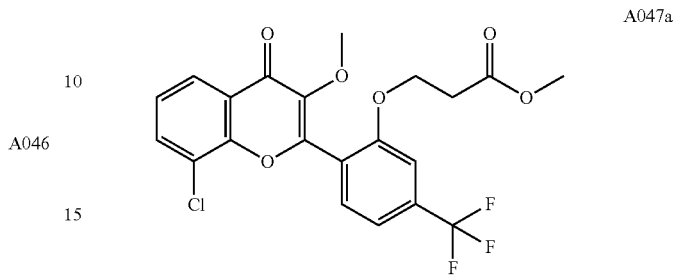

A047a

To a solution of 3-[2-(8-chloro-3-hydroxy-4-oxo-chromen-2-yl)-5-(trifluoromethyl)phenoxy]propanoic acid (Example A046, 70.0 mg, 0.16 mmol) and cesium carbonate (150 mg, 0.49 mmol) in DMF (5 mL) was added iodomethane (75 mg, 0.48 mmol) and the mixture was stirred at 40° C. for 2 hours. After the reaction was completed, the reaction mixture was diluted with water (30 mL) and extracted with EtOAc (20 mL) three times. The combined organic layer was washed with brine (20 mL), dried over Na$_2$SO$_4$ and concentrated in vacuo. The residue was purified by column chromatography on silica gel (eluent with PE:EtOAc=3:1) to give methyl 3-[2-(8-chloro-3-methoxy-4-oxo-chromen-2-yl)-5-(trifluoromethyl)phenoxy]propanoate (50 mg, 57.4% yield) as a yellow oil. MS obsd. (ESI$^+$) [(M+H)$^+$]:457.1.

Step 2: Preparation of 3-[2-(8-chloro-3-methoxy-4-oxo-chromen-2-yl)-5-(trifluoromethyl)phenoxy]propanoic acid

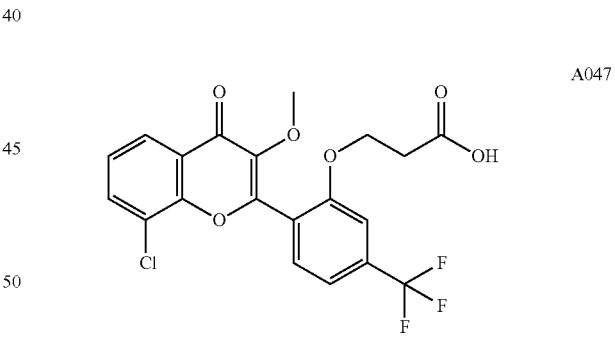

A047

A mixture of methyl 3-[2-(8-chloro-3-methoxy-4-oxo-chromen-2-yl)-5-(trifluoromethyl)phenoxy]propanoate (50 mg, 57.4% yield) in hydrochloric acid (36%~38%) was stirred at 100° C. for 2 hours. After the reaction was completed, the mixture was concentrated in vacuo and the residue was purified by Prep-HPLC to give 3-[2-(8-chloro-3-methoxy-4-oxo-chromen-2-yl)-5-(trifluoromethyl)phenoxy]propanoic acid (21.6 mg, 45.7% yield) as a white solid. $^1$H NMR (DMSO-d$_6$, 400 MHz): δ ppm 12.24-12.32 (m, 1H), 8.07-8.12 (m, 1H), 8.01 (dd, J=7.8, 1.5 Hz, 1H), 7.76-7.81 (m, 1H), 7.58-7.61 (m, 1H), 7.51 (s, 2H), 4.39 (t, J=6.1 Hz, 2H), 3.75 (s, 3H), 2.62 (t, J=6.1 Hz, 2H). MS obsd. (ESI$^+$) [(M+H)$^+$]:443.1.

Example A048: 2-[2-(8-chloro-4-oxo-chromen-2-yl)-5-(trifluoromethoxy)phenoxy]acetic acid

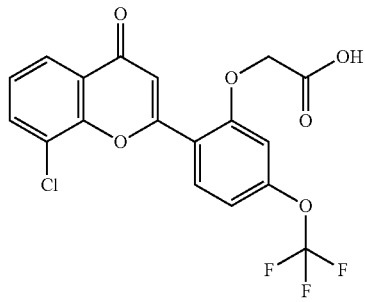
A048

Step 1: Preparation of methyl 2-[2-(8-chloro-4-oxo-chromen-2-yl)-5-(trifluoromethoxy)phenoxy]acetate

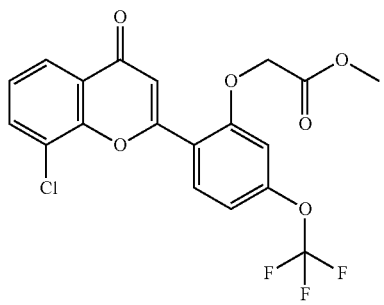
A048

To a solution of 8-chloro-2-[2-hydroxy-4-(trifluoromethoxy)phenyl]chromen-4-one (Int-9, 1.2 g, 3.36 mmol, as the "CORE" in Table 3) and methyl 2-bromoacetate (772 mg, 5.05 mmol, as the "SM3" in Table 3) in DMF (10 mL) was added $K_2CO_3$ (1.39 g, 10.1 mmol) and the mixture was stirred at 50° C. overnight. After the reaction was completed, the reaction mixture was diluted with water (20 mL) and adjusted to PH~4 by addition of 4N HCl. The resulting suspension was extracted with EtOAc (30 ml) three times. The combined organic layer was washed with brine, dried over $Na_2SO_4$ and concentrated in vacuo. The residue was purified by column chromatography on silica gel (eluted with PE:EtOAc=100:1 to 3:1) to give methyl 2-[2-(8-chloro-4-oxo-chromen-2-yl)-5-(trifluoromethoxy)phenoxy]acetate (1.0 g, 69.3% yield) as a yellow solid. MS obsd. (ESI$^+$) [(M+H)$^+$]: 429.1.

Step 2: Preparation of 2-[2-(8-chloro-4-oxo-chromen-2-yl)-5-(trifluoromethoxy)phenoxy]acetic acid

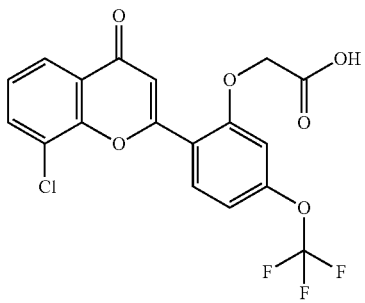
A048

To a mixture solution of methyl 2-[2-(8-chloro-4-oxo-chromen-2-yl)-5-(trifluoromethoxy)phenoxy]acetate (1.0 g, 2.33 mmol) in THF (5 ml) and water (5 ml) was added LiOH (335 mg, 14 mmol) and the mixture was stirred at room temperature for 2 hours. After the reaction was completed, the reaction was adjusted to pH~4 by addition of 4N HCl and then extracted with EtOAc (50 mL) three times. The combined organic layer was washed with brine, dried over anhydrous $Na_2SO_4$ and concentrated in vacuo. The residue was purified by Prep-HPLC to give 2-[2-(8-chloro-4-oxo-chromen-2-yl)-5-(trifluoromethoxy)phenoxy]acetic acid (700 mg, 72.4% yield) as a white foam. $^1$H NMR (DMSO-$d_6$, 400 MHz): δ ppm 8.08-8.18 (m, 1H), 7.96-8.05 (m, 2H), 7.46-7.57 (m, 1H), 7.31-7.37 (m, 1H), 7.21-7.31 (m, 2H), 5.07 (s, 2H). MS obsd. (ESI$^+$) [(M+H)$^+$]:415.1.

The following Example A049 to Example A072 were prepared in analogy to the procedure described for the preparation of Example A048, replacing 8-chloro-2-[2-hydroxy-4-(trifluoromethoxy)phenyl]chromen-4-one (Int-9) with "CORE", and replacing methyl 2-bromoacetate with "SM3" in step1. The "CORE" and "SM3" are the reagent indicated in Table 3.

TABLE 3

Compounds synthesis and characterization

| Example No. | Compounds Name and Structure | CORE and SM3 | $^1$H NMR and (ESI$^+$) |
|---|---|---|---|
| A049 | 2-[2-(8-chloro-4-oxo-chromen-2-yl)-5-methyl-phenoxy]acetic acid | CORE: Int-2 SM3: methyl 2-bromoacetate | $^1$H NMR (DMSO-$d_6$, 400 MHz): δ ppm 13.07-13.37 (m, 1H), 7.97-8.02 (m, 2H), 7.89-7.96 (m, 1H), 7.44-7.53 (m, 1H), 7.34-7.40 (m, 1H), 7.00-7.09 (m, 2H), 4.85-4.96 (m, 2H), 2.35-2.43 (m, 3H). MS obsd. (ESI$^+$) [(M + H)$^+$]: 345.1. |

TABLE 3-continued

Compounds synthesis and characterization

| Example No. | Compounds Name and Structure | CORE and SM3 | $^1$H NMR and (ESI$^+$) |
|---|---|---|---|
| A050 | 2-[2-(8-chloro-4-oxo-chromen-2-yl)-4,5-dimethoxy-phenoxy]acetic acid | CORE: Int-10 SM3: methyl 2-bromoacetate | $^1$H NMR (DMSO-d$_6$, 400 MHz): δ ppm 7.94-8.05 (m, 2H), 7.59-7.69 (m, 1H), 7.39-7.52 (m, 2H), 6.86 (s, 1H), 4.96 (s, 2H), 3.86-3.95 (m, 3H), 3.75-3.84 (m, 3H). MS obsd. (ESI$^+$) [(M + H)$^+$]: 391.0 |
| A051 | 2-[2-(8-chloro-4-oxo-chromen-2-yl)-5-(trifluoromethyl)phenoxy] acetic acid | CORE: Int-1 SM3: methyl 2-bromoacetate | $^1$H NMR (DMSO-d$_6$, 400 MHz): δ ppm 12.82-13.52 (m, 1H), 8.21 (d, J = 8.1 Hz, 1H), 7.90-8.09 (m, 2H), 7.61 (d, J = 8.3 Hz, 1H), 7.44-7.57 (m, 2H), 7.38 (s, 1H), 5.02 (s, 2H). MS obsd. (ESI$^+$) [(M + H)$^+$]: 399.1. |
| A052 | 4-[2-(8-chloro-4-oxo-chromen-2-yl)-5-(trifluoromethyl)phenoxy] butanoic acid | CORE: Int-1 SM3: methyl 4-bromobutanoate | $^1$H NMR (DMSO-d$_6$, 400 MHz): δ ppm 12.01-12.20 (m, 1H), 8.08-8.15 (m, 1H), 8.03 (dd, J = 7.9, 1.2 Hz, 2H), 7.47-7.60 (m, 3H), 7.07 (s, 1H), 4.29 (t, J = 6.5 Hz, 2H), 2.37-2.44 (m, 2H), 1.97-2.06 (m, 2H). MS obsd. (ESI$^+$) [(M + H)$^+$]: 427.2. |
| A053 | 4-[2-(8-chloro-4-oxo-chromen-2-yl)-5-(trifluoromethoxy)phenoxy] butanoic acid | CORE: Int-9 SM3: methyl 4-bromobutanoate | $^1$H NMR (DMSO-d$_6$, 400 MHz): δ ppm 12.23 (s, 1H), 8.04-8.08 (m, 1H), 7.99-8.03 (m, 2H), 7.48-7.53 (m, 1H), 7.29-7.32 (m, 1H), 7.20-7.25 (m, 1H), 7.01-7.04 (m, 1H), 4.20-4.26 (m, 2H), 2.37-2.44 (m, 2H), 1.98-2.06 (m, 2H). MS obsd. (ESI$^+$) [(M + H)$^+$]: 443.1. |

TABLE 3-continued

Compounds synthesis and characterization

| Example No. | Compounds Name and Structure | CORE and SM3 | ¹H NMR and (ESI⁺) |
|---|---|---|---|
| A054 | 4-[5-bromo-2-(8-chloro-4-oxo-chromen-2-yl)-4-methyl-phenoxy]butanoic acid 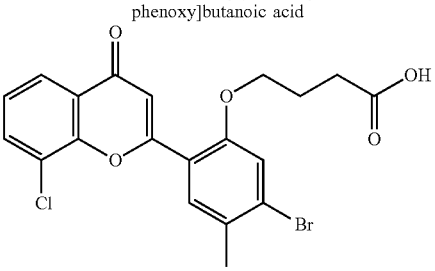 | CORE: Int-6 SM3: methyl 4-bromobutanoate | ¹H NMR (DMSO-d₆, 400 MHz): δ ppm 12.17 (s, 1H), 7.96-8.04 (m, 2H), 7.83-7.90 (m, 1H), 7.46-7.55 (m, 2H), 6.96-7.02 (m, 1H), 4.15-4.22 (m, 2H), 2.35-2.41 (m, 5H), 1.92-2.05 (m, 2H). MS obsd. (ESI⁺) [(M + H)⁺]: 451.1 |
| A055 | 4-[5-bromo-2-(8-chloro-4-oxo-chromen-2-yl)phenoxy]butanoic acid 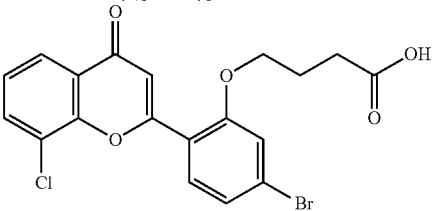 | CORE: Int-4 SM3: methyl 4-bromobutanoate | ¹H 1 NMR (DMSO-d₆, 400 MHz): δ ppm 12.03-12.24 (m, 1H), 7.96-8.04 (m, 2H), 7.84-7.92 (m, 1H), 7.46-7.54 (m, 2H), 7.37-7.45 (m, 1H), 7.01-7.05 (m, 1H), 4.16-4.26 (m, 2H), 2.36-2.44 (m, 2H), 1.96-2.06 (m, 2H). MS obsd. (ESI⁺) [(M + H)⁺]: 437.1 |
| A056 | 4-[2-(8-chloro-4-oxo-chromen-2-yl)-4,5-dimethoxy-phenoxy]butanoic acid 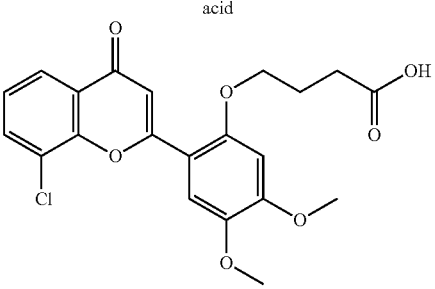 | CORE: Int-10 SM3: methyl 4-bromobutanoate | ¹H NMR (DMSO-d₆, 400 MHz): δ ppm 11.78-12.40 (br s, 1H), 7.73-8.23 (m, 2H), 7.32-7.63 (m, 2H), 6.94-7.15 (s, 1H), 6.44-6.92 (m, 1H), 4.05-4.30 (m, 2H), 3.84-3.94 (m, 3H), 3.63-3.84 (m, 3H), 2.41-2.47 (m, 2H), 1.88-2.08 (m, 2H). MS obsd. (ESI⁺) [(M + H)⁺]: 419.1 |
| A057 | 4-[5-chloro-2-(8-chloro-4-oxo-chromen-2-yl)-4-methyl-phenoxy]butanoic acid 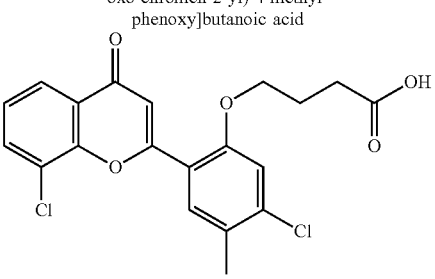 | CORE: Int-5 SM3: methyl 4-bromobutanoate | ¹H NMR (DMSO-d₆, 400 MHz): δ ppm 12.27 (s, 1H), 7.96-8.04 (m, 2H), 7.83-7.89 (m, 1H), 7.46-7.53 (m, 1H), 7.34-7.40 (m, 1H), 6.97-7.02 (m, 1H), 4.14-4.22 (m, 2H), 2.32-2.43 (m, 5H), 1.95-2.05 (m, 2H). MS obsd. (ESI⁺) [(M + H)⁺]: 407.1. |

TABLE 3-continued

Compounds synthesis and characterization

| Example No. | Compounds Name and Structure | CORE and SM3 | $^1$H NMR and (ESI$^+$) |
|---|---|---|---|
| A058 | 4-[5-bromo-2-(8-chloro-4-oxo-chromen-2-yl)-4-methoxy-phenoxy]butanoic acid | CORE: Int-7<br>SM3: methyl 4-bromobutanoate | $^1$H NMR (DMSO-d$_6$, 400 MHz): δ ppm 12.22 (s, 1H), 7.96-8.05 (m, 2H), 7.59-7.68 (m, 1H), 7.45-7.57 (m, 2H), 7.03-7.09 (m, 1H), 4.13-4.20 (m, 2H), 3.93 (s, 3H), 2.35-2.42 (m, 2H), 1.93-2.03 (m, 2H). MS obsd. (ESI$^+$) [(M + H)$^+$]: 467.1. |
| A059 | 4-[2-(8-chloro-4-oxo-chromen-2-yl)-5-methyl-phenoxy]butanoic acid | CORE: Int-2<br>SM3: methyl 4-bromobutanoate | $^1$H NMR (DMSO-d$_6$, 400 MHz): δ ppm 12.26 (s, 1H), 7.95-8.03 (m, 2H), 7.81-7.91 (m, 1H), 7.42-7.52 (m, 1H), 7.09-7.15 (m, 1H), 6.96-7.07 (m, 2H), 4.12-4.22 (m, 2H), 2.39-2.45 (m, 5H), 1.97-2.08 (m, 2H). MS obsd. (ESI$^+$) [(M + H)$^+$]: 373.1 |
| A060 | 4-[2-(8-chloro-4-oxo-chromen-2-yl)-5-methoxy-4-methyl-phenoxy]butanoic acid | CORE: Int-12<br>SM3: methyl 4-bromobutanoate | $^1$H NMR (DMSO-d$_6$, 400 MHz): δ ppm 12.05 (s, 1H), 7.97 (d, J = 7.82 Hz, 2H), 7.69-7.80 (m, 1H), 7.42-7.52 (m, 1H), 7.02 (s, 1H), 6.75-6.84 (m, 1H), 4.19-4.28 (m, 2H), 3.92 (s, 3H), 2.39-2.46 (m, 2H), 2.16 (s, 3H), 1.99-2.10 (m, 2H). MS obsd. (ESI$^+$) [(M + H)$^+$]: 403.1. |
| A061 | 3-[2-(8-chloro-4-oxo-chromen-2-yl)-5-(trifluoromethoxy)phenoxy]-2,2-dimethyl-propanoic acid | CORE: Int-9<br>SM3: methyl 2,2-dimethyl-3-(tosyloxy)propanoate | $^1$H NMR (DMSO-d$_6$, 400 MHz): δ ppm 7.98-8.07 (m, 3H), 7.44-7.56 (m, 1H), 7.29-7.38 (m, 1H), 7.18-7.28 (m, 1H), 6.91-7.02 (m, 1H), 4.24 (s, 2H), 1.24 (s, 6H). MS obsd. (ESI$^+$) [(M + H)$^+$]: 457.1. |

TABLE 3-continued

Compounds synthesis and characterization

| Example No. | Compounds Name and Structure | CORE and SM3 | $^1$H NMR and (ESI$^+$) |
|---|---|---|---|
| A062 | 3-[2-(8-chloro-4-oxo-chromen-2-yl)-5-(trifluoromethyl)phenoxy]-2,2-dimethyl-propanoic acid | CORE: Int-1<br>SM3: methyl 2,2-dimethyl-3-(tosyloxy)propanoate | $^1$H NMR (DMSO-d$_6$, 400 MHz): δ ppm 12.16-12.41 (m, 1H), 8.25-8.33 (m, 1H), 8.07 (d, J = 8.2 Hz, 1H), 7.67-7.81 (m, 3H), 7.54-7.63 (m, 1H), 7.29-7.38 (m, 1H), 3.76-3.95 (m, 2H), 1.00 (s, 6H). MS obsd. (ESI$^+$) [(M + H)$^+$]: 441.1. |
| A063 | 3-[2-(8-chloro-4-oxo-chromen-2-yl)-5-methyl-phenoxy]-2,2-dimethyl-propanoic acid | CORE: Int-2<br>SM3: methyl 2,2-dimethyl-3-(tosyloxy)propanoate | $^1$H NMR (DMSO-d$_6$, 400 MHz): δ ppm 12.35 (s, 1H), 7.94-8.02 (m, 2H), 7.81-7.89 (m, 1H), 7.42-7.54 (m, 1H), 7.10-7.18 (m, 1H), 6.96-7.07 (m, 2H), 4.19 (s, 2H), 2.40 (s, 3H), 1.26 (s, 6H). MS obsd. (ESI$^+$) [(M + H)$^+$]: 387.1. |
| A064 | 3-[5-chloro-2-(8-chloro-4-oxo-chromen-2-yl)-4-methyl-phenoxy]-2,2-dimethyl-propanoic acid | CORE: Int-15<br>SM3: methyl 2,2-dimethyl-3-(tosyloxy)propanoate | $^1$H NMR (DMSO-d$_6$, 400 MHz): δ ppm 7.95-8.05 (m, 2H), 7.81-7.90 (m, 1H), 7.46-7.54 (m, 1H), 7.35-7.43 (m, 1H), 6.95 (s, 1H), 4.21 (s, 2H), 2.36 (s, 3H), 1.23 (s, 6H). MS obsd. (ESI$^+$) [(M + H)$^+$]: 421.1. |
| A065 | 5-[2-(8-chloro-4-oxo-chromen-2-yl)-5-(trifluoromethyl)phenoxy]pentanoic acid | CORE: Int-1<br>SM3: methyl 5-bromopentanoate | $^1$H NMR (DMSO-d$_6$, 400 MHz): δ ppm 11.85-12.14 (br s, 1H), 8.09-8.17 (m, 1H), 7.98-8.08 (m, 2H), 7.44-7.61 (m, 3H), 7.06-7.14 (m, 1H), 4.23-4.32 (m, 2H), 2.29 (t, J = 7.3 Hz, 2H), 1.76-1.88 (m, 2H), 1.60-1.72 (m, 2H). MS obsd. (ESI$^+$) [(M + H)$^+$]: 441.3. |

TABLE 3-continued

Compounds synthesis and characterization

| Example No. | Compounds Name and Structure | CORE and SM3 | $^1$H NMR and (ESI$^+$) |
|---|---|---|---|
| A066 | 7-[2-(8-chloro-4-oxo-chromen-2-yl)-5-(trifluoromethyl)phenoxy]heptanoic acid 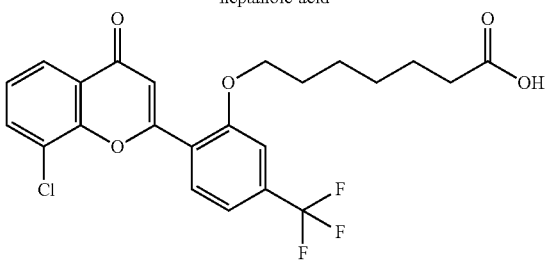 | CORE: Int-1 SM3: methyl 7-bromoheptanoate | $^1$H NMR (DMSO-d$_6$, 400 MHz): δ ppm 11.92 (br s, 1H), 8.10-8.17 (m, 1H), 7.98-8.07 (m, 2H), 7.45-7.58 (m, 3H), 7.10 (s, 1H), 4.21-4.30 (m, 2H), 2.11-2.20 (m, 2H), 1.75-1.87 (m, 2H), 1.40-1.54 (m, 4H), 1.26-1.39 (m, 2H). MS obsd. (ESI$^+$) [(M + H)$^+$]: 469.2 |
| A067 | 2-[1-[[2-(8-chloro-4-oxo-chromen-2-yl)-4,5-dimethoxy-phenoxy]methyl]cyclopropyl]acetic acid 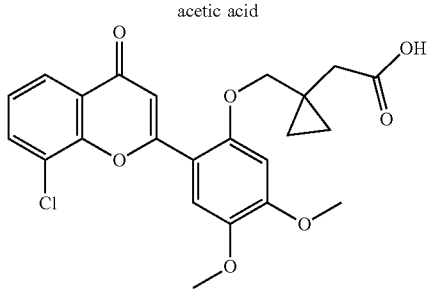 | CORE: Int-10 SM3: methyl 2-[1-(bromomethyl)cyclopropyl]acetate (CAS #: 855473-50-6, Cat.#: PBGJ3164, from PharmaBlock (NanJing) R&D Co. Ltd). | $^1$H NMR (DMSO-d$_6$, 400 MHz): δ ppm 13.11-13.25 (m, 1H), 8.95-9.08 (m, 2H), 8.63 (s, 1H), 8.46-8.56 (m, 1H), 8.23 (s, 1H), 7.87 (s, 1H), 5.12-5.15 (m, 2H), 4.94 (s, 3H), 4.86 (s, 3H), 3.45-3.49 (m, 2H), 1.61-1.74 (m, 4H). MS obsd. (ESI$^+$) [(M + H)$^+$]: 445.1. |
| A068 | 2-[1-[[5-bromo-2-(8-chloro-4-oxo-chromen-2-yl)-4-methyl-phenoxy]methyl]cyclopropyl]acetic acid 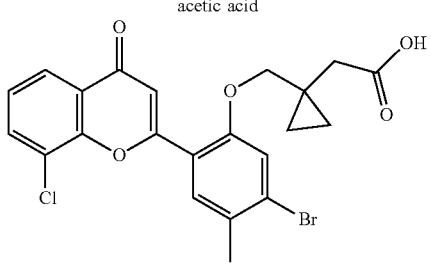 | CORE: Int-6 SM3: methyl 2-[1-(bromomethyl)cyclopropyl]acetate | $^1$H NMR (DMSO-d$_6$, 400 MHz): δ ppm 7.94-8.05 (m, 2H), 7.83-7.90 (m, 1H), 7.41-7.56 (m, 2H), 7.04-7.13 (m, 1H), 4.11 (s, 2H), 2.38 (s, 5H), 0.51-0.69 (m, 4H). MS obsd. (ESI$^+$) [(M + H)$^+$]: 477.1. |
| A069 | 2-[1-[[5-bromo-2-(8-chloro-4-oxo-chromen-2-yl)phenoxy]methyl]cyclopropyl]acetic acid 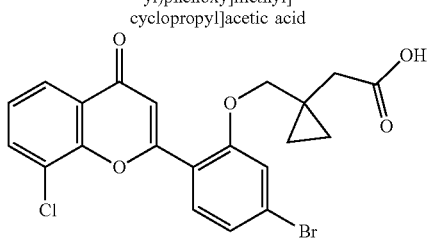 | CORE: Int-4 SM3: methyl 2-[1-(bromomethyl)cyclopropyl]acetate | $^1$H NMR (DMSO-d$_6$, 400 MHz): δ ppm 12.19 (s, 1H), 7.96-8.07 (m, 2H), 7.79-7.94 (m, 1H), 7.47-7.56 (m, 1H), 7.36-7.45 (m, 2H), 7.05-7.17 (m, 1H), 4.17 (s, 2H), 2.43 (s, 2H), 0.53-0.72 (m, 4H). MS obsd. (ESI$^+$) [(M + H)$^+$]: 463.1. |

TABLE 3-continued

Compounds synthesis and characterization

| Example No. | Compounds Name and Structure | CORE and SM3 | $^1$H NMR and (ESI$^+$) |
|---|---|---|---|
| A070 | 2-[5-bromo-2-(8-chloro-4-oxo-chromen-2-yl)phenoxy]-2-methyl-propanoic acid | CORE: Int-4<br>SM3: methyl 2-bromo-2-methyl-propanoate | $^1$H NMR (DMSO-d$_6$, 400 MHz): δ ppm 13.54 (br s, 1H), 8.01 (dd, J = 7.9, 1.9 Hz, 2H), 7.84 (d, J = 8.4 Hz, 1H), 7.38-7.56 (m, 2H), 7.05 (d, J = 1.7 Hz, 1H), 6.97 (s, 1H), 1.62 (s, 6H). MS obsd. (ESI$^+$) [(M + H)$^+$]: 437.0. |
| A071 | 5-[2-(8-chloro-4-oxo-chromen-2-yl)-5-(trifluoromethoxy)phenoxy]-2,2-dimethyl-pentanoic acid | CORE: Int-9<br>SM3: methyl 5-bromo-2,2-dimethyl-pentanoate | $^1$H NMR (DMSO-d$_6$, 400 MHz): δ ppm 12.03 (br s, 1H), 7.98-8.08 (m, 3H), 7.45-7.56 (m, 1H), 7.16-7.30 (m, 2H), 7.00-7.08 (m, 1H), 4.13-4.23 (m, 2H), 1.69-1.78 (m, 2H), 1.59-1.65 (m, 2H), 1.08-1.15 (m, 8H). MS obsd. (ESI$^+$) [(M + H)$^+$]: 485.1. |
| A072 | 3-[[5-bromo-2-(8-chloro-4-oxo-chromen-2-yl)phenoxy]methyl]benzoic acid | CORE: Int-4<br>SM3: methyl 3-(bromomethyl)benzoate | $^1$H NMR (DMSO-d$_6$, 400 MHz): δ ppm 12.79-13.18 (br s, 1H), 8.04-8.09 (m, 1H), 7.88-8.01 (m, 4H), 7.74 (d, J = 7.8 Hz, 1H), 7.62 (d, J = 1.7 Hz, 1H), 7.40-7.57 (m, 3H), 7.00 (s, 1H), 5.44 (s, 2H). MS obsd. (ESI$^+$) [(M + H)$^+$]: 485.0. |
| A073 | 2-[5-bromo-2-(8-chloro-4-oxo-chromen-2-yl)-4-methyl-phenoxy]acetic acid | CORE: Int-6<br>SM3: methyl 2-bromoacetate | $^1$H NMR (DMSO-d$_6$, 400 MHz): δ ppm 7.97-8.05 (m, 2H), 7.90-7.96 (m, 1H), 7.41-7.54 (m, 2H), 7.27-7.35 (m, 1H), 4.96 (s, 2H), 2.36-2.43 (m, 3H). MS obsd. (ESI$^+$) [(M + H)$^+$]: 423.1. |

Example A074: 3-[[2-[2-(8-chloro-4-oxo-chromen-2-yl)-5-(trifluoromethyl)phenoxy]acetyl]amino]cyclobutanecarboxylic acid

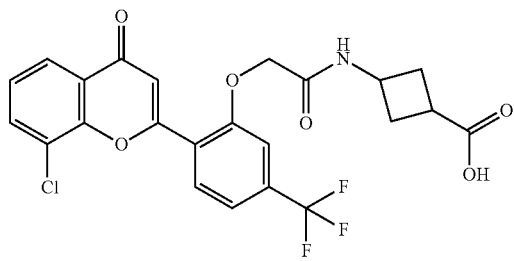

A074

Step 1: Preparation of methyl 3-[[2-[2-(8-chloro-4-oxo-chromen-2-yl)-5-(trifluoromethyl)phenoxy]acetyl]amino]cyclobutanecarboxylate

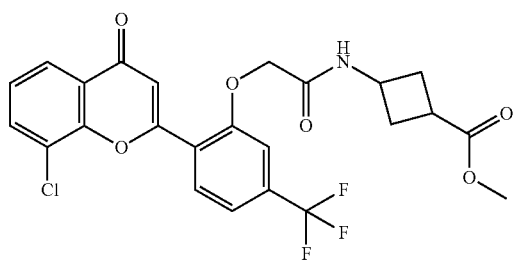

A074a

To a solution of 2-[2-(8-chloro-4-oxo-chromen-2-yl)-5-(trifluoromethyl)phenoxy]acetic acid (Example A051, 200.0 mg, 0.5 mmol), methyl 3-aminocyclobutanecarboxylate (77.8 mg, 0.60 mmol) and DIPEA (0.25 mL, 1.42 mmol) in DMF (5 mL) was added HATU (269.26 mg, 0.710 mmol) and the reaction mixture was stirred at room temperature for 2 hours. After reaction was completed, the reaction was quenched with water (30 mL) and extracted with EtOAc (30 mL) three times. The combined organic layer was washed with brine (40 mL), dried over $Na_2SO_4$ and concentrated in vacuo. The residue was purified by column chromatography on silica gel (eluent with PE:EtOAc=1:1) to afford methyl 3-[[2-[2-(8-chloro-4-oxo-chromen-2-yl)-5-(trifluoromethyl)phenoxy]acetyl]amino]cyclobutanecarboxylate (150 mg, 58.1% yield) as a light yellow oil. MS obsd. (ESI$^+$) [(M+H)$^+$]: 510.0.

Step 2: Preparation of 3-[[2-[2-(8-chloro-4-oxo-chromen-2-yl)-5-(trifluoromethyl)phenoxy]acetyl]amino]cyclobutanecarboxylic acid

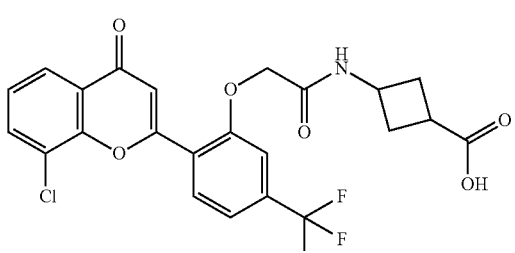

A074

To a solution of methyl 3-[[2-[2-(8-chloro-4-oxo-chromen-2-yl)-5-(trifluoromethyl)phenoxy]acetyl]amino]cyclobutanecarboxylate (150.0 mg, 0.29 mmol) in a mixed solvent of THF (8 mL) and water (2 mL) was added lithium hydroxide (44 mg, 2.0 mmol) and the mixture was stirred at 25° C. for 2 hours. After the reaction was completed, the mixture was adjusted to pH~3 by addition of HCl (1 M). The resulting suspension was then filtered and the solid was collected to give 3-[[2-[2-(8-chloro-4-oxo-chromen-2-yl)-5-(trifluoromethyl)phenoxy]acetyl]amino]cyclobutanecarboxylic acid (114.7 mg, 58.09% yield) as a white solid. $^1$H NMR (DMSO-d$_6$, 400 MHz): δ ppm 11.99-12.28 (br s, 1H), 8.44-8.52 (m, 1H), 8.16 (d, J=7.9 Hz, 1H), 8.03 (d, J=7.9 Hz, 2H), 7.61 (dd, J=8.1, 0.7 Hz, 1H), 7.52 (t, J=7.9 Hz, 1H), 7.39-7.44 (m, 1H), 7.27 (s, 1H), 4.77-4.88 (m, 2H), 4.11-4.26 (m, 1H), 2.66-2.80 (m, 1H), 2.33-2.42 (m, 2H), 1.99-2.11 (m, 2H). MS obsd. (ESI$^+$) [(M+H)$^+$]: 496.0.

Example A075: (2R)-1-[3-[5-bromo-2-(8-chloro-4-oxo-chromen-2-yl)phenoxy]propanoyl]pyrrolidine-2-carboxylic acid

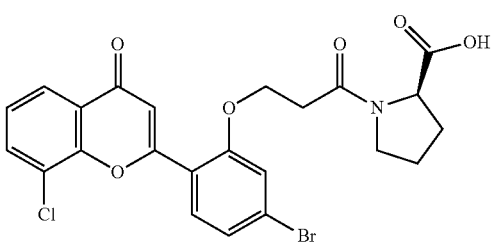

A075

Step 1: Preparation of tert-butyl (2R)-1-[3-[5-bromo-2-(8-chloro-4-oxo-chromen-2-yl)phenoxy]propanoyl]pyrrolidine-2-carboxylate

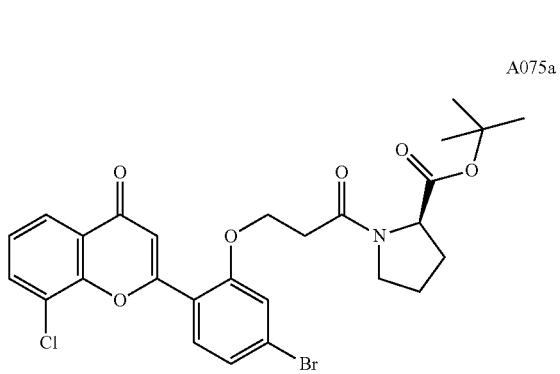 [SMILES: CC(C)(C)OC(=O)[C@H]1CCCN1C(=O)CCOc1cc(Br)ccc1-c1cc(=O)c2cccc(Cl)c2o1]

A075a

To a solution of 3-[5-bromo-2-(8-chloro-4-oxo-chromen-2-yl)phenoxy]propanoic acid (Example A004, 200.0 mg, 0.470 mmol, as the "EX" in Table 4), tert-butyl (2R)-pyrrolidine-2-carboxylate (121.26 mg, 0.710 mmol, as the "AMINE" in Table 4) and DIPEA (0.25 mL, 1.42 mmol) in DMF (5 mL) was added HATU (269.26 mg, 0.710 mmol) and the reaction mixture was stirred at room temperature for 2 hours. After reaction was completed, the reaction was quenched with water (30 mL) and extracted with EtOAc (30 mL) three times. The combined organic layer was washed with brine (40 mL), dried over $Na_2SO_4$ and concentrated in vacuo. The residue was purified by column chromatography on silica gel (eluted with PE:EtOAc=1:1) to afford tert-butyl (2R)-1-[3-[5-bromo-2-(8-chloro-4-oxo-chromen-2-yl)phenoxy]propanoyl]pyrrolidine-2-carboxylate (200 mg, 73.44% yield) as a light yellow oil. MS obsd. (ESI$^+$) [(M+H)$^+$]: 576.0.

Step 2: Preparation of (2R)-1-[3-[5-bromo-2-(8-chloro-4-oxo-chromen-2-yl)phenoxy]propanoyl]pyrrolidine-2-carboxylic acid

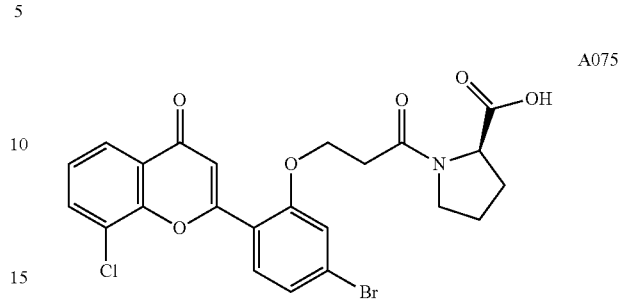

A075

To a solution of tert-butyl (2R)-1-[3-[5-bromo-2-(8-chloro-4-oxo-chromen-2-yl)phenoxy]propanoyl]pyrrolidine-2-carboxylate (200.0 mg, 0.350 mmol) in DCM (2 mL) was added TFA (2.0 mL, 25.96 mmol) and the mixture was then stirred at room temperature for 4 hours. After the reaction was completed, the mixture was concentrated in vacuo and the residue was purified by Prep-HPLC to give (2R)-1-[3-[5-bromo-2-(8-chloro-4-oxo-chromen-2-yl)phenoxy]propanoyl]pyrrolidine-2-carboxylic acid (85.1 mg, 46.97% yield) as a white solid. $^1$H NMR (DMSO-d$_6$, 400 MHz): δ ppm 12.38 (s, 1H), 7.99-8.01 (m, 2H), 7.88 (d, J=8.5 Hz, 1H), 7.46-7.54 (m, 2H), 7.43 (d, J=8.4 Hz, 1H), 6.98 (d, J=8.7 Hz, 1H), 4.37-4.49 (m, 2H), 4.26 (dd, J=8.9, 3.3 Hz, 1H), 3.50-3.61 (m, 2H), 3.39-3.46 (m, 1H), 2.87-2.92 (m, 1H), 2.74 (dt, J=7.4, 4.5 Hz, 1H), 2.09-2.15 (m, 1H), 1.81-1.92 (m, 2H). MS obsd. (ESI$^+$) [(M+H)$^+$]: 520.0.

The following Example A076 to Example A083 were prepared in analogy to the procedure described for the preparation of Example A075, replacing 3-[5-bromo-2-(8-chloro-4-oxo-chromen-2-yl)phenoxy]propanoic acid (Example A004) with "EX", tert-butyl (2R)-pyrrolidine-2-carboxylate "AMINE" in step1. The "EX" and "AMINE" are the reagents indicated in Table 4.

TABLE 4

Compounds synthesis and characterization

| Example No. | Compounds Name and Structure | EX and AMINE | $^1$H NMR and (ESI$^+$) |
|---|---|---|---|
| A076 | (2S)-1-[3-[5-bromo-2-(8-chloro-4-oxo-chromen-2-yl)phenoxy]propanoyl]pyrrolidine-2-carboxylic acid | EX: A004 AMINE: tert-butyl (2S)-pyrrolidine-2-carboxylate | $^1$H NMR (DMSO-d$_6$, 400 MHz): δ ppm 12.34 (s, 1H), 7.99-8.01 (m, 2H), 7.88 (d, J = 8.4 Hz, 1H), 7.46-7.56 (m, 2H), 7.43 (d, J = 8.4 Hz, 1H), 6.98 (d, J = 8.7 Hz, 1H), 4.37-4.49 (m, 2H), 4.26 (dd, J = 8.9, 3.3 Hz, 1H), 3.50-3.67 (m, 2H), 3.39-3.46 (m, 1H), 2.87-2.92 (m, 1H), 2.76 (dt, J = 7.4, 4.5 Hz, 1H), 2.09-2.19 (m, 1H), 1.81-1.92 (m, 2H). MS obsd. (ESI$^+$) [(M + H)$^+$]: 520.0. |

TABLE 4-continued

Compounds synthesis and characterization

| Example No. | Compounds Name and Structure | EX and AMINE | 1H NMR and (ESI+) |
|---|---|---|---|
| A077 | (2R)-1-[2-[2-(8-chloro-4-oxo-chromen-2-yl)-5-methyl-phenoxy]acetyl]pyrrolidine-2-carboxylic acid | EX: A004 AMINE: tert-butyl (2R)-pyrrolidine-2-carboxylate | $^1$H NMR (DMSO-$d_6$, 400 MHz): δ ppm 7.87-8.02 (m, 3H), 7.39-7.53 (m, 2H), 7.00-7.08 (m, 2H), 5.06 (s, 2H), 4.26-4.36 (m, 1H), 3.53-3.69 (m, 2H), 2.38 (s, 3H), 1.82-2.25 (m, 4H) MS obsd. (ESI$^+$) [(M + H)$^+$]: 442.1. |
| A078 | (2S)-1-[2-[2-(8-chloro-4-oxo-chromen-2-yl)-5-methyl-phenoxy]acetyl]pyrrolidine-2-carboxylic acid | EX: A004 AMINE: tert-butyl (2S)-pyrrolidine-2-carboxylate | $^1$H NMR (DMSO-$d_6$, 400 MHz): δ ppm 7.88-8.02 (m, 3H), 7.40-7.52 (m, 2H), 6.98-7.07 (m, 2H), 5.02 (s, 2H), 4.25-4.36 (m, 1H), 3.55-3.68 (m, 2H), 2.33 (s, 3H), 2.10-2.26 (m, 1H), 1.81-2.01 (m, 3H) MS obsd. (ESI$^+$) [(M + H)$^+$]: 442.1. |
| A079 | (2R)-1-[2-[5-bromo-2-(8-chloro-4-oxo-chromen-2-yl)-4-methyl-phenoxy]acetyl]pyrrolidine-2-carboxylic acid | EX: A073 AMINE: tert-butyl (2R)-pyrrolidine-2-carboxylate | $^1$H NMR (DMSO-$d_6$, 400 MHz): δ ppm 7.97-8.03 (m, 2H), 7.90-7.94 (m, 1H), 7.47-7.53 (m, 2H), 7.39-7.42 (m, 1H), 5.14 (s, 2H), 4.26-4.33 (m, 1H), 3.53-3.64 (m, 2H), 2.39 (s, 3H), 2.10-2.23 (m, 1H), 1.82-2.01 (m, 3H) MS obsd. (ESI$^+$) [(M + H)$^+$]: 520.1. |
| A080 | (2S)-1-[2-[5-bromo-2-(8-chloro-4-oxo-chromen-2-yl)-4-methyl-phenoxy]acetyl]pyrrolidine-2-carboxylic acid | EX: A073 AMINE: tert-butyl (2S)-pyrrolidine-2-carboxylate | $^1$H NMR (DMSO-$d_6$, 400 MHz): δ ppm 7.97-8.05 (m, 2H), 7.93 (s, 1H), 7.41 (s, 3H), 5.06 (s, 2H), 4.23-4.35 (m, 1H), 3.52-3.69 (m, 2H), 2.39 (s, 3H), 2.09-2.24 (m, 1H), 1.81-2.03 (m, 3H) MS obsd. (ESI$^+$) [(M + H)$^+$]: 520.1 |

TABLE 4-continued

Compounds synthesis and characterization

| Example No. | Compounds Name and Structure | EX and AMINE | $^1$H NMR and (ESI$^+$) |
|---|---|---|---|
| A081 | (2R)-1-[2-[2-(8-chloro-4-oxo-chromen-2-yl)-5-(trifluoromethyl)phenoxy]acetyl]pyrrolidine-2-carboxylic acid | EX: A051 AMINE: tert-butyl (2R)-pyrrolidine-2-carboxylate | $^1$H NMR (DMSO-d$_6$, 400 MHz): δ ppm 8.17-8.23 (m, 1H), 8.02 (dd, J = 7.9, 3.4 Hz, 2H), 7.53 (br d, J = 13.2 Hz, 3H), 7.46 (s, 1H), 5.24 (s, 2H), 4.26-4.32 (m, 1H), 3.58-3.67 (m, 2H), 2.12-2.22 (m, 2H), 1.83-2.01 (m, 2H). MS obsd. (ESI$^+$) [(M + H)$^+$]: 496.0. |
| A082 | (2S)-1-[2-[2-(8-chloro-4-oxo-chromen-2-yl)-5-(trifluoromethyl)phenoxy]acetyl]pyrrolidine-2-carboxylic acid | EX: A051 AMINE: tert-butyl (2S)-pyrrolidine-2-carboxylate | $^1$H NMR (DMSO-d$_6$, 400 MHz): δ ppm 8.21 (d, J = 8.1 Hz, 1H), 7.99-8.05 (m, 2H), 7.49-7.61 (m, 3H), 7.43-7.48 (m, 1H), 5.18-5.27 (s, 2H), 4.26-4.33 (m, 1H), 3.55-3.66 (m, 2H), 2.12-2.24 (m, 2H), 1.87-2.00 (m, 2H). MS obsd. (ESI$^+$) [(M + H)$^+$]: 496.0. |
| A083 | (3S)-1-[2-[2-(8-chloro-4-oxo-chromen-2-yl)-5-(trifluoromethyl)phenoxy]acetyl]pyrrolidine-3-carboxylic acid | EX: A051 AMINE: tert-butyl (3S)-pyrrolidine-3-carboxylate | $^1$H NMR (DMSO-d$_6$, 400 MHz): δ ppm 8.15-8.24 (m, 1H), 8.02 (s, 2H), 7.46-7.66 (m, 4H), 5.18 (s, 2H), 3.70-3.79 (m, 1H), 3.46-3.65 (m, 2H), 2.92-3.15 (m, 1H), 2.57-2.71 (m, 1H), 1.90-2.21 (m, 2H). MS obsd. (ESI$^+$) [(M + H)$^+$]: 496.0. |

Example A084: 3-[2-(8-chloro-4-oxo-chromen-2-yl)-5-(trifluoromethyl)phenoxy]-N-cyclopropylsulfonyl-propanamide

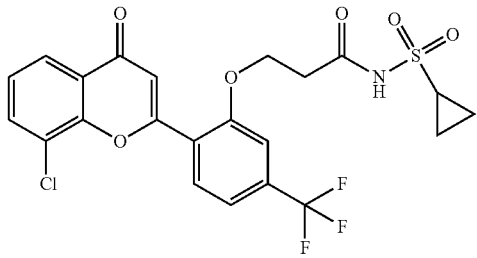

To a solution of methyl 3-[2-(8-chloro-4-oxo-chromen-2-yl)-5-(trifluoromethyl)phenoxy]propanoate (Example A002, 1450.0 mg, 3.4 mmol) and cyclopropanesulfonamide (617.48 mg, 5.1 mmol) in 1,2-dichloroethane (100 mL) cooled at 0° C. was added titanium tetrachloride (1611.15 mg, 8.49 mmol). After addition, the mixture was stirred at 110° C. for 16 hours. After the reaction was completed, the reaction was quenched by pour into ice water (50 mL) and the resulting solution was extracted with EtOAc (50 mL) three times. The combined organic layer was washed with brine, dried over $Na_2SO_4$ and concentrated in vacuo. The residue was then purified by column chromatography on silica gel (PE:EtOAc=2:1) to give the crude 3-[2-(8-chloro-4-oxo-chromen-2-yl)-5-(trifluoromethyl)phenoxy]-N-eyelopropylsulfonyl-propanamide, which was further purified by Prep-HPLC to afford 3-[2-(8-chloro-4-oxo-chromen-2-yl)-5-(trifluoromethyl)phenoxy]-N-cyclopropylsulfonyl-propanamide as a white solid. $^1$H NMR (DMSO-$d_6$, 400 MHz): δ ppm 11.87 (s, 1H), 8.16 (d, J=7.9 Hz, 1H), 8.02 (td, J=7.6, 1.5 Hz, 2H), 7.56-7.64 (m, 2H), 7.46-7.55 (m, 1H), 7.03 (s, 1H), 4.46-4.55 (m, 2H), 2.93-2.99 (m, 1H), 2.86-2.93 (m, 2H), 0.90-1.10 (m, 4H). MS obsd. (ESI$^+$) [(M+H)$^+$]:516.1.

Example A085: 3-[2-(8-chloro-4-oxo-chromen-2-yl)-4,5-dimethoxy-phenoxy]-N-cyclopropylsulfonyl-propanamide

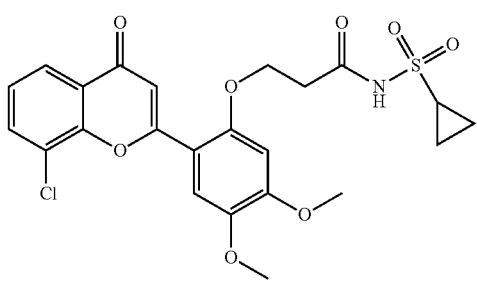

Step1: Preparation of methyl 3-[2-(8-chloro-4-oxo-chromen-2-yl)-4,5-dimethoxy-phenoxy]propanoate

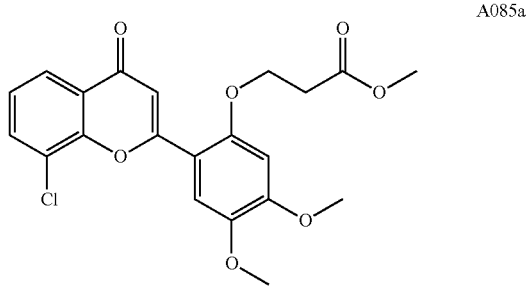 [SMILES: COC(=O)CCOc1cc(OC)c(OC)cc1-c1cc(=O)c2cccc(Cl)c2o1]

Example A038 was prepared in analogy to the procedure described for the preparation of Example A002 by using 3-[2-(8-chloro-4-oxo-chromen-2-yl)-4,5-dimethoxy-phenoxy]propanoic acid (Example A010) as the starting material instead of 3-[2-(8-chloro-4-oxo-chromen-2-yl)-5-(trifluoromethyl)phenoxy]propanoic acid (Example A001).

Step1: Preparation of 3-[2-(8-chloro-4-oxo-chromen-2-yl)-4,5-dimethoxy-phenoxy]-N-cyclopropylsulfonyl-propanamide

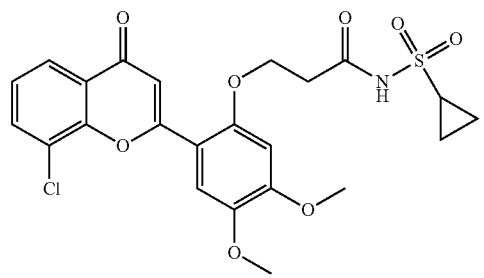

Example A085 was prepared in analogy to the procedure described for the preparation of example A084 by using methyl 3-[2-(8-chloro-4-oxo-chromen-2-yl)-4,5-dimethoxy-phenoxy]propanoate as the starting material instead of methyl 3-[2-(8-chloro-4-oxo-chromen-2-yl)-5-(trifluoromethyl)phenoxy]propanoate. $^1$H NMR (DMSO-$d_6$, 400 MHz): δ ppm 11.81-11.96 (br s, 1H), 7.96-8.04 (m, 2H), 7.60 (s, 1H), 7.47 (t, J=1.9 Hz, 1H), 7.03 (s, 1H), 6.91 (s, 1H), 4.43 (t, J=5.7 Hz, 2H), 3.90-3.98 (m, 3H), 3.73-3.86 (m, 3H), 2.94-3.02 (m, 1H), 2.79-2.95 (m, 2H), 0.92-1.10 (m, 4H). MS obsd. (ESI$^+$) [(M+H)$^+$]:508.0.

Example A086: 2-[2-(8-chloro-4-oxo-chromen-2-yl)-5-(trifluoromethyl)phenoxy]-N-(2-hydroxyethyl)acetamide

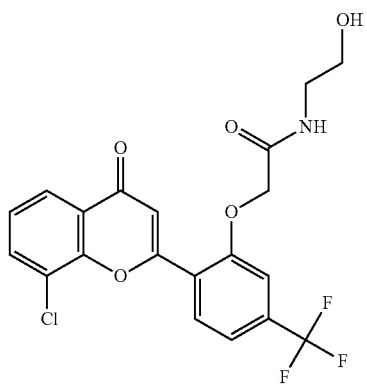

A086

To a solution of 2-[2-(8-chloro-4-oxo-chromen-2-yl)-5-(trifluoromethyl)phenoxy]acetic acid (Example A051, 93.0 mg, 0.230 mmol, as the "EX" in Table 5), 2-hydroxyethylamine (0.03 mL, 0.470 mmol, as the "AMINE" in Table 5), DIPEA (0.12 mL, 0.700 mmol) in DMF (8 mL) was added HATU (133.0 mg, 0.350 mmol) and the mixture was stirred at room temperature for 18 hours. After the reaction was completed, the reaction was diluted with water (20 mL) and extracted with EtOAc (30 mL) three times. The combined organic layer was washed with brine, dried over $Na_2SO_4$ and concentrated in vacuo. The residue was purified by Prep-HPLC to give 2-[2-(8-chloro-4-oxo-chromen-2-yl)-5-(trifluoromethyl)phenoxy]-N-(2-hydroxyethyl)acetamide (59 mg, 0.130 mmol, 56.11% yield) as a white solid. $^1$H NMR (DMSO-$d_6$, 400 MHz): δ ppm 8.11-8.20 (m, 2H), 7.99-8.05 (m, 2H), 7.61 (dd, J=8.1, 1.0 Hz, 1H), 7.52 (s, 1H), 7.44-7.47 (m, 1H), 7.26-7.29 (m, 1H), 4.84-4.90 (m, 2H), 4.60-4.73 (m, 1H), 3.42 (s, 2H), 3.15-3.21 (m, 2H). MS obsd. (ESI$^+$) [(M+H)$^+$]: 442.0.

The following Example A087 to A083 were prepared in analogy to the procedure described for the preparation of Example A086, replacing 2-[2-(8-chloro-4-oxo-chromen-2-yl)-5-(trifluoromethyl)phenoxy]acetic acid (Example A051) with "EX", 2-hydroxyethylamine with "AMINE" in by the reagent indicated in Table 5.

TABLE 5

Compounds synthesis and characterization

| Example No. | Compounds Name and Structure | EX and AMINE | $^1$H NMR and (ESI$^+$) |
|---|---|---|---|
| A087 | 8-chloro-2-[2-[2-(3-methylsulfonylpyrrolidin-1-yl)-2-oxo-ethoxy]-4-(trifluoromethyl)phenyl]chromen-4-one | EX: A051 AMINE: 3-methylsulfonyl pyrrolidine | $^1$H NMR (DMSO-$d_6$, 400 MHz): δ ppm 8.16-8.26 (m, 1H), 7.95-8.06 (m, 2H), 7.45-7.67 (m, 4H), 5.15-5.31 (m, 2H), 3.96-4.15 (m, 1H), 3.87-3.94 (m, 1H), 3.71-3.82 (m, 1H), 3.43-3.71 (m, 2H), 3.08 (d, J = 9.2 Hz, 3H), 2.20-2.43 (m, 2H). MS obsd. (ESI$^+$) [(M + H)$^+$]: 529.9. |
| A088 | 2-[4-bromo-2-[2-[(3S)-3-hydroxypyrrolidin-1-yl]-2-oxo-ethoxy]-5-methyl-phenyl]-8-chloro-chromen-4-one | EX: A073 AMINE: (3S)-pyrrolidin-3-ol | $^1$H NMR (DMSO-$d_6$, 400 MHz): δ ppm 7.96-8.05 (m, 2H), 7.93 (s, 1H), 7.47-7.57 (m, 2H), 7.43 (d, J = 1.3 Hz, 1H), 5.08 (s, 2H), 4.25-4.40 (m, 1H), 3.53-3.64 (m, 2H), 3.42-3.51 (m, 1H), 2.39 (s, 3H), 1.67-2.01 (m, 3H). MS obsd. (ESI$^+$) [(M + H)$^+$]: 492.0. |

TABLE 5-continued

Compounds synthesis and characterization

| Example No. | Compounds Name and Structure | EX and AMINE | $^1$H NMR and (ESI$^+$) |
|---|---|---|---|
| A089 | 2-[4-bromo-2-[2-[(3R)-3-hydroxypyrrolidin-1-yl]-2-oxo-ethoxy]-5-methyl-phenyl]-8-chloro-chromen-4-one | EX: A073 AMINE: (3R)-pyrrolidin-3-ol | $^1$H NMR (DMSO-d$_6$, 400 MHz): δ ppm 7.96-8.06 (m, 2H), 7.92 (s, 1H), 7.48-7.57 (m, 2H), 7.43 (d, J = 1.3 Hz, 1H), 5.08 (s, 2H), 4.25-4.43 (m, 1H), 3.53-3.69 (m, 2H), 3.42-3.51 (m, 1H), 2.39 (s, 3H), 1.67-2.01 (m, 3H). MS obsd. (ESI$^+$) [(M + H)$^+$]: 491.8. |
| A090 | 2-[4-bromo-5-methyl-2-[2-oxo-2-[rac-(3S,4R)-3,4-dihydroxypyrrolidin-1-yl]ethoxy]phenyl]-8-chloro-chromen-4-one | EX: A073 AMINE: (3S,4R)-pyrrolidine-3,4-diol | $^1$H NMR (CDCl$_3$, 400 MHz): δ ppm 8.11 (d, J = 8.2 Hz, 1H), 7.86-7.99 (m, 1H), 7.65-7.82 (m, 2H), 7.34-7.47 (m, 2H), 4.64-4.87 (s, 2H), 4.20-4.41 (m, 2H), 3.53-3.79 (m, 4H), 2.59-2.68 (m, 1H), 2.41-2.50 (s, 3H). MS obsd. (ESI$^+$) [(M + H)$^+$]: 507.8. |
| A091 | 2-[2-(8-chloro-4-oxo-chromen-2-yl)-4,5-dimethoxy-phenoxy]-N-cyclopropylsulfonyl-acetamide | EX: A050 AMINE: cyclopropane-sulfonamide | $^1$H NMR (DMSO-d$_6$, 400 MHz): δ ppm 7.95-8.02 (m, 2H), 7.60-7.66 (m, 1H), 7.42-7.53 (m, 2H), 6.75-6.83 (m, 1H), 4.62-4.71 (s, 2H), 3.84-3.93 (s, 3H), 3.78-3.84 (s, 3H), 2.77-2.88 (m, 1H), 0.70-0.89 (m, 4H). MS obsd. (ESI$^+$) [(M + H)$^+$]: 494.0. |

TABLE 5-continued

Compounds synthesis and characterization

| Example No. | Compounds Name and Structure | EX and AMINE | ¹H NMR and (ESI⁺) |
|---|---|---|---|
| A092 | 8-chloro-2-[2-(2-morpholino-2-oxo-ethoxy)-4-(trifluoromethyl)phenyl]chromen-4-one | EX: A051 AMINE: morpholine | ¹H NMR (DMSO-$d_6$, 400 MHz): δ ppm 8.22-8.27 (m, 1H), 7.99-8.06 (m, 2H), 7.45-7.65 (m, 4H), 5.26 (s, 2H), 3.54-3.68 (m, 4H), 3.43-3.54 (m, 4H). MS obsd. (ESI⁺) [M + H]⁺: 468.0. |
| A093 | (2S)-1-[2-[2-(8-chloro-4-oxo-chromen-2-yl)-5-methyl-phenoxy]acetyl]-N-methylsulfonyl-pyrrolidine-2-carboxamide | EX: A049 AMINE: methane-sulfonamide | ¹H NMR (DMSO-$d_6$, 400 MHz): δ ppm 11.88 (s, 1H), 7.91-8.02 (m, 3H), 7.41-7.52 (m, 2H), 6.99-7.10 (m, 2H), 5.01-5.10 (m, 2H), 4.31-4.41 (m, 1H), 3.54-3.69 (m, 2H), 3.19 (s, 3H), 2.39 (s, 3H), 2.11-2.24 (m, 1H), 1.77-2.03 (m, 3H). MS obsd. (ESI⁺) [(M + H)⁺: 519.1. |
| A094 | (2R)-1-[2-[2-(8-chloro-4-oxo-chromen-2-yl)-5-methyl-phenoxy]acetyl]-N-methylsulfonyl-pyrrolidine-2-carboxamide | EX: A049 AMINE: methane-sulfonamide | ¹H NMR (DMSO-$d_6$, 400 MHz): δ ppm 11.95 (s, 1H), 7.91-8.03 (m, 3H), 7.41-7.53 (m, 2H), 6.98-7.10 (m, 2H), 5.02-5.10 (m, 2H), 4.31-4.41 (m, 1H), 3.52-3.73 (m, 2H), 3.20 (s, 3H), 2.39 (s, 3H), 2.11-2.23 (m, 1H), 1.78-2.03 (m, 3H). MS obsd. (ESI⁺) [(M + H)⁺: 519.1. |

Example A095: (2S)-2-amino-3-[2-(8-chloro-4-oxo-chromen-2-yl)-5-(trifluoromethyl)phenoxy]propanoic acid

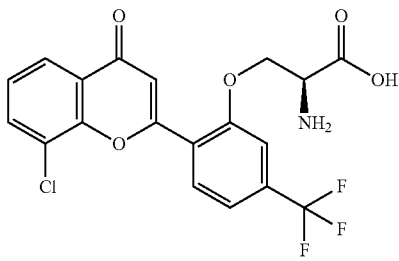

A095

Step 1: Preparation of methyl (2S)-2-amino-3-[2-(8-chloro-4-oxo-chromen-2-yl)-5-(trifluoromethyl)phenoxy]propanoate

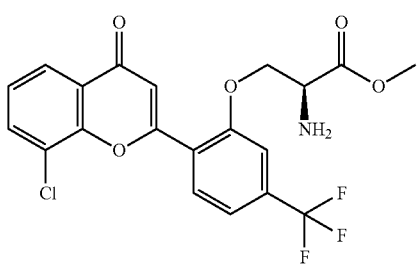

A095a

To a solution of 8-chloro-2-[2-hydroxy-4-(trifluoromethyl)phenyl]chromen-4-one (Int-1, 1000 mg, 2.94 mmol), methyl trityl-L-serinate (1.27 g, 3.52 mmol) and triphenylphosphine (1.92 g, 7.34 mmol) in THF (10 ml) was added DIAD (1.19 g, 1.14 ml, 5.87 mmol) and the mixture was then stirred at room temperature overnight. The mixture was then diluted with water (30 mL) and extracted with EtOAc (30 mL) three times. The combined organic layer was washed with 1 N HCl (20 mL), brine (20 mL), dried over Na$_2$SO$_4$ and concentrated in vacuo.

The residue was dissolved in DCM (20 mL) and to the resulting solution was added TFA (3 mL). The mixture was then stirred at room temperature for 2 hours. The mixture was then concentrated in vacuo and the residue was triturated with EtOAc (30 mL). The suspension was then filtered and the solid was collected to give methyl (2S)-2-amino-3-[2-(8-chloro-4-oxo-chromen-2-yl)-5-(trifluoromethyl)phenoxy]propanoate (1.1 g, 80% yield) as a white solid. MS obsd. (ESI$^+$) [(M+H)$^+$]: 442.1.

Step 2: Preparation of (2S)-2-amino-3-[2-(8-chloro-4-oxo-chromen-2-yl)-5-(trifluoromethyl)phenoxy]propanoic acid

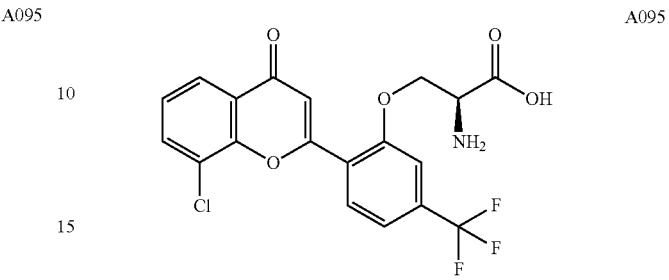

A095

To a solution of methyl (2S)-2-amino-3-[2-(8-chloro-4-oxo-chromen-2-yl)-5-(trifluoromethyl)phenoxy]propanoate (500 mg, 1.13 mmol) in the mixed solvent of THF (10 ml) and water (1 ml) was added LiOH (27.1 mg, 1.13 mmol). The mixture was then stirred at room temperature for 2 hours. The reaction was then quenched by addition of AcOH (1 mL) and the resulting suspension was filtered. The solid was collected and suspended in a mixed solvent of EtOAc (10 mL) and water (10 mL). The suspension was then filtered. The solid was collected and dried in vacuo to give (2S)-2-amino-3-[2-(8-chloro-4-oxo-chromen-2-yl)-5-(trifluoromethyl)phenoxy]propanoic acid (200 mg, 39.2% yield) as a white solid. $^1$H NMR (DMSO-d$_6$, 400 MHz): δ ppm 7.98 (m, 4H), 7.67 (s, 1H), 7.48-7.62 (m, 2H), 7.08 (s, 1H), 4.61-4.69 (m, 1H), 4.41-4.49 (m, 1H), 3.69 (m, 1H), 3.44 (s, 3H). MS obsd. (ESI$^+$) [(M+H)$^+$]: 428.3.

Example A096: (2S)-3-[2-(8-chloro-4-oxo-chromen-2-yl)-5-(trifluoromethyl)phenoxy]-2-(cyclopropylsulfonylamino)propanoic acid

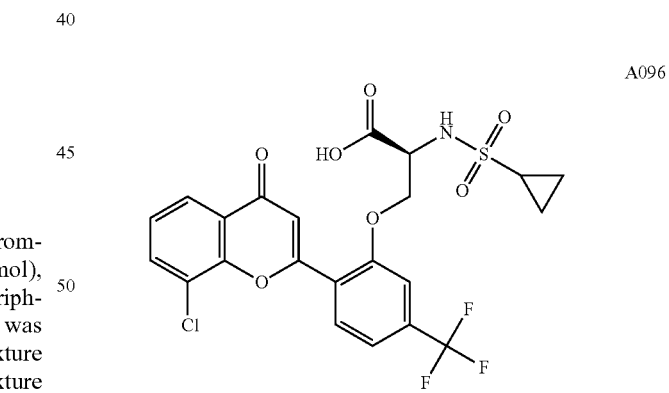

A096

To a solution of (2S)-2-amino-3-[2-(8-chloro-4-oxo-chromen-2-yl)-5-(trifluoromethyl)phenoxy]propanoic acid (40 mg, 93.5 μmol) and TEA (284 mg, 2.81 mmol) in the DCM (10 mL) was added cyclopropanesulfonyl chloride (263 mg, 1.87 mmol) and the mixture was then stirred at room temperature overnight. The mixture was then adjusted to pH~5.0 by addition of AcOH. The resulting mixture was washed with water (10 mL), brine, dried over MgSO$_4$ and then concentrated in vacuo. The residue was then purified by Prep-HPLC to give (2S)-3-[2-(8-chloro-4-oxo-chromen-2-yl)-5-(trifluoromethyl)phenoxy]-2-(cyclopropylsulfonylamino)propanoic acid (11 mg, 21.7% yield) as a white solid. ¹H NMR (DMSO-d₆, 400 MHz): δ ppm 8.11-8.16 (m, 1H), 7.99-8.07 (m, 2H), 7.72-7.85 (m, 1H), 7.57-7.67 (m, 2H), 7.48-7.55 (m, 1H), 7.05-7.13 (m, 1H), 4.45-4.57 (m, 2H), 4.30-4.41 (m, 1H), 2.58-2.62 (m, 1H), 0.71-0.96 (m, 4H). MS obsd. (ESI⁺) [(M+H)⁺]: 532.1.

Example A097: (2S)-3-[2-(8-chloro-4-oxo-chromen-2-yl)-5-(trifluoromethyl)phenoxy]-2-(p-tolylsulfonylamino)propanoic acid

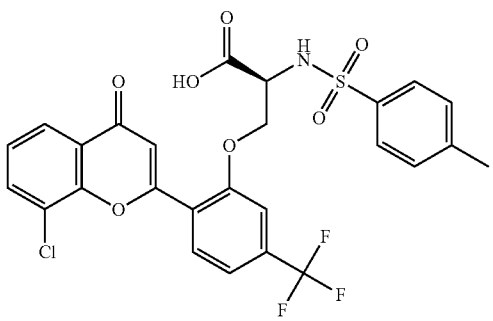

A097

Example A097 was prepared in analogy to the procedure described for the preparation of example A096 by using 4-methylbenzenesulfonyl chloride as the starting material instead of clopropanesulfonyl chloride. ¹H NMR (DMSO-d₆. 400 MHz): δ ppm 8.09 (d, J=8.3 Hz, 1H), 8.03 (d, J=7.8 Hz, 2H), 7.54-7.63 (m, 3H), 7.48-7.54 (m, 1H), 7.44-7.48 (m, 1H), 7.15-7.19 (m, 2H), 7.01-7.06 (m, 1H), 4.39-4.47 (m, 1H), 4.29-4.38 (m, 1H), 4.03-4.12 (m, 1H), 2.21-2.27 (s, 3H). MS obsd. (ESI⁺) [(M+H)⁺]:583.3.

Example A098: methyl (2S)-3-[2-(8-chloro-4-oxo-chromen-2-yl)-5-(trifluoromethyl)phenoxy]-2-(ethylsulfamoylamino)propanoate

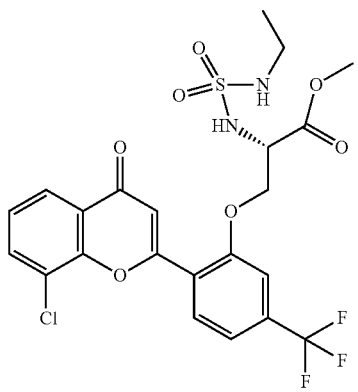

A098

To a solution of methyl (2S)-2-amino-3-[2-(8-chloro-4-oxo-chromen-2-yl)-5-(trifluoromethyl)phenoxy]propanoate (200 mg, 0.45 mmol) and TEA (202 mg, 2 2 mol) in DCM (10 mL) was added ethylsulfamoyl chloride (143 mg, 1 mmol) and the mixture was then stirred at room temperature for 2 hours. The mixture was then diluted with EtOAc (50 mL) and the resulting solution was washed with water (15 mL), brine (15 mL), dried over Na₂SO₄. The organic layer was then concentrated in vacuo and the residue was purified by column chromatography on silica gel (eluent with PE:EtOAc 10:1 to 3:1) to give methyl (2S)-3-[2-(8-chloro-4-oxo-chromen-2-yl)-5-(trifluoromethyl)phenoxy]-2-(ethylsulfamoylamino)propanoate (120 mg, 45.9% yield) as a white solid. ¹H NMR (DMSO-d₆, 400 MHz): δ ppm 8.13 (d, J=7.8 Hz, 1H), 8.03 (d, J=7.8 Hz, 2H), 7.71-7.76 (m, 1H), 7.59-7.65 (m, 2H), 7.52 (t, J=7.9 Hz, 1H), 7.00 (s, 1H), 6.95 (t, J=5.7 Hz, 1H), 4.51-4.56 (m, 1H), 4.43-4.49 (m, 1H), 4.25-4.32 (m, 1H), 3.64 (s, 3H), 2.77-2.86 (m, 2H), 0.97 (t, J=7.2 Hz, 3H). MS obsd. (ESI⁺) [(M+H)⁺]:549.1.

Example A099: (2S)-3-[2-(8-chloro-4-oxo-chromen-2-yl)-5-(trifluoromethyl)phenoxy]-2-(ethylsulfamoylamino)propanoic acid

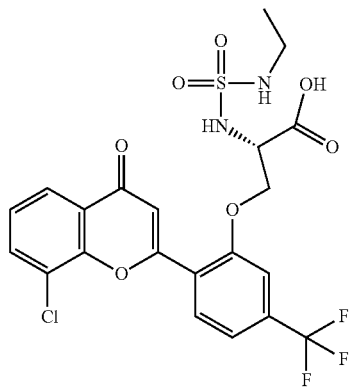

A099

To a solution of methyl (2S)-3-[2-(8-chloro-4-oxo-chromen-2-yl)-5-(trifluoromethyl)phenoxy]-2-(ethylsulfamoylamino)propanoate (160 mg, 291 μmol) in DCE (15 mL) was added trimethylstannanol (158 mg, 874 μmol) and the mixture was then stirred at 90° C. for 10 hours. After the reaction was completed, the mixture was concentrated in vacuo and the residue was dissolved with 4 N HCl (20 mL). The mixture was then extracted with EtOAc (20 mL) three times. The combined organic layer was concentrated in vacuo and the residue was purified by Prep-HPLC to give (2S)-3-[2-(8-chloro-4-oxo-chromen-2-yl)-5-(trifluoromethyl)phenoxy]-2-(ethylsulfamoylamino)propanoic acid (43.5 mg, 26.5% yield) as a white solid. ¹H NMR (DMSO-d₆, 400 MHz): δ ppm 8.13 (d, J=7.9 Hz, 1H), 8.02 (d, J=7.8 Hz, 2H), 7.58-7.65 (m, 2H), 7.51 (t, J=7.9 Hz, 1H), 7.24 (d, J=7.0 Hz, 1H), 7.09 (s, 1H), 6.90 (t, J=5.6 Hz, 1H), 4.45-4.56 (m, 2H), 4.11-4.17 (m, 1H), 2.76-2.87 (m, 2H), 0.95 (t, J=7.3 Hz, 3H). MS obsd. (ESI⁺) [(M+H)⁺]:535.0.

Example B001: 3-[5-bromo-2-(8-chloro-4-oxo-chromen-2-yl)phenoxy]cyclobutanecarboxylic acid

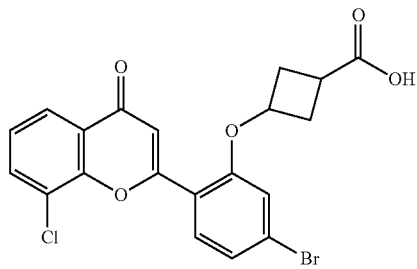

B001

Step 1: Preparation of methyl 3-methylsulfonyloxycyclobutanecarboxylate

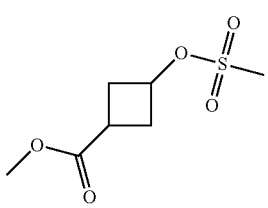

B001a

To a solution of methyl 3-hydroxycyclobutanecarboxylate (1 g, 7.68 mmol, as the "SM4" in Table 6) and TEA (1.17 g, 1.61 mL, 11.5 mmol) in dichloromethane (10 mL) was added methanesulfonyl chloride (1.14 g, 778 µL, 9.99 mmol) at 0° C. and the mixture was then stirred at room temperature overnight. The mixture was then diluted with dichloromethane (50 mL), the resulting solution was then washed with water (20 mL) twice, saturated NaHCO₃ (20 mL) twice, brine (20 mL), dried over anhydrous Na₂SO₄ and concentrated in vacuo to give the crude methyl 3-methyl-sulfonyloxycyclobutanecarboxylate (1.6 g, 100%) as a colorless oil. MS obsd. (ESI⁺) [(M+H)⁺]: 209.2.

Step 2: Preparation of methyl 3-[5-bromo-2-(8-chloro-4-oxo-chromen-2-yl)phenoxy]cyclobutanecarboxylate

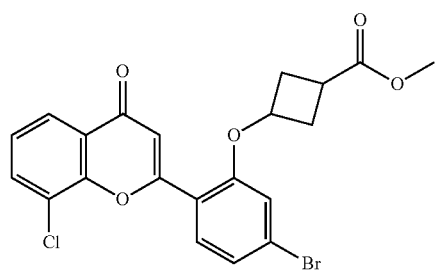

B001b

To a mixture of 2-(4-bromo-2-hydroxy-phenyl)-8-chloro-chromen-4-one (Int-4, 100 mg, 284 µmol, as the "CORE" in Table 6), methyl 3-methylsulfonyloxycyclobutanecarboxylate (592 mg, 2.84 mmol) in DMF (5 ml) was added K₂CO₃ (393 mg, 2.84 mmol) and the mixture was stirred at 120° C. for 12 hours. After the reaction was completed, the mixture was diluted with water (15 mL) and extracted with EtOAc (20 mL) three times. The combined organic layer was washed with brine, dried over Na₂SO₄ and concentrated in vacuo to give the crude methyl 3-[5-bromo-2-(8-chloro-4-oxo-chromen-2-yl)phenoxy]cyclobutanecarboxylate, which was used in the next step directly without further purification.

Step 3: Preparation of 3-[5-bromo-2-(8-chloro-4-oxo-chromen-2-yl)phenoxy]cyclobutanecarboxylic acid

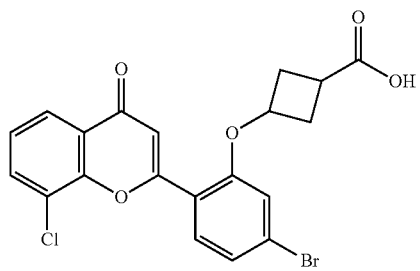

B001

A solution of methyl 3-[5-bromo-2-(8-chloro-4-oxo-chromen-2-yl)phenoxy]cyclobutanecarboxylate (crude prepared above) in the mixed solvent of THF (10 mL) and LiOH solution (2N, 2 mL) was stirred at room temperature for 2 hours. After the reaction was completed, the reaction was adjusted to pH~4 by addition of 2 N HCl. The resulting mixture was concentrated in vacuo and the residue was purified by Prep-HPLC to give 3-[5-bromo-2-(8-chloro-4-oxo-chromen-2-yl)phenoxy]cyclobutanecarboxylic acid (30 mg, 22% yield over 2 steps).

¹H NMR (DMSO-d₆, 400 MHz): δ ppm 8.01 (d, J=7.83 Hz, 2H), 7.88 (s, 1H), 7.51 (t, J=7.70 Hz, 1H), 7.43 (d, J=8.56 Hz, 1H), 7.20 (s, 1H), 7.04-7.09 (m, 1H), 4.87-5.15 (m, 1H), 3.07-3.12 (m, 1H), 2.68-2.76 (m, 2H), 2.43-2.47 (m, 2H). MS obsd. (ESI⁺) [(M+H)⁺]:449.1.

Example B002-A and Example B002-B

Cis-3-[2-(8-chloro-4-oxo-chromen-2-yl)phenoxy]cyclobutanecarboxylic acid and traits-3-[2-(8-chloro-4-oxo-chromen-2-yl)phenoxy]cyclobutanecarboxylic acid

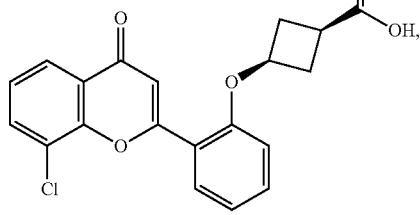
B002-A

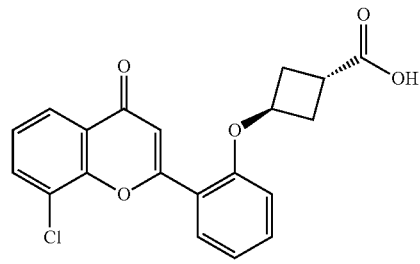
B002-B

Step 1: Preparation of methyl 3-[2-(8-chloro-4-oxo-chromen-2-yl)phenoxy]cyclobutanecarboxylate

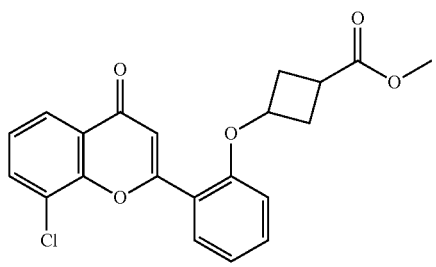
B002a

To a mixture of 8-chloro-2-(2-hydroxyphenyl)chromen-4-one (Int-3, 100 mg, 367 µmol), methyl 3-methylsulfonyloxycyclobutanecarboxylate (305 mg, 1.47 mmol) in DMF (5 ml) was added $Cs_2CO_3$ (478 mg, 1.47 mmol) and the mixture was stirred at 120° C. for 12 hours. After the reaction was completed, the mixture was diluted with water (15 mL) and extracted with EtOAc (20 mL) three times. The combined organic layer was washed with brine, dried over $Na_2SO_4$ and concentrated in vacuo to give the crude methyl 3-[2-(8-chloro-4-oxo-chromen-2-yl)phenoxy]cyclobutanecarboxylate, which was used in the next directly without further purification.

Step 2: Preparation of Cis-3-[2-(8-chloro-4-oxo-chromen-2-yl)phenoxy]cyclobutanecarboxylic acid and trans-3-[2-(8-chloro-4-oxo-chromen-2-yl)phenoxy]cyclobutanecarboxylic acid

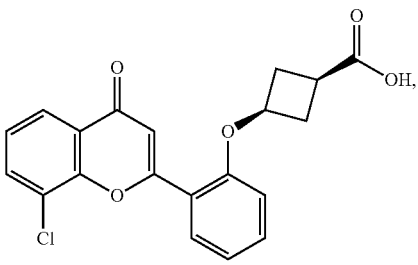
B002-A

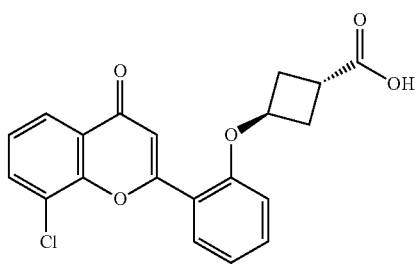 [SMILES: O=c1cc(-c2ccccc2O[C@H]2C[C@H](C(=O)O)C2)oc2c(Br)cccc12]
B002-B

A solution of methyl 3-[2-(8-chloro-4-oxo-chromen-2-yl)phenoxy]cyclobutanecarboxylate (crude prepared above) in the mixed solvent of THF (10 mL) and LiOH solution (2N, 2 mL) was stirred at room temperature for 2 hours. After the reaction was completed, the reaction was adjusted to pH~4 by addition of 2 N HCl, the resulting mixture was concentrated in vacuo to give the crude-[2-(8-chloro-4-oxo-chromen-2-yl)phenoxy]cyclobutanecarboxylic acid. The crude was further purified by Prep-HPLC to give two diastereomers of cis-3-[2-(8-chloro-4-oxo-chromen-2-yl)phenoxy]cyclobutanecarboxylic acid (Example B002-A, 9 mg, % yield) and trans-3-[2-(8-chloro-4-oxo-chromen-2-yl)phenoxy]cyclobutanecarboxylic acid (Example B002-B, 56 mg, % yield).

Example B002-A: $^1$H NMR (DMSO-$d_6$, 400 MHz): δ ppm 8.01 (qd, J=1.52, 7.92 Hz, 2H), 7.97 (dd, J=1.71, 7.83 Hz, 1H), 7.57 (ddd, J=1.71, 7.34, 8.56 Hz, 1H), 7.50 (t, J=7.83 Hz, 1H), 7.17-7.23 (m, 1H), 7.08-7.13 (m, 1H), 7.07 (s, 1H), 4.79-4.91 (m, 1H), 2.80 (d, J=4.65 Hz, 3H), 2.27 (d, J=7.09 Hz, 2H). MS obsd. (ESI$^+$) [(M+H)$^+$]: 371.0.

Example B002-B: $^1$H NMR (DMSO-$d_6$, 400 MHz): δ ppm 12.33-12.41 (m, 1H), 8.01 (d, J=7.83 Hz, 2H), 7.97 (dd, J=1.71, 7.83 Hz, 1H), 7.53-7.61 (m, 1H), 7.50 (t, J=7.95 Hz, 1H), 7.16-7.23 (m, 1H), 7.10 (s, 1H), 7.03 (d, J=8.31 Hz, 1H), 5.02 (s, 1H), 3.10-3.20 (m, 1H), 2.69-2.79 (m, 2H), 2.37-2.47 (m, 2H). MS obsd. (ESI$^+$) [(M+H)$^+$]: 371.1.

The following Example B003 to Example B010 were prepared in analogy to the procedure described for the preparation of Example B001, replacing methyl 3-hydroxycyclobutanecarboxylate with "SM4" in step1, and replacing 2-(4-bromo-2-hydroxy-phenyl)-8-chloro-chromen-4-one (Int-4) with "CORE" in step 2. "SM4" and "CORE" are the reagents indicated in Table 6.

TABLE 6

Compounds synthesis and characterization

| Example No. | Compounds Name and Structure | CORE and SM4 | ¹H NMR and (ESI⁺) |
|---|---|---|---|
| B003 | 3-[2-(8-chloro-4-oxo-chromen-2-yl)-5-(trifluoromethyl)phenoxy]cyclobutanecarboxylic acid | CORE: Int-1 SM4: 3-hydroxycyclo-butanecarboxylate | $^1$H NMR (DMSO-d$_6$, 400 MHz): δ ppm 12.4 (br s, 1H), 8.12-8.14 (m, 1H), 8.02-8.05 (m, 2H), 7.50-7.52 (m, 2H), 7.25 (s, 1H), 7.12 (s, 1H), 5.16-5.19 (m, 1H), 3.12-3.17 (m, 1H), 2.68-2.76 (m, 2H), 2.40-2.47 (m, 2H). MS obsd. (ESI⁺) [(M + H)⁺]: 439.1. |
| B004 | 3-[5-bromo-2-(8-chloro-4-oxo-chromen-2-yl)-4-methoxy-phenoxy]cyclobutane-carboxylic acid | CORE: Int-7 SM4: 3-hydroxycyclo-butanecarboxylate | $^1$H NMR (DMSO-d$_6$, 400 MHz): δ ppm 12.42 (s, 1H), 7.96-8.04 (m, 2H), 7.61-7.66 (m, 1H), 7.47-7.53 (m, 1H), 7.21-7.36 (m, 1H), 7.04-7.13 (m, 1H), 4.77-5.07 (m, 1H), 3.90 (s, 3H), 2.63-3.17 (m, 3H), 2.18-2.44 (m, 2H). MS obsd. (ESI⁺) [(M + H)⁺]: 479.1. |
| B005 | 3-[2-(8-chloro-4-oxo-chromen-2-yl)-5-(trifluoromethoxy)phenoxy]cyclobutanecarboxylic acid | CORE: Int-9 SM4: 3-hydroxycyclo-butanecarboxylate | $^1$H NMR (DMSO-d$_6$, 400 MHz): δ ppm 12.27 (s, 1H), 7.99-8.10 (m, 3H), 7.44-7.57 (m, 1H), 7.17-7.27 (m, 1H), 6.97-7.10 (m, 2H), 4.85-5.15 (m, 1H), 2.71-3.21 (m, 3H), 2.37-2.45 (m, 1H), 2.20-2.29 (m, 1H). MS obsd. (ESI⁺) [(M + H)⁺]: 455.1. |

TABLE 6-continued

Compounds synthesis and characterization

| Example No. | Compounds Name and Structure | CORE and SM4 | 1H NMR and (ESI+) |
|---|---|---|---|
| B006 | 3-[2-(8-chloro-4-oxo-chromen-2-yl)-4,5-dimethoxy-phenoxy]cyclobutane-carboxylic acid | CORE: Int-10<br>SM4: 3-hydroxycyclo-butanecarboxylate | 1H NMR (DMSO-d$_6$, 400 MHz): δ ppm 12.25-12.34 (br s, 1H), 7.94-8.03 (m, 2H), 7.52-7.65 (m, 1H), 7.43-7.52 (m, 1H), 7.11-7.17 (m, 1H), 6.56 (s, 1H), 5.03-5.12 (m, 1H), 3.89 (s, 3H), 3.81 (s, 3H), 3.09-3.19 (m, 1H), 2.69-2.80 (m, 2H), 2.38-2.46 (m, 2H). MS obsd. (ESI+) [(M + H)+]: 431.1. |
| B007 | 3-[4-bromo-2-(8-chloro-4-oxo-chromen-2-yl)-5-(trifluoromethoxy)phenoxy]cyclobutanecarboxylic acid | CORE: Int-16<br>SM4: 3-hydroxycyclo-butanecarboxylate | 1H NMR (DMSO-d$_6$, 400 MHz): δ ppm 8.25-8.28 (m, 1H), 7.99-8.06 (m, 2H), 7.47-7.55 (m, 1H), 7.18-7.24 (m, 1H), 7.02-7.05 (m, 1H), 4.90-5.15 (m, 1H), 2.72-2.82 (m, 1H), 2.37-2.45 (m, 2H), 2.19-2.29 (m, 2H). MS obsd. (ESI+) [(M + H)+]: 533.1. |
| B009 | 3-[2-bromo-6-(8-chloro-4-oxo-chromen-2-yl)-4-methyl-phenoxy]cyclobutane-carboxylic acid | CORE: Int-18<br>SM4: 3-hydroxycyclo-butanecarboxylate | 1H NMR (DMSO-d$_6$, 400 MHz): δ ppm 12.09 (s, 1H), 8.00-8.06 (m, 2H), 7.72-7.77 (m, 1H), 7.59-7.64 (m, 1H), 7.48-7.56 (m, 1H), 6.80-6.86 (m, 1H), 4.27-4.61 (m, 1H), 2.64-2.92 (m, 1H), 2.21-2.42 (m, 7H). MS obsd. (ESI+) [(M + H)+]: 463.1. |

TABLE 6-continued

Compounds synthesis and characterization

| Example No. | Compounds Name and Structure | CORE and SM4 | $^1$H NMR and (ESI$^+$) |
|---|---|---|---|
| B010 | 4-[5-bromo-2-(8-chloro-4-oxo-chromen-2-yl)phenoxy]cyclohexanecarboxylic acid | CORE: Int-4 SM4: methyl 4-hydroxycyclohexanecarboxylate | $^1$H NMR (DMSO-d$_6$, 400 MHz): δ ppm 11.91-12.13 (br s, 1H), 7.96-8.05 (m, 2H), 7.81-7.87 (m, 1H), 7.45-7.57 (m, 2H), 7.34-7.42 (m, 1H), 7.02 (s, 1H), 4.84-4.94 (m, 0.8 H), 4.63-4.73 (m, 0.2 H), 2.27-2.38 (m, 1H), 1.83-1.92 (m, 2H), 1.57-1.79 (m, 6H) MS obsd. (ESI$^+$) [(M + H)$^+$]: 477.1. |

The following compounds B011 to B029 were prepared in analogy to the procedure described for the preparation of example B002-A and B002-B, replacing methyl 3-methylsulfonyloxycyclobutanecarboxylate with "SM4" in step1, 8-chloro-2-(2-hydroxyphenyl)chromen-4-one with "CORE" in step 1. The "CORE" and "SM4" are the reagent indicated in Table 6.

TABLE 6

Compounds synthesis and characterization

| Example No. | Compounds Name and Structure | CORE and SM4 | $^1$H NMR and (ESI$^+$) |
|---|---|---|---|
| B011-A | Cis-3-[2-(8-chloro-4-oxo-chromen-2-yl)-5-methoxy-phenoxy]cyclobutane-carboxylic acid | CORE: Int-13 SM4: methyl 3-methylsulfonyl-oxycyclobutane-carboxylate | $^1$H NMR (DMSO-d$_6$, 400 MHz): δ ppm 7.92-8.03 (m, 3H), 7.43-7.53 (m, 1H), 7.01-7.07 (m, 1H), 6.78-6.87 (m, 1H), 6.52-6.61 (m, 1H), 4.80-4.95 (m, 1H), 3.90 (s, 3H), 2.72-2.89 (m, 3H), 2.17-2.36 (m, 2H). MS obsd. (ESI$^+$) [(M + H)$^+$]: 401.1. |
| B011-B | Trans-3-[2-(8-chloro-4-oxo-chromen-2-yl)-5-methoxy-phenoxy]cyclobutane-carboxylic acid | CORE: Int-13 SM4: methyl 3-methylsulfonyl-oxycyclobutane-carboxylate | $^1$H NMR (DMSO-d$_6$, 400 MHz): δ ppm 12.49 (s, 1H), 7.95-8.03 (m, 3H), 7.43-7.52 (m, 1H), 7.05-7.11 (m, 1H), 6.78-6.85 (m, 1H), 6.43-6.50 (m, 1H), 4.99-5.11 (m, 1H), 3.86 (s, 3H), 3.10-3.21 (m, 1H), 2.70-2.81 (m, 2H), 2.38-2.47 (m, 2H). MS obsd. (ESI$^+$) [(M + H)$^+$]: 401.1. |

TABLE 6-continued

Compounds synthesis and characterization

| Example No. | Compounds Name and Structure | CORE and SM4 | $^1$H NMR and (ESI$^+$) |
|---|---|---|---|
| B012-A | Cis-3-[5-chloro-2-(8-chloro-4-oxo-chromen-2-yl)-4-methyl-phenoxy]cyclobutane-carboxylic acid | CORE: Int-5 SM4: methyl 3-methylsulfonyl-oxycyclobutane-carboxylate | $^1$H NMR (DMSO-d$_6$, 400 MHz): δ ppm 7.95-8.03 (m, 2H), 7.84-7.92 (m, 1H), 7.45-7.53 (m, 1H), 7.10-7.18 (m, 1H), 7.03 (s, 1H), 4.75-4.91 (m, 1H), 2.62-2.79 (m, 3H), 2.35 (s, 3H), 2.11-2.29 (m, 2H). MS obsd. (ESI$^+$) [(M + H)$^+$]: 419.1. |
| B012-B | Trans-3-[5-chloro-2-(8-chloro-4-oxo-chromen-2-yl)-4-methyl-phenoxy]cyclobutane-carboxylic acid | CORE: Int-5 SM4: methyl 3-methylsulfonyl-oxycyclobutane-carboxylate | $^1$H NMR (DMSO-d$_6$, 400 MHz): δ ppm 7.97-8.05 (m, 2H), 7.85-7.92 (m, 1H), 7.45-7.54 (m, 1H), 7.04 (s, 2H), 4.98-5.09 (m, 1H), 3.02-3.16 (m, 1H), 2.64-2.77 (m, 2H), 2.35-2.43 (m, 5H). MS obsd. (ESI$^+$) [(M + H)$^+$]: 419.1. |
| B013-A | Cis-3-[5-bromo-2-(8-chloro-4-oxo-chromen-2-yl)-4-methyl-phenoxy]cyclobutane-carboxylic acid | CORE: Int-6 SM4: methyl 3-methylsulfonyl-oxycyclobutane-carboxylate | $^1$H NMR (DMSO-d$_6$, 400 MHz): δ ppm 7.91-8.01 (m, 2H), 7.79-7.87 (m, 1H), 7.42-7.52 (m, 1H), 7.20-7.29 (m, 1H), 6.97-7.03 (m, 1H), 4.80-4.91 (m, 1H), 2.65-2.84 (m, 3H), 2.34 (s, 3H), 2.15-2.30 (m, 2H). MS obsd. (ESI$^+$) [(M + H)$^+$]: 463.1. |

TABLE 6-continued

Compounds synthesis and characterization

| Example No. | Compounds Name and Structure | CORE and SM4 | ¹H NMR and (ESI⁺) |
|---|---|---|---|
| B013-B | Trans-3-[5-bromo-2-(8-chloro-4-oxo-chromen-2-yl)-4-methyl-phenoxy]cyclobutanecarboxylic acid | CORE: Int-6 SM4: methyl 3-methylsulfonyl-oxycyclobutane-carboxylate | ¹H NMR (DMSO-d₆, 400 MHz): δ ppm 7.96-8.02 (m, 2H), 7.79-7.86 (m, 1H), 7.46-7.52 (m, 1H), 7.14-7.18 (m, 1H), 7.03 (s, 1H), 4.97-5.07 (m, 1H), 3.07-3.18 (m, 1H), 2.65-2.75 (m, 2H), 2.35-2.43 (m, 5H). MS obsd. (ESI⁺) [(M + H)⁺]: 463.1. |
| B014 | Trans-3-[4-bromo-2-(8-chloro-4-oxo-chromen-2-yl)-5-methoxy-phenoxy]cyclobutanecarboxylic acid | CORE: Int-34 SM4: methyl 3-methylsulfonyl-oxycyclobutane-carboxylate | ¹H NMR (DMSO-d₆, 400 MHz): δ ppm 8.12-8.15 (m, 1H), 7.97-8.02 (m, 2H), 7.44-7.52 (m, 1H), 7.06-7.10 (m, 1H), 6.61 (s, 1H), 5.12-5.20 (m, 1H), 4.07-4.13 (m, 1H), 3.98 (s, 3H), 2.72-2.83 (m, 2H), 2.40-2.47 (m, 2H). MS obsd. (ESI⁺) [(M + H)⁺]: 479.1. |
| B015-A | Cis-3-[2-(8-chloro-4-oxo-chromen-2-yl)-5-(trifluoromethoxy)phenoxy]cyclobutanecarboxylic acid | CORE: Int-9 SM4: methyl 3-methylsulfonyl-oxycyclobutane-carboxylate | ¹H NMR (DMSO-d₆, 400 MHz): δ ppm 12.33 (s, 1H), 7.96-8.12 (m, 3H), 7.47-7.55 (m, 1H), 7.19-7.28 (m, 1H), 7.06-7.13 (m, 1H), 7.03-7.05 (m, 1H), 4.87-4.96 (m, 1H), 2.74-2.86 (m, 3H), 2.23-2.29 (m, 2H). MS obsd. (ESI⁺) [(M + H)⁺]: 455.1. |

TABLE 6-continued

Compounds synthesis and characterization

| Example No. | Compounds Name and Structure | CORE and SM4 | $^1$H NMR and (ESI$^+$) |
|---|---|---|---|
| B016 | Cis-3-[2-(8-chloro-4-oxo-chromen-2-yl)-4-methyl-phenoxy]cyclobutane-carboxylic acid | CORE: Int-31 SM4: methyl 3-methylsulfonyl-oxycyclobutane-carboxylate | $^1$H NMR (DMSO-d$_6$, 400 MHz): δ ppm 12.40 (s, 1H), 7.97-8.03 (m, 2H), 7.73-7.78 (m, 1H), 7.45-7.54 (m, 1H), 7.33-7.41 (m, 1H), 7.03-7.06 (m, 1H), 6.97-7.02 (m, 1H), 4.73-4.84 (m, 1H), 2.69-2.86 (m, 3H), 2.38 (s, 3H), 2.16-2.29 (m, 2H). MS obsd. (ESI$^+$) [(M + H)$^+$]: 385.1. |
| B017 | 3-[2-(8-chloro-4-oxo-chromen-2-yl)-5-methoxy-4-methyl-phenoxy]cyclobutane-carboxylic acid | CORE: Int-12 SM4: methyl 3-methylsulfonyl-oxycyclobutane-carboxylate | $^1$H NMR (DMSO-d$_6$, 400 MHz): δ ppm 12.31 (s, 1H), 7.95-8.03 (m, 2H), 7.75-7.82 (m, 1H), 7.41-7.52 (m, 1H), 7.04-7.08 (m, 1H), 6.45-6.50 (m, 1H), 5.06-5.16 (m, 1H), 3.91 (s, 3H), 3.11-3.20 (m, 1H), 2.71-2.83 (m, 2H), 2.39-2.47 (m, 2H), 2.16 (s, 3H). MS obsd. (ESI$^+$) [(M + H)$^+$]: 415.1. |
| B018-A | Cis-3-[2-(8-chloro-4-oxo-chromen-2-yl)-5-methyl-phenoxy]cyclobutane-carboxylic acid | CORE: Int-2 SM4: methyl 3-methylsulfonyl-oxycyclobutane-carboxylate | $^1$H NMR (DMSO-d$_6$, 400 MHz): δ ppm 12.25-12.44 (m, 1H), 7.96-8.03 (m, 2H), 7.84-7.91 (m, 1H), 7.45-7.53 (m, 1H), 7.05-7.08 (m, 1H), 6.99-7.05 (m, 1H), 6.89-6.95 (m, 1H), 4.78-4.88 (m, 1H), 2.74-2.86 (m, 3H), 2.43 (s, 3H), 2.19-2.30 (m, 2H). MS obsd. (ESI$^+$) [(M + H)$^+$]: 385.1. |
| B018-B | Trans-3-[2-(8-chloro-4-oxo-chromen-2-yl)-5-methyl-phenoxy]cyclobutane-carboxylic acid | CORE: Int-2 SM4: methyl 3-methylsulfonyl-oxycyclobutane-carboxylate | $^1$H NMR (DMSO-d$_6$, 400 MHz): δ ppm 8.00 (d, J = 7.95 Hz, 2H), 7.84-7.91 (m, 1H), 7.44-7.54 (m, 1H), 7.06-7.12 (m, 1H), 6.99-7.05 (m, 1H), 6.81-6.87 (m, 1H), 4.94-5.06 (m, 1H), 3.07-3.19 (m, 1H), 2.69-2.84 (m, 2H), 2.35-2.46 (m, 5H). MS obsd. (ESI$^+$) [(M + H)$^+$]: 385.1. |

TABLE 6-continued

Compounds synthesis and characterization

| Example No. | Compounds Name and Structure | CORE and SM4 | $^1$H NMR and (ESI$^+$) |
|---|---|---|---|
| B019-A | Cis-3-[2-(8-chloro-4-oxo-chromen-2-yl)-5-ethyl-phenoxy]cyclobutane-carboxylic acid | CORE: Int-29 SM4: methyl 3-methylsulfonyl-oxycyclobutane-carboxylate | $^1$H NMR (DMSO-d$_6$, 400 MHz): δ ppm 12.35 (br s, 1H), 7.94-8.05 (m, 2H), 7.81-7.92 (m, 1H), 7.42-7.53 (m, 1H), 6.99-7.09 (m, 2H), 6.86-6.95 (m, 1H), 4.85 (br d, J = 4.5 Hz, 1H), 2.74-2.86 (m, 3H), 2.62-2.72 (m, 2H), 2.11-2.35 (m, 2H), 1.22 (td, J = 7.4, 1.8 Hz, 3H). MS obsd. (ESI$^+$) [(M + H)$^+$]: 399.1. |
| B019-B | Trans-3-[2-(8-chloro-4-oxo-chromen-2-yl)-5-ethyl-phenoxy]cyclobutane-carboxylic acid | CORE: Int-29 SM4: methyl 3-methylsulfonyl-oxycyclobutane-carboxylate | $^1$H NMR (DMSO-d$_6$, 400 MHz): δ ppm 112.40 (br s, 1H), 7.98 (dd, J = 7.9, 2.0 Hz, 2H), 7.88 (d, J = 8.1 Hz, 1H), 7.47 (t, J = 7.9 Hz, 1H), 7.05-7.12 (m, 1H), 6.97-7.05 (m, 1H), 6.77-6.86 (m, 1H), 4.95-5.06 (m, 1H), 3.06-3.20 (m, 1H), 2.60-2.81 (m, 4H), 2.36-2.48 (m, 2H), 1.21 (t, J = 7.6 Hz, 3H). MS obsd. (ESI$^+$) [(M + H)$^+$]: 399.1. |
| B020-A | Cis-3-[2-(8-chloro-4-oxo-chromen-2-yl)-5-isopropyl-phenoxy]cyclobutane-carboxylic acid | CORE: Int-30 SM4: methyl 3-methylsulfonyl-oxycyclobutane-carboxylate | $^1$H NMR (DMSO-d$_6$, 400 MHz): δ ppm 12.34 (s, 1H), 7.95 (dd, J = 39.5, 8.0 Hz, 3H), 7.49 (t, J = 7.9 Hz, 1H), 7.07 (d, J = 20.5 Hz, 2H), 6.92 (d, J = 1.0 Hz, 1H), 4.84-4.92 (m, 1H), 2.97 (dq, J = 14.0, 7.0 Hz, 1H), 2.80 (d, J = 4.1 Hz, 3H), 2.18-2.31 (m, 2H), 1.25 (d, J = 6.9 Hz, 6H). MS obsd. (ESI$^+$) [(M + H)$^+$]: 413.1. |
| B020-B | Trans-3-[2-(8-chloro-4-oxo-chromen-2-yl)-5-isopropyl-phenoxy]cyclobutane-carboxylic acid | CORE: Int-30 SM4: methyl 3-methylsulfonyl-oxycyclobutane-carboxylate | $^1$H NMR (DMSO-d$_6$, 400 MHz): δ ppm 12.38 (s, 1H), 7.95 (dd, J = 38.4, 8.0 Hz, 3H), 7.49 (t, J = 7.9 Hz, 1H), 7.00-7.19 (m, 2H), 6.83 (d, J = 1.1 Hz, 1H), 5.00-5.09 (m, 1H), 3.07-3.20 (m, 1H), 2.92-3.04 (m, 1H), 2.74 (ddd, J = 13.4, 7.0, 4.1 Hz, 2H), 2.35-2.47 (m, 2H), 1.22 (t, J = 10.9 Hz, 6H). MS obsd. (ESI$^+$) [(M + H)$^+$]: 413.1. |

TABLE 6-continued

Compounds synthesis and characterization

| Example No. | Compounds Name and Structure | CORE and SM4 | $^1$H NMR and (ESI$^+$) |
|---|---|---|---|
| B021 | Trans-3-[2-(8-chloro-4-oxo-chromen-2-yl)-4-methoxy-phenoxy]cyclobutane-carboxylic acid | CORE: Int-32 SM4: methyl 3-methylsulfonyl-oxycyclobutane-carboxylate | $^1$H NMR (DMSO-d$_6$, 400 MHz): δ ppm 12.42 (s, 1H), 7.99-8.05 (m, 2H), 7.46-7.56 (m, 2H), 7.13 (s, 2H), 6.95-7.01 (m, 1H), 4.90-4.99 (m, 1H), 3.80 (s, 3H), 3.06-3.15 (m, 1H), 2.63-2.74 (m, 2H), 2.34-2.44 (m, 2H). MS obsd. (ESI$^+$) [(M + H)$^+$]: 401.1. |
| B022-A | Cis-3-[2-(8-bromo-4-oxo-chromen-2-yl)phenoxy]cyclobutane-carboxylic acid | CORE: Int-28 SM4: methyl 3-methylsulfonyl-oxycyclobutane-carboxylate | $^1$H NMR (DMSO-d$_6$, 400 MHz): δ ppm 8.08-8.11 (m, 1H), 7.93-7.99 (m, 2H), 7.47-7.54 (m, 1H), 7.37 (t, J = 7.8 Hz, 1H), 7.13 (t, J = 7.6 Hz, 1H), 7.01-7.06 (m, 1H), 6.93-6.99 (m, 1H), 4.95 (quin, J = 6.5 Hz, 1H), 3.03-3.10 (m, 2H), 2.63-2.69 (m, 2H), 2.34-2.38 (m, 1H). MS obsd. (ESI$^+$) [(M + H)$^+$]: 415.0. |
| B022-B | Trans-3-[2-(8-bromo-4-oxo-chromen-2-yl)phenoxy]cyclobutane-carboxylic acid | CORE: Int-28 SM4: methyl 3-methylsulfonyl-oxycyclobutane-carboxylate | $^1$H NMR (DMSO-d$_6$, 400 MHz): δ ppm 8.13-8.18 (m, 1H), 8.00-8.07 (m, 2H), 7.54-7.62 (m, 1H), 7.44 (t, J = 7.9 Hz, 1H), 7.18-7.23 (m, 1H), 7.07-7.13 (m, 2H), 4.85 (br dd, J = 9.0, 5.3 Hz, 1H), 2.76-2.83 (m, 3H), 2.24-2.32 (m, 2H). MS obsd. (ESI$^+$) [(M + H)$^+$]: 415.0. |
| B023 | Trans-3-[[6-(8-chloro-4-oxo-chromen-2-yl)-2,3-dihydrobenzofuran-5-yl]oxy]cyclobutanecarboxylic acid | CORE: Int-33 SM4: methyl 3-methylsulfonyl-oxycyclobutane-carboxylate | $^1$H NMR (DMSO-d$_6$, 400 MHz): δ ppm 7.96-8.05 (m, 2H), 7.42-7.55 (m, 1H), 7.26-7.35 (m, 1H), 7.07-7.14 (m, 1H), 6.95-7.04 (m, 1H), 4.84-5.01 (m, 1H), 4.48-4.62 (m, 2H), 3.23-3.30 (m, 2H), 3.04-3.15 (m, 1H), 2.64-2.75 (m, 2H), 2.30-2.45 (m, 2H). MS obsd. (ESI$^+$) [(M + H)$^+$]: 413.1. |

TABLE 6-continued

Compounds synthesis and characterization

| Example No. | Compounds Name and Structure | CORE and SM4 | $^1$H NMR and (ESI$^+$) |
|---|---|---|---|
| B024 | Trans-3-[5-bromo-2-(8-chloro-4-oxo-chromen-2-yl)-4-(trifluoromethyl)phenoxy]cyclobutanecarboxylic acid | CORE: Int-27 SM4: methyl 3-methylsulfonyl-oxycyclobutane-carboxylate | $^1$H NMR (DMSO-d$_6$, 400 MHz): δ ppm 8.31-8.37 (m, 1H), 7.97-8.08 (m, 2H), 7.43-7.57 (m, 2H), 7.07-7.17 (m, 1H), 5.15-5.27 (m, 1H), 3.03-3.20 (m, 1H), 2.70-2.82 (m, 2H), 2.38-2.46 (m, 2H). MS obsd. (ESI$^+$) [(M + H)$^+$]: 516.9. |
| B025-A | Cis-3-[[5-bromo-2-(8-chloro-4-oxo-chromen-2-yl)phenoxy]methyl]cyclobutane-carboxylic acid | CORE: Int-4 SM4: methyl 3-(p-tolylsulfonyl-oxymethyl)cyclo-butanecarboxylate | $^1$H NMR (DMSO-d$_6$, 400 MHz): δ ppm 7.95-8.05 (m, 2H), 7.82-7.92 (m, 1H), 7.46-7.54 (m, 2H), 7.39-7.46 (m, 1H), 6.97-7.04 (m, 1H), 4.09-4.21 (m, 2H), 2.93-3.12 (m, 1H), 2.62-2.79 (m, 1H), 2.20-2.38 (m, 2H), 1.93-2.06 (m, 2H). MS obsd. (ESI$^+$) [(M + H)$^+$]: 416.1. |
| B025-B | Trans-3-[[5-bromo-2-(8-chloro-4-oxo-chromen-2-yl)phenoxy]methyl]cyclo-butanecarboxylic acid | CORE: Int-4 SM4: methyl 3-(p-tolylsulfonyl-oxymethyl)cyclo-butanecarboxylate | $^1$H NMR (DMSO-d$_6$, 400 MHz): δ ppm 7.96-8.04 (m, 2H), 7.84-7.94 (m, 1H), 7.39-7.56 (m, 3H), 6.99-7.10 (m, 1H), 4.15-4.30 (m, 2H), 3.03-3.15 (m, 1H), 2.71-2.86 (m, 1H), 2.23-2.38 (m, 2H), 2.04-2.19 (m, 2H). MS obsd. (ESI$^+$) [(M + H)$^+$]: 416.1. |
| B026-A | Cis-3-[[2-(8-chloro-4-oxo-chromen-2-yl)phenoxy]methyl]cyclo-butanecarboxylic acid | CORE: Int-3 SM4: methyl 3-(p-tolylsulfonyloxy-methyl)cyclo-butanecarboxylate | $^1$H NMR (DMSO-d$_6$, 400 MHz): δ ppm 7.95-8.03 (m, 3H), 7.57 (d, J = 1.47 Hz, 1H), 7.49 (t, J = 7.83 Hz, 1H), 7.25 (d, J = 8.07 Hz, 1H), 7.16-7.23 (m, 1H), 7.04 (s, 1H), 4.12 (d, J = 7.09 Hz, 2H), 3.00-3.12 (m, 1H), 2.73 (s, 1H), 2.25-2.36 (m, 2H), 1.96-2.06 (m, 2H). MS obsd. (ESI$^+$) [(M + H)$^+$]: 385.1. |

TABLE 6-continued

Compounds synthesis and characterization

| Example No. | Compounds Name and Structure | CORE and SM4 | $^1$H NMR and (ESI$^+$) |
|---|---|---|---|
| B026-B | Trans-3-[[2-(8-chloro-4-oxo-chromen-2-yl)phenoxy]methyl]cyclo-butanecarboxylic acid | CORE: Int-3 SM4: methyl 3-(p-tolylsulfonyloxy-methyl)cyclo-butanecarboxylate | $^1$H NMR (DMSO-d$_6$, 400 MHz): δ ppm 7.94-8.05 (m, 3H), 7.56-7.64 (m, 1H), 7.46-7.54 (m, 1H), 7.16-7.33 (m, 2H), 7.01-7.10 (m, 1H), 4.14-4.24 (m, 2H), 3.00-3.15 (m, 1H), 2.74-2.84 (m, 1H), 2.25-2.35 (m, 2H), 2.06-2.21 (m, 2H). MS obsd. (ESI$^+$) [(M + H)$^+$]: 385.1. |
| B027-A | Cis-[2-(8-chloro-4-oxo-chromen-2-yl)-4-methoxy-phenoxy]methyl]cyclobutane-carboxylic acid | CORE: Int-32 SM4: methyl 3-(p-tolylsulfonyloxy-methyl)cyclo-butanecarboxylate | $^1$H NMR (DMSO-d$_6$, 400 MHz): δ ppm 12.14 (s, 1H), 7.95-8.06 (m, 2H), 7.44-7.57 (m, 2H), 7.14-7.25 (m, 2H), 7.07-7.11 (m, 1H), 4.02-4.08 (m, 2H), 3.80 (s, 3H), 2.96-3.09 (m, 1H), 2.64-2.75 (m, 1H), 2.21-2.34 (m, 2H), 1.91-2.04 (m, 2H). MS obsd. (ESI$^+$) [(M + H)$^+$]: 415.1. |
| B027-B | Trans-[2-(8-chloro-4-oxo-chromen-2-yl)-4-methoxy-phenoxy]methyl]cyclobutane-carboxylic acid | CORE: Int-32 SM4: methyl 3-(p-tolylsulfonyloxy-methyl)cyclo-butanecarboxylate | $^1$H NMR (DMSO-d$_6$, 400 MHz): δ ppm 7.95-8.05 (m, 2H), 7.45-7.56 (m, 2H), 7.16-7.27 (m, 2H), 7.08-7.13 (m, 1H), 4.09-4.17 (m, 2H), 3.87 (s, 3H), 3.02-3.12 (m, 1H), 2.72-2.81 (m, 1H), 2.25-2.36 (m, 2H), 2.06-2.18 (m, 2H). MS obsd. (ESI$^+$) [(M + H)$^+$]: 415.1. |
| B028-A | Cis-3-[5-bromo-2-(8-chloro-4-oxo-chromen-2-yl)phenoxy]cyclopentane-carboxylic acid | CORE: Int-4 SM4: methyl 3-(p-tolylsulfonyloxy) cyclopentane-carboxylate | $^1$H NMR (DMSO-d$_6$, 400 MHz): δ ppm 11.96-12.16 (m, 1H), 7.96-8.04 (m, 2H), 7.83-7.92 (m, 1H), 7.38-7.54 (m, 3H), 6.97-7.09 (m, 1H), 5.06-5.17 (m, 1H), 2.75-2.89 (m, 1H), 2.29-2.45 (m, 1H), 1.87-2.04 (m, 5H). MS obsd. (ESI$^+$) [(M + H)$^+$]: 463.0. |

TABLE 6-continued

Compounds synthesis and characterization

| Example No. | Compounds Name and Structure | CORE and SM4 | $^1$H NMR and (ESI$^+$) |
|---|---|---|---|
| B028-B | Trans-3-[5-bromo-2-(8-chloro-4-oxo-chromen-2-yl)phenoxy]cyclopentane-carboxylic acid | CORE: Int-4 SM4: methyl 3-(p-tolylsulfonyloxy)cyclopentane-carboxylate | $^1$H NMR (DMSO-d$_6$, 400 MHz): δ ppm 12.08-12.31 (m, 1H), 7.95-8.06 (m, 2H), 7.81-7.92 (m, 1H), 7.34-7.56 (m, 3H), 6.92-7.02 (m, 1H), 5.15-5.25 (m, 1H), 2.85-2.99 (m, 1H), 1.91-2.22 (m, 5H), 1.77-1.89 (m, 1H). MS obsd. (ESI$^+$) [(M + H)$^+$]: 463.0. |
| B029 | Trans-3-[[5-bromo-2-(8-chloro-4-oxo-chromen-2-yl)-3-pyridyl]oxy]cyclobutane-carboxylic acid | CORE: Int-26 SM4: methyl 3-methylsulfonyl-oxycyclobutane-carboxylate | $^1$H NMR (DMSO-d$_6$, 400 MHz): δ ppm 8.47-8.57 (m, 1H), 7.99-8.07 (m, 2H), 7.77-7.82 (m, 1H), 7.35-7.59 (m, 1H), 6.94-7.08 (m, 1H), 5.02-5.19 (m, 1H), 3.04-3.19 (m, 1H), 2.69-2.80 (m, 2H), 2.38-2.48 (m, 2H). MS obsd. (ESI$^+$) [(M + H)$^+$]: 450.1. |

Example B035-A and Example B035-B: cis-3-[2-(8-chloro-4-oxo-chromen-2-yl)-5-cyclopropyl-phenoxy]cyclobutanecarboxylic acid and trans-3-[2-(8-chloro-4-oxo-chromen-2-yl)-5-cyclopropyl-phenoxy]cyclobutanecarboxylic acid -continued

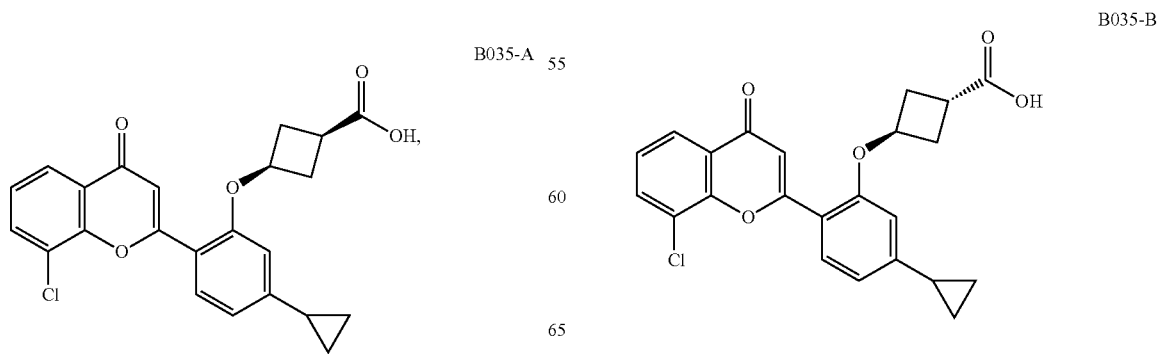

Step 1: Preparation of methyl 3-[2-(8-chloro-4-oxo-chromen-2-yl)-5-cyclopropyl-phenoxy]cyclobutan-ecarboxylate

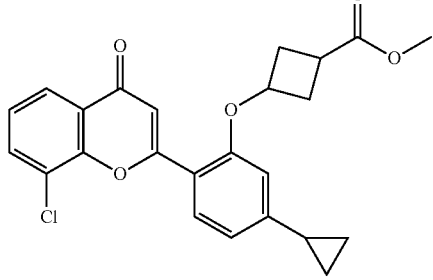

To a mixture of methyl 3-[5-bromo-2-(8-chloro-4-oxo-chromen-2-yl)phenoxy]cyclobutanecarboxylate (Example B001b, 800.0 mg, 1.73 mmol), potassium cyclopropyltrifluoroborate (1021.19 mg, 6.9 mmol), 2-dicyclohexylphosphino-2',6'-dimethoxybiphenyl (70.83 mg, 0.170 mmol) in the mixed solvent of toluene (10 mL) and water (1 mL) was added Pd(OAc)$_2$ (387.33 mg, 1.73 mmol) under N$_2$ atmosphere and the reaction was stirred at 90° C. for 3 hours. After the reaction was completed, the mixture was concentrated in vacuo and the residue was purified by column chromatography on solica gel (eluent with PE:EtOAc=100:1 to 2:1) to give methyl 3-[2-(8-chloro-4-oxo-chromen-2-yl)-5-cyclopropyl-phenoxy]cyclobutanecarboxylate (430 mg, 57.8% yield) as a yellow solid. MS obsd. (ESI$^+$)[(M+H)$^+$]: 425.1.

Step 2: Preparation of 3-[2-(8-chloro-4-oxo-chromen-2-yl)-5-cyclopropyl-phenoxy]cyclobutan-ecarboxylic acid cis-3-[2-(8-chloro-4-oxo-chromen-2-yl)-5-cyclopropyl-phenoxy]cyclobutanecarboxylic acid and trans-3-[2-(8-chloro-4-oxo-chromen-2-yl)-5-cyclopropyl-phenoxy]cyclobutanecarboxylic acid

B035-A

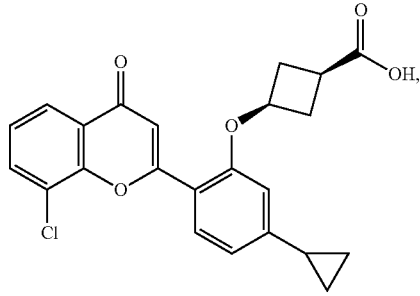

B035-B

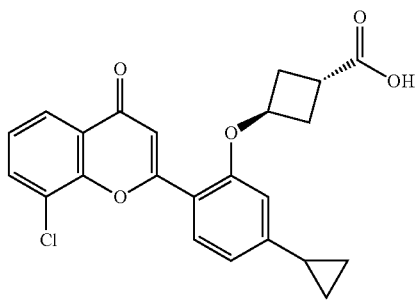

Example B035-A and B035-B was prepared in analogy to the procedure described for the preparation of example B002-A and B002-B by using methyl 3-[2-(8-chloro-4-oxo-chromen-2-yl)-5-cyclopropyl-phenoxy]cyclobutanecarboxylate as the starting material instead of methyl 3-[2-(8-chloro-4-oxo-chromen-2-yl)phenoxy]cyclobutanecarboxylate in step 2. Example B035-A: $^1$H NMR (DMSO-d$_6$, 400 MHz): δ ppm 7.94-8.04 (m, 2H), 7.82-7.90 (m, 1H), 7.42-7.57 (m, 1H), 7.03-7.11 (m, 1H), 6.83-6.92 (m, 1H), 6.72-6.79 (m, 1H), 4.79-4.96 (m, 1H), 2.73-2.87 (m, 3H), 2.20-2.36 (m, 2H), 1.97-2.10 (m, 1H), 0.99-1.15 (m, 2H), 0.76-0.89 (m, 2H). MS obsd. (ESI$^+$)[(M+H)$^+$]: 411.0.

Example B035-B: $^1$H NMR (DMSO-d$_6$, 400 MHz): δ ppm 7.95-8.03 (m, 2H), 7.80-7.92 (m, 1H), 7.43-7.55 (m, 1H), 7.04-7.15 (m, 1H), 6.77-6.88 (m, 1H), 6.65-6.75 (m, 1H), 4.98-5.13 (m, 1H), 3.04-3.21 (m, 1H), 2.69-2.82 (m, 2H), 2.34-2.46 (m, 2H), 2.01-2.11 (m, 1H), 1.00-1.13 (m, 2H), 0.71-0.85 (m, 2H). MS obsd. (ESI$^+$)[(M+H)$^+$]: 411.0.

Example B036-A and Example B036-B: Cis-3-[5-bromo-2-(8-chloro-5-hydroxy-4-oxo-chromen-2-yl)phenoxy]cyclobutanecarboxylic acid and trans-3-[5-bromo-2-(8-chloro-5-hydroxy-4-oxo-chromen-2-yl)phenoxy]cyclobutanecarboxylic acid

B036-A

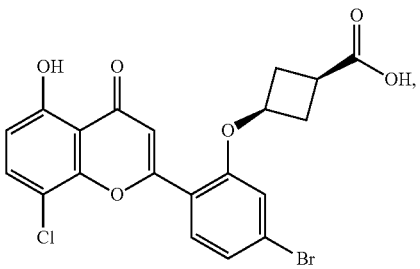

B036-B

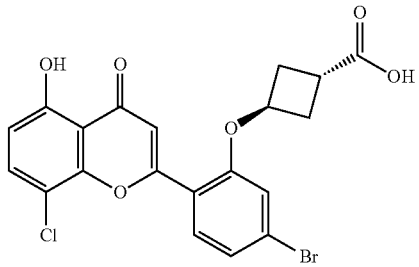

Step 1: Preparation of methyl 3-(5-bromo-2-formyl-phenoxy)cyclobutanecarboxylate

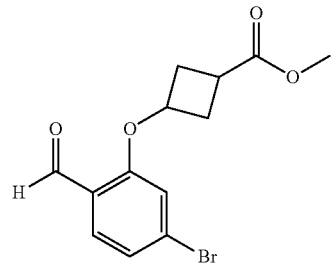
B036a

To a mixture of 4-bromo-2-hydroxy-benzaldehyde (500 mg, 2.5 mmol), methyl 3-methylsulfonyloxycyclobutanecarboxylate (750 mg, 4.2 mmol) in DMF (10 ml) was added $K_2CO_3$ (690 mg, 5.0 mmol) and the mixture was stirred at 120° C. for 2 hours. After the reaction was completed, the mixture was diluted with water (15 mL) and extracted with EtOAc (30 mL) three times. The combined organic layer was washed with brine, dried over $Na_2SO_4$ and concentrated in vacuo to give the crude methyl 3-(5-bromo-2-formyl-phenoxy)cyclobutanecarboxylate (657 mg, 82.1% yield), which was used in the next directly without further purification. MS obsd. (ESI$^+$) [(M+H)$^+$]:312.9.

Step 2: Preparation of 3-[5-bromo-2-[(E)-3-[3-chloro-2,6-bis(methoxymethoxy)phenyl]-3-oxo-prop-1-enyl]phenoxy]cyclobutanecarboxylic acid

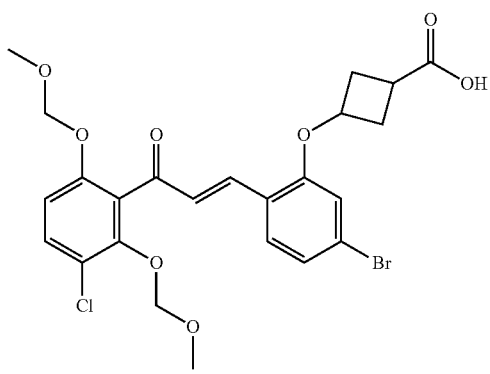
B036b

To a solution of 1-[3-chloro-2,6-bis(methoxymethoxy)phenyl]ethanone (83.1 mg, 0.3 mmol) and methyl 3-(5-bromo-2-formyl-phenoxy)cyclobutanecarboxylate (80 mg, 0.3 mmol) in ethanol (5 mL) was added KOH (171 mg, 3.05 mmol) and the mixture was then stirred at 40° C. for 16 hours. After the reaction was completed, the mixture was diluted with water (20 mL) and adjusted to PH~6 by addition of 1N HCl. The resulting mixture was extracted with EtOAc (20 mL) three times, the combined organic layer was washed with brine (20 mL) twice, dried over $Na_2SO_4$ and concentrated in vacuo to give 3-[5-bromo-2-[(E)-3-[3-chloro-2,6-bis(methoxymethoxy)phenyl]-3-oxo-prop-1-enyl]phenoxy]cyclobutanecarboxylic acid (150 mg, 97.4% yield) as an orange oil. MS obsd. (ESI$^+$) [(M+H)$^+$]:555.1.

Step 3: Preparation of Cis-3-[5-bromo-2-(8-chloro-5-hydroxy-4-oxo-chromen-2-yl)phenoxy]cyclobutanecarboxylic acid and trans-3-[5-bromo-2-(8-chloro-5-hydroxy-4-oxo-chromen-2-yl)phenoxy]cyclobutanecarboxylic acid

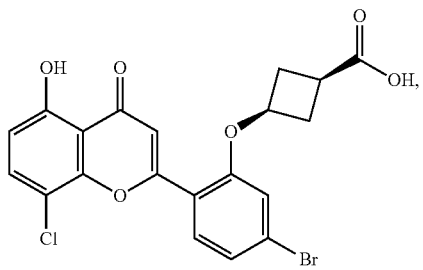
B036-A

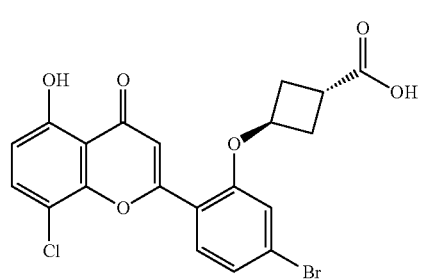 [SMILES: O=c1cc(-c2ncc(Br)cc2O[C@H]2C[C@H](C(=O)O)C2)oc2c(Cl)cccc12]
B036-B

To a solution of 3-[5-bromo-2-[(E)-3-[3-chloro-2,6-bis(methoxymethoxy)phenyl]-3-oxo-prop-1-enyl]phenoxy]cyclobutanecarboxylic acid (150 mg, 0.29 mmol) in DMSO (8 ml) was added $I_2$ (5.1 mg, 0.02 mmol) and the mixture was stirred 140° C. at for 2 hours. After the reaction was completed, the mixture was diluted with water (30 mL) and extracted with EtOAc (30 mL) three times. The combined organic layer was washed with brine, dried over $Na_2SO_4$ and concentrated in vacuo. The residue was purified by Prep-HPLC to give two diastereomers of cis-3-[5-bromo-2-(8-chloro-5-hydroxy-4-oxo-chromen-2-yl)phenoxy]cyclobutanecarboxylic acid (Example B036-A, 9 mg, % yield) and trans-3-[5-bromo-2-(8-chloro-5-hydroxy-4-oxo-chromen-2-yl)phenoxy]cyclobutanecarboxylic acid (Example B036-B, 56 mg, % yield).

Example B036-A: $^1$H NMR (DMSO-d$_6$, 400 MHz): δ ppm 12.58 (s, 1H), 12.23-12.39 (br, 1H), 7.87 (dd, J=16.1, 8.7 Hz, 2H), 7.44 (dd, J=8.5, 1.8 Hz, 1H), 7.31 (d, J=1.7 Hz, 1H), 7.11 (s, 1H), 6.87 (d, J=8.9 Hz, 1H), 4.88-5.00 (m, 1H), 2.75-2.83 (m, 3H), 2.21-2.29 (m, 2H). MS obsd. (ESI$^+$) [(M+H)$^+$]:465.1.

Example B036-B: $^1$H NMR (DMSO-d$_6$, 400 MHz): δ ppm 12.58 (s, 1H), 7.88 (s, 2H), 7.41-7.47 (m, 1H), 7.14 (s, 1H), 6.96 (s, 1H), 6.88 (d, J=8.8 Hz, 1H), 5.07-5.12 (m, 1H), 3.11-3.18 (m, 2H), 2.72-2.77 (m, 2H), 2.39-2.442 (m, 1H). MS obsd. (ESI$^+$) [(M+H)$^+$]:465.1.

Example B037-A and Example B037-B

Cis-3-[2-(8-chloro-5-hydroxy-4-oxo-chromen-2-yl)-5-methyl-phenoxy]cyclobutanecarboxylic acid and Trans-3-[2-(8-chloro-5-hydroxy-4-oxo-chromen-2-yl)-5-methyl-phenoxy]cyclobutanecarboxylic acid

Example B038-A and Example B038-B: Cis-3-[2-(8-chloro-5-hydroxy-4-oxo-chromen-2-yl)-5-(trifluoromethyl)phenoxy]cyclobutanecarboxylic acid and Trans-3-[2-(8-chloro-5-hydroxy-4-oxo-chromen-2-yl)-5-(trifluoromethyl)phenoxy]cyclobutanecarboxylic acid

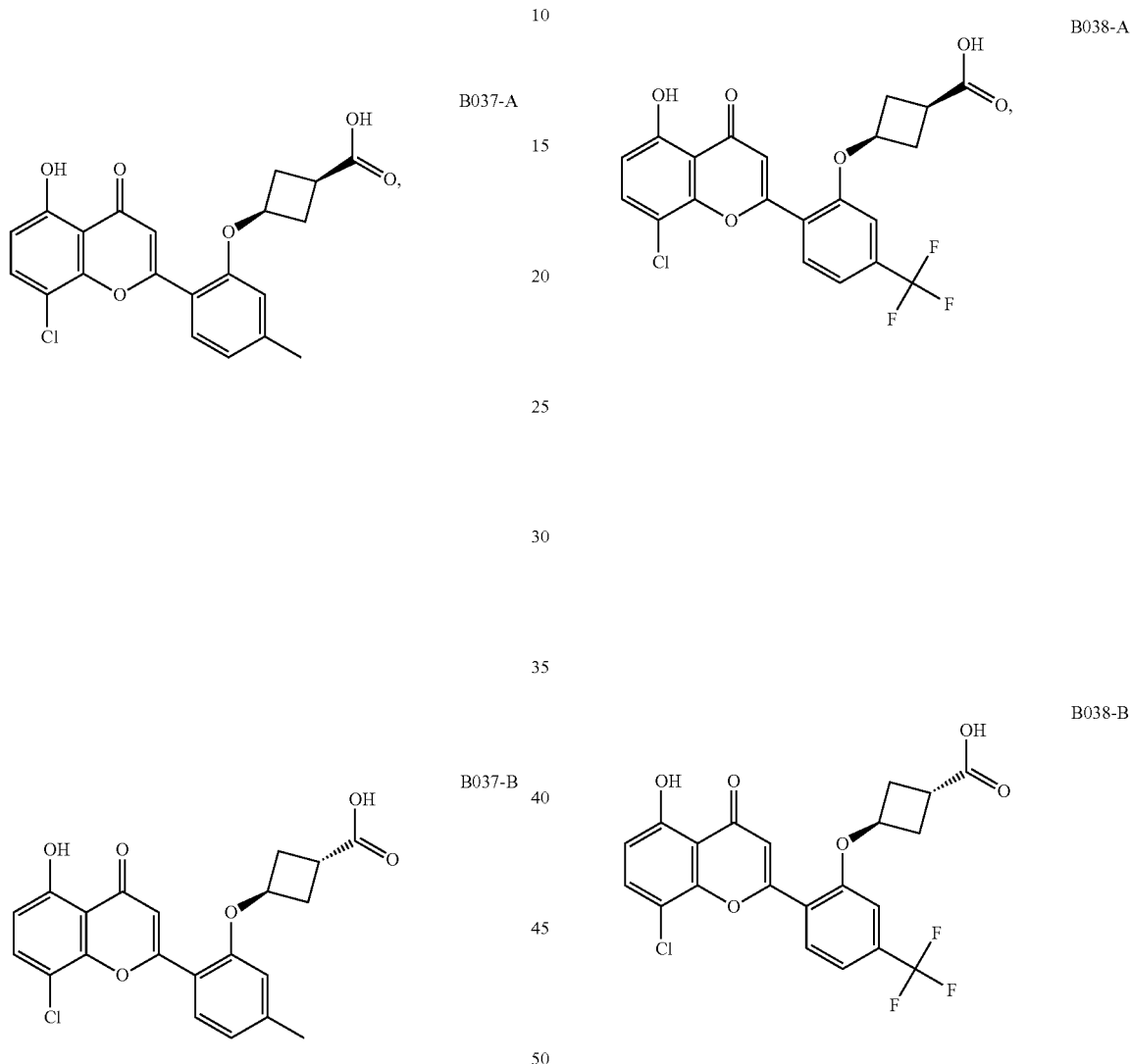

Example B037-A and B037-B were prepared in analogy to the procedure described for the preparation of example B036-A and B036-B by using 2-hydroxy-4-methyl-benzaldehyde as the starting material instead of 4-bromo-2-hydroxy-benzaldehyde in step 1.

Example B037-A: $^1$H NMR (DMSO-d$_6$, 400 MHz): δ ppm 12.57 (s, 1H), 12.36 (s, 1H), 7.76-7.92 (m, 2H), 7.07-7.15 (m, 1H), 6.95-7.02 (m, 1H), 6.79-6.93 (m, 2H), 4.76-4.88 (m, 1H), 2.74-2.91 (m, 3H), 2.35 (s, 3H), 2.18-2.33 (m, 2H). MS obsd. (ESI$^+$) [(M+H)$^+$]:401.0.

Example B037-B: $^1$H NMR (DMSO-d$_6$, 400 MHz): δ ppm 12.61 (s, 1H), 12.36 (s, 1H), 7.76-7.92 (m, 2H), 7.11-7.16 (m, 1H), 6.96-7.04 (m, 1H), 6.80-6.89 (m, 2H), 4.95-5.06 (m, 1H), 3.06-3.20 (m, 1H), 2.69-2.84 (m, 2H), 2.39-2.45 (m, 5H). MS obsd. (ESI$^+$) [(M+H)$^+$]:401.0.

Example B038-A and B038-B were prepared in analogy to the procedure described for the preparation of example B036-A and B036-B by using 2-hydroxy-4-(trifluoromethyl)benzaldehyde as the starting material instead of 4-bromo-2-hydroxy-benzaldehyde in step 1.

Example B038-A: $^1$H NMR (DMSO-d$_6$, 400 MHz): δ ppm 12.58 (s, 1H), 12.36 (s, 1H), 8.08-8.17 (m, 1H), 7.83-7.91 (m, 1H), 7.53-7.62 (m, 1H), 7.30-7.38 (m, 1H), 7.12-7.19 (m, 1H), 6.83-6.93 (m, 1H), 4.96-5.09 (m, 1H), 2.70-2.88 (m, 3H), 2.19-2.37 (m, 2H). MS obsd. (ESI$^+$) [(M+H)$^+$]:455.0.

Example B038-B: $^1$H NMR (DMSO-d$_6$, 400 MHz): δ ppm 12.51 (s, 1H), 8.05-8.18 (m, 1H), 7.75-7.90 (m, 1H), 7.49-7.61 (m, 1H), 7.13-7.29 (m, 2H), 6.79-6.92 (m, 1H), 5.11-5.24 (m, 1H), 3.06-3.18 (m, 1H), 2.65-2.82 (m, 2H), 2.33-2.46 (m, 2H). MS obsd. (ESI$^+$) [(M+H)$^+$]:455.1.

Example B039-A and Example B039-B: Cis-3-[2-(8-chloro-5-hydroxy-4-oxo-chromen-2-yl)-5-ethoxy-phenoxy]cyclobutanecarboxylic acid and Trans-3-[2-(8-chloro-5-hydroxy-4-oxo-chromen-2-yl)-5-ethoxy-phenoxy]cyclobutanecarboxylic acid

Example B040-A and Example B040-B: cis-3-[5-bromo-2-(8-chloro-5-hydroxy-4-oxo-chromen-2-yl)-4-methyl-phenoxy]cyclobutanecarboxylic acid and trans-3-[5-bromo-2-(8-chloro-5-hydroxy-4-oxo-chromen-2-yl)-4-methyl-phenoxy]cyclobutanecarboxylic acid

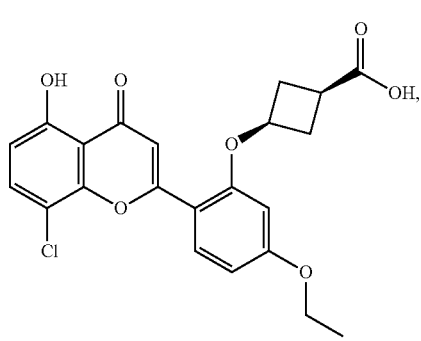

B039-A

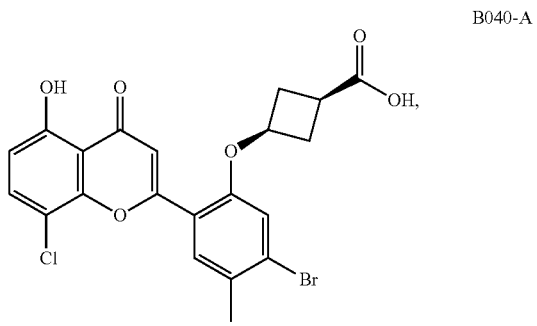

B040-A

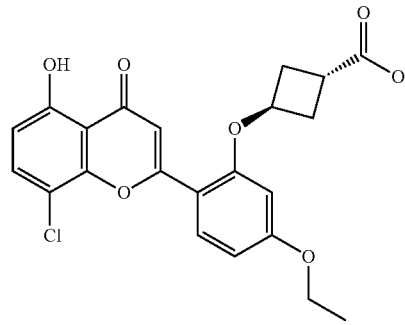

B039-B

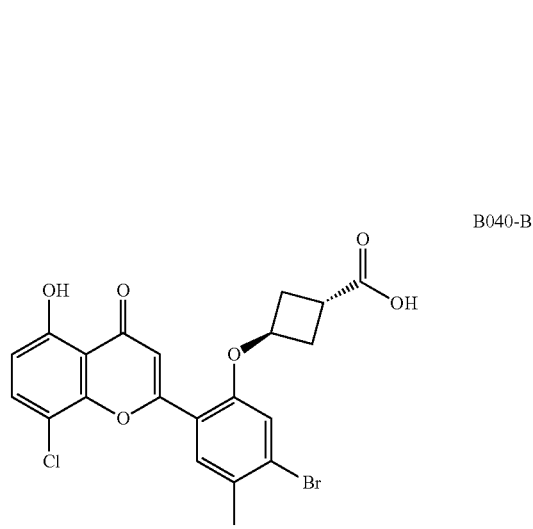

B040-B

Example B039-A and B039-B were prepared in analogy to the procedure described for the preparation of example B036-A and B036-B by using 4-ethoxy-2-hydroxy-benzaldehyde as the starting material instead of 4-bromo-2-hydroxy-benzaldehyde in step 1.

Example B039-A: $^1$H NMR (DMSO-d$_6$, 400 MHz): δ ppm 12.69 (s, 1H), 12.17-12.50 (br s, 1H), 7.92-8.02 (m, 1H), 7.73-7.85 (m, 1H), 7.04-7.16 (m, 1H), 6.73-6.89 (m, 2H), 6.47-6.60 (m, 1H), 4.83-4.94 (m, 1H), 4.04-4.21 (m, 2H), 2.73-2.89 (m, 3H), 2.19-2.39 (m, 2H), 1.29-1.42 (m, 3H). MS obsd. (ESI$^+$) [(M+H)$^+$]:431.1.

Example B039-B: $^1$H NMR (DMSO-d$_6$, 400 MHz): δ ppm 12.79 (s, 1H), 7.92-8.02 (m, 1H), 7.73-7.87 (m, 1H), 7.07-7.18 (m, 1H), 6.71-6.91 (m, 2H), 6.32-6.47 (m, 1H), 4.96-5.10 (m, 1H), 4.08-4.22 (m, 2H), 3.07-3.21 (m, 1H), 2.69-2.82 (m, 2H), 2.36-2.45 (m, 2H), 1.29-1.40 (m, 3H). MS obsd. (ESI$^+$) [(M+H)$^+$]:431.1.

Example B040-A and B040-B were prepared in analogy to the procedure described for the preparation of example B036-A and B036-B by using 4-bromo-2-hydroxy-5-methyl-benzaldehyde as the starting material instead of 4-bromo-2-hydroxy-benzaldehyde in step 1.

Example B040-A: $^1$H NMR (DMSO-d$_6$, 400 MHz): δ ppm 12.64 (s, 1H), 12.34 (s, 1H), 7.78-7.90 (m, 2H), 7.27-7.34 (m, 1H), 7.04-7.11 (m, 1H), 6.78-6.92 (m, 1H), 4.81-4.95 (m, 1H), 2.65-2.86 (m, 3H), 2.36 (s, 3H), 2.17-2.30 (m, 2H). MS obsd. (ESI$^+$) [(M+H)$^+$]:479.0.

Example B040-B: $^1$H NMR (DMSO-d$_6$, 400 MHz): δ ppm 12.52 (s, 1H), 12.38 (s, 1H), 7.79-7.89 (m, 2H), 7.17-7.23 (m, 1H), 7.06-7.13 (m, 1H), 6.75-6.92 (m, 1H), 4.95-5.11 (m, 1H), 3.07-3.19 (m, 1H), 2.66-2.79 (m, 2H), 2.38-2.45 (m, 2H), 2.35 (s, 3H). MS obsd. (ESI$^+$) [(M+H)$^+$]: 479.0.

Example B041 4-[2-(8-chloro-5-hydroxy-4-oxo-chromen-2-yl)-5-(trifluoromethyl)phenoxy]butanoic acid

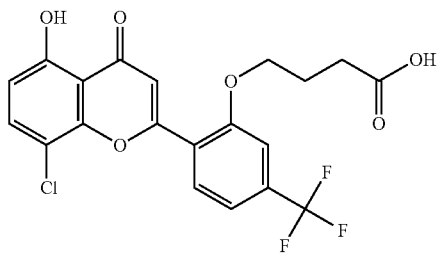

B041

Example B041 was prepared in analogy to the procedure described for the preparation of example B036-A and B036-B by using 2-hydroxy-4-(trifluoromethyl)benzaldehyde and methyl 4-bromobutanoate as the starting material and methyl 3-methylsulfonyloxycyclobutanecarboxylate instead of 4-bromo-2-hydroxy-benzaldehyde in step 1.

Example B041: $^1$H NMR (DMSO-$d_6$, 400 MHz): δ ppm 12.63 (s, 1H), 8.09-8.17 (m, 1H), 7.82-7.89 (m, 1H), 7.54-7.63 (m, 2H), 7.11-7.18 (m, 1H), 6.82-6.96 (m, 1H), 4.21-4.36 (m, 2H), 2.38-2.45 (m, 2H), 1.99-2.08 (m, 2H). MS obsd. (ESI$^+$) [(M+H)$^+$]:443.1.

Example B042 3-[2-(8-chloro-5-hydroxy-4-oxo-chromen-2-yl)-4,5-dimethoxy-phenoxy]cyclobutanecarboxylic acid

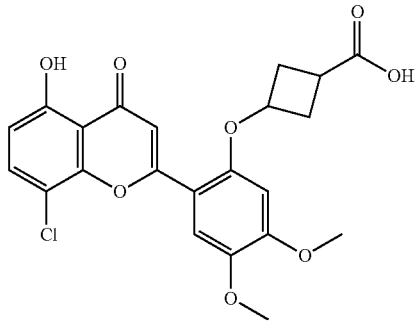

B042

Example B042 were prepared in analogy to the procedure described for the preparation of example B036-A and B036-B by using 2-hydroxy-4,5-dimethoxy-benzaldehyde as the starting material instead of 4-bromo-2-hydroxy-benzaldehyde in step 1. After purified by Prep-HPLC in step 3, the cis- and trans-two diastereomers were afforded as a mixture.

Example B042: $^1$H NMR (DMSO-$d_6$, 400 MHz): δ ppm 13.51 (s, 1H), 12.11-12.37 (br, 1H), 7.84 (d, J=9.0 Hz, 1H), 7.52 (s, 1H), 7.31 (d, J=9.0 Hz, 1H), 7.06-7.16 (m, 1H), 6.62-6.69 (m, 1H), 4.82-4.96 (m, 1H), 3.90 (s, 3H), 3.80-3.86 (m, 3H), 2.75-2.86 (m, 3H), 2.21-2.29 (m, 2H). MS obsd. (ESI$^+$) [(M+H)$^+$]:447.0.

Example B043-A and B043-B

Cis-3-[2-(8-chloro-4-oxo-chromen-2-yl)-5-(trifluoromethyl)phenoxy]-N-cyclopropylsulfonyl-cyclobutanecarboxamide and trans-3-[2-(8-chloro-4-oxo-chromen-2-yl)-5-(trifluoromethyl)phenoxy]-N-cyclopropylsulfonyl-cyclobutanecarboxamide

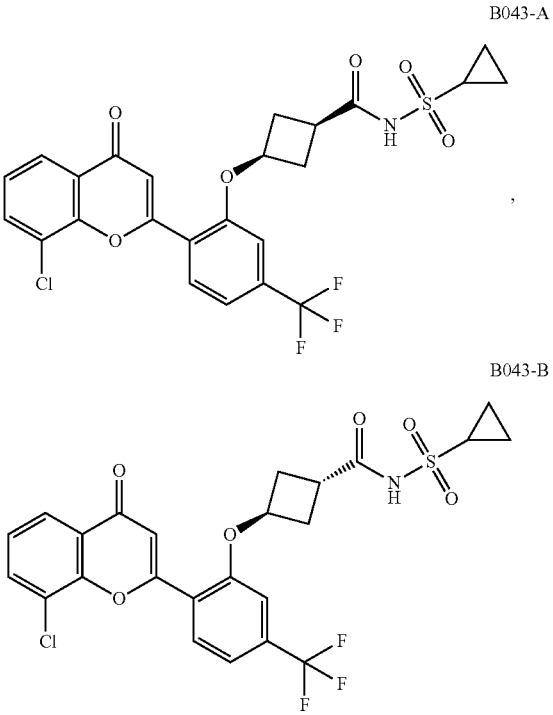

Step 1: Preparation of methyl 3-[2-(8-chloro-4-oxo-chromen-2-yl)-5-(trifluoromethyl)phenoxy]cyclobutanecarboxylate

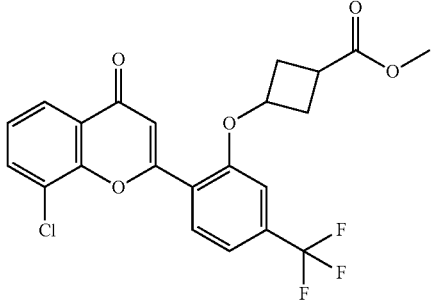

B043a

To a solution of 8-chloro-2-[2-hydroxy-4-(trifluoromethyl)phenyl]chromen-4-one (Int-1, 470.0 mg, 1.38 mmol, as the "CORE" in Table 7), methyl 3-(p-tolylsulfonyloxy)cyclobutanecarboxylate (615 mg, 4.1 mmol) in DMF (5 mL) was added Cs$_2$CO$_3$ (2.25 g, 6.9 mmol) and the reaction mixture was stirred at 100° C. for 16 hours. After the reaction was completed, the mixture was diluted with water (15 mL) and extracted with EtOAc (20 mL) three times. The combined organic layer was washed with brine, dried over Na₂SO₄ and concentrated in vacuo to give the crude methyl 3-[2-(8-chloro-4-oxo-chromen-2-yl)-5-(trifluoromethyl)phenoxy]cyclobutanecarboxylate (600 mg, 96.0% yield) as a brown solid, which was used in the next step directly. MS obsd. (ESI⁺) [(M+Na)⁺]: 475.0.

Step 2: Preparation of 3-[2-(8-chloro-4-oxo-chromen-2-yl)-5-(trifluoromethyl)phenoxy]cyclobutanecarboxylic acid

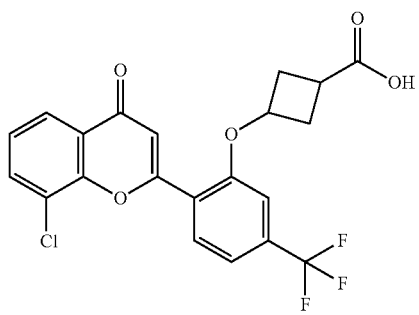

B043b

To a solution of methyl 3-[2-(8-chloro-4-oxo-chromen-2-yl)-5-(trifluoromethyl)phenoxy]cyclobutanecarboxylate (600 mg, 1.2 mmol) in THF (8 mL) and water (8 mL) was added LiOH (408 mg, 9.3 mmol). The reaction mixture was stirred at room temperature for 2 hours. After the reaction was completed, the mixture was diluted with water (15 mL) and extracted with EtOAc (20 mL) three times. The combined organic layer was washed with brine, dried over Na₂SO₄ and concentrated in vacuo to give the crude product of 3-[2-(8-chloro-4-oxo-chromen-2-yl)-5-(trifluoromethyl)phenoxy]cyclobutanecarboxylic acid (570 mg, 98.8% yield), which was used in the next step directly without further purification. MS obsd. (ESI⁺)[(M+H)⁺]: 439.0.

Step 3: Preparation of B043-A and B043-B

Cis-3-[2-(8-chloro-4-oxo-chromen-2-yl)-5-(trifluoromethyl)phenoxy]-N-cyclopropylsulfonyl-cyclobutanecarboxamide and trans-3-[2-(8-chloro-4-oxo-chromen-2-yl)-5-(trifluoromethyl)phenoxy]-N-cyclopropylsulfonyl-cyclobutanecarboxamide

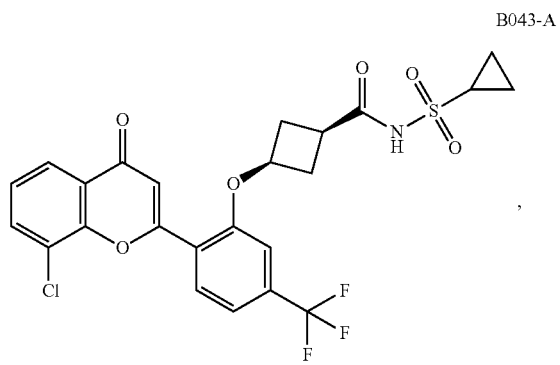

B043-A

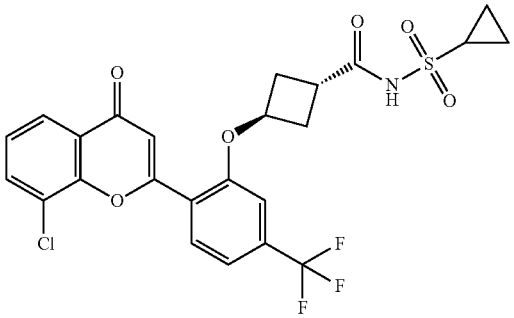

B043-B

To a solution of 3-[2-(8-chloro-4-oxo-chromen-2-yl)-5-(trifluoromethyl)phenoxy]cyclobutanecarboxylic acid (0.33 g, 752 μmol) and DIPEA (292 mg, 2.26 mmol) in DMF (10 mL) was added HATU (429 mg, 1.13 mmol) and the mixture was stirred at room temperature for 30 minutes. Then to the resulting solution was added solution of cyclopropanesulfonamide (364 mg, 3.01 mmol, as the "AMINE" in Table 7) and DMAP (368 mg, 3.01 mmol) in DMF (5 mL). The reaction was then stirred at room temperature overnight. After the reaction was completed, the reaction mixture was quenched with water (30 mL) and extracted with DCM (30 mL) three times. The combined organic layer was washed with brine, dried over MgSO₄ and concentrated in vacuo to give the crude 3-[2-(8-chloro-4-oxo-chromen-2-yl)-5-(trifluoromethyl)phenoxy]-N-cyclopropylsulfonyl-cyclobutanecarboxamide. The crude was further purified by Prep-HPLC to give cis-3-[2-(8-chloro-4-oxo-chromen-2-yl)-5-(trifluoromethyl)phenoxy]-N-cyclopropylsulfonyl-cyclobutanecarboxamide (Example B043-A) and trans-3-[2-(8-chloro-4-oxo-chromen-2-yl)-5-(trifluoromethyl)phenoxy]-N-cyclopropylsulfonyl-cyclobutanecarboxamide (Example B043-B). The configuration of Example B043-A and Example B043-B were further confirmed by NOESY.

Example B043-A: ¹H NMR (DMSO-d₆, 400 MHz): δ ppm 11.86 (s, 1H), 8.10-8.19 (m, 1H), 7.95-8.08 (m, 2H), 7.48-7.63 (m, 2H), 7.30-7.41 (m, 1H), 7.00-7.14 (m, 1H), 4.98-5.14 (m, 1H), 2.87-3.01 (m, 2H), 2.72-2.83 (m, 2H), 2.21-2.36 (m, 2H), 0.99-1.14 (m, 4H). MS obsd. (ESI⁺) [(M+H)⁺]:542.1.

Example B043-B: ¹H NMR (DMSO-d₆, 400 MHz): δ ppm 11.82 (s, 1H), 8.11-8.18 (m, 1H), 7.95-8.09 (m, 2H), 7.48-7.66 (m, 2H), 7.18-7.27 (m, 1H), 7.08-7.17 (m, 1H), 5.06-5.22 (m, 1H), 3.97-4.10 (m, 1H), 2.90-3.04 (m, 1H), 2.68-2.80 (m, 2H), 2.37-2.47 (m, 2H), 1.06-1.12 (m, 4H). MS obsd. (ESI⁺) [(M+H)⁺]:542.1.

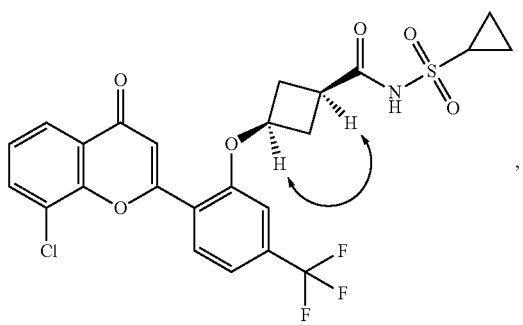

,

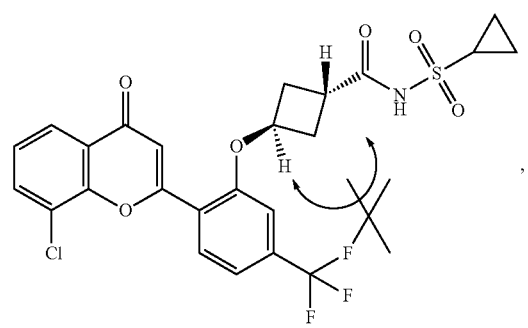

(NOESY correlation observed) (no NOESY correlation observed) Example B044-A and B044-B: cis-3-[5-bromo-2-(8-chloro-4-oxo-chromen-2-yl)phenoxy]-N-methylsulfonyl-cyclobutanecarboxamide and trans-3-[5-bromo-2-(8-chloro-4-oxo-chromen-2-yl)phenoxy]-N-methylsulfonyl-cyclobutanecarboxamide

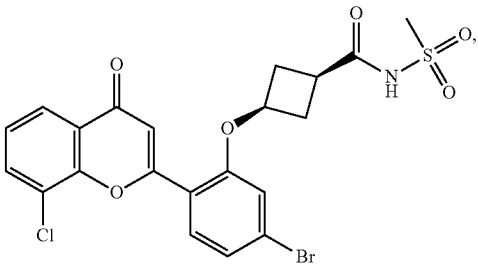

B044-A

,

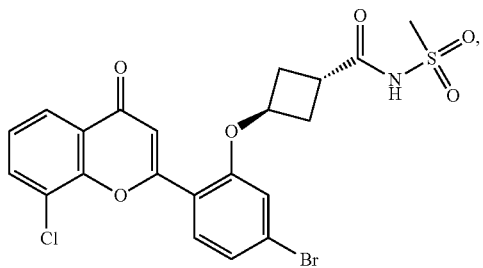

B044-B

To a solution of 3-[5-bromo-2-(8-chloro-4-oxo-chromen-2-yl)phenoxy]cyclobutanecarboxylic acid (Example B001, 250 mg, 556 μmol) and DIPEA (719 mg, 971 μl, 5.56 mmol) in DCM (5 ml) were added HATU (423 mg, 1.11 mmol) and methanesulfonamide (106 mg, Ell mmol) and the mixture was stirred at room temperature for 12 hours. After the reaction was completed, the reaction was concentrated in vacuo and the residue was purified by Prep-HPLC to give cis-3-[5-bromo-2-(8-chloro-4-oxo-chromen-2-yl)phenoxy]-N-methylsulfonyl-cyclobutanecarboxamide (Example B044-A, 4 mg, 1.4% yield) and trans-3-[5-bromo-2-(8-chloro-4-oxo-chromen-2-yl)phenoxy]-N-methylsulfonyl-cyclobutanecarboxamide (Example B044-B, 12 mg, 4.1% yield).

Example B044-A: $^1$H NMR (DMSO-$d_6$, 400 MHz): δ ppm 11.78 (s, 1H), 7.97-8.04 (m, 2H), 7.84-7.92 (m, 1H), 7.47-7.54 (m, 1H), 7.40-7.47 (m, 1H), 7.26-7.34 (m, 1H), 7.02-7.08 (m, 1H), 4.89-5.03 (m, 1H), 3.17 (s, 3H), 2.70-2.94 (m, 3H), 2.23-2.35 (m, 2H). MS obsd. (ESI$^+$) [(M+H)$^+$]:526.1.

Example B044-B: $^1$H NMR (DMSO-$d_6$, 400 MHz): δ ppm 11.81 (s, 1H), 7.97-8.06 (m, 2H), 7.84-7.93 (m, 1H), 7.48-7.56 (m, 1H), 7.38-7.46 (m, 1H), 7.19-7.21 (m, 1H), 7.07-7.12 (m, 1H), 4.98-5.10 (m, 1H), 3.31 (s, 3H), 3.22-3.27 (m, 1H), 2.71-2.79 (m, 2H), 2.35-2.45 (m, 2H). MS obsd. (ESI$^+$) [(M+H)$^+$]:526.1.

The following Example B047 to Example B035 were prepared in analogy to the procedure described for the preparation of Example B043-A, B043-B, replacing 8-chloro-2-[2-hydroxy-4-(trifluoromethyl)phenyl]chromen-4-one(Int-1) with "CORE" in step 1, cyclopropanesulfonamide with "AMINE" in step 3. The "CORE" and "AMINE" are the reagents indicated in Table 7.

TABLE 7

| Example No. | Compounds Name and Structure | CORE and AMINE | $^1$H NMR and (ESI$^+$) |
|---|---|---|---|
| B047-A | Cis-3-[2-(8-chloro-4-oxo-chromen-2-yl)-5-(trifluoromethoxy)phenoxy]-N-methylsulfonyl-cyclobutanecarboxamide | CORE: Int-9 AMINE: methane-sulfonamide | $^1$H NMR (DMSO-d$_6$, 400 MHz): δ ppm 11.92 (s, 1H), 8.05-8.12 (m, 1H), 7.97-8.05 (m, 2H), 7.45-7.55 (m, 1H), 7.19-7.28 (m, 1H), 7.07-7.14 (m, 1H), 7.00-7.06 (m, 1H), 4.90-5.03 (m, 1H), 3.25 (s, 3H), 2.83-2.94 (m, 1H), 2.71-2.81 (m, 2H), 2.21-2.36 (m, 2H). MS obsd. (ESI$^+$) [(M + H)$^+$]: 532.1. |
| B047-B | Trans-3-[2-(8-chloro-4-oxo-chromen-2-yl)-5-(trifluoromethoxy)phenoxy]-N-methylsulfonyl-cyclobutanecarboxamide | CORE: Int-9 AMINE: methane-sulfonamide | $^1$H NMR (DMSO-d$_6$, 400 MHz): δ ppm 11.80 (s, 1H), 7.97-8.13 (m, 3H), 7.42-7.58 (m, 1H), 7.16-7.30 (m, 1H), 7.04-7.11 (m, 1H), 6.96-7.04 (m, 1H), 4.99-5.14 (m, 1H), 3.28-3.31 (m, 4H), 2.71-2.80 (m, 2H), 2.36-2.46 (m, 2H). MS obsd. (ESI$^+$) [(M + H)$^+$]: 532.1. |
| B048-A | Cis-3-[2-(8-chloro-4-oxo-chromen-2-yl)-5-(trifluoromethyl)phenoxy]-N-methylsulfonyl-cyclobutanecarboxamide | CORE: Int-1 AMINE: methane-sulfonamide | $^1$H NMR (DMSO-d$_6$, 400 MHz): δ ppm 8.32-8.40 (m, 1H), 8.10-8.21 (m, 2H), 7.66-7.73 (m, 1H), 7.26-7.39 (m, 2H), 6.95-7.03 (m, 1H), 4.69-4.81 (m, 1H), 3.18 (s, 3H), 2.66-2.94 (m, 5H). MS obsd. (ESI$^+$) [(M + H)$^+$]: 516.1. |

TABLE 7-continued

Compounds synthesis and characterization

| Example No. | Compounds Name and Structure | CORE and AMINE | ¹H NMR and (ESI⁺) |
|---|---|---|---|
| B048-B | Trans-3-[2-(8-chloro-4-oxo-chromen-2-yl)-5-(trifluoromethyl)phenoxy]-N-methylsulfonyl-cyclobutanecarboxamide | CORE: Int-1 AMINE: methane-sulfonamide | ¹H NMR (DMSO-d$_6$, 400 MHz): δ ppm 8.42-8.52 (m, 1H), 8.10-8.27 (m, 2H), 7.66-7.76 (m, 1H), 7.29-7.41 (m, 2H), 6.92-7.03 (m, 1H), 4.92-5.16 (m, 1H), 3.25-3.39 (m, 1H), 3.19 (s, 3H), 2.71-2.87 (m, 4H). MS obsd. (ESI⁺) [(M + H)⁺]: 516.1. |
| B049-A | Cis-3-[5-bromo-2-(8-chloro-4-oxo-chromen-2-yl)-4-methyl-phenoxy]-N-methylsulfonyl-cyclobutanecarboxamide | CORE: Int-6 AMINE: methane-sulfonamide | ¹H NMR (DMSO-d$_6$, 400 MHz): δ ppm 7.95-8.05 (m, 2H), 7.83-7.92 (m, 1H), 7.43-7.55 (m, 1H), 7.27-7.36 (m, 1H), 7.01 (s, 1H), 4.87-4.98 (m, 1H), 3.23 (s, 3H), 2.81-2.92 (m, 1H), 2.69-2.78 (m, 2H), 2.38 (s, 3H), 2.21-2.31 (m, 2H). MS obsd. (ESI⁺) [(M + H)⁺]: 540.1. |
| B049-B | Trans-3-[5-bromo-2-(8-chloro-4-oxo-chromen-2-yl)4-methyl-phenoxy]-N-methylsulfonyl-cyclobutanecarboxamide | CORE: Int-6 AMINE: methane-sulfonamide | ¹H NMR (DMSO-d$_6$, 400 MHz): δ ppm 7.98-8.06 (m, 2H), 7.86-7.92 (m, 1H), 7.46-7.54 (m, 1H), 7.19 (s, 1H), 7.05 (s, 1H), 4.96-5.07 (m, 1H), 3.19-3.23 (m, 4H), 2.63-2.77 (m, 2H), 2.26-2.38 (s, 5H). MS obsd. (ESI⁺) [(M + H)⁺]: 540.1. |

TABLE 7-continued

Compounds synthesis and characterization

| Example No. | Compounds Name and Structure | CORE and AMINE | ¹H NMR and (ESI⁺) |
|---|---|---|---|
| B050-A | Cis-3-[2-(8-chloro-4-oxo-chromen-2-yl)-5-methoxy-4-methyl-phenoxy]-N-methylsulfonyl-cyclobutanecarboxamide | CORE: Int-12 AMINE: methane-sulfonamide | ¹H NMR (DMSO-$d_6$, 400 MHz): δ ppm 11.88 (s, 1H), 7.94-8.01 (m, 2H), 7.74-7.81 (m, 1H), 7.42-7.52 (m, 1H), 6.99-7.07 (m, 1H), 6.55-6.63 (m, 1H), 4.90-5.03 (m, 1H), 3.92 (s, 3H), 3.27 (s, 3H), 2.74-2.96 (m, 3H), 2.24-2.36 (m, 2H), 2.18 (s, 3H). MS obsd. (ESI⁺) [(M + H)⁺]: 492.1. |
| B050-B | Trans-3-[2-(8-chloro-4-oxo-chromen-2-yl)-5-methoxy-4-methyl-phenoxy]-N-methylsulfonyl-cyclobutanecarboxamide | CORE: Int-12 AMINE: methane-sulfonamide | ¹H NMR (DMSO-$d_6$, 400 MHz): δ ppm 11.70 (s, 1H), 7.94-8.02 (m, 2H), 7.74-7.81 (m, 1H), 7.42-7.52 (m, 1H), 7.04-7.10 (m, 1H), 6.44-6.49 (m, 1H), 5.03-5.12 (m, 1H), 3.91 (s, 3H), 3.22-3.31 (m, 4H), 2.73-2.82 (m, 2H), 2.36-2.47 (m, 2H), 2.16 (s, 3H). MS obsd. (ESI⁺) [(M + H)⁺]: 492.1. |
| B051-A | Cis-3-[2-(8-chloro-4-oxo-chromen-2-yl)-5-methyl-phenoxy]-N-methylsulfonyl-cyclobutanecarboxamide | CORE: Int-2 AMINE: methane-sulfonamide | ¹H NMR (DMSO-$d_6$, 400 MHz): δ ppm 7.96-8.02 (m, 2H), 7.84-7.91 (m, 1H), 7.44-7.52 (m, 1H), 6.98-7.08 (m, 2H), 6.90-6.96 (m, 1H), 4.81-4.93 (m, 1H), 3.27 (s, 3H), 2.72-2.95 (m, 3H), 2.42 (s, 3H), 2.23-2.34 (m, 2H). MS obsd. (ESI⁺) [(M + H)⁺]: 462.1. |
| B051-B | Trans-3-[2-(8-chloro-4-oxo-chromen-2-yl)-5-methyl-phenoxy]-N-methylsulfonyl-cyclobutanecarboxamide | CORE: Int-2 AMINE: methane-sulfonamide | ¹H NMR (DMSO-$d_6$, 400 MHz): δ ppm 11.84 (s, 1H), 7.97-8.03 (m, 2H), 7.84-7.93 (m, 1H), 7.45-7.52 (m, 1H), 7.06-7.14 (m, 1H), 6.99-7.04 (m, 1H), 6.79-6.87 (m, 1H), 4.92-5.06 (m, 1H), 3.22-3.28 (m, 4H), 2.71-2.81 (m, 2H), 2.39-2.44 (m, 5H). MS obsd. (ESI⁺) [(M + H)⁺]: 462.1. |

TABLE 7-continued

Compounds synthesis and characterization

| Example No. | Compounds Name and Structure | CORE and AMINE | $^1$H NMR and (ESI$^+$) |
|---|---|---|---|
| B052-A | Cis-3-[2-(8-chloro-4-oxo-chromen-2-yl)-5-methyl-phenoxy]-N-cyclopropylsulfonyl-cyclobutanecarboxamide | CORE: Int-2 AMINE: cyclopropane-sulfonamide | $^1$H NMR (DMSO-d$_6$, 400 MHz): δ ppm 11.64 (s, 1H), 7.99 (d, J = 7.95 Hz, 2H), 7.80-7.91 (m, 1H), 7.43-7.54 (m, 1H), 7.06 (s, 2H), 6.89-6.97 (m, 1H), 4.82-4.96 (m, 1H), 2.85-3.04 (m, 2H), 2.73-2.85 (m, 2H), 2.40 (s, 3H), 2.18-2.35 (m, 2H), 1.1-1.05 (m, 4H). MS obsd. (ESI$^+$) [(M + H)$^+$]: 488.1. |
| B052-B | Trans-3-[2-(8-chloro-4-oxo-chromen-2-yl)-5-methyl-phenoxy]-N-cyclopropylsulfonyl-cyclobutanecarboxamide | CORE: Int-2 AMINE: cyclopropane-sulfonamide | $^1$H NMR (DMSO-d$_6$, 400 MHz): δ ppm 11.67 (s, 1H), 7.96-8.05 (m, 2H), 7.82-7.93 (m, 1H), 7.42-7.54 (m, 1H), 7.08-7.13 (m, 1H), 6.97-7.06 (m, 1H), 6.79-6.84 (m, 1H), 4.93-5.05 (m, 1H), 3.22-3.33 (m, 1H), 2.94-3.06 (m, 1H), 2.69-2.82 (m, 2H), 2.39-2.45 (m, 5H), 1.07-1.13 (m, 4H). MS obsd. (ESI$^+$) [(M + H)$^+$]: 488.1. |
| B053-A | Cis-3-[5-bromo-2-(8-chloro-4-oxo-chromen-2-yl)-4-methoxy-phenoxy]-N-methylsulfonyl-cyclobutanecarboxamide | CORE: Int-7 AMINE: methane-sulfonamide | $^1$H NMR (DMSO-d$_6$, 400 MHz): δ ppm 11.86 (s, 1H), 7.97-8.04 (m, 2H), 7.62-7.67 (m, 1H), 7.45-7.56 (m, 1H), 7.33-7.39 (m, 1H), 7.03-7.11 (m, 1H), 4.78-4.94 (m, 1H), 3.90 (s, 3H), 3.24 (s, 3H), 2.79-2.94 (m, 1H), 2.69-2.76 (m, 2H), 2.20-2.30 (m, 2H). MS obsd. (ESI$^+$) [(M + H)$^+$]: 556.1. |

TABLE 7-continued

Compounds synthesis and characterization

| Example No. | Compounds Name and Structure | CORE and AMINE | ¹H NMR and (ESI⁺) |
|---|---|---|---|
| B053-A | Trans-3-[5-bromo-2-(8-chloro-4-oxo-chromen-2-yl)-4-methoxy-phenoxy]-N-methylsulfonyl-cyclobutanecarboxamide | CORE: Int-7 AMINE: methane-sulfonamide | ¹H NMR (DMSO-$d_6$, 400 MHz): δ ppm 11.81 (s, 1H), 7.96-8.07 (m, 2H), 7.62-7.67 (m, 1H), 7.47-7.55 (m, 1H), 7.23-7.26 (m, 1H), 7.09-7.13 (m, 1H), 4.92-5.05 (m, 1H), 3.93 (s, 3H), 3.14-3.19 (m, 1H), 2.64-2.76 (m, 2H), 2.31-2.43 (m, 2H). MS obsd. (ESI⁺) [(M + H)⁺]: 556.1. |
| B054 | Cis-3-[5-bromo-2-(8-chloro-4-oxo-chromen-2-yl)-4-methoxy-phenoxy]-N-cyclopropylsulfonyl-cyclobutanecarboxamide | CORE: Int-7 AMINE: cyclopropane-sulfonamide | ¹H NMR (DMSO-$d_6$, 400 MHz): δ ppm 11.84 (s, 1H), 7.96-8.04 (m, 2H), 7.61-7.67 (m, 1H), 7.46-7.55 (m, 1H), 7.33-7.38 (m, 1H), 7.05-7.11 (m, 1H), 4.84-4.95 (m, 1H), 3.92 (s, 3H), 2.92-3.00 (m, 1H), 2.82-2.92 (m, 1H), 2.64-2.78 (m, 2H), 2.18-2.29 (m, 2H), 1.03-1.10 (m, 4H). MS obsd. (ESI⁺) [(M + H)⁺]: 582.1. |
| B055-A | Cis-3-[4-bromo-2-(8-chloro-4-oxo-chromen-2-yl)-5-methoxy-phenoxy]-N-methylsulfonyl-cyclobutanecarboxamide | CORE: Int-34 AMINE: methane-sulfonamide | ¹H NMR (DMSO-$d_6$, 400 MHz): δ ppm 11.84 (s, 1H), 8.12-8.18 (m, 1H), 7.95-8.03 (m, 2H), 7.44-7.53 (m, 1H), 7.02-7.07 (m, 1H), 6.69-6.74 (m, 1H), 4.99-5.11 (m, 1H), 4.02 (s, 3H), 3.26 (s, 3H), 2.75-2.95 (m, 3H), 2.24-2.38 (m, 2H). MS obsd. (ESI⁺) [(M + H)⁺]: 556.1. |

TABLE 7-continued

Compounds synthesis and characterization

| Example No. | Compounds Name and Structure | CORE and AMINE | $^1$H NMR and (ESI$^+$) |
|---|---|---|---|
| B055-B | Trans-3-[4-bromo-2-(8-chloro-4-oxo-chromen-2-yl)-5-methoxy-phenoxy]-N-methylsulfonyl-cyclobutanecarboxamide | CORE: Int-34 AMINE: methane-sulfonamide | $^1$H NMR (DMSO-d$_6$, 400 MHz): δ ppm 11.70 (s, 1H), 8.12-8.17 (m, 1H), 7.96-8.05 (m, 2H), 7.45-7.54 (m, 1H), 7.06-7.12 (m, 1H), 6.56-6.62 (m, 1H), 5.07-5.18 (m, 1H), 3.98 (s, 3H), 3.10-3.33 (m, 4H), 2.74-2.84 (m, 2H), 2.38-2.47 (m, 2H). MS obsd. (ESI$^+$) [(M + H)$^+$]: 556.1. |
| B056-A | Cis-3-[4-bromo-2-(8-chloro-4-oxo-chromen-2-yl)-5-methoxy-phenoxy]-N-cyclopropylsulfonyl-cyclobutanecarboxamide | CORE: Int-34 AMINE: cyclopropane-sulfonamide | $^1$H NMR (DMSO-d$_6$, 400 MHz): δ ppm 8.13 (s, 1H), 7.94-8.03 (m, 2H), 7.43-7.52 (m, 1H), 7.04 (s, 1H), 6.67-6.74 (m, 1H), 4.98-5.10 (m, 1H), 4.04 (s, 3H), 2.76-3.04 (m, 4H), 2.19-2.37 (m, 2H), 1.01-1.14 (m, 4H). MS obsd. (ESI$^+$) [(M + H)$^+$]: 582.1. |
| B057 | 3-[2-(8-chloro-4-oxo-chromen-2-yl)-4,5-dimethoxy-phenoxy]-N-methylsulfonyl-cyclobutanecarboxamide | CORE: Int-10 AMINE: methane-sulfonamide | $^1$H NMR (DMSO-d$_6$, 400 MHz): δ ppm 7.96-8.05 (m, 2H), 7.56-7.63 (m, 1H), 7.42-7.56 (m, 1H), 7.11-7.17 (m, 1H), 6.49-6.64 (m, 1H), 5.00-5.15 (m, 1H), 3.87 (s, 3H), 3.84 (s, 3H), 3.28 (s, 3H), 2.69-2.82 (m, 2H), 2.36-2.46 (m, 3H). MS obsd. (ESI$^+$) [(M + H)$^+$]: 508.0. |

Example B070: 3-[2-(8-chloro-4-oxo-chromen-2-yl)-5-(trifluoromethyl)phenoxy]cyclobutanecarbonitrile

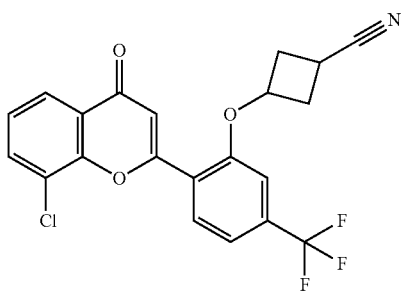

B070

Step 1: Preparation of (3-cyanocyclobutyl) 4-methylbenzenesulfonate

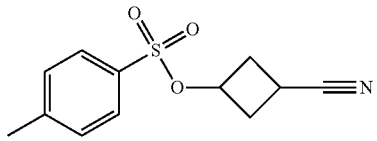

B070a

To a solution of 3-hydroxycyclobutane-1-carbonitrile (500 mg, 5.15 mmol), DMAP (1.01 g, 8.24 mmol) in DCM (25 mL) was added 4-methylbenzenesulfonyl chloride (1.18 g, 6.2 mmol) and the mixture was then stirred at room temperature overnight. After the reaction was completed, the mixture was concentrated in vacuo and the residue was partitioned between EtOAc (30 mL) and water (20 mL). The organic layer was separated out and washed by brine, dried over $Na_2SO_4$, then concentrated in vacuo to give the crude (3-cyanocyclobutyl) 4-methylbenzenesulfonate (0.517 g, 40% yield) as a colorless oil, which was used in the next step directly without further purification.

Step 2: Preparation of 3-[2-(8-chloro-4-oxo-chromen-2-yl)-5-(trifluoromethyl)phenoxy]cyclobutanecarbonitrile

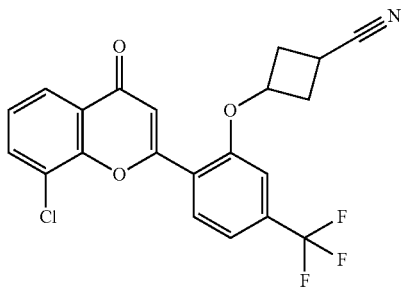

B070

A mixture of 8-chloro-2-[2-hydroxy-4-(trifluoromethyl)phenyl]chromen-4-one (Int-1, 117 mg, 342 μmol), 3-cyanocyclobutyl 4-methylbenzenesulfonate (86 mg, 342 μmol) and $K_2CO_3$ (236 mg, 1.71 mmol) in DMF (5 mL) was stirred at 70° C. overnight. After the reaction was completed, the mixture was diluted with water (15 mL) and extracted with EtOAc (30 mL) three times. The combined organic layer was washed with brine, dried over $Na_2SO_4$ and concentrated in vacuo. The residue was purified by Prep-HPLC to give 3-[2-(8-chloro-4-oxo-chromen-2-yl)-5-(trifluoromethyl)phenoxy]cyclobutanecarbonitrile (31 mg, 21.4% yield) as a white solid. $^1$H NMR (DMSO-$d_6$, 400 MHz): δ ppm 8.09-8.17 (m, 1H), 7.97-8.07 (m, 2H), 7.47-7.62 (m, 2H), 7.35-7.44 (m, 1H), 7.04-7.11 (m, 1H), 5.28-5.45 (m, 1H), 3.44-3.55 (m, 1H), 2.85-2.97 (m, 2H), 2.55-2.68 (m, 2H). MS obsd. (ESI$^+$) [(M+H)$^+$]: 419.1.

Example B071: 3-[5-bromo-2-(8-chloro-4-oxo-chromen-2-yl)phenoxy]-N,N-dimethyl-propane-1-sulfonamide

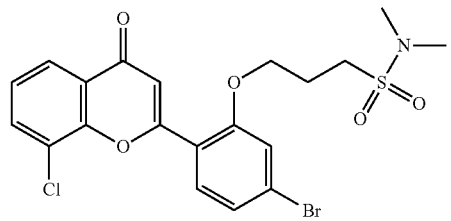

B071

To a suspension of 2-(4-bromo-2-hydroxy-phenyl)-8-chloro-chromen-4-one (Int-4, 150 mg, 427 μmol) and 3-chloro-N,N-dimethylpropane-1-sulfonamide (111 mg, 597 μmol) in DMF (5 mL) was added $K_2CO_3$ (354 mg, 2.56 mmol) and the mixture was then stirred at 40° C. for 4 hours. The mixture was then purified by Prep-HPLC to give 3-[5-bromo-2-(8-chloro-4-oxo-chromen-2-yl)phenoxy]-N,N-dimethyl-propane-1-sulfonamide (112 mg, 51.4% yield) as a white solid. $^1$H NMR (DMSO-$d_6$, 400 MHz): δ ppm 8.01 (dd, J=7.9, 1.3 Hz, 2H), 7.85 (d, J=8.3 Hz, 1H), 7.43-7.52 (m, 3H), 6.98 (s, 1H), 4.31 (t, J=6.1 Hz, 2H), 3.13-3.22 (m, 2H), 2.74 (s, 6H), 2.13-2.23 (m, 2H). MS obsd. (ESI$^+$) [(M+H)$^+$]: 500.2.

Example B072: 3-[2-(8-chloro-4-oxo-chromen-2-yl)-5-(trifluoromethyl)phenoxy]propane-1-sulfonamide

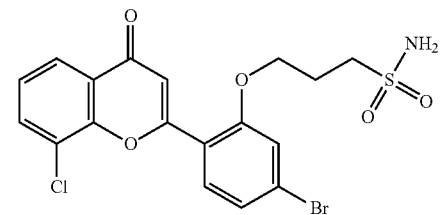

B072

Step 1: Preparation of 3-[5-bromo-2-(8-chloro-4-oxo-chromen-2-yl)phenoxy]-N-tert-butyl-propane-1-sulfonamide

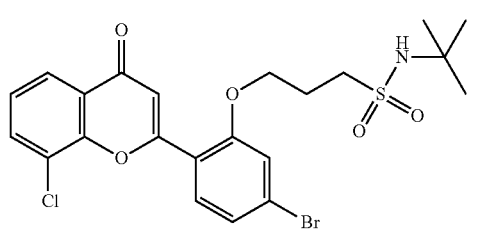

B072a

To a suspension of 2-(4-bromo-2-hydroxy-phenyl)-8-chloro-chromen-4-one (Int-4, 150 mg, 440 μmol) and N-(tert-butyl)-3-chloropropane-1-sulfonamide (132 mg, 616 μmol) in DMF (5 mL) was added $K_2CO_3$ (365 mg, 2.64 mmol). The mixture was then stirred at 40° C. for 4 hours. After the reaction was completed, the mixture was poured into water (20 mL) and extracted with EtOAc (30 mL) three times. The combined organic layer was concentrated in vacuo to give the crude 3-[5-bromo-2-(8-chloro-4-oxo-chromen-2-yl)phenoxy]-N-tert-butyl-propane-1-sulfonamide (200 mg, 87.7% yield) as a white solid, which was used in the next step directly without further purification. MS obsd. (ESI+) [(M+H)+]: 518.3.

Step 2: Preparation of 3-[2-(8-chloro-4-oxo-chromen-2-yl)-5-(trifluoromethyl)phenoxy]propane-1-sulfonamide

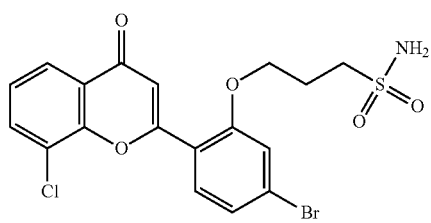

B072

To a suspension of 3-[5-bromo-2-(8-chloro-4-oxo-chromen-2-yl)phenoxy]-N-tert-butyl-propane-1-sulfonamide (30 mg, 57.9 μmol) in AcOH (4 mL) was added concentrated HCl (1 mL) and the mixture was stirred at 110° C. for 4 hours. The mixture was then diluted with water (15 mL) and extracted with EtOAc (20 mL) three times. The combined organic layer was concentrated in vacuo and the residue was purified by Prep-HPLC to give 3-[2-(8-chloro-4-oxo-chromen-2-yl)-5-(trifluoromethyl)phenoxy]propane-1-sulfonamide (15 mg, 55.0% yield) as a white solid. $^1$H NMR (DMSO-$d_6$, 400 MHz): δ ppm 8.14 (s, 1H), 8.01-8.06 (m, 2H), 7.49-7.62 (m, 3H), 7.07 (s, 1H), 6.88 (s, 2H), 4.40 (t, J=6.5 Hz, 2H), 3.09-3.17 (m, 2H), 2.17-2.26 (m, 2H). MS obsd. (ESI+) [(M+H)+]: 462.3.

Example B073: 3-[2-(8-chloro-4-oxo-chromen-2-yl)-5-(trifluoromethyl)phenoxy]-2-hydroxy-propanoic acid

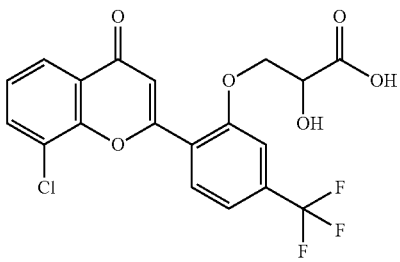

B073

Step 1: Preparation of methyl 3-[2-(8-chloro-4-oxo-chromen-2-yl)-5-(trifluoromethyl)phenoxy]-2-hydroxy-propanoate

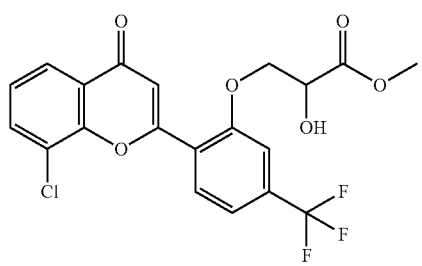

B073a

To a suspension of 8-chloro-2-[2-hydroxy-4-(trifluoromethyl)phenyl]chromen-4-one (Int-1, 100 mg, 294 μmol) and methyl oxirane-2-carboxylate (300 mg, 2.94 mmol) in DMSO (5 mL) was added $K_2CO_3$ (243 mg, 1.76 mmol) and the mixture was then stirred at 80° C. for 40 hours. The mixture was then poured into water (20 mL) and extracted with EtOAc (20 mL) three times. The combined organic layer was concentrated in vacuo to give the crude methyl 3-[2-(8-chloro-4-oxo-chromen-2-yl)-5-(trifluoromethyl) phenoxy]-2-hydroxy-propanoate (50 mg, 25% purity), which was used in the next step directly without further purification. MS obsd. (ESI+) [(M+H)+]: 443.1

Step 2: Preparation of 3-[2-(8-chloro-4-oxo-chromen-2-yl)-5-(trifluoromethyl)phenoxy]-2-hydroxy-propanoic acid

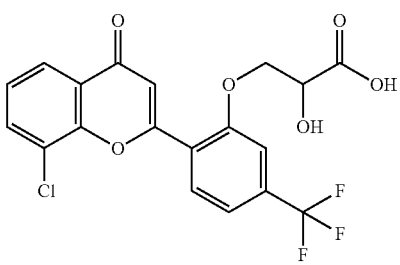

B073

To a solution of methyl 3-[2-(8-chloro-4-oxo-chromen-2-yl)-5-(trifluoromethyl)phenoxy]-2-hydroxy-propanoate (20 mg, 45.2 μmol) in a mixed solvent of THF (6 mL), MeOH (3 mL) and water (1 mL) was added LiOH (54.1 mg, 2.26 mmol) and the mixture was stirred at room temperature for 4 hours. The mixture was then adjusted to PH-6.0 by addition of AcOH and the resulting mixture was concentrated in vacuo. The residue was purified by Prep-HPLC to give 3-[2-(8-chloro-4-oxo-chromen-2-yl)-5-(trifluoromethyl)phenoxy]-2-hydroxy-propanoic acid (7.1 mg, 34.8% yield) as an off-white solid. $^1$H NMR (DMSO-$d_6$, 400 MHz): δ ppm 12.80-12.99 (m, 1H), 8.16 (s, 1H), 8.02 (dd, J=7.8, 2.3 Hz, 2H), 7.65 (s, 2H), 7.49-7.58 (m, 1H), 7.22 (s, 1H), 5.69-5.78 (m, 1H), 4.41-4.55 (m, 3H). MS obsd. (ESI$^+$) [(M+H)$^+$]: 429.1.

Example B075: (2S,4S)-4-[5-bromo-2-(8-chloro-4-oxo-chromen-2-yl)phenoxy]pyrrolidine-2-carboxylic acid

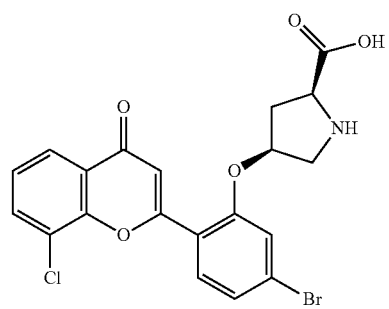

B075

Step 1: Preparation of O1-tert-butyl O2-methyl (2S,4S)-4-[5-bromo-2-(8-chloro-4-oxo-chromen-2-yl)phenoxy]pyrrolidine-1,2-dicarboxylate

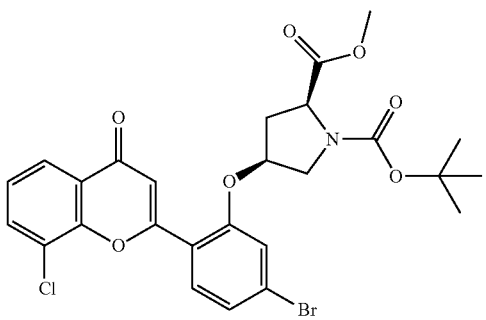

B075a

A mixture of 2-(4-bromo-2-hydroxy-phenyl)-8-chloro-chromen-4-one (Int-4, 100 mg, 284 μmol), O1-tert-butyl O2-methyl (2R,4S)-4-(p-tolylsulfonyloxy)pyrrolidine-1,2-dicarboxylate (114 mg, 284 μmol) and K$_2$CO$_3$ (197 mg, 1.42 mmol) in DMF (15 mL) was stirred at 50° C. overnight. The mixture was then poured into water (50 mL) and extracted with EtOAc (50 mL) three times. The combined organic layer was concentrated in vacuo and the residue was purified by column chromatography on silica gel (eluted with PE:EtOAc=100:1 to 3:1) to give O1-tert-butyl O2-methyl (2S,4S)-4-[5-bromo-2-(8-chloro-4-oxo-chromen-2-yl)phenoxy]pyrrolidine-1,2-dicarboxylate (150 mg, 91.1% yield) as a yellow solid. MS obsd. (ESI$^+$) [(M+H)$^+$]: 578.1.

Step 2: Preparation of methyl (2S,4S)-4-[5-bromo-2-(8-chloro-4-oxo-chromen-2-yl)phenoxy]pyrrolidine-2-carboxylate

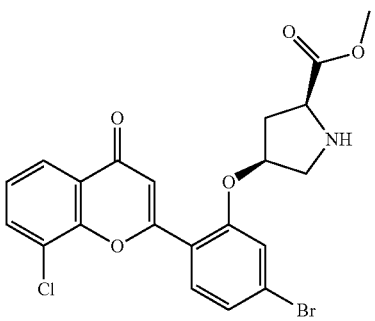

B075b

To a solution of O1-tert-butyl O2-methyl (2S,4S)-4-[5-bromo-2-(8-chloro-4-oxo-chromen-2-yl)phenoxy]pyrrolidine-1,2-dicarboxylate (1.3 g, 2.25 mmol) in DCM (30 mL) was added TFA (1.28 g, 865 μl, 11.2 mmol) and the mixture was then stirred at room temperature overnight. After the reaction was completed, the mixture was concentrated in vacuo to give the crude methyl (2S,4S)-4-[5-bromo-2-(8-chloro-4-oxo-chromen-2-yl)phenoxy]pyrrolidine-2-carboxylate (1.08 g, 100% yield) as a white solid, which was used in the next step directly without further purification. MS obsd. (ESI$^+$) [(M+H)$^+$]: 578.1.

Step 3: Preparation of (2S,4S)-4-[5-bromo-2-(8-chloro-4-oxo-chromen-2-yl)phenoxy]pyrrolidine-2-carboxylic acid

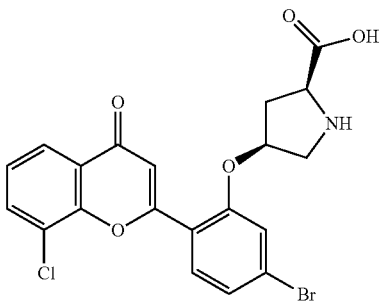

B075

To a solution of methyl (2S,4S)-4-[5-bromo-2-(8-chloro-4-oxo-chromen-2-yl)phenoxy]pyrrolidine-2-carboxylate (150 mg, 313 μmol) in the mixed solvent of THF (20 ml) and MeOH (10 ml) was added LiOH (30 mg, 1.25 mmol) and the mixture was then stirred at room temperature for 4 hours. The mixture was then quenched by addition of AcOH (0.5 mL) and the resulting mixture was concentrated in vacuo. The residue was purified by Prep-HPLC to give (2S,4S)-4-[5-bromo-2-(8-chloro-4-oxo-chromen-2-yl)phenoxy]pyrrolidine-2-carboxylic acid (45 mg, 29.4%) yield as white solid. $^1$H NMR (DMSO-$d_6$, 400 MHz): δ ppm 8.00 (d, J=7.8 Hz, 2H), 7.83 (d, J=8.3 Hz, 1H), 7.43-7.55 (m, 3H), 6.95 (s, 1H), 5.34 (br s, 1H), 4.37-4.40 (m, 1H), 3.62-3.69 (m, 1H), 3.51-3.56 (m, 1H), 2.60-2.84 (m, 2H), 2.37-2.66 (m, 1H). MS obsd. (ESI$^+$) [(M+H)$^+$]: 464.0.

Example B076: (2S,4R)-1-(benzenesulfonyl)-4-[2-(8-chloro-4-oxo-chromen-2-yl)-5-(trifluoromethyl)phenoxy]pyrrolidine-2-carboxylic acid

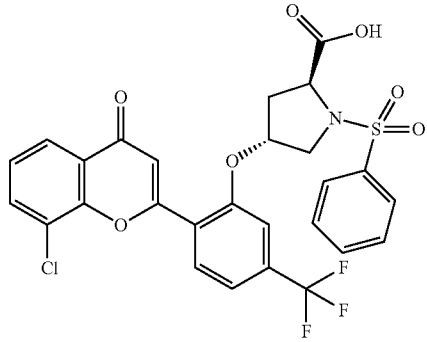

B076

Step 1: Preparation of O1-tert-butyl O2-methyl (2S,4R)-4-[2-(8-chloro-4-oxo-chromen-2-yl)-5-(trifluoromethyl)phenoxy]pyrrolidine-1,2-dicarboxylate

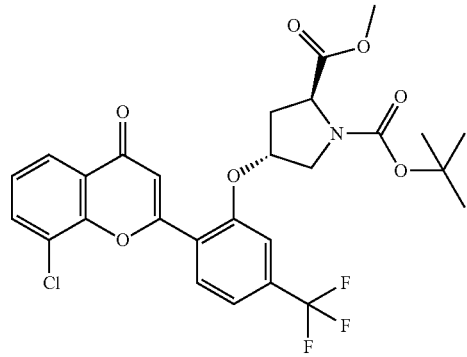

B076a

A mixture of 8-chloro-2-[2-hydroxy-4-(trifluoromethyl)phenyl]chromen-4-one (Int-1, 323 mg, 948 μmol, as the "CORE" in Table 8), 1-(tert-butyl) 2-methyl (2S,4S)-4-((methylsulfonyl)oxy)pyrrolidine-1,2-dicarboxylate (460 mg, 1.42 mmol, as the "SM5" in Table 8) and K$_2$CO$_3$ (524 mg, 3.79 mmol) in DMF (10 mL) was stirred at 80° C. overnight. After the reaction was completed, the mixture was diluted with water (30 mL) and extracted with EtOAc (30 mL) three times. The combined organic layer was concentrated in vacuo and the residue was purified by column chromatography on silica gel to give O1-tert-butyl O2-methyl (2S,4R)-4-[2-(8-chloro-4-oxo-chromen-2-yl)-5-(trifluoromethyl)phenoxy]pyrrolidine-1,2-dicarboxylate (400 mg, 74.3% yield) as a light yellow solid.

Step 2: Preparation of methyl (2S,4R)-4-[2-(8-chloro-4-oxo-chromen-2-yl)-5-(trifluoromethyl)phenoxy]pyrrolidine-2-carboxylate

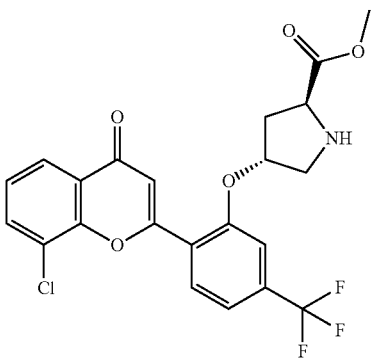

B076b

To a solution of O1-tert-butyl O2-methyl (2S,4R)-4-[2-(8-chloro-4-oxo-chromen-2-yl)-5-(trifluoromethyl)phenoxy]pyrrolidine-1,2-dicarboxylate (400 mg, 704 μmol) in DCM (10 mL) was added TLA (402 mg, 3.52 mmol) and the mixture was then stirred at room temperature overnight. The mixture was then concentrated in vacuo to give the crude methyl (2S,4R)-4-[2-(8-chloro-4-oxo-chromen-2-yl)-5-(trifluoromethyl)phenoxy]pyrrolidine-2-carboxylate (320 mg, 97.1% yield) as a white solid, which was used in the next step directly without further purification. MS obsd. (ESI$^+$) [(M+H)$^+$]: 468.9.

Step 3: Preparation of (2S,4R)-1-(benzenesulfonyl)-4-[2-(8-chloro-4-oxo-chromen-2-yl)-5-(trifluoromethyl)phenoxy]pyrrolidine-2-carboxylic acid

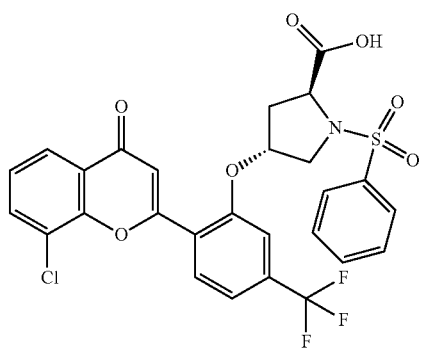

B076

To a solution of methyl (2S,4R)-4-[2-(8-chloro-4-oxo-chromen-2-yl)-5-(trifluoromethyl)phenoxy]pyrrolidine-2-carboxylate (120 mg, 250 μmol) in the mixed solvent of THF (10 ml) and Water (1 ml) was added LiOH (20.5 mg, 855 μmol) and the mixture was then stirred at room temperature for 2 hours. After complete conversion of methyl (2S,4R)-4-[2-(8-chloro-4-oxo-chromen-2-yl)-5-(trifluoromethyl)phenoxy]pyrrolidine-2-carboxylate to the (2S,4R)-4-[2-(8-chloro-4-oxo-chromen-2-yl)-5-(trifluoromethyl)phenoxy]pyrrolidine-2-carboxylic acid, to the resulting solution was added benzenesulfonyl chloride (195 mg, 1.1 mmol, as the "SM6" in Table 8) and the mixture was then stirred at room temperature for 30 minutes. The mixture was diluted with water (15 mL) and adjusted to pH 3.0 by addition of 2 N HCl. The resulting suspension was then extracted with EtOAc (30 mL) twice. The combined organic layer (60 mL) was washed with brine, dried over $Na_2SO_4$, concentrated in vacuo and the residue was purified by Prep-HPLC to give (2S,4R)-1-(benzenesulfonyl)-4-[2-(8-chloro-4-oxo-chromen-2-yl)-5-(trifluoromethyl)phenoxy]pyrrolidine-2-carboxylic acid (87 mg, 65.1% yield) as a white solid. $^1$H NMR (DMSO-$d_6$, 400 MHz): δ ppm 8.02-8.09 (m, 3H), 7.51-7.61 (m, 4H), 7.45 (s, 1H), 7.07-7.17 (m, 3H), 6.65 (s, 1H), 5.35 (br s, 1H), 4.16 (dd, J=9.5, 7.2 Hz, 1H), 3.85 (dd, J=12.7, 3.4 Hz, 1H), 3.60 (br d, J=12.1 Hz, 1H), 2.61 (br dd, J=13.9, 7.2 Hz, 1H), 2.35 (ddd, J=13.9, 9.6, 4.5 Hz, 1H). MS obsd. (ESI$^+$) [(M+H)$^+$]: 594.4.

The following Example B077 to Example B088 were prepared in analogy to the procedure described for the preparation of Example B076, replacing 8-chloro-2-[2-hydroxy-4-(trifluoromethyl)phenyl]chromen-4-one with "CORE", 1-(tert-butyl) 2-methyl (2S,4S)-4-((methylsulfonyl)oxy)pyrrolidine-1,2-dicarboxylate with "SM5" in step1 and benzenesulfonyl chloride with "SM6" in step 3. The "CORE", "SM5" and "SM6" are the reagents indicated in Table 8.

TABLE 8

Compounds synthesis and characterization

| Example No. | Compounds Name and Structure | CORE and SM4 | $^1$H NMR and (ESI$^+$) |
|---|---|---|---|
| B077 | (2S,4R)-4-[2-(8-chloro-4-oxo-chromen-2-yl)-5-(trifluoromethyl)phenoxyl-1-cyclopropylsulfonyl-pyrrolidine-2-carboxylic acid | CORE: Int-1<br>SM5: 1-(tert-butyl) 2-methyl (2S,4S)-4-((methylsulfonyl)oxy)pyrrolidine-1,2-dicarboxlate (Int-Pro2)<br>SM6: cyclopropanesulfonyl chloride | $^1$H NMR (DMSO-$d_6$, 400 MHz): δ ppm 8.00-8.14 (m, 3H), 7.59-7.65 (m, 2H), 7.52 (t, J = 7.9 Hz, 1H), 7.00 (s, 1H), 5.48 (br s, 1H), 4.38 (t, J = 8.2 Hz, 1H), 3.76 (br d, J = 2.9 H, 1H), 2.60-2.70 (m, 2H), 2.29-2.42 (m, 2H), 0.64-0.91 (m, 4H). MS obsd. (ESI$^+$) [(M + H)$^+$]: 558.4. |
| B078 | (2S,4S)-4-[2-(8-chloro-4-oxo-chromen-2-yl)-5-(trifluoromethyl)phenoxy]-1-cyclopropylsulfonyl-pyrrolidine-2-carboxylic acid | CORE: Int-1<br>SM5: O1-tert-butyl O2-methyl (2R,4S)-4-(p-tolylsulfonyloxy)pyrrolidine-1,2-dicarboxylate (Int-Pro1)<br>SM6: cyclopropane sulfonyl chloride | $^1$H NMR (DMSO-$d_6$, 400 MHz): δ ppm 12.56-12.73 (m, 1H), 8.16 (d, J = 8.1 Hz, 1H), 8.01 (dd, J = 7.9, 2.5 Hz, 2H), 7.54-7.63 (m, 2H), 7.50 (t, J = 7.9 Hz, 1H), 7.16 (s, 1H), 5.48 (br s, 1H), 4.49-4.52 (m, 1H), 3.89-3.93 (m, 1H), 3.64 (d, J = 11.2 Hz, 1H), 2.91-2.99 (m, 1H), 2.72-2.78 (m, 1H), 2.34 (d, J = 13.7 Hz, 1H), 0.90-1.14 (m, 4H). MS obsd. (ESL$^+$) [(M + H)$^+$]: 558.1. |
| C079 | (2S,4S)-4-[2-(8-chloro-4-oxo-chromen-2-yl)-5-(trifluoromethybphenoxy)-1-(3-methoxyphenyl)sulfonyl-pyrrolidine-2-carboxylic acid | CORE: Int-1<br>SM5: O1-tert-butyl O2-methyl (2R,4S)-4-(p- | $^1$H NMR (DMSO-$d_6$, 400 MHz): δ ppm 7.98-8.10 (m, 3H), 7.52-7.59 (m, 3H), 7.45-7.51 (m, 2H), 7.34- |

TABLE 8-continued

Compounds synthesis and characterization

| Example No. | Compounds Name and Structure | CORE and SM4 | $^1$H NMR and (ESI$^+$) |
|---|---|---|---|
| | (structure shown) | tolylsulfonyloxy)pyrrolidine-1,2-dicarboxylate (Int-Pro1) SM6: 3-methoxybenzenesulfonyl chloride | 7.41 (m, 1H), 7.25-7.30 (m, 1H), 6.96-6.99 (m, 1H), 5.27 (br d, J = 3.3 Hz, 1H), 4.49 (t, J = 6.1 Hz, 1H), 3.83 (s, 3H), 3.73 (dd, J = 12.2, 5.8 Hz, 1H), 3.56 (br d, J = 1.5 Hz, 1H), 2.25-2.30 (m, 2H). MS obsd. (ESI$^+$) [(M + H)$^+$]: 624.3. |
| B080 | (2S,4S)-1-(benzenesulfonyl)-4-[2-(8-chloro-4-oxo-chromen-2-yl)-5-(trifluoromethyl)phenoxy]methyl pyrrolidine-2-carboxylic acid (structure shown) | CORE: Int-1 SM5: O1-tert-butyl O2-(2R,4S)-4-(p-tolylsulfonyloxy)pyrrolidine-1,2-dicarboxylate (Int-Pro1) SM6: benzenesulfonyl chloride | $^1$H NMR (DMSO-d$_6$, 400MHz):12.96-13.13 (m, 1H), 8.00-8.11 (m, 4H), 7.04-7.20 (m, 3H), 6.65 (s, 1H), 5.30-5.40 (m, 1H), 4.15 (dd, J = 9.5, 7.2 Hz, 1H), 3.85 (dd, J = 12.6, 3.4 Hz, 1H), 3.60 (br d, J = 12.8 Hz, 1H), 2.57-2.64 (m, 1H), 2.30-2.38 (m, 1H). MS obsd. (ESI) [(M + H)$^+$]: 594.3. |
| B081 | (2S,4S)-1-(benzenesulfonyl)-4-[2-(8-chloro-4-oxo-chromen-2-yl)-4,5-dimethoxy-phenoxy]pyrrolidine-2-carboxylic acid (structure shown) | CORE: Int-10 SM5: O1-tert-butyl O2-methyl (2R,4S)-4-(p-tolylsulfonyloxy)pyrrolidine-1,2-dicarboxylate (Int-Pro1) SM6: benzenesulfonyl chloride | $^1$H NMR (DMSO-d$_6$, 400 MHz): δ ppm 7.90-8.03 (m, 4H), 7.69-7.75 (m, 1H), 7.61-7.67 (m, 2H), 7.44-7.53 (m, 2H), 6.98 (s, 1H), 6.69 (s, 1H), 5.03-5.10 (m, 1H), 4.45 (t, J = 6.3 Hz, 1H), 3.86 (s, 3H), 3.80 (s, 3H), 3.67 (dd, J = 11.6, 5.6 Hz, 1H), 3.53 (br dd, J = 11.5, 2.2 Hz, 2H), 2.30 (dd, J = 6.2, 4.0 Hz, 1H). MS obsd. (ESL$^+$) [(M + H)$^+$: 586.3. |
| B082 | (2S,4S)-1-(benzenesulfonyl)-4-[5-bromo-2-(8-chloro-4-oxo-chromen-2-yl)phenoxy]pyrrolidine-2-carboxylic acid | CORE: Int-4 SM5: O1-tert-butyl O2-methyl (2R,4S)-4-(p- | $^1$H NMR (DMSO-d$_6$, 400 MHz): δ ppm 7.91-8.03 (m, 4H), 7.79-7.86 (m, 1H), 7.67-7.74 (m, 1H), 7.59- |

TABLE 8-continued

Compounds synthesis and characterization

| Example No. | Compounds Name and Structure | CORE and SM4 | ¹H NMR and (ESI⁺) |
|---|---|---|---|
| | | tolylsulfonyloxy)pyrrolidine-1,2-dicarboxylate (Int-Pro1) SM6: benzenesulfonyl chloride | 7.66 (m, 2H), 7.46-7.53 (m, 1H), 7.34-7.44 (m, 2H), 6.97-7.02 (m, 1H), 4.99-5.07 (m, 1H), 4.29-4.38 (m, 1H), 3.70-3.78 (m, 1H), 3.43-3.51 (m, 1H), 2.16-2.36 (m, 2H). MS obsd. (ESL⁺) [(M + H)⁺]:602.1. |
| B083 | (2S,4S)-4-[5-bromo-2-(8-chloro-4-oxo-chromen-2-yl)phenoxy]-1-cyclopropylsulfonyl-pyrrolidine-2-carboxylic acid | CORE: Int-4 SM5: O1-tert-butyl O2-methyl (2R,4S)-4-(p-tolylsulfonyloxpy)pyrrolidine-1,2-dicarboxylate (Int-Pro1) SM6: cyclopropane-sulfonyl chloride | ¹H NMR (DMSO-d₆, 400 MHz): δ ppm 8.00 (dd, J = 7.9, 1.9 Hz, 2H), 7.86-7.97 (m, 1H), 7.39-7.55 (m, 3H), 7.12 (s, 1H), 5.32-5.39 (m, 1H), 4.45-4.56 (m, 1H), 3.88-3.93 (m, 1H), 3.63 (br d, J = 11.1 Hz, 1H), 2.95-3.04 (m, 1H), 2.68-2.79 (m, 1H), 2.35 (br d, J = 14.1 Hz, 1H), 0.91-1.17 (m, 4H) .MS obsd. (ESI⁺) [(M + H)⁺]: 568.3. |
| B084 | (2S,4S)-1-(benzenesulfonyl)-4-[5-chloro-2-(8-chloro-4-oxo-chromen-2-yl)-4-methyl-phenoxy]pyrrolidine-2-carboxylic acid | CORE: Int-5 SM5: O1-tert-butyl O2-methyl (2R,4S)-4-(p-tolylsulfonyloxy)pyrrolidine-1,2-dicarboxylate (Int-Pro1) SM6: benzenesulfonyl chloride | ¹H NMR (DMSO-d₆, 400 MHz): δ ppm 12.79 (s, 1H), 7.96-8.04 (m, 2H), 7.89-7.96 (m, 2H), 7.81-7.85 (m, 1H), 7.68-7.75 (m, 1H), 7.58-7.67 (m, 2H), 7.45-7.53 (m, 1H), 7.24-7.31 (m, 1H), 6.90-6.95 (m, 1H), 5.06-5.12 (m, 1H), 4.40-4.48 (m, 1H), 3.63-3.72 (m, 1H), 3.48-3.55 (m, 1H), 2.37 (s, 3H), 2.23-2.29 (m, 2H). MS obsd. (ESI⁺) [(M + H)⁺]: 574.1. |
| B085 | (2S,4S)-1-(benzenesulfonyl)-4-[2-(8-chloro-4-oxo-chromen-2-yl)-5-(trifluoromethoxy)phenoxy]pyrrolidine-2-carboxylic acid | CORE: Int-9 SM5: O1-tert-butyl O2-methyl (2R,4S)-4-(p- | ¹H NMR (DMSO-d₆, 400 MHz): δ ppm 7.97-8.06 (m, 3H), 7.89-7.96 (m, 2H), 7.68-7.78 (m, 1H), 7.59- |

TABLE 8-continued

Compounds synthesis and characterization

| Example No. | Compounds Name and Structure | CORE and SM4 | $^1$H NMR and (ESI$^+$) |
|---|---|---|---|
| | | tolylsulfonyloxy) pyrrolidine-1,2-dicarboxylate (Int-Pro1) SM6: benzenesulfonyl chloride | 7.68 (m, 2H), 7.46-7.55 (m, 1H), 7.17-7.26 (m, 2H), 6.94-6.98 (m, 1H), 5.11-5.19 (m, 1H), 4.41-4.51 (m, 1H), 3.66-3.75 (m, 2H), 2.23-2.33 (m, 2H) .MS obsd. (ESI$^+$) [(M + H)$^+$]: 610.1. |
| B086 | (2S,4S)-1-benzoyl-4-[5-bromo-2-(8-chloro-4-oxo-chromen-2-yl) phenoxy]pyrrolidine-2-carboxylic acid | CORE: Int-4 SM5: O1-tert-butyl O2-methyl (2R,4S)-4-(p-tolylsulfonyloxy) pyrrolidine-1,2-dicarboxylate (Int-Pro1) SM6: benzoyl chloride | $^1$HNMR (DMSO-d$_6$, 400 MHz): δ ppm 7.97-8.09 (m, 2H), 7.87 (br d, J = 8.6 Hz, 1H), 7.39-7.58 (m, 8H), 7.09 (s, 1H), 5.23-5.32 (m, 1H), 4.65-4.71 (m, 1H), 4.48-4.54 (m, 1H), 3.73-3.84 (m, 1H), 2.74-2.82 (m, 1H), 2.26-2.32 (m, 1H). MS obsd. (ESI$^+$) [(M + H)$^+$]: 570.1. |
| B087 | (2R,4S)-1-(benzenesulfonyl)-4-[2-(8-chloro-4-oxo-chromen-2-yl)-5-(trifluoromethyl)phenoxy] pyrrolidine-2-carboxylic acid | CORE: Int-1 SM5: O1-tert-butyl O2-methyl (2R,4R)-4-(p-tolylsulfonyloxy) pyrrolidine-1,2-dicarboxylate (Int-Pro3) SM6: benzenesulfonyl chloride | $^1$H NMR (DMSO-d$_6$, 400 MHz): δ ppm 8.04-8.11 (m, 3H), 7.53-7.59 (m, 4H), 7.06-7.18 (m, 3H), 6.62-6.67 (m, 1H), 5.24-5.41 (m, 1H), 4.14-4.23 (m, 1H), 3.81-3.90 (m, 1H), 3.60 br d, J = 12.2 Hz, 1H), 2.58-2.66 (m, 1H), 2.28-2.41 (m, 1H). MS obsd. (ESI$^+$) [(M + H)$^+$]: 594.6. |
| B088 | (2R,4R)-1-(benzenesulfonyl)-4-[2-(8-chloro-4-oxo-chromen-2-yl)-5-(trifluoromethyl)phenoxy] pyrrolidine-2-carboxylic acid | CORE: Int-1 SM5: O1-tert-butyl O2-methyl (2S,4R)-4-(p- | $^1$H NMR (DMSO-d$_6$, 400 MHz): δ ppm 7.98-8.13 (m, 3H), 7.91-7.97 (m, 2H), 7.72 (s, 1H), 7.39-7.66 |

TABLE 8-continued

Compounds synthesis and characterization

| Example No. | Compounds Name and Structure | CORE and SM4 | ¹H NMR and (ESI⁺) |
|---|---|---|---|
| | 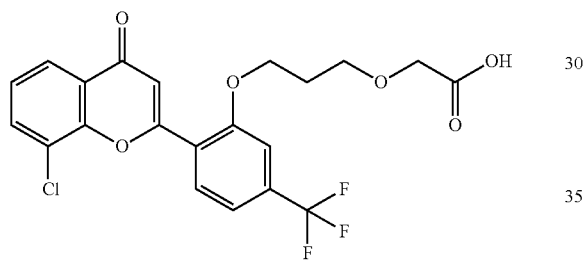 | tolylsulfonyloxy)y)pyrrolidine-1,2-dicarboxylate (Int-Pro4) SM6: benzenesulfonyl chloride | (m, 5H), 7.00 (s, 1H), 5.26 (br d, J = 3.3 Hz, 1H), 4.46 (dd, J = 7.6, 4.5 Hz, 1H), 3.70 (dd, J = 11.7, 5.4 Hz, 1H), 3.54 (dd, J = 11.7, 1.5 Hz, 1H), 2.51-2.54 (m, 1H), 2.24-2.30 (m, 1H). MS obsd. (ESI⁺) [(M + H)⁺]: 594.1. |

Example C001: 2-[3-[2-(8-chloro-4-oxo-chromen-2-yl)-5-(trifluoromethyl)phenoxy]propoxy]acetic acid

C001

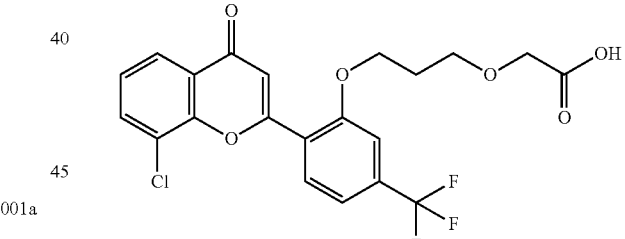

Step 1: Preparation of tert-butyl 2-[3-[2-(8-chloro-4-oxo-chromen-2-yl)-5-(trifluoromethyl)phenoxy]propoxy]acetate C001a

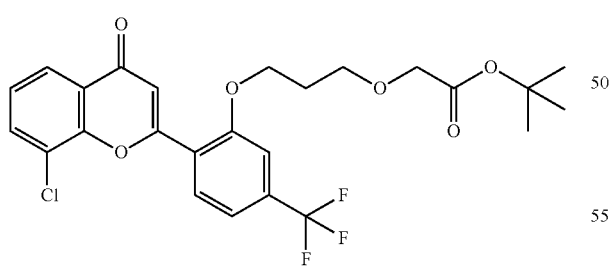

To a mixture of 8-chloro-2-[2-hydroxy-4-(trifluoromethyl)phenyl]chromen-4-one (Int-1, 500.0 mg, 1.47 mmol, as the "CORE" in Table 9), K₂CO₃ (608.5 mg, 4.4 mmol) in DMF (10 mL) was added tert-butyl 2-[2-(p-tolylsulfonyloxy)ethoxy]acetate (Int-T3, 533.4 mg, 1.61 mmol, as the "Tail" in Table 9) and the mixture was stirred at 80° C. for 4 hours. After the reaction was completed, the mixture was diluted with water (15 mL) and extracted with EtOAc (15 mL) three times. The combined organic layer was washed with brine, dried over Na₂SO₄ and concentrated in vacuo. The residue was purified by column chromatography on silica gel (eluted with PE:EtOAc=3:1 to 1:1) to give tert-butyl 2-[3-[2-(8-chloro-4-oxo-chromen-2-yl)-5-(trifluoromethyl)phenoxy]propoxy]acetate (632 mg, 83.9% yield) as a colorless oil. MS obsd. (ESI⁺) [(M+H)⁺]: 513.1.

Step 2: Preparation of 2-[3-[2-(8-chloro-4-oxo-chromen-2-yl)-5-(trifluoromethyl)phenoxy]propoxy]acetic acid

C001

To a mixture of tert-butyl 2-[3-[2-(8-chloro-4-oxo-chromen-2-yl)-5-(trifluoromethyl)phenoxy]propoxy]acetate (2000.0 mg, 3.9 mmol) in DCM (50 mL) was added TFA (5.0 mL, 64.9 mmol) and the mixture was stirred at room temperature for 4 hours. After the reaction was completed, the mixture was concentrated in vacuo. The residue was triturated with EtOAc (30 mL) and then filtered, the solid was collected and dried in vacuo to give 2-[3-[2-(8-chloro-4-oxo-chromen-2-yl)-5-(trifluoromethyl)phenoxy]propoxy]acetic acid (1580 mg, 88.7% yield) as a white solid. ¹H NMR (DMSO-d₆, 400 MHz): δ ppm 8.21-8.27 (m, 1H), 8.08-8.15 (m, 1H), 7.87-7.99 (m, 1H), 7.45-7.58 (m, 3H), 7.29-7.36 (m, 1H), 4.36-4.48 (m, 2H), 4.01-4.10 (m, 2H), 3.73-3.83 (m, 2H), 2.16-2.30 (m, 2H). MS obsd. (ESI⁺) [(M+H)⁺]: 457.1.

Example C002: 2-[3-[2-(8-chloro-4-oxo-chromen-2-yl)-5-methyl-phenoxy]propoxy]acetic acid

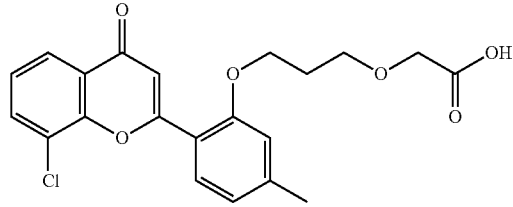

Example C002 was prepared in analogy to the procedure described for the preparation of Example C001 by using 8-chloro-2-(2-hydroxy-4-methyl-phenyl)chromen-4-one (Int-2) as the starting materials instead of 8-chloro-2-[2-hydroxy-4-(trifluoromethyl)phenyl]chromen-4-one (Int-1) in Step 1. $^1$H NMR (DMSO-$d_6$, 400 MHz): δ ppm 12.42 (s, 1H), 7.96-8.03 (m, 2H), 7.83-7.93 (m, 1H), 7.44-7.53 (m, 1H), 7.10-7.16 (m, 1H), 7.07-7.10 (m, 1H), 6.99-7.04 (m, 1H), 4.19-4.29 (m, 2H), 3.97-4.04 (m, 2H), 3.60-3.70 (m, 2H), 2.43 (s, 3H), 2.01-2.10 (m, 2H). MS obsd. (ESI$^+$) [(M+H)$^+$]: 403.1.

Example C003-A and Example C003-B: Cis-3-[2-[5-bromo-2-(8-chloro-4-oxo-chromen-2-yl)phenoxy]ethoxy]cyclobutanecarboxylic acid and tram-3-[2-[5-bromo-2-(8-chloro-4-oxo-chromen-2-yl)phenoxy]ethoxy]cyclobutanecarboxylic acid

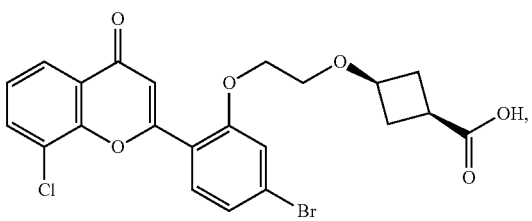

C003-A

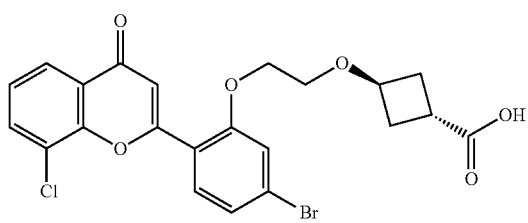

C003-B

Step 1: Preparation of methyl 3-[2-[5-bromo-2-(8-chloro-4-oxo-chromen-2-yl)phenoxy]ethoxy]cyclobutanecarboxylate

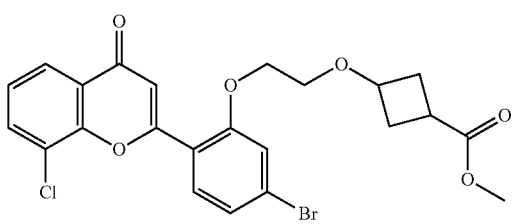

C003a

To a mixture of 2-(4-bromo-2-hydroxy-phenyl)-8-chloro-chromen-4-one (Int-4, 300.0 mg, 0.850 mmol) and methyl 3-[2-(p-tolylsulfonyloxy)ethoxy]cyclobutanecarboxylate (Int-T1, 336.24 mg, 1.02 mmol) in DMF (5 mL) was added K$_2$CO$_3$ (176.89 mg, 1.28 mmol) at 25° C. and the mixture was then stirred at 80° C. for 16 hours. After the reaction was completed, the mixture was poured into water (50 mL) and extracted with EtOAc (100 mL) twice. The combined organic layer was washed with brine, dried over Na$_2$SO$_4$ and concentrated in vacuo. The residue was purified by column chromatography on silica gel (eluted with PE:EtOAc=3:1 to 1:1) to give methyl 3-[2-[5-bromo-2-(8-chloro-4-oxo-chromen-2-yl)phenoxy]ethoxy]cyclobutanecarboxylate (300 mg, 69.4% yield) as a yellow solid. $^1$H NMR (DMSO-$d_6$, 400 MHz): δ ppm 7.95-8.02 (m, 2H), 7.90 (s, 1H), 7.85-7.94 (m, 1H), 7.46-7.53 (m, 2H), 7.37-7.43 (m, 1H), 7.31 (s, 1H), 4.27-4.35 (m, 2H), 4.20 (t, J=6.8 Hz, 0.6H), 3.96 (t, J=7.0 Hz, 0.4H), 3.66-3.73 (m, 2H), 3.53-3.61 (m, 3H), 3.02-3.11 (m, 0.6H), 2.60-2.67 (m, 0.4H), 2.36-2.42 (m, 2H), 2.17-2.29 (m, 2H). MS obsd. (ESI$^+$) [(M+H)$^+$]: 509.3.

Step 2: Preparation of Cis-3-[2-[5-bromo-2-(8-chloro-4-oxo-chromen-2-yl)phenoxy]ethoxy]cyclobutanecarboxylic acid and tram-3-[2-[5-bromo-2-(8-chloro-4-oxo-chromen-2-yl)phenoxy]ethoxy]cyclobutanecarboxylic acid

C003-A

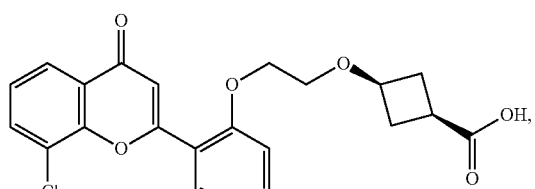

C003-B

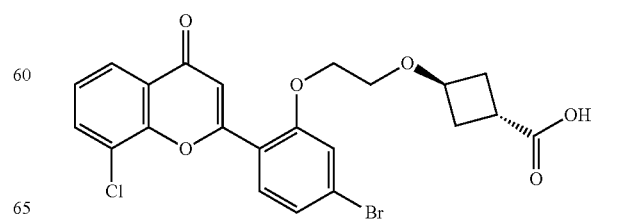

To a mixture of methyl 3-[2-[5-bromo-2-(8-chloro-4-oxo-chromen-2-yl)phenoxy]ethoxy]cyclobutanecarboxylate (300.0 mg, 0.590 mmol) in THF (3 mL) and water (1 mL) was added LiOH.H$_2$O (74.37 mg, 1.77 mmol) at 25° C. and the mixture was then stirred at 25° C. for 3 hours. After the reaction was completed, the mixture was poured into water (30 mL) and adjusted to pH ~5 by addition of HCl (4 N). The resulting solution was then extracted with EtOAc (50 mL) twice. The combined organic layer was washed with brine, dried over Na$_2$SO$_4$ and concentrated in vacuo to give the crude 3-[2-[5-bromo-2-(8-chloro-4-oxo-chromen-2-yl)phenoxy]ethoxy]cyclobutanecarboxylic acid. The crude was purified by Prep-HPLC to give two sets of diastereomers of the 3-[2-[5-bromo-2-(8-chloro-4-oxo-chromen-2-yl)phenoxy]ethoxy]cyclobutanecarboxylic acid with cis- and trans-configuration, one of which is characterized as Example C003-A (25 mg, 8.3%) and the other is Example C003-B (48 mg, 16.0%).

Example C003-A: $^1$H NMR (DMSO-d$_6$, 400 MHz): δ ppm 12.10 (br s, 1H), 7.98 (br d, J=7.7 Hz, 2H), 7.90 (br d, J=8.4 Hz, 1H), 7.35-7.57 (m, 3H), 7.13-7.27 (m, 1H), 4.23-4.40 (m, 2H), 3.86-4.01 (m, 1H), 3.68-3.72 (m, 2H), 2.30-2.47 (m, 3H), 1.94-2.06 (m, 2H). MS obsd. (ESI$^+$) [(M+H)$^+$]:495.0.

Example C003-B: $^1$H NMR (DMSO-d$_6$, 400 MHz): δ ppm 11.28-12.64 (m, 1H), 7.72-8.19 (m, 3H), 7.14-7.67 (m, 4H), 4.07-4.39 (m, 3H), 3.51-3.56 (m, 2H), 2.83-3.08 (m, 1H), 2.40 (br s, 2H), 2.24 (br s, 2H). MS obsd. (ESI$^+$) [(M+H)$^+$]:495.0.

Example C004: 3-[2-[5-chloro-2-(8-chloro-4-oxo-chromen-2-yl)phenoxy]ethoxy]cyclobutanecarboxylic acid

C004

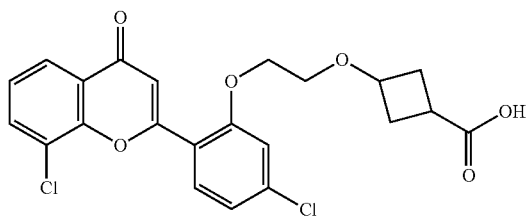

Step 1: Preparation of methyl 3-[2-[5-chloro-2-(8-chloro-4-oxo-chromen-2-yl)phenoxy]ethoxy]cyclobutanecarboxylate C004a

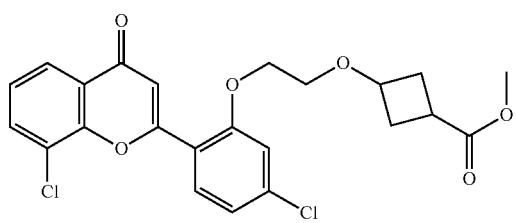

To a solution of 8-chloro-2-(4-chloro-2-hydroxy-phenyl)chromen-4-one (Int-35, 200.0 mg, 0.650 mmol) and K$_2$CO$_3$ (180.0 mg, 1.3 mmol) in DMF (5 mL) was added methyl 3-[2-(p-tolylsulfonyloxy)ethoxy]cyclobutanecarboxylate (213.84 mg, 0.650 mmol) and the reaction mixture was stirred at 80° C. for 16 hours. The reaction mixture was then poured into water (30 mL) and extracted with EtOAc (30 mL) twice. The combined organic layer was washed with brine, dried over Na$_2$SO$_4$ and concentrated in vacuo to give the crude methyl 3-[2-[5-chloro-2-(8-chloro-4-oxo-chromen-2-yl)phenoxy]ethoxy]cyclobutanecarboxylate (210 mg, 55.68% yield) as a yellow solid, which was used in the next step directly without further purification.

Step 2: Preparation of 3-[2-[5-chloro-2-(8-chloro-4-oxo-chromen-2-yl)phenoxy]ethoxy]cyclobutanecarboxylic acid

C004

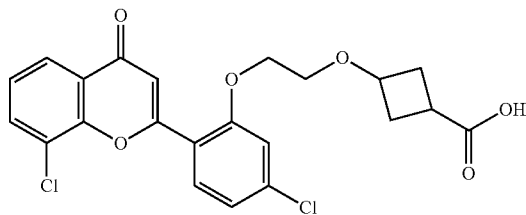

To a solution of methyl 3-[2-[5-chloro-2-(8-chloro-4-oxo-chromen-2-yl)phenoxy]ethoxy]cyclobutanecarboxylate (210.0 mg, 0.450 mmol) in DMF (5 mL) was added sodium hydroxide (54.4 mg, 1.36 mmol) at 20° C. and the reaction mixture was stirred at 20° C. for 3 hours. After the reaction was completed, the mixture was concentrated in vacuo and the residue was purified by Prep-HPLC to give the product 3-[2-[5-chloro-2-(8-chloro-4-oxo-chromen-2-yl)phenoxy]ethoxy]cyclobutanecarboxylic acid (20.4 mg, 9.85% yield) as a yellow solid. $^1$H NMR (DMSO-d$_6$, 400 MHz): δ ppm 7.91-8.02 (m, 3H), 7.46 (t, J=7.9 Hz, 1H), 7.19-7.38 (m, 3H), 4.27-4.34 (m, 2H), 4.15-4.22 (m, 1H), 3.662-3.72 (m, 2H), 2.86-2.95 (m, 1H), 2.35-2.41 (m, 2H), 2.10-2.24 (m, 2H). MS obsd. (ESI$^+$) [(M+H)$^+$]: 449.6.

Example C005: 2-[2-[2-(8-chloro-4-oxo-chromen-2-yl)-5-(trifluoromethyl)phenoxy]ethoxy]acetic acid

C005

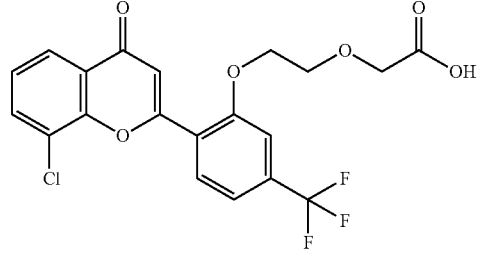

Step 1: Preparation of methyl 2-[2-[2-(8-chloro-4-oxo-chromen-2-yl)-5-(trifluoromethyl)phenoxy]ethoxy]acetate

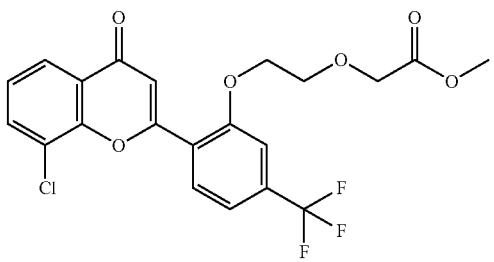

C005a

Compound C005a was prepared in analogy to the procedure described for the preparation of compound C003a by using 8-chloro-2-[2-hydroxy-4-(trifluoromethyl)phenyl]chromen-4-one (Int-1) and methyl 2-[2-(p-tolylsulfonyloxy)ethoxy]acetate (Int-T4) as the starting materials instead of 2-(4-bromo-2-hydroxy-phenyl)-8-chloro-chromen-4-one (Int-4) and methyl 3-[2-(p-tolylsulfonyloxy)ethoxy]cyclobutanecarboxylate (Int-T1) in Step 1.

Step 2: Preparation of 2-[2-[2-(8-chloro-4-oxo-chromen-2-yl)-5-(trifluoromethyl)phenoxy]ethoxy]acetic acid

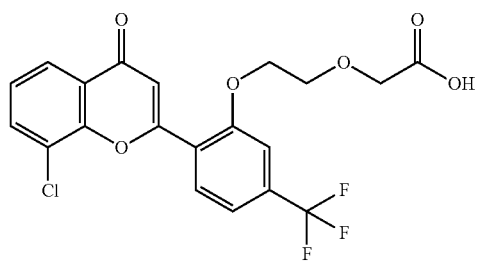

C005

To a solution of methyl 2-[2-[2-(8-chloro-4-oxo-chromen-2-yl)-5-(trifluoromethyl)phenoxy]ethoxy]acetate (400 mg, 876 μmol) in the THF (20 mL)/water (5 mL) was added LiOH (220 mg, 5.25 mmol). The reaction was stirred at room temperature for 4 hours. After the reaction was completed, the mixture was concentrated in vacuo and the residue was purified by Prep-HPLC to give 2-[2-[2-(8-chloro-4-oxo-chromen-2-yl)-5-(trifluoromethyl)phenoxy]ethoxy]acetic acid (128.4, 31.8% yield) as a white solid. $^1$H NMR (DMSO-$d_6$, 400 MHz): δ ppm 8.11-8.20 (m, 1H), 7.96-8.05 (m, 2H), 7.48-7.64 (m, 3H), 7.21-7.28 (m, 1H), 4.40-4.48 (m, 2H), 4.13 (s, 2H), 3.83-3.97 (m, 2H). (ESI$^+$) [(M+H)$^+$]: 443.1.

Example C006: 2-[2-[5-bromo-2-(8-chloro-4-oxo-chromen-2-yl)phenoxy]ethoxy]acetic acid

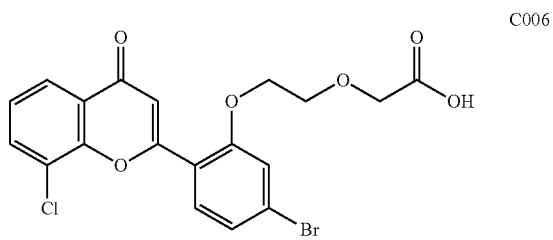 [SMILES: O=C(O)COCCOc1cc(Br)ccc1-c1cc(=O)c2cccc(Cl)c2o1]

C006

Step 1: Preparation of methyl 2-[2-[5-bromo-2-(8-chloro-4-oxo-chromen-2-yl)phenoxy]ethoxy]acetate

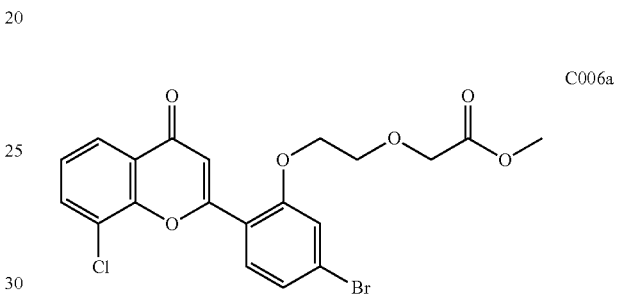

C006a

Compound C006a was prepared in analogy to the procedure described for the preparation of compound C003a by using methyl 2-[2-(p-tolylsulfonyloxy)ethoxy]acetate (Int-T4) as the starting materials instead of methyl 3-[2-(p-tolylsulfonyloxy)ethoxy]cyclobutanecarboxylate (Int-T1) in Step 1.

Step 2: Preparation of 2-[2-[5-bromo-2-(8-chloro-4-oxo-chromen-2-yl)phenoxy]ethoxy]acetic acid

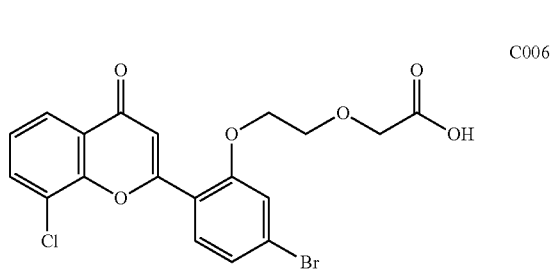 [SMILES: O=C(O)COCCOc1cc(Br)ccc1-c1cc(=O)c2cccc(Cl)c2o1]

C006

To a solution of methyl 2-[2-[5-bromo-2-(8-chloro-4-oxo-chromen-2-yl)phenoxy]ethoxy]acetate (400 mg, 855 μmol) in a mixed solvent of MeOH (10 ml) and THF (10 ml) was added LiOH (20.5 mg, 855 μmol) and the mixture was stirred at room temperature for 4 hours. After the reaction was completed, the mixture was adjusted to pH ~ 5.0 by addition of concentrated HCl. The resulting solution was concentrated in vacuo and the residue was triturated with EtOH (15 mL). The suspension was then filtered, the solid was collected and dried in vacuo to give 2-[2-[5-bromo-2-(8-chloro-4-oxo-chromen-2-yl)phenoxy]ethoxy]acetic acid (220 mg, 50.5% yield) as a yellow solid. $^1$H NMR (DMSO-$d_6$, 400 MHz): δ ppm 8.00 (dd, J=7.9, 2.1 Hz, 2H), 7.92 (d, J=8.6 Hz, 1H), 7.47-7.57 (m, 2H), 7.43 (dd, J=8.5, 1.8 Hz, 1H), 7.23 (s, 1H), 4.31-4.37 (m, 2H), 3.82-3.89 (m, 2H), 3.68-3.73 (m, 2H). (ESI+) [(M+H)+]: 453.0.

The following Example C009 to Example C019 were prepared in analogy to the procedure described for the preparation of Example C001. By replacing tert-butyl 2-[2-(p-tolylsulfonyloxy)ethoxy]acetate with "Tail", 8-chloro-2-[2-hydroxy-4-(trifluoromethyl)phenyl]chromen-4-one with "CORE" in step 1. The Tail" and "CORE" are the reagents indicated in Table 9.

TABLE 9

Compounds synthesis and characterization

| Example No. | Compounds Name and Structure | CORE, TAIL | ¹NMR and (ESI+) |
|---|---|---|---|
| C009 | 2-[3-[5-chloro-2-(8-chloro-4-oxo-chromen-2-yl)phenoxy]propoxy]acetic acid | CORE:Int-35 TAIL:Int-T3 | ¹H NMR (DMSO-$d_6$, 400 MHz): δ ppm 7.91-8.05 (m, 3H), 7.45-7.54 (m, 1H), 7.37-7.43 (m, 1H), 7.25-7.33 (m, 1H), 7.02-7.11 (m, 1H), 4.21-4.33 (m, 2H), 4.05 (s, 2H), 3.59-3.66 (m, 2H), 1.98-2.11 (m, 2H). (ESI+) [(M + H)+]: 423.1. |
| C010 | 2-[3-[5-bromo-2-(8-chloro-4-oxo-chromen-2-yl)phenoxy]propoxy]acetic acid | CORE:Int-4 TAIL:Int-T3 | ¹H NMR (DMSO-$d_6$, 400 MHz): δ ppm 7.94-8.05 (m, 2H), 7.78-7.93 (m, 1H), 7.36-7.58 (m, 3H), 7.02-7.11 (m, 1H), 4.20-4.33 (m, 2H), 3.89-4.03 (m, 2H), 3.59-3.68 (m, 2H), 1.98-2.12 (m, 2H). (ESI+) [(M + H)+]: 465.1. |
| C011 | 2-[3-[5-bromo-2-(8-chloro-4-oxo-chromen-2-yl)-4-methyl-phenoxy]propoxy]acetic acid | CORE:Int-6 TAIL:Int-T3 | ¹H NMR (DMSO-$d_6$, 400 MHz): δ ppm 7.99 (br d, J = 3.55 Hz, 2H), 7.84-7.89 (m, 1H), 7.45-7.53 (m, 2H), 6.98-7.08 (m, 1H), 4.18-4.27 (m, 2H), 3.95 (s, 2H), 3.56-3.64 (m, 2H), 2.36 (s, 3H), 1.94-2.09 (m, 2H). (ESI+) [(M + H)+]: 481.1. |
| C012 | 2-[3-[2-(8-chloro-4-oxo-chromen-2-yl)-4,5-dimethoxy-phenoxy]propoxy]acetic acid | CORE:Int-10 TAIL:Int-T3 | ¹H NMR (DMSO-$d_6$, 400 MHz): δ ppm 7.90-8.03 (m, 2H), 7.52-7.63 (m, 1H), 7.39-7.52 (m, 1H), 7.06-7.15 (m, 1H), 6.79-6.89 (m, 1H), 4.17-4.31 (m, 2H), 4.07 (s, 2H), 3.93 (s, 3H), 3.80 (s, 3H), 3.60-3.71 (m, 2H), 2.00-2.13 (m, 2H). (ESI+) [(M + H)+]: 449.1. |

TABLE 9-continued

Compounds synthesis and characterization

| Example No. | Compounds Name and Structure | CORE, TAIL | ¹NMR and (ESI⁺) |
|---|---|---|---|
| C013 | 2-[3-[5-bromo-2-(8-chloro-4-oxo-chromen-2-yl)-4-methoxy-phenoxy]propoxy]acetic acid | CORE:Int-7 TAIL:Int-T3 | ¹H NMR (DMSO-$d_6$, 400 MHz): δ ppm 12.46 (s, 1H), 7.96-8.04 (m, 2H), 7.62-7.68 (m, 1H), 7.54-7.57 (m, 1H), 7.47-7.53 (m, 1H), 7.04-7.13 (m, 1H), 4.17-4.27 (m, 2H), 3.97-4.03 (m, 2H), 3.94 (s, 3H), 3.58-3.65 (m, 2H), 1.94-2.07 (m, 2H). (ESI⁺) [(M + H)⁺]: 497.1. |
| C014 | 2-[3-[2-(8-chloro-4-oxo-chromen-2-yl)-5-(trifluoromethoxy)phenoxy]propoxy]acetic acid | CORE:Int-9 TAIL:Int-T3 | ¹H NMR (DMSO-$d_6$, 400 MHz): δ ppm 7.97-8.10 (m, 3H), 7.44-7.54 (m, 1H), 7.19-7.32 (m, 2H), 7.03-7.09 (m, 1H), 4.25-4.33 (m, 2H), 4.04 (s, 2H), 3.59-3.66 (m, 2H), 2.00-2.09 (m, 2H). (ESI⁺) [(M + H)⁺]: 473.1. |
| C015 | 2-[3-[[6-(8-chloro-4-oxo-chromen-2-yl)-1,3-benzodioxol-5-yl]oxy]propoxy]acetic acid | CORE:Int-11 TAIL:Int-T3 | ¹H NMR (DMSO-$d_6$, 400 MHz): δ ppm 7.94-8.03 (m, 2H), 7.41-7.53 (m, 2H), 7.00-7.11 (m, 2H), 6.20 (s, 2H), 4.14-4.26 (m, 2H), 4.03 (s, 2H), 3.59-3.67 (m, 2H), 1.94-2.08 (m, 2H). (ESI⁺) [(M + H)⁺]: 433.1. |
| C016 | 2-[3-[5-chloro-2-(8-chloro-4-oxo-chromen-2-yl)-4-methoxy-phenoxy]propoxy]acetic acid | CORE:Int-8 TAIL:Int-T3 | ¹H NMR (DMSO-$d_6$, 400 MHz): δ ppm 12.63 (s, 1H), 7.97-8.06 (m, 2H), 7.65-7.71 (m, 1H), 7.47-7.56 (m, 1H), 7.41-7.45 (m, 1H), 7.05-7.13 (m, 1H), 4.18-4.27 (m, 2H), 4.05 (s, 2H), 3.91 (s, 3H), 3.57-3.66 (m, 2H), 1.94-2.07 (m, 2H). (ESI⁺) [(M + H)⁺]: 453.1. |
| C017 | 2-[3-[2-(8-bromo-4-oxo-chromen-2-yl)-5-methyl-phenoxy]propoxy]acetic acid | CORE:Int-24 TAIL:Int-T3 | ¹H NMR (DMSO-$d_6$, 400 MHz): δ ppm 8.07-8.16 (m, 1H), 7.98- |

TABLE 9-continued

Compounds synthesis and characterization

| Example No. | Compounds Name and Structure | CORE,TAIL | ¹NMR and (ESI⁺) |
|---|---|---|---|
| | (structure: 8-bromo-chromen-4-one with 2-(4-methylphenoxy) bearing propoxy-acetic acid tail) | | 8.05 (m, 1H), 7.89-7.97 (m, 1H), 7.37-7.49 (m, 1H), 7.07-7.16 (m, 2H), 6.97-7.06 (m, 1H), 4.16-4.29 (m, 2H), 4.01 (s, 2H), 3.58-3.70 (m, 2H), 2.40 (s, 3H), 1.96-2.11 (m, 2H). (ESI⁺) [(M + H)⁺]: 447.1. |
| C018 | 2-[3-[2-(8-bromo-4-oxo-chromen-2-yl)-5-chloro-4-methyl-phenoxy]propoxy]acetic acid (structure shown) | CORE:Int-25 TAIL:Int-T3 | ¹H NMR (DMSO-$d_6$, 400 MHz): δ ppm 8.11-8.16 (m, 1H), 8.01-8.05 (m, 1H), 7.92-7.96 (m, 1H), 7.40-7.47 (m, 1H), 7.35-7.39 (m, 1H), 7.06 (s, 1H), 4.22-4.28 (m, 2H), 4.00 (s, 2H), 3.58-3.66 (m, 2H), 2.37 (s, 3H), 1.99-2.09 (m, 2H). (ESI⁺) [(M + H)⁺]: 481.1. |
| C019 | 2-[3-[5-chloro-2-(8-chloro-4-oxo-chromen-2-yl)-4-methyl-phenoxy]propoxy]acetic acid (structure shown) | CORE:Int-5 TAIL:Int-T3 | ¹H NMR (DMSO-$d_6$, 400 MHz): δ ppm 7.96-8.04 (m, 2H), 7.85-7.91 (m, 1H), 7.46-7.54 (m, 1H), 7.34-7.39 (m, 1H), 7.00-7.08 (m, 1H), 4.20-4.30 (m, 2H), 3.95-4.04 (m, 2H), 3.59-3.68 (m, 2H), 2.40 (s, 3H), 1.95-2.08 (m, 2H). (ESI⁺) [(M + H)⁺]: 437.1. |

The following compounds C020 to C058 were prepared in analogy to the procedure described for the preparation of example C005. By replacing methyl 2-[2-(p-tolylsulfonyloxy)ethoxy] acetate with "Tail", 8-chloro-2-[2-hydroxy-4-(trifluoromethyl)phenyl]chromen-4-one with "CORE" in step 1. The "Tail" and "CORE" are the reagents indicated in Table 8.

| Example No. | Compounds Name and Structure | CORE,TAIL, | ¹H NMR and (ESI⁺) |
|---|---|---|---|
| C020 | 2-[2-[5-bromo-2-(8-chloro-4-oxo-chromen-2-yl)-4-methoxy-phenoxy]ethoxy]acetic acid | CORE:Int-7 TAIL:Int-T4 | ¹H NMR (DMSO-$d_6$, 400 MHz): δ ppm 12.56 (s, 1H), 7.94-8.05 (m, 2H), 7.66 (s, |

| Example No. | Compounds Name and Structure | CORE, TAIL | ¹H NMR and (ESI⁺) |
|---|---|---|---|
| | 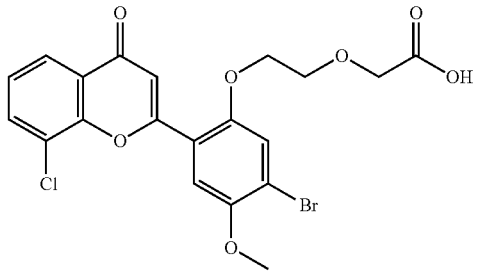 [SMILES: COc1cc(-c2cc(=O)c3cccc(Cl)c3o2)c(OCCOCC(=O)O)cc1Br] | | 1H), 7.55-7.62 (m, 1H), 7.45-7.53 (m, 1H), 7.23 (s, 1H), 4.26-4.36 (m, 2H), 4.10 (s, 2H), 3.91 (s, 3H), 3.84-3.89 (m, 2H). (ESI⁺) [(M + H)⁺]: 483.1. |
| C021 | 2-[2-[5-bromo-2-(8-chloro-4-oxo-chromen-2-yl)-4-methyl-phenoxy]ethoxy]acetic acid 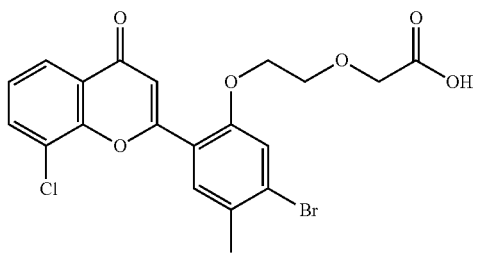 [SMILES: Cc1cc(-c2cc(=O)c3cccc(Cl)c3o2)c(OCCOCC(=O)O)cc1Br] | CORE:Int-6 TAIL:Int-T4 | ¹H NMR (DMSO-d₆, 400 MHz): δ ppm 7.99 (br d, J = 4.28 Hz, 2H), 7.90 (s, 1H), 7.52 (d, J = 17.85 Hz, 2H), 7.16 (s, 1H), 4.31-4.37 (m, 2H), 4.09 (s, 2H), 3.83-3.93 (m, 2H), 2.38 (s, 3H). (ESI⁺) [(M + H)⁺]: 467.1. |
| C022 | 2-[2-[2-(8-chloro-4-oxo-chromen-2-yl)-4,5-dimethoxy-phenoxy]ethoxy]acetic acid 491 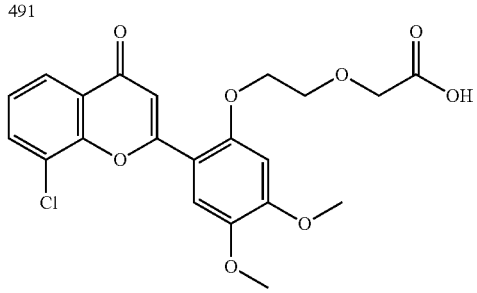 | CORE:Int-10 TAIL:Int-T4 | ¹H NMR (DMSO-d₆, 400 MHz): δ ppm 12.65 (br s, 1H), 7.97 (br dd, J = 7.8, 2.8 Hz, 2H), 7.59 (s, 1H), 7.46 (t, J = 7.9 Hz, 1H), 7.22 (s, 1H), 6.91 (s, 1H), 4.27-4.43 (m, 2H), 4.14 (s, 2H), 3.91 (m, 5H), 3.81 (s, 3H). . (ESI⁺) [(M + H)⁺]: 435.1. |
| C023 | 2-[2-[2-(8-chloro-4-oxo-chromen-2-yl)-5-(trifluoromethoxy)phenoxy]ethoxy]acetic acid 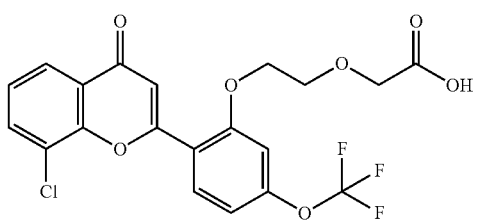 [SMILES: O=C(O)COCCOc1cc(OC(F)(F)F)ccc1-c1cc(=O)c2cccc(Cl)c2o1] | CORE:Int-9 TAIL:Int-T4 | ¹H NMR (DMSO-d₆, 400 MHz): δ ppm 12.51 (s, 1H), 8.07-8.13 (m, 1H), 7.95-8.04 (m, 2H), 7.45-7.56 (m, 1H), 7.30-7.36 (m, 1H), 7.22-7.28 (m, 1H), 7.15-7.19 (m, 1H), 4.32-4.42 (m, 2H), 4.10 (s, 2H), 3.84-3.94 (m, 2H). (ESI⁺) [(M + H)⁺]: 459.1. |
| C024 | 2-[3-[2-(8-chloro-4-oxo-chromen-2-yl)-5-(trifluoromethyl)phenoxy]butoxy]acetic acid | CORE:Int-1 TAIL:Int-T8 | ¹H NMR (DMSO-d₆, 400 MHz): δ ppm 8.08-8.16 (m, 1H), 8.02 (d, 2H, J = 7.8 Hz), 7.47- |

| Example No. | Compounds Name and Structure | CORE,TAIL | ¹H NMR and (ESI⁺) |
|---|---|---|---|
| | 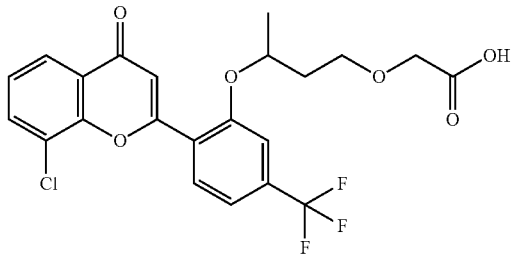 [SMILES: CC(CCOCC(=O)O)Oc1cc(C(F)(F)F)ccc1-c1cc(=O)c2cccc(Cl)c2o1] | | 7.62 (m, 3H), 7.07 (s, 1H), 4.99 (td, 1H, J = 5.7, 11.5 Hz), 3.96 (s, 2H), 1.75-2.05 (m, 2H), 1.31-1.41 (m, 3H), 1.07-1.20 (m, 2H). (ESI⁺) [(M + H)⁺]:471.3. |

The following compounds C025 to C024 were prepared in analogy to the procedure described for the preparation of example C003-A and C003-B. By replacing methyl 3-[2-(p-tolylsulfonyloxy)ethoxy]cyclobutanecarboxylate (Int-T1) with "Tail", 2-(4-bromo-2-hydroxy-phenyl)-8-chloro-chromen-4-one (Int-4) with "CORE" in step 1. The "CORE" and "Tail" are the reagents indicated in Table 9.

TABLE 9

Compounds synthesis and characterization

| Example No. | Compounds Name and Structure | CORE,TAIL | ¹H NMR and (ESI⁺) |
|---|---|---|---|
| C025-A | Cis-3-[2-[2-(8-chloro-4-oxo-chromen-2-yl)phenoxy]ethoxy]cyclobutane-carboxylic acid<br>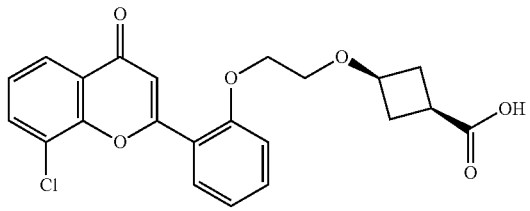 [SMILES: O=c1cc(-c2ccccc2OCCO[C@H]2C[C@@H](C(=O)O)C2)oc2c(Cl)cccc12] | CORE:Int-3<br>TAIL:Int-T1 | ¹H NMR (DMSO-d₆, 400 MHz): δ ppm 12.08 (br s, 1H), 7.97-8.04 (m, 3H), 7.59 (br t, J = 7.9 Hz, 1H), 7.49 (t, J = 7.9 Hz, 1H), 7.18-7.31 (m, 3H), 4.22-4.34 (m, 2H), 3.95 (quin, J = 7.3 Hz, 1H), 3.68-3.76 (m, 2H), 2.37-2.59 (m, 3H), 1.93-2.05 (m, 2H). (ESI⁺) [(M + H)⁺]: 415.1. |
| C025-B | Trans-3-[2-[2-(8-chloro-4-oxo-chromen-2-yl)phenoxy]ethoxy]cyclobutane-carboxylic acid<br>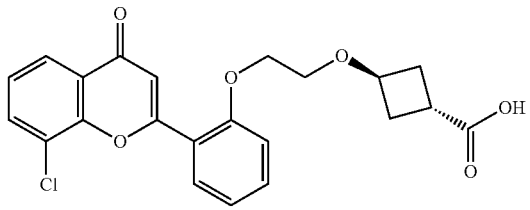 [SMILES: O=c1cc(-c2ccccc2OCCO[C@H]2C[C@H](C(=O)O)C2)oc2c(Cl)cccc12] | CORE:Int-3<br>TAIL:Int-T1 | ¹H NMR (DMSO-d₆, 400 MHz): δ ppm 12.06 (br s, 1H), 7.9 8.03 (m, 3H), 7.59 (ddd, J = 8.5, 7.2, 1.7 Hz, 1H), 7.50 (t, J = 7.9 Hz, 1H), 7.18-7.30 (m, 3H), 4.24-4.31 (m, 2H), 3.89-4.01 (m, 1H), 3.66-3.76 (m, 2H), 3.40 (br d, J = 3.8 Hz, 1H), 2.36-2.48 (m, 2H), 1.94-2.03 (m, 2H). (ESI⁺) [(M + H)⁺]: 415.3. |
| C026 | Cis-3-[2-[2-(8-chloro-4-oxo-chromen-2-yl)-5-(trifluoromethyl)phenoxy]ethoxy]cyclobutanecarboxylic acid | CORE:Int-1<br>TAIL:Int-T1 | ¹H NMR (DMSO-d₆, 400 MHz): δ ppm 8.17 8.26 (m, 1H), 7.99-8.07 (m, 2H), 7.49-7.64 (m, 3H), 7.37 (s, |

TABLE 9-continued

Compounds synthesis and characterization

| Example No. | Compounds Name and Structure | CORE,TAIL | $^1$H NMR and (ESI$^+$) |
|---|---|---|---|
| | | | 1H), 4.32-4.45 (m, 2H), 4.18 (quin, J = 6.7 Hz, 1H), 3.64-3.73 (m, 2H), 2.82-3.06 (m, 1H), 2.31-2.47 (m, 2H), 2.10-2.26 (m, 2H).. (ESI$^+$) [(M + H)$^+$]: 483.2. |
| C027 | Trans-3-2-[[5-bromo-2-(8-chloro-4-oxo-chromen-2-yl)-3-pyridyl]oxy]ethoxy]cyclobutanecarboxylic acid | CORE:Int-26 TAIL:Int-T1 | $^1$H NMR (DMSO-d$_6$, 400 MHz): δ ppm 8.15 (br dd, J = 7.9, 1.6 Hz, 1H), 7.79 (br dd, J = 7.8, 1.5 Hz, 2H), 7.28-7.45 (m, 2H), 7.00 (s, 1H), 4.24-4.50 (m, 2H), 4.22 (br s, 1H), 3.72-3.83 (m, 2H), 3.28 (s, 1H), 2.55 (br dd, J = 11.7, 6.4 Hz, 2H), 2.21-2.34 (m, 2H). (ESI$^+$) [(M + H)$^+$]: 496.0. |
| C028 | Cis-3-[2-[5-bromo-2-(8-chloro-6-fluoro-4-oxo-chromen-2-yl)phenoxy]ethoxy]cyclobutanecarboxylic acid | CORE:Int-37 TAIL:Int-T1 | $^1$H NMR (DMSO-d$_6$, 400 MHz): δ ppm 12.10 (br s, 1H), 8.11 (dd, J = 8.2, 3.1 Hz, 1H), 7.89 (d, J = 8.6 Hz, 1H), 7.71 (dd, J = 8.1, 3.1 Hz, 1H), 7.52 (d, J = 1.7 Hz, 1H), 7.43 (dd, J = 8.4, 1.7 Hz, 1H), 7.22 (s, 1H), 4.27-4.37 (m, 2H), 3.94 (quin, J = 7.4 Hz, 1H), 3.66-3.73 (m, 2H), 2.52-2.57 (m, 1H), 2.37-2.48 (m, 2H), 1.93-2.03 (m, 2H). (ESI$^+$) [(M + H)$^+$]: 513.1. |
| C029-A | Cis-3-[2-[2-(8-chloro-7-methyl-4-oxo-chromen-2-yl)phenoxy]ethoxy]cyclobutanecarboxylic acid | CORE:Int-38 TAIL:Int-T1 | $^1$H NMR (DMSO-d$_6$, 400 MHz): δ ppm 8.02 (br d, J = 7.6 Hz, 1H), 7.90 (d, J = 8.1 Hz, 1H), 7.58 (br t, J = 7.5 Hz, 1H), 7.49 (d, J = 8.1 Hz, 1H), 7.16-7.31 (m, 3H), 4.13-4.40 (m, 2H), 3.95 (dt, J = 14.7, 7.4 Hz, 1H), 3.65-3.77 (m, 2H), 2.52-2.58 (m, 3H), 2.36-2.48 (m, 3H), 1.77-2.04 (m, 2H). (ESI$^+$) [(M + H)$^+$]: 429.1. |
| C029-B | Trans-3-[2-[2-(8-chloro-7-methyl-4-oxo-chromen-2-yl)phenoxy]ethoxy]cyclobutane-carboxylic acid | CORE:Int-38 TAIL:Int-T1 | $^1$H NMR (DMSO-d$_6$, 400 MHz): δ ppm 12.15 (s, 1H), 8.03 (dt, J = 10.0, 5.0 Hz, 1H), |

TABLE 9-continued

Compounds synthesis and characterization

| Example No. | Compounds Name and Structure | CORE,TAIL | ¹H NMR and (ESI⁺) |
|---|---|---|---|
| | | | 7.89 (d, J = 8.1 Hz, 1H), 7.53-7.61 (m, 1H), 7.47 (d, J = 8.2 Hz, 1H), 7.33 (s, 1H), 7.16-7.29 (m, 2H), 4.24-4.36 (m, 2H), 4.17 (dd, J = 13.6, 6.8 Hz, 1H), 3.56-3.77 (m, 2H), 2.95 (ddd, J = 13.9, 9.9, 3.8 Hz, 1H), 2.52 (s, 3H), 2.38 (ddd, J = 13.0, 6.8, 3.6 Hz, 2H), 2.16-2.27 (m, 2H). (ESI⁺) [(M + H)⁺]: 429.1. |
| C030-A | Cis-3-[2-[5-bromo-2-(8-chloro-7-fluoro-4-oxo-chromen-2-yl)phenoxy]ethoxy] cyclobutanecarboxylic acid | CORE:Int-39 TAIL:Int-T1 | ¹H NMR (DMSO-d₆, 400 MHz): δ ppm 8.16 (br dd, J = 8.9, 6.0 Hz, 2H), 7.87-8.06 (m, 1H), 7.40 (s, 1H), 7.28-7.36 (m, 1H), 7.11-7.25 (m, 1H), 4.19-4.37 (m, 2H), 4.08 (dt, J = 12.5, 6.3 Hz, 1H), 3.70-3.88 (m, 2H), 2.83 (dt, J = 16.3, 8.3 Hz, 1H), 2.48-2.70 (m, 2H), 2.27-2.47 (m, 2H). (ESI⁺) [(M + H)⁺]: 513.0. |
| C030-B | Trans-3-[2-[5-bromo-2-(8-chloro-7-fluoro-4-oxo-chromen-2-yl)phenoxy]ethoxy] cyclobutanecarboxylic acid | CORE:Int-39 TAIL:Int-T1 | ¹NMR (DMSO-d₆, 400 MHz): δ ppm 8.15 (dd, J = 8.9, 6.0 Hz, 1H), 7.98 (d, J = 8.6 Hz, 1H), 7.45 (s, 1H), 7.19-7.35 (m, 3H), 4.20-4.35 (m, 2H), 3.71-3.93 (m, 2H), 3.30-3.42 (m, 1H), 2.51-2.71 (m, 2H), 2.39 (ddd, J = 12.7, 9.7, 5.3 Hz, 2H), 1.26 (m, 1H). (ESI⁺) [(M + H)⁺]: 513.0. |
| C031-A | Cis-3-[2-[5-bromo-2-(8-chloro-4-oxo-chromen-2-yl)-4-methyl-phenoxy]ethoxy] cyclobutanecarboxylic acid | CORE:Int-6 TAIL:Int-T1 | ¹NMR (DMSO-d₆, 400 MHz): δ ppm 7.94-8.03 (m, 2H), 7.83-7.91 (m, 1H), 7.41-7.53 (m, 2H), 7.13-7.20 (m, 1H), 4.23-4.31 (m, 2H), 3.86-4.00 (m, 1H), 3.60-3.74 (m,3H), 2.38-2.45 (m, 5H), 1.90-2.03 (m, 2H). (ESI⁺) [(M + H)⁺]: 507.1. |
| C032-A | Cis-3-[2-[4-bromo-2-(8-chloro-4-oxo-chromen-2-yl)-5-fluoro- | CORE:Int-40 TAIL:Int-T1 | ⁺NMR (DMSO-d₆, 400 MHz): δ ppm 12.03 (s, 1H), 8.21 (t, J = |

TABLE 9-continued

Compounds synthesis and characterization

| Example No. | Compounds Name and Structure | CORE, TAIL | $^1$H NMR and (ESI$^+$) |
|---|---|---|---|
| | phenoxy]ethoxy] cyclobutanecarboxylic acid 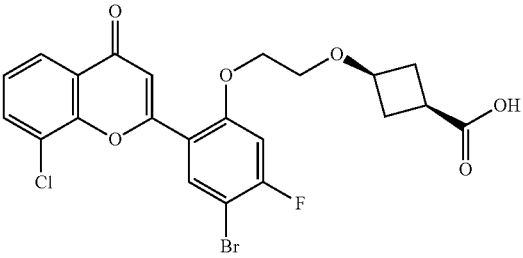 [SMILES: O=c1cc(-c2cc(Br)c(F)cc2OCCO[C@H]2C[C@@H](C(=O)O)C2)oc2c(Cl)cccc12] | | 8.0 Hz, 1H), 7.98-8.03 (m, 2H), 7.45-7.52 (m, 2H), 7.16 (s, 1H), 4.30-4.32 (m, 2H), 3.89-3.95 (m, 1H), 3.69-3.71 (m, 2H), 2.36-2.50 (m, 3H), 1.93-2.01 (m, 2H). (ESI$^+$) [(M + H)$^+$]: 511.0. |
| C033-A | Cis-3-[2-[2-(8-chloro-4-oxo-chromen-2-yl)-4-fluoro-phenoxy]ethoxy] cyclobutanecarboxylic acid 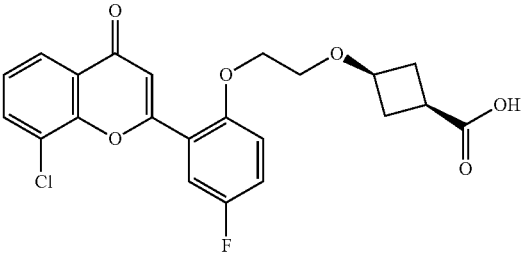 [SMILES: O=c1cc(-c2cc(F)ccc2OCCO[C@H]2C[C@@H](C(=O)O)C2)oc2c(Cl)cccc12] | CORE:Int-41 TAIL:Int-T1 | $^1$H NMR (DMSO-d$_6$, 400 MHz): δ ppm 11.96 (br s, 1H), 8.01 (td, J = 7.6, 1.5 Hz, 2H), 7.76 (dd, J = 9.7, 3.2 Hz, 1H), 7.42-7.56 (m, 2H), 7.33 (dd, J = 9.2, 4.6 Hz, 1H), 7.28 (s, 1H), 4.23-4.31 (m, 2H), 3.94 (quin, J = 7.3 Hz, 1H), 3.66-3.75 (m, 2H), 3.29-3.31 (m, 1H), 2.33-2.47 (m, 2H), 1.93-2.04 (m, 2H). (ESI$^+$) [(M + H)$^+$]: 433.1. |
| C033-B | Trans-3- [2-[2-(8-chloro-4-oxo-chromen-2-yl)-4-fluoro-phenoxy]ethoxy] cyclobutanecarboxylic acid 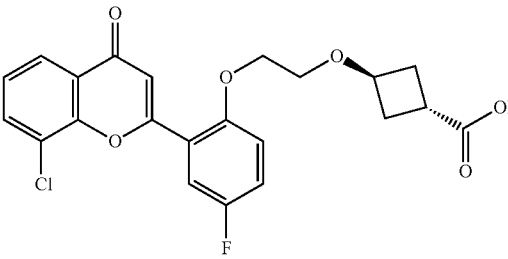 [SMILES: O=c1cc(-c2cc(F)c(Br)cc2OCCO[C@H]2C[C@H](C(=O)O)C2)oc2c(Cl)cccc12] | CORE:Int-41 TAIL:Int-T1 | $^1$NMR (DMSO-d$_6$, 400 MHz): δ ppm 12.12 (br s, 1H), 7.92-8.12 (m, 2H), 7.77 (br dd, J = 9.5, 3.1 Hz, 1H), 7.37-7.56 (m, 3H), 7.32 (br dd, J = 9.1, 4.5 Hz, 1H), 4.27 (br s, 2H), 4.12-4.23 (m, 1H), 3.68 (br s, 2H), 2.87-3.04 (m, 1H), 2.31-2.45 (m, 2H), 2.12-2.30 (m, 2H). (ESI$^+$) [(M + H)$^+$]: 433.1. |
| C034-A | Cis-3-[2-[2-(8-chloro-4-oxo-chromen-2-yl)-5-fluoro-phenoxy]ethoxy] cyclobutanecarboxylic acid 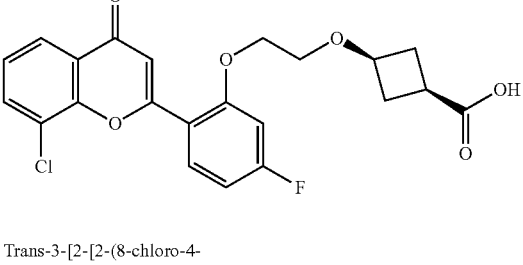 | CORE:Int-42 TAIL:Int-T1 | $^1$H NMR (DMSO-d$_6$, 400 MHz): δ ppm 12.12 (br s, 1H), 7.96-8.07 (m, 3H), 7.49 (t, J = 7.9 Hz, 1H), 7.17-7.25 (m, 2H), 7.08 (td, J = 8.4, 2.4 Hz, 1H), 4.26-4.34 (m, 2H), 3.82-4.09 (m, 1H), 3.54-3.77 (m, 2H), 2.53-2.58 (m, 1H), 2.37-2.49 (m, 2H), 1.94-2.08 (m, 2H). (ESI$^+$) [(M + H)$^+$]: 433.2. |
| C034-B | Trans-3-[2-[2-(8-chloro-4-oxo-chromen-2-yl)-5-fluoro-phenoxy]ethoxy] | CORE:Int-42 TAIL:Int-T1 | $^1$H NMR (DMSO-d$_6$, 400 MHz): δ ppm 7.95-8.01 (m, 2H), 7.47 (t, J = |

| Example No. | Compounds Name and Structure | CORE, TAIL | ¹H NMR and (ESI⁺) |
|---|---|---|---|
| | cyclobutanecarboxylic acid | | 7.9 Hz, 1H), 7.19 (s, 1H), 6.75-6.82 (m, 2H), 4.23-4.33 (m, 2H), 4.16 (q, J = 6.9 Hz, 1H), 3.97 (quin, J = 7.2 Hz, 1H), 3.67-3.78 (m, 2H), 2.36-2.47 (m, 2H), 1.94-2.08 (m, 2H). (ESI⁺) [(M + H)⁺]: 433.2. |
| C035-A | Cis-3-[2-[2-(8-chloro-4-oxo-chromen-2-yl)-5-ethoxy-phenoxy]ethoxy] cyclobutanecarboxylic acid | CORE:Int-43 TAIL:Int-T1 | ¹H NMR (DMSO-d₆, 400 MHz): δ ppm 7.95-8.01 (m, 3H), 7.47 (t, J = 7.9 Hz, 1H), 7.19 (s, 1H), 6.75-6.82 (m, 2H), 4.23-4.33 (m, 2H), 4.16 (q, J = 6.9 Hz, 2H), 3.97 (quin, J = 7.2 Hz, 1H), 3.67-3.78 (m, 2H), 2.54-2.64 (m, 1H), 2.36-2.47 (m, 2H), 1.94-2.08 (m, 2H), 1.37 (t, J = 7.0 Hz, 3H). (ESI⁺) [(M + H)⁺]: 459.3. |
| C035-B | Trans-3-[2-[2-(8-chloro-4-oxo-chromen-2-yl)-5-ethoxy-phenoxy]ethoxy] cyclobutanecarboxylic acid | CORE:Int-43 TAIL:Int-T1 | ¹H NMR (DMSO-d₆, 400 MHz): δ ppm 7.96-8.03 (m, 3H), 7.47 (t, J = 7.9 Hz, 1H), 7.32 (s, 1H), 6.76-6.83 (m, 2H), 4.25-4.32 (m, 2H), 4.09-4.24 (m, 3H), 3.64-3.73 (m, 2H), 2.93-3.01 (m, 1H), 2.35-2.47 (m, 2H), 2.18-2.32 (m, 2H), 1.37 (t, J = 7.0 Hz, 3H). (ESI⁺) [(M + H)⁺]: 459.2. |
| C036-A | Cis-3-[2-[2-(8-chloro-6-fluoro-4-oxo-chromen-2-yl)phenoxy]ethoxy] cyclobutanecarboxylic acid | CORE:Int-44 TAIL:Int-T1 | ¹NMR (DMSO-d₆, 400 MHz): δ ppm 12.10 (br s, 1H), 8.11 (dd, J = 8.2, 3.1 Hz, 1H), 7.99 (dd, J = 7.9, 1.7 Hz, 1H), 7.72 (dd, J = 8.1, 3.1 Hz, 1H), 7.59 (ddd, J = 8.5, 7.2, 1.8 Hz, 1H), 7.18-7.31 (m, 3H), 4.17-4.38 (m, 2H), 3.82-4.08 (m, 1H), 3.48-3.75 (m, 2H), 2.53-2.62 (m, 1H), 2.37-2.49 (m, 2H), 1.94-2.03 (m, 2H). (ESI⁺) [(M + H)⁺]: 433.1. |
| C036-B | Trans-3-[2-[2-(8-chloro-6-fluoro-4-oxo-chromen-2-yl)phenoxy]ethoxy] cyclobutanecarboxylic acid | CORE:Int-44 TAIL:Int-T1 | ¹H NMR (DMSO-d₆, 400 MHz): δ ppm 12.16 (br s, 1H), 8.09 (dd, J = 8.2, 3.1 Hz, 1H), 8.01 (dd, J = 7.9, |

TABLE 9-continued

Compounds synthesis and characterization

| Example No. | Compounds Name and Structure | CORE, TAIL | ¹H NMR and (ESI⁺) |
|---|---|---|---|
| | (structure) | | 1.7 Hz, 1H), 7.71 (dd, J = 8.1, 3.1 Hz, 1H), 7.58 (ddd, J = 8.5, 7.2, 1.7 Hz, 1H), 7.37 (s, 1H), 7.27 (d, J = 8.1 Hz, 1H), 7.20 (t, J = 7.3 Hz, 1H), 4.14-4.32 (m, 3H), 3.65-3.73 (m, 2H), 2.88-3.02 (m, 1H), 2.38 (qd, J = 6.6, 3.8 Hz, 2H), 2.17-2.29 (m, 2H). (ESI⁺) [(M + H)⁺]: 433.1. |
| C037-A | Cis-3-[2-[2-(8-chloro-4-oxo-chromen-2-yl)-6-fluoro-phenoxy]ethoxy]cyclobutanecarboxylic acid | CORE:Int-45 TAIL:Int-T1 | ¹H NMR (DMSO-d₆, 400 MHz): δ ppm 7.99-8.16 (m, 2H), 7.74 (br d, J = 7.6 Hz, 1H), 7.44-7.66 (m, 2H), |
| | (structure) | | 7.36 (td, J = 8.1, 5.3 Hz, 1H), 7.09 (s, 1H), 4.27 (br s, 2H), 3.64-3.88 (m, 1H), 3.41-3.63 (m, 2H), 2.37-2.48 (m, 1H), 2.15-2.30 (m, 2H),1.78-1.99 (m, 2H). (ESI⁺) [(M + H)⁺]: 433.0. |
| C037-B | Trans-3-[2-[2-(8-chloro-4-oxo-chromen-2-yl)-6-fluoro-phenoxy]ethoxy]cyclobutanecarboxylic acid | CORE:Int-45 TAIL:Int-T1 | ¹H NMR (DMSO-d₆, 400 MHz): δ ppm 8.01-8.25 (m, 2H), 7.63-7.88 (m, 1H), 7.45-7.63 (m, 2H), 7.24- |
| | (structure) | | 7.44 (m, 1H), 7.14 (s, 1H), 4.26-4.42 (m, 2H), 3.86-4.15 (m, 1H), 3.44-3.56 (m, 2H), 2.55-2.80 (m, 1H), 2.08-2.28 (m, 2H), 1.89-2.06 (m, 2H).MS obsd. (ESI⁺) [(M + H)⁺]: 433.0. |
| C038-A | Cis-3-[2-[2-(8-chloro-4-oxo-chromen-2-yl)-5-methyl-phenoxy]ethoxy]cyclobutane-carboxylic acid | CORE:Int-2 TAIL:Int-T1 | ¹H NMR (DMSO-d₆, 400 MHz): δ ppm 11.98-12.25 (m, 1H), 7.89-8.05 (m, 3H), 7.48 (t, J = 7.9 Hz, |
| | (structure) | | 1H), 7.35 (s, 1H), 7.12 (s, 1H), 7.03 (d, J = 8.1 Hz, 1H), 4.23-4.32 (m, 2H), 4.15-4.23 (m, 1H), 3.66-3.72 (m, 2H), 2.88-2.99 (m, 1H), 2.36-2.45 (m, 5H), 2.15-2.27 (m, 2H). MS obsd. (ESI⁺) [(M + H)⁺]: 429.1. |
| C038-B | Trans-3-[2-[2-(8-chloro-4-oxo-chromen-2-yl)-5-methyl-phenoxy]ethoxy]cyclobutanecarboxylic acid | CORE:Int-2 TAIL:Int-T1 | ¹NMR (DMSO-d₆, 400 MHz): δ ppm 12.02-12.21 (m, 1H), 7.99 (d, J = 7.8 Hz, 2H), 7.89-7.95 (m, |

TABLE 9-continued

Compounds synthesis and characterization

| Example No. | Compounds Name and Structure | CORE, TAIL | ¹H NMR and (ESI⁺) |
|---|---|---|---|
| | (structure: 8-chloro-chromone with 2-(methylphenoxy)ethoxy cyclobutanecarboxylic acid) | | 1H), 7.48(t, J = 7.8 Hz, 1H), 7.20-7.25 (m, 1H), 7.12 (s, 1H), 7.03 (d, J = 7.9 Hz, 1H), 4.21-4.29 (m, 2H), 3.92-3.99 (m, 1H), 3.69-3.75 (m, 2H), 2.42 (s, 3H), 1.91-2.06 (m, 2H). MS obsd. (ESI⁺) [(M + H)⁺]: 429.1. |
| C039-A | Cis-3-[2-[2-(8-chloro-4-oxo-chromen-2-yl)-5-methoxy-phenoxy]ethoxy] cyclobutanecarboxylic acid | CORE:Int-13 TAIL:Int-T1 | ¹H NMR (DMSO-d₆, 400 MHz): δ ppm 7.97 (d, J = 7.82 Hz, 3H), 7.42-7.54 (m, 1H), 7.19 (s, 1H), 6.76-6.87 |
| | (structure) | | (m, 2H), 4.21-4.34 (m, 2H), 3.92-4.01 (m, 1H), 3.87 (s, 3H), 3.69-3.77 (m, 2H), 2.52-2.56 (m, 1H), 2.38-2.48 (m, 2H), 1.95-2.06 (m, 2H). MS obsd. (ESI⁺) [(M + H)⁺]: 445.1. |
| C039-B | Trans-3-[2-[2-(8-chloro-4-oxo-chromen-2-yl)-5-methoxy-phenoxy]ethoxy] cyclobutanecarboxylic acid | CORE:Int-13 TAIL:Int-T1 | ¹H NMR (DMSO-d₆, 400 MHz): δ ppm 12.23 (s, 1H), 7.93-8.08 (m, 3H), 7.39-7.51 (m, 1H), 7.30-7.36 (m, 1H), 6.73- |
| | (structure) | | 6.86 (m, 2H), 4.26-4.33 (m, 2H), 4.14-4.24 (m, 1H), 3.87 (s, 3H), 3.65-3.73 (m, 2H), 2.88-3.03 (m, 1H), 2.36-2.44 (m, 2H), 2.18-2.29 (m, 2H). (ESI⁺) [(M + H)⁺]: 445.1. |
| C040-A | Cis-3- [2-[4-bromo-2-(8-chloro-4-oxo-chromen-2-yl)-5-methoxy-phenoxy]ethoxy] cyclobutanecarboxylic acid | CORE:Int-34 TAIL:Int-T1 | ¹H NMR (DMSO-d₆, 400 MHz): δ ppm 12.05 (s, 1H), 8.14 (s, 1H), 7.92-8.02 (m, 2H), 7.43-7.52 (m, 1H), 7.19 (s, 1H), |
| | (structure) | | 6.88-7.00 (m, 1H), 4.30-4.42 (m, 2H), 3.85-3.99 (m, 4H), 3.65-3.81 (m, 2H), 2.53-2.58 (m, 1H), 2.39-2.48 (m, 2H), 1.96-2.06 (m, 2H). (ESI⁺) [(M + H)⁺]: 523.1. |
| C040-B | Trans-3-[2-[4-bromo-2-(8-chloro-4-oxo-chromen-2-yl)-5-methoxy-phenoxy]ethoxy] cyclobutanecarboxylic acid | CORE:Int-34 TAIL:Int-T1 | ¹H NMR (DMSO-d₆, 400 MHz): δ ppm 8.16 (s, 1H), 7.91-8.03 (m, 2H), 7.42-7.54 (m, 1H), 7.32 (s, 1H), 6.88-7.01 (m, 1H), |

TABLE 9-continued

Compounds synthesis and characterization

| Example No. | Compounds Name and Structure | CORE, TAIL | $^1$H NMR and (ESI$^+$) |
|---|---|---|---|
| | (structure) | | 4.33-4.43 (m, 2H), 4.11-4.25 (m, 1H), 3.99 (s, 3H), 3.67-3.76 (m, 2H), 2.88-3.02 (m, 1H), 2.35-2.45 (m, 2H), 2.16-2.28 (m, 2H). (ESI$^+$) [(M + H)$^+$]: 523.1. |
| C041-A | Cis-3-[2-[2-(8-chloro-4-oxo-chromen-2-yl)-5-methoxy-4-methyl-phenoxy]ethoxy] cyclobutanecarboxylic acid (structure) | CORE:Int-12 TAIL:Int-T1 | $^1$H NMR (DMSO-d$_6$, 400 MHz): δ ppm 12.04 (s, 1H), 7.94-8.01 (m, 2H), 7.74-7.82 (m, 1H), 7.43-7.50 (m, 1H), 7.17-7.21 (m, 1H), 6.78-6.85 (m, 1H), 4.29-4.36 (m, 2H), 3.95-4.02 (m, 1H), 3.92 (s, 3H), 3.70-3.76 (m, 2H), 2.52-2.56 (m, 1H), 2.38-2.47 (m, 2H), 2.17 (s, 3H), 1.95-2.06 (m, 2H). (ESI$^+$) [(M + H)$^+$]: 459.1. |
| C041-B | Trans-3-[2-[2-(8-chloro-4-oxo-chromen-2-yl)-5-methoxy-4-methyl-phenoxy]ethoxy] cyclobutanecarboxylic acid (structure) | CORE:Int-12 TAIL:Int-T1 | $^1$H NMR (DMSO-d$_6$, 400 MHz): δ ppm 7.97 (d, J = 7.95 Hz, 2H), 7.77-7.86 (m, 1H), 7.41-7.51 (m, 1H), 7.28-7.37 (m, 1H), 6.78-6.85 (m, 1H), 4.29-4.36 (m, 2H), 4.11-4.24 (m, 1H), 3.92 (s, 3H), 3.66-3.75 (m, 2H), 2.88-3.04 (m, 1H), 2.35-2.44 (m, 2H), 2.19-2.28 (m, 2H), 2.18 (s, 3H). (ESI$^+$) [(M + H)]: 459.1. |
| C042-A | Cis-3-[2-[5-bromo-2-(8-chloro-4-oxo-chromen-2-yl)-4-(trifluoromethyl)phenoxy] ethoxy]cyclobutane-carboxylic acid (structure) | CORE:Int-27 TAIL:Int-T1 | $^1$H NMR (DMSO-d$_6$, 400 MHz): δ ppm 8.36 (s, 1H), 8.00 (td, J = 8.1, 1.6 Hz, 2H), 7.81 (s, 1H), 7.50 (t, J = 7.9 Hz, 1H), 7.23 (s, 1H), 4.40-4.47 (m, 2H), 3.92 (quin, J = 7.2 Hz, 1H), 3.66-3.77 (m, 2H), 2.25-2.47 (m, 3H), 1.90-2.08 (m, 2H). (ESI$^+$) [(M + H)$^+$]: 561.0. |

TABLE 9-continued

Compounds synthesis and characterization

| Example No. | Compounds Name and Structure | CORE, TAIL | $^1$H NMR and (ESI$^+$) |
|---|---|---|---|
| C042-B | Trans-3-[2-[5-bromo-2-(8-chloro-4-oxo-chromen-2-yl)-4-(trifluoromethyl)phenoxy]ethoxy]cyclobutanecarboxylic acid | CORE:Int-27 TAIL:Int-T1 | $^1$H NMR (DMSO-d$_6$, 400 MHz): δ ppm 12.18 (br s, 1H), 8.40 (s, 1H), 7.97-8.07 (m, 2H), 7.82 (s, 1H), 7.47-7.56 (m, 1H), 7.37 (s, 1H), 4.45 (br s, 2H), 4.19 (quin, J = 6.8 Hz, 1H), 3.71 (br d, J = 3.9 Hz, 2H), 2.88-3.01 (m, 1H), 2.34-2.45 (m, 2H), 2.15-2.32 (m, 2H).MS obsd. (ESI$^+$) [(M + H)$^+$]: 561.0. |
| C043-A | Cis-3-[2-[[6-(8-chloro-4-oxo-chromen-2-yl)-1,3-benzodioxol-5-yl]oxy]ethoxy]cyclobutanecarboxylic acid | CORE:Int-11 TAIL:Int-T1 | $^1$H NMR (DMSO-d$_6$, 400 MHz): δ ppm 12.10 (br s, 1H), 7.98 (d, J = 1.7 Hz, 1H), 7.96 (d, J = 2.1 Hz, 1H), 7.44-7.50 (m, 2H), 7.18 (s, 1H), 7.07 (s, 1H), 6.14 (s, 2H), 4.19-4.28 (m, 2H), 3.88-4.07 (m, 1H), 3.64-3.72 (m, 2H), 2.53-2.66 (m, 3H), 2.36-2.48 (m, 2H). MS obsd. (ESI$^+$) [(M + H)$^+$]: 459.1. |
| C043-B | Trans-3-[2-[[6-(8-chloro-4-oxo-chromen-2-yl)-1,3-benzodioxol-5-yl]oxy]ethoxy]cyclobutane carboxylic acid | CORE:Int-11 TAIL:Int-T1 | $^1$H NMR (DMSO-d$_6$, 400 MHz): δ ppm 12.09 (br s, 1H), 7.98 (d, J = 7.9 Hz, 2H), 7.44-7.52 (m, 2H), 7.31 (s, 1H), 7.07 (s, 1H), 6.14 (s, 2H), 4.13-4.30 (m, 3H), 3.61-3.70 (m, 2H), 2.90-2.99 (m, 1H), 2.32-2.46 (m, 2H), 2.16-2.29 (m, 2H).MS obsd. (ESI$^+$) [(M + H)$^+$]: 459.1. |
| C044-A | Cis-3-[2-[5-bromo-2-(8-chloro-4-oxo-chromen-2-yl)-4-fluoro-phenoxy]ethoxy]cyclobutanecarboxylic acid | CORE:Int-46 TAIL:Int-T1 | $^1$NMR (DMSO-d$_6$, 400 MHz): δ ppm 12.10 (br s, 1H), 8.00 (ddd, J = 9.8, 8.1, 1.5 Hz, 2H), 7.86 (d, J = 9.5 Hz, 1H), 7.67 (d, J = |

TABLE 9-continued

Compounds synthesis and characterization

| Example No. | Compounds Name and Structure | CORE, TAIL | $^1$H NMR and (ESI$^+$) |
|---|---|---|---|
| | (structure) | | 5.7 Hz, 1H), 7.50 (t, J = 7.9 Hz, 1H), 7.25 (s, 1H), 4.27-4.37 (m, 2H), 3.81-4.07 (m, 1H), 3.66-3.73 (m, 2H), 2.67 (br s, 1H), 2.33-2.47 (m, 2H), 1.93-2.03 (m, 2H).MS obsd. (ESI$^+$) [(M + H)$^+$]: 511.0. |
| C044-B | Trans- 3-[2-[5-bromo-2-(8-chloro-4-oxo-chromen-2-yl)-4-fluoro-phenoxy]ethoxy]cyclobutanecarboxylic acid (structure) | CORE:Int-46 TAIL:Int-T1 | $^1$H NMR (DMSO-d$_6$, 400 MHz): δ ppm 12.18 (br s, 1H), 7.99 (m, 2H), 7.85 (d, J = 9.5 Hz, 1H), 7.64 (d, J = 5.7 Hz, 1H), 7.49 (m, 1H), 7.37 (s, 1H), 4.24-4.34 (m, 3H), 3.66 (m, 1H), 2.95 (m, 2H), 2.33-2.03 (m, 4H). MS obsd. (ESI$^+$) [(M + H)$^+$]: 510.9. |
| C045-A | Cis-3-[2-[2-(8-chloro-6-fluoro-4-oxo-chromen-2-yl)-5-fluoro-phenoxy]ethoxy]cyclobutanecarboxylic acid (structure) | CORE:Int-47 TAIL:Int-T1 | $^1$H NMR (DMSO-d$_6$, 400 MHz): δ ppm 8.11 (dd, J = 8.1, 3.1 Hz, 1H), 8.03 (dd, J = 8.9, 6.8 Hz, 1H), 7.71 (dd, J = 8.1, 3.1 Hz, 1H), 7.23 (dd, J = 11.4, 2.3 Hz, 1H), 7.18 (s, 1H), 7.08 (td, J = 8.4, 2.4 Hz, 1H), 4.21-4.37 (m, 2H), 3.81-4.03 (m, 1H), 3.47-3.75 (m, 2H), 2.52-2.60 (m, 1H), 2.33-2.47 (m, 2H), 1.93-2.03 (m, 2H).MS obsd. (ESI$^+$) [(M + H)$^+$]: 451.3. |
| C045-B | Trans-3-[2-[2-(8-chloro-6-fluoro-4-oxo-chromen-2-yl)-5-fluoro-phenoxy]ethoxy]cyclobutanecarboxylic acid (structure) | CORE:Int-47 TAIL:Int-T1 | $^1$H NMR (DMSO-d$_6$, 400 MHz): δ ppm 8.10 (dd, J = 8.1, 3.0 Hz, 1H), 8.04 (dd, J = 8.9, 6.8 Hz, 1H), 7.71 (dd, J = 7.9, 3.1 Hz, 1H), 7.31 (s, 1H), 7.22 (dd, J = 11.3, 2.4 Hz, 1H), 7.07 (td, J = 8.4, 2.4 Hz, 1H), 4.25-4.35 (m, 2H), 4.18 (quin, J = 6.7 Hz, 1H), 3.52-3.78 (m, 2H), 2.82-3.08 (m, 1H), 2.30-2.47 (m, 2H), 2.16-2.26 (m, 2H). MS obsd. (ESI$^+$) [(M + H)$^+$]: 451.3. |
| C046-A | Cis-3-[2-[2-(8-bromo-4-oxo-chromen-2-yl)phenoxy]ethoxy] | CORE:Int-28 TAIL:Int-T | $^1$H NMR (DMSO-d$_6$, 400 MHz): δ ppm 11.92-12.18 (m, 1H), |

TABLE 9-continued

Compounds synthesis and characterization

| Example No. | Compounds Name and Structure | CORE,TAIL | ¹H NMR and (ESI⁺) |
|---|---|---|---|
| | cyclobutanecarboxylic acid | | 8.14 (dd, J = 7.7, 1.5 Hz, 1H), 8.05 (td, J = 8.4, 1.6 Hz, 2H), 7.56-7.63 (m, 1H), 7.43 (t, J = 7.8 Hz, 1H), 7.18-7.32 (m, 3H), 4.23-4.34 (m, 2H), 3.95 (quin, J = 7.3 Hz, 1H), 3.67-3.78 (m, 2H), 2.45-2.48 (m, 1H), 2.36-2.44 (m, 2H), 1.91-2.03 (m, 2H). MS obsd. (ESI⁺) [(M + H)⁺]: 459.1. |
| C046-B | Trans-3-[2-[2-(8-bromo-4-oxo-chromen-2-yl)phenoxy]ethoxy] cyclobutanecarboxylic acid | CORE:Int-28 TAIL:Int-T1 | ¹H NMR (DMSO-d₆, 400 MHz): δ ppm 12.01-12.28 (m, 1H), 7.99-8.16 (m, 3H), 7.55-7.63 (m, 1H), 7.41-7.47 (m, 1H), 7.38 (s, 1H), 7.18-7.33 (m, 2H), 4.23-4.33 (m, 2H), 4.14-4.23 (m, 1H), 3.66-3.73 (m, 2H), 2.90-2.99 (m, 1H), 2.33-2.43 (m, 2H), 2.15-2.27 (m, 2H). MS obsd. (ESI⁺) [(M + H)⁺]: 459.1. |
| C047-A | Cis-3-[2-[2-[4-oxo-8-(trifluoromethyl)chromen-2-yl]phenoxy]ethoxy] cyclobutanecarboxylic acid | CORE:Int-48 TAIL:Int-T1 | ¹H NMR (DMSO-d₆, 400 MHz): δ ppm 8.34 (dd, J = 7.9, 1.2 Hz, 1H), 8.22 (d, J = 7.5 Hz, 1H), 7.89 (dd, J = 7.9, 1.7 Hz, 1H), 7.66 (t, J = 7.8 Hz, 1H), 7.57-7.63 (m, 1H), 7.26-7.34 (m, 2H), 7.22 (t, J = 7.6 Hz, 1H), 4.26-4.31 (m, 2H), 3.90-4.01 (m, 1H), 3.69-3.75 (m, 2H), 2.50-2.58 (m, 1H), 2.37-2.45 (m, 2H), 1.95-2.05 (m, 2H). MS obsd. (ESI⁺) [(M + H)⁺]: 449.2. |
| C047-B | Trans-3-[2-[2-[4-oxo-8-(trifluoromethyl)chromen-2-yl]phenoxy]ethoxy] cyclobutanecarboxylic acid | CORE:Int-48 TAIL:Int-T1 | ¹H NMR (DMSO-d₆, 400 MHz): δ ppm 12.00-12.37 (m, 1H), 8.35 (dd, J = 7.9, 1.0 Hz, 1H), 8.22 (d, J = 7.6 Hz, 1H), 7.91 (dd, J = 7.9, 1.7 Hz, 1H), 7.54-7.71 (m, 2H), 7.42 (s, 1H), 7.22 (t, J = 7.6 Hz, 2H), 4.27-4.34 (m, 2H), 4.15-4.22 (m, 1H), 3.69 (dd, J = 5.1, 3.5 Hz, 2H), 2.90-2.99 (m, 1H), 2.33-2.43 (m, 2H), 2.16-2.27 (m, 2H). MS obsd. (ESI⁺) [(M + H)⁺]: 449.2. |
| C048-A | Cis-3-[2-[5-bromo-2-[8-chloro-4-oxo-7- | CORE:Int-49 TAIL:Int-T1 | ¹H NMR (DMSO-d₆, 400 MHz): δ ppm |

TABLE 9-continued

Compounds synthesis and characterization

| Example No. | Compounds Name and Structure | CORE,TAIL | $^1$H NMR and (ESI$^+$) |
|---|---|---|---|
| | (trifluoromethyl)chromen-2-yl]phenoxy]ethoxy] cyclobutanecarboxylic acid | | 12.12 (br s, 1H), 7.98-8.23 (m, 1H), 7.53-7.78 (m, 2H), 7.36 (s, 1H), 7.09-7.32 (m, 2H), 4.28 (brs, 2H), 4.04 (s, 1H), 3.69 (brs, 2H), 2.54-2.60 (m, 1H), 2.31-2.47 (m, 2H), 2.22 (brs, 2H). MS obsd. (ESI$^+$) [(M + H)$^+$]: 561.0. |
| C048-B | Trans-3-[2-[5-bromo-2-[8-chloro-4-oxo-7-(trifluoromethyl)chromen-2-yl]phenoxy]ethoxy] cyclobutanecarboxylic acid | CORE:Int-49 TAIL:Int-T1 | $^1$H NMR (DMSO-d$_6$, 400 MHz): δ ppm 12.12 (brs, 1 H), 7.98-8.23 (m, 1H), 7.53-7.78 (m, 2H), 7.36 (s, 1H), 7.09-7.32 (m, 2H), 4.28 (brs, 2H), 4.11-4.24 (m, 1H), 3.69 (brs, 2H), 2.96 (m, 1H), 2.31-2.47 (m, 2H), 2.22 (brs, 2H). MS obsd. (ESI$^+$) [(M + H)$^+$]: 561.0. |
| C049-A | Cis-3-[2-[5-bromo-2-[8-chloro -4-oxo-5-(trifluoromethyl)chromen-2-yl]phenoxy]ethoxy] cyclobutanecarboxylic acid | CORE:Int-50 TAIL:Int-T1 | $^1$H NMR (DMSO-d$_6$, 400 MHz): δ ppm 8.17 (d, J = 8.44 Hz, 1H), 7.86-7.98 (m, 2H), 7.54 (d, J = 1.71 Hz, 1H), 7.45 (dd, J = 8.44, 1.71 Hz, 1H), 7.24 (s, 1 H), 4.28-4.41 (m, 2H), 3.95 (quin, J = 7.34 Hz, 1H), 3.67-3.76 (m, 2H), 2.32-2.47 (m, 3H), 1.93-2.03 (m, 2 H).. (ESI$^+$) [(M + H)$^+$]: 561.0. |
| C049-B | Trans-3-[2-[5-bromo-248-chloro -4-oxo-5-(trifluoromethyl)chromen-2-yl]phenoxy]ethoxy] cyclobutanecarboxylic acid | CORE:Int-50 TAIL:Int-T1 | $^1$H NMR (DMSO-d$_6$, 400 MHz): δ ppm 8.17 (br d, J = 8.1 Hz, 1H), 7.96 (br dd, J = 8.6, 2.2 Hz, 1H), 7.88 (br d, J = 8.3 Hz, 1H), 7.53 (br s, 1H), 7.45 (br d, J = 8.6 Hz, 1H), 7.36 (s, 1H), 4.34 (br s, 2H), 4.18 (dt, J = 13.6, 6.7 Hz, 1H), 3.64-3.71 (m, 2H), 2.89 (br d, J = 10.5 Hz, 1H), 2.29-2.47 (m, 2H), 2.09-2.28 (m, 2H). MS obsd. (ESL$^+$) [(M + H)$^+$]: 561.0. |

TABLE 9-continued

Compounds synthesis and characterization

| Example No. | Compounds Name and Structure | CORE, TAIL | ¹H NMR and (ESI⁺) |
|---|---|---|---|
| C050-A | Cis-3-[2-[2-(8-chloro-4-oxo-chromen-2-yl)-4-methyl-phenoxy]ethoxy]cyclobutanecarboxylic acid | CORE:Int-31 TAIL:Int-T1 | ¹H NMR (DMSO-$d_6$, 400 MHz): δ ppm 7.97-8.02 (m, 2H), 7.77-7.81 (m, 1H), 7.45-7.53 (m, 1H), 7.37-7.43 (m, 1H), 7.15-7.22 (m, 2H), 4.19-4.26 (m, 2H), 3.87-3.98 (m, 1H), 3.65-3.72 (m, 2H), 2.31-2.48 (m, 6H), 1.91-2.02 (m, 2H). MS obsd. (ESI⁺) [(M + H)⁺]: 429.1. |
| C050-B | Trans-3-[2-[2-(8-chloro-4-oxo-chromen-2-yl)-4-methyl-phenoxy]ethoxy]cyclobutanecarboxylic acid | CORE:Int-31 TAIL:Int-T1 | ¹H NMR (DMSO-$d_6$, 400 MHz): δ ppm 11.99-12.16 (m, 1H), 7.97-8.03 (m, 2H), 7.75-7.81 (m, 1H), 7.44-7.54 (m, 1H), 7.34-7.42 (m, 1H), 7.14-7.22 (m, 2H), 4.18-4.27 (m, 2H), 4.05-4.14 (m, 1H), 3.66-3.72 (m, 2H), 3.14-3.20 (m, 1H), 2.30-2.44 (m, 5H), 1.92-2.03 (m, 2H). MS obsd. (ESI⁺) [(M + H)⁺]: 429.1. |
| C051-A | Cis-3-[2-[2-(8-chloro-4-oxo-chromen-2-yl)-4-ethoxy-phenoxy]ethoxy]cyclobutanecarboxylic acid | CORE:Int-51 TAIL:Int-T1 | ¹H NMR (DMSO-$d_6$, 400 MHz): δ ppm 7.95-8.03 (m, 2H), 7.46-7.56 (m, 2H), 7.11-7.29 (m, 3H), 4.17-4.24 (m, 2H), 4.02-4.12 (m, 2H), 3.86-3.98 (m, 1H), 3.62-3.73 (m, 2H), 2.45-2.49 (m, 1H), 2.33-2.46 (m, 2H), 1.91-2.03 (m, 2H), 1.30-1.41 (m, 3H). MS obsd. (ESI⁺) [(M + H)⁺]: 459.1. |
| C051-B | Trans-3-[2-[2-(8-chloro-4-oxo-chromen-2-yl)-4-ethoxy-phenoxy]ethoxy]cyclobutanecarboxylic acid | CORE:Int-51 TAIL:Int-T1 | ¹H NMR (DMSO-$d_6$, 400 MHz): δ ppm 7.99 (d, J = 7.95 Hz, 2H), 7.53-7.56 (m, 1H), 7.45-7.51 (m, 1H), |

TABLE 9-continued

Compounds synthesis and characterization

| Example No. | Compounds Name and Structure | CORE,TAIL | ¹H NMR and (ESI⁺) |
|---|---|---|---|
| | 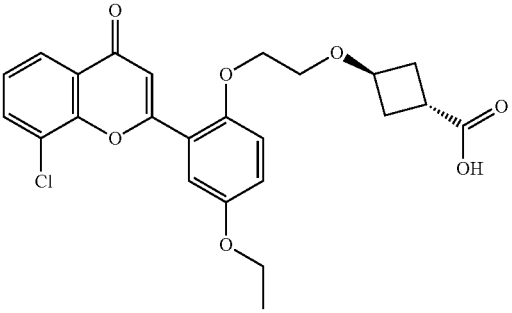 | | 7.38 (s, 1H), 7.12-7.21 (m, 2H), 4.11-4.23 (m, 3H), 4.02-4.10 (m, 2H), 3.62-3.68 (m, 2H), 2.88-3.00 (m, 1H), 2.32-2.42 (m, 2H), 2.13-2.26 (m, 2H), 1.31-1.35 (m, 3H). MS obsd. (ESI⁺) [(M + H)⁺]: 459.1. |
| C052-A | Cis-3-[2-[2-(8-chloro-4-oxo-chromen-2-yl)-5-(trifluoromethoxy)phenoxy]ethoxy]cyclobutanecarboxylic acid 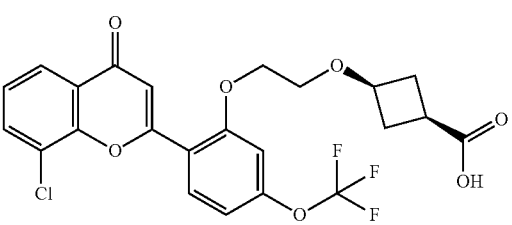 | CORE:Int-9 TAIL:Int-T1 | ¹H NMR (DMSO-d₆, 400 MHz): δ ppm 12.03 (s, 1H), 8.05-8.13 (m, 1H), 7.96-8.04 (m, 2H), 7.47-7.54 (m, 1H), 7.29-7.36 (m, 1H), 7.14-7.27 (m, 2H), 4.27-4.37 (m, 2H), 3.86-3.99 (m, 1H), 3.65-3.75 (m, 2H), 2.31-2.46 (m, 3H), 1.91-2.03 (m, 2H). MS obsd. (ESI⁺) [(M + H)⁺]: 499.1. |
| C053-B | Trans-3-[2-[4-bromo-2-(8-chloro-6-fluoro-4-oxo-chromen-2-yl)phenoxy]ethoxy]cyclobutanecarboxylic acid 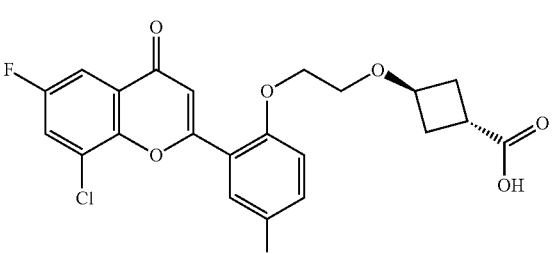 | CORE:Int-52 TAIL:Int-T1 | ¹H NMR (DMSO-d₆, 400 MHz): δ ppm 8.20 (d, J = 2.4 Hz, 1H), 7.79 (dd, J = 7.8, 2.9 Hz, 1H), 7.49-7.68 (m, 2H), 7.28-7.48 (m, 1H), 6.82-7.05 (m, 1H), 4.19-4.38 (m, 3H), 3.74-3.91 (m, 2H), 3.32 (m, 1H), 2.51-2.73 (m, 2H), 2.30-2.49 (m, 2H). MS obsd. (ESI⁺) [(M + H)⁺]: 510.9. |
| C054-A | Cis-3-[2-[2-(8-chloro-7-fluoro-4-oxo-chromen-2-yl)phenoxy]ethoxy]cyclobutanecarboxylic acid 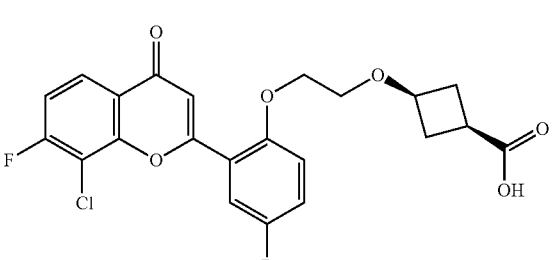 | CORE:Int-53 TAIL:Int-T1 | ¹H NMR (DMSO-d₆, 400 MHz): δ ppm 12.06 (br s, 1H), 7.98-8.13 (m, 2H), 7.55-7.65 (m, 2H), 7.19-7.32 (m, 2H), 4.23-4.35 (m, 2H), 3.88-4.01 (m, 1H), 3.66-3.78 (m, 2H), 2.54-2.61 (m, 1H), 2.32-2.47 (m, 2H), 1.91-2.04 (m, 2H). MS obsd. (ES⁺) [(M + H)⁺]: 433.1. |
| C055-A | Cis-3-[2-[5-chloro-2-(8-chloro-4-oxo-chromen-2-yl)-4-methyl-phenoxy]ethoxy] | CORE:Int-5 TAIL:Int-T1 | ¹H NMR (DMSO-d₆, 400 MHz): δ ppm 12.04 (br s, 1H), 8.00 (ddd, J =7.8, 6.2, 1.6 |

TABLE 9-continued

Compounds synthesis and characterization

| Example No. | Compounds Name and Structure | CORE, TAIL | ¹H NMR and (ESI⁺) |
|---|---|---|---|
| | cyclobutanecarboxylic acid | | Hz, 2H), 7.91 (s, 1H), 7.49 (t, J = 7.8 Hz, 1H), 7.39 (s, 1H), 7.18 (s, 1H), 4.22-4.41 (m, 2H), 3.86-4.07 (m, 1H), 3.59-3.79 (m, 2H), 2.67 (br s, 1H), 2.28-2.48 (m, 5H), 1.88-2.04 (m, 2H). MS obsd. (ESI⁺) [(M + H)⁺]: 463.1. |
| C056-A | Cis-3- [3-[5-bromo-2-(8-chloro-4-oxo-chromen-2-yl)phenoxy]propoxy] cyclobutanecarboxylic acid | CORE:Int-4 TAIL:Int-T2 | ¹H NMR (DMSO-d₆, 400 MHz): δ ppm 8.00 (d, J = 7.8 Hz, 2H), 7.88 (d, J = 8.4 Hz, 1H), 7.48-7.55 (m, 2H), 7.42 (dd, J = 8.4, 1.7 Hz, 1H), 7.03 (s, 1H), 4.25 (t, J = 6.0 Hz, 2H), 3.80 (t, J = 7.2 Hz, 1H), 3.35-3.50 (m, 2H), 2.30-2.47 (m, 4H), 1.87-2.04 (m, 3H). MS obsd. (ESI⁺) [(M + H)⁺]: 507.0. |
| C056-B | Trans-3-[3-[5-bromo-2-(8-chloro-4-oxo-chromen-2-yl)phenoxy]propoxy] cyclobutanecarboxylic acid | CORE:Int-4 TAIL:Int-T2 | ¹H NMR (DMSO-d₆, 400 MHz): δ ppm 12.14 (br s, 1H), 8.00 (d, J = 7.9 Hz, 2H), 7.87 (d, J = 8.4 Hz, 1H), 7.32-7.58 (m, 3H), 7.01-7.07 (m, 1H), 4.26 (t, J = 5.9 Hz, 2H), 3.99-4.11 (m, 1H), 3.36-3.51 (m, 2H), 2.79-2.94 (m, 1H), 2.25-2.42 (m, 2H), 1.89-2.14 (m, 4H). MS obsd. (ESI⁺) [(M + H)⁺]: 507.0. |
| C057-A | Cis-3-[2-[5-bromo-4-chloro-2-(8-chloro-4-oxo-chromen-2-yl)phenoxy]ethoxy] cyclobutanecarboxylic acid | CORE:Int-54 TAIL:Int-T1 | ¹H NMR (DMSO-d₆, 400 MHz): δ ppm 8.08 (s, 1H), 8.00 (ddd, J = 9.4, 7.9, 1.5 Hz, 2H), 7.72 (s, 1H), 7.50 (t, J = 7.9 Hz, 1H), 7.20 (s, 1H), 4.29-4.37 (m, 2H), 3.90-3.95 (m, 1H), 3.62-3.75 (m, 2H), 2.52-2.54 (m, 1H), 2.31-2.48 (m, 2H), 1.90-2.08 (m, 2H) MS obsd. (ES⁺) [(M + H)⁺]: 562.9. |

TABLE 9-continued

Compounds synthesis and characterization

| Example No. | Compounds Name and Structure | CORE,TAIL | ¹H NMR and (ESI⁺) |
|---|---|---|---|
| C058-A | Cis-3-[2-[2-(8-chloro-7-cyclopropyl-4-oxo-chromen-2-yl)phenoxy]ethoxy]cyclobutanecarboxylic acid 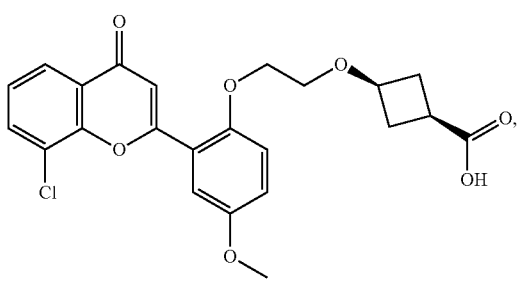 | CORE:Int-55 TAIL:Int-T1 | ¹H NMR (DMSO-$d_6$, 400 MHz): δ ppm 8.16 (dd, J = 7.9, 1.7 Hz, 1H), 8.04 (d, J =8.4 Hz, 1H), 7.44-7.53 (m, 2H), 7.17 (t, J = 7.4 Hz, 1H), 7.05 (d, J = 8.2 Hz, 1H), 6.90 (d, J = 8.4 Hz, 1H), 4.19-4.35 (m, 2H), 3.66-3.94 (m, 3H), 2.73-2.85 (m, 1H), 2.53-2.64 (m, 2H), 2.29-2.49 (m, 3H), 1.13-1.28 (m, 2H), 0.81-0.92 (m, 2H).MS obsd. (ESI⁺) [(M + H)⁺]: 455.1. |

Example C060-A and Example C060-B: Cis-3-[2-[2-(8-chloro-4-oxo-chromen-2-yl)-4-methoxy-phenoxy]ethoxy]cyclobutanecarboxylic acid and Trans-3-[2-[2-(8-chloro-4-oxo-chromen-2-yl)-4-methoxy-phenoxy]ethoxy]cyclobutanecarboxylic acid

C060-A

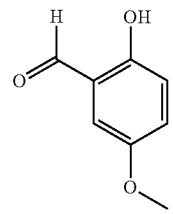

C060-B

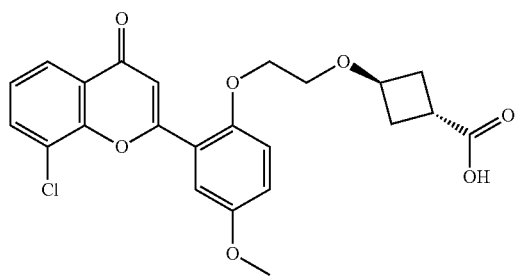

Step 1: Preparation of 2-hydroxy-5-methoxy-benzaldehyde

C060a

Compound C060a was prepared in analogy to the procedure described for the preparation of compound Int-5a by using 4-methoxyphenol as the starting material instead of 3-chloro-4-methyl-phenol in Step 1.

Step 2: Preparation of methyl 3-[2-(2-formyl-4-methoxy-phenoxy)ethoxy]cyclobutanecarboxylate C060b

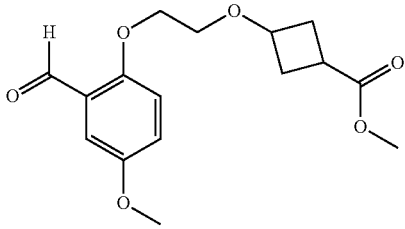

To a mixture of 2-hydroxy-5-methoxybenzaldehyde (550 mg, 3.61 mmol), methyl 3-[2-(p-tolylsulfonyloxy)ethoxy]cyclobutanecarboxylate (Int-T1, 600 mg, 1.95 mmol) in DMF (10 mL) was added $K_2CO_3$ (1.5 g, 10.8 mmol) and the mixture was then stirred at 50° C. for 16 hours. After the reaction was completed, the mixture was diluted with water (50 mL) and extracted with EtOAc (50 mL) three times. The combined organic layer was washed with brine, dried over Na₂SO₄ and concentrated in vacuo. The residue was purified by column chromatography on silica gel (eluted with PE:EtOAc=100:1 to 3:1) to give methyl 3-[2-(2-formyl-4-methoxy-phenoxy)ethoxy]cyclobutanecarboxylate (600 mg, 53.8% yield) as a yellow oil. (ESI⁺)[(M+H)⁺]309.1.

Step 3: Preparation of 3-[2-[2-[(E)-3-(3-chloro-2-hydroxy-phenyl)-3-oxo-prop-1-enyl]-4-methoxy-phenoxy]ethoxy]cyclobutanecarboxylic acid

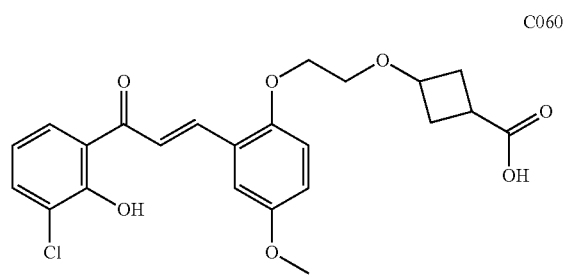

C060c

A mixture of KOH (395 mg, 7.03 mmol), methyl 3-(2-(2-formyl-4-methoxyphenoxy)ethoxy)cyclobutane-1-carboxylate (361 mg, 1.17 mmol) and 1-(3-chloro-2-hydroxy-phenyl)ethan-1-one (200 mg, 1.17 mmol) in ethanol (50 mL) was stirred at 80° C. overnight. After the reaction was completed, the mixture was adjusted to PH~2 by addition of 6N HCl, the resulting suspension was then filtered, the solid was collected and dried in vacuo to give 3-[2-[2-[(E)-3-(3-chloro-2-hydroxy-phenyl)-3-oxo-prop-1-enyl]-4-methoxy-phenoxy]ethoxy]cyclobutanecarboxylic acid (500 mg, 95.4% yield) as a yellow solid. (ESI⁺)[(M+H)⁺]447.1.

Step 4: Preparation of Cis-3-[2-[2-(8-chloro-4-oxo-chromen-2-yl)-4-methoxy-phenoxy]ethoxy]cyclobutanecarboxylic acid and Trans-3-[2-[2-(8-chloro-4-oxo-chromen-2-yl)-4-methoxy-phenoxy]ethoxy]cyclobutanecarboxylic acid

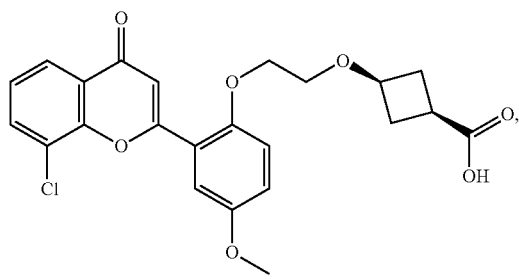

C060-A

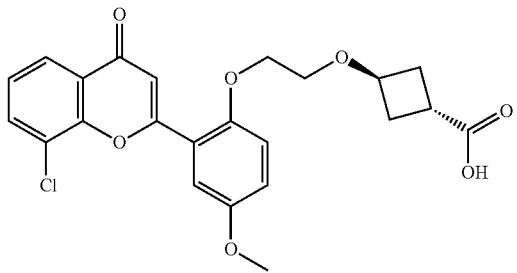

C060-B

To a mixture solution of 3-[2-[2-[(E)-3-(3-chloro-2-hydroxy-phenyl)-3-oxo-prop-1-enyl]-4-methoxy-phenoxy]ethoxy]cyclobutanecarboxylic acid (500 mg, 1.12 mmol) in DMSO (30 mL) was added I₂ (28.4 mg, 112 μmol) and the mixture was then stirred at 125° C. for 3 hours. After the reaction was completed, the reaction was quenched with 2N Na₂S₂O₃ solution (15 mL) and the resulting suspension was filtered. The solid cake was collected to give the crude 3-[2-[2-(8-chloro-4-oxo-chromen-2-yl)-4-methoxy-phenoxy]ethoxy]cyclobutanecarboxylic acid, which was further purified by Prep-HPLC to give two sets of diastereomers of the 3-[2-[2-(8-chloro-4-oxo-chromen-2-yl)-4-methoxy-phenoxy]ethoxy]cyclobutanecarboxylic acid with cis- and trans-configuration, one of which is characterized as Example C060-A (90 mg, 17.7%) and the other is Example C060-B (90 mg, 17.7%) as yellow powder.

Example C060-A ¹H NMR (DMSO-d₆, 400 MHz): δ ppm. 12.17 (s, 1H), 7.94-8.03 (m, 2H), 7.44-7.58 (m, 2H), 7.15-7.26 (m, 3H), 4.16-4.27 (m, 2H), 3.88-4.01 (m, 1H), 3.81 (s, 3H), 3.62-3.72 (m, 2H), 2.51-2.54 (m, 1H), 2.35-2.45 (m, 2H), 1.92-2.04 (m, 2H). (ESI⁺) [(M+H)⁺]: 445.1.

Example CMO-B ¹H NMR (DMSO-d₆, 400 MHz): δ ppm 12.15 (s, 1H), 8.00 (d, J=8.1 Hz, 2H), 7.57 (d, J=2.9 Hz, 1H), 7.49 (t, J=7.9 Hz, 1H), 7.39 (s, 1H), 7.06-7.25 (m, 2H), 4.19-4.28 (m, 2H), 4.09-4.19 (m, 1H), 3.89 (s, 3H), 3.58-3.69 (m, 2H), 2.76-3.01 (m, 1H), 2.32-2.42 (m, 2H), 2.14-2.28 (m, 2H). (ESI⁺)[(M+H)⁺]445.1.

Example C061: 3-[2-[[4-(8-chloro-4-oxo-chromen-2-yl)-3-pyridyl]oxy]ethoxy]cyclobutanecarboxylic acid

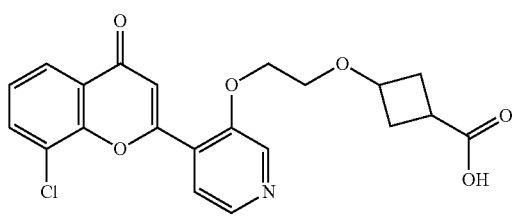 [SMILES: O=c1cc(-c2ccccc2OCCO[C@H]2C[C@H](C(=O)O)C2)oc2c(Br)cccc12]

C061

Step 1: Preparation of methyl 3-[2-[(4-formyl-3-pyridyl)oxy]ethoxy]cyclobutanecarboxylate

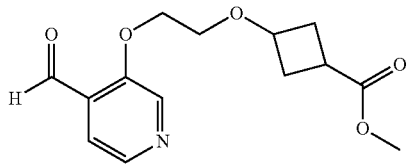

C061a

Compound C061a was prepared in analogy to the procedure described for the preparation of compound C060b by using 3-hydroxypyridine-4-carbaldehyde as the starting material instead of 2-hydroxy-5-methoxybenzaldehyde in Step 2.

Step 2: Preparation of methyl 3-[2-[[4-[(E)-3-(3-chloro-2-hydroxy-phenyl)-3-oxo-prop-1-enyl]-3-pyridyl]oxy]ethoxy]cyclobutanecarboxylate

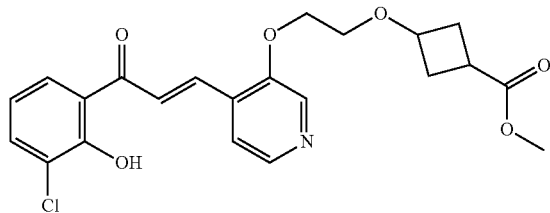

C061b

To a solution of 1-(3-chloro-2-hydroxy-phenyl)ethanone (128.27 mg, 0.750 mmol), potassium tert-butoxide (126.56 mg, 1.13 mmol) in THF (30 mL) was added methyl 3-[2-[(4-formyl-3-pyridyl)oxy]ethoxy]cyclobutanecarboxylate (210.0 mg, 0.750 mmol) and the mixture was stirred at room temperature for 3 hours. The mixture was concentrated in vacuo and the residue was adjusted to pH~5 by addition of 1N HCl. The mixture was extracted with EtOAc (20 mL) three times. The combined organic layer was dried over Na$_2$SO$_4$ and concentrated in vacuo to give methyl 3-[2-[[4-[(E)-3-(3-chloro-2-hydroxy-phenyl)-3-oxo-prop-1-enyl]-3-pyridyl]oxy]ethoxy]cyclobutanecarboxylate (273 mg, 84.0% yield) as a light brown oil. MS obsd. (ESI$^+$) [(M+H)$^+$]: 432.1.

Step 3: Preparation of methyl 3-[2-[[4-(8-chloro-4-oxo-chromen-2-yl)-3-pyridyl]oxy]ethoxy]cyclobutanecarboxylate

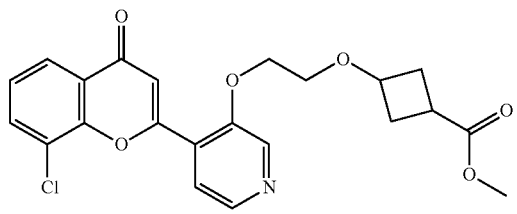

C061c

A mixture of methyl 3-[2-[[4-[(E)-3-(3-chloro-2-hydroxy-phenyl)-3-oxo-prop-1-enyl]-3-pyridyl]oxy]ethoxy]cyclobutanecarboxylate (273.0 mg, 0.630 mmol) and iodine (8.02 mg, 0.030 mmol) in DMSO (5 mL) was stirred at 140° C. for 3 hours. The mixture was diluted with water (20 mL) and the resulting suspension was filtered. The solid was collected and dried in vacuo to give methyl 3-[2-[[4-(8-chloro-4-oxo-chromen-2-yl)-3-pyridyl]oxy]ethoxy]cyclobutanecarboxylate (200 mg, 73.6% yield) as a yellow solid. MS obsd. (ESI$^+$)[(M+H)$^+$]: 430.0.

Step 4: Preparation of 3-[2-[[4-(8-chloro-4-oxo-chromen-2-yl)-3-pyridyl]oxy]ethoxy]cyclobutanecarboxylic acid

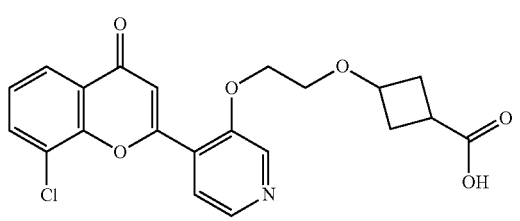 [SMILES: O=c1cc(-c2ccccc2OCCO[C@H]2C[C@H](C(=O)O)C2)oc2c(Br)cccc12]

C061

A mixture of methyl 3-[2-[[4-(8-chloro-4-oxo-chromen-2-yl)-3-pyridyl]oxy]ethoxy]cyclobutanecarboxylate (300.0 mg, 0.700 mmol) and LiOH (0.02 mL, 2.09 mmol) in a mixed solvent of THF (5 mL) and water (5 mL) was stirred at room temperature for 0.5 hour. The mixture was concentrated in vacuo and the residue was purified by Prep-HPLC to give 3-[2-[[4-(8-chloro-4-oxo-chromen-2-yl)-3-pyridyl]oxy]ethoxy]cyclobutanecarboxylic acid (16.4 mg, 5.48% yield) as a yellow solid. $^1$H NMR (DMSO-d$_6$, 400 MHz): δ ppm 12.19 (s, 1H), 8.60 (s, 1H), 8.44 (d, J=5.1 Hz, 1H), 8.07 (d, J=5.1 Hz, 1H), 7.97 (d, J=7.9 Hz, 1H), 7.82 (d, J=7.5 Hz, 1H), 7.37 (t, J=7.7 Hz, 1H), 7.15 (d, J=9.0 Hz, 1H), 4.33-4.46 (m, 2H), 4.15-4.24 (m, 0.4H), 3.94-4.04 (m, 0.6H), 3.72 (d, J=4.2 Hz, 2H), 2.81-3.04 (m, 1H), 2.44 (dd, J=10.8, 6.4 Hz, 2H), 2.11-2.29 (m, 1H), 1.91-2.05 (m, 1H). MS obsd. (ESI$^+$)[(M+H)$^+$]: 416.1.

Example C062: 3-[2-[2-(8-chloro-4-oxo-chromen-2-yl)-5-(2-oxooxazolidin-3-yl)phenoxy]ethoxy]cyclobutanecarboxylic acid

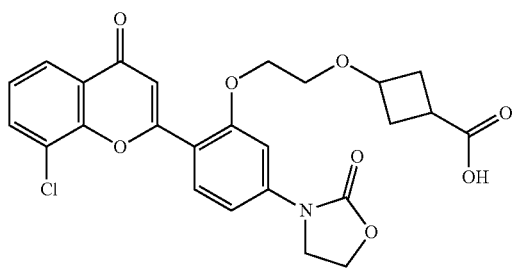

C062

Step 1: Preparation of methyl 3-[2-[2-(8-chloro-4-oxo-chromen-2-yl)-5-(2-oxooxazolidin-3-yl)phenoxy]ethoxy]cyclobutanecarboxylate

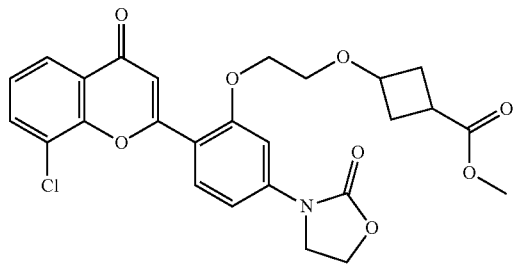

C062a

To a solution of methyl 3-[2-[5-bromo-2-(8-chloro-4-oxo-chromen-2-yl)phenoxy]ethoxy]cyclobutanecarboxylate (C003a, 300.0 mg, 0.590 mmol), 2-oxazolidone (154.35 mg, 1.77 mmol) and Cs$_2$CO$_3$ (385.01 mg, 1.18 mmol) in DMF (4 mL) were added CuI (202.1 mg, 1.18 mmol), N,N-dimethylethylenediamine (208.33 mg, 2.36 mmol) under N$_2$ atmosphere. The mixture was then stirred at 110° C. for 4 hours. After the reaction was completed, the mixture was filtered and the filtrate was concentrated in vacuo. The residue was purified by column chromatography on silica gel (eluted with PE:EtOAc=5:1 to 2:1) to give methyl 3-[2-[2-(8-chloro-4-oxo-chromen-2-yl)-5-(2-oxooxazolidin-3-yl)phenoxy]ethoxy]cyclobutanecarboxylate (290 mg, 93.6% yield) as yellow solid. $^1$H NMR (DMSO-d$_6$, 400 MHz): δ ppm 7.94-8.06 (m, 3H), 7.41-7.54 (m, 2H), 7.28-7.38 (m, 1H), 7.23 (s, 1H), 4.40-4.58 (m, 2H), 4.10-4.33 (m, 5H), 3.73 (br d, J=2.8 Hz, 2H), 3.52-3.65 (s, 3H), 2.23-2.48 (m, 4H), 1.99-2.09 (m, 1H). (ESI$^+$)[(M+H)$^+$]:514.2.

Step 2: Preparation of 3-[2-[2-(8-chloro-4-oxo-chromen-2-yl)-5-(2-oxooxazolidin-3-yl)phenoxy]ethoxy]cyclobutanecarboxylic acid

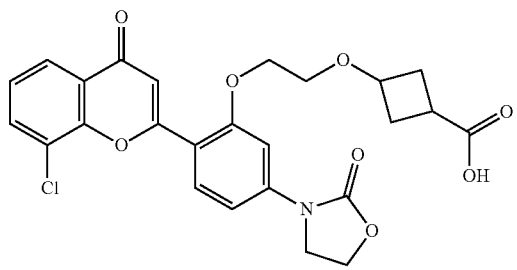

C062

To a solution of methyl 3-[2-[2-(8-chloro-4-oxo-chromen-2-yl)-5-(2-oxooxazolidin-3-yl)phenoxy]ethoxy]cyclobutanecarboxylate (150.0 mg, 0.290 mmol) in THF (5 mL)/water (0.500 mL) was added LiOH (11 mg, 0.500 mmol). The mixture was stirred at room temperature for 30 minutes. After the reaction was completed, the mixture was adjusted to pH~5 by addition of 2M HCl. The resulting suspension was then filtered and the solid was collected. The solid was then purified by preparative HPLC to give 3-[2-[2-(8-chloro-4-oxo-chromen-2-yl)-5-(2-oxooxazolidin-3-yl) phenoxy]ethoxy]cyclobutanecarboxylic acid (60 mg, 38.24% yield) as a yellow solid. $^1$H NMR (DMSO-d$_6$, 400 MHz): δ ppm 12.15 (br s, 1H), 8.07 (t, J=8.9 Hz, 1H), 8.01-7.94 (m, 2H), 7.53 (s, 1H), 7.48 (t, J=7.9 Hz, 1H), 7.39-7.31 (m, 2H), 4.55-4.45 (m, 2H), 4.28 (br s, 2H), 3.91-4.22 (m, 3H), 3.80-3.68 (m, 2H), 3.04-2.91 (m, 1H), 2.43-2.36 (m, 2H), 2.29-2.20 (m, 1H), 2.10-1.92 (m, 1H). (ESI$^+$)[(M+H)$^+$]:500.3.

Example C063-A and Example C063-B: Cis-3-[2-[2-(8-chloro-4-oxo-chromen-2-yl)-5-(2-oxopyrrolidin-1-yl)phenoxy]ethoxy]cyclobutanecarboxylic acid and Trans-3-[2-[2-(8-chloro-4-oxo-chromen-2-yl)-5-(2-oxopyrrolidin-1-yl)phenoxy]ethoxy]cyclobutanecarboxylic acid

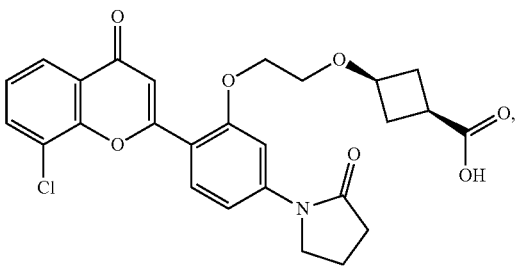

C063-A

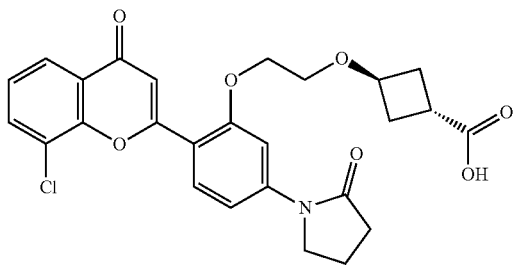

C063-B

Step 1: Preparation of methyl 3-[2-[2-(8-chloro-4-oxo-chromen-2-yl)-5-(2-oxopyrrolidin-1-yl)phenoxy]ethoxy]cyclobutanecarboxylate

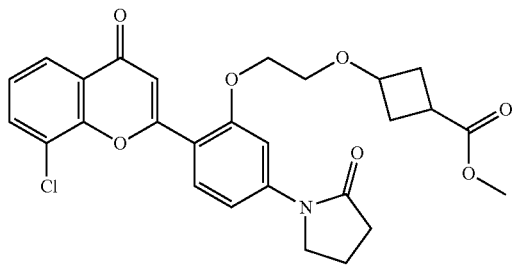

C063a

Compound C063a was prepared in analogy to the procedure described for the preparation of example C062a by using pyrrolidin-2-one as the starting material instead of 2-oxazolidone. (ESI$^+$)[(M+H)$^+$]:512.1.

Step 2: Preparation of Cis-3-[2-[2-(8-chloro-4-oxo-chromen-2-yl)-5-(2-oxopyrrolidin-1-yl)phenoxy]ethoxy]cyclobutanecarboxylic acid and Trans-3-[2-[2-(8-chloro-4-oxo-chromen-2-yl)-5-(2-oxopyrrolidin-1-yl)phenoxy]ethoxy]cyclobutanecarboxylic acid Example C064-A and Example C064-B: Cis-3-[2-[2-(8-chloro-4-oxo-chromen-2-yl)-5-methylsulfanyl-phenoxy]ethoxy]cyclobutanecarboxylic acid and trans-3-[2-[2-(8-chloro-4-oxo-chromen-2-yl)-5-methylsulfanyl-phenoxy]ethoxy]cyclobutanecarboxylic acid

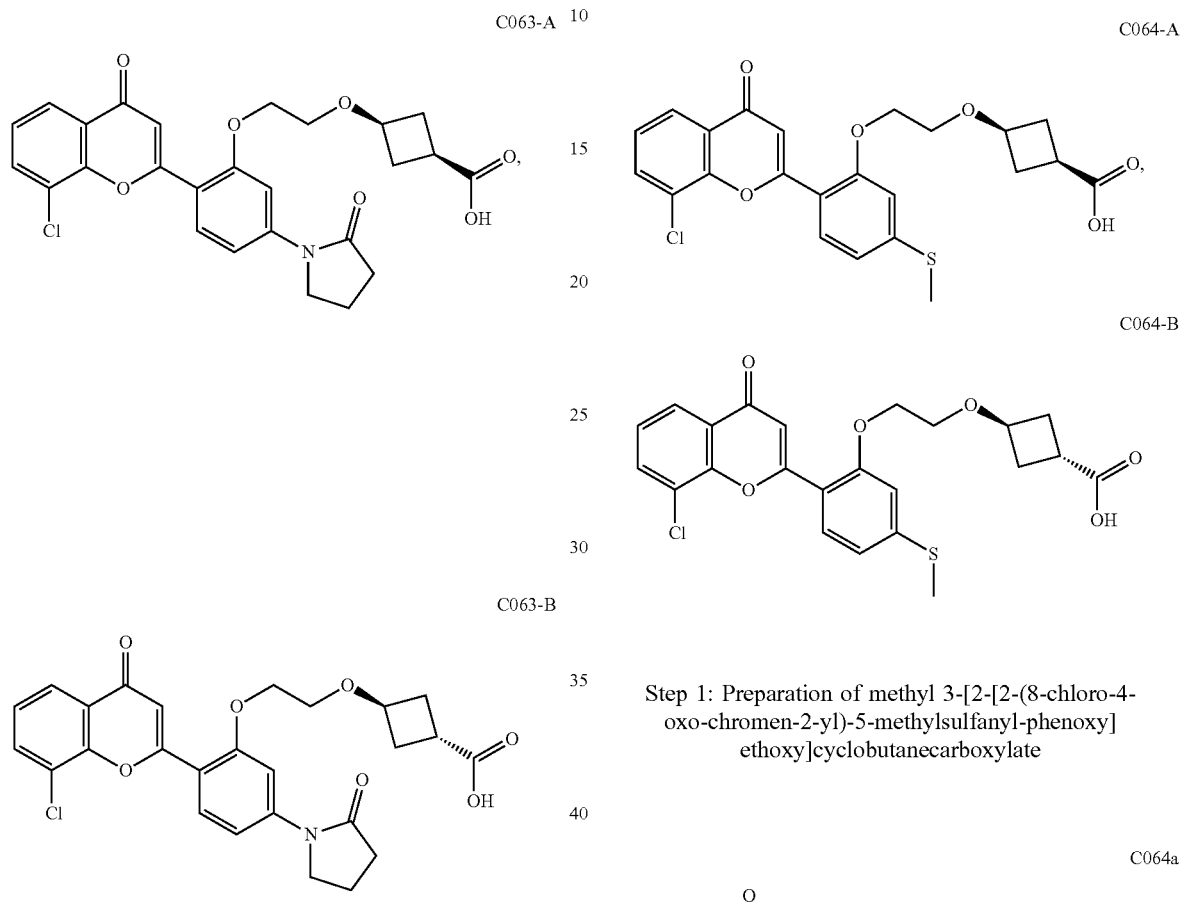

Example C063-A and C063-B were prepared in analogy to the procedure described for the preparation of example C003-A and C003-B by using methyl 3-[2-[2-(8-chloro-4-oxo-chromen-2-yl)-5-(2-oxopyrrolidin-1-yl)phenoxy]ethoxy]cyclobutanecarboxylate as the starting material instead of methyl 3-[2-[5-bromo-2-(8-chloro-4-oxo-chromen-2-yl)phenoxy]ethoxy]cyclobutanecarboxylate in Step 2.

Example C063-A: $^1$H NMR (DMSO-$d_6$, 400 MHz): δ ppm 7.96-8.07 (m, 3H), 7.69-7.74 (m, 1H), 7.43-7.52 (m, 2H), 7.25 (s, 1H), 4.23-4.29 (m, 2H), 3.87-4.01 (m, 3H), 3.70-3.79 (m, 2H), 2.55-2.59 (m, 2H), 2.41-2.47 (m, 2H), 2.07-2.17 (m, 2H), 1.94-2.06 (m, 3H). MS obsd. (ESI$^+$) [(M+H)$^+$]:498.2.

Example C063-B: $^1$H NMR (DMSO-$d_6$, 400 MHz): δ ppm 8.07 (d, J=8.8 Hz, 1H), 7.99 (d, J=7.8 Hz, 2H), 7.71 (d, J=1.7 Hz, 1H), 7.44-7.51 (m, 2H), 7.38 (s, 1H), 4.24-4.30 (m, 2H), 4.19 (t, J=6.8 Hz, 1H), 3.92 (t, J=7.1 Hz, 2H), 3.70-3.75 (m, 2H), 2.93-3.01 (m, 1H), 2.55-2.60 (m, 2H), 2.36-2.44 (m, 2H), 2.21-2.28 (m, 2H), 2.06-2.15 (m, 2H). MS obsd. (ESI$^+$) [(M+H)$^+$]:498.2.

Step 1: Preparation of methyl 3-[2-[2-(8-chloro-4-oxo-chromen-2-yl)-5-methylsulfanyl-phenoxy]ethoxy]cyclobutanecarboxylate A mixture of methyl 3-[2-[5-bromo-2-(8-chloro-4-oxo-chromen-2-yl)phenoxy]ethoxy]cyclobutanecarboxylate (C003a, 50 mg, 98.5 μmol), DABCO (22.1 mg, 197 μmol), CuI (37.5 mg, 197 μmol) in DMSO (5 mL) was microwaved at 170° C. for 2.5 hour. After the reaction was completed, the mixture was diluted with EtOAc (30 mL) and the suspension was then filtered through silica pad. The filtrate was concentrated in vacuo to give a dark solution of methyl 3-[2-[2-(8-chloro-4-oxo-chromen-2-yl)-5-methylsulfanyl-phenoxy]ethoxy]cyclobutanecarboxylate in DMSO, which was used in the next step directly without further purification. (ESI$^+$)[(M+H)$^+$]:475.1

Step 2: Preparation of Cis-3-[2-[2-(8-chloro-4-oxo-chromen-2-yl)-5-methylsulfanyl-phenoxy]ethoxy]cyclobutanecarboxylic acid and trans-3-[2-[2-(8-chloro-4-oxo-chromen-2-yl)-5-methylsulfanyl-phenoxy]ethoxy]cyclobutanecarboxylic acid Example C065-A and Example C065-B: Cis-methyl 3-[2-[2-(8-chloro-4-oxo-chromen-2-yl)-5-methylsulfonyl-phenoxy]ethoxy]cyclobutanecarboxylate and Trans-methyl 3-[2-[2-(8-chloro-4-oxo-chromen-2-yl)-5-methylsulfonyl-phenoxy]ethoxy]cyclobutanecarboxylate

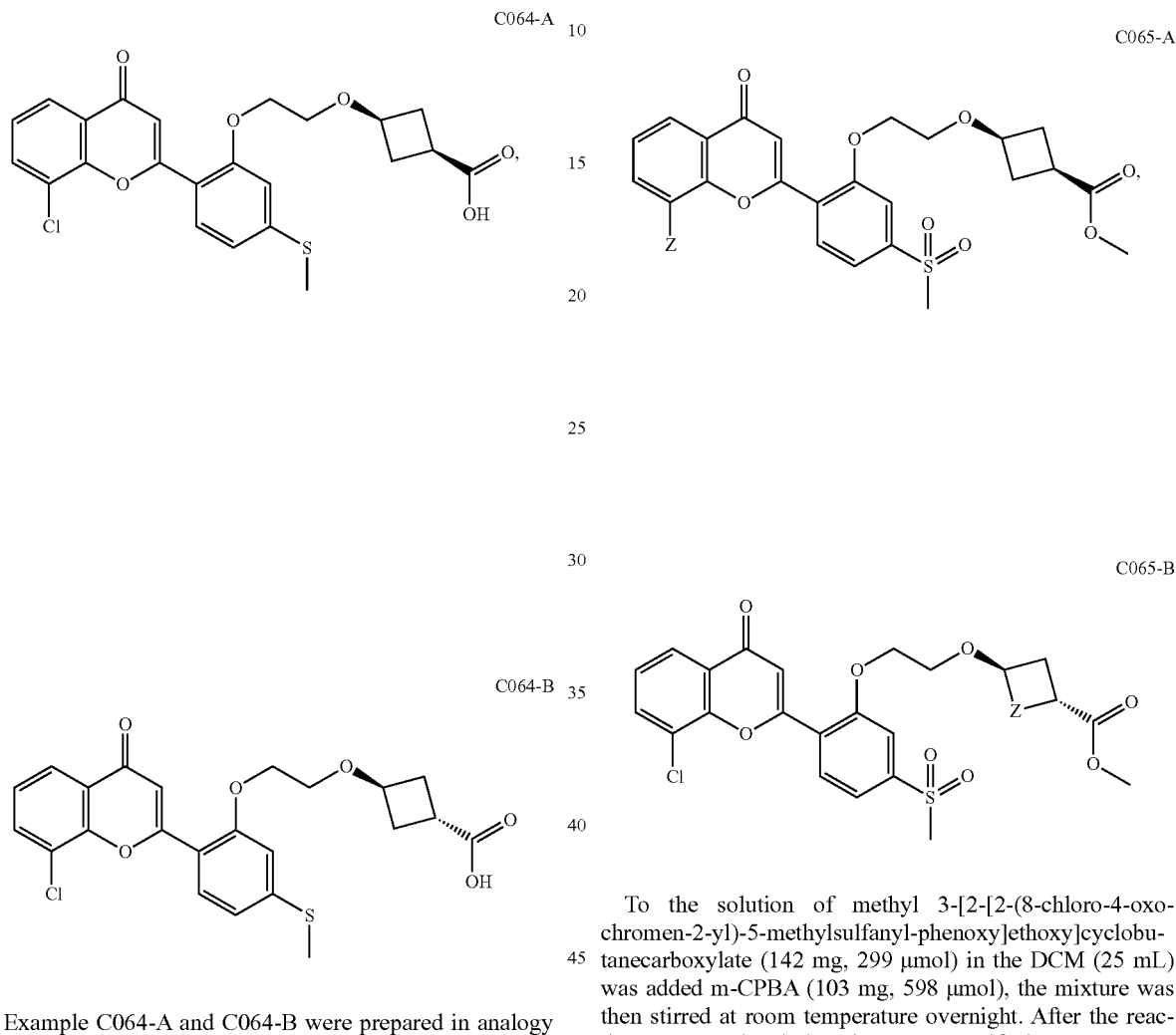

Example C064-A and C064-B were prepared in analogy to the procedure described for the preparation of example C003-A and C003-B by using methyl 3-[2-[2-(8-chloro-4-oxo-chromen-2-yl)-5-(2-oxopyrrolidin-1-yl)phenoxy]ethoxy]cyclobutanecarboxylate as the starting material instead of methyl 3-[2-[5-bromo-2-(8-chloro-4-oxo-chromen-2-yl)phenoxy]ethoxy]cyclobutanecarboxylate in Step 2.

Example C064-A: $^1$H NMR (DMSO-$d_6$, 400 MHz): δ ppm 7.95-8.05 (m, 3H), 7.49 (t, J=1.9 Hz, 1H), 7.19-7.29 (m, 1H), 7.05-7.14 (m, 2H), 4.26-4.39 (m, 2H), 3.93-4.04 (m, 1H), 3.68-3.79 (m, 2H), 2.57-2.62 (m, 4H), 2.39-2.47 (m, 2H), 1.97-2.08 (m, 2H). MS obsd. (ESI$^+$) [(M+H)$^+$]: 461.2.

Example C064-B: $^1$H NMR (DMSO-$d_6$, 400 MHz): δ ppm 7.96-8.02 (m, 3H), 7.49 (t, J=7.9 Hz, 1H), 7.36 (s, 1H), 7.07-7.13 (m, 2H), 4.31-4.36 (m, 2H), 4.15-4.24 (m, 1H), 3.67-3.72 (m, 2H), 2.89-3.00 (m, 1H), 2.58 (s, 3H), 2.40 (qd, J=6.6, 3.7 Hz, 2H), 2.16-2.28 (m, 2H). MS obsd. (ESI$^+$) [(M+H)$^+$]: 461.2.

To the solution of methyl 3-[2-[2-(8-chloro-4-oxo-chromen-2-yl)-5-methylsulfanyl-phenoxy]ethoxy]cyclobutanecarboxylate (142 mg, 299 μmol) in the DCM (25 mL) was added m-CPBA (103 mg, 598 μmol), the mixture was then stirred at room temperature overnight. After the reaction was completed, the mixture was purified Prep-HPLC to give two sets of diastereomers of the methyl 3-[2-[2-(8-chloro-4-oxo-chromen-2-yl)-5-methylsulfanyl-phenoxy]ethoxy]cyclobutanecarboxylate with cis- and trans-configuration, one of which is characterized as Example C065-A (3.5 mg, 1.9% yield) and the other is Example C065-B (6.5 mg, 3.9% yield) as white solid.

Example C065-A: $^1$H NMR (DMSO-$d_6$, 400 MHz): δ ppm 8.19 (d, J=8.7 Hz, 1H), 8.03 (ddd, J=7.9, 6.5, 1.5 Hz, 2H), 7.72-7.76 (m, 2H), 7.52 (s, 1H), 7.24 (s, 1H), 4.39-4.43 (m, 2H), 3.92-3.99 (m, 1H), 3.70-3.75 (m, 2H), 3.56 (s, 3H), 3.31 (s, 3H), 2.58-2.64 (m, 1H), 2.38-2.43 (m, 2H), 1.98-2.03 (m, 2H). MS obsd. (ESI$^+$) [(M+H)$^+$]: 507.3.

Example C065-B: $^1$H NMR (DMSO-$d_6$, 400 MHz): δ ppm 8.18-8.24 (m, 1H), 7.99-8.06 (m, 2H), 7.73-7.77 (m, 2H), 7.52 (t, J=7.9 Hz, 1H), 7.34 (s, 1H), 4.38-4.45 (m, 2H), 4.19 (quin, J=6.6 Hz, 1H), 3.69-3.75 (m, 2H), 3.59 (s, 3H), 3.33 (s, 3H), 2.99-3.07 (m, 1H), 2.35-2.42 (m, 2H), 2.09-2.26 (m, 2H). MS obsd. (ESI$^+$) [(M+H)$^+$]: 507.3.

Example C066-A and Example C066-B: Cis-3-[2-[2-(8-chloro-4-oxo-chromen-2-yl)-5-thiazol-2-yl-phenoxy]ethoxy]cyclobutanecarboxylic acid and Trans-3-[2-[2-(8-chloro-4-oxo-chromen-2-yl)-5-thiazol-2-yl-phenoxy]ethoxy]cyclobutanecarboxylic acid

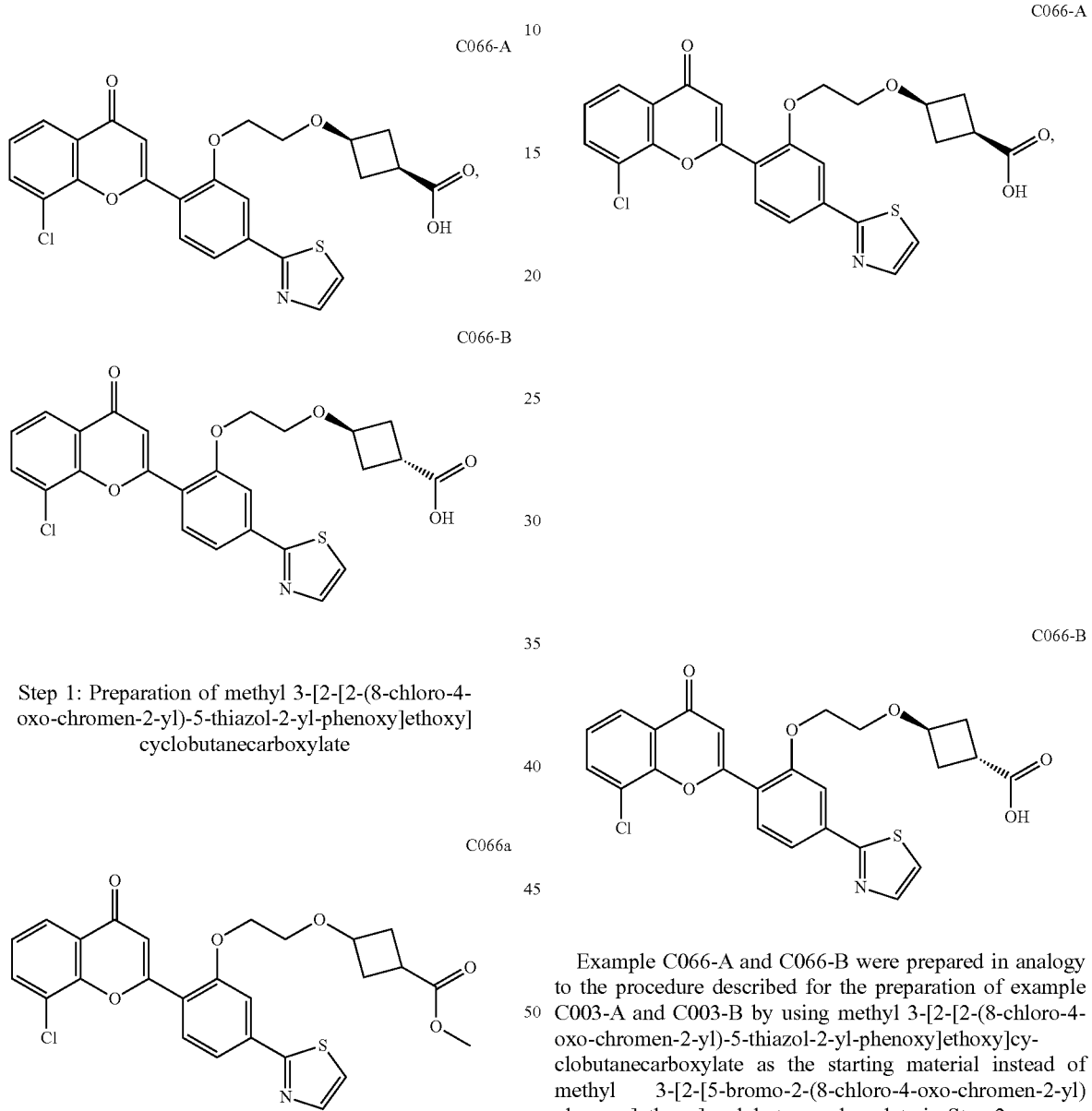

Step 1: Preparation of methyl 3-[2-[2-(8-chloro-4-oxo-chromen-2-yl)-5-thiazol-2-yl-phenoxy]ethoxy]cyclobutanecarboxylate A mixture of methyl 3-[2-[5-bromo-2-(8-chloro-4-oxo-chromen-2-yl)phenoxy]ethoxy]cyclobutanecarboxylate (C003a, 80 mg, 158 μmol), Pd(OAc)$_2$ (35.4 mg, 158 μmol), CuI (60 mg, 315 μmol), thiazole (26.8 mg, 315 μmol) in DMF (2 ml) was stirred at 150° C. under microwave condition for 3 hours. After the reaction was completed, the mixture was diluted with EtOAc (30 ml) and then filtered, the filtrate was concentrated in vacuo to give the crude methyl 3-[2-[2-(8-chloro-4-oxo-chromen-2-yl)-5-thiazol-2-yl-phenoxy]ethoxy]cyclobutanecarboxylate (80 mg, 100% yield) as a yellow solid. MS obsd. (ESI$^+$) [(M+H)$^+$]: 512.2.

Step 2: Preparation of Cis-3-[2-[2-(8-chloro-4-oxo-chromen-2-yl)-5-thiazol-2-yl-phenoxy]ethoxy]cyclobutanecarboxylic acid and traits-3-[2-[2-(8-chloro-4-oxo-chromen-2-yl)-5-thiazol-2-yl-phenoxy]ethoxy]cyclobutanecarboxylic acid Example C066-A and C066-B were prepared in analogy to the procedure described for the preparation of example C003-A and C003-B by using methyl 3-[2-[2-(8-chloro-4-oxo-chromen-2-yl)-5-thiazol-2-yl-phenoxy]ethoxy]cyclobutanecarboxylate as the starting material instead of methyl 3-[2-[5-bromo-2-(8-chloro-4-oxo-chromen-2-yl)phenoxy]ethoxy]cyclobutanecarboxylate in Step 2.

Example C066-A: $^1$H NMR (DMSO-d$_6$, 400 MHz): δ ppm 8.14 (d, J=8.6 Hz, 1H), 7.98-8.05 (m, 3H), 7.93 (d, J=3.2 Hz, 1H), 7.79 (td, J=4.2, 1.5 Hz, 2H), 7.48-7.54 (m, 1H), 7.31 (s, 1H), 4.39-4.44 (m, 2H), 3.93-4.00 (m, 1H), 3.73-3.79 (m, 2H), 2.47-2.49 (m, 1H), 2.36-2.46 (m, 2H), 1.98-2.05 (m, 2H). MS obsd. (ESI$^+$) [(M+H)$^+$]: 498.1.

Example C066-B: $^1$H NMR (DMSO-d$_6$, 400 MHz): δ ppm 8.17 (d, J=8.7 Hz, 1H), 8.00-8.05 (m, 3H), 7.94 (d, J=3.2 Hz, 1H), 7.76-7.83 (m, 2H), 7.48-7.54 (m, 1H), 7.44 (s, 1H), 4.41-4.46 (m, 2H), 4.16-4.24 (m, 1H), 3.72-3.76 (m, 2H), 2.94-2.99 (m, 1H), 2.38-2.44 (m, 2H), 2.21-2.27 (m, 2H). MS obsd. (ESI$^+$) [(M+H)$^+$]: 498.1.

Example C067-A and Example C067-B: Cis-3-[2-[2-(8-chloro-4-oxo-chromen-2-yl)-5-morpholino-phenoxy]ethoxy]cyclobutanecarboxylic acid and trans-3-[2-[2-(8-chloro-4-oxo-chromen-2-yl)-5-morpholino-phenoxy]ethoxy]cyclobutanecarboxylic acid

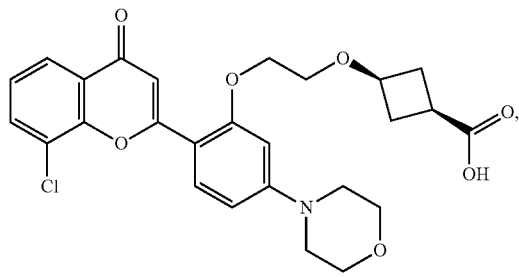
C067-A

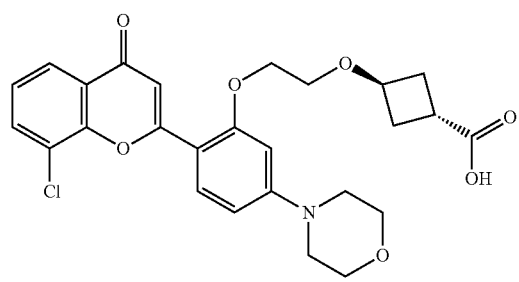
C067-B

The mixture of methyl 3-[2-[5-bromo-2-(8-chloro-4-oxo-chromen-2-yl)phenoxy]ethoxy]cyclobutanecarboxylate (C003a, 80 mg, 158 μmol), morpholine (41.2 mg, 473 μmol), K$_2$CO$_3$ (65.3 mg, 473 μmol) and RuPhos Pd G2 (12.2 mg, 15.8 μmol) in 1,4-Dioxane (3 ml) was stirred at 100° C. overnight. After the reaction was completed, to the reaction mixture was added LiOH solution (1N, 1 mL) and then the mixture was stirred at 50° C. for 2 hours. The mixture was adjusted to pH~5 by addition of AcOH and the mixture was concentrated in vacuo. The residue was purified by prep-HPLC to give two sets of diastereomers of the 3-[2-[2-(8-chloro-4-oxo-chromen-2-yl)-5-morpholino-phenoxy]ethoxy]cyclobutanecarboxylic acid with cis- and trans- configuration, one of which is characterized as Example C067-A (9.5 mg, 11.5% yield) and the other is Example C067-B (3.5 mg, 4.2% yield) as white solid.

Example C067-A: $^1$H NMR (DMSO-d$_6$, 400 MHz): δ ppm 12.11 (br s, 1H), 7.90-8.00 (m, 3H), 7.45 (t, J=7.9 Hz, 1H), 7.19 (s, 1H), 6.78 (dd, J=9.0, 2.2 Hz, 1H), 6.66 (d, J=2.2 Hz, 1H), 4.23-4.33 (m, 2H), 3.95-4.06 (m, 1H), 3.70-3.82 (m, 6H), 2.52-2.58 (m, 1H), 2.40-2.46 (m, 2H), 1.93-2.11 (m, 2H). MS obsd. (ESI$^+$) [(M+H)$^+$]: 500.3.

Example C067-B: $^1$H NMR (DMSO-d$_6$, 400 MHz): δ ppm 12.01-12.32 (m, 1H), 7.90-7.99 (m, 3H), 7.37-7.50 (m, 1H), 7.28-7.34 (m, 1H), 6.78 (dd, J=9.0, 2.2 Hz, 1H), 6.65 (d, J=2.0 Hz, 1H), 4.26-4.37 (m, 2H), 4.15-4.24 (m, 1H), 3.68-3.81 (m, 6H), 2.93-3.05 (m, 1H), 2.40 (ddd, J=9.8, 6.7, 3.4 Hz, 2H), 2.17-2.30 (m, 2H). MS obsd. (ESI$^+$) [(M+H)$^+$]: 500.3.

Example C068: cis-3-[2-[2-(8-chloro-4-oxo-chromen-2-yl)-5-pyrrolidin-1-yl-phenoxy]ethoxy]cyclobutanecarboxylic acid

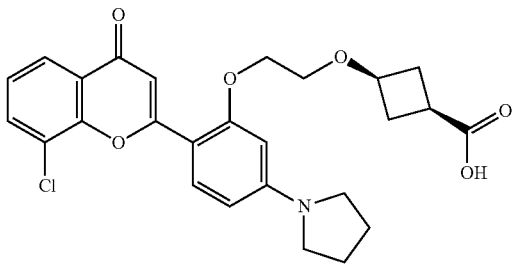
C068

Step 1: Preparation of cis-tert-butyl 3-[2-[5-bromo-2-(8-chloro-4-oxo-chromen-2-yl)phenoxy]ethoxy]cyclobutanecarboxylate

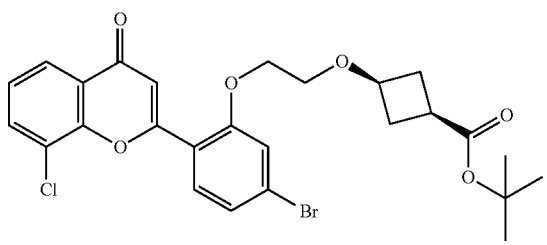
C068a

Compound C068a was prepared in analogy to the procedure described for the preparation of compound C003a by using cis-tert-butyl 3-[2-(p-tolylsulfonyloxy)ethoxy]cyclobutanecarboxylate as the starting material instead of methyl 3-[2-(p-tolylsulfonyloxy)ethoxy]cyclobutanecarboxylate.

Step 2: Preparation of cis-tert-butyl 3-[2-[2-(8-chloro-4-oxo-chromen-2-yl)-5-pyrrolidin-1-yl-phenoxy]ethoxy]cyclobutanecarboxylate

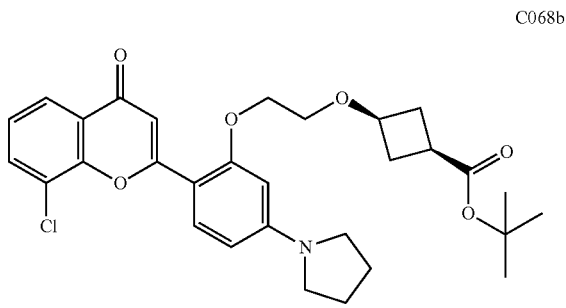
C068b

A mixture of cis-tert-butyl 3-[2-[5-bromo-2-(8-chloro-4-oxo-chromen-2-yl)phenoxy]ethoxy]cyclobutanecarboxylate (330.0 mg, 0.600 mmol), pyrrolidine (213.42 mg, 3 mmol), Pd₂(dba)₃ (54.96 mg, 0.060 mmol), 9,9-dimethyl-4,5-bis(diphenylphosphino)xanthene (34.73 mg, 0.060 mmol) and Cs₂CO₃ (586.6 mg, 1.8 mmol) in 1,4-dioxane (7 mL) was stirred at 105° C. for 5 hours. The mixture was filtered and the filtrate was concentrated in vacuo. The residue was purified by column chromatography on silica gel (eluted with PE:EtOAc=10:1 to 1:1) to give cis-tert-butyl 3-[2-[2-(8-chloro-4-oxo-chromen-2-yl)-5-pyrrolidin-1-yl-phenoxy]ethoxy]cyclobutanecarboxylate (250 mg, 77.13% yield) as light yellow oil. MS obsd. (ESI⁺) [(M+H)⁺]: 540.1.

Step 3: Preparation of cis-3-[2-[2-(8-chloro-4-oxo-chromen-2-yl)-5-pyrrolidin-1-yl-phenoxy]ethoxy]cyclobutanecarboxylic acid

C068

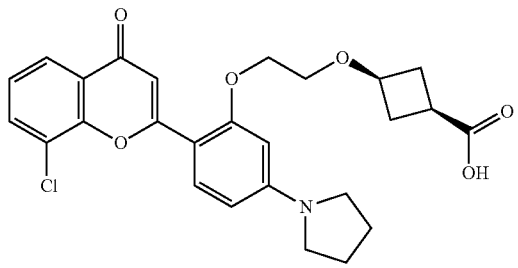

To a solution of cis-tert-butyl 3-[2-[2-(8-chloro-4-oxo-chromen-2-yl)-5-pyrrolidin-1-yl-phenoxy]ethoxy]cyclobutanecarboxylate (250.0 mg, 0.460 mmol) in DCM (5 mL) was added TFA (2.5 mL, 32.45 mmol) and the mixture was stirred at room temperature for 1 hour. The mixture was concentrated in vacuo and the residue was triturated with mixed solvent of EtOAc (3 mL) and PE (15 mL). The suspension was then filtered, the solid was collected and dried in vacuo to give cis-3-[2-[2-(8-chloro-4-oxo-chromen-2-yl)-5-pyrrolidin-1-yl-phenoxy]ethoxy]cyclobutanecarboxylic acid (137.5 mg, 59.6% yield) as light red solid. ¹H NMR (DMSO-d₆, 400 MHz): δ ppm 12.39-11.69 (m, 1H), 7.89-7.96 (m, 3H), 7.42 (t, J=7.9 Hz, 1H), 7.15 (s, 1H), 6.37 (d, J=9.0 Hz, 1H), 6.19 (s, 1H), 4.16-4.36 (m, 2H), 3.86-4.12 (m, 1H), 3.65-3.83 (m, 2H), 2.53-2.64 (m, 4H), 2.39-2.48 (m, 3H), 1.93-2.08 (m, 6H). MS obsd. (ESI⁺) [(M+H)⁺]: 484.7.

Example C069-A and Example C069-B: Cis-3-[2-[2-(8-chloro-4-oxo-chromen-2-yl)-5-cyclopropyl-phenoxy]ethoxy]cyclobutanecarboxylic acid and Trans-3-[2-[2-(8-chloro-4-oxo-chromen-2-yl)-5-cyclopropyl-phenoxy]ethoxy]cyclobutanecarboxylic acid

C069-A

C069-B

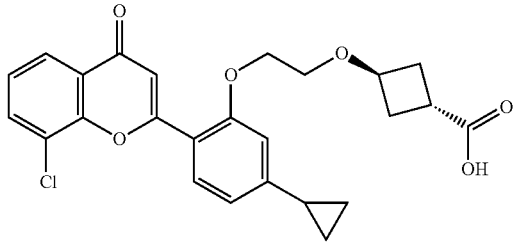

A mixture of methyl 3-[2-[5-bromo-2-(8-chloro-4-oxo-chromen-2-yl)phenoxy]ethoxy]cyclobutanecarboxylate (C003a, 80 mg, 158 μmol), potassium cyclopropyltrifluoroborate (35 mg, 236 μmol), Pd(Ph₃P)₄ (18.2 mg, 15.8 μmol) and K₂CO₃ (54.4 mg, 394 μmol) in 1,4-Dioxane (5 mL) and water (1 mL) was stirred at 100° C. for 3 hours. Then to the resulting mixture was added LiOH (22 mg, 1 mmol) and the mixture was stirred at 50° C. for 30 minutes. After the reaction was completed, the mixture was adjusted to PH~5 by addition of 6N HCl. The mixture was then concentrated in vacuo and the residue was purified by Prep-HPLC to give two sets of diastereomers of the 3-[2-[2-(8-chloro-4-oxo-chromen-2-yl)-5-cyclopropyl-phenoxy]ethoxy]cyclobutanecarboxylic acid with cis- and trans-configuration, one of which is characterized as Example C069-A (10 mg, 13.5% yield) and the other is Example C069-B (22 mg, 30% yield) as white solid.

Example C069-A: ¹H NMR (DMSO-d₆, 400 MHz): δ ppm 7.98 (d, J=7.34 Hz, 2H), 7.90 (d, J=7.58 Hz, 1H), 7.45-7.53 (m, 1H), 7.21 (br. s., 1H), 6.96 (br. s., 1H), 6.90 (d, J=7.58 Hz, 1H), 4.29 (br. s., 2H), 3.95 (d, J=5.87 Hz, 1H), 3.72 (br. s., 2H), 2.43 (br. s., 3H), 2.01 (br. s., 3H), 1.06 (d, J=6.11 Hz, 2H), 0.80-0.90 (m, 2H). MS obsd. (ESI⁺) [(M+H)⁺]: 455.1.

Example C069-B: ¹H NMR (DMSO-d₆, 400 MHz): δ ppm 7.88-8.05 (m, 3H), 7.41-7.54 (m, 1H), 7.29-7.37 (m, 1H), 6.90 (dd, J=8.3, 1.4 Hz, 2H), 4.26-4.38 (m, 2H), 4.13-4.24 (m, 1H), 3.64-3.73 (m, 2H), 2.90-3.02 (m, 1H), 2.35-2.44 (m, 2H), 2.15-2.27 (m, 2H), 1.91-2.06 (m, 1H), 1.02-1.11 (m, 2H), 0.69-0.90 (m, 2H). MS obsd. (ESI⁺) [(M+H)⁺]: 455.1.

Example C070: Cis-3-[2-[2-bromo-6-(8-chloro-6-fluoro-4-oxo-chromen-2-yl)phenoxy]ethoxy]cyclobutanecarboxylic acid

C070

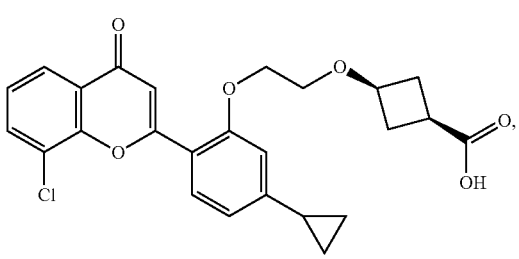

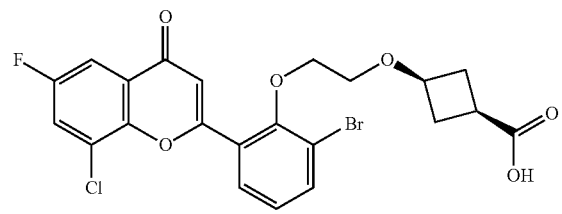

301

Step 1: Preparation of 2-(3-bromo-2-hydroxy-phenyl)-8-chloro-6-fluoro-chromen-4-one

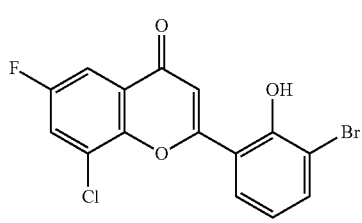

C070a

Compound C070a was prepared in analogy to the procedure described for the preparation of compound Int-5 by using 3-bromo-2-hydroxy-benzaldehyde (CAS #: 1829-34-1, Cat. #: SY013143, from Accela ChemBio Inc) as the starting material instead of 4-chloro-2-hydroxy-5-methyl-benzaldehyde in Step 2 and using 1-(3-chloro-5-fluoro-2-hydroxy-phenyl)ethanone as the starting material instead of 1-(3-chloro-2-hydroxy-phenyl)ethanone in Step 3.

Step 2: Preparation of Cis-3-[2-[2-bromo-6-(8-chloro-6-fluoro-4-oxo-chromen-2-yl)phenoxy]ethoxy]cyclobutanecarboxylic acid

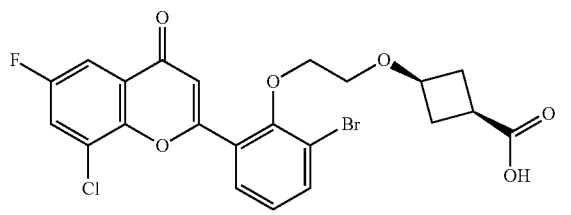

C070

Example C070a was prepared in analogy to the procedure described for the preparation of example C004 by using 2-(3-bromo-2-hydroxy-phenyl)-8-chloro-6-fluoro-chromen-4-one as the starting material instead of 8-chloro-2-(4-chloro-2-hydroxy-phenyl)chromen-4-one in Step 1. $^1$H NMR (DMSO-$d_6$, 400 MHz): δ ppm 12.10 (br s, 1H), 7.79-7.89 (m, 4H), 7.47-7.66 (m, 1H), 7.34 (t, J=7.7 Hz, 1H), 3.97-4.09 (m, 2H), 3.90 (quin, J=6.7 Hz, 1H), 3.26-3.45 (m, 3H), 2.08-2.29 (m, 2H), 1.73-2.00 (m, 2H). (ESI$^+$)[(M+H)$^+$]: 511.1.

Example C071: Cis-3-[2-[5-bromo-2-(8-chloro-4-oxo-chromen-2-yl)-3-fluoro-phenoxy]ethoxy]cyclobutanecarboxylic acid

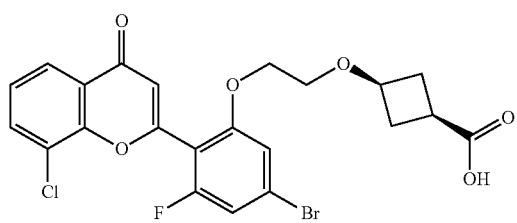

C071

302

Step 1: Preparation of 2-(4-bromo-2-fluoro-6-hydroxy-phenyl)-8-chloro-chromen-4-one

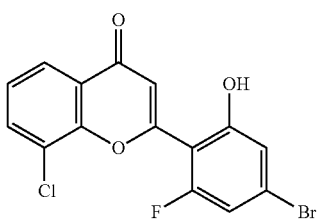

C071a

Compound C070a was prepared in analogy to the procedure described for the preparation of compound Int-5 by using 4-bromo-2-fluoro-6-hydroxy-benzaldehyde (CAS #: 1427438-90-1, Cat. #: BD260521, from Bide Pharmtach) as the starting material instead of 4-chloro-2-hydroxy-5-methyl-benzaldehyde in Step 2.

Step 2: Preparation of cis-tert-butyl 3-[2-[5-bromo-2-(8-chloro-4-oxo-chromen-2-yl)-3-fluoro-phenoxy]ethoxy]cyclobutanecarboxylate

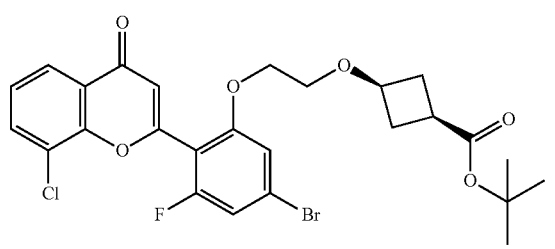

C071b

A solution of 2-(4-bromo-2-fluoro-6-hydroxy-phenyl)-8-chloro-chromen-4-one (200.0 mg, 0.540 mmol), cis-tert-butyl 3-[2-(p-tolylsulfonyloxy)ethoxy]cyclobutanecarboxylate (200.48 mg, 0.540 mmol) and $K_2CO_3$ (74.79 mg, 0.540 mmol) in DMF (15 mL) was stirred at 80° C. for 8 hours. After the reaction was completed, the mixture was concentrated in vacuo and the residue was purified by column chromatography on silica gel (eluted with PE:EtOAc=20:1 to 3:1) to give cis-tert-butyl 3-[2-[5-bromo-2-(8-chloro-4-oxo-chromen-2-yl)-3-fluoro-phenoxy]ethoxy]cyclobutanecarboxylate (170 mg, 55.32% yield, purity 36.42%) as a light yellow oil. MS obsd. (ESI$^+$)[(M+H)$^+$]: 567.0.

Step 3: Preparation of cis-3-[2-[5-bromo-2-(8-chloro-4-oxo-chromen-2-yl)-3-fluoro-phenoxy]ethoxy]cyclobutanecarboxylic acid

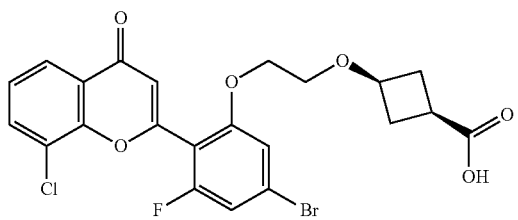

C071

To a solution of cis-tert-butyl 3-[2-[5-bromo-2-(8-chloro-4-oxo-chromen-2-yl)-3-fluoro-phenoxy]ethoxy]cyclobutanecarboxylate (170.0 mg, 0.300 mmol) in DCM (5 mL) was added TFA (2.5 mL, 32.45 mmol) and the mixture was stirred at 20° C. for 5 hours. After the reaction was completed, the mixture was concentrated in vacuo and the residue was purified by Prep-HPLC to give cis-3-[2-[5-bromo-2-(8-chloro-4-oxo-chromen-2-yl)-3-fluoro-phenoxy]ethoxy]cyclobutanecarboxylic acid (89.7 mg, 58.55% yield) as an off-white solid. $^1$H NMR (DMSO-$d_6$, 400 MHz): δ ppm 12.07 (br s, 1H), 7.99-8.07 (m, 2H), 7.53 (t, J=7.9 Hz, 1H), 7.38-7.45 (m, 2H), 6.71 (s, 1H), 4.19-4.32 (m, 2H), 3.77 (quin, J=7.2 Hz, 1H), 3.41-3.62 (m, 2H), 2.16-2.34 (m, 3H), 1.74-1.85 (m, 2H). (ESI$^+$)[(M+H)$^+$]: 511.5.

Example C072: Cis-3-[2-[2-(8-chloro-4-oxo-chromen-2-yl)-4,5-dimethoxy-phenoxy]ethoxy]cyclobutanecarboxylic acid

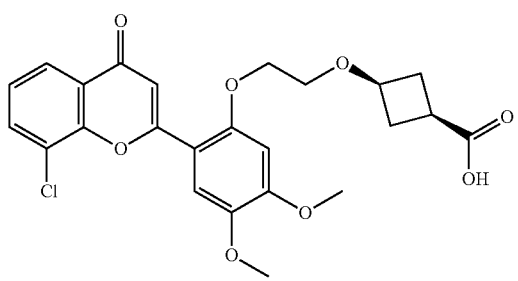

C072

Example C072 was prepared in analogy to the procedure described for the preparation of example C071 by using 8-chloro-2-(2-hydroxy-4,5-dimethoxy-phenyl)chromen-4-one (Int-10) as the starting material instead of 2-(4-bromo-2-fluoro-6-hydroxy-phenyl)-8-chloro-chromen-4-one in Step 2. $^1$H NMR (DMSO-$d_6$, 400 MHz): δ ppm 7.98 (dd, J=7.9, 2.9 Hz, 2H), 7.60 (s, 1H), 7.47 (t, J=7.9 Hz, 1H), 7.25 (s, 1H), 6.91 (s, 1H), 4.28-4.35 (m, 2H), 3.88-4.00 (m, 4H), 3.82 (s, 3H), 3.67-3.76 (m, 2H), 2.38-2.47 (m, 2H), 1.96-2.06 (m, 2H). (ESI$^+$)[(M+H)$^+$]: 475.1.

Example C073: Cis-3-[2-[5-bromo-2-(8-chloro-4-oxo-chromen-2-yl)-4-methoxy-phenoxy]ethoxy]cyclobutanecarboxylic acid

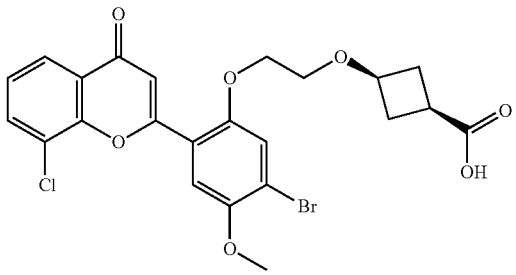

C073

Example C073 was prepared in analogy to the procedure described for the preparation of example C071 by using 2-(4-bromo-2-hydroxy-5-methoxy-phenyl)-8-chloro-chromen-4-one as the starting material instead of 2-(4-bromo-2-fluoro-6-hydroxy-phenyl)-8-chloro-chromen-4-one in Step 2. $^1$H NMR (DMSO-$d_6$, 400 MHz): δ ppm 12.08 (br s, 1H), 8.00 (br t, J=7.5 Hz, 2H), 7.54-7.70 (m, 2H), 7.50 (t, J=7.8 Hz, 1H), 7.23-7.30 (m, 1H), 4.17-4.36 (m, 2H), 3.87-3.96 (m, 4H), 3.63-3.73 (m, 2H), 2.54-2.61 (m, 1H), 2.33-2.48 (m, 2H), 1.93-2.03 (m, 2H). (ESI$^+$)[(M+H)$^+$]: 523.2.

Example C074: Cis-3-[2-[[7-(8-chloro-4-oxo-chromen-2-yl)-2,3-dihydro-1,4-benzodioxin-6-yl]oxy]ethoxy]cyclobutanecarboxylic acid

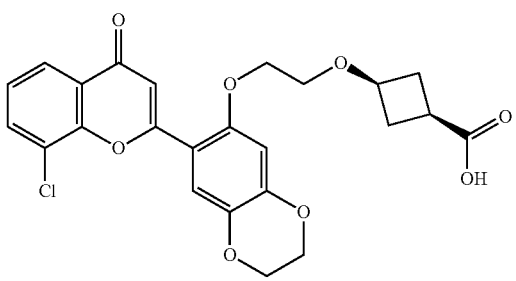

C074

Step 1: Preparation of 6-hydroxy-2,3-dihydro-1,4-benzodioxine-7-carbaldehyde

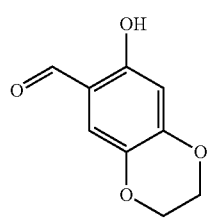

C074a

Compound C074a was prepared in analogy to the procedure described for the preparation of compound Int-5a by using 2,3-dihydro-1,4-benzodioxin-6-ol as the starting material instead of 3-chloro-4-methyl-phenol in Step 1.

Step 2: Preparation of 8-chloro-2-(6-hydroxy-2,3-dihydro-1,4-benzodioxin-7-yl)chromen-4-one

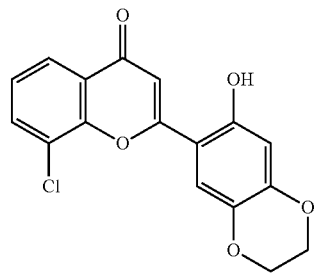

C074b

Compound C070a was prepared in analogy to the procedure described for the preparation of compound Int-5 by using 6-hydroxy-2,3-dihydro-1,4-benzodioxine-7-carbaldehyde as the starting material instead of 4-chloro-2-hydroxy-5-methyl-benzaldehyde in Step 2.

Step 3: Preparation of cis-3-[2-[[7-(8-chloro-4-oxo-chromen-2-yl)-2,3-dihydro-1,4-benzodioxin-6-yl]oxy]ethoxy]cyclobutanecarboxylic acid

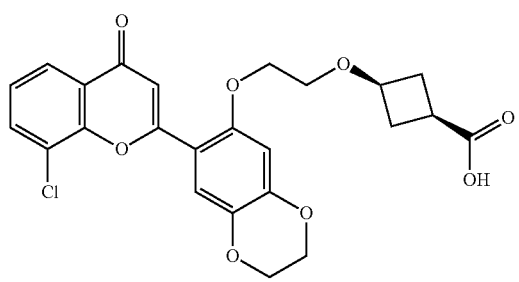

C074

Example C074 was prepared in analogy to the procedure described for the preparation of example C071 by using 8-chloro-2-(6-hydroxy-2,3-dihydro-1,4-benzodioxin-7-yl)chromen-4-one as the starting material instead of 2-(4-bromo-2-fluoro-6-hydroxy-phenyl)-8-chloro-chromen-4-one in Step 2. $^1$H NMR (DMSO-d$_6$, 400 MHz): δ ppm 7.95-7.98 (m, 2H), 7.52 (s, 1H), 7.49 (s, 1H), 7.45 (m, 1H), 7.22 (s, 1H), 6.80 (s, 1H), 4.35 (dd, J=5.3, 2.1 Hz, 2H), 4.27 (dd, J=5.3, 2.1 Hz, 2H), 4.17-4.19 (m, 2H), 3.95 (m, 1H), 3.67-3.70 (m, 2H), 2.53 (br s, 1H), 2.41-2.44 (m, 2H), 2.01-2.02 (m, 2H). (ESI$^+$)[(M+H)$^+$]:473.0.

Example C075: Cis-3-[2-[2-(8-chloro-4-oxo-chromen-2-yl)-4-(difluoromethyl)-5-methyl-phenoxy]ethoxy]cyclobutanecarboxylic acid

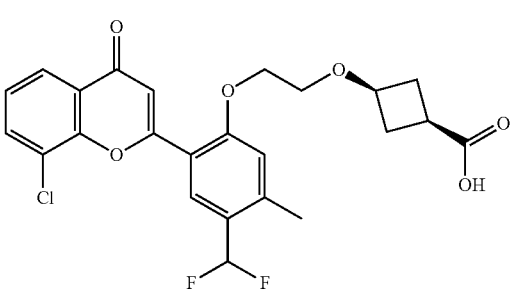

C075

Step 1: Preparation of 4-benzyloxy-2-methyl-benzaldehyde

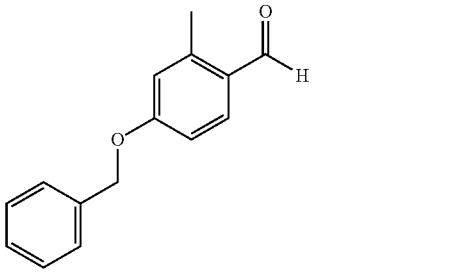

C075a

To a solution of 4-hydroxy-2-methyl-benzaldehyde (2000.0 mg, 14.69 mmol) in DMF (15 mL) were added potassium carbonate (2436.24 mg, 17.63 mmol) and benzyl bromide (1.83 mL, 15.42 mmol), then the mixture was stirred at 25° C. for 16 hours. After the reaction was completed, the reaction was quenched with water (150 mL) and the resulting solution was extracted with EtOAc (80 mL) three times. The combined organic layer was washed with brine (100 mL), dried over MgSO$_4$, filtered and the filtrate was concentrated in vacuo. The residue was purified by column chromatography on silica gel (eluted with PE:EtOAc=5:1) to give 4-benzyloxy-2-methyl-benzaldehyde (3200 mg, 96.27% yield) as a white solid. MS obsd. (ESI$^+$) [(M+H)$^+$]: 227.1.

Step 2: Preparation of 4-benzyloxy-5-bromo-2-methyl-benzaldehyde

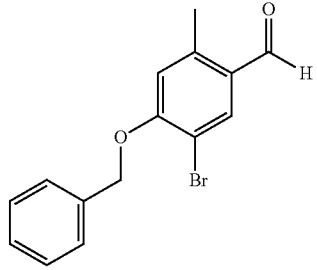

C075b

To a solution of 4-benzyloxy-2-methyl-benzaldehyde (3200.0 mg, 14.14 mmol) in methanol (40 mL) cooled in ice-bath was added pyridinium tribromide (6784.53 mg, 21.21 mmol) and the mixture was stirred at 25° C. for 3 hours. After the reaction was completed, the reaction was quenched with 10% $Na_2SO_3$ solution (150 mL) and the resulting solution was extracted with EtOAc (100 mL) three times. The combined organic layer was washed with brine (100 mL), dried over $Na_2SO_4$ and concentrated in vacuo. The residue was purified by column chromatography on silica gel (eluted with PE:EtOAc=5:1) to give 4-benzyloxy-5-bromo-2-methyl-benzaldehyde (3519 mg, 81.54% yield) as a white solid. MS obsd. (ESI$^+$) [(M+E1)$^+$]: 305.0.

Step 3: Preparation of methyl 2-benzyloxy-5-formyl-4-methyl-benzoate

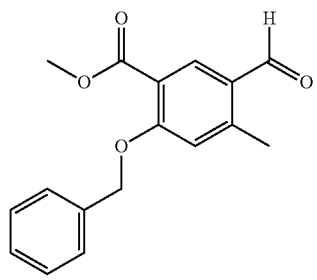

C075c

A mixture of 4-benzyloxy-5-bromo-2-methyl-benzaldehyde (3519.0 mg, 11.53 mmol), (dppf)$_2$PdCl$_2$ (2845.97 mg, 3.46 mmol), TEA (4.82 mL, 34.59 mmol) in methanol (100 mL) was stirred under CO (0.5 MPa) at 80° C. for 16 hours. After the reaction was completed and the reaction mixture was concentrated in vacuo. The residue was purified by column chromatography on silica gel (eluted with PE:EtOAc=5:1) to give methyl 2-benzyloxy-5-formyl-4-methyl-benzoate (2044 mg, 62.35% yield) as a white solid. MS obsd. (ESI$^+$) [(M+H)$^+$]: 285.2.

Step 4: Preparation of methyl 2-benzyloxy-5-(difluoromethyl)-4-methyl-benzoate

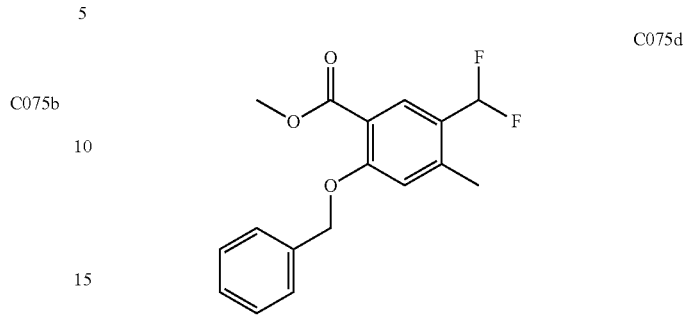

C075d

To a solution of methyl 2-benzyloxy-5-formyl-4-methyl-benzoate (2300.0 mg, 8.09 mmol) in DCM (40 mL) was added DAST (5.34 mL, 40.45 mmol) and then the reaction mixture was stirred at 25° C. for 16 hours. After the reaction was completed, the mixture was poured into ice water (100 mL) and the resulting mixture was extracted with DCM (50 mL) three times. The combined organic layer was washed with brine (50 mL), dried over MgSO$_4$, filtered and the filtrate was concentrated in vacuo. The residue was purified by column chromatography on silica gel (PE/EtOAc=10/1) to give methyl 2-benzyloxy-5-(difluoromethyl)-4-methyl-benzoate (2229 mg, 89.96% yield) as a white solid. MS obsd. (ESI$^+$) [(M+Na)$^+$]: 329.1.

Step 5: Preparation of [2-benzyloxy-5-(difluoromethyl)-4-methyl-phenyl]methanol

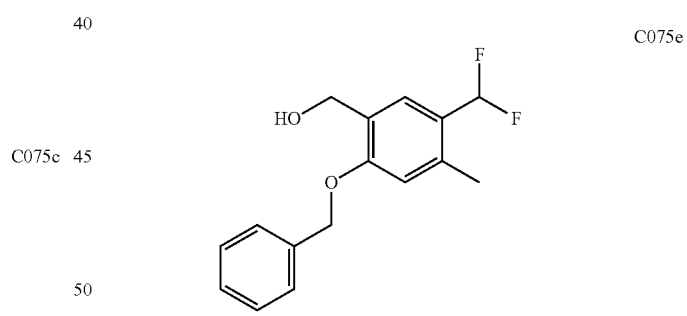

C075e

To a solution of methyl 2-benzyloxy-5-(difluoromethyl)-4-methyl-benzoate (2229.0 mg, 7.28 mmol) in THF (50 mL) was added LiAlH$_4$ (1104.68 mg, 29.11 mmol) at 0° C. and the mixture was stirred at 0° C. for 2 hours. After the reaction was completed, the reaction was quenched with 15% NaOH aqueous solution (1.1 mL) and water (3.3 mL). The resulting mixture was filtered and the filtrate was concentrated in vacuo to give [2-benzyloxy-5-(difluoromethyl)-4-methyl-phenyl]methanol (1824 mg, 90.07% yield) as a white solid, which was used in the next step directly without further purification. MS obsd. (ESI$^+$)[(M+Na)$^+$]: 301.1.

Step 6: Preparation of 2-benzyloxy-5-(difluoromethyl)-4-methyl-benzaldehyde

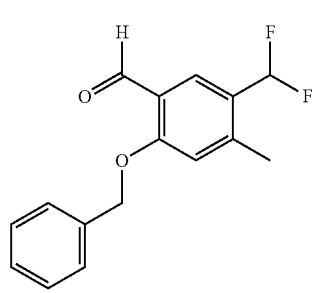
C075f

To a solution of [2-benzyloxy-5-(difluoromethyl)-4-methyl-phenyl]methanol (1824.0 mg, 6.55 mmol) in DCM (50 mL) was added MnO$_2$ (5698.06 mg, 65.54 mmol) and the mixture was stirred at 25° C. for 16 hours. After the reaction was completed, the mixture was filtered and the filtrate was concentrated in vacuo. The residue was purified by column chromatography on silica gel (eluted with PE:EtOAc=10:1) to give 2-benzyloxy-5-(difluoromethyl)-4-methyl-benzaldehyde (1696 mg, 93.66% yield) as a white solid. MS obsd. (ESI$^+$) [(M+Na)$^+$]: 299.1.

Step 7: Preparation of (E)-3-[2-benzyloxy-5-(difluoromethyl)-4-methyl-phenyl]-1-(3-chloro-2-hydroxy-phenyl)prop-2-en-1-one

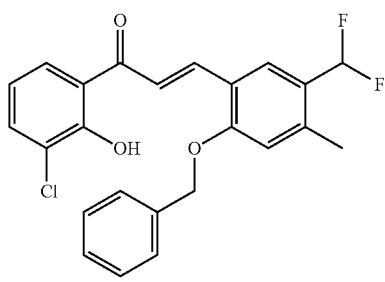
C075g

To a solution of 1-(3-chloro-2-hydroxy-phenyl)ethanone (950.0 mg, 5.57 mmol) and 2-benzyloxy-5-(difluoromethyl)-4-methyl-benzaldehyde (1692.4 mg, 6.13 mmol) in ethanol (100 mL) was added KOH (3124.4 mg, 55.69 mmol) and the mixture was stirred at 35° C. for 16 hours. After the reaction was completed and the reaction mixture was adjusted to pH~6 by addition of 1N HCl to give a yellow suspension. The suspension was filtered, the solid was washed with water and then dried in vacuo to give the crude (E)-3-[2-benzyloxy-5-(difluoromethyl)-4-methyl-phenyl]-1-(3-chloro-2-hydroxy-phenyl)prop-2-en-1-one (2240 mg, 93.79% yield) as a yellow solid which was used in the next step directly without further purification.

Step 8: Preparation of 2-[2-benzyloxy-5-(difluoromethyl)-4-methyl-phenyl]-8-chloro-chromen-4-one

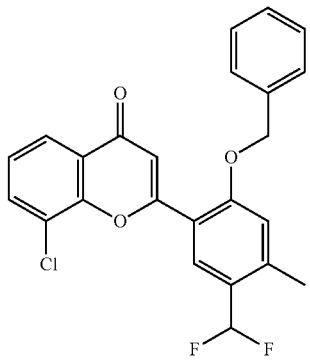
C075h

To a solution of (E)-3-[2-benzyloxy-5-(difluoromethyl)-4-methyl-phenyl]-1-(3-chloro-2-hydroxy-phenyl)prop-2-en-1-one (1250.0 mg, 2.91 mmol) in DMSO (250 mL) was added I$_2$ (51.78 mg, 0.200 mmol) and then the reaction mixture was stirred at 140° C. for 6 hours. After the reaction was completed, the reaction mixture was quenched with water (500 mL) and the resulting suspension was filtered. The solid was washed with EtOH and then dried in vacuo to give 2-[2-benzyloxy-5-(difluoromethyl)-4-methyl-phenyl]-8-chloro-chromen-4-one (1114 mg, 89.54% yield) as a light yellow solid which was used in the next step directly without further purification. MS obsd. (ESI$^+$) [(M+H)$^+$]: 427.0.

Step 9: Preparation of 8-chloro-2-[5-(difluoromethyl)-2-hydroxy-4-methyl-phenyl]chromen-4-one

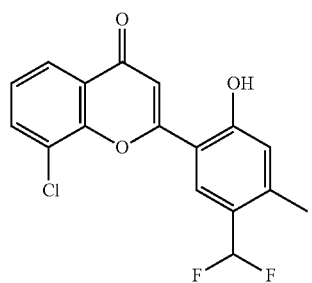
C075i

To a solution of 2-[2-benzyloxy-5-(difluoromethyl)-4-methyl-phenyl]-8-chloro-chromen-4-one (1100.0 mg, 2.58 mmol) in methanol (80 mL) was added Pd/C (10% Pd on carbon, 55% water) (110.0 mg, 2.58 mmol) and the reaction was stirred under H$_2$ atmosphere at 25° C. for 12 hours. After the reaction was completed, the mixture was filtered through celite, the filtrate was concentrated in vacuo to give the crude 8-chloro-2-[5-(difluoromethyl)-2-hydroxy-4-methyl-phenyl]chromen-4-one (600 mg, 69.14% yield) as a dark brown solid, which was used in the next step directly without further purification. MS obsd. (ESI$^+$) [(M+H)$^+$]: 337.0.

Step 10: Preparation of Cis-3-[2-[2-(8-chloro-4-oxo-chromen-2-yl)-4-(difluoromethyl)-5-methyl-phenoxy]ethoxy]cyclobutanecarboxylic acid

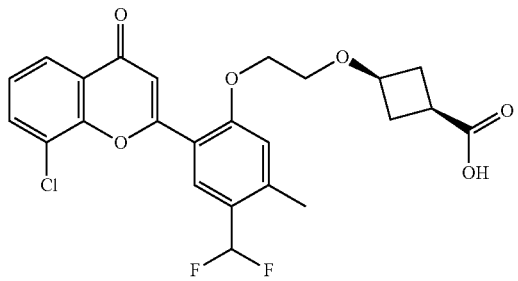

C075

Example C075 was prepared in analogy to the procedure described for the preparation of example C071 by using 8-chloro-2-[5-(difluoromethyl)-2-hydroxy-4-methyl-phenyl]chromen-4-one as the starting material instead of 2-(4-bromo-2-fluoro-6-hydroxy-phenyl)-8-chloro-chromen-4-one in Step 2. $^1$H NMR (DMSO-$d_6$, 400 MHz): δ ppm 12.08 (br s, 1H), 8.18 (s, 1H), 7.97-8.03 (m, 2H), 7.49 (t, J=7.9 Hz, 1H), 7.11-7.39 (m, 1H), 7.24 (s, 2H), 4.30-4.37 (m, 2H), 3.96 (quin, J=7.3 Hz, 1H), 3.69-3.78 (m, 2H), 2.38-2.52 (m, 6H), 1.95-2.05 (m, 2H). (ESI$^+$)[(M+H)$^+$]:478.9.

Example C076: Cis-3-[2-[2-(8-chloro-4-oxo-chromen-2-yl)-5-hydroxy-4-methoxy-phenoxy] ethoxy]cyclobutanecarboxylic acid

C076

Step 1: Preparation of 2-hydroxy-5-methoxy-4-[(4-methoxyphenyl)methoxy]benzaldehyde C076a To a mixture of 2,4-dihydroxy-5-methoxybenzaldehyde (785 mg, 4.67 mmol), sodium bicarbonate (471 mg, 5.6 mmol) in DMF (15 mL) was added 1-(chloromethyl)-4-methoxybenzene (877 mg, 5.6 mmol) and the mixture was stirred at 85° C. for 24 hours. After the reaction was completed, the reaction mixture was diluted with water (100 mL) and the resulting suspension was filtered. The solid was collected and dried in vacuo to give the crude 2-hydroxy-5-methoxy-4-[(4-methoxyphenyl)methoxy]benzaldehyde (1.06 g, 71%) as a brown solid, which was directly used for next step directly without further purification. MS obsd. (ESI$^+$) [(M+H)$^+$]: 288.7.

Step 2: Preparation of cis-tert-butyl 3-[2-[2-formyl-4-methoxy-5-[(4-methoxyphenyl)methoxy]phenoxy] ethoxy]cyclobutanecarboxylate

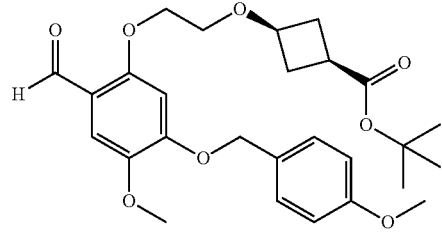

C076b

A mixture of 2-hydroxy-5-methoxy-4-((4-methoxybenzyl)oxy)benzaldehyde (1.06 g, 3.31 mmol), cis-tert-butyl 3-[2-(p-tolylsulfonyloxy)ethoxy]cyclobutanecarboxylate (1.35 g, 3.64 mmol) and K$_2$CO$_3$ (915 mg, 6.62 mmol) in DMF (10 mL) was heated to 50° C. for 20 hours. After the reaction mixture was completed, the reaction mixture was diluted with water (50 mL) and EtOAc (50 ml) three times. The combined organic layer was washed with brine, dried over anhydrous Na$_2$SO$_4$ and concentrated in vacuo to give the crude cis-tert-butyl 3-[2-[2-formyl-4-methoxy-5-[(4-methoxyphenyl)methoxy]phenoxy]ethoxy]cyclobutanecarboxylate (1.91 g, 93.9% yield) as a dark brown oil, which was used in the next step directly without further purification. MS obsd. (ESI$^+$) [(M+H)$^+$]: 486.8.

Step 3: Preparation of Cis-3-[2-[2-(8-chloro-4-oxo-chromen-2-yl)-5-hydroxy-4-methoxy-phenoxy] ethoxy]cyclobutanecarboxylic acid

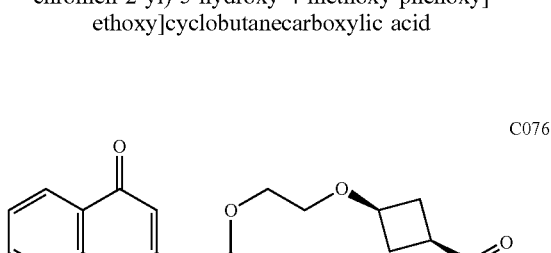

C076

A mixture of cis-tert-butyl 3-[2-[2-formyl-4-methoxy-5-[(4-methoxyphenyl)methoxy]phenoxy]ethoxy]cyclobutanecarboxylate (1.6 g, 2.63 mmol), 1-(3-chloro-2-hydroxyphenyl)ethan-1-one (494 mg, 2.89 mmol) and pyrrolidine (93.6 mg, 1.32 mmol) in DMSO (10 mL) was stirred at 100° C. for 30 minutes. After the reaction was completed, the reaction mixture was diluted with water (50 ml), extracted with EtOAc (50 mL) three times. The combined organic layer was washed with 2 N HCl, water, brine, dried over anhydrous $Na_2SO_4$ and then concentrated in vacuo to give light brown oil. The brown oil was dissolved in DMSO (10 mL) and to the resulting solution was added $I_2$ (66.8 mg, 0.26 mmol), the mixture was then stirred at 140° C. for 3 hours. After the reaction was completed, the reaction mixture was cooled to room temperature and then diluted with water (50 mL). The resulting mixture was extracted with EtOAc (50 mL) three times. The combined organic layer was directly concentrated in vacuo to give the crude Cis-[2-[2-(8-chloro-4-oxo-chromen-2-yl)-5-hydroxy-4-methoxy-phenoxy]ethoxy]cyclobutanecarboxylic acid (2.76 g) as a dark oil which was directly used for next step without purification. $^1$H NMR (DMSO-$d_6$, 400 MHz): δ ppm 10.17 (s, 1H), 7.94-8.01 (m, 2H), 7.61 (s, 1H), 7.46 (s, 1H), 7.20-7.23 (m, 1H), 7.06-7.10 (m, 1H), 6.93-6.98 (m, 1H), 4.11-4.19 (m, 2H), 3.96 (br t, J=6.8 Hz, 1H), 3.83 (s, 3H), 3.66-3.73 (m, 2H), 2.76-2.80 (m, 1H), 2.38-2.45 (m, 2H), 1.91-2.05 (m, 2H). (ESI$^+$)[(M+H)$^+$]:MS obsd. (ESI$^+$) [(M+H)$^+$]: 461.1

Example C077: Cis-3-[2-[2-(8-chloro-4-oxo-chromen-2-yl)-4-methoxy-5-propoxy-phenoxy]ethoxy]cyclobutanecarboxylic acid

C077

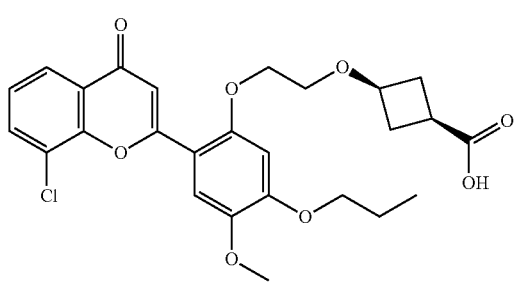

Step 1: Preparation of cis-propyl 3-[2-[2-(8-chloro-4-oxo-chromen-2-yl)-4-methoxy-5-propoxy-phenoxy]ethoxy]cyclobutanecarboxylate C077a

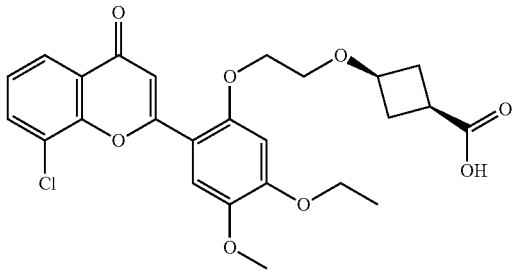

To a mixture of cis-3-[2-[2-(8-chloro-4-oxo-chromen-2-yl)-5-hydroxy-4-methoxy-phenoxy]ethoxy]cyclobutanecarboxylic acid (346 mg, 0.3 mmol), $K_2CO_3$ (166 mg, 1.2 mmol) and NaI (45 mg, 0.3 mmol) in DMF (3 mL) was added 1-bromopropane (111 mg, 0.9 mmol) and the mixture was then stirred at 70° C. for 16 hours. After the reaction was completed, the reaction mixture was diluted with water (30 mL) and extracted with EtOAc (100 mL) three times. The combined organic layer was washed with water, brine, dried over anhydrous $Na_2SO_4$ and concentrated in vacuo to give the crude cis-propyl 3-[2-[2-(8-chloro-4-oxo-chromen-2-yl)-4-methoxy-5-propoxy-phenoxy]ethoxy]cyclobutanecarboxylate (152 mg, 92.9% yield) as a dark brown oil, which was used in the next step directly without further purification. MS obsd. (ESI$^+$) [(M+H)$^+$]: 545.2

Step 2: Preparation of Cis-3-[2-[2-(8-chloro-4-oxo-chromen-2-yl)-4-methoxy-5-propoxy-phenoxy]ethoxy]cyclobutanecarboxylic acid

C077

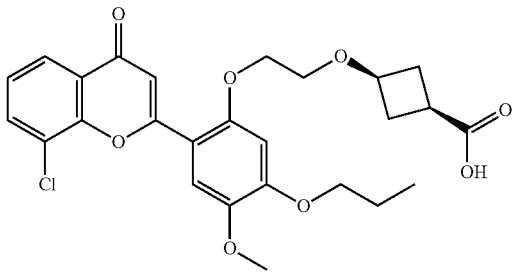

To a solution of cis-propyl 3-[2-[2-(8-chloro-4-oxo-chromen-2-yl)-4-methoxy-5-propoxy-phenoxy]ethoxy]cyclobutanecarboxylate (152 mg, 0.28 mmol) in THF (4 ml) and water (1 ml) was added lithium hydroxide monohydrate (58.2 mg, 1.39 mmol) and the mixture was then stirred at room temperature for 16 hours. After the reaction was completed, the mixture was adjusted to PH~3 by addition of 1N HCl. The reaction was then concentrated in vacuo and the residue was purified by Prep-HPLC to give cis-3-[2-[2-(8-chloro-4-oxo-chromen-2-yl)-4-methoxy-5-propoxy-phenoxy]ethoxy]cyclobutanecarboxylic acid (50 mg, 35.6% yield) as a yellow solid. $^1$H NMR (DMSO-$d_6$, 400 MHz) δ ppm 12.10 (s, 1H), 8.00-7.94 (m, 2H), 7.60 (s, 1H), 7.47 (t, J=7.9 Hz, 1H), 7.24 (s, 1H), 6.89 (s, 1H), 4.32-4.25 (m, 2H), 4.08 (t, J=6.6 Hz, 2H), 4.01-3.91 (m, 1H), 3.82 (s, 3H), 3.73-3.67 (m, 2H), 2.59-2.52 (m, 1H), 2.47-2.39 (m, 2H), 2.06-1.95 (m, 2H), 1.85-1.73 (m, 2H), 1.01 (t, J=7.4 Hz, 3H). MS obsd. (ESI$^+$) [(M+H)$^+$]: 503.3.

Example 078: Cis-3-[2-[2-(8-chloro-4-oxo-chromen-2-yl)-5-ethoxy-4-methoxy-phenoxy]ethoxy]cyclobutanecarboxylic acid

C078

Example C078 was prepared in analogy to the procedure described for the preparation of example C077 by using iodoethane as the starting material instead of 1-bromopropane in Step 1. $^1$H NMR (DMSO-$d_6$, 400 MHz): δ ppm 12.10 (br s, 1H), 7.97 (dq, J=7.9, 1.7 Hz, 2H), 7.55-7.62 (m, 1H), 7.47 (t, J=7.9 Hz, 1H), 7.24 (s, 1H), 6.88 (s, 1H), 4.26-4.33 (m, 2H), 4.13-4.22 (m, 2H), 3.90-4.03 (m, 1H), 3.78-3.86 (m, 3H), 3.64-3.75 (m, 2H), 2.53-2.58 (m, 1H), 2.38-2.47 (m, 2H), 1.92-2.07 (m, 2H), 1.38 (t, J=7.0 Hz, 3H). (ESI$^+$)[(M+H)$^+$]:489.2.

Example 079: Cis-3-[2-[2-(8-chloro-4-oxo-chromen-2-yl)-5-(cyclopropylmethoxy)-4-methoxy-phenoxy]ethoxy]cyclobutanecarboxylic acid

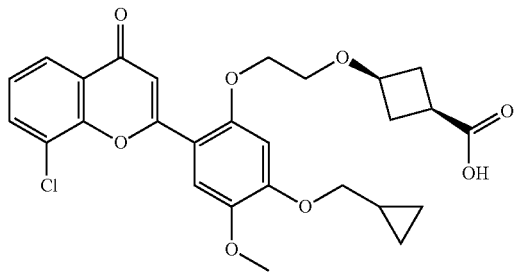

C079

Example C079 was prepared in analogy to the procedure described for the preparation of example C077 by using bromomethylcyclopropane as the starting material instead of 1-bromopropane in Step 1. $^1$H NMR (DMSO-$d_6$, 400 MHz) δ ppm 12.04 (br s, 1H), 8.01-7.94 (m, 2H), 7.60 (s, 1H), 7.47 (t, J=7.9 Hz, 1H), 7.24 (s, 1H), 6.85 (s, 1H), 4.30-4.25 (m, 2H), 4.01-3.91 (m, 3H), 3.83 (s, 3H), 3.72-3.68 (m, 2H), 2.59-2.52 (m, 1H), 2.47-2.38 (m, 2H), 2.05-1.95 (m, 2H), 1.34-1.26 (m, 1H), 0.65-0.58 (m, 2H), 0.39-0.32 (m, 2H). MS obsd. (ESI$^+$) [(M+H)$^+$]: 515.1.

Example 080: Cis-3-[2-[2-(8-chloro-4-oxo-chromen-2-yl)-4-methoxy-5-(2,2,2-trifluoroethoxy)phenoxy]ethoxy]cyclobutanecarboxylic acid

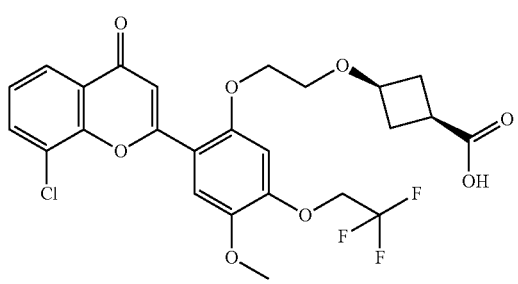

C080

Example C080 was prepared in analogy to the procedure described for the preparation of example C077 by using 1,1,1-trifluoro-2-iodoethane as the starting material instead of 1-bromopropane in Step 1. $^1$H NMR (DMSO-$d_6$, 400 MHz) δ ppm 12.05 (br s, 1H), 8.02-7.95 (m, 2H), 7.65 (s, 1H), 7.48 (t, J=7.9 Hz, 1H), 7.24 (s, 1H), 7.05 (s, 1H), 4.92 (q, J=8.8 Hz, 2H), 4.32-4.26 (m, 2H), 4.00-3.89 (m, 1H), 3.85 (s, 3H), 3.73-3.68 (m, 2H), 2.52 (d, J=1.8 Hz, 1H), 2.46-2.37 (m, 2H), 2.06-1.94 (m, 2H). MS obsd. (ESI$^+$) [(M+H)$^+$]: 543.1

Example C081: Cis-3-[2-[2-(8-chloro-4-oxo-chromen-2-yl)-5-(difluoromethoxy)-4-methoxy-phenoxy]ethoxy]cyclobutanecarboxylic acid

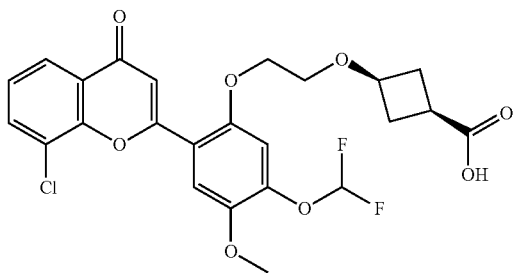

C081

Example C081 was prepared in analogy to the procedure described for the preparation of example C077 by using sodium chlorodifluoroacetate as the starting material instead of 1-bromopropane in Step 1. $^1$H NMR (DMSO-$d_6$, 400 MHz) δ ppm 12.01 (br s, 1H), 8.05-7.97 (m, 2H), 7.73 (s, 1H), 7.53-7.47 (m, 1H), 7.31-7.10 (m, 2H), 4.29-4.22 (m, 2H), 3.97-3.87 (m, 4H), 3.71-3.65 (m, 2H), 2.52-2.59 (m, 1H), 2.44-2.35 (m, 2H), 2.04-1.93 (m, 2H). MS obsd. (ESI$^+$) [(M+H)$^+$]: 511.2.

Example C082: cis-3-[2-[2-(8-chloro-4-oxo-chromen-2-yl)-4-(cyclopropylmethoxy)-5-methoxy-phenoxy]ethoxy]cyclobutanecarboxylic acid

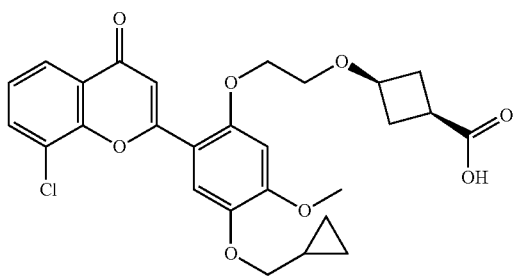

C082

Step 1: Preparation of 2-fluoro-5-hydroxy-4-methoxy-benzaldehyde

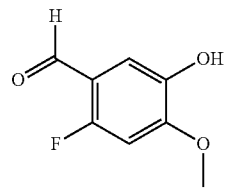

C082a

A mixture of 6-fluoroveratraldehyde (3600.0 mg, 19.55 mmol) in sulfuric acid (36.0 mL) was stirred at 95° C. under nitrogen for 6 hours. Then the resulting mixture was poured into ice water (150 g) and the resulting suspension was filtered. The filtered cake was washed with water (100 mL) twice and dried in vacuo to give 2-fluoro-5-hydroxy-4-methoxy-benzaldehyde (3025 mg, 1 90.95% yield, purity) as a brown solid. MS obsd. (ESI$^+$) [(M+H)$^+$]: 171.1.

Step 2: Preparation of 5-(cyclopropylmethoxy)-2-fluoro-4-methoxy-benzaldehyde

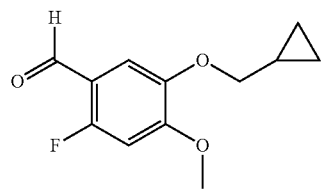

C082b

To a solution of 2-fluoro-5-hydroxy-4-methoxy-benzaldehyde (1000.0 mg, 5.88 mmol), bromomethylcyclopropane (0.86 mL, 8.82 mmol) in DMF (25 mL) was added K$_2$CO$_3$ (3249.23 mg, 23.51 mmol) and the mixture was stirred at 80° C. for 2 hours. After the reaction was completed, the reaction mixture was diluted with water (100 mL) and the resulting mixture was extracted with EtOAc (50 mL) three times. The combined organic layer was washed with brine (50 mL) twice, dried over Na$_2$SO$_4$ and concentrated in vacuo. The residue was purified by column chromatography on silica gel (eluted with PE:EtOAc=6:1) to give 5-(cyclopropylmethoxy)-2-fluoro-4-methoxy-benzaldehyde (1050 mg, 79.67% yield) as a white solid. MS obsd. (ESI$^+$) [(M+H)$^+$]: 225.2.

Step 3: Preparation of 5-(cyclopropylmethoxy)-4-methoxy-2-[(4-methoxyphenyl)methoxy]benzaldehyde

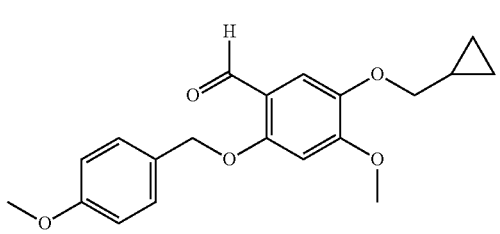

C082c

To a mixture of 5-(cyclopropylmethoxy)-2-fluoro-4-methoxy-benzaldehyde (1000.0 mg, 4.46 mmol), Cs$_2$CO$_3$ (726.53 mg, 2.23 mmol) was added 4-methoxybenzyl alcohol (6161.53 mg, 44.6 mmol) and the mixture was stirred at 120° C. under microwave condition for 1 hour. The mixture was purified by reversed phase column chromatography (eluent with water/MeOH=1:3) to give 5-(cyclopropylmethoxy)-4-methoxy-2-[(4-methoxyphenyl)methoxy]benzaldehyde (515 mg, 33.73% yield) as a white solid. MS obsd. (ESI$^+$) [(M+Na)$^+$]: 365.0.

Step 4: Preparation of 8-chloro-2-[5-(cyclopropylmethoxy)-2-hydroxy-4-methoxy-phenyl]chromen-4-one

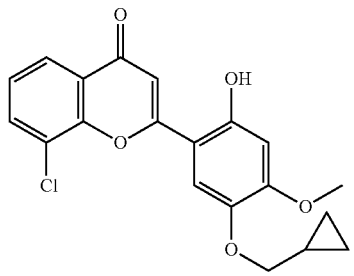

C082d

Compound C082d was prepared in analogy to the procedure described for the preparation of compound C075i by using 5-(cyclopropylmethoxy)-4-methoxy-2-[(4-methoxyphenyl)methoxy]benzaldehyde as the starting material instead of 2-benzyloxy-5-(difluoromethyl)-4-methyl-benzaldehyde in Step 7.

Step 5: Preparation of cis-tert-butyl 3-[2-[2-(8-chloro-4-oxo-chromen-2-yl)-4-(cyclopropylmethoxy)-5-methoxy-phenoxy]ethoxy]cyclobutanecarboxylate

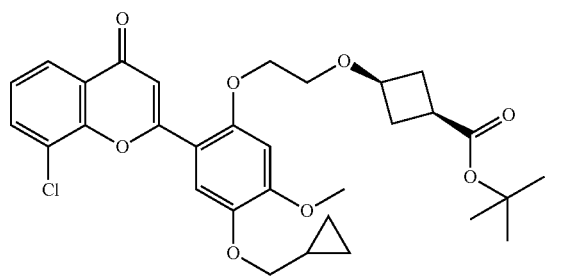

C082e

Compound C082e was prepared in analogy to the procedure described for the preparation of compound C071b by using 8-chloro-2-[5-(cyclopropylmethoxy)-2-hydroxy-4-methoxy-phenyl]chromen-4-one as the starting material instead of 2-(4-bromo-2-fluoro-6-hydroxy-phenyl)-8-chloro-chromen-4-one in Step 7.

Step 6: Preparation of cis-3-[2-[2-(8-chloro-4-oxo-chromen-2-yl)-4-(cyclopropylmethoxy)-5-methoxy-phenoxy]ethoxy]cyclobutanecarboxylic acid

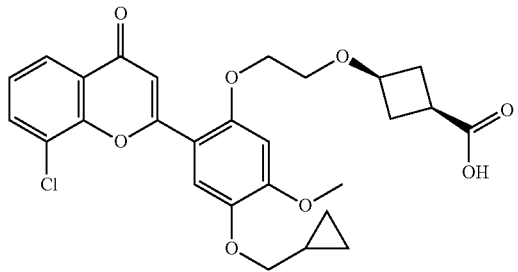

C082

To a solution of cis-tert-butyl 3-[2-[2-(8-chloro-4-oxo-chromen-2-yl)-4-(cyclopropylmethoxy)-5-methoxy-phenoxy]ethoxy]cyclobutanecarboxylate (80.0 mg, 0.140 mmol) in DCM (15 mL) was added TFA (1.2 mL, 15.58 mmol) and the mixture was stirred at 25° C. for 1 hour. The mixture was then concentrated in vacuo and the residue was purified by Prep-HPLC to give cis-3-[2-[2-(8-chloro-4-oxo-chromen-2-yl)-4-(cyclopropylmethoxy)-5-methoxy-phenoxy]ethoxy]cyclobutanecarboxylic acid (43 mg, 58.35% yield) as a light yellow solid. $^1$H NMR (DMSO-$d_6$, 400 MHz): δ ppm. 12.12 (br s, 1H), 7.97 (dq, J=7.9, 1.7 Hz, 2H), 7.59 (s, 1H), 7.47 (t, J=7.9 Hz, 1H), 7.22 (s, 1H), 6.90 (s, 1H), 4.28-4.34 (m, 2H), 3.89-3.98 (m, 4H), 3.84 (d, J=7.0 Hz, 2H), 3.68-3.74 (m, 2H), 2.35-2.47 (m, 3H), 1.96-2.05 (m, 2H), 1.20-1.30 (m, 1H), 0.55-0.60 (m, 2H), 0.29-0.37 (m, 2H). MS obsd. (ESI$^+$)[(M+H)$^+$]: 514.9.

Example C083: cis-3-[2-[2-(8-chloro-4-oxo-chromen-2-yl)-4-hydroxy-5-methoxy-phenoxy]ethoxy]cyclobutanecarboxylic acid

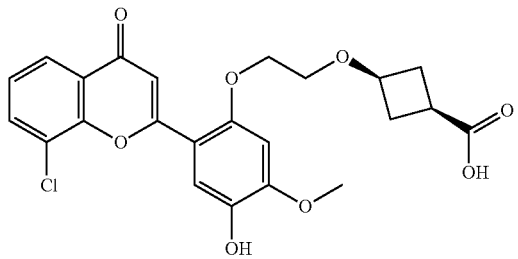

C083

A mixture of cis-tert-butyl 3-[2-[2-(8-chloro-4-oxo-chromen-2-yl)-4-(cyclopropylmethoxy)-5-methoxy-phenoxy]ethoxy]cyclobutanecarboxylate (50.0 mg, 0.090 mmol) in TFA (3.0 mL, 38.94 mmol) was stirred at 40° C. for 1 hour. The mixture was then concentrated in vacuo and the residue was purified by Prep-HPLC to give cis-3-[2-[2-(8-chloro-4-oxo-chromen-2-yl)-4-hydroxy-5-methoxy-phenoxy]ethoxy]cyclobutanecarboxylic acid (25.2 mg, 62.38% yield) as a yellow solid. $^1$H NMR (DMSO-$d_6$, 400 MHz): δ ppm 9.11 (s, 1H), 7.97 (ddd, J=7.9, 1.6 Hz, 2H), 7.53 (s, 1H), 7.46 (t, J=7.9 Hz, 1H), 7.25 (s, 1H), 6.85 (s, 1H), 4.24-4.29 (m, 2H), 3.96 (t, J=7.0 Hz, 1H), 3.90 (s, 3H), 3.67-3.73 (m, 2H), 2.52-2.56 (m, 1H), 2.35-2.47 (m, 2H), 1.97-2.08 (m, 2H). (ESI$^+$)[(M+H)$^+$]: 460.9.

Example C084: cis-3-[2-[2-(8-chloro-4-oxo-chromen-2-yl)-4-ethoxy-5-methoxy-phenoxy]ethoxy]cyclobutanecarboxylic acid

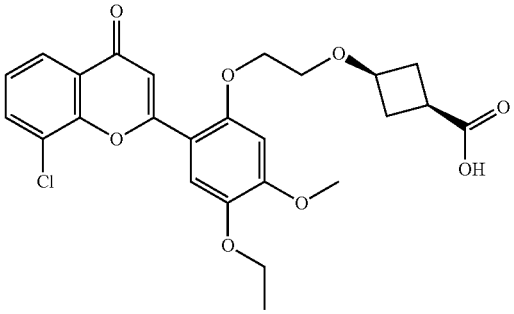 [SMILES: CCOc1ccc(OCCO[C@H]2C[C@@H](C(=O)O)C2)c(-c2cc(=O)c3cccc(Cl)c3o2)c1]

C084

Example C084 was prepared in analogy to the procedure described for the preparation of example C082 by using iodoethane as the starting material instead of bromomethylcyclopropane in Step 2. $^1$H NMR (DMSO-$d_6$, 400 MHz): δ ppm 7.94-8.00 (m, 2H), 7.59 (s, 1H), 7.47 (t, J=7.9 Hz, 1H), 7.24 (s, 1H), 6.89 (s, 1H), 4.24-4.36 (m, 2H), 3.88-4.09 (m, 6H), 3.65-3.77 (m, 2H), 2.52-2.58 (m, 1H), 2.38-2.48 (m, 2H), 1.96-2.08 (m, 2H), 1.36 (t, J=7.0 Hz, 3H). (ESI$^+$)[(M+H)$^+$]:489.0.

Example C085: cis-3-[2-[2-(8-chloro-4-oxo-chromen-2-yl)-5-methoxy-4-(2,2,2-trifluoroethoxy)phenoxy]ethoxy]cyclobutanecarboxylic acid

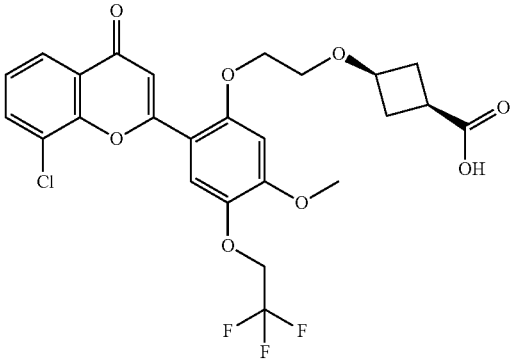

C085

Example C085 was prepared in analogy to the procedure described for the preparation of example C082 by using 2,2,2-trifluoroethyl trifluoromethanesulfonate as the starting material instead of bromomethylcyclopropane in Step 2. $^1$H NMR (DMSO-$d_6$, 400 MHz): δ ppm 12.11 (br s, 1H), 7.96-8.01 (m, 2H), 7.69 (s, 1H), 7.48 (t, J=7.9 Hz, 1H), 7.20 (s, 1H), 6.96 (s, 1H), 4.70 (q, J=9.0 Hz, 2H), 4.28-4.38 (m, 1H), 3.95 (s, 3H), 3.67-3.77 (m, 2H), 2.52-2.57 (m, 3H), 2.38-2.47 (m, 2H), 1.95-2.04 (m, 2H). (ESI$^+$)[(M+H)$^+$]: 543.1.

Example C086: cis-3-[2-[2-(8-chloro-4-oxo-chromen-2-yl)-4-(difluoromethoxy)-5-methoxy-phenoxy]ethoxy]cyclobutanecarboxylic acid

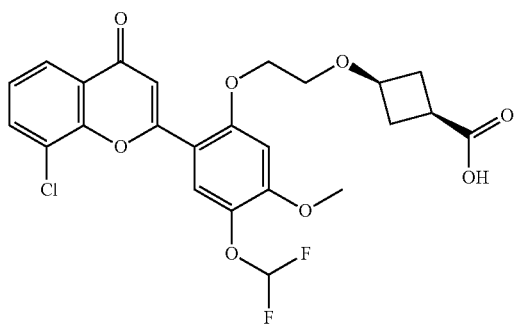

C086

Example C086 was prepared in analogy to the procedure described for the preparation of example C082 by using sodium chlorodifluoroacetate as the starting material instead of bromomethylcyclopropane in Step 2. $^1$H NMR (DMSO-$d_6$, 400 MHz): δ ppm 12.12 (br s, 1H), 7.94-8.03 (m, 2H), 7.85 (s, 1H), 7.48 (t, J=7.9 Hz, 1H), 7.24 (s, 1H), 6.95 (br d, 1H), 6.87 (s, 1H), 4.34-4.42 (m, 2H), 3.89-4.06 (m, 4H), 3.70-3.83 (m, 2H), 2.52-2.59 (m, 1H), 2.37-2.47 (m, 2H), 1.95-2.07 (m, 2H). (ESI$^+$)[(M+H)$^+$]:511.1.

Example C087: cis-3-[2-[2-(8-chloro-4-oxo-chromen-2-yl)-4,5-bis(difluoromethoxy)phenoxy]ethoxy]cyclobutanecarboxylic acid

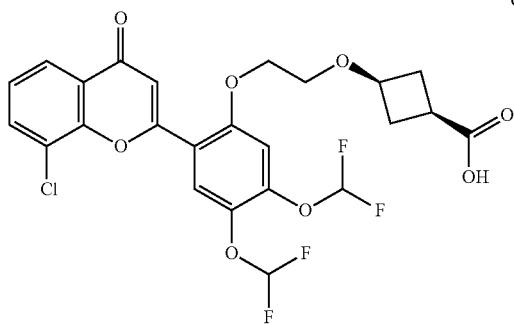

C087

Step 1: Preparation of cis-tert-butyl 3-[2-[[6-(8-chloro-4-oxo-chromen-2-yl)-1,3-benzodioxol-5-yl]oxy]ethoxy]cyclobutanecarboxylate C087a Compound C087a was prepared in analogy to the procedure described for the preparation of compound C071b by using 8-chloro-2-(6-hydroxy-1,3-benzodioxol-5-yl)chromen-4-one as the starting material instead of 2-(4-bromo-2-fluoro-6-hydroxy-phenyl)-8-chloro-chromen-4-one in Step 7.

Step 2: Preparation of cis-3-[2-[2-(8-chloro-4-oxo-chromen-2-yl)-4,5-dihydroxy-phenoxy]ethoxy]cyclobutanecarboxylic acid C087b

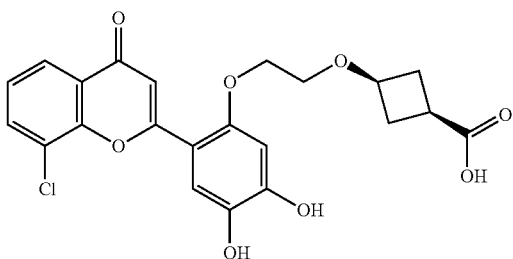

To a solution of cis-tert-butyl 3-[2-[[6-(8-chloro-4-oxo-chromen-2-yl)-1,3-benzodioxol-5-yl]oxy]ethoxy]cyclobutanecarboxylate (250.0 mg, 0.490 mmol) in DCM (20 mL) was added AlCl$_3$ (517.88 mg, 3.88 mmol) and the mixture was stirred at 30° C. for 1 hour. The reaction was quenched with water (25 mL) and the resulting mixture was extracted with DCM (25 mL) twice. The combined organic layer was washed with brine, dried over MgSO$_4$, filtered and the filtrate was concentrated in vacuo to give the crude cis-3-[2-[2-(8-chloro-4-oxo-chromen-2-yl)-4,5-dihydroxy-phenoxy]ethoxy]cyclobutanecarboxylic acid (210 mg, 89.1% yield) as a red solid. (ESI$^+$)[(M+H)$^+$]:477.1.

Step 3: Preparation of cis-methyl 3-[2-[2-(8-chloro-4-oxo-chromen-2-yl)-4,5-dihydroxy-phenoxy]ethoxy]cyclobutanecarboxylate

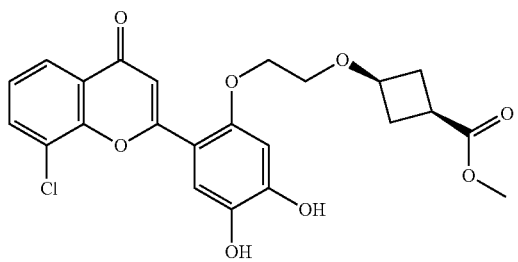

C087c

To a solution of cis-3-[2-[2-(8-chloro-4-oxo-chromen-2-yl)-4,5-dihydroxy-phenoxy]ethoxy]cyclobutanecarboxylic acid (350.0 mg, 0.780 mmol) in MeOH (40 mL) was added $SOCl_2$ (1.0 mL, 0.780 mmol) and the resulting mixture was stirred at 30° C. for 3 hours. Then the reaction mixture was concentrated in vacuo and the residue was purified by column chromatography on silica gel (eluted with PE/EtOAc=3:1 to 1:10) to give cis-methyl 3-[2-[2-(8-chloro-4-oxo-chromen-2-yl)-4,5-dihydroxy-phenoxy]ethoxy]cyclobutanecarboxylate (280 mg, 77.56% yield) as a light yellow solid.

Step 4: Preparation of cis-methyl 3-[2-[2-(8-chloro-4-oxo-chromen-2-yl)-4,5-bis(difluoromethoxy)phenoxy]ethoxy]cyclobutanecarboxylate

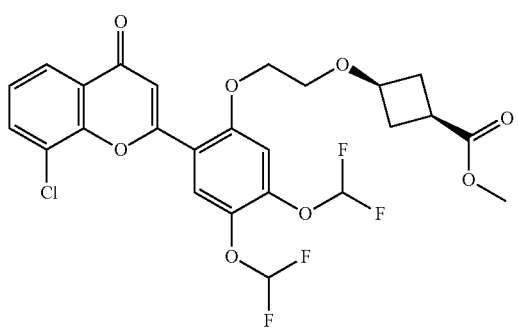

C087d

To a solution of cis-methyl 3-[2-[2-(8-chloro-4-oxo-chromen-2-yl)-4,5-dihydroxy-phenoxy]ethoxy]cyclobutanecarboxylate (120.0 mg, 0.260 mmol), (2-chloro-2,2-difluoro-acetyl)oxysodium (79.4 mg, 0.520 mmol) in DMF (8 mL) was added $Cs_2CO_3$ (254.51 mg, 0.780 mmol) and the mixture was stirred at 80° C. for 3 hours. The mixture was then concentrated in vacuo and the residue was purified by column chromatography on silica gel (eluted with PE:EtOAc=3:1) to give cis-methyl 3-[2-[2-(8-chloro-4-oxo-chromen-2-yl)-4,5-bis(difluoromethoxy)phenoxy]ethoxy]cyclobutanecarboxylate (65 mg, 044.51% yield) as a yellow solid. MS obsd. (ESI$^+$)[(M+H)$^+$]: 561.1.

Step 5: Preparation of cis-3-[2-[2-(8-chloro-4-oxo-chromen-2-yl)-4,5-bis(difluoromethoxy)phenoxy]ethoxy]cyclobutanecarboxylic acid

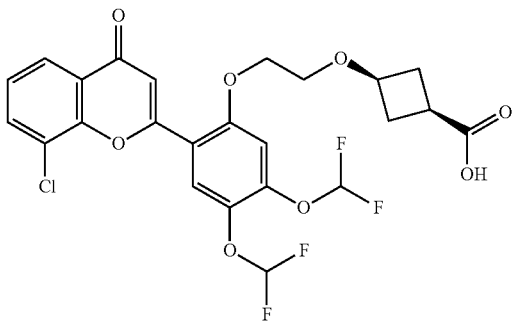

C087

To a solution of cis-methyl 3-[2-[2-(8-chloro-4-oxo-chromen-2-yl)-4,5-bis(difluoromethoxy)phenoxy]ethoxy]cyclobutanecarboxylate (60.0 mg, 0.110 mmol) in THF (5 mL) and water (1 mL) was added LiOH (11 mg, 0.50 mmol). The reaction mixture was stirred at room temperature for 2 hours. Then the mixture was adjusted to pH ~5 by addition of 2N HCl. The resulting mixture was concentrated in vacuo and the residue was purified by Prep-HPLC to give 3-[2-[2-(8-chloro-4-oxo-chromen-2-yl)-4,5-bis(difluoromethoxy)phenoxy]ethoxy]cyclobutanecarboxylic acid (12 mg, 20.1% yield) as an off-white solid. $^1$H NMR (DMSO-$d_6$, 400 MHz): δ ppm 7.99-8.04 (m, 2H), 7.96 (s, 1H), 7.50 (t, J=7.9 Hz, 1H), 7.43 (dd, 1H), 7.28 (m, 1H), 7.23 (s, 1H), 7.18 (dd, 1H), 4.28-4.40 (m, 2H), 3.82-4.06 (m, 1H), 3.66-3.76 (m, 2H), 2.25-2.46 (m, 3H), 1.93-2.04 (m, 2H). MS obsd. (ESI$^+$)[(M+H)$^+$]: 547.1.

Example C088: Cis-3-[2-[2-(8-chloro-4-oxo-chromen-2-yl)-4,5-diethoxy-phenoxy]ethoxy]cyclobutanecarboxylic acid

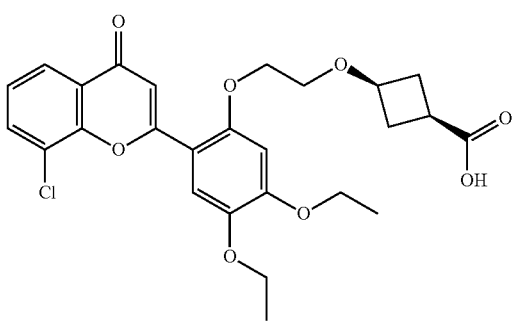

C088

Example C088 was prepared in analogy to the procedure described for the preparation of example C077 by using cis-3-[2-[2-(8-chloro-4-oxo-chromen-2-yl)-4,5-dihydroxy-phenoxy]ethoxy]cyclobutanecarboxylic acid and iodoethane as the starting material instead of cis-3-[2-[2-(8-chloro-4-oxo-chromen-2-yl)-5-hydroxy-4-methoxy-phenoxy]ethoxy]cyclobutanecarboxylic acid and 1-bromopropane in Step 1. $^1$H NMR (DMSO-$d_6$, 400 MHz): δ ppm 12.09 (s, 1H), 7.97

(dd, J=7.8, 3.3 Hz, 2H), 7.60 (s, 1H), 7.47 (t, J=7.9 Hz, 1H), 7.24 (s, 1H), 6.88 (s, 1H), 4.25-4.29 (m, 2H), 4.19 (dd, J=13.9, 6.9 Hz, 2H), 4.08 (dd, J=13.9, 6.9 Hz, 2H), 3.93-4.09 (m, 1H), 3.70 (s, 2H), 2.42 (dd, J=12.1, 4.8 Hz, 3H), 1.94-2.07 (m, 2H), 1.37 (dd, J=15.3, 7.0 Hz, 6H). (ESI$^+$) [(M+H)$^+$]:503.0.

Example C089: Cis-3-[2-[2-(8-chloro-4-oxo-chromen-2-yl)-5-methoxy-4-(trifluoromethoxy)phenoxy]ethoxy]cyclobutanecarboxylic acid

C089

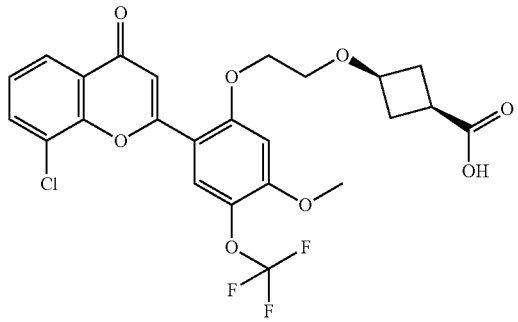

Step 1: Preparation of cis-tert-butyl 3-[2-[5-bromo-2-formyl-4-(trifluoromethoxy)phenoxy]ethoxy]cyclobutanecarboxylate

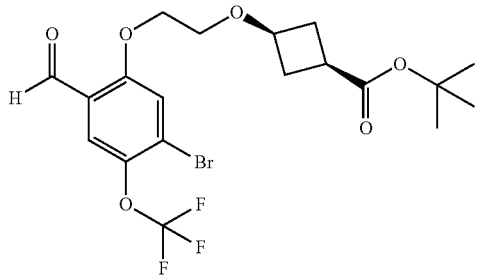 [SMILES: CC(C)(C)OC(=O)[C@H]1C[C@@H](OCCOc2cc(Br)c(OC(F)(F)F)cc2C=O)C1]

To a mixture of 4-bromo-2-hydroxy-5-(trifluoromethoxy)benzaldehyde (221.8 mg, 0.780 mmol), cis-tert-butyl 3-[2-(p-tolylsulfonyloxy)ethoxy]cyclobutanecarboxylate (432.44 mg, 1.17 mmol) in DMF (20 mL) was added K$_2$CO$_3$ (537.77 mg, 3.89 mmol) and the reaction was stirred at 80° C. for 4 hours. The reaction was diluted with water (200 mL) and the resulting mixture was extracted with EtOAc (150 mL) three times. The combined organic layer was washed with water (100 mL) twice, brine (100 mL), dried over Na$_2$SO$_4$ and concentrated in vacuo. The residue was purified by column chromatography on silica gel (eluent with PE:EtOAc=4:1) to give cis-tert-butyl 3-[2-[5-bromo-2-formyl-4-(trifluoromethoxy)phenoxy]ethoxy]cyclobutanecarboxylate (300 mg, 79.77% yield) as a colorless oil. MS obsd. (ESI$^+$) [(M+Na)$^+$]: 505.0.

Step 2: Preparation of cis-tert-butyl 3-[2-[2-formyl-5-hydroxy-4-(trifluoromethoxy)phenoxy]ethoxy]cyclobutanecarboxylate

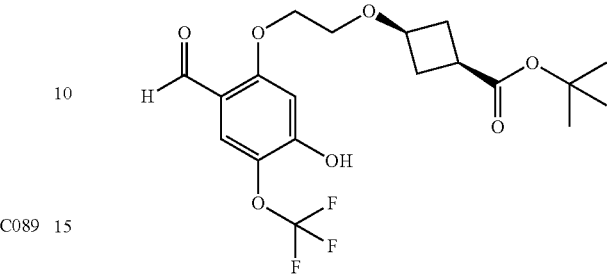

To a solution of cis-tert-butyl 3-[2-[5-bromo-2-formyl-4-(trifluoromethoxy)phenoxy]ethoxy]cyclobutanecarboxylate (200.0 mg, 0.410 mmol), 4-methoxybenzyl alcohol (171.53 mg, 1.24 mmol), tBuXPhos (7.03 mg, 0.020 mmol) in 1,4-dioxane (15 mL) was added Pd$_2$(dba)$_3$ (7.58 mg, 0.010 mmol) under N$_2$ atmosphere. The mixture was stirred at 100° C. for 16 hours. The mixture was cooled to room temperature and concentrated in vacuo. The residue was purified by prep-HPLC to give cis-tert-butyl 3-[2-[2-formyl-5-hydroxy-4-(trifluoromethoxy)phenoxy]ethoxy]cyclobutanecarboxylate (70 mg, 40.24% yield) as dense oil. MS obsd. (ESI$^+$) [(M+Na)$^+$]: 443.1.

Step 3: Preparation of cis-tert-butyl 3-[2-[2-formyl-5-methoxy-4-(trifluoromethoxy)phenoxy]ethoxy]cyclobutanecarboxylate

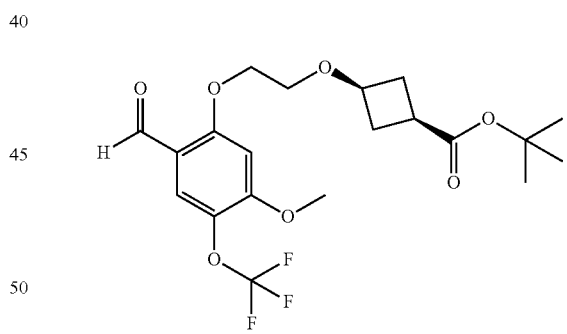

To a solution of cis-tert-butyl 3-[2-[2-formyl-5-hydroxy-4-(trifluoromethoxy)phenoxy]ethoxy]cyclobutanecarboxylate (70.0 mg, 0.170 mmol), K$_2$CO$_3$ (45.96 mg, 0.330 mmol) in ACN (2 mL) was added iodomethane (28.36 mg, 0.200 mmol) and the mixture was stirred at 30° C. for 10 hours. The mixture was concentrated in vacuo and the residue was purified by column chromatography on silica gel (eluted with PE:EtOAc=3:1) to give cis-tert-butyl 3-[2-[2-formyl-5-methoxy-4-(trifluoromethoxy)phenoxy]ethoxy]cyclobutanecarboxylate (65 mg, 89.8% yield) as a colorless oil. MS obsd. (ESI$^+$)[(M+Na)$^+$]: 457.0.

Step 4: Preparation of cis-tert-butyl 3-[2-[2-[(E)-3-(3-chloro-2-hydroxy-phenyl)-3-oxo-prop-1-enyl]-5-methoxy-4-(trifluoromethoxy)phenoxy]ethoxy]cyclobutanecarboxylate

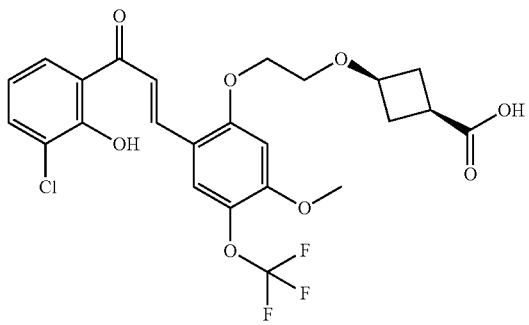 [SMILES: COc1cc(OCCO[C@H]2C[C@@H](C(=O)O)C2)c(/C=C/C(=O)c2cccc(Cl)c2O)cc1OC(F)(F)F]

A mixture of 1-(3-chloro-2-hydroxy-phenyl)ethanone (27.49 mg, 0.160 mmol), cis-tert-butyl 3-[2-[2-formyl-4-methoxy-5-(trifluoromethoxy)phenoxy]ethoxy]cyclobutanecarboxylate (70.0 mg, 0.160 mmol), KOH (90.42 mg, 1.61 mmol) in EtOH (5 mL) was stirred at 40° C. for 20 hours. The mixture was poured into 1N HCl (15 mL) and the resulting suspension was filtered. The solid was collected and dried in vacuo to give cis-tert-butyl 3-[2-[2-[(E)-3-(3-chloro-2-hydroxy-phenyl)-3-oxo-prop -1-enyl]-5-methoxy-4-(trifluoromethoxy)phenoxy]ethoxy]cyclobutanecarboxylate (80 mg, 84.58% yield) as a yellow solid. MS obsd. (ESI$^+$)[(M+H)$^+$]: 531.1.

Step 4: Preparation of cis-3-[2-[2-(8-chloro-4-oxo-chromen-2-yl)-5-methoxy-4-(trifluoromethoxy)phenoxy]ethoxy]cyclobutanecarboxylic acid

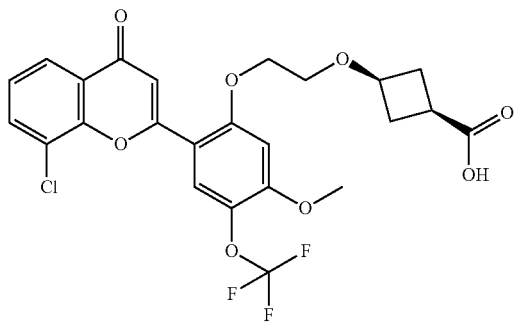 [SMILES: COc1cc(OCCO[C@H]2C[C@@H](C(=O)O)C2)c(-c2cc(=O)c3cccc(Cl)c3o2)cc1OC(F)(F)F]

A mixture of cis-3-[2-[2-[(E)-3-(3-chloro-2-hydroxy-phenyl)-3-oxo-prop-1-enyl]-5-methoxy-4-(trifluoromethoxy) phenoxy]ethoxy]cyclobutanecarboxylic acid (80.0 mg, 0.150 mmol) and iodine (4.3 mg, 0.020 mmol) in DMSO (2 mL) was stirred at 140° C. for 3 hours. The resulting mixture was purified by prep-HPLC to give cis-3-[2-[2-(8-chloro-4-oxo-chromen-2-yl)-5-methoxy-4-(trifluoromethoxy)phenoxy]ethoxy]cyclobutanecarboxylic acid (26 mg, 32.3% yield) as an off-white solid. $^1$H NMR (DMSO-d$_6$, 400 MHz) δ ppm 12.11 (br s, 1H), 7.99 (dd, J=7.2, 5.7 Hz, 3H), 7.48 (t, J=7.9 Hz, 1H), 7.24 (s, 1H), 7.07 (s, 1H), 4.41 (s, 2H), 4.01 (s, 3H), 3.92-3.99 (m, 1H), 3.76 (d, J=4.5 Hz, 2H), 2.39-2.47 (m, 3H), 2.01 (dd, J=20.0, 8.8 Hz, 2H). MS obsd. (ESI$^+$) [(M+H)$^+$]: 529.0.

Example C090: Cis-3-[2-[2-(8-chloro-4-oxo-chromen-2-yl)-5-hydroxy-4-(trifluoromethoxy)phenoxy]ethoxy]cyclobutanecarboxylic acid

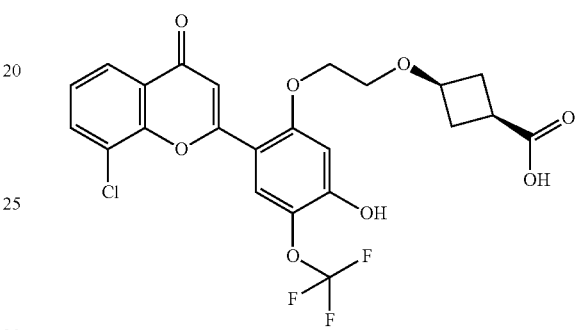

Step 1: Preparation of cis-tert-butyl 3-[2-[2-formyl-5-[(4-methoxyphenyl)methoxy]-4-(trifluoromethoxy)phenoxy]ethoxy]cyclobutanecarboxylate

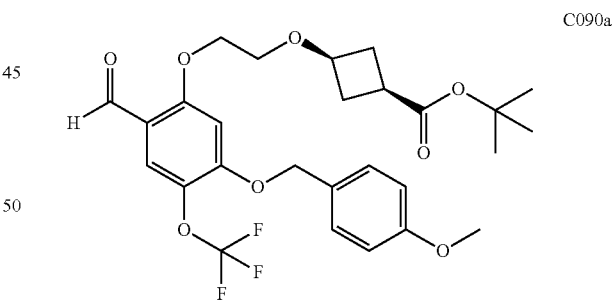

C090a

To a solution of cis-tert-butyl 3-[2-[2-formyl-5-hydroxy-4-(trifluoromethoxy)phenoxy]ethoxy]cyclobutanecarboxylate (140.0 mg, 0.330 mmol), K$_2$CO$_3$ (91.92 mg, 0.670 mmol) in ACN (12 mL) was added 4-methoxybenzylchloride (0.05 mL, 0.400 mmol) and the mixture was stirred at 60° C. for 16 hours. The mixture was concentrated in vacuo and the residue was purified by column chromatography on silica gel (eluted with PE:EtOAc=3:1) to give cis-tert-butyl 3-[2-[2-formyl-5-[(4-methoxyphenyl)methoxy]-4-(trifluoromethoxy)phenoxy]ethoxy]cyclobutanecarboxylate (160 mg, 0.300 mmol) as a colorless oil. MS obsd. (ESI$^+$) [(M+H)$^+$]: 563.2.

Step 2: Preparation of cis-3-[2-[2-(8-chloro-4-oxo-chromen-2-yl)-5-[(4-methoxyphenyl)methoxy]-4-(trifluoromethoxy)phenoxy]ethoxy]cyclobutanecarboxylic acid C090b

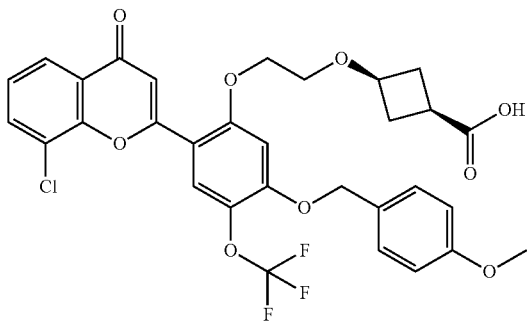

Compound C090b was prepared in analogy to the procedure described for the preparation of example C082 by using cis-tert-butyl 3-[2-[2-formyl-5-[(4-methoxyphenyl)methoxy]-4-(trifluoromethoxy)phenoxy]ethoxy]cyclobutanecarboxylate as the starting material instead of cis-tert-butyl 3-[2-[2-formyl-4-methoxy-5-(trifluoromethoxy)phenoxy]ethoxy]cyclobutanecarboxylate in Step 3. MS obsd. (ESI$^+$) [(M+H)$^+$]: 635.1.

Step 3: Preparation of cis-3-[2-[2-(8-chloro-4-oxo-chromen-2-yl)-5-hydroxy-4-(trifluoromethoxy)phenoxy]ethoxy]cyclobutanecarboxylic acid

C090

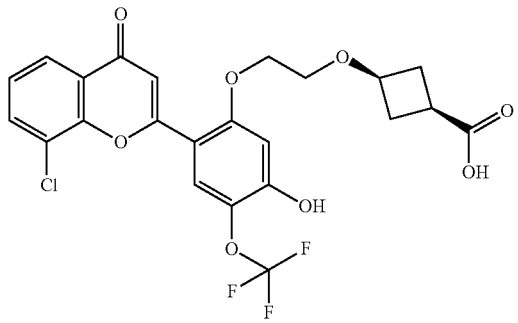 [SMILES: O=c1cc(-c2cc(OC(F)(F)F)c(O)cc2OCCO[C@H]2C[C@@H](C(=O)O)C2)oc2c(Cl)cccc12]

A mixture of cis-3-[2-[2-(8-chloro-4-oxo-chromen-2-yl)-5-[(4-methoxyphenyl)methoxy]-4-(trifluoromethoxy)phenoxy]ethoxy]cyclobutanecarboxylic acid (95.99 mg, 0.150 mmol) and TFA (0.001 mL, 0.020 mmol) in DMSO (2 mL) was stirred at 140° C. for 3 hours. The mixture was concentrated in vacuo, the residue was purified by Prep-HPLC to give cis-3-[2-[2-(8-chloro-4-oxo-chromen-2-yl)-5-hydroxy-4-(trifluoromethoxy)phenoxy]ethoxy]cyclobutanecarboxylic acid (5 mg, 6.06% yield) as a grey solid. $^1$H NMR (DMSO-d$_6$, 400 MHz) δ ppm 12.09 (br s, 1H), 11.29 (s, 1H), 7.97 (dd, J=14.9, 7.0 Hz, 3H), 7.47 (t, J=7.9 Hz, 1H), 7.21 (s, 1H), 6.80 (s, 1H), 4.18-4.28 (m, 2H), 3.92-3.99 (m, 1H), 3.68-3.77 (m, 2H), 2.39-2.44 (m, 3H), 1.94-2.05 (m, 2H). MS obsd. (ESI$^+$) [(M+H)$^+$]: 515.1.

Example C091: Cis-3-[2-[6-(8-chloro-4-oxo-chromen-2-yl)-2-oxo-indolin-5-yl]oxyethoxy]cyclobutanecarboxylic acid

C091

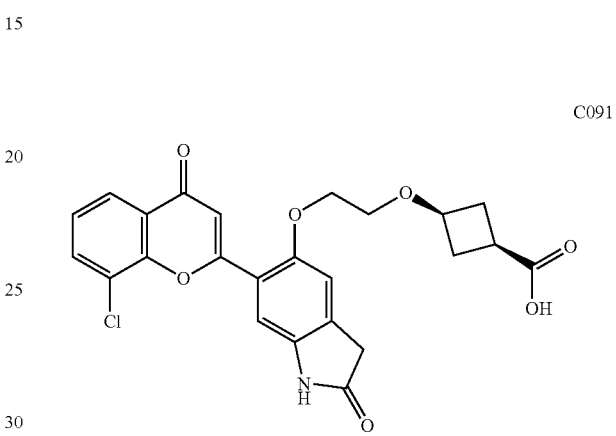

Step 1: Preparation of cis-methyl 4-bromo-2-[2-(3-tert-butoxycarbonylcyclobutoxy)ethoxy]benzoate C091a

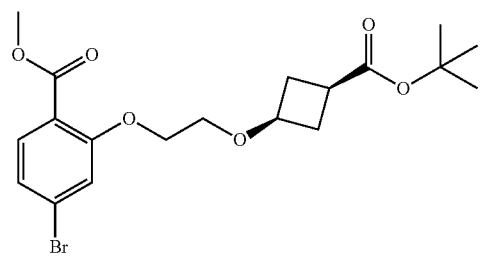

To a mixture of methyl 4-bromo-2-hydroxybenzoate (2 g, 8.66 mmol), K$_2$CO$_3$ (2.39 g, 17.3 mmol) in DMF (20 mL) was added cis-tert-butyl 3-[2-(p-tolylsulfonyloxy)ethoxy]cyclobutanecarboxylate (3.85 g, 10.4 mmol) and the resulting mixture was stirred at 50° C. for 16 hours. After the reaction was completed, the reaction mixture was diluted with water (60 mL) and extracted with EtOAc (100 mL) three times. The combined organic layer was washed with brine, dried over anhydrous Na$_2$SO$_4$ and concentrated in vacuo to give the crude cis-methyl 4-bromo-2-[2-(3-tert-butoxycarbonylcyclobutoxy)ethoxy]benzoate (4.41 g, 95.6% yield) as a yellow oil, which was used in the next step directly without further purification. MS obsd. (ESI$^+$) [(M+H)$^+$]: 428.9.

Step 2: Preparation of cis-3-[2-(5-bromo-2-methoxycarbonyl-4-nitro-phenoxy)ethoxy]cyclobutanecarboxylic acid

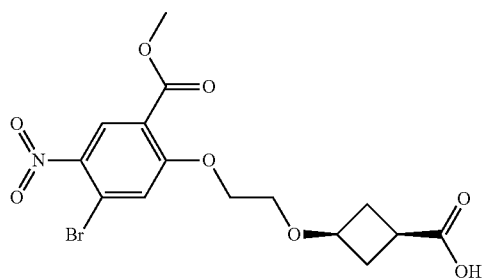

C091b

To a solution of cis-methyl 4-bromo-2-[2-(3-tert-butoxycarbonylcyclobutoxy)ethoxy]benzoate (4.31 g, 8.43 mmol) in Conc.H$_2$SO$_4$ (50 mL) was added KNO$_3$ (938 mg, 9.28 mmol) at 0° C. in small portions while keeping inner temperature below 5° C. After addition, the mixture stirred at 0° C. for another 20 minutes and then the reaction mixture was poured into ice-water (200 g). The resulted suspension was extracted with EtOAc (100 mL) three times, the combined organic layer was washed with brine, dried over anhydrous Na$_2$SO$_4$ and concentrated in vacuo to give the crude cis-3-[2-(5-bromo-2-methoxycarbonyl-4-nitro-phenoxy)ethoxy]cyclobutanecarboxylic acid (3.54 g, 100% yield) as a yellow solid, which was used in the next step directly without further purification. MS obsd. (ESI$^+$) [(M+H)$^+$]: 417.8

Step 3: Preparation of cis-3-[2-[5-bromo-2-[3-(3-chloro-2-hydroxy-phenyl)-3-oxo-propanoyl]-4-nitro-phenoxy]ethoxy]cyclobutanecarboxylic acid

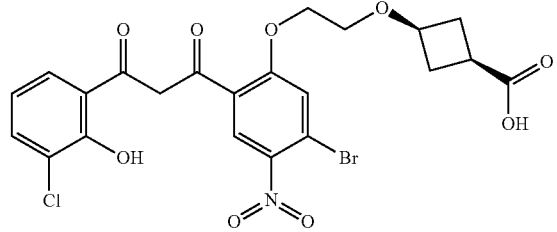

C091c

To LiHMDS solution (1 mol/L in THF, 5 mL, 5 mmol) was added cooled at −78° C. was added 1-(3-chloro-2-hydroxyphenyl)ethan-1-one solution (2 mol/L in THF, 2 mL, 2 mmol) dropwise and resulting solution was stirred at −78° C. 30 min. Then to the resulting mixture was added cis-3-[2-(5-bromo-2-methoxycarbonyl-4-nitro-phenoxy)ethoxy]cyclobutanecarboxylic acid (935 mg, 2 mmol, dissolved in THF (3 mL)) at −78° C. and the reaction was then warmed to room temperature and stirred at room temperature for 16 hours. Then reaction mixture was diluted with water (25 mL) and adjusted to pH 5.0 by addition of AcOH, the resulting mixture was extracted with EtOAc (60 mL) three times. The combined organic layer was washed with brine, dried over anhydrous Na$_2$SO$_4$ and concentrated in vacuo to give the crude cis-3-[2-[5-bromo-2-[3-(3-chloro-2-hydroxy-phenyl)-3-oxo-propanoyl]-4-nitro-phenoxy]ethoxy]cyclobutanecarboxylic acid (710 mg, 63.8% yield) as a brown solid, which was used in the next step directly without further purification. MS obsd. (ESI$^+$) [(M+H)$^+$]: 556.0.

Step 4: Preparation of cis-3-[2-[5-bromo-2-(8-chloro-4-oxo-chromen-2-yl)-4-nitro-phenoxy]ethoxy]cyclobutanecarboxylic acid

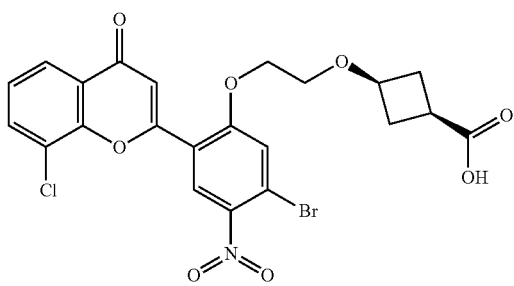

C091d

To a mixture of cis-3-[2-[5-bromo-2-[3-(3-chloro-2-hydroxy-phenyl)-3-oxo-propanoyl]-4-nitro-phenoxy]ethoxy]cyclobutanecarboxylic acid (710 mg, 1.28 mmol) in AcOH (10 mL) was added Con. H$_2$SO$_4$ (0.05 mL) and the resulting mixture was stirred at 100° C. for 1 hour. The mixture was concentrated in vacuo and the residue was purified by column chromatography on silica gel (eluted with PE:EtOAc 5:1 to 1:10) to give cis-3-[2-[5-bromo-2-(8-chloro-4-oxo-chromen-2-yl)-4-nitro-phenoxy]ethoxy]cyclobutanecarboxylic acid (360 mg, 52% yield) as a brown foam, which was used in the next step directly without further purification. MS obsd. (ESI$^+$) [(M+H)$^+$]: 537.9

Step 5: Preparation of cis-3-[2-[2-(8-chloro-4-oxo-chromen-2-yl)-5-(2-methoxy-1-methoxycarbonyl-2-oxo-ethyl)-4-nitro-phenoxy]ethoxy]cyclobutanecarboxylic acid

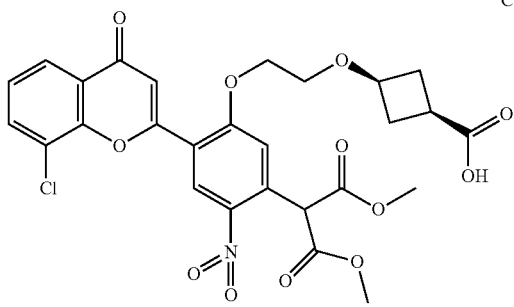

C091e

A mixture of cis-3-[2-[5-bromo-2-(8-chloro-4-oxo-chromen-2-yl)-4-nitro-phenoxy]ethoxy]cyclobutanecarboxylic acid (333 mg, 0.62 mmol), dimethyl malonate (98 mg, 0.74 mmol) and K$_2$CO$_3$ (342 mg, 2.47 mmol) in DMF (5 mL) was stirred at 70° C. overnight. After cooling to room temperature, the reaction mixture was diluted with water (30 mL), adjusted to PH~3 by addition of 1N HCl and the resulting mixture was extracted with EtOAc (50 mL) three

333 times. The combined organic layer was washed with brine, dried over anhydrous Na$_2$SO$_4$ and concentrated in vacuo to give the crude cis-3-[2-[2-(8-chloro-4-oxo-chromen-2-yl)-5-(2-methoxy-1-methoxycarbonyl-2-oxo-ethyl)-4-nitro-phenoxy]ethoxy]cyclobutanecarboxylic acid (265 mg, 73% yield) as a brown oil, which was used in the next step directly without further purification. MS obsd. (ESI$^+$) [(M+H)$^+$]: 590.1

Step 6: Preparation of cis-3-[2-[2-(8-chloro-4-oxo-chromen-2-yl)-5-(2-methoxy-2-oxo-ethyl)-4-nitro-phenoxy]ethoxy]cyclobutanecarboxylic acid C091f

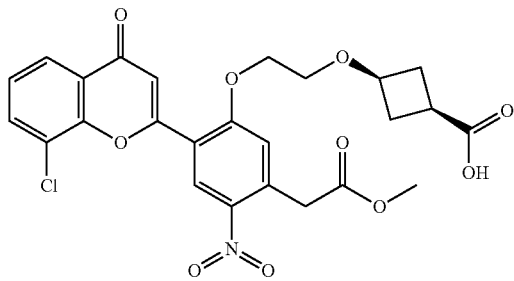

A mixture of cis-3-[2-[2-(8-chloro-4-oxo-chromen-2-yl)-5-(2-methoxy-1-methoxycarbonyl-2-oxo-ethyl)-4-nitro-phenoxy]ethoxy]cyclobutanecarboxylic acid (240 mg, 0.41 mmol), lithium chloride (51.7 mg, 1.22 mmol) in DMSO (3 mL) and water (0.3 mL) was stirred at 100° C. for 16 hours. After cooling to room temperature, the reaction mixture was diluted with water (20 mL) and adjusted to pH~3 by addition of 1N HCl. The resulting mixture was extracted with EtOAc (50 mL) three times. The combined organic layer was washed with brine, dried over anhydrous Na$_2$SO$_4$ and concentrated in vacuo to give the crude cis-3-[2-[2-(8-chloro-4-oxo-chromen-2-yl)-5-(2-methoxy-2-oxo-ethyl)-4-nitro-phenoxy]ethoxy]cyclobutanecarboxylic acid (306 mg) as a brown oil, which was used in the next step directly without further purification. MS obsd. (ESI$^+$) [(M+E1)$^+$]: 532.1

Step 7: Preparation of cis-3-[2-[6-(8-chloro-4-oxo-chromen-2-yl)-2-oxo-indolin-5-yl]oxyethoxy]cy-clobutanecarboxylic acid

C091

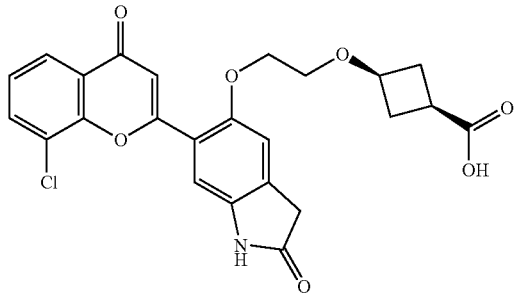

A mixture of cis-3-[2-[2-(8-chloro-4-oxo-chromen-2-yl)-5-(2-methoxy-2-oxo-ethyl)-4-nitro-phenoxy]ethoxy]cy-

334 clobutanecarboxylic acid (168 mg, 0.32 mmol), sodium hydrosulfite (275 mg, 1.58 mmol) in EtOH (6 mL) and water (2 mL) was stirred at 110° C. for 4 hours. After cooling to room temperature, the reaction mixture was diluted with water and adjusted to PH~3 by addition of 2 N HCl. The resulting mixture was extracted with EtOAc (50 mL) three times. The combined organic layer was washed with brine, dried over anhydrous Na$_2$SO$_4$ and concentrated in vacuo. The residue was purified by Prep-HPLC to give cis-3-[2-[6-(8-chloro-4-oxo-chromen-2-yl)-2-oxo-indolin-5-yl]oxy-ethoxy]cyclobutanecarboxylic acid (6 mg, 4%) as a yellow solid. $^1$H NMR (DMSO-d$_6$, 400 MHz) δ ppm 10.46 (s, 1H), 8.02-7.97 (m, 2H), 7.49 (t, J=7.9 Hz, 1H), 7.44 (s, 1H), 7.28-7.24 (m, 2H), 4.25-4.19 (m, 2H), 3.95-3.85 (m, 1H), 3.69-3.66 (m, 2H), 3.59 (s, 2H), 2.42-2.32 (m, 3H), 2.05-1.93 (m, 2H). MS obsd. (ESI$^+$) [(M+H)$^+$]: 470.1

Example C092: cis-3-[2-[6-(8-chloro-4-oxo-chromen-2-yl)-3,3-dimethyl-2-oxo-indolin-5-yl]oxyethoxy]cyclobutanecarboxylic acid

C092

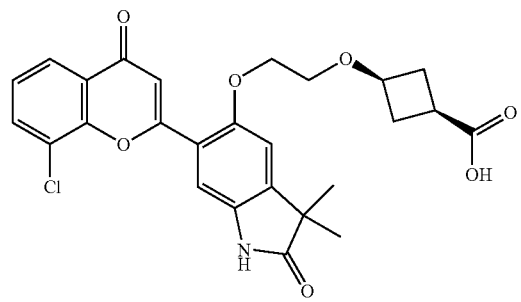

Step 1: Preparation of cis-methyl 3-[2-[2-(8-chloro-4-oxo-chromen-2-yl)-5-(2-methoxy-1,1-dimethyl-2-oxo-ethyl)-4-nitro-phenoxy]ethoxy]cyclobutanecar-boxylate C092a

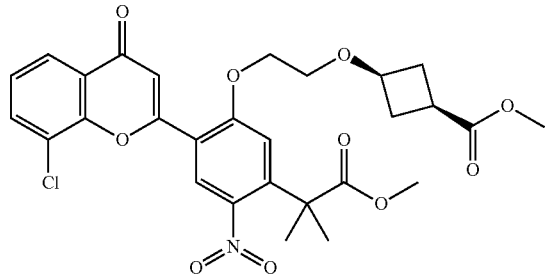

To a solution of cis-3-[2-[2-(8-chloro-4-oxo-chromen-2-yl)-5-(2-methoxy-2-oxo-ethyl)-4-nitro-phenoxy]ethoxy]cy-clobutanecarboxylic acid (160 mg, 0.3 mmol), MeI (170 mg, 1.2 mmol) in DMF (2 mL) was added NaH (48 mg, 1.2 mmol) at 0° C. and the mixture was then stirred at room temperature for 6 hours. The reaction mixture was diluted with water (20 mL) and extracted with EtOAc (20 mL) three times. The combined organic layer was washed with brine, dried over anhydrous Na$_2$SO$_4$ and concentrated in vacuo to give the crude cis-methyl 3-[2-[2-(8-chloro-4-oxo-chromen-2-yl)-5-(2-methoxy-1,1-dimethyl-2-oxo-ethyl)-4-nitro-phenoxy]ethoxy]cyclobutanecarboxylate (162 mg, 92.9% yield) as a brown oil, which was used in the next step directly without further purification. MS obsd. (ESI$^+$) [(M+H)$^+$]: 574.2

Step 2: Preparation of cis-methyl 3-[2-[6-(8-chloro-4-oxo-chromen-2-yl)-3,3-dimethyl-2-oxo-indolin-5-yl]oxyethoxy]cyclobutanecarboxylate

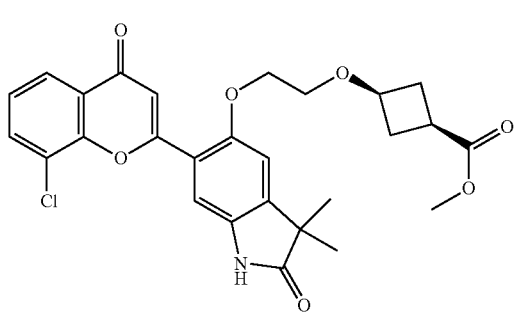

C092b

A mixture of cis-methyl 3-[2-[2-(8-chloro-4-oxo-chromen-2-yl)-5-(2-methoxy-1,1-dimethyl-2-oxo-ethyl)-4-nitro-phenoxy]ethoxy]cyclobutanecarboxylate (crude, 162 mg, 0.28 mmol) and iron (221 mg, 3.95 mmol) in AcOH (3 mL) was stirred at 100° C. for 6 hours. After cooling to room temperature, the reaction mixture was diluted with THF (30 mL) and then filtered. The filtrate was concentrated in vacuo to give the crude cis-methyl 3-[2-[6-(8-chloro-4-oxo-chromen-2-yl)-3,3-dimethyl-2-oxo-indolin-5-yl]oxyethoxy]cyclobutanecarboxylate (213 mg) as a brown oil, which was used in the next step directly without further purification. MS obsd. (ESI$^+$) [(M+H)$^+$]: 512.4

Step 3: Preparation of cis-3-[2-[6-(8-chloro-4-oxo-chromen-2-yl)-3,3-dimethyl-2-oxo-indolin-5-yl]oxyethoxy]cyclobutanecarboxylic acid

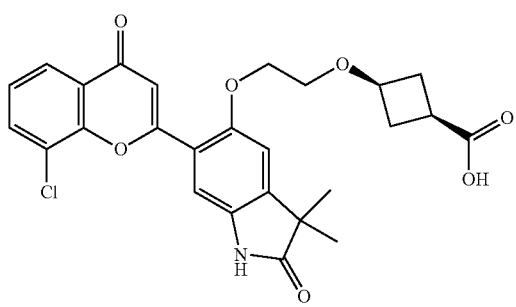

C092

A mixture of cis-methyl 3-[2-[6-(8-chloro-4-oxo-chromen-2-yl)-3,3-dimethyl-2-oxo-indolin-5-yl]oxyethoxy]cyclobutanecarboxylate (213 mg, 0.17 mmol, crude prepared above), lithium hydroxide monohydrate (140 mg, 3.33 mmol) in THF (4 mL) and water (1 mL) was stirred at room temperature for 3 hours. The mixture was adjusted to PH~3 by addition of 1N HCl and concentrated in vacuo. The residue was purified by Prep-HPLC to give ds-3-[2-[6-(8-chloro-4-oxo-chromen-2-yl)-3,3-dimethyl-2-oxo-indolin-5-yl]oxyethoxy]cyclobutanecarboxylic acid (12 mg, 14% yield) as a yellow solid. $^1$H NMR (DMSO-d$_6$, 400 MHz) δ ppm 10.42 (s, 1H), 8.00 (d, J=7.9 Hz, 2H), 7.52-7.39 (m, 3H), 7.21 (s, 1H), 4.30-4.22 (m, 2H), 4.00-3.88 (m, 1H), 3.72-3.63 (m, 2H), 2.44-2.35 (m, 3H), 2.03-1.93 (m, 2H), 1.31 (s, 6H). MS obsd. (ESI$^+$) [(M+H)$^+$]: 512.4

Example C093: Cis-3-[2-[6-(8-chloro-4-oxo-chromen-2-yl)-1,3,3-trimethyl-2-oxo-indolin-5-yl]oxyethoxy]cyclobutanecarboxylic acid

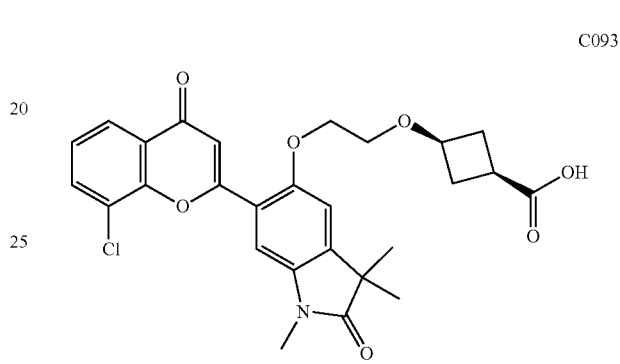

C093

Step 1: Preparation of cis-methyl 3-[2-[6-(8-chloro-4-oxo-chromen-2-yl)-1,3,3-trimethyl-2-oxo-indolin-5-yl]oxyethoxy]cyclobutanecarboxylate

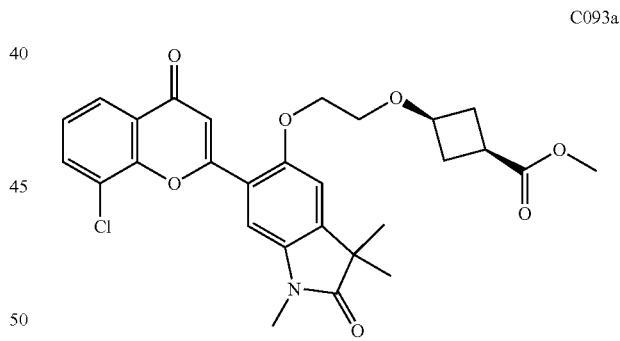

C093a

To a solution of cis-3-[2-[6-(8-chloro-4-oxo-chromen-2-yl)-2-oxo-indolin-5-yl]oxyethoxy]cyclobutanecarboxylic acid (390 mg, 0.58 mmol) in DMF (6 mL) was added NaH (232 mg, 5.81 mmol) at 0° C. and the mixture was stirred at 0° C. for 30 minutes. Then to the resulting mixture was added MeI (660 mg, 4.65 mmol) and the reaction mixture was stirred at room temperature for 16 hours. The reaction mixture was diluted with water (50 mL) and the resulting suspension was filtered. The solid was collected and dried in vacuo to give the crude cis-methyl 3-[2-[6-(8-chloro-4-oxo-chromen-2-yl)-1,3,3-trimethyl-2-oxo-indolin-5-yl]oxyethoxy]cyclobutanecarboxylate (331 mg, 87% yield) as a brown solid, which was used in the next step directly without further purification. MS obsd. (ESI$^+$) [(M+H)$^+$]: 526.5

Step 2: Preparation of cis-3-[2-[6-(8-chloro-4-oxo-chromen-2-yl)-1,3,3-trimethyl-2-oxo-indolin-5-yl]oxyethoxy]cyclobutanecarboxylic acid

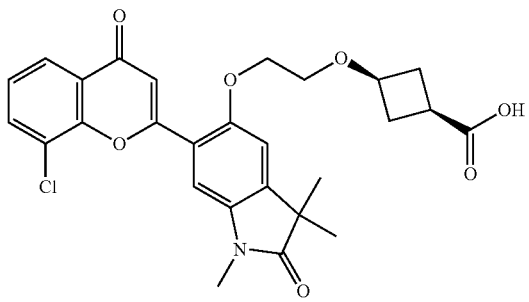
C093

A mixture of cis-methyl 3-[2-[6-(8-chloro-4-oxo-chromen-2-yl)-1,3,3-trimethyl-2-oxo-indolin-5-yl]oxyethoxy]cyclobutanecarboxylate (331 mg, 0.5 mmol) and lithium hydroxide monohydrate (211 mg, 5 mmol) in THF (4 mL) and water (1 mL) was stirred at room temperature for 2 hours. The mixture was adjusted to pH~3 by addition of 1N HCl and concentrated in vacuo. The residue was purified by Prep-HPLC to give cis-3-[2-[6-(8-chloro-4-oxo-chromen-2-yl)-1,3,3-trimethyl-2-oxo-indolin-5-yl]oxyethoxy]cyclobutanecarboxylic acid (12 mg, 4% yield) as a yellow solid. $^1$H NMR (DMSO-d$_6$, 400 MHz) δ ppm 8.05-7.98 (m, 2H), 7.54-7.47 (m, 3H), 7.17 (s, 1H), 4.33-4.25 (m, 2H), 3.96-3.87 (m, 1H), 3.72-3.64 (m, 2H), 3.18 (s, 3H), 2.45-2.30 (m, 3H), 2.03-1.90 (m, 2H), 1.34 (s, 6H). MS obsd. (ESI$^+$) [(M+H)$^+$]: 512.1.

Example C094: cis-3-[2-[2-[8-chloro-4-oxo-5-(trifluoromethyl)chromen-2-yl]phenoxy]ethoxy]cyclobutanecarboxylic acid

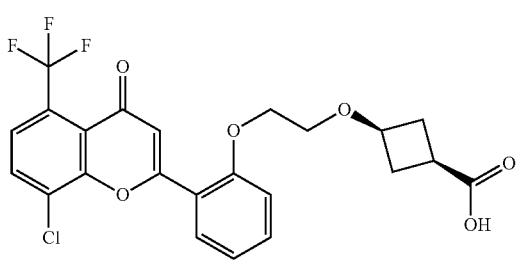
C094

Step 1: Preparation of 5-bromo-8-chloro-2-(2-hydroxyphenyl)chromen-4-one

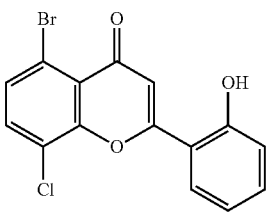
C094a

Compound C094a was prepared in analogy to the procedure described for the preparation of compound Int-1 by using 1-(6-bromo-3-chloro-2-hydroxy-phenyl)ethanone and 2-hydroxybenzaldehyde as the starting material instead of 1-(3-chloro-2-hydroxy-phenyl)ethanone and 2-methoxy-4-(trifluoromethyl)benzaldehyde in Step 1.

Step 2: Preparation of cis-tert-butyl 3-[2-[2-(5-bromo-8-chloro-4-oxo-chromen-2-yl)phenoxy]ethoxy]cyclobutanecarboxylate

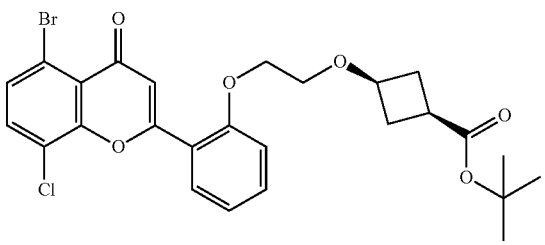
C094b

A solution of 5-bromo-8-chloro-2-(2-hydroxyphenyl)chromen-4-one (200.0 mg, 0.570 mmol), cis-tert-butyl 3-[2-(p-tolylsulfonyloxy)ethoxy]cyclobutanecarboxylate (210.74 mg, 0.570 mmol) and potassium carbonate (235.86 mg, 1.71 mmol) in DMF (10 mL) was stirred at 80° C. for 3 hours. The mixture was then concentrated in vacuo and the residue was purified by column chromatography on silica gel (eluted with PE:EtOAc=20:1 to 3:1) to give cis-tert-butyl 3-[2-[2-(5-bromo-8-chloro-4-oxo-chromen-2-yl)phenoxy]ethoxy]cyclobutanecarboxylate (145 mg, 46.36% yield) as light yellow oil. MS obsd. (ESI$^+$)[(M+H)$^+$]: 549.0.

Step 3: Preparation of cis-3-[2-[2-[8-chloro-4-oxo-5-(trifluoromethyl)chromen-2-yl]phenoxy]ethoxy]cyclobutanecarboxylic acid

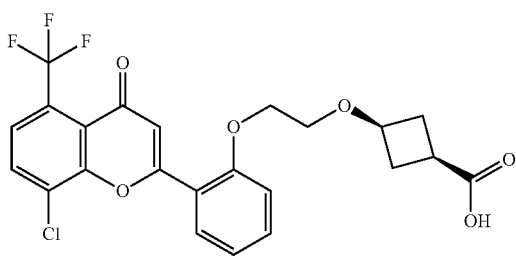

C094

A mixture of cis-tert-butyl 3-[2-[2-(5-bromo-8-chloro-4-oxo-chromen-2-yl)phenoxy]ethoxy]cyclobutanecarboxylate (145.0 mg, 0.260 mmol), methyl 2,2-difluoro-2-(fluorosulfonyl)acetate (253.31 mg, 1.32 mmol) and copper (I) iodide (100.45 mg, 0.530 mmol) in DMF (3.5 mL) was stirred at 120° C. for 12 hours. The mixture was then concentrated in vacuo and the residue was purified by Prep-HPLC to give cis-3-[2-[2-[8-chloro-4-oxo-5-(trifluoromethyl)chromen-2-yl]phenoxy]ethoxy]cyclobutanecarboxylic acid (24.9 mg, 19.56% yield) as an off-white solid. $^1$H NMR (DMSO-d$_6$, 400 MHz): δ ppm 12.02 (br s, 1H), 8.17 (d, J=8.4 Hz, 1H), 8.05 (d, J=7.8 Hz, 1H), 7.88 (d, J=8.4 Hz, 1H), 7.60 (t, J=7.9 Hz, 1H), 7.19-7.34 (m, 3H), 4.24-4.34 (m, 2H), 3.96 (quin, J=7.3 Hz, 1H), 3.68-3.77 (m, 2H), 2.36-2.46 (m, 3H), 1.92-2.04 (m, 2H). MS obsd. (ESI$^+$): [(M+H)$^+$]:483.5.

Example C095: cis-3-[2-[2-[8-chloro-4-oxo-5-(trifluoromethyl)chromen-2-yl]-5-ethoxy-phenoxy]ethoxy]cyclobutanecarboxylic acid

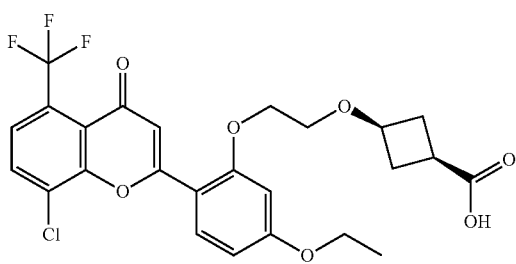

C095

Step 1: Preparation of 5-bromo-8-chloro-2-(4-ethoxy-2-hydroxy-phenyl)chromen-4-one

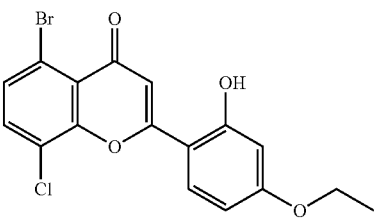

C095a

Compound C095a was prepared in analogy to the procedure described for the preparation of compound Int-5 by using 2-hydroxy-5-methoxy-benzaldehyde as the starting material instead of 4-chloro-2-hydroxy-5-methyl-benzaldehyde in Step 2 and 1-(6-bromo-3-chloro-2-hydroxy-phenyl)ethanone as the starting material instead of 1-(3-chloro-2-hydroxy-phenyl)ethanone in step 3.

Step 2: Preparation of cis-3-[2-[2-[8-chloro-4-oxo-5-(trifluoromethyl)chromen-2-yl]-5-ethoxy-phenoxy]ethoxy]cyclobutanecarboxylic acid

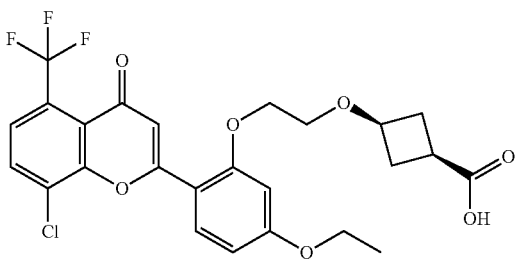

C095

Example C095 was prepared in analogy to the procedure described for the preparation of example C094 by using 5-bromo-8-chloro-2-(4-ethoxy-2-hydroxy-phenyl)chromen-4-one as the starting material instead of 5-bromo-8-chloro-2-(2-hydroxyphenyl)chromen-4-one in Step 2. $^1$H NMR (DMSO-<fc, 400 MHz): δ ppm 12.06 (br s, 1H), 8.14 (d, J=8.4 Hz, 1H), 8.01 (d, J=8.7 Hz, 1H), 7.85 (d, J=8.4 Hz, 1H), 7.21 (s, 1H), 6.77-6.83 (m, 2H), 4.24-4.33 (m, 2H), 4.16 (q, J=6.9 Hz, 2H), 3.98 (quin, J=7.2 Hz, 1H), 3.68-3.77 (m, 2H), 2.39-2.48 (m, 3H), 1.95-2.04 (m, 2H), 1.37 (t, J=7.0 Hz, 3H). (ESI$^+$)[(M+H)$^+$]:527.1.

Example C096: Cis-3-[2-[2-[8-chloro-4-oxo-5-(trifluoromethyl)chromen-2-yl]-4,5-dimethoxy-phenoxy]ethoxy]cyclobutanecarboxylic acid

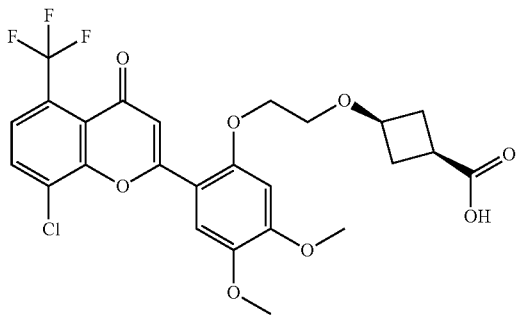

C096

Step 1: Preparation of 5-bromo-8-chloro-2-(2-hydroxy-4,5-dimethoxy-phenyl)chromen-4-one

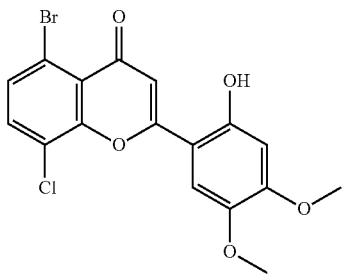

C096a

Compound C096a was prepared in analogy to the procedure described for the preparation of compound Int-5 by using 2-hydroxy-4,5-dimethoxy-benzaldehyde as the starting material instead of 4-chloro-2-hydroxy-5-methyl-benzaldehyde in Step 2 and 1-(6-bromo-3-chloro-2-hydroxyphenyl)ethanone as the starting material instead of 1-(3-chloro-2-hydroxy-phenyl)ethanone in step 3.

Step 2: Preparation of cis-3-[2-[2-[8-chloro-4-oxo-5-(trifluoromethyl)chromen-2-yl]-4,5-dimethoxy-phenoxy]ethoxy]cyclobutanecarboxylic acid

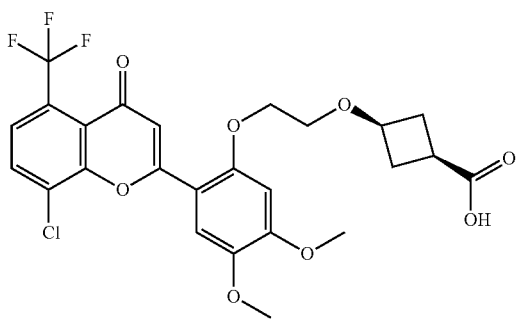

C096

Example C096 was prepared in analogy to the procedure described for the preparation of example C094 by using 5-bromo-8-chloro-2-(2-hydroxy-4,5-dimethoxy-phenyl)chromen-4-one as the starting material instead of 5-bromo-8-chloro-2-(2-hydroxyphenyl)chromen-4-one in Step 2. $^1$H NMR (DMSO-$d_6$, 400 MHz): δ ppm 8.11-8.17 (m, J=8.3 Hz, 1H), 7.81-7.89 (m, J=8.4 Hz, 1H), 7.62 (s, 1H), 7.26 (s, 1H), 6.91 (s, 1H), 4.21-4.41 (m, 2H), 3.86-4.00 (m, 4H), 3.82 (s, 3H), 3.68-3.77 (m, 2H), 2.38-2.46 (m, 3H), 1.90-2.12 (m, 2H). (ESI$^+$)[(M+H)$^+$]:543.1.

Example C097: 3-[2-[2-[8-chloro-4-oxo-7-(trifluoromethyl)chromen-2-yl]-5-ethoxy-phenoxy]ethoxy]cyclobutanecarboxylic acid

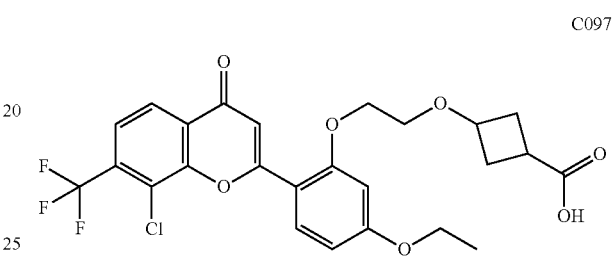

C097

Step 1: Preparation of 8-chloro-2-(4-ethoxy-2-hydroxy-phenyl)-7-(trifluoromethyl)chromen-4-one

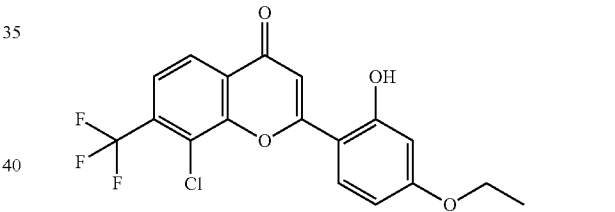

C097a

Compound C095a was prepared in analogy to the procedure described for the preparation of compound Int-5 by using 2-hydroxy-5-methoxy-benzaldehyde as the starting material instead of 4-chloro-2-hydroxy-5-methyl-benzaldehyde in Step 2 and 1-[3-chloro-2-hydroxy-4-(trifluoromethyl)phenyl]ethanone as the starting material instead of 1-(3-chloro-2-hydroxy-phenyl)ethanone in step 3.

Step 2: Preparation of 3-[2-[2-[8-chloro-4-oxo-7-(trifluoromethyl)chromen-2-yl]-5-ethoxy-phenoxy]ethoxy]cyclobutanecarboxylic acid

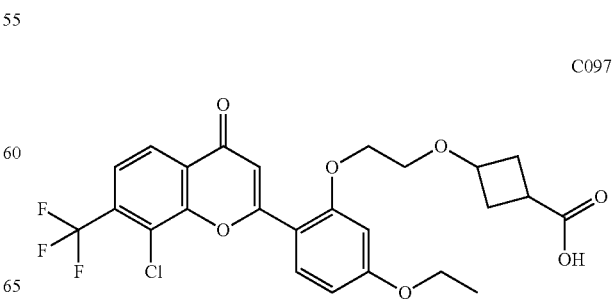

C097

Example C097 was prepared in analogy to the procedure described for the preparation of example C004 by using 8-chloro-2-(4-ethoxy-2-hydroxy-phenyl)-7-(trifluoromethyl)chromen-4-one as the starting material instead of 8-chloro-2-(4-chloro-2-hydroxy-phenyl)chromen-4-one in Step 2. $^1$H NMR (DMSO-$d_6$, 400 MHz): δ ppm 8.13 (d, J=8.4 Hz, 1H), 8.03 (d, J=8.8 Hz, 1H), 7.90 (d, J=8.4 Hz, 1H), 7.29 (s, 1H), 6.77-6.85 (m, 2H), 4.29 (br s, 2H), 4.17 (q, J=7.0 Hz, 2H), 3.97 (br t, J=7.2 Hz, 1H), 3.73 (br s, 2H), 2.43 (br d, J=7.0 Hz, 3H), 1.95-2.06 (m, 2H), 1.37 (t, J=6.9 Hz, 3H). (ESI$^+$)[(M+H)$^+$]:527.1.

Example C098: cis-3-[2-[2-(8-chloro-5-hydroxy-4-oxo-chromen-2-yl)-4,5-dimethoxy-phenoxy]ethoxy]cyclobutanecarboxylic acid

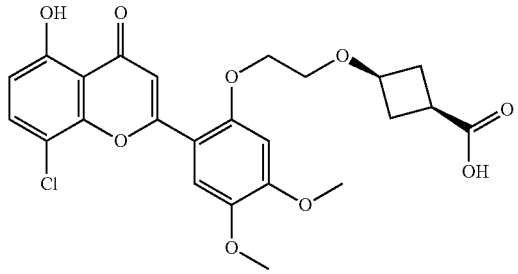

C098

Step 1: Preparation of cis-tert-butyl 3-[2-(2-formyl-4,5-dimethoxy-phenoxy)ethoxy]cyclobutanecarboxylate

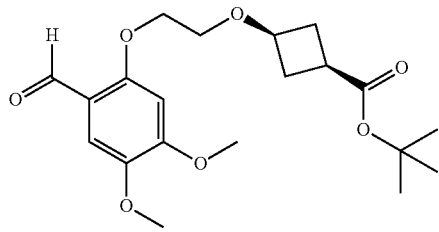

C098a

A mixture of cis-tert-butyl 3-[2-(p-tolylsulfonyloxy)ethoxy]cyclobutanecarboxylate (2.44 g, 6.59 mmol), 2-hydroxy-4,5-dimethoxybenzaldehyde (600 mg, 3.29 mmol) and K$_2$CO$_3$ (1.37 g, 9.88 mmol) in DMF (20 mL) was stirred at 60° C. overnight.

After the reaction was completed, the mixture was diluted with water (40 mL) and extracted with EtOAc (50 mL) three times. The combined organic layer was washed with brine, dried over Na$_2$SO$_4$ and concentrated in vacuo. The residue was purified by column chromatography on silica gel (eluted with PE:EtOAc=10:1 to 3:1) to give cis-tert-butyl 3-[2-(2-formyl-4,5-dimethoxy-phenoxy)ethoxy]cyclobutanecarboxylate (600 mg, 47.9% yield) as a colorless oil. MS obsd. (ESI$^+$): [(M+H)$^+$]:381.3.

Step 2: Preparation of cis-tert-butyl 3-[2-[2-[(E)-3-[3-chloro-2,6-bis(methoxymethoxy)phenyl]-3-oxo-prop-1-enyl]-4,5-dimethoxy-phenoxy]ethoxy]cyclobutanecarboxylate

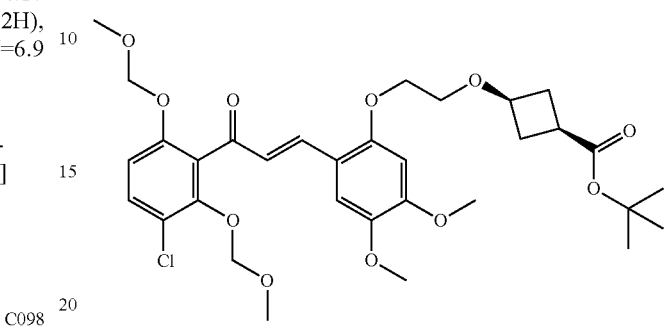

C098b

A mixture of 1-(3-chloro-2-hydroxy-6-(methoxymethoxy)phenyl)ethan-1-one (160 mg, 694 μmol), cis-tert-butyl 3-[2-(2-formyl-4,5-dimethoxy-phenoxy)ethoxy]cyclobutanecarboxylate (200 mg, 526 μmol) and KOH (29.5 mg, 526 μmol) in EtOH (10 mL) was stirred at room temperature for 2 hours. After the reaction was completed, the mixture was diluted with water (50 mL) and extracted with EtOAc (30 mL) three times. The combined organic layer was concentrated in vacuo to give the crude cis-tert-butyl 3-[2-[2-[(E)-3-[3-chloro-2,6-bis(methoxymethoxy)phenyl]-3-oxo-prop-1-enyl]-4,5-dimethoxy-phenoxy]ethoxy]cyclobutanecarboxylate (305 mg, 100% yield) as a brown solid, which was used in the next step directly without further purification. MS obsd. (ESI$^+$): [(M+H)$^+$]:581.2.

Step 3: Preparation of cis-3-[2-[2-(8-chloro-5-hydroxy-4-oxo-chromen-2-yl)-4,5-dimethoxy-phenoxy]ethoxy]cyclobutanecarboxylic acid

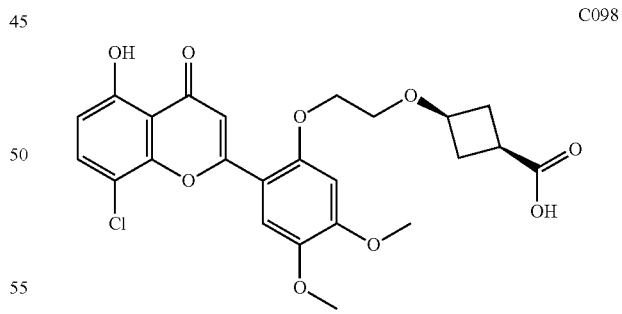

C098

To a suspension of cis-tert-butyl 3-[2-[2-[(T)-3-[3-chloro-2,6-bis(methoxymethoxy)phenyl]-3-oxo-prop-1-enyl]-4,5-dimethoxy-phenoxy]ethoxy]cyclobutanecarboxylate (300 mg, 471 μmol) in DCM (20 Ml) was added TFA (1 mL) and the mixture was then stirred at room temperature for 2 hours. Then the mixture was then washed with water (10 mL) and the organic phase was concentrated in vacuo. The residue was dissolved in DMSO (5 mL) and to the resulting solution was added I$_2$ (12 mg, 471 μmol). The mixture was stirred at 140° C. for 1 hour. After cooling to room temperature, the mixture was purified by Prep-HPLC to give cis-3-[2-[2-(8-chloro-5-hydroxy-4-oxo-chromen-2-yl)-4,5-dimethoxyphenoxy]ethoxy]cyclobutanecarboxylic acid (19.1 mg, 7.4% yield) as an orange solid. $^1$H NMR (DMSO-d$_6$, 400 MHz): δ ppm 12.80 (s, 1H), 11.97-12.19 (m, 1H), 7.81 (d, J=8.9 Hz, 1H), 7.61 (s, 1H), 7.34 (s, 1H), 6.88-6.94 (m, 1H), 6.83 (d, J=8.8 Hz, 1H), 4.26-4.37 (m, 2H), 3.95-4.00 (m, 1H), 3.90 (s, 3H), 3.81 (s, 3H), 3.70-3.74 (m, 2H), 2.56-2.61 (m, 1H), 2.41-2.45 (m, 2H), 1.97-2.07 (m, 2H). MS obsd. (ESI$^+$): [(M+H)$^+$]:491.3.

Example C099: cis-3-[2-[2-(8-chloro-5-hydroxy-4-oxo-chromen-2-yl)-5-(trifluoromethyl)phenoxy]ethoxy]cyclobutanecarboxylic acid

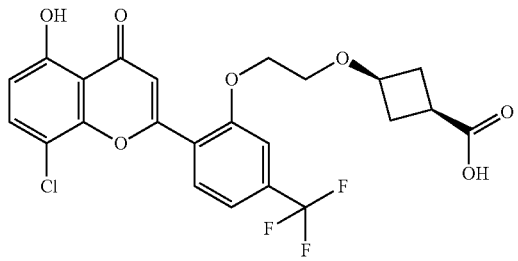

C099

Example C099 was prepared in analogy to the procedure described for the preparation of example C098 by using 2-hydroxy-4-(trifluoromethyl)benzaldehyde as the starting material instead of 2-hydroxy-4,5-dimethoxybenzaldehyde in step 1. $^1$H NMR (DMSO-d$_6$, 400 MHz): δ ppm 12.54 (s, 1H), 8.18 (br d, J=7.8 Hz, 1H), 7.87 (d, J=8.8 Hz, 1H), 7.48-7.73 (m, 2H), 7.36 (s, 1H), 6.89 (d, J=9.0 Hz, 1H), 4.30-4.49 (m, 2H), 3.95 (br t, J=7.5 Hz, 1H), 3.62-3.78 (m, 2H), 2.36-2.46 (m, 3H), 1.93-2.17 (m, 2H). (ESI$^+$)[(M+H)$^+$]: 499.0.

Example C100: 2-[3-[2-(8-chloro-5-hydroxy-4-oxo-chromen-2-yl)-5-(trifluoromethyl)phenoxy]propoxy]acetic acid

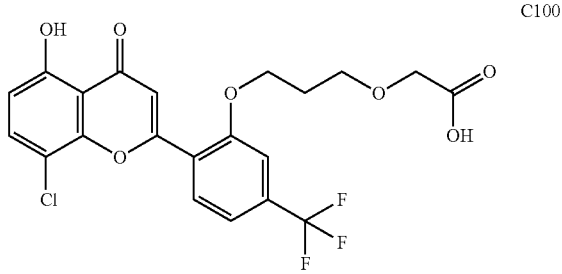 [SMILES: O=C(O)COCCCOc1cc(C(F)(F)F)ccc1-c1cc(=O)c2c(O)ccc(Cl)c2o1]

C100

Example C100 was prepared in analogy to the procedure described for the preparation of example C098 by using 2-hydroxy-4-(trifluoromethyl)benzaldehyde and tert-butyl 2-[3-(p-tolylsulfonyloxy)propoxy]acetate as the starting material instead of 2-hydroxy-4,5-dimethoxybenzaldehyde and cis-tert-butyl 3-[2-(p-tolylsulfonyloxy)ethoxy]cyclobutanecarboxylate in step 1. $^1$H NMR (DMSO-d$_6$, 400 MHz): δ ppm 12.51-12.60 (m, 2H), 8.14 (d, J=8.4 Hz, 1H), 7.87 (d, J=8.8 Hz, 1H), 7.56-7.61 (m, 2H), 7.19 (s, 1H), 6.89 (d, J=8.9 Hz, 1H), 4.36 (t, J=6.2 Hz, 2H), 4.01 (s, 2H), 3.64 (t, J=6.1 Hz, 2H), 2.01-2.11 (m, 2H). (ESI$^+$)[(M+H)$^+$]:473.1.

Example C101: Cis-3-[2-[5-bromo-2-(8-chloro-3-methoxy-4-oxo-chromen-2-yl)phenoxy]ethoxy]cyclobutanecarboxylic acid

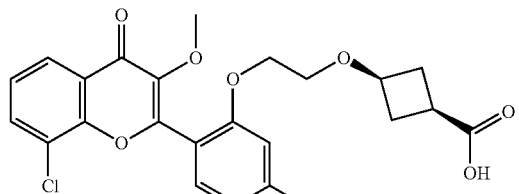

C101

Step 1: Preparation of cis-tert-butyl 3-[2-(5-bromo-2-formyl-phenoxy)ethoxy]cyclobutanecarboxylate

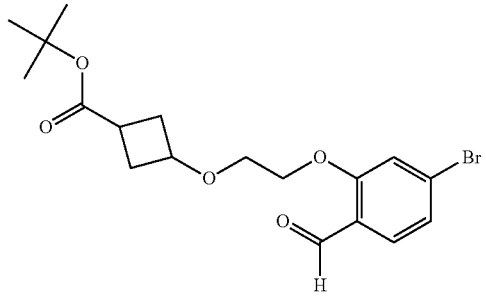

C101a

To a solution of 4-bromo-2-hydroxybenzaldehyde (200.0 mg, 0.990 mmol), K$_2$CO$_3$ (412.51 mg, 2.98 mmol) in DMF (10 mL) was added cis-tert-butyl 3-[2-(p-tolylsulfonyloxy)ethoxy]cyclobutanecarboxylate (368.58 mg, 0.990 mmol) and the reaction mixture was stirred at 80° C. for 6 hours. Then the reaction was diluted with water (25 mL) and the resulting mixture was extracted with EtOAc (20 mL) three times. The combined organic layer was washed with brine, dried over Na$_2$SO$_4$ and concentrated in vacuo to give cis-tert-butyl 3-[2-(5-bromo-2-formyl-phenoxy)ethoxy]cyclobutanecarboxylate (350 mg, 88.1% yield) as a yellow solid. MS obsd. (ESI$^+$) [(M+Na)$^+$]: 421.0.

Step 2: Preparation of cis-3-[2-[5-bromo-2-[(E)-3-(3-chloro-2-hydroxy-phenyl)-3-oxo-prop-1-enyl]phenoxy]ethoxy]cyclobutanecarboxylic acid

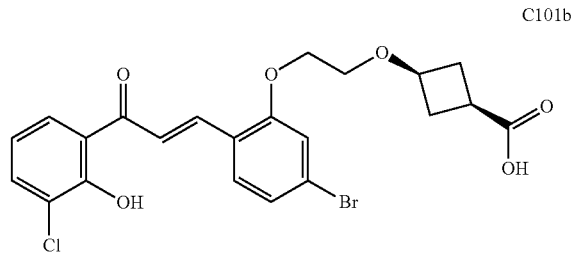 [SMILES: O=C(/C=C/c1ccc(Br)cc1OCCO[C@H]1C[C@@H](C(=O)O)C1)c1cccc(Cl)c1O]

C101b

A mixture of 1-(3-chloro-2-hydroxy-phenyl)ethanone (250.0 mg, 1.47 mmol), cis-tert-butyl 3-[2-(5-bromo-2-formyl-phenoxy)ethoxy]cyclobutanecarboxylate (312.5 mg, 0.780 mmol) and KOH (411.15 mg, 7.33 mmol) in EtOH (20 mL) was stirred at 30° C. for 8 hours. Then the mixture was adjusted to PH~2 by addition of 1N HCl and the resulting suspension was filtered. The solid was washed with water and dried in vacuo to give the crude cis-3-[2-[5-bromo-2-[(E)-3-(3-chloro-2-hydroxy-phenyl)-3-oxo-prop-1-enyl]phenoxy]ethoxy]cyclobutanecarboxylic acid (400 mg, 55.06% yield) as a light yellow solid, which was used in the next step directly without further purification. MS obsd. (ESI$^+$)[(M+Na)$^+$]: 516.9.

Step 3: Preparation of cis-3-[2-[5-bromo-2-(8-chloro-3-hydroxy-4-oxo-chromen-2-yl)phenoxy]ethoxy]cyclobutanecarboxylic acid

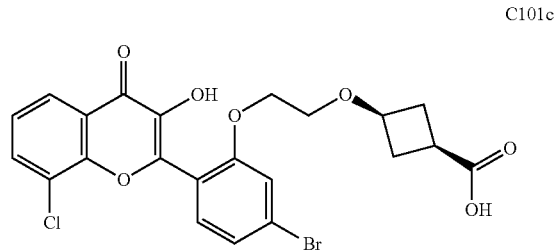 [SMILES: O=c1c(O)c(-c2ccc(Br)cc2OCCO[C@H]2C[C@@H](C(=O)O)C2)oc2c(Cl)cccc12]

C101c

To a solution of cis-3-[2-[5-bromo-2-[(E)-3-(3-chloro-2-hydroxy-phenyl)-3-oxo-prop-1-enyl]phenoxy]ethoxy]cyclobutanecarboxylic acid (70.0 mg, 0.140 mmol) in EtOH (2 mL) were added hydrogen peroxide (35.22 mg, 0.310 mmol) and sodium hydroxide (11.3 mg, 0.280 mmol). The mixture was stirred at 25° C. for 16 hours. Then the mixture was poured into water (15 mL) and the resulting suspension was filtered. The solid was collected and purified by Prep-HPLC to give cis-3-[2-[5-bromo-2-(8-chloro-3-hydroxy-4-oxo-chromen-2-yl)phenoxy]ethoxy]cyclobutanecarboxylic acid (15 mg, 18.4% yield) as a white solid. $^1$H NMR (400 MHz, DMSO) δ ppm: 8.04-8.20 (m, 1H), 7.96 (dd, J=7.7, 1.3 Hz, 1H), 7.39-7.56 (m, 3H), 7.32 (dd, J=8.2, 1.6 Hz, 1H), 4.17-4.20 (m, 2H), 3.73 (t, J=6.9 Hz, 1H), 3.51-3.61 (m, 2H), 2.05-2.21 (m, 3H), 1.74 (dd, J=18.1, 7.8 Hz, 2H). MS obsd. (ESI$^+$)[(M+H)$^+$]: 509.0.

Step 4: Preparation of cis-methyl 3-[2-[5-bromo-2-(8-chloro-3-methoxy-4-oxo-chromen-2-yl)phenoxy]ethoxy]cyclobutanecarboxylate

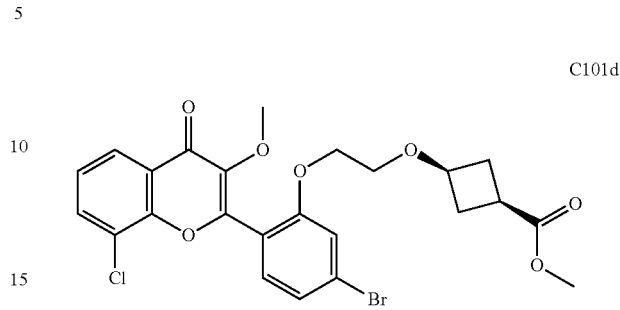

C101d

To a solution of cis-3-[2-[5-bromo-2-(8-chloro-3-hydroxy-4-oxo-chromen-2-yl)phenoxy]ethoxy]cyclobutanecarboxylic acid (25.0 mg, 0.050 mmol), Cs$_2$CO$_3$ (47.94 mg, 0.150 mmol) in DMF (2 mL) was added iodomethane (13.92 mg, 0.100 mmol) and the mixture was stirred at 40° C. for 2 hours. The reaction mixture was then quenched with water (30 mL) and extracted with EtOAc (40 mL) three times. The combined organic layer was washed with brine (40 mL), dried over Na$_2$SO$_4$ and concentrated in vacuo. The residue was purified by column chromatography on silica gel (eluted with PE:EtOAc=3:1) to give civ-methyl 3-[2-[5-bromo-2-(8-chloro-3-methoxy-4-oxo-chromen-2-yl)phenoxy]ethoxy]cyclobutanecarboxylate (18 mg, 70.07% yield) as a colorless oil. MS obsd. (ESI$^+$) [(M+Na)$^+$]: 559.0.

Step 5: Preparation of Cis-3-[2-[5-bromo-2-(8-chloro-3-methoxy-4-oxo-chromen-2-yl)phenoxy]ethoxy]cyclobutanecarboxylic acid

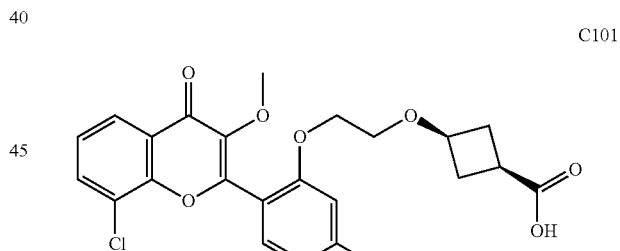

C101

To a solution of civ-methyl 3-[2-[5-bromo-2-(8-chloro-3-methoxy-4-oxo-chromen-2-yl)phenoxy]ethoxy]cyclobutanecarboxylate (18.0 mg, 0.030 mmol) in THF (8 mL) and water (1 mL) was added lithium hydroxide (8.02 mg, 0.330 mmol) and the mixture was stirred at 25° C. for 16 hours. The mixture was adjusted to pH~6 by addition of 1N HCl and the resulting solution was concentrated in vacuo. The residue was purified by Prep-HPLC to give cis-3-[2-[5-bromo-2-(8-chloro-3-methoxy-4-oxo-chromen-2-yl)phenoxy]ethoxy]cyclobutanecarboxylic acid (12.1 mg, 68.33% yield) as a white solid. $^1$H NMR (DMSO-d$_6$, 400 MHz): δ ppm 8.09 (dd, J=7.9, 1.5 Hz, 1H), 8.00 (dd, J=7.7, 1.5 Hz, 1H), 7.48-7.53 (m, 3H), 7.35 (dd, J=8.1, 1.7 Hz, 1H), 4.18-4.25 (m, 2H), 3.71-3.78 (m, 4H), 3.36-3.58 (m, 2H), 2.10-2.26 (m, 3H), 1.70-1.81 (m, 2H). MS obsd. (ESI$^+$) [(M+H)$^+$]: 523.0.

Example C102: Cis-3-[2-[[6-(8-chloro-4-oxo-chromen-2-yl)-2,2-difluoro-1,3-benzodioxol-5-yl]oxy]ethoxy]cyclobutanecarboxylic acid

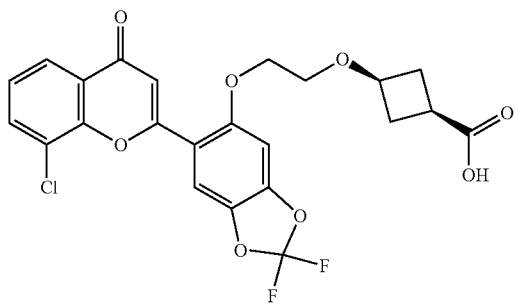 [SMILES: COC(=O)[C@H]1C[C@@H](OCCOc2cc3c(cc2-c2cc(=O)c4cccc(Cl)c4o2)OC(F)(F)O3)C1]

C102

Step 1: Preparation of civ-methyl 3-[2-[[6-(8-chloro-4-oxo-chromen-2-yl)-2-thioxo-1,3-benzodioxol-5-yl]oxy]ethoxy]cyclobutanecarboxylate

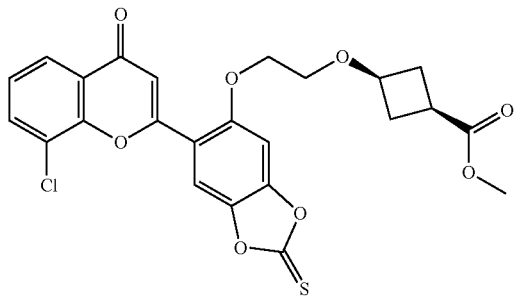

C102a

To a solution of cis-methyl 3-[2-[2-(8-chloro-4-oxo-chromen-2-yl)-4,5-dihydroxy-phenoxy]ethoxy]cyclobutanecarboxylate (100.0 mg, 0.220 mmol), DMAP (58.32 mg, 0.480 mmol) in DCM (20 mL) was added thiophosgene (29.94 mg, 0.260 mmol) and the mixture was stirred at room temperature for 4 hours. The resulting solution was washed with water (20 mL), brine (15 mL), dried over MgSO$_4$ and concentrated in vacuo to give the crude cis-methyl 3-[2-[[6-(8-chloro-4-oxo-chromen-2-yl)-2-thioxo-1,3-benzodioxol-5-yl]oxy]ethoxy]cyclobutanecarboxylate (102 mg, 93.47% yield) as a light yellow solid. MS obsd. (ESI$^+$) [(M+H)$^+$]: 503.1.

Step 2: Preparation of cis-methyl 3-[2-[[6-(8-chloro-4-oxo-chromen-2-yl)-2,2-difluoro-1,3-benzodioxol-5-yl]oxy]ethoxy]cyclobutanecarboxylate

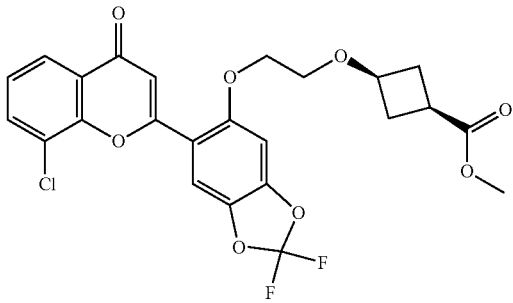

To a solution of cis-methyl 3-[2-[[6-(8-chloro-4-oxo-chromen-2-yl)-2-thioxo-1,3-benzodioxol-5-yl]oxy]ethoxy]cyclobutanecarboxylate (230.0 mg, 0.460 mmol), NIS (246.9 mg, 1.1 mmol) in DCM (10 mL) was added tetrabutylammonium dihydrogen trifluoride (413.6 mg, 1.37 mmol) at 0° C. and the mixture was stirred at room temperature for 2 hours. The reaction was quenched with water (10 mL) and the resulting mixture was extracted with DCM (20 mL) twice. The combined organic layer was dried over Na$_2$SO$_4$ and concentrated in vacuo, the residue was purified by prep-HPLC to give cis-methyl 3-[2-[[6-(8-chloro-4-oxo-chromen-2-yl)-2,2-difluoro-1,3-benzodioxol-5-yl]oxy]ethoxy]cyclobutanecarboxylate (21.3 mg, 9.15% yield) as a yellow solid. MS obsd. (ESI$^+$)[(M+H)$^+$]: 509.1.

Step 3: Preparation of cis-3-[2-[[6-(8-chloro-4-oxo-chromen-2-yl)-2,2-difluoro-1,3-benzodioxol-5-yl]oxy]ethoxy]cyclobutanecarboxylic acid

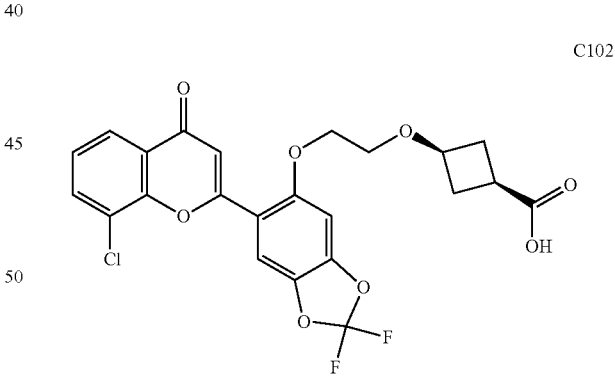

C102

A solution of cis-methyl 3-[2-[[6-(8-chloro-4-oxo-chromen-2-yl)-2,2-difluoro-1,3-benzodioxol-5-yl]oxy]ethoxy]cyclobutanecarboxylate (20.0 mg, 0.040 mmol) in hydrochloric acid (10 mL, 120 mmol) was stirred at 100° C. for 20 minutes. The reaction mixture was concentrated in vacuo and the residue was purification by prep-HPLC to give cis-3-[2-[[6-(8-chloro-4-oxo-chromen-2-yl)-2,2-difluoro-1,3-benzodioxol-5-yl]oxy]ethoxy]cyclobutanecarboxylic acid (14.1 mg, 70.96% yield) as a white solid. $^1$H NMR (400 MHz, DMSO) δ ppm: 12.11 (s, 1H), 7.97-8.04 (m, 2H), 7.88 (s, 1H), 7.58 (s, 1H), 7.50 (t, J=7.9 Hz, 1H), 7.15 (s, 1H), 4.28-4.30 (m, 2H), 3.86-3.93 (m, 1H), 3.68-

3.70 (m, 2H), 2.36-2.46 (m, 3H), 1.92-1.99 (m, 2H). MS obsd. (ESI⁺)[(M+H)⁺]: 495.1.

Example C103: 3-[3-[2-(8-chloro-4-oxo-chromen-2-yl)-5-(trifluoromethyl)phenoxy]propoxy]cyclobutanecarboxylic acid

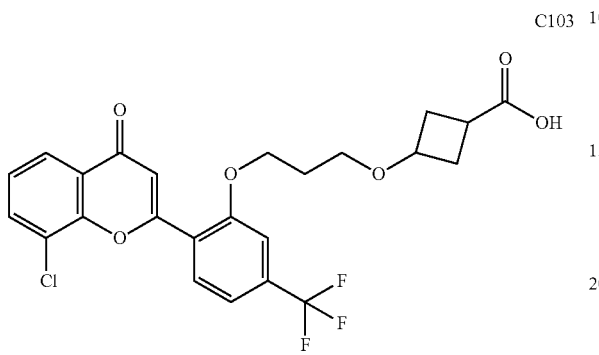

C103

Example C103 was prepared in analogy to the procedure described for the preparation of example C004 by using 8-chloro-2-[2-hydroxy-4-(trifluoromethyl)phenyl]chromen-4-one and methyl 3-[3-[3-(p-tolylsulfonyloxy)propoxy]cyclobutanecarboxylate as the starting material instead of 8-chloro-2-(4-chloro-2-hydroxy-phenyl)chromen-4-one and methyl 3-[2-(p-tolylsulfonyloxy)ethoxy]cyclobutanecarboxylate in step 1. ¹H NMR (400 MHz, DMSO) δ ppm: 12.03-12.13 (m, 1H), 8.10-8.15 (m, 1H), 8.03 (ddt, J=7.8, 3.0, 1.5 Hz, 2H), 7.48-7.59 (m, 3H), 7.05-7.12 (m, 1H), 4.27-4.37 (m, 2H), 4.01-4.05 (m, 0.3H), 3.76-3.85 (m, 0.7H), 3.41-3.48 (m, 2H), 2.80-2.90 (m, 0.3H), 2.51-2.54 (m, 0.7H), 2.26-2.39 (m, 2H), 1.86-2.11 (m, 4H). MS obsd. (ESI⁺)[(M+H)⁺]: 496.9.

Example C104: 3-[3-[2-(8-chloro-4-oxo-chromen-2-yl)-5-(trifluoromethyl)phenoxy]propoxy]cyclopentanecarboxylic acid

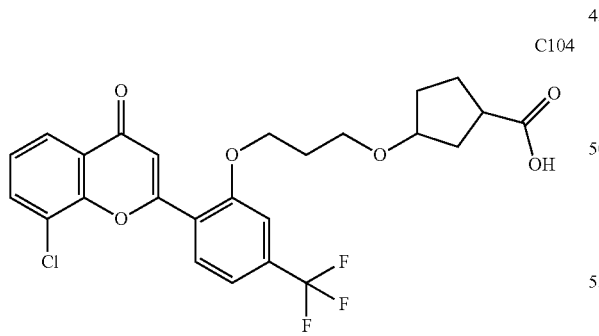

C104

Example C104 was prepared in analogy to the procedure described for the preparation of example C004 by using 8-chloro-2-[2-hydroxy-4-(trifluoromethyl)phenyl]chromen-4-one and methyl 3-[3-(p-tolylsulfonyloxy)propoxy]cyclopentanecarboxylate as the starting material instead of 8-chloro-2-(4-chloro-2-hydroxy-phenyl)chromen-4-one and methyl 3-[2-(p-tolylsulfonyloxy)ethoxy]cyclobutanecarboxylate in step 1. ¹H NMR (DMSO-d₆, 400 MHz): δ ppm 8.11-8.23 (m, 1H), 8.05 (br dd, 1H, J=6.4, 8.0 Hz), 7.88-8.00 (m, 1H), 7.38-7.50 (m, 3H), 7.21-7.26 (m, 1H), 4.32 (br d, 2H, J=5.6 Hz), 3.89-4.01 (m, 1H), 3.59 (t, 2H, J=5.9 Hz), 2.83 (br t, 1H, J=7.9 Hz), 2.13 (br t, 2H, J=5.3 Hz), 1.93 (br d, 2H, J=7.3 Hz), 1.79-1.99 (m, 2H), 1.64-1.77 (m, 2H). (ESI⁺)[(M+H)⁺]:510.9.

Example C105: 3-[3-[5-bromo-2-(8-chloro-4-oxo-chromen-2-yl)phenoxy]propoxy]cyclopentanecarboxylic acid

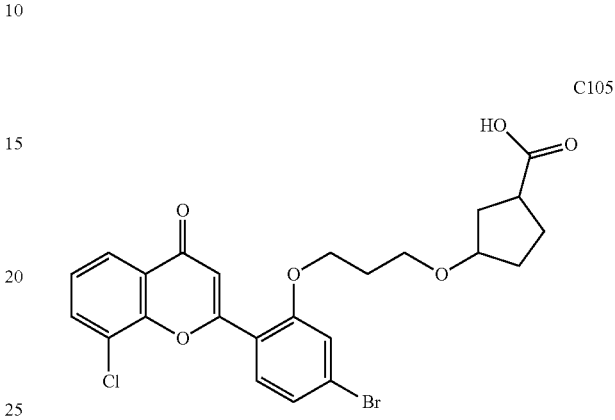

C105

Example C105 was prepared in analogy to the procedure described for the preparation of example C004 by using 2-(4-bromo-2-hydroxy-phenyl)-8-chloro-chromen-4-one and methyl 3-[3-(p-tolylsulfonyloxy)propoxy]cyclopentanecarboxylate as the starting material instead of 8-chloro-2-(4-chloro-2-hydroxy-phenyl)chromen-4-one and methyl 3-[2-(p-tolylsulfonyloxy)ethoxy]cyclobutanecarboxylate in step 1. ¹H NMR (DMSO-d₆, 400 MHz): δ ppm 12.01 (br s, 1H), 7.96-8.03 (m, 2H), 7.83-7.91 (m, 1H), 7.38-7.55 (m, 3H), 7.02-7.06 (m, 1H), 4.19-4.29 (m, 2H), 3.80-3.93 (m, 1H), 3.48 (t, J=6.2 Hz, 2H), 2.68-2.78 (m, 1H), 1.94-2.07 (m, 2H), 1.68-1.89 (m, 4H), 1.53-1.66 (m, 2H). (ESI⁺)[(M+H)⁺]:521.0.

Example C106: 3-[2-[5-bromo-2-(8-chloro-4-oxo-chromen-2-yl)phenoxy]ethoxy]cyclopentanecarboxylic acid

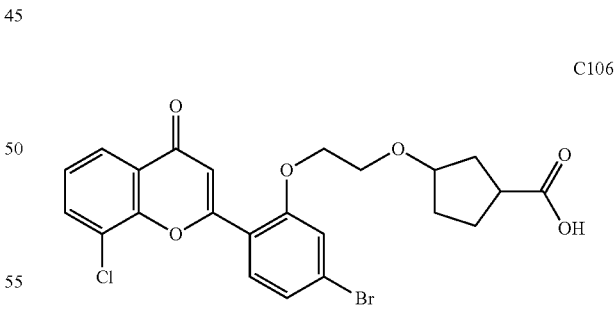

C106

Example C106 was prepared in analogy to the procedure described for the preparation of example C004 by using 2-(4-bromo-2-hydroxy-phenyl)-8-chloro-chromen-4-one and methyl 3-[2-(p-tolylsulfonyloxy)ethoxy]cyclopentanecarboxylate as the starting material instead of 8-chloro-2-(4-chloro-2-hydroxy-phenyl)chromen-4-one and methyl 3-[2-(p-tolylsulfonyloxy)ethoxy]cyclobutanecarboxylate in step 1. ¹H NMR (DMSO-d₆, 400 MHz): 5 ppm 12.01 (br s, 1H), 7.91-8.02 (m, 3H), 7.41-7.54 (m, 3H), 7.25 (s, 1H), 4.27-4.37 (m, 2H), 4.04 (dq, J=5.4, 2.6 Hz, 1H), 3.67-3.78

(m, 2H), 2.76-2.85 (m, 1H), 1.74-1.95 (m, 4H), 1.59-1.71 (m, 2H). (ESI⁺)[(M+H)⁺]:507.1.

Example C107: 4-[2-[5-bromo-2-(8-chloro-4-oxo-chromen-2-yl)phenoxy]ethoxy]benzoic acid

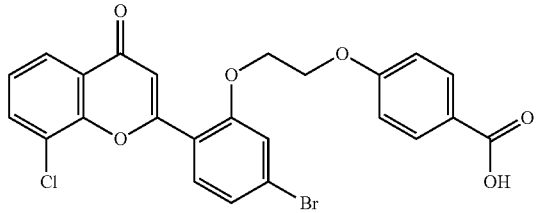

C107

Step 1: Preparation of 2-[4-bromo-2-(2-bromoethoxy)phenyl]-8-chloro-chromen-4-one

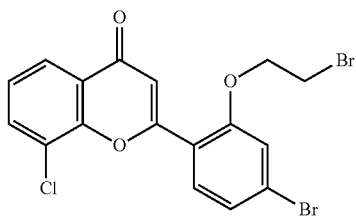

C107a

To the solution of 2-(4-bromo-2-hydroxy-phenyl)-8-chloro-chromen-4-one (500 mg, 1.42 mmol), 1,2-dibromoethane (1.07 g, 5.69 mmol) in DMF was added K₂CO₃ (197 mg, 1.42 mmol) and the mixture was then stirred at 50° C. overnight. After the reaction was completed, the mixture was partitioned between EtOAc (10 mL) and water (30 ml). The resulting suspension was filtered. The solid was collected and dried in vacuo to give 2-[4-bromo-2-(2-bromoethoxy)phenyl]-8-chloro-chromen-4-one (450 mg, 69% yield) as a yellow solid. MS obsd. (ESI⁺) [(M+H)⁺]:457.0.

Step 2: Preparation of methyl 4-[2-[5-bromo-2-(8-chloro-4-oxo-chromen-2-yl)phenoxy]ethoxy]benzoate

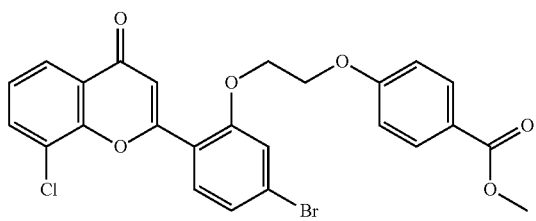

C107b

A mixture of 2-[4-bromo-2-(2-bromoethoxy)phenyl]-8-chloro-chromen-4-one (110 mg, 239 μmol), methyl 4-hydroxybenzoate (60 mg, 392 μmol), K₂CO₃ (54.3 mg, 393 μmol) in a mixed solvent of THF (5 mL) and DMF (2 mL) was stirred at 30° C. overnight. After the reaction was completed, the reaction mixture was diluted with EtOAc (40 mL). The resulting solution was washed with water (20 mL), brine (15 mL), dried over Na₂SO₄ and concentrated in vacuo to give the crude methyl 4-[2-[5-bromo-2-(8-chloro-4-oxo-chromen-2-yl)phenoxy]ethoxy]benzoate (120 mg, 100% yield) as a yellow oil, which was used in the next step directly. MS obsd. (ESI⁺) [(M+H)⁺]:527.0.

Step 3: Preparation of 4-[2-[5-bromo-2-(8-chloro-4-oxo-chromen-2-yl)phenoxy]ethoxy]benzoic acid

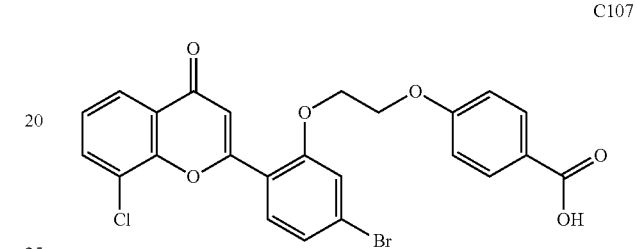

C107

To a solution of methyl 4-(2-(5-bromo-2-(8-chloro-4-oxo-4H-chromen-2-yl)phenoxy)ethoxy)benzoate (120 mg, 227 μmol) in a mixed solvent of THF (5 ml), MeOH (5 ml) and water (1 mL) was added LiOH (43.4 mg, 1.81 mmol). The mixture was then stirred at room temperature for 48 hours. The reaction mixture was diluted with water (10 mL) and methanol (10 mL) and the resulting suspension was filtered. The solid was collected and purified by Prep-HPLC to give 4-[2-[5-bromo-2-(8-chloro-4-oxo-chromen-2-yl)phenoxy]ethoxy]benzoic acid (16 mg, 12.3% yield) as an off-white solid. ¹H NMR (400 MHz, DMSO) δ ppm: 7.97 (td, J=7.5, 1.5 Hz, 2H), 7.91 (d, J=8.4 Hz, 1H), 7.85 (d, J=8.8 Hz, 2H), 7.60-7.65 (m, 1H), 7.45-7.50 (m, 2H), 7.19 (s, 1H), 7.08 (d, J=8.8 Hz, 2H), 4.61 (dd, J=5.9, 2.3 Hz, 2H), 4.47 (dd, J=5.6, 2.5 Hz, 2H). MS obsd. (ESI⁺) [(M+H)⁺]:515.1.

Example C108: 3-[2-[5-bromo-2-(8-chloro-4-oxo-chromen-2-yl)phenoxy]ethoxy]benzoic acid

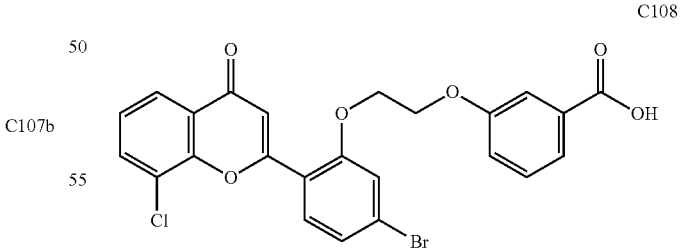

C108

Example C108 was prepared in analogy to the procedure described for the preparation of example C107 by using methyl 3-hydroxybenzoate as the starting material instead of methyl 4-hydroxybenzoate in step 2. ¹H NMR (400 MHz, DMSO) δ ppm: 7.89-8.02 (m, 3H), 7.61-7.67 (m, 1H), 7.43-7.54 (m, 4H), 7.36-7.40 (m, 1H), 7.27 (br d, J=1.7 Hz, 1H), 7.20 (s, 1H), 4.56-4.66 (m, 2H), 4.31-4.49 (m, 2H). MS obsd. (ESI⁺) [(M+H)⁺]:515.1.

Example C109: 2-[3-[2-(8-chloro-4-oxo-chromen-2-yl)-5-(trifluoromethyl)phenoxy]propoxy]-2-methyl-propanoic acid

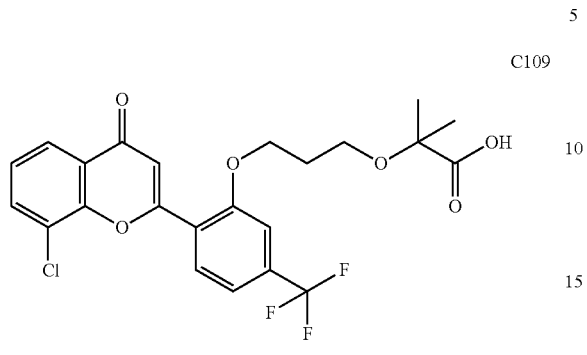

C109

Example C109 was prepared in analogy to the procedure described for the preparation of example C107 by using 8-chloro-2-[2-hydroxy-4-(trifluoromethyl)phenyl]chromen-4-one and 1,3-dibromopropane as the starting material instead of 2-(4-bromo-2-hydroxy-phenyl)-8-chloro-chromen-4-one and 1,2-dibromoethane in step 1 and using methyl 2-hydroxy-2-methyl-propanoate as the starting material instead of methyl 4-hydroxybenzoate in step 2. $^1$H NMR (DMSO-d$_6$, 400 MHz): δ ppm 8.23 (d, 1H, J=7.9 Hz), 8.13 (dd, 1H, J=1.5, 8.0 Hz), 7.95 (dd, 1H, J=1.5, 7.8 Hz), 7.48-7.55 (m, 3H), 7.25 (s, 1H), 4.35-4.41 (m, 4H), 2.31 (m, 2H), 1.38 (s, 6H). (ESI$^+$)[(M+H)$^+$]:485.3.

Example C110: cis-3-[3-[5-bromo-2-(8-chloro-4-oxo-chromen-2-yl)phenoxy]-2,2-dimethyl-propoxy]cyclobutanecarboxylic acid and trans-3-[3-[5-bromo-2-(8-chloro-4-oxo-chromen-2-yl)phenoxy]-2,2-dimethyl-propoxy]cyclobutanecarboxylic acid

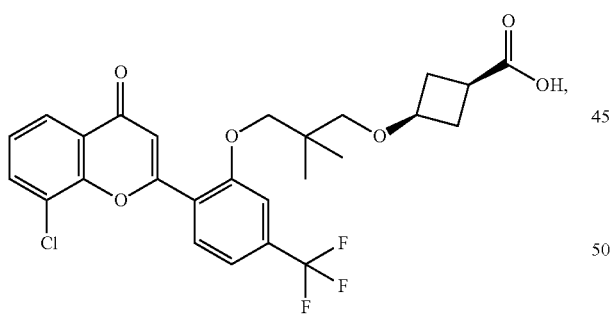

C110-A

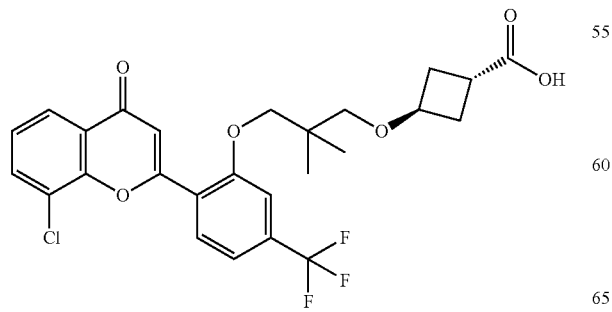

C110-B

Step 1: Preparation of 3-benzyloxy-2,2-dimethyl-propan-1-ol

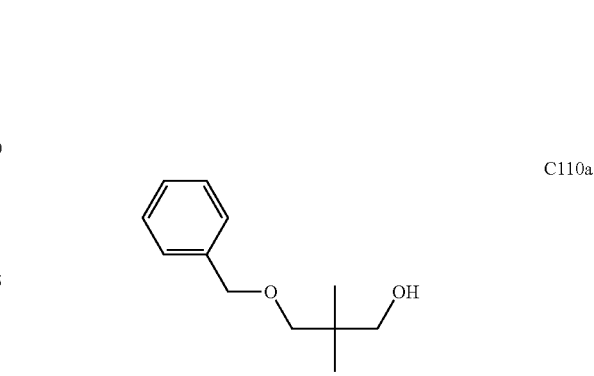

C110a

To a solution of 2,2-dimethylpropane-1,3-diol (2800.0 mg, 26.88 mmol) in THF (60 mL) were added NaH (1290.45 mg, 32.26 mmol), benzyl bromide (3.2 mL, 26.88 mmol) and tetrabutylammonium iodide (9930.17 mg, 26.88 mmol) at 0° C. The resulting mixture was stirred at 25° C. for 16 hours. Then the reaction mixture was quenched with saturated aqueous NH$_4$Cl (50 mL) and extracted with EtOAc (50 mL) three times. The combined organic layer was washed with brine (80 mL), dried over anhydrous Na$_2$SO$_4$ and concentrated in vacuo. The residue was purified by column chromatography on silica gel (eluted with PE:EtOAc=100:1 to 5:1) to give 3-benzyloxy-2,2-dimethyl-propan-1-ol (3800 mg, 72.74% yield) as a colorless oil. MS obsd. (ESI$^+$)[(M+H)$^+$]: 195.2.

Step 2: Preparation of methyl 3-[2,2-dimethyl-3-(p-tolylsulfonyloxy)propoxy]cyclobutanecarboxylate

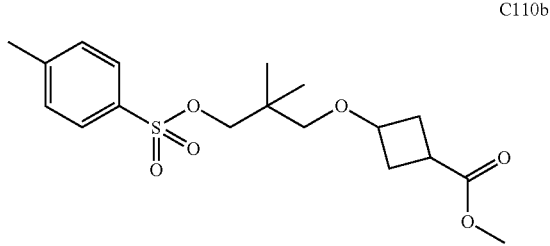

C110b

Compound C110b was prepared in analogy to the procedure described for the preparation of compound Int-T1 by using 3-benzyloxy-2,2-dimethyl-propan-1-ol as the starting material instead of 2-benzyloxyethanol in Step 1.

Step 3: Preparation of cis-3-[3-[5-bromo-2-(8-chloro-4-oxo-chromen-2-yl)phenoxy]-2,2-dimethyl-propoxy]cyclobutanecarboxylic acid and trans-3-[3-[5-bromo-2-(8-chloro-4-oxo-chromen-2-yl)phenoxy]-2,2-dimethyl-propoxy]cyclobutanecarboxylic acid Example C111: (3R)-1-[2-[2-[5-bromo-2-(8-chloro-4-oxo-chromen-2-yl)phenoxy]ethoxy]acetyl]pyrrolidine-3-carboxylic acid

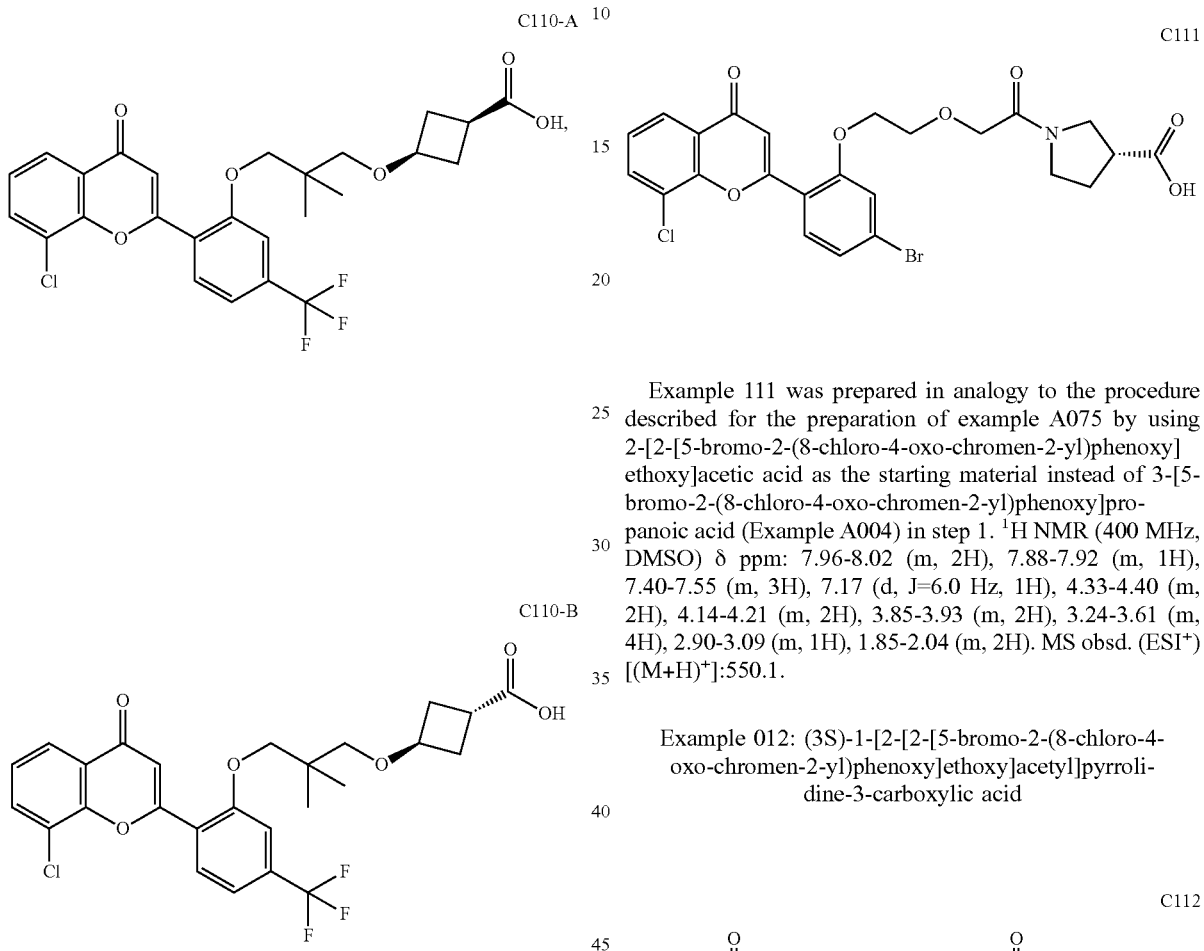

Example C110-A and C110-B were prepared in analogy to the procedure described for the preparation of example C003-A and example C003-B by using 8-chloro-2-[2-hydroxy-4-(trifluoromethyl)phenyl]chromen-4-one and methyl 3-[2,2-dimethyl-3-(p-tolylsulfonyloxy)propoxy]cyclobutanecarboxylate as the starting materials instead of 2-(4-bromo-2-hydroxy-phenyl)-8-chloro-chromen-4-one and methyl 3-[2-(p-tolylsulfonyloxy)ethoxy]cyclobutanecarboxylate in Step 1.

Example C110-A: $^1$H NMR (DMSO-$d_6$, 400 MHz): δ ppm 12.06 (br s, 1H), 8.01 (dq, J=7.9, 1.4 Hz, 2H), 7.84 (d, J=8.6 Hz, 1H), 7.39-7.56 (m, 3H), 7.00 (s, 1H), 3.94 (s, 2H), 3.69-3.86 (m, 1H), 3.14 (s, 2H), 2.44-2.48 (m, 1H), 2.15-2.38 (m, 2H), 1.76-1.95 (m, 2H), 0.87-1.04 (m, 6H). (ESI$^+$) [(M+H)$^+$]:535.0.

Example C110-B: $^1$H NMR (DMSO-$d_6$, 400 MHz): δ ppm 12.11 (br s, 1H), 8.01 (d, J=8.1 Hz, 2H), 7.85 (d, J=8.6 Hz, 1H), 7.40-7.59 (m, 3H), 7.02 (s, 1H), 3.91-4.06 (m, 3H), 3.13 (s, 2H), 2.73-2.98 (m, 1H), 2.16-2.34 (m, 2H), 1.95-2.10 (m, 2H), 0.98 (s, 6H). (ESI$^+$)[(M+H)$^+$]:535.0.

Example 111 was prepared in analogy to the procedure described for the preparation of example A075 by using 2-[2-[5-bromo-2-(8-chloro-4-oxo-chromen-2-yl)phenoxy]ethoxy]acetic acid as the starting material instead of 3-[5-bromo-2-(8-chloro-4-oxo-chromen-2-yl)phenoxy]propanoic acid (Example A004) in step 1. $^1$H NMR (400 MHz, DMSO) δ ppm: 7.96-8.02 (m, 2H), 7.88-7.92 (m, 1H), 7.40-7.55 (m, 3H), 7.17 (d, J=6.0 Hz, 1H), 4.33-4.40 (m, 2H), 4.14-4.21 (m, 2H), 3.85-3.93 (m, 2H), 3.24-3.61 (m, 4H), 2.90-3.09 (m, 1H), 1.85-2.04 (m, 2H). MS obsd. (ESI$^+$) [(M+H)$^+$]:550.1.

Example 012: (3S)-1-[2-[2-[5-bromo-2-(8-chloro-4-oxo-chromen-2-yl)phenoxy]ethoxy]acetyl]pyrrolidine-3-carboxylic acid

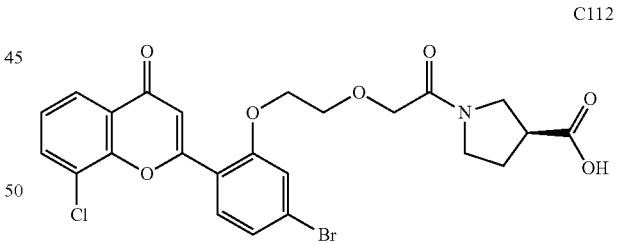

Example 111 was prepared in analogy to the procedure described for the preparation of example A075 by using 2-[2-[5-bromo-2-(8-chloro-4-oxo-chromen-2-yl)phenoxy]ethoxy]acetic acid and tert-butyl (2S)-pyrrolidine-2-carboxylate as the starting material instead of 3-[5-bromo-2-(8-chloro-4-oxo-chromen-2-yl)phenoxy]propanoic acid (Example A004) and tert-butyl (2R)~pyrrolidine-2-carboxylate in step 1. $^1$H NMR (400 MHz, DMSO) δ ppm: 12.40-12.56 (m, 1H), 7.97-8.04 (m, 2H), 7.86-7.93 (m, 1H), 7.41-7.55 (m, 3H), 7.17 (d, J=6.1 Hz, 1H), 4.31-4.44 (m, 2H), 4.11-4.20 (m, 2H), 3.89 (br d, J=2.6 Hz, 2H), 3.37-3.61 (m, 4H), 2.90-3.08 (m, 1H), 1.86-2.09 (m, 2H). MS obsd. (ESI$^+$) [(M+H)$^+$]:550.0.

Example 013: 2-[3-[5-bromo-2-(8-chloro-4-oxo-chromen-2-yl)phenoxy]-2-hydroxy-propoxy]acetic acid

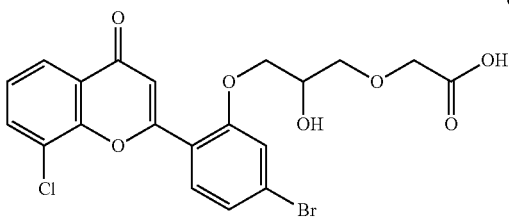
C113

Step 1: Preparation of 2-[4-bromo-2-(oxiran-2-yl-methoxy)phenyl]-8-chloro-chromen-4-one

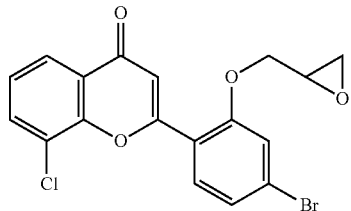
C113a

A mixture of 2-(4-bromo-2-hydroxy-phenyl)-8-chloro-chromen-4-one (300 mg, 853 µmol), 2-(chloromethyl)oxirane (789 mg, 8.53 mmol) and K₂CO₃ (1.77 g, 12.8 mmol) in DMF (25 mL) was stirred at 50° C. overnight. The mixture was then poured into water (75 mL) and extracted with EtOAc (100 mL) twice. The combined organic layer was washed with brine, dried over Na₂SO₄ and concentrated in vacuo. The residue was then triturated with MTBE (20 mL) and the suspension was then filtered. The filtered cake was collected and dried in vacuo to give 2-[4-bromo-2-(oxiran-2-ylmethoxy)phenyl]-8-chloro-chromen-4-one (300 mg, 86.2% yield) as a yellow solid. MS obsd. (ESI⁺) [(M+H)⁺]: 406.9.

Step 2: Preparation of methyl 2-[3-[5-bromo-2-(8-chloro-4-oxo-chromen-2-yl)phenoxy]-2-hydroxy-propoxy]acetate

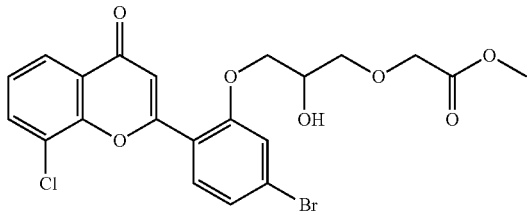
C113b

To a solution of 2-[4-bromo-2-(oxiran-2-ylmethoxy)phenyl]-8-chloro-chromen-4-one (220.0 mg, 0.540 mmol) in methyl glycolate (486.15 mg, 5.4 mmol) was added boron fluoride ethyl ether (182.98 mg, 2.7 mmol) and the mixture was stirred at 25° C. for 1 hour. The mixture was concentrated in vacuo and the residue was purified column chromatography on silica gel (eluted with PE:EtOAc=5:1 to 1:1) to give methyl 2-[3-[5-bromo-2-(8-chloro-4-oxo-chromen-2-yl)phenoxy]-2-hydroxy-propoxy]acetate (150 mg, 55.84% yield) as a colorless oil. MS obsd. (ESI⁺)[(M+H)⁺]: 497.0.

Step 3: Preparation of 2-[3-[5-bromo-2-(8-chloro-4-oxo-chromen-2-yl)phenoxy]-2-hydroxy-propoxy] acetic acid

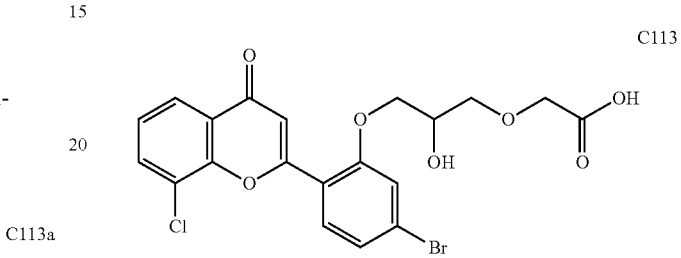
C113

To a solution of methyl 2-[3-[5-bromo-2-(8-chloro-4-oxo-chromen-2-yl)phenoxy]-2-hydroxy-propoxy]acetate (250.0 mg, 0.500 mmol) in THF (5 mL) and water (1 mL) was add LiOH (55 mg, 2.51 mmol) and the mixture was stirred at 25° C. for 3 hours. The mixture was then adjusted to pH~6 by addition of 2N HCl and the resulting mixture was concentrated in vacuo. The residue was then purified by Prep-HPLC to give 2-[3-[5-bromo-2-(8-chloro-4-oxo-chromen-2-yl)phenoxy]-2-hydroxy-propoxy]acetic acid (130 mg, 0.03% yield) as a white solid. ¹H NMR (DMSO-d₆, 400 MHz) δ ppm 8.00 (d, J=7.7 Hz, 2H), 7.90 (d, J=8.5 Hz, 1H), 7.56-7.46 (m, 2H), 7.42 (dd, J=8.5, 1.8 Hz, 1H), 7.19 (s, 1H), 4.16 (ddd, J=15.8, 9.9, 5.3 Hz, 2H), 4.02-3.90 (m, 1H), 3.83-3.72 (m, 2H), 3.64-3.50 (m, 2H). MS obsd. (ESI⁺)[(M+H)⁺]: 483.0.

Example 014: 2-[3-[5-bromo-2-(8-chloro-4-oxo-chromen-2-yl)phenoxy]-2-hydroxy-propoxy]acetamide

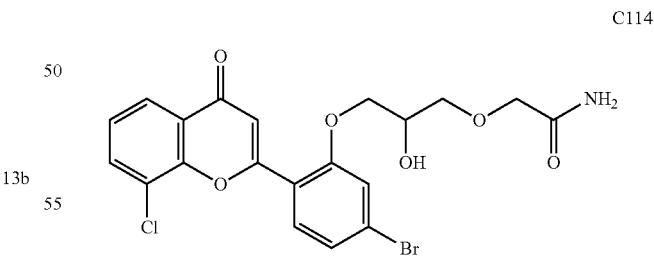
C114

A solution of methyl 2-[3-[5-bromo-2-(8-chloro-4-oxo-chromen-2-yl)phenoxy]-2-hydroxy-propoxy]acetate (100.0 mg, 0.200 mmol) in ammonia (1 mL) was stirred at room temperature for 3 hours. The mixture was concentrated in vacuo and the residue was then purified by Prep-HPLC to give 2-[3-[5-bromo-2-(8-chloro-4-oxo-chromen-2-yl)phenoxy]-2-hydroxy-propoxy]acetamide (30 mg, 29.08% yield) as a white solid. ¹H NMR (DMSO-d₆, 400 MHz) δ ppm 8.01 (dd, J=1N, 1.9 Hz, 2H), 7.91 (d, J=8.5 Hz, 1H), 7.54 (d, J=1.6 Hz, 1H), 7.50 (t, J=1N Hz, 1H), 7.44 (dd, J=8.5, 1.7 Hz, 1H), 7.32 (d, J=17.4 Hz, 2H), 7.23 (s, 1H), 5.40 (d, J=5.0 Hz, 1H), 4.29 (dd, J=10.1, 3.9 Hz, 1H), 4.19 (dd, J=10.0, 6.1 Hz, 1H), 4.07 (dd, J=9.4, 5.1 Hz, 1H), 3.83 (d, J=1.7 Hz, 2H), 3.55 (qd, J=9.8, 5.4 Hz, 2H). MS obsd. (ESI$^+$)[(M+H)$^+$]:482.0.

Example 015: 2-[3-[2-(8-chloro-4-oxo-chromen-2-yl)-5-(trifluoromethyl)phenoxy]-2-hydroxy-propoxy] acetic acid

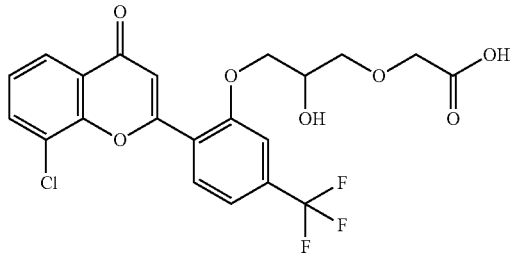

C115

Example 115 was prepared in analogy to the procedure described for the preparation of example 013 by using 8-chloro-2-[2-hydroxy-4-(trifluoromethyl)phenyl]chromen-4-one as the starting material instead of 2-(4-bromo-2-hydroxy-phenyl)-8-chloro-chromen-4-one in step 1. $^1$H NMR (DMSO-d$_6$, 400 MHz) δ ppm 8.13-8.18 (m, 1H), 7.99-8.06 (m, 2H), 7.56-7.61 (m, 2H), 7.49-7.55 (m, 1H), 7.20-7.27 (m, 1H), 5.22-5.32 (m, 1H), 4.31-4.37 (m, 1H), 4.21-4.26 (m, 1H), 4.05 (s, 2H), 3.52-3.59 (m, 1H), 3.52-3.55 (m, 1H). MS obsd. (ESI$^+$)[(M+H)$^+$]:473.2.

Example 016: 2-[2-[5-bromo-2-(8-chloro-4-oxo-chromen-2-yl)phenoxy]ethoxy]-N-cyclopropylsulfonyl-acetamide

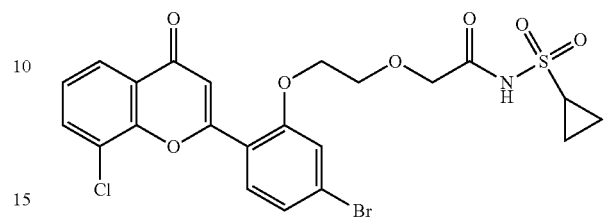

C116

To a mixture of 2-[2-[5-bromo-2-(8-chloro-4-oxo-chromen-2-yl)phenoxy]ethoxy]acetic acid (100 mg, 220 μmol, as the "EX" in Table 10), cyclopropanesulfonamide (34.7 mg, 287 μmol, as the "AMINE" in Table 10), DMAP (40.4 mg, 331 μmol) in DCM (10 mL) was added HATU (134 mg, 353 μmol) and the mixture was then stirred at room temperature overnight. After the reaction was completed, the reaction solution was diluted with DCM (30 mL), the resulting solution was washed by water (15 mL), brine (15 ml), dried over MgSO$_4$ and filtered. The filtrate was concentrated in vacuo and the residue was purified by Prep-HPLC to give 2-[2-[5-bromo-2-(8-chloro-4-oxo-chromen-2-yl)phenoxy]ethoxy]-N-cyclopropylsulfonyl-acetamide (26.5 mg, 20.5% yield) as a white solid. $^1$H NMR (DMSO-d$_6$, 400 MHz) δ ppm 11.68 (s, 1H), 8.00 (ddd, J=7.8, 6.4, 1.5 Hz, 2H), 7.88-7.94 (m, 1H), 7.38-7.57 (m, 3H), 7.19 (s, 1H), 4.30-4.43 (m, 2H), 4.12-4.19 (m, 2H), 3.78-3.96 (m, 2H), 2.88-2.99 (m, 1H), 1.03-1.13 (m, 4H). MS obsd. (ESI$^+$)[(M+H)$^+$]:556.1.

The following compounds 017 to 026 were prepared in analogy to the procedure described for the preparation of Example 016, replacing 2-[2-[5-bromo-2-(8-chloro-4-oxo-chromen-2-yl)phenoxy]ethoxy]acetic acid with "EX", cyclopropanesulfonamide with "AMINE". The "EX" and "AMINE" are the reagents indicated in Table 10.

TABLE 10

| | Compounds synthesis and characterization | | |
|---|---|---|---|
| Example No. | Compounds Name and Structure | EX and AMINE | $^1$H NMR and (ESI$^+$) |
| C117 | 2-[3-[2-(8-chloro-4-oxo-chromen-2-yl)-5-(trifluoromethyl)phenoxy] propoxy]-N-cyclopropylsulfonyl-acetamide | EX: C001 AMINE: cyclopropane-sulfonamide | $^1$H NMR (DMSO-d$_6$, 400 MHz): δ ppm 11.65 (s, 1H), 8.14 (br d, J = 8.4 Hz, 1H), 8.03 (br t, J = 6.5 Hz, 2H), 7.49-7.64 (m, 3H), 7.12 (s, 1H), 4.36 (br t, J = 6.1 Hz, 2H), 4.06 (s, 2H), 3.64 (br t, J = 6.0 Hz, 2H), 2.68-2.95 (m, 1H), 2.07 (br t, J = 6.1 Hz, 2H), 0.97-1.12 (m, 4H). (ESI$^+$)[(M + H)$^+$]: 560.1. |

TABLE 10-continued

Compounds synthesis and characterization

| Example No. | Compounds Name and Structure | EX and AMINE | $^1$H NMR and (ESI$^+$) |
|---|---|---|---|
| C118 | 2-[2-[2-(8-chloro-4-oxo-chromen-2-yl)-5-(trifluoromethyl)phenoxy]ethoxy]-N-cyclopropylsulfonyl-acetamide | EX: C005 AMINE: cyclopropane-sulfonamide | $^1$H NMR (DMSO-d$_6$, 400 MHz): δ ppm 11.66 (s, 1H), 8.17 (d, J = 8.2 Hz, 1H), 8.00-8.06 (m, 2H), 7.50-7.65 (m, 3H), 7.24 (s, 1H), 4.43-4.50 (m, 2H), 4.16 (s, 2H), 3.93 (br d, J = 4.2 Hz, 2H), 2.90-2.97 (m, 1H), 0.99-1.14 (m, 4H). (ESI$^+$)[(M + H)$^+$]: 546.0. |
| C119 | Cis-3-[2-[2-(8-chloro-4-oxo-chromen-2-yl)-4,5-dimethoxy-phenoxy]ethoxy]-N-cyclopropylsulfonyl-cyclobutanecarboxamide | EX: C072 AMINE: cyclopropane-sulfonamide | $^1$H NMR (DMSO-d$_6$, 400 MHz): δ ppm 11.63 (br s, 1H), 7.97 (ddd, J = 10.0, 8.1, 1.5 Hz, 2H), 7.61 (s, 1H), 7.47 (t, J = 7.9 Hz, 1H), 7.25 (s, 1H), 6.91 (s, 1H), 4.26-4.38 (m, 2H), 3.84-4.02 (m, 4H), 3.82 (s, 3H), 3.66-3.77 (m, 2H), 2.83-2.97 (m, 1H), 2.52-2.64 (m, 1H), 2.33-2.46 (m, 2H), 1.96-2.08 (m, 2H), 0.96-1.06 (m, 4H).. (ESI$^+$)[(M + H)$^+$]: 577.8. |
| C120 | 2-[2-[2-(8-chloro-4-oxo-chromen-2-yl)-5-(trifluoromethyl)phenoxy]ethoxy]-N-methylsulfonyl-acetamide | EX: C005 AMINE: methane-sulfonamide | $^1$H NMR (DMSO-d$_6$, 400 MHz): δ ppm 11.70 (s, 1H), 8.17 (d, 1H, J = 8.1 Hz), 7.98-8.05 (m, 2H), 7.49-7.63 (m, 3H), 7.25 (s, 1H), 4.40-4.52 (m, 2H), 4.16 (s, 2H), 3.88-3.98 (m, 2H), 3.24 (s, 3H). (ESI$^+$)[(M + H)$^+$]: 520.1. |
| C121 | Cis-3-[2-[2-(8-chloro-4-oxo-chromen-2-yl)-5-(trifluoromethyl)phenoxy]ethoxy]-N-methylsulfonyl-cyclobutanecarboxamide | EX: C026-A AMINE: methane-sulfonamide | $^1$H NMR (DMSO-d$_6$, 400 MHz): δ ppm 8.17 (d, J = 8.1 Hz, 1H), 7.98-8.07 (m, 2H), 7.47-7.63 (m, 3H), 7.22-7.29 (m, 1H), 4.37-4.45 (m, 2H), 3.93 (quin, J = 7.4 Hz, 1H), 3.67-3.77 (m, 2H), 2.98-3.08 (m, 3H), 2.43-2.47 (m, 1H), 2.27-2.37 (m, 2H), 1.87-2.05 (m, 2H). (ESI$^+$)[(M + H)$^+$]: 560.1. |

TABLE 10-continued

Compounds synthesis and characterization

| Example No. | Compounds Name and Structure | EX and AMINE | ¹H NMR and (ESI⁺) |
|---|---|---|---|
| C122 | Cis-3-[2-[5-bromo-2-(8-chloro-4-oxo-chromen-2-yl)phenoxy]ethoxy]-N-methylsulfonyl-cyclobutanecarboxamide | EX: C003-A AMINE: methanesulfonamide | ¹H NMR (DMSO-d₆, 400 MHz): δ ppm 8.00 (ddd, J = 9.1, 7.8, 1.5 Hz, 2H), 7.90-7.95 (m, 1H), 7.40-7.55 (m, 3H), 7.20-7.24 (m, 1H), 4.29-4.36 (m, 2H), 3.89-3.98 (m, 1H), 3.66-3.72 (m, 2H), 3.10 (s, 3H), 2.53-2.57 (m, 1H), 2.30-2.39 (m, 2H), 1.94-2.06 (m, 2H). (ESI⁺)[(M + H)⁺]: 570.0. |
| C123 | Trans-3-[2-[5-bromo-2-(8-chloro-4-oxo-chromen-2-yl)phenoxy]ethoxy]-N-methylsulfonyl-cyclobutanecarboxamide | EX: C003-B AMINE: methanesulfonamide | ¹H NMR (DMSO-d₆, 400 MHz): δ ppm 8.01 (d, J = 7.8 Hz, 2H), 7.94 (d, J = 8.6 Hz, 1H), 7.41-7.56 (m, 3H), 7.33 (s, 1H), 4.31-4.36 (m, 2H), 4.10-4.17 (m, 1H), 3.63-3.70 (m, 2H), 3.28 (s, 3H), 2.87-2.93 (m, 1H), 2.25-2.33 (m, 2H), 1.98-2.12 (m, 2H). (ESI⁺)[(M + H)⁺]: 569.9. |
| C124 | 3-[3-[2-(8-chloro-4-oxo-chromen-2-yl)-5-(trifluoromethyl)phenoxy]propoxy]-N-methylsulfonyl-cyclopentanecarboxamide | EX: C104 AMINE: methanesulfonamide | ¹H NMR (DMSO-d₆, 400 MHz): δ ppm 8.1-8.2 (m, 1H), 7.89-8.02 (m, 1H), 7.80-7.91 (m, 1H), 7.28-7.41 (m, 3H), 7.11-7.19 (m, 1H), 4.23 (t, 2H, J = 6.0 Hz), 3.82-4.01 (m, 1H), 3.38-3.59 (m, 2H), 3.01-3.09 (s, 3H), 2.48-2.93 (m, 1H), 2.01-2.12 (m, 2H), 1.51-1.92 (m, 6H). (ESI⁺)[(M + H)⁺]: 587.9. |
| C125 | 3-[2-[2-(8-chloro-4-oxo-chromen-2-yl)-4,5-dimethoxy-phenoxy]ethoxy]-N-methylsulfonyl-cyclobutanecarboxamide | EX: C072 AMINE: methanesulfonamide | ¹H NMR (DMSO-d₆, 400 MHz): δ ppm 7.97 (dd, J = 7.0, 5.7 Hz, 2H), 7.61 (s, 1H), 7.47 (t, J = 7.8 Hz, 1H), 7.24 (s, 1H), 6.91 (s, 1H), 4.25-4.37 (m, 2H), 3.87-3.98 (m, 4H), 3.82 (s, 3H), 3.63-3.77 (m, 2H), 3.02 (s, 3H), 2.28-2.42 (m, 3H), 1.95-2.05 (m, 2H). (ESI⁺)[(M + H)⁺]: 552.1. |

TABLE 10-continued

Compounds synthesis and characterization

| Example No. | Compounds Name and Structure | EX and AMINE | $^1$H NMR and (ESI$^+$) |
|---|---|---|---|
| C126 | 2-[4-bromo-2-[2-[2-(3-hydroxypyrrolidin-1-yl)-2-oxo-ethoxy]ethoxy]phenyl]-8-chloro-chromen-4-one | EX:C006 AMINE: pyrrolidin-3-ol | $^1$H NMR (DMSO-d$_6$, 400 MHz) δ ppm 7.96-8.05 (m, 2H), 7.91 (dd, J = 8.6, 1.8 Hz, 1H), 7.38-7.56 (m, 3H), 7.18 (d, J = 2.9 Hz, 1H), 4.84-4.96 (m, 1H), 4.38 (t, J = 4.4 Hz, 2H), 4.10-4.24 (m, 3H), 3.82-3.94 (m, 2H), 3.35-3.40 (m, 2H), 3.11-3.25 (m, 2H), 1.63-1.88 (m, 2H). MS obsd. (ESI$^+$)[(M + H)$^+$]: 522.1. |

Similar flavone compounds, 7-hydroxy-2-(2-hydroxyphenyl)chromen-4-one (compound F-1) in patent WO2015061294 for treating HBV infection as STING agonist and 6-methoxy-2-(2-methoxyphenyl)chromen-4-one (compound F-2) disclosed in patent WO 2001003681 for treating infections, were chosen as reference compounds in present invention.

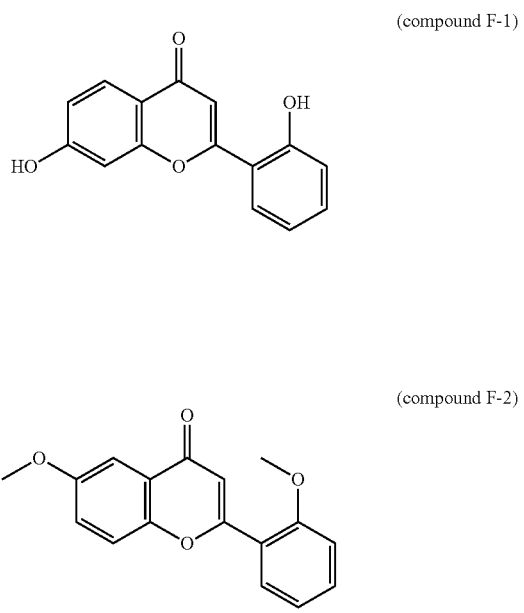

(compound F-1)

(compound F-2)

BIOLOGICAL EXAMPLES

Biological Example 1: Engineered HepDES19 Primary Screen Assay

The assay was employed to screen for novel cccDNA inhibitors. HepDES19 is a cccDNA-producing cell line. In this cell line, HBeAg in the cell culture supernatant as surrogate marker, as HBeAg production depends on cccDNA level and activity. HepDES19 is an engineered cell line which contains a 1.1 unit length HBV genome, and pgRNA transcription from the transgene is controlled by Tetracycline (Tet). In the absence of Tet, pgRNA transcription will be induced, but HBV e antigen (HBeAg) could not be produced from this pgRNA due to very short leader sequence before the HBeAg start codon and the start codon is disrupted. Only after cccDNA is formed, the missing leader sequence and start codon mutation would be restored from the 3'-terminal redundancy of pgRNA, and then HBeAg could be synthesized. Therefore, HBeAg could be used as a surrogate marker for cccDNA (Zhou, T. et al., Antiviral Res. (2006), 72(2), 116-124; Guo, H. et al., J. Virol. (2007), 81(22), 12472-12484).

HepDES19 cells were seeded at 2×10$^6$ cells per T150 flask and cultured with the culture medium (Dulbecco's Modified Eagle Medium: Nutrient Mixture F-12 [DMEM-F12, Gibco Cat. 11320-82], 10% Fetal Bovine Serum [FBS, Clontech Cat. 631101], 0.1 mM Non-Essential Amino Acids Solution [NEAA, Gibco Cat. 11140-050], 50 µg/mL Penicillin-Streptomycin [PS, Invitrogen Cat. 15140-163], 500 µg/mL Geneticin [G418, Invitrogen Cat. 10131-027]) containing 3 µg/mL Tet (Sigma, Cat. 87128) for 5 days. Cells were then seeded at 4×10$^6$ cells per T150 in the same culture medium as described above in the absence of Tet for 8 days. Cells were then harvested and frozen at density of 2×10$^6$ cells per mL. For compound testing, the frozen cells were thawed and seeded into 96-well plates at a density of 6×10$^4$ cells per well. At 24 hours after seeding, half log serial dilutions of compounds made with Dimethyl sulfoxide (DMSO, Sigma, Cat. D2650) were further diluted with the same culture medium as described above before they were added to the cells to reach desired final compound concentrations and 1% DMSO concentration. Plates were then incubated at 37° C. for another 5 days before measurement of HBeAg level and cell viability. Intracellular HBeAg level were measured with enzyme-linked immunosorbent assay (ELISA) kit (Shanghai Kehua Diagnostic Medical Products Co., Ltd). Cell viability was assessed using Cell Counting Kit-8 (DonJindo, Cat. CK04-20). IC$_{50}$ values were derived from the dose-response curve using 4 parameter logistic curve fit method.

The compounds of the present invention were tested for their capacity to inhibit extracellular HBeAg level as described herein. The compounds of this invention were found to have IC$_{50}$ below 50 µM. Particular compounds of formula (I) were found to have IC$_{50}$ below 5.0 µM. Results of HepDES19 primary screen assay are given in Table D1.

TABLE D1

Activity data in HepDES19 primary screen assay

| Example No. | IC$_{50}$ (μM) |
|---|---|
| A001 | 1.64 |
| A002 | 0.795 |
| A003 | 0.362 |
| A004 | 0.374 |
| A005 | 1.37 |
| A006 | 1.23 |
| A007 | 3.15 |
| A008 | 2.26 |
| A009 | 0.403 |
| A010 | 1.4 |
| A011 | 0.415 |
| A012 | 0.65 |
| A013 | 0.656 |
| A014 | 3.22 |
| A015 | 11.1 |
| A016 | 1.03 |
| A017 | 3.17 |
| A018 | 3.32 |
| A019 | 2.96 |
| A020 | 0.78 |
| A021 | 4.04 |
| A022 | 0.983 |
| A023 | 29.6 |
| A024 | 0.57 |
| A025 | 3.55 |
| A026 | 2.97 |
| A031 | 0.377 |
| A032 | 13.0 |
| A033 | 0.479 |
| A034 | 13.4 |
| A038 | 4.79 |
| A039 | 0.142 |
| A040 | 0.525 |
| A041 | 6.06 |
| A042 | 17.8 |
| A043 | 2.25 |
| A044 | 2.52 |
| A045 | 2.03 |
| A046 | 7.86 |
| A047 | 1.83 |
| A048 | 9.38 |
| A049 | 0.0872 |
| A050 | 11.8 |
| A051 | 2.41 |
| A052 | 0.213 |
| A053 | 0.491 |
| A054 | 1.47 |
| A055 | 0.0955 |
| A056 | 3.11 |
| A057 | 1.33 |
| A058 | 0.549 |
| A059 | 0.622 |
| A060 | 5.36 |
| A061 | 15.9 |
| A062 | 13.0 |
| A063 | 1.35 |
| A064 | 9.59 |
| A065 | 1.9 |
| A066 | 2.44 |
| A067 | 1.68 |
| A068 | 5.7 |
| A069 | 2.73 |
| A070 | 0.63 |
| A071 | 6.46 |
| A072 | 0.366 |
| A074 | 2.38 |
| A075 | 2.85 |
| A076 | 14.1 |
| A077 | 9.0 |
| A078 | 10.2 |
| A079 | 19.0 |
| A080 | 17.5 |
| A081 | 0.26 |
| A082 | 1.19 |
| A083 | 5.57 |
| A084 | 1.45 |
| A085 | 4.92 |
| A086 | 1.0 |
| A087 | 4.98 |
| A088 | 1.11 |
| A089 | 11.9 |
| A090 | 4.79 |
| A091 | 0.888 |
| A092 | 1.13 |
| A093 | 1.32 |
| A094 | 0.858 |
| A095 | 3.29 |
| A096 | 0.114 |
| A097 | 0.983 |
| A098 | 0.036 |
| A099 | 0.0663 |
| B001 | 0.213 |
| B002-A | 0.162 |
| B002-B | 0.112 |
| B003 | 0.468 |
| B004 | 0.556 |
| B005 | 0.219 |
| B006 | 5.48 |
| B007 | 2.31 |
| B009 | 5.98 |
| B010 | 2.76 |
| B011-A | 0.851 |
| B011-B | 3.48 |
| B012-A | 3.27 |
| B012-B | 2.72 |
| B013-A | 0.919 |
| B013-B | 2.45 |
| B014 | 15.5 |
| B015-A | 3.79 |
| B016 | 3.1 |
| B017 | 4.85 |
| B018-A | 0.146 |
| B018-B | 0.548 |
| B019-A | 1.03 |
| B019-B | 3.63 |
| B020-A | 2.84 |
| B020-B | 9.44 |
| B021 | 3.06 |
| B022-A | 0.112 |
| B022-B | 0.141 |
| B023 | 3.39 |
| B024 | 1.64 |
| B025-A | 4.92 |
| B025-B | 2.27 |
| B026-A | 0.0394 |
| B026-B | 0.138 |
| B027-A | 2.47 |
| B027-B | 11.0 |
| B028-A | 0.471 |
| B028-B | 0.213 |
| B029 | 14.1 |
| B035-A | 0.16 |
| B035-B | 2.02 |
| B036-A | 0.926 |
| B036-B | 0.407 |
| B037-A | 4.43 |
| B037-B | 0.149 |
| B038-A | 1.05 |
| B038-B | 0.312 |
| B039-A | 6.76 |
| B039-B | 11.5 |
| B040-A | 0.302 |
| B040-B | 2.93 |
| B041 | 0.289 |
| B042 | 0.865 |
| B043-A | 1.4 |
| B043-B | 1.14 |
| B044-A | 4.62 |
| B044-B | 3.72 |
| B047-A | 1.96 |
| B047-B | 3.76 |
| B048-A | 0.632 |

TABLE D1-continued

Activity data in HepDES19 primary screen assay

| Example No. | IC$_{50}$ (µM) |
|---|---|
| B048-B | 3.08 |
| B049-A | 12.2 |
| B049-B | 8.74 |
| B050-A | 7.03 |
| B050-B | 6.08 |
| B051-A | 6.18 |
| B051-B | 9.22 |
| B052-A | 10.7 |
| B052-B | 16.3 |
| B053-A | 3.36 |
| B053-B | 0.912 |
| B054 | 1.65 |
| B055-A | 3.59 |
| B055-B | 3.88 |
| B056-A | 9.44 |
| B057 | 1.08 |
| B070 | 0.435 |
| B071 | 0.988 |
| B072 | 0.95 |
| B073 | 1.04 |
| B075 | 0.774 |
| B076 | 0.111 |
| B077 | 0.657 |
| B078 | 0.541 |
| B079 | 1.52 |
| B080 | 1.2 |
| B081 | 3.11 |
| B082 | 1.98 |
| B083 | 0.704 |
| B084 | 0.533 |
| B085 | 4.57 |
| B086 | 4.89 |
| B087 | 3.0 |
| B088 | 1.85 |
| C001 | 3.05 |
| C002 | 0.348 |
| C003a | 0.4 |
| C003-A | 1.07 |
| C003-B | 1.34 |
| C004 | 1.32 |
| C005 | 17.7 |
| C006 | 1.26 |
| C009 | 2.66 |
| C010 | 0.696 |
| C011 | 10.6 |
| C012 | 5.26 |
| C013 | 0.252 |
| C014 | 2.19 |
| C015 | 7.87 |
| C016 | 2.46 |
| C017 | 0.492 |
| C018 | 4.82 |
| C019 | 0.185 |
| C020 | 5.55 |
| C021 | 9.25 |
| C022 | 5.53 |
| C023 | 3.99 |
| C024 | 0.909 |
| C025-A | 0.191 |
| C025-B | 0.205 |
| C026 | 0.526 |
| C027 | 1.8 |
| C028 | 3.32 |
| C029-A | 3.36 |
| C029-B | 1.32 |
| C030-A | 1.37 |
| C030-B | 12.8 |
| C031-A | 6.19 |
| C032-A | 19.2 |
| C033-A | 1.34 |
| C033-B | 0.927 |
| C034-A | 0.526 |
| C034-B | 1.81 |
| C035-A | 12.5 |
| C035-B | 17.9 |
| C036-A | 0.261 |
| C036-B | 0.77 |
| C037-A | 0.0975 |
| C037-B | 0.531 |
| C038-A | 0.643 |
| C038-B | 1.53 |
| C039-A | 8.91 |
| C039-B | 17.5 |
| C040-A | 13.2 |
| C040-B | 17.1 |
| C041-A | 7.84 |
| C041-B | 9.64 |
| C042-A | 12.7 |
| C042-B | 15.3 |
| C043-A | 2.68 |
| C043-B | 9.42 |
| C044-A | 2.01 |
| C044-B | 1.57 |
| C045-A | 2.62 |
| C045-B | 2.88 |
| C046-A | 0.192 |
| C046-B | 0.251 |
| C047-A | 16.6 |
| C047-B | 14.0 |
| C048-A | 5.12 |
| C049-A | 0.0775 |
| C049-B | 0.103 |
| C050 | 15.6 |
| C050-B | 0.137 |
| C051-A | 4.14 |
| C051-B | 9.41 |
| C052-A | 5.99 |
| C053-B | 5.59 |
| C054 | 2.99 |
| C055-A | 4.03 |
| C056-A | 2.39 |
| C056-B | 2.18 |
| C057-A | 5.01 |
| C058-A | 5.1 |
| C060 | 9.81 |
| C061 | 3.35 |
| C062 | 1.51 |
| C062a | 2.45 |
| C063-A | 4.95 |
| C063-B | 14.9 |
| C064-A | 1.94 |
| C064-B | 2.93 |
| C065-B | 12.2 |
| C066-A | 1.02 |
| C066-B | 1.02 |
| C067-B | 8.36 |
| C068 | 4.74 |
| C069-A | 5.09 |
| C069-B | 1.29 |
| C070 | 13.1 |
| C071 | 10.8 |
| C072 | 6.31 |
| C073 | 0.92 |
| C074 | 7.28 |
| C075 | 10.9 |
| C076 | 0.502 |
| C077 | 3.21 |
| C078 | 15.0 |
| C079 | 5.5 |
| C080 | 4.0 |
| C081 | 0.779 |
| C082 | 3.97 |
| C083 | 4.59 |
| C084 | 15.1 |
| C085 | 0.271 |
| C086 | 5.03 |
| C087 | 6.35 |
| C088 | 10.3 |
| C089 | 3.78 |
| C090 | 6.57 |
| C091 | 0.418 |
| C092 | 11.2 |

TABLE D1-continued

Activity data in HepDES19 primary screen assay

| Example No. | IC$_{50}$ (µM) |
|---|---|
| C093 | 7.79 |
| C094 | 0.04 |
| C095 | 3.29 |
| C096 | 3.48 |
| C097 | 1.31 |
| C098 | 8.56 |
| C099 | 15.7 |
| C100 | 0.691 |
| C101 | 2.38 |
| C102 | 7.0 |
| C103 | 2.28 |
| C104 | 4.46 |
| C105 | 1.74 |
| C106 | 2.1 |
| C107 | 0.991 |
| C108 | 1.25 |
| C109 | 0.995 |
| C110-A | 0.433 |
| C110-B | 3.74 |
| C111 | 1.25 |
| C112 | 11.4 |
| C113 | 1.28 |
| C114 | 1.24 |
| C115 | 19.2 |
| C116 | 9.13 |
| C117 | 2.52 |
| C118 | 14.7 |
| C119 | 3.48 |
| C120 | 1.05 |
| C121 | 5.89 |
| C122 | 1.05 |
| C123 | 6.53 |
| C124 | 2.84 |
| C125 | 4.91 |
| C126 | 4.4 |
| F-1 | >50 |
| F-2 | >50 |

Biological Example 2: Cryopreserved Primary Human Hepatocytes (PHH) Assay

This assay is used to confirm the anti-HBV effect of the compounds in HBV PHH infection assay. Cryopreserved PHH (BioreclamationIVT, Lot YJM) was thawed at 37° C. and gently transferred into pre-warmed InVitroGRO HT medium (BioreclamationIVT, Cat. S03317). The mixture was centrifuged at 70 relative centrifugal force (RCF) for 3 minutes at RT, and the supernatant was discarded. Pre-warmed InVitroGRO CP medium (BioreclamationIVT, Cat #S03316) was added to the cell pellet to gently re-suspend cells. The cells were seeded at the density of 5.8×10$^4$ cells per well to collagen I coated 96-well plate (Gibco, Cat. A1142803) with the InVitroGRO CP medium. All plates were incubated at 37° C. with 5% CO$_2$ and 85% humidity.

At 20 hours after plating, the medium was changed to PHH culture medium (Dulbecco's Modified Eagle Medium (DMEM)/F12 (1:1) (Gibco, Cat. 11320-033), 10% fetal bovine semm (Gibco Cat. 10099141), 100 U/mL penicillin, 100 µg/mL streptomycin (Gibco, Cat. 151401-122), ng/mL human epidermal growth factor (Invitrogen Cat. PHG0311L), 20 ng/mL dexamethasone (Sigma, Cat. D4902) and 250 ng/mL human recombinant insulin (Gibco, Cat. 12585-014)). And the cells were incubated at 37° C. with 5% CO$_2$ and 85% humidity for 4 hours. The medium was then changed to pre-warmed PHH culture medium containing 4% polyethylene glycol (PEG) MW8000 (Sigma, Cat. P1458-50 ML) and 1% DMSO (Sigma, Cat. D2650). 5.8×10$^6$ genomic equivalents of HBV were added into the medium.

At 24 hours post-infection, the cells were gently washed with PBS and refreshed with PHH culture medium supplemented with 1% DMSO, and 0.25 mg/mL Matrix gel (Corning, Cat. 356237) at 200 µL per well. All plates were immediately placed in at 37° C. CO$_2$ incubator.

24 hours later, serial dilutions of compounds made with DMSO were further diluted with the same culture medium (PHH culture medium supplemented with 1% DMSO and 0.25 mg/mL Matrix gel as described above) before they were added to the cells to reach desired final compound concentrations and 1% DMSO concentration. The medium containing the compounds were refreshed every three days.

At 9 days post-compound treatment, extracellular HBsAg level were measured with Chemiluminescence Immuno Assay (CLIA) kit (Autobio, HBsAg Quantitative CLIA). Extracellular HBV DNA was extracted by MagNA Pure 96 system (Roche) and then determined by quantitative PCR with the following primers and probe:

```
HBV-Forward Primer (SEQ ID NO: 1):
AAGAAAAACCCCGCCTGTAA (5' to 3');

HBV-Reverse Primer (SEQ ID NO: 2):
CCTGTTCTGACTACTGCCTCTCC (5' to 3');

HBV-Probe: 5' + tetramethylrhodamine +
SEQ ID NO: 3 + black hole quencher 2-3',
wherein SEQ ID NO: 3 is
CCTGATGTGATGTTCTCCATGTTCAGC.
```

HBsAg IC$_{50}$ and HBV DNA IC$_{50}$ values were derived from the dose-response curve using 4 parameter logistic curve fit method. The compounds of formula (I) have HBsAg IC$_{50}$<20 µM, particularly <1 µM; and HBV DNA IC$_{50}$<50 µM. Results of Cryopreserved PHH assay are given in Table D2.

TABLE D2

HBsAg IC$_{50}$ data in Cryopreserved PHH assay

| Example No. | HBsAg IC$_{50}$ (µM) |
|---|---|
| A001 | 1.19 |
| A002 | 1.82 |
| A004 | 6.61 |
| A005 | 0.553 |
| A006 | 1.08 |
| A007 | 2.73 |
| A008 | 0.948 |
| A009 | 1.48 |
| A010 | 3.0 |
| A011 | 0.931 |
| A012 | 2.11 |
| A013 | 1.91 |
| A016 | 0.828 |
| A017 | 1.84 |
| A020 | 7.5 |
| A022 | 0.754 |
| A024 | 4.09 |
| A026 | 2.97 |
| A039 | 7.08 |
| A040 | 7.94 |
| A043 | 6.69 |
| A044 | 1.77 |
| A049 | 1.26 |
| A052 | 6.91 |
| A053 | 3.57 |
| A054 | 4.21 |
| A055 | 2.38 |
| A056 | 9.21 |
| A057 | 9.76 |
| A083 | 9.74 |
| A084 | 1.02 |

TABLE D2-continued

HBsAg IC$_{50}$ data in Cryopreserved PHH assay

| Example No. | HBsAg IC$_{50}$ (μM) |
|---|---|
| A090 | 9.35 |
| A092 | 2.8 |
| A096 | 1.24 |
| A097 | 4.03 |
| A099 | 0.14 |
| B001 | 1.03 |
| B002-A | 2.02 |
| B002-B | 3.35 |
| B003 | 4.37 |
| B004 | 5.52 |
| B005 | 6.97 |
| B007 | 2.24 |
| B010 | 7.08 |
| B011-A | 2.32 |
| B012-A | 6.01 |
| B012-B | 2.56 |
| B013-A | 7.3 |
| B013-B | 1.02 |
| B015-A | 2.57 |
| B017 | 4.87 |
| B018-A | 0.887 |
| B018-B | 4.7 |
| B019-A | 3.96 |
| B022-A | 3.83 |
| B024 | 6.84 |
| B025-B | 3.06 |
| B026-A | 4.97 |
| B026-B | 3.19 |
| B035-A | 1.46 |
| B036-A | 9.5 |
| B037-A | 2.04 |
| B043-B | 3.7 |
| B047-A | 5.54 |
| B050-B | 9.46 |
| B051-A | 3.21 |
| B051-B | 5.3 |
| B052-A | 8.48 |
| B052-B | 7.98 |
| B055-B | 4.0 |
| B070 | 0.788 |
| B071 | 4.95 |
| B073 | 5.97 |
| B076 | 1.31 |
| B082 | 4.8 |
| B083 | 3.24 |
| C002 | 2.43 |
| C003-A | 8.77 |
| C006 | 3.74 |
| C010 | 9.38 |
| C011 | 8.5 |
| C013 | 9.32 |
| C014 | 7.8 |
| C015 | 3.36 |
| C016 | 7.14 |
| C017 | 2.94 |
| C019 | 3.0 |
| C025-A | 2.58 |
| C025-B | 2.02 |
| C026 | 8.95 |
| C031-A | 1.16 |
| C033-A | 1.97 |
| C033-B | 4.33 |
| C034-A | 4.69 |
| C034-B | 9.11 |
| C036-A | 2.42 |
| C036-B | 5.58 |
| C038-A | 8.61 |
| C041-A | 5.93 |
| C042-B | 8.96 |
| C043-A | 8.67 |
| C043-B | 5.2 |
| C044-A | 9.58 |
| C049-A | 7.31 |
| C055-A | 9.27 |
| C062 | 6.79 |
| C063-A | 6.61 |
| C067-B | 4.74 |
| C073 | 7.56 |
| C077 | 9.37 |
| C078 | 6.32 |
| C080 | 3.51 |
| C081 | 8.77 |
| C082 | 9.52 |
| C084 | 5.21 |
| C085 | 9.02 |
| C086 | 5.46 |
| C096 | 7.78 |
| C103 | 7.56 |
| C113 | 8.89 |
| C114 | 9.19 |
| C119 | 7.21 |
| C120 | 4.12 |
| C122 | 4.81 |
| C125 | 7.17 |

Biological Example 3: cccDNA Southern Blot Assay

HepDES19 cells were seeded at 4*10$^6$ cells per T150 in the culture medium (Dulbecco's Modified Eagle Medium: Nutrient Mixture F-12 [DMEM-F12, Gibco Cat. 11320-82], 10% Fetal Bovine Serum [FBS, Clontech Cat. 631101], 0.1 mM Non-Essential Amino Acids Solution [NEAA, Gibco Cat. 11140-050], 50 μg/mL Penicillin-Streptomycin [PS, Invitrogen Cat. 15140-163], 500 μg/mL Geneticin [G418, Invitrogen Cat. 10131-027]) in the absence of Tet for 8 days. These cells were seeded at the density of 1×10$^6$ cells per well in 6-well plate. At 24 hours after seeding, serial dilutions of compounds made with DMSO (Sigma, Cat. D2650) were further diluted with the same culture medium as described above before they were added to the cells to reach desired final compound concentrations and 1% DMSO concentration. After 5 days' compound treatment, the cells growing in one well from 6-well plate were re-suspended with 500 μL re-suspension buffer (50 mM tris [hydroxymethyl]amino methane pH 7.5), 10 mM ethylenediaminetetraacetic acid (EDTA), 50 μg/mL RNase A [Qiagen, Cat. 158922], 500 μL of 1.2% sodium dodecyl sulfate (SDS) was then added into the re-suspended cells to lyse the cells. After 15 minutes' incubation, 700 μL precipitation buffer (3M cesium chloride, 1M potassium acetate, 0.67M acetic acid) was added and the lysate was incubated at 4° C. for 2 h. The lysate was centrifuged at 15000 revolutions per minute (RPM) at 4° C. for 15 minutes. The supernatant was collected and loaded onto Qiagen miniprep columns (QIAprep spin Mini prep kit, Cat. No. 27016). After centrifugation for 1 minute at 15000 RPM, the column was washed once with 750 μL wash buffer PE (QIAprep spin Mini prep kit, Cat. No. 27016). 80 μL of double distilled water was loaded to the columns to elute Hirt DNA.

Hirt DNA of each sample was loaded into 1.2% 1x tris-acetate electrophoresis (TAE) agarose gel and separated at 90 voltages for 3 hours. The gel was then treated in 50 mM NaAc—HAc, pH4.2 for 30 min at room temperature (RT), and then denatured by soaking in denaturation buffer (0.5 M sodium hydroxide, 1.5 M sodium chloride) at room temperature for 30~45 minutes. The gel was then treated with neutralization buffer (1M tris [hydroxymethyl]amino methane pH7.4 and 1.5M NaCl) at room temperature for 30~45 minutes.

The gel was transferred onto a pre-wet Nylon membrane (GE life science, Hybond N+) by capillary transfer method overnight, followed by UV crosslinking. The membrane was transferred into a hybridization tube, then rinsed with double distilled water at 60° C. for 5 min. 10 mL of hybridization buffer (Lab kits, China) was added, the resulting sample was rotated in hybridization oven at 60° C. for 1 hour. Digoxigenin (DIG)-labelled HBV probe was denatured at 95° C. for 10 minutes, and then 7 μL of denatured probe was added to the hybridization tube, which was rotated in hybridization oven at 60° C. overnight.

On the second day, the membrane was washed according to the procedure of DIG wash and block buffer set kit (Roche, Cat. 11 585 762 001), and then incubated with 50 mL antibody solution (Antibody anti-Digoxigenin-AP Fab fragment [Roche Cat. 11093274910] diluted in fresh lxblocking buffer at 1:10,000) for 1 hour. The membrane was washed with 50 mL washing buffer (1×Maleic buffer with 0.3% Tween-20) for 15 minutes twice, and equilibrated with 20 mL detection buffer (0.1M tris [hydroxymethyl] amino methane pH9.5, 0.1M sodium chloride) for 5 minutes. CDP-Star substrate (Roche, Cat. 12041677001) was added to the membrane for 5 minutes, and then the membrane was scanned by Bio-Rad Visualize Image System (Biorad, ChemiDoc-MP, Serial No. 731BR00916).

Results of cccDNA Southern Blot assay are given in FIG. 1. The results indicate that the compounds of this invention dose-dependently reduced cccDNA level in HepDES19 cells.

Biological Example 4: Human Microsome Stability Assay

The human microsomal stability assay is used for early assessment of metabolic stability of a test compound in human liver microsomes.

Human liver microsomes (Cat. NO.: 452117, Corning, USA; Cat. NO.: H2610, Xenotech, USA) were preincubated with test compound for 10 minutes at 37° C. in 100 mM potassium phosphate buffer, pH 7.4. The reactions were initiated by adding NADPH regenerating system. The final incubation mixtures contained 1 μM test compound, 0.5 mg/mL liver microsomal protein, 1 mM $MgCl_2$, 1 mM NADP, 1 unit/mL isocitric dehydrogenase and 6 mM isocitric acid in 100 mM potassium phosphate buffer, pH 7.4. After incubation times of 0, 3, 6, 9, 15 and 30 minutes at 37° C., 300 μL of cold ACN (including internal standard) was added to 100 μL incubation mixture to terminate the reaction. Following precipitation and centrifugation, the amount of compound remaining in the samples was determined by LC-MS/MS. Controls of no NADPH regenerating system at zero and 30 minutes were also prepared and analyzed. The compounds of present invention showed good human liver microsome stability determined in the above assay, results are shown in Table D3 below.

TABLE D3

Human liver microsome stability of the compounds of present invention

| Example No. | Clearance of Human microsome (mL/min/kg) |
|---|---|
| A001 | 10.0 |
| A003 | 6.15 |
| A004 | 6.15 |
| A005 | 6.66 |
| A007 | 6.15 |
| A008 | 6.15 |
| A009 | 6.57 |
| A010 | 6.15 |
| A015 | 6.15 |
| A017 | 9.98 |
| A018 | 6.15 |
| A019 | 6.15 |
| A021 | 6.15 |
| A022 | 6.15 |
| A024 | 6.61 |
| A026 | 6.15 |
| A031 | 6.15 |
| A032 | 6.15 |
| A033 | 6.15 |
| A034 | 6.15 |
| A039 | 6.37 |
| A040 | 6.15 |
| A041 | 6.15 |
| A042 | 6.15 |
| A043 | 6.15 |
| A044 | 6.15 |
| A046 | 6.15 |
| A047 | 6.15 |
| A049 | 6.15 |
| A050 | 6.15 |
| A051 | 6.15 |
| A052 | 8.01 |
| A053 | 7.66 |
| A054 | 6.15 |
| A056 | 6.15 |
| A057 | 6.15 |
| A058 | 6.15 |
| A059 | 8.34 |
| A060 | 6.15 |
| A061 | 8.78 |
| A062 | 9.88 |
| A063 | 6.15 |
| A064 | 9.5 |
| A065 | 6.15 |
| A067 | 6.15 |
| A069 | 6.15 |
| A070 | 6.15 |
| A071 | 7.4 |
| A073 | 6.15 |
| A074 | 6.15 |
| A075 | 6.15 |
| A076 | 6.15 |
| A077 | 8.57 |
| A078 | 6.15 |
| A079 | 6.6 |
| A080 | 6.15 |
| A081 | 6.15 |
| A082 | 6.15 |
| A083 | 6.15 |
| A084 | 7.5 |
| A085 | 6.15 |
| A086 | 9.68 |
| A088 | 7.09 |
| A089 | 6.69 |
| A091 | 6.15 |
| A093 | 6.15 |
| A094 | 6.15 |
| A095 | 9.59 |
| A096 | 6.15 |
| A097 | 8.78 |
| A099 | 9.53 |
| B002-A | 6.15 |
| B002-B | 6.15 |
| B003 | 6.15 |
| B004 | 6.15 |
| B005 | 6.15 |
| B007 | 6.15 |
| B009 | 6.19 |
| B010 | 6.15 |
| B011-A | 8.35 |

TABLE D3-continued

Human liver microsome stability of the compounds of present invention

| Example No. | Clearance of Human microsome (mL/min/kg) |
|---|---|
| B012-A | 6.15 |
| B015-A | 6.15 |
| B016 | 6.15 |
| B018-A | 6.15 |
| B019-B | 8.92 |
| B020-B | 8.46 |
| B021 | 6.15 |
| B022-B | 6.15 |
| B022-A | 6.15 |
| B023 | 6.15 |
| B024 | 7.41 |
| B026-A | 6.15 |
| B026-B | 6.15 |
| B027-B | 6.15 |
| B028-B | 9.98 |
| B029 | 6.15 |
| B035-A | 8.46 |
| B05-B | 6.51 |
| B036-A | 6.15 |
| B037-A | 9.86 |
| B038-A | 6.84 |
| B038-B | 9.59 |
| B039-B | 6.15 |
| B040-B | 6.29 |
| B041 | 6.15 |
| B042 | 6.15 |
| B043-A | 6.15 |
| B043-B | 6.15 |
| B044-A | 6.15 |
| B044-B | 6.15 |
| B047-A | 6.15 |
| B047-B | 6.15 |
| B048-A | 6.15 |
| B048-B | 6.15 |
| B049-A | 7.5 |
| B050-A | 6.15 |
| B050-B | 7.69 |
| B051-A | 6.15 |
| B051-B | 6.97 |
| B052-A | 6.15 |
| B052-B | 6.15 |
| B053-A | 6.15 |
| B053-B | 6.15 |
| B054 | 6.15 |
| B056-A | 6.48 |
| B057 | 6.15 |
| B072 | 8.89 |
| B073 | 6.15 |
| B076 | 6.15 |
| B077 | 6.15 |
| B078 | 6.15 |
| B080 | 6.15 |
| B082 | 6.15 |
| B083 | 6.15 |
| B084 | 6.15 |
| B086 | 6.15 |
| B087 | 6.15 |
| B088 | 6.15 |
| C001 | 6.15 |
| C002 | 6.15 |
| C003a | 6.15 |
| C005 | 8.08 |
| C006 | 6.15 |
| C009 | 6.15 |
| C011 | 6.15 |
| C012 | 6.15 |
| C013 | 6.15 |
| C014 | 8.04 |
| C015 | 6.15 |
| C016 | 6.15 |
| C017 | 6.15 |
| C018 | 6.74 |
| C019 | 6.71 |
| C020 | 6.15 |
| C021 | 7.66 |
| C022 | 6.15 |
| C023 | 6.15 |
| C024 | 6.15 |
| C025-A | 6.15 |
| C025-B | 6.15 |
| C026 | 6.81 |
| C027 | 6.15 |
| C028 | 8.85 |
| C032-A | 9.6 |
| C033-A | 6.15 |
| C033-B | 6.15 |
| C034-A | 6.15 |
| C034-B | 6.75 |
| C035-A | 8.64 |
| C035-B | 9.78 |
| C036-A | 6.15 |
| C036-B | 6.15 |
| C037-A | 6.15 |
| C037-B | 6.15 |
| C038-A | 6.15 |
| C038-B | 6.15 |
| C039-A | 6.15 |
| C039-B | 6.15 |
| C040-A | 8.52 |
| C042-A | 7.57 |
| C042-B | 6.15 |
| C043-A | 6.15 |
| C043-B | 7.72 |
| C044-A | 6.15 |
| C044-B | 9.33 |
| C045-A | 6.53 |
| C045-B | 9.43 |
| C046-A | 6.15 |
| C046-B | 6.15 |
| C047-A | 6.15 |
| C047-B | 6.15 |
| C050 | 6.15 |
| C050-B | 6.15 |
| C051-A | 6.15 |
| C051-B | 7.85 |
| C052-A | 9.08 |
| C054 | 6.52 |
| C056-A | 6.15 |
| C057-A | 8.0 |
| C060 | 6.15 |
| C063-A | 9.09 |
| C068 | 6.15 |
| C070 | 9.42 |
| C071 | 6.15 |
| C072 | 6.15 |
| C073 | 7.85 |
| C074 | 6.15 |
| C075 | 6.15 |
| C076 | 6.15 |
| C077 | 6.15 |
| C078 | 6.15 |
| C079 | 6.15 |
| C080 | 6.15 |
| C081 | 6.15 |
| C082 | 6.15 |
| C083 | 6.15 |
| C084 | 6.15 |
| C085 | 6.15 |
| C086 | 6.15 |

TABLE D3-continued

Human liver microsome stability of the compounds of present invention

| Example No. | Clearance of Human microsome (mL/min/kg) |
|---|---|
| C087 | 6.15 |
| C088 | 6.15 |
| C089 | 6.15 |
| C092 | 6.15 |
| C093 | 6.15 |
| C094 | 6.15 |
| C095 | 9.62 |
| C096 | 6.15 |
| C098 | 6.15 |
| C099 | 7.11 |
| C100 | 6.15 |
| C101 | 6.15 |
| C102 | 7.11 |
| C103 | 6.15 |
| C104 | 6.15 |
| C105 | 6.15 |
| C110-A | 6.15 |
| C110-B | 6.15 |
| C111 | 6.15 |
| C112 | 6.15 |
| C113 | 6.15 |
| C115 | 6.15 |
| C116 | 6.15 |
| C117 | 7.45 |
| C118 | 6.15 |
| C119 | 6.39 |
| C120 | 6.15 |
| C121 | 8.68 |
| C122 | 7.32 |
| C125 | 6.15 |

The invention claimed is:
1. A compound of formula (I),

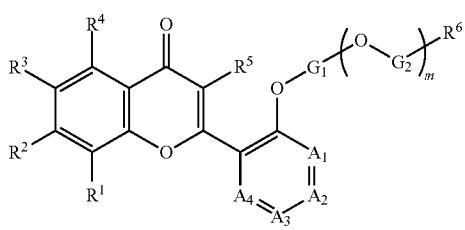

wherein:
$R^1$ is selected from halogen and halo$C_{1-6}$alkyl;
$R^2$ is selected from H, halogen, $C_{1-6}$alkyl, $C_{1-6}$alkoxy, $C_{3-7}$cycloalkyl and halo$C_{1-6}$alkyl;
$R^3$ is selected from H, halogen and $C_{1-6}$alkoxy;
$R^4$ is selected from H, hydroxy and halo$C_{1-6}$alkyl;
$R^5$ is selected from H, halogen, $C_{1-6}$alkyl, $C_{1-6}$alkoxy and hydroxy;
$R^6$ is selected from carboxy, $C_{1-6}$alkoxycarbonyl, carboxy$C_{1-6}$alkoxycarbonyl, carboxy$C_{3-7}$cycloalkylaminocarbonyl, carboxyheterocyclylcarbonyl, $C_{3-7}$cycloalkylsulfonylaminocarbonyl, hydroxy$C_{1-6}$alkylaminocarbonyl, $C_{1-6}$alkylsulfonylheterocyclylcarbonyl, heterocyclylcarbonyl, hydroxyheterocyclylcarbonyl, (hydroxy)$_2$heterocyclylcarbonyl, $C_{1-6}$alkylsulfonylaminocarbonylheterocyclylcarbonyl, $C_{1-6}$alkylsulfonylaminocarbonyl, cyano, ($C_{1-6}$alkyl)$_2$aminosulfonyl, aminocarbonyl, aminosulfonyl, $C_{3-7}$cycloalkylaminocarbonylcarbonyl and $C_{3-7}$cycloalkylaminocarbonyl;
$A_1$ is selected from N and $CR^7$, wherein $R^7$ is selected from H, halogen and halo$C_{1-6}$alkyl;
$A_2$ is selected from N and $CR^8$, wherein $R^8$ is selected from H, halogen, hydroxy, $C_{1-6}$alkyl, $C_{1-6}$alkoxy, $C_{3-7}$cycloalkyl, halo$C_{1-6}$alkyl, halo$C_{1-6}$alkoxy, halo$C_{1-6}$ alkyl$C_{1-6}$alkoxy, $C_{1-6}$alkylsulfanyl, $C_{1-6}$alkylsulfonyl, $C_{3-7}$cycloalkyl$C_{1-6}$alkoxy and heterocyclyl, wherein heterocyclyl is unsubstituted or substituted one or two or three times by oxo;
$A_3$ is selected from N and $CR^9$, wherein $R^9$ is selected from H, amino, halogen, hydroxy, $C_{1-6}$alkyl, $C_{1-6}$alkoxy, halo$C_{1-6}$alkyl, halo$C_{1-6}$alkoxy, halo$C_{1-6}$alkyl$C_{1-6}$alkoxy and $C_{3-7}$cycloalkyl$C_{1-6}$alkoxy;
or $R^8$ and $R^9$, together with the atoms to which they are attached, form a heterocyclyl ring, wherein the heterocyclyl ring is unsubstituted or substituted by one or two or three or four substituents independently selected from halogen, $C_{1-6}$alkyl and oxo;
$A_4$ is selected from N and $CR^{10}$, wherein $R^{10}$ is selected from H and halogen;
$G_1$ is selected from $C_{1-6}$alkyl, $C_{3-7}$cycloalkyl, $C_{3-7}$cycloalkyl$C_{1-6}$alkyl, phenyl$C_{1-6}$alkyl, $C_{1-6}$alkyl$C_{3-7}$cycloalkyl$C_{1-6}$alkyl and heterocyclyl, wherein $G_1$ is unsubstituted or substituted by one or two or three substituents independently selected from hydroxy, amino, $C_{3-7}$cycloalkylsulfonylamino, $C_{1-6}$alkylphenylsulfonylamino, phenylsulfonyl, $C_{3-7}$cycloalkylsulfonyl, $C_{1-6}$alkoxyphenylsulfonyl, phenylcarbonyl, phenylcarbonylamino, $C_{1-6}$alkylcarbonylamino, $C_{1-6}$alkylaminosulfonylamino, aminocarbonyamino, ($C_{1-6}$alkoxy)$_2$phenylaminosulfonylamino, $C_{1-6}$alkoxycarbonylcarbonylamino, ($C_{1-6}$alkyl)$_2$aminosulfonylamino, $C_{1-6}$alkylaminocarbonylamino, $C_{1-6}$alkylaminosulfonyl, aminosulfonylamino, $C_{3-7}$cycloalkylaminosulfonylamino and phenyl$C_{1-6}$alkylaminosulfonylamino;
$G_2$ is selected from $C_{1-6}$alkyl, $C_{3-7}$cycloalkyl and phenyl; and
m is selected from 0 and 1;
or a pharmaceutically acceptable salt thereof.

2. A compound according to claim 1, wherein:
$R^6$ is selected from carboxy, $C_{1-6}$alkoxycarbonyl, carboxy$C_{1-6}$alkoxycarbonyl, carboxy$C_{3-7}$cycloalkylaminocarbonyl, carboxypyrrolidinylcarbonyl, $C_{3-7}$cycloalkylsulfonylaminocarbonyl, hydroxy$C_{1-6}$alkylaminocarbonyl, $C_{1-6}$alkylsulfonylpyrrolidinylcarbonyl, morpholinylcarbonyl, hydroxypyrrolidinylcarbonyl, (hydroxy)$_2$pyrrolidinylcarbonyl, $C_{1-6}$alkylsulfonylaminocarbonylpyrrolidinylcarbonyl, $C_{1-6}$alkylsulfonylaminocarbonyl, cyano, ($C_{1-6}$alkyl)$_2$aminosulfonyl, aminocarbonyl, aminosulfonyl, $C_{3-7}$cycloalkylaminocarbonylcarbonyl and $C_{3-7}$cycloalkylaminocarbonyl;
$A_2$ is selected from N and $CR^8$; wherein $R^8$ is selected from H, halogen, hydroxy, $C_{1-6}$alkyl, $C_{1-6}$alkoxy, $C_{3-7}$cycloalkyl, halo$C_{1-6}$alkyl, halo$C_{1-6}$alkoxy, halo$C_{1-6}$ alkyl$C_{1-6}$alkoxy, $C_{1-6}$alkylsulfanyl, $C_{1-6}$alkylsulfonyl, $C_{3-7}$cycloalkyl$C_{1-6}$alkoxy, thiazolyl, morpholinyl, pyrrolidinyl and oxazolidinyl, wherein pyrrolidinyl and oxazolidinyl are unsubstituted or substituted by one or two or three times by oxo;
or $R^8$ and $R^9$, together with the atoms to which they are attached, form a 5- or 6-membered heterocyclyl ring, wherein the 5- or 6-membered heterocyclyl ring is unsubstituted or substituted by one or two or three or four substituents independently selected from halogen, $C_{1-6}$alkyl and oxo; and
$G_1$ is selected from $C_{1-6}$alkyl, $C_{3-7}$cycloalkyl, $C_{3-7}$cycloalkyl$C_{1-6}$alkyl, phenyl$C_{1-6}$alkyl, $C_{1-6}$alkyl$C_{3-7}$cycloalkyl$C_{1-6}$alkyl and pyrrolidinyl, wherein $G_1$ is unsubstituted or substituted by one or two or three substituents independently selected from hydroxy, amino, $C_{3-7}$cycloalkylsulfonylamino, $C_{1-6}$alkylphenylsulfonylamino, phenylsulfonyl, $C_{3-7}$cycloalkylsulfonyl, $C_{1-6}$alkoxyphenylsulfonyl, phenylcarbonyl, phenylcarbonylamino, $C_{1-6}$alkylcarbonylamino, $C_{1-6}$alkylaminosulfonylamino, aminocarbonyamino, ($C_{1-6}$alkoxy)$_2$phenylaminosulfonylamino, $C_{1-6}$alkoxycarbonylcarbonylamino, ($C_{1-6}$alkyl)$_2$aminosulfonylamino, $C_{1-6}$alkylaminocarbonylamino, $C_{1-6}$alkylaminosulfonyl, aminosulfonylamino, $C_{3-7}$cycloalkylaminosulfonylamino and phenyl$C_{1-6}$alkylaminosulfonylamino;
or a pharmaceutically acceptable salt thereof.

3. A compound according to claim 1, wherein:
$R^1$ is selected from F, Cl, Br and $CF_3$;
$R^2$ is selected from H, F, Cl, Br, methyl, methoxy, $CF_3$ and cyclopropyl;
$R^3$ is selected from H, F and methoxy;
$R^4$ is selected from H, hydroxy and $CF_3$;
$R^5$ is selected from H, hydroxy, methyl and methoxy;
$R^6$ is selected from carboxy, methoxycarbonyl, carboxyisopropoxycarbonyl, carboxycyclobutylaminocarbonyl, carboxypyrrolidinylcarbonyl, cyclopropylsulfonylaminocarbonyl, hydroxyethylaminocarbonyl, methylsulfonylpyrrolidinylcarbonyl, hydroxypyrrolidinylcarbonyl, (hydroxy)$_2$pyrrolidinylcarbonyl, morpholinylcarbonyl, methylsulfonylaminocarbonylpyrrolidinylcarbonyl, methylsulfonylaminocarbonyl, cyano, (methyl)$_2$aminosulfonyl, aminocarbonyl, aminosulfonyl, cyclopropylaminocarbonylcarbonyl and cyclopropylaminocarbonyl;

$A_1$ is selected from N and $CR^7$, wherein $R^7$ is selected from H, F, Cl, Br and $CF_3$;

$A_2$ is selected from N and $CR^8$, wherein $R^8$ is selected from H, F, Cl, Br, $CF_3$, hydroxy, methyl, ethyl, isopropyl, methoxy, ethoxy, propoxy, cyclopropyl, trifluoromethoxy, difluoromethoxy, trifluoromethylmethoxy, methylsulfonyl, methylsulfanyl, cyclopropylmethoxy, thiazolyl, morpholinyl, pyrrolidinyl and oxazolidinyl; wherein pyrrolidinyl and oxazolidinyl are unsubstituted or substituted one or two or three times independently by oxo;

$A_3$ is selected from N and $CR^9$; wherein $R^9$ is selected from H, amino, hydroxy, F, Cl, Br, $CF_3$, methyl, methoxy, ethoxy, difluoromethoxy, trifluoromethoxy, trifluoromethylmethoxy, difluoromethyl and cyclopropylmethoxy;

or $R^8$ and $R^9$, together with the atoms to which they are attached, form a 5- or 6-membered heterocyclyl ring, wherein the 5- or 6-membered heterocyclyl ring is unsubstituted or substituted by one or two or three or four substituents independently selected from F, methyl and oxo;

$A_4$ is selected from N and $CR^{10}$; wherein $R^{10}$ is selected from H and F;

$G_1$ is selected from methyl, ethyl, propyl, isopropyl, butyl, isobutyl, neopentyl, hexyl, isohexyl, cyclobutyl, cyclopentyl, cyclohexyl, cyclobutylmethyl, phenylmethyl, methylcyclopropylmethyl and pyrrolidinyl, wherein $G_1$ is unsubstituted or substituted by one or two or three substituents independently selected from hydroxy, amino, cyclopropylsulfonylamino, methylphenylsulfonylamino, phenylsulfonyl, cyclopropylsulfonyl, methoxyphenylsulfonyl, phenylcarbonyl, phenylcarbonylamino, methylcarbonylamino, ethylaminosulfonylamino, aminocarbonylamino, (methoxy)$_2$phenylcarbamoylamino, ethyoxycarbonylcarbonylamino, dimethylaminosulfonylamino, ethylaminocarbonylamino, ethylaminosulfonyl, aminosulfonylamino, methylaminosulfonylamino, isopropylaminosulfonylamino, cyclopropylaminosulfonylamino and phenylmethylaminosulfonylamino; and $G_2$ is selected from methyl, isopropyl, cyclobutyl, cyclopentyl and phenyl;

or a pharmaceutically acceptable salt thereof.

4. A compound according to claim 1, or a pharmaceutically acceptable salt thereof, wherein:

$R^1$ is halogen;

$R^2$ is selected from H, halogen, $C_{1-6}$alkoxy and $C_{3-7}$cycloalkyl;

$R^4$ is selected from H and hydroxy;

$R^s$ is selected from H, $C_{1-6}$alkyl, $C_{1-6}$alkoxy and hydroxy;

$R^6$ is selected from carboxy, $C_{1-6}$alkoxycarbonyl, carboxy$C_{1-6}$alkoxycarbonyl, carboxy$C_{3-7}$cycloalkylaminocarbonyl, carboxypyrrolidinylcarbonyl, $C_{3-7}$cycloalkylsulfonylaminocarbonyl, hydroxy$C_{1-6}$alkylaminocarbonyl, $C_{1-6}$alkylsulfonylpyrrolidinylcarbonyl, morpholinylcarbonyl, hydroxypyrrolidinylcarbonyl, (hydroxy)$_2$ pyrrolidinylcarbonyl, $C_{1-6}$alkylsulfonylaminocarbonylpyrrolidinylcarbonyl, ($C_{1-6}$alkyl)$_2$aminosulfonyl and aminosulfonyl;

$A_1$ is $CR^7$, wherein $R^7$ is selected from H and halogen;

$A_2$ is $CR^8$, wherein $R^8$ is selected from H, hydroxy, halogen, $C_{1-6}$alkyl, $C_{1-6}$alkoxy, halo$C_{1-6}$alkyl, halo$C_{1-6}$alkoxy and halo$C_{1-6}$alkyl$C_{1-6}$alkoxy;

$A_3$ is selected from N and $CR^9$, wherein $R^9$ is selected from H, halogen, hydroxy, $C_{1-6}$alkyl, $C_{1-6}$alkoxy and halo$C_{1-6}$alkoxy;

or $R^8$ and $R^9$, together with the atoms to which they are attached, form a 5-membered heterocyclyl ring;

$G_1$ is selected from $C_{1-6}$alkyl and $C_{1-6}$alkyl$C_{3-7}$cycloalkyl$C_{1-6}$alkyl; wherein $C_{1-6}$alkyl is unsubstituted or substituted by one or two or three substituents independently selected from hydroxy, amino, $C_{3-7}$cycloalkylsulfonylamino, $C_{1-6}$alkylphenylsulfonylamino and $C_{1-6}$alkylaminosulfonylamino; and m is 0;

or a pharmaceutically acceptable salt thereof.

5. A compound according to claim 4, wherein:

$R^1$ is selected from F, Cl and Br;

$R^2$ is selected from H, F, Cl, Br, methoxy and $CF_3$;

$R^3$ is selected from H, F and methoxy;

$R^5$ is selected from H and hydroxy;

$R^6$ is selected from carboxy, methoxycarbonyl, carboxyisopropoxycarbonyl, carboxycyclobutylaminocarbonyl, carboxypyrrolidinylcarbonyl, cyclopropylsulfonylaminocarbonyl, hydroxyethylaminocarbonyl, methylsulfonylpyrrolidinylcarbonyl, hydroxypyrrolidinylcarbonyl, (hydroxy)$_2$pyrrolidinylcarbonyl, morpholinylcarbonyl, methylsulfonylaminocarbonylpyrrolidinylcarbonyl, (methyl)$_2$aminosulfonyl and aminosulfonyl;

$A_1$ is $CR^7$, wherein $R^7$ is selected from H, F, Cl and Br;

$A_2$ is $CR^8$, wherein $R^8$ is selected from H, F, Cl, Br, $CF_3$, hydroxy, methyl, methoxy, trifluoromethoxy and trifluoromethylmethoxy;

$A_3$ is $CR^9$, wherein $R^9$ is selected from H, hydroxy, F, Cl, Br, methyl, methoxy and trifluoromethoxy;

or $R^8$ and $R^9$, together with the atoms to which they are attached, form a 5-membered heterocyclyl ring;

$A_4$ is selected from N and $CR^{10}$, wherein $R^{10}$ is selected from H and F; and $G_1$ is selected from methyl, ethyl, propyl, isopropyl, butyl, isobutyl, neopentyl, hexyl, isohexyl and methylcyclopropylmethyl; wherein ethyl is unsubstituted or substituted by one or two or three substituents independently selected from hydroxy, amino, cyclopropylsulfonylamino, methylphenylsulfonylamino and ethylaminosulfonylamino;

or a pharmaceutically acceptable salt thereof.

6. A compound according to claim 4, wherein:

$R^2$ is H;

$R^3$ is H;

$R^4$ is H;

$R^s$ is H;

$R^6$ is selected from carboxy and $C_{1-6}$alkoxycarbonyl;

$A_1$ is CH;

$A_2$ is $CR^8$, wherein $R^8$ is selected from halogen, $C_{1-6}$alkoxy, halo$C_{1-6}$alkyl and halo$C_{1-6}$ alkoxy;

$A_3$ is $CR^9$, wherein $R^9$ is selected from H, methyl and methoxy;

$A_4$ is CH; and $G_1$ is $C_{1-6}$alkyl; wherein $C_{1-6}$alkyl is unsubstituted or substituted by one substituent independently selected from $C_{3-7}$cycloalkylsulfonylamino and $C_{1-6}$alkylaminosulfonylamino;

or a pharmaceutically acceptable salt thereof.

7. A compound according to claim 6, wherein:
$R^1$ is selected from Cl and Br;
$R^6$ is selected from carboxy and methoxycarbonyl;
$A_2$ is $CR^8$, wherein $R^8$ is selected from Cl, Br, $CF_3$, methoxy and trifluoromethoxy; and
$G_1$ is ethyl; wherein ethyl is unsubstituted or substituted by one substituent independently selected from cyclopropylsulfonylamino and ethylaminosulfonylamino;
or a pharmaceutically acceptable salt thereof.

8. A compound according to claim 1, selected from:
3-[2-(8-chloro-4-oxo-chromen-2-yl)-5-(trifluoromethyl)phenoxy]propanoic acid;
methyl 3-[2-(8-chloro-4-oxo-chromen-2-yl)-5-(trifluoromethyl)phenoxy]propanoate;
3-[2-(8-chloro-6-fluoro-4-oxo-chromen-2-yl)-5-(trifluoromethyl)phenoxy]propanoic acid;
3-[5-bromo-2-(8-chloro-4-oxo-chromen-2-yl)phenoxy]propanoic acid;
3-[5-chloro-2-(8-chloro-4-oxo-chromen-2-yl)-4-methyl-phenoxy]propanoic acid;
3-[5-bromo-2-(8-chloro-4-oxo-chromen-2-yl)-4-methyl-phenoxy]propanoic acid;
3-[5-bromo-2-(8-chloro-4-oxo-chromen-2-yl)-4-methoxy-phenoxy]propanoic acid;
3-[5-chloro-2-(8-chloro-4-oxo-chromen-2-yl)-4-methoxy-phenoxy]propanoic acid;
3-[2-(8-chloro-4-oxo-chromen-2-yl)-5-(trifluoromethoxy)phenoxy]propanoic acid;
3-[2-(8-chloro-4-oxo-chromen-2-yl)-4,5-dimethoxy-phenoxy]propanoic acid;
3-[[6-(8-chloro-4-oxo-chromen-2-yl)-1,3-benzodioxol-5-yl]oxy]propanoic acid;
3-[2-(8-chloro-4-oxo-chromen-2-yl)-5-methoxy-4-methyl-phenoxy]propanoic acid;
3-[2-(8-chloro-4-oxo-chromen-2-yl)-5-methyl-phenoxy]propanoic acid;
3-[5-bromo-2-(8-chloro-4-oxo-chromen-2-yl)-4-(trifluoromethoxy)phenoxy]propanoic acid;
3-[2-(8-chloro-4-oxo-chromen-2-yl)-4-methoxy-5-methyl-phenoxy]propanoic acid;
3-[4-bromo-2-(8-chloro-4-oxo-chromen-2-yl)-5-(trifluoromethoxy)phenoxy]propanoic acid;
3-[2-(8-chloro-4-oxo-chromen-2-yl)-4-methyl-5-(trifluoromethoxy)phenoxy]propanoic acid;
3-[2-bromo-6-(8-chloro-4-oxo-chromen-2-yl)-4-methyl-phenoxy]propanoic acid;
3-[2-(8-chloro-4-oxo-chromen-2-yl)-5-methyl-4-(trifluoromethoxy)phenoxy]propanoic acid;
3-[5-bromo-2-(8-chloro-4-oxo-chromen-2-yl)-3-fluoro-phenoxy]propanoic acid;
3-[2-(8-chloro-4-oxo-chromen-2-yl)-3-fluoro-5-methyl-phenoxy]propanoic acid;
3-[2-(8-bromo-4-oxo-chromen-2-yl)-5-(trifluoromethoxy)phenoxy]propanoic acid;
3-[2-(7-bromo-8-chloro-4-oxo-chromen-2-yl)-5-(trifluoromethoxy)phenoxy]propanoic acid;
3-[2-(8-bromo-4-oxo-chromen-2-yl)-5-methyl-phenoxy]propanoic acid;
3-[2-(8-bromo-4-oxo-chromen-2-yl)-5-chloro-4-methyl-phenoxy]propanoic acid;
3-[[5-bromo-2-(8-chloro-4-oxo-chromen-2-yl)-3-pyridyl]oxy]propanoic acid;
3-[2-(8-chloro-7-fluoro-4-oxo-chromen-2-yl)-5-(trifluoromethyl)phenoxy]propanoic acid;
3-[2-(8-chloro-7-methoxy-4-oxo-chromen-2-yl)-5-(trifluoromethyl)phenoxy]propanoic acid;
3-[2-(8-chloro-6-methoxy-4-oxo-chromen-2-yl)-5-(trifluoromethyl)phenoxy]propanoic acid;
3-[2-(8-chloro-3-methyl-4-oxo-chromen-2-yl)-5-(trifluoromethyl)phenoxy]propanoic acid;
methyl 3-[5-chloro-2-(8-chloro-4-oxo-chromen-2-yl)-4-methyl-phenoxy]propanoate;
3-[2-(8-chloro-4-oxo-chromen-2-yl)-5-(trifluoromethyl)phenoxy]butanoic acid;
3-[3-[2-(8-chloro-4-oxo-chromen-2-yl)-5-(trifluoromethyl)phenoxy]butanoyloxy]butanoic acid;
3-[2-(8-chloro-4-oxo-chromen-2-yl)-4-methoxy-5-(2,2,2-trifluoroethoxy)phenoxy]propanoic acid;
3-[2-[8-chloro-4-oxo-7-(trifluoromethyl)chromen-2-yl]-5-(trifluoromethoxy)phenoxy]-propanoic acid;
3-[2-(8-chloro-4-oxo-chromen-2-yl)-4-methoxy-5-(trifluoromethyl)phenoxy]propanoic acid;
3-[2-(8-chloro-4-oxo-chromen-2-yl)-4-methyl-5-(trifluoromethyl)phenoxy]propanoic acid;
3-[2-(8-chloro-5-hydroxy-4-oxo-chromen-2-yl)-5-(trifluoromethyl)phenoxy]propanoic acid;
3-[2-(8-chloro-3-hydroxy-4-oxo-chromen-2-yl)-5-(trifluoromethyl)phenoxy]propanoic acid;
3-[2-(8-chloro-3-methoxy-4-oxo-chromen-2-yl)-5-(trifluoromethyl)phenoxy]propanoic acid;
2-[2-(8-chloro-4-oxo-chromen-2-yl)-5-(trifluoromethoxy)phenoxy]acetic acid;
2-[2-(8-chloro-4-oxo-chromen-2-yl)-5-methyl-phenoxy]acetic acid;
2-[2-(8-chloro-4-oxo-chromen-2-yl)-4,5-dimethoxy-phenoxy]acetic acid;
2-[2-(8-chloro-4-oxo-chromen-2-yl)-5-(trifluoromethyl)phenoxy]acetic acid;
4-[2-(8-chloro-4-oxo-chromen-2-yl)-5-(trifluoromethyl)phenoxy]butanoic acid;
4-[2-(8-chloro-4-oxo-chromen-2-yl)-5-(trifluoromethoxy)phenoxy]butanoic acid;
4-[5-bromo-2-(8-chloro-4-oxo-chromen-2-yl)-4-methyl-phenoxy]butanoic acid;
4-[5-bromo-2-(8-chloro-4-oxo-chromen-2-yl)phenoxy]butanoic acid;
4-[2-(8-chloro-4-oxo-chromen-2-yl)-4,5-dimethoxy-phenoxy]butanoic acid
4-[5-chloro-2-(8-chloro-4-oxo-chromen-2-yl)-4-methyl-phenoxy]butanoic acid
4-[5-bromo-2-(8-chloro-4-oxo-chromen-2-yl)-4-methoxy-phenoxy]butanoic acid
4-[2-(8-chloro-4-oxo-chromen-2-yl)-5-methyl-phenoxy]butanoic acid
4-[2-(8-chloro-4-oxo-chromen-2-yl)-5-methoxy-4-methyl-phenoxy]butanoic acid;
3-[2-(8-chloro-4-oxo-chromen-2-yl)-5-(trifluoromethoxy)phenoxy]-2,2-dimethyl-propanoic acid;
3-[2-(8-chloro-4-oxo-chromen-2-yl)-5-(trifluoromethyl)phenoxy]-2,2-dimethyl-propanoic acid;
3-[2-(8-chloro-4-oxo-chromen-2-yl)-5-methyl-phenoxy]-2,2-dimethyl-propanoic acid;
3-[5-chloro-2-(8-chloro-4-oxo-chromen-2-yl)-4-methyl-phenoxy]-2,2-dimethyl-propanoic acid;
5-[2-(8-chloro-4-oxo-chromen-2-yl)-5-(trifluoromethyl)phenoxy]pentanoic acid;
7-[2-(8-chloro-4-oxo-chromen-2-yl)-5-(trifluoromethyl)phenoxy]heptanoic acid;
2-[1-[[2-(8-chloro-4-oxo-chromen-2-yl)-4,5-dimethoxy-phenoxy]methyl]cyclopropyl]acetic acid;
2-[1-[[5-bromo-2-(8-chloro-4-oxo-chromen-2-yl)-4-methyl-phenoxy]methyl]cyclopropyl]acetic acid;

2-[1-[[5-bromo-2-(8-chloro-4-oxo-chromen-2-yl)phenoxy]methyl]cyclopropyl]acetic acid;
2-[5-bromo-2-(8-chloro-4-oxo-chromen-2-yl)phenoxy]-2-methyl-propanoic acid;
5-[2-(8-chloro-4-oxo-chromen-2-yl)-5-(trifluoromethoxy)phenoxy]-2,2-dimethyl-pentanoic acid;
2-[5-bromo-2-(8-chloro-4-oxo-chromen-2-yl)-4-methyl-phenoxy]acetic acid;
3-[[2-[2-(8-chloro-4-oxo-chromen-2-yl)-5-(trifluoromethyl)phenoxy]acetyl]amino]cyclobutanecarboxylic acid;
(2R)-1-[3-[5-bromo-2-(8-chloro-4-oxo-chromen-2-yl)phenoxy]propanoyl]pyrrolidine-2-carboxylic acid;
(2S)-1-[3-[5-bromo-2-(8-chloro-4-oxo-chromen-2-yl)phenoxy]propanoyl]pyrrolidine-2-carboxylic acid;
(2R)-1-[2-[2-(8-chloro-4-oxo-chromen-2-yl)-5-methyl-phenoxy]acetyl]pyrrolidine-2-carboxylic acid;
(2S)-1-[2-[2-(8-chloro-4-oxo-chromen-2-yl)-5-methyl-phenoxy]acetyl]pyrrolidine-2-carboxylic acid;
(2R)-1-[2-[5-bromo-2-(8-chloro-4-oxo-chromen-2-yl)-4-methyl-phenoxy]acetyl]pyrrolidine-2-carboxylic acid;
(2S)-1-[2-[5-bromo-2-(8-chloro-4-oxo-chromen-2-yl)-4-methyl-phenoxy]acetyl]pyrrolidine-2-carboxylic acid;
(2R)-1-[2-[2-(8-chloro-4-oxo-chromen-2-yl)-5-(trifluoromethyl)phenoxy]acetyl]pyrrolidine-2-carboxylic acid;
(2S)-1-[2-[2-(8-chloro-4-oxo-chromen-2-yl)-5-(trifluoromethyl)phenoxy]acetyl]pyrrolidine-2-carboxylic acid;
(3S)-1-[2-[2-(8-chloro-4-oxo-chromen-2-yl)-5-(trifluoromethyl)phenoxy]acetyl]pyrrolidine-3-carboxylic acid;
3-[2-(8-chloro-4-oxo-chromen-2-yl)-5-(trifluoromethyl)phenoxy]-N-cyclopropylsulfonyl-propanamide;
3-[2-(8-chloro-4-oxo-chromen-2-yl)-4,5-dimethoxy-phenoxy]-N-cyclopropylsulfonyl-propanamide;
2-[2-(8-chloro-4-oxo-chromen-2-yl)-5-(trifluoromethyl)phenoxy]-N-(2-hydroxyethyl)acetamide;
8-chloro-2-[2-[2-(3-methylsulfonylpyrrolidin-1-yl)-2-oxo-ethoxy]-4-(trifluoromethyl)phenyl]chromen-4-one;
2-[4-bromo-2-[2-[(3S)-3-hydroxypyrrolidin-1-yl]-2-oxo-ethoxy]-5-methyl-phenyl]-8-chloro-chromen-4-one;
2-[4-bromo-2-[2-[(3R)-3-hydroxypyrrolidin-1-yl]-2-oxo-ethoxy]-5-methyl-phenyl]-8-chloro-chromen-4-one;
2-[4-bromo-5-methyl-2-[2-oxo-2-[rac-(3S,4R)-3,4-dihydroxypyrrolidin-1-yl]ethoxy]phenyl]-8-chloro-chromen-4-one;
2-[2-(8-chloro-4-oxo-chromen-2-yl)-4,5-dimethoxy-phenoxy]-N-cyclopropylsulfonyl-acetamide;
8-chloro-2-[2-(2-morpholino-2-oxo-ethoxy)-4-(trifluoromethyl)phenyl]chromen-4-one;
(2S)-1-[2-[2-(8-chloro-4-oxo-chromen-2-yl)-5-methyl-phenoxy]acetyl]-N-methylsulfonyl-pyrrolidine-2-carboxamide;
(2R)-1-[2-[2-(8-chloro-4-oxo-chromen-2-yl)-5-methyl-phenoxy]acetyl]-N-methylsulfonyl-pyrrolidine-2-carboxamide;
(2S)-2-amino-3-[2-(8-chloro-4-oxo-chromen-2-yl)-5-(trifluoromethyl)phenoxy]propanoic acid;
(2S)-3-[2-(8-chloro-4-oxo-chromen-2-yl)-5-(trifluoromethyl)phenoxy]-2-(cyclopropylsulfonylamino)propanoic acid;
(2S)-3-[2-(8-chloro-4-oxo-chromen-2-yl)-5-(trifluoromethyl)phenoxy]-2-(p-tolylsulfonylamino)propanoic acid;
methyl (2S)-3-[2-(8-chloro-4-oxo-chromen-2-yl)-5-(trifluoromethyl)phenoxy]-2-(ethylsulfamoylamino)propanoate;
(2S)-3-[2-(8-chloro-4-oxo-chromen-2-yl)-5-(trifluoromethyl)phenoxy]-2-(ethylsulfamoylamino)propanoic acid;
4-[2-(8-chloro-5-hydroxy-4-oxo-chromen-2-yl)-5-(trifluoromethyl)phenoxy]butanoic acid;
3-[5-bromo-2-(8-chloro-4-oxo-chromen-2-yl)phenoxy]-N,N-dimethyl-propane-1-sulfonamide;
3-[2-(8-chloro-4-oxo-chromen-2-yl)-5-(trifluoromethyl)phenoxy]propane-1-sulfonamide; and
3-[2-(8-chloro-4-oxo-chromen-2-yl)-5-(trifluoromethyl)phenoxy]-2-hydroxy-propanoic acid;
or a pharmaceutically acceptable salt thereof.

9. A compound according to claim 1, wherein:
$R^1$ is halogen;
$R^2$ is H;
$R^3$ is H;
$R^4$ is selected from H and hydroxy;
$R^5$ is H;
$R^6$ is selected from carboxy, $C_{3-7}$cycloalkylsulfonylaminocarbonyl and $C_{1-6}$alkylsulfonylaminocarbonyl;
$A_1$ is CH;
$A_2$ is $CR^8$, wherein $R^8$ is selected from H, halogen, $C_{1-6}$alkyl, $C_{1-6}$alkoxy, $C_{3-7}$cycloalkyl, halo$C_{1-6}$alkyl and halo$C_{1-6}$alkoxy;
$A_3$ is $CR^9$, wherein $R^9$ is selected from H, halogen, $C_{1-6}$alkyl, $C_{1-6}$alkoxy and halo$C_{1-6}$alkyl;
or $R^8$ and $R^9$, together with the atoms to which they are attached, form a 5-membered heterocyclyl ring;
$A_4$ is CH;
$G_1$ is selected from $C_{3-7}$cycloalkyl, $C_{3-7}$cycloalkyl$C_{1-6}$alkyl, phenyl$C_{1-6}$alkyl and pyrrolidinyl; wherein pyrrolidinyl is unsubstituted or substituted by one or two or three substituents independently selected from phenylsulfonyl, $C_{3-7}$cycloalkylsulfonyl, $C_{1-6}$alkoxyphenylsulfonyl and phenylcarbonyl; and
m is 0;
or a pharmaceutically acceptable salt thereof.

10. A compound according to claim 9, wherein:
$R^6$ is selected from carboxy and $C_{3-7}$cycloalkylsulfonylaminocarbonyl;
$A_2$ is $CR^8$, wherein $R^8$ is selected from halogen and halo$C_{1-6}$alkyl;
$A_3$ is $CR^9$, wherein $R^9$ is selected from H and $C_{1-6}$alkyl; and
$G_1$ is selected from $C_{3-7}$cycloalkyl and pyrrolidinyl; wherein pyrrolidinyl is substituted one time by phenylsulfonyl;
or a pharmaceutically acceptable salt thereof.

11. A compound according to claim 1, selected from:
3-[[5-bromo-2-(8-chloro-4-oxo-chromen-2-yl)phenoxy]methyl]benzoic acid;
3-[5-bromo-2-(8-chloro-4-oxo-chromen-2-yl)phenoxy]cyclobutanecarboxylic acid;
cis-3-[2-(8-chloro-4-oxo-chromen-2-yl)phenoxy]cyclobutanecarboxylic acid;
trans-3-[2-(8-chloro-4-oxo-chromen-2-yl)phenoxy]cyclobutanecarboxylic acid;
3-[2-(8-chloro-4-oxo-chromen-2-yl)-5-(trifluoromethyl)phenoxy]cyclobutanecarboxylic acid;
3-[5-bromo-2-(8-chloro-4-oxo-chromen-2-yl)-4-methoxy-phenoxy]cyclobutanecarboxylic acid;
3-[2-(8-chloro-4-oxo-chromen-2-yl)-5-(trifluoromethoxy)phenoxy]cyclobutanecarboxylic acid;

3-[2-(8-chloro-4-oxo-chromen-2-yl)-4,5-dimethoxy-phenoxy]cyclobutanecarboxylic acid;
3-[4-bromo-2-(8-chloro-4-oxo-chromen-2-yl)-5-(trifluoromethoxy)phenoxy]cyclobutanecarboxylic acid;
3-[2-bromo-6-(8-chloro-4-oxo-chromen-2-yl)-4-methyl-phenoxy]cyclobutanecarboxylic acid;
4-[5-bromo-2-(8-chloro-4-oxo-chromen-2-yl)phenoxy]cyclohexanecarboxylic acid;
cis-3-[2-(8-chloro-4-oxo-chromen-2-yl)-5-methoxy-phenoxy]cyclobutanecarboxylic acid;
trans-3-[2-(8-chloro-4-oxo-chromen-2-yl)-5-methoxy-phenoxy]cyclobutanecarboxylic acid;
cis-3-[5-chloro-2-(8-chloro-4-oxo-chromen-2-yl)-4-methyl-phenoxy]cyclobutanecarboxylic acid;
trans-3-[5-chloro-2-(8-chloro-4-oxo-chromen-2-yl)-4-methyl-phenoxy]cyclobutanecarboxylic acid;
cis-3-[5-bromo-2-(8-chloro-4-oxo-chromen-2-yl)-4-methyl-phenoxy]cyclobutanecarboxylic acid;
trans-3-[5-bromo-2-(8-chloro-4-oxo-chromen-2-yl)-4-methyl-phenoxy]cyclobutanecarboxylic acid;
trans-3-[4-bromo-2-(8-chloro-4-oxo-chromen-2-yl)-5-methoxy-phenoxy]cyclobutanecarboxylic acid;
cis-3-[2-(8-chloro-4-oxo-chromen-2-yl)-5-(trifluoromethoxy)phenoxy]cyclobutanecarboxylic acid;
cis-3-[2-(8-chloro-4-oxo-chromen-2-yl)-4-methyl-phenoxy]cyclobutanecarboxylic acid
trans-3-[2-(8-chloro-4-oxo-chromen-2-yl)-5-methoxy-4-methyl-phenoxy]cyclobutanecarboxylic acid;
cis-3-[2-(8-chloro-4-oxo-chromen-2-yl)-5-methyl-phenoxy]cyclobutanecarboxylic acid;
trans-3-[2-(8-chloro-4-oxo-chromen-2-yl)-5-methyl-phenoxy]cyclobutanecarboxylic acid;
cis-3-[2-(8-chloro-4-oxo-chromen-2-yl)-5-ethyl-phenoxy]cyclobutanecarboxylic acid;
trans-3-[2-(8-chloro-4-oxo-chromen-2-yl)-5-ethyl-phenoxy]cyclobutanecarboxylic acid;
cis-3-[2-(8-chloro-4-oxo-chromen-2-yl)-5-isopropyl-phenoxy]cyclobutanecarboxylic acid;
trans-3-[2-(8-chloro-4-oxo-chromen-2-yl)-5-isopropyl-phenoxy]cyclobutanecarboxylic acid;
trans-3-[2-(8-chloro-4-oxo-chromen-2-yl)-4-methoxy-phenoxy]cyclobutanecarboxylic acid;
trans-3-[2-(8-bromo-4-oxo-chromen-2-yl)phenoxy]cyclobutanecarboxylic acid;
cis-3-[2-(8-bromo-4-oxo-chromen-2-yl)phenoxy]cyclobutanecarboxylic acid;
trans-3-[[6-(8-chloro-4-oxo-chromen-2-yl)-2,3-dihydrobenzofuran-5-yl]oxy]cyclobutanecarboxylic acid;
trans-3-[5-bromo-2-(8-chloro-4-oxo-chromen-2-yl)-4-(trifluoromethyl)phenoxy]cyclobutanecarboxylic acid;
cis-3-[[5-bromo-2-(8-chloro-4-oxo-chromen-2-yl)phenoxy]methyl]cyclobutanecarboxylic acid;
trans-3-[[5-bromo-2-(8-chloro-4-oxo-chromen-2-yl)phenoxy]methyl]cyclobutanecarboxylic acid;
cis-3-[[2-(8-chloro-4-oxo-chromen-2-yl)phenoxy]methyl]cyclobutanecarboxylic acid;
trans-3-[[2-(8-chloro-4-oxo-chromen-2-yl)phenoxy]methyl]cyclobutanecarboxylic acid;
cis-3-[[2-(8-chloro-4-oxo-chromen-2-yl)-4-methoxy-phenoxy]methyl]cyclobutanecarboxylic acid;
trans-3-[[2-(8-chloro-4-oxo-chromen-2-yl)-4-methoxy-phenoxy]methyl]cyclobutanecarboxylic acid;
cis-3-[5-bromo-2-8-chloro-4-oxo-chromen-2-yl)phenoxy]cyclopentanecarboxylic acid;
trans-3-[5-bromo-2-(8-chloro-4-oxo-chromen-2-yl)phenoxy]cyclopentanecarboxylic acid;
trans-3-[[5-bromo-2-(8-chloro-4-oxo-chromen-2-yl)-3-pyridyl]oxy]cyclobutanecarboxylic acid;
cis-3-[2-(8-chloro-4-oxo-chromen-2-yl)-5-cyclopropyl-phenoxy]cyclobutanecarboxylic acid;
trans-3-[2-(8-chloro-4-oxo-chromen-2-yl)-5-cyclopropyl-phenoxy]cyclobutanecarboxylic acid;
cis-3-[5-bromo-2-(8-chloro-5-hydroxy-4-oxo-chromen-2-yl)phenoxy]cyclobutanecarboxylic acid;
cis-3-[2-(8-chloro-5-hydroxy-4-oxo-chromen-2-yl)-5-methyl-phenoxy]cyclobutanecarboxylic acid;
trans-3-[2-(8-chloro-5-hydroxy-4-oxo-chromen-2-yl)-5-methyl-phenoxy]cyclobutanecarboxylic acid;
trans-3-[5-bromo-2-(8-chloro-5-hydroxy-4-oxo-chromen-2-yl)phenoxy]cyclobutanecarboxylic acid;
cis-3-[2-(8-chloro-5-hydroxy-4-oxo-chromen-2-yl)-5-(trifluoromethyl)phenoxy]cyclobutanecarboxylic acid;
trans-3-[2-(8-chloro-5-hydroxy-4-oxo-chromen-2-yl)-5-(trifluoromethyl)phenoxy]cyclobutanecarboxylic acid;
cis-3-[2-(8-chloro-5-hydroxy-4-oxo-chromen-2-yl)-5-ethoxy-phenoxy]cyclobutanecarboxylic acid;
trans-3-[2-(8-chloro-5-hydroxy-4-oxo-chromen-2-yl)-5-ethoxy-phenoxy]cyclobutanecarboxylic acid;
cis-3-[5-bromo-2-(8-chloro-5-hydroxy-4-oxo-chromen-2-yl)-4-methyl-phenoxy]cyclobutanecarboxylic acid;
trans-3-[5-bromo-2-(8-chloro-5-hydroxy-4-oxo-chromen-2-yl)-4-methyl-phenoxy]cyclobutanecarboxylic acid;
3-[2-(8-chloro-5-hydroxy-4-oxo-chromen-2-yl)-4,5-dimethoxy-phenoxy]cyclobutanecarboxylic acid;
cis-3-[2-(8-chloro-4-oxo-chromen-2-yl)-5-(trifluoromethyl)phenoxy]-N-cyclopropylsulfonyl-cyclobutanecarboxamide;
trans-3-[2-(8-chloro-4-oxo-chromen-2-yl)-5-(trifluoromethyl)phenoxy]-N-cyclopropylsulfonyl-cyclobutanecarboxamide;
cis-3-[5-bromo-2-(8-chloro-4-oxo-chromen-2-yl)phenoxy]-N-methylsulfonyl-cyclobutanecarboxamide;
trans-3-[5-bromo-2-(8-chloro-4-oxo-chromen-2-yl)phenoxy]-N-methylsulfonyl-cyclobutanecarboxamide;
cis-3-[2-(8-chloro-4-oxo-chromen-2-yl)-5-(trifluoromethoxy)phenoxy]-N-methylsulfonyl-cyclobutanecarboxamide;
trans-3-[2-(8-chloro-4-oxo-chromen-2-yl)-5-(trifluoromethoxy)phenoxy]-N-methylsulfonyl-cyclobutanecarboxamide;
cis-3-[2-(8-chloro-4-oxo-chromen-2-yl)-5-(trifluoromethyl)phenoxy]-N-methylsulfonyl-cyclobutanecarboxamide;
trans-3-[2-(8-chloro-4-oxo-chromen-2-yl)-5-(trifluoromethyl)phenoxy]-N-methylsulfonyl-cyclobutanecarboxamide;
cis-3-[5-bromo-2-(8-chloro-4-oxo-chromen-2-yl)-4-methyl-phenoxy]-N-methylsulfonyl-cyclobutanecarboxamide;
trans-3-[5-bromo-2-(8-chloro-4-oxo-chromen-2-yl)-4-methyl-phenoxy]-N-methylsulfonyl-cyclobutanecarboxamide;
cis-3-[2-(8-chloro-4-oxo-chromen-2-yl)-5-methoxy-4-methyl-phenoxy]-N-methylsulfonyl-cyclobutanecarboxamide;
trans-3-[2-(8-chloro-4-oxo-chromen-2-yl)-5-methoxy-4-methyl-phenoxy]-N-methylsulfonyl-cyclobutanecarboxamide;
cis-3-[2-(8-chloro-4-oxo-chromen-2-yl)-5-methyl-phenoxy]-N-methylsulfonyl-cyclobutanecarboxamide;
trans-3-[2-(8-chloro-4-oxo-chromen-2-yl)-5-methyl-phenoxy]-N-methylsulfonyl-cyclobutanecarboxamide;

cis-3-[2-(8-chloro-4-oxo-chromen-2-yl)-5-methyl-phenoxy]-N-cyclopropylsulfonyl-cyclobutanecarboxamide;
trans-3-[2-(8-chloro-4-oxo-chromen-2-yl)-5-methyl-phenoxy]-N-cyclopropylsulfonyl-cyclobutanecarboxamide;
cis-3-[5-bromo-2-(8-chloro-4-oxo-chromen-2-yl)-4-methoxy-phenoxy]-N-methylsulfonyl-cyclobutanecarboxamide;
trans-3-[5-bromo-2-(8-chloro-4-oxo-chromen-2-yl)-4-methoxy-phenoxy]-N-methylsulfonyl-cyclobutanecarboxamide;
cis-3-[5-bromo-2-(8-chloro-4-oxo-chromen-2-yl)-4-methoxy-phenoxy]-N-cyclopropylsulfonyl-cyclobutanecarboxamide;
cis-3-[4-bromo-2-(8-chloro-4-oxo-chromen-2-yl)-5-methoxy-phenoxy]-N-methylsulfonyl-cyclobutanecarboxamide;
trans-3-[4-bromo-2-(8-chloro-4-oxo-chromen-2-yl)-5-methoxy-phenoxy]-N-methylsulfonyl-cyclobutanecarboxamide;
cis-3-[4-bromo-2-(8-chloro-4-oxo-chromen-2-yl)-5-methoxy-phenoxy]-N-cyclopropylsulfonyl-cyclobutanecarboxamide;
3-[2-(8-chloro-4-oxo-chromen-2-yl)-4,5-dimethoxy-phenoxy]-N-methylsulfonyl-cyclobutanecarboxamide;
3-[2-(8-chloro-4-oxo-chromen-2-yl)-5-(trifluoromethyl)phenoxy]cyclobutanecarbonitrile;
(2S,4S)-4-[5-bromo-2-(8-chloro-4-oxo-chromen-2-yl)phenoxy]pyrrolidine-2-carboxylic acid;
(2S,4R)-1-(benzenesulfonyl)-4-[2-(8-chloro-4-oxo-chromen-2-yl)-5-(trifluoromethyl)phenoxy]pyrrolidine-2-carboxylic acid;
(2S,4R)-4-[2-(8-chloro-4-oxo-chromen-2-yl)-5-(trifluoromethyl)phenoxy]-1-cyclopropylsulfonyl-pyrrolidine-2-carboxylic acid;
(2S,4S)-4-[2-(8-chloro-4-oxo-chromen-2-yl)-5-(trifluoromethyl)phenoxy]-1-cyclopropylsulfonyl-pyrrolidine-2-carboxylic acid;
(2S,4S)-4-[2-(8-chloro-4-oxo-chromen-2-yl)-5-(trifluoromethyl)phenoxy]-1-(3-methoxyphenyl)sulfonyl-pyrrolidine-2-carboxylic acid;
(2S,4S)-1-(benzenesulfonyl)-4-[2-(8-chloro-4-oxo-chromen-2-yl)-5-(trifluoromethyl)phenoxy]pyrrolidine-2-carboxylic acid;
(2S,4S)-1-(benzenesulfonyl)-4-[2-(8-chloro-4-oxo-chromen-2-yl)-4,5-dimethoxy-phenoxy]pyrrolidine-2-carboxylic acid;
(2S,4S)-1-(benzenesulfonyl)-4-[5-bromo-2-(8-chloro-4-oxo-chromen-2-yl)phenoxy]pyrrolidine-2-carboxylic acid;
(2S,4S)-4-[5-bromo-2-(8-chloro-4-oxo-chromen-2-yl)phenoxy]-1-cyclopropylsulfonyl-pyrrolidine-2-carboxylic acid;
(2S,4S)-1-(benzenesulfonyl)-4-[5-chloro-2-(8-chloro-4-oxo-chromen-2-yl)-4-methyl-phenoxy]pyrrolidine-2-carboxylic acid;
(2S,4S)-1-(benzenesulfonyl)-4-[2-(8-chloro-4-oxo-chromen-2-yl)-5-(trifluoromethoxy)phenoxy]pyrrolidine-2-carboxylic acid;
(2S,4S)-1-benzoyl-4-[5-bromo-2-(8-chloro-4-oxo-chromen-2-yl)phenoxy]pyrrolidine-2-carboxylic acid;
(2R,4S)-1-(benzenesulfonyl)-4-[2-(8-chloro-4-oxo-chromen-2-yl)-5-(trifluoromethyl)phenoxy]pyrrolidine-2-carboxylic acid; and
(2R,4R)-1-(benzenesulfonyl)-4-[2-(8-chloro-4-oxo-chromen-2-yl)-5-(trifluoromethyl)phenoxy]pyrrolidine-2-carboxylic acid;
or a pharmaceutically acceptable salt thereof.

12. A compound according to claim 1, wherein:
$R^2$ is selected from H, halogen, $C_{1-6}$alkyl, $C_{3-7}$cycloalkyl and halo$C_{1-6}$alkyl;
$R^3$ is selected from H and halogen;
$R^5$ is selected from H and $C_{1-6}$alkoxy;
$R^6$ is selected from carboxy, $C_{1-6}$alkoxycarbonyl, carboxypyrrolidinylcarbonyl, $C_{3-7}$cycloalkylsulfonylaminocarbonyl, hydroxypyrrolidinylcarbonyl, $C_{1-6}$alkylsulfonylaminocarbonyl and aminocarbonyl;
$A_1$ is $CR^7$, wherein $R^7$ is selected from H and halogen;
$A_2$ is selected from N and $CR^8$, wherein $R^8$ is selected from H, halogen, hydroxy, $C_{1-6}$alkyl, $C_{1-6}$alkoxy, $C_{3-7}$cycloalkyl, halo$C_{1-6}$alkyl, halo$C_{1-6}$alkoxy, $C_{1-6}$alkylsulfanyl, $C_{1-6}$alkylsulfonyl, $C_{3-7}$cycloalkyl$C_{1-6}$alkoxy, thiazolyl, morpholinyl, pyrrolidinyl and oxazolidinyl, wherein pyrrolidinyl and oxazolidinyl are unsubstituted or substituted one or two or three times by oxo;
$A_3$ is $CR^9$; wherein $R^9$ is selected from H, amino, halogen, hydroxy, $C_{1-6}$alkyl, $C_{1-6}$alkoxy, halo$C_{1-6}$alkyl, halo$C_{1-6}$alkoxy, halo$C_{1-6}$alkyl$C_{1-6}$alkoxy and $C_{3-7}$cycloalkyl$C_{1-6}$ alkoxy;
or $R^8$ and $R^9$, together with the atoms to which they are attached, form a 5- or 6-membered heterocyclyl ring; wherein 5- or 6-membered heterocyclyl ring is unsubstituted or substituted by one or two or three or four substituents independently selected from halogen, $C_{1-6}$alkyl and oxo;
$G_1$ is $C_{1-6}$alkyl; wherein $C_{1-6}$alkyl is unsubstituted or substituted one or two or three times by hydroxy; and
m is 1;
or a pharmaceutically acceptable salt thereof.

13. A compound according to claim 12, wherein:
$R^1$ is selected from F, Cl, Br and $CF_3$;
$R^2$ is selected from H, F, Cl, Br, methyl, $CF_3$ and cyclopropyl;
$R^3$ is selected from H and F;
$R^4$ is selected from H, hydroxy and $CF_3$;
$R^s$ is selected from H and methoxy;
$R^6$ is selected from carboxy, methoxycarbonyl, carboxypyrrolidinylcarbonyl, cyclopropylsulfonylaminocarbonyl, hydroxypyrrolidinylcarbonyl, methylsulfonylaminocarbonyl and aminocarbonyl;
$A_1$ is $CR^7$, wherein $R^7$ is selected from H, F, Cl and Br;
$A_2$ is selected from N and $CR^8$, wherein $R^8$ is selected from H, F, Cl, Br, $CF_3$, hydroxy, methyl, methoxy, ethoxy, propoxy, cyclopropyl, trifluoromethoxy, difluoromethoxy, trifluoromethylmethoxy, methylsulfonyl, methylsulfanyl, cyclopropylmethoxy, thiazolyl, morpholinyl, pyrrolidinyl and oxazolidinyl; wherein pyrrolidinyl and oxazolidinyl are unsubstituted or substituted one or two or three times independently by oxo;
$A_3$ is $CR^9$, wherein $R^9$ is selected from H, amino, hydroxy, F, Cl, Br, $CF_3$, methyl, methoxy, ethoxy, difluoromethoxy, trifluoromethoxy, trifluoromethylmethoxy, difluoromethyl and cyclopropylmethoxy;
or $R^8$ and $R^9$, together with the atoms to which they are attached, form a 5- or 6-membered heterocyclyl ring; wherein 5- or 6-membered heterocyclyl ring is unsubstituted or substituted by one or two or three or four substituents independently selected from F, methyl and oxo;

A₄ is selected from N and CR¹⁰, wherein R¹⁰ is selected from H and F;
G₁ is selected from ethyl, propyl, butyl and neopentyl, wherein propyl is unsubstituted or substituted one or two or three times by hydroxy; and
G₂ is selected from methyl, isopropyl, cyclobutyl, cyclopentyl and phenyl;
or a pharmaceutically acceptable salt thereof.

14. A compound according to claim 12, wherein:
R¹ is halogen;
R² is H;
R³ is H;
R⁴ is H;
Rˢ is H;
R⁶ is carboxy;
A₁ is CH;
A₂ is CR⁸, wherein R⁸ is selected from halogen, C₁₋₆alkyl, C₁₋₆alkoxy and haloC₁₋₆ alkyl;
A₃ is CR⁹, wherein R⁹ is selected from H, C₁₋₆alkyl and C₁₋₆alkoxy;
A₄ is CH;
G₁ is C₁₋₆alkyl; and
G₂ is selected from C₁₋₆alkyl and C₃₋₇cycloalkyl;
or a pharmaceutically acceptable salt thereof.

15. A compound according to claim 14, wherein:
R¹ is selected from Cl and Br;
A₂ is CR⁸, wherein R⁸ is selected from Cl, CF₃, methyl and methoxy;
A₃ is CR⁹, wherein R⁹ is selected from H, methyl and methoxy;
G₁ is selected from ethyl and propyl; and
G₂ is selected from methyl and cyclobutyl;
or a pharmaceutically acceptable salt thereof.

16. A compound according to claim 12, selected from:
2-[3-[2-(8-chloro-4-oxo-chromen-2-yl)-5-(trifluoromethyl)phenoxy]propoxy]acetic acid;
2-[3-[2-(8-chloro-4-oxo-chromen-2-yl)-5-methyl-phenoxy]propoxy]acetic acid;
methyl 3-[2-[5-bromo-2-(8-chloro-4-oxo-chromen-2-yl)phenoxy]ethoxy]cyclobutanecarboxylate;
cis-3-[2-[5-bromo-2-(8-chloro-4-oxo-chromen-2-yl)phenoxy]ethoxy]cyclobutanecarboxylic acid;
trans-3-[2-[5-bromo-2-(8-chloro-4-oxo-chromen-2-yl)phenoxy]ethoxy]cyclobutanecarboxylic acid;
3-[2-[5-chloro-2-(8-chloro-4-oxo-chromen-2-yl)phenoxy]ethoxy]cyclobutanecarboxylic acid;
2-[2-[2-(8-chloro-4-oxo-chromen-2-yl)-5-(trifluoromethyl)phenoxy]ethoxy]acetic acid;
2-[2-[5-bromo-2-(8-chloro-4-oxo-chromen-2-yl)phenoxy]ethoxy]acetic acid;
2-[3-[5-chloro-2-(8-chloro-4-oxo-chromen-2-yl)phenoxy]propoxy]acetic acid;
2-[3-[5-bromo-2-(8-chloro-4-oxo-chromen-2-yl)phenoxy]propoxy]acetic acid;
2-[3-[5-bromo-2-(8-chloro-4-oxo-chromen-2-yl)-4-methyl-phenoxy]propoxy]acetic acid;
2-[3-[2-(8-chloro-4-oxo-chromen-2-yl)-4,5-dimethoxy-phenoxy]propoxy]acetic acid;
2-[3-[5-bromo-2-(8-chloro-4-oxo-chromen-2-yl)-4-methoxy-phenoxy]propoxy]acetic acid;
2-[3-[2-(8-chloro-4-oxo-chromen-2-yl)-5-(trifluoromethoxy)phenoxy]propoxy]acetic acid;
2-[3-[[6-(8-chloro-4-oxo-chromen-2-yl)-1,3-benzodioxol-5-yl]oxy]propoxy]acetic acid;
2-[3-[5-chloro-2-(8-chloro-4-oxo-chromen-2-yl)-4-methoxy-phenoxy]propoxy]acetic acid;
2-[3-[2-(8-bromo-4-oxo-chromen-2-yl)-5-methyl-phenoxy]propoxy]acetic acid;
2-[3-[2-(8-bromo-4-oxo-chromen-2-yl)-5-chloro-4-methyl-phenoxy]propoxy]acetic acid;
2-[3-[5-chloro-2-(8-chloro-4-oxo-chromen-2-yl)-4-methyl-phenoxy]propoxy]acetic acid;
2-[2-[5-bromo-2-(8-chloro-4-oxo-chromen-2-yl)-4-methoxy-phenoxy]ethoxy]acetic acid;
2-[2-[5-bromo-2-(8-chloro-4-oxo-chromen-2-yl)-4-methyl-phenoxy]ethoxy]acetic acid;
2-[2-[2-(8-chloro-4-oxo-chromen-2-yl)-4,5-dimethoxy-phenoxy]ethoxy]acetic acid;
2-[2-[2-(8-chloro-4-oxo-chromen-2-yl)-5-(trifluoromethoxy)phenoxy]ethoxy]acetic acid;
2-[3-[2-(8-chloro-4-oxo-chromen-2-yl)-5-(trifluoromethyl)phenoxy]butoxy]acetic acid;
cis-3-[2-[2-(8-chloro-4-oxo-chromen-2-yl)phenoxy]ethoxy]cyclobutanecarboxylic acid;
trans-3-[2-[2-(8-chloro-4-oxo-chromen-2-yl)phenoxy]ethoxy]cyclobutanecarboxylic acid;
cis-3-[2-[2-(8-chloro-4-oxo-chromen-2-yl)-5-(trifluoromethyl)phenoxy]ethoxy]cyclobutanecarboxylic acid;
trans-3-[2-[[5-bromo-2-(8-chloro-4-oxo-chromen-2-yl)-3-pyridyl]oxy]ethoxy]cyclobutanecarboxylic acid;
cis-3-[2-[5-bromo-2-(8-chloro-6-fluoro-4-oxo-chromen-2-yl)phenoxy]ethoxy]cyclobutanecarboxylic acid;
cis-3-[2-[2-(8-chloro-7-methyl-4-oxo-chromen-2-yl)phenoxy]ethoxy]cyclobutanecarboxylic acid;
trans-3-[2-[2-(8-chloro-7-methyl-4-oxo-chromen-2-yl)phenoxy]ethoxy]cyclobutanecarboxylic acid;
cis-3-[2-[5-bromo-2-(8-chloro-7-fluoro-4-oxo-chromen-2-yl)phenoxy]ethoxy]cyclobutanecarboxylic acid;
trans-3-[2-[5-bromo-2-(8-chloro-7-fluoro-4-oxo-chromen-2-yl)phenoxy]ethoxy]cyclobutanecarboxylic acid;
cis-3-[2-[5-bromo-2-(8-chloro-4-oxo-chromen-2-yl)-4-methyl-phenoxy]ethoxy]cyclobutanecarboxylic acid;
cis-3-[2-[4-bromo-2-(8-chloro-4-oxo-chromen-2-yl)-5-fluoro-phenoxy]ethoxy]cyclobutanecarboxylic acid;
cis-3-[2-[2-(8-chloro-4-oxo-chromen-2-yl)-4-fluoro-phenoxy]ethoxy]cyclobutanecarboxylic acid;
trans-3-[2-[2-(8-chloro-4-oxo-chromen-2-yl)-4-fluoro-phenoxy]ethoxy]cyclobutanecarboxylic acid;
cis-3-[2-[2-(8-chloro-4-oxo-chromen-2-yl)-5-fluoro-phenoxy]ethoxy]cyclobutanecarboxylic acid;
trans-3-[2-[2-(8-chloro-4-oxo-chromen-2-yl)-5-fluoro-phenoxy]ethoxy]cyclobutanecarboxylic acid;
cis-3-[2-[2-(8-chloro-4-oxo-chromen-2-yl)-5-ethoxy-phenoxy]ethoxy]cyclobutanecarboxylic acid;
trans-3-[2-[2-(8-chloro-4-oxo-chromen-2-yl)-5-ethoxy-phenoxy]ethoxy]cyclobutanecarboxylic acid;
cis-3-[2-[2-(8-chloro-6-fluoro-4-oxo-chromen-2-yl)phenoxy]ethoxy]cyclobutanecarboxylic acid;
trans-3-[2-[2-(8-chloro-6-fluoro-4-oxo-chromen-2-yl)phenoxy]ethoxy]cyclobutanecarboxylic acid;
cis-3-[2-[2-(8-chloro-4-oxo-chromen-2-yl)-6-fluoro-phenoxy]ethoxy]cyclobutanecarboxylic acid;
trans-3-[2-[2-(8-chloro-4-oxo-chromen-2-yl)-6-fluoro-phenoxy]ethoxy]cyclobutanecarboxylic acid;
cis-3-[2-[2-(8-chloro-4-oxo-chromen-2-yl)-5-methyl-phenoxy]ethoxy]cyclobutanecarboxylic acid;
trans-3-[2-[2-(8-chloro-4-oxo-chromen-2-yl)-5-methyl-phenoxy]ethoxy]cyclobutanecarboxylic acid;
cis-3-[2-[2-(8-chloro-4-oxo-chromen-2-yl)-5-methoxy-phenoxy]ethoxy]cyclobutanecarboxylic acid;
trans-3-[2-[2-(8-chloro-4-oxo-chromen-2-yl)-5-methoxy-phenoxy]ethoxy]cyclobutanecarboxylic acid;

cis-3-[2-[4-bromo-2-(8-chloro-4-oxo-chromen-2-yl)-5-methoxy-phenoxy]ethoxy]cyclobutanecarboxylic acid;
trans-3-[2-[4-bromo-2-(8-chloro-4-oxo-chromen-2-yl)-5-methoxy-phenoxy]ethoxy]cyclobutanecarboxylic acid;
cis-3-[2-[2-(8-chloro-4-oxo-chromen-2-yl)-5-methoxy-4-methyl-phenoxy]ethoxy]cyclobutanecarboxylic acid;
trans-3-[2-[2-(8-chloro-4-oxo-chromen-2-yl)-5-methoxy-4-methyl-phenoxy]ethoxy]cyclobutanecarboxylic acid;
cis-3-[2-[5-bromo-2-(8-chloro-4-oxo-chromen-2-yl)-4-(trifluoromethyl)phenoxy]ethoxy]cyclobutanecarboxylic acid;
trans-3-[2-[5-bromo-2-(8-chloro-4-oxo-chromen-2-yl)-4-(trifluoromethyl)phenoxy]ethoxy]cyclobutanecarboxylic acid;
cis-3-[2-[[6-(8-chloro-4-oxo-chromen-2-yl)-1,3-benzodioxol-5-yl]oxy]ethoxy]cyclobutanecarboxylic acid;
trans-3-[2-[[6-(8-chloro-4-oxo-chromen-2-yl)-1,3-benzodioxol-5-yl]oxy]ethoxy]cyclobutanecarboxylic acid;
cis-3-[2-[5-bromo-2-(8-chloro-4-oxo-chromen-2-yl)-4-fluoro-phenoxy]ethoxy]cyclobutanecarboxylic acid;
trans-3-[2-[5-bromo-2-(8-chloro-4-oxo-chromen-2-yl)-4-fluoro-phenoxy]ethoxy]cyclobutanecarboxylic acid;
cis-3-[2-[2-(8-chloro-6-fluoro-4-oxo-chromen-2-yl)-5-fluoro-phenoxy]ethoxy]cyclobutanecarboxylic acid;
trans-3-[2-[2-(8-chloro-6-fluoro-4-oxo-chromen-2-yl)-5-fluoro-phenoxy]ethoxy]cyclobutanecarboxylic acid;
cis-3-[2-[2-(8-bromo-4-oxo-chromen-2-yl)phenoxy]ethoxy]cyclobutanecarboxylic acid;
trans-3-[2-[2-(8-bromo-4-oxo-chromen-2-yl)phenoxy]ethoxy]cyclobutanecarboxylic acid;
cis-3-[2-[2-[4-oxo-8-(trifluoromethyl)chromen-2-yl]phenoxy]ethoxy]cyclobutanecarboxylic acid;
trans-3-[2-[2-[4-oxo-8-(trifluoromethyl)chromen-2-yl]phenoxy]ethoxy]cyclobutanecarboxylic acid;
cis-3-[2-[5-bromo-2-[8-chloro-4-oxo-7-(trifluoromethyl)chromen-2-yl]phenoxy]ethoxy]cyclobutanecarboxylic acid;
trans-3-[2-[5-bromo-2-[8-chloro-4-oxo-7-(trifluoromethyl)chromen-2-yl]phenoxy]ethoxy]cyclobutanecarboxylic acid;
cis-3-[2-[5-bromo-2-[8-chloro-4-oxo-5-(trifluoromethyl)chromen-2-yl]phenoxy]ethoxy]cyclobutanecarboxylic acid;
trans-3-[2-[5-bromo-2-[8-chloro-4-oxo-5-(trifluoromethyl)chromen-2-yl]phenoxy]ethoxy]cyclobutanecarboxylic acid;
3-[2-[2-(8-chloro-4-oxo-chromen-2-yl)-4-methyl-phenoxy]ethoxy]cyclobutanecarboxylic acid;
trans-3-[2-[2-(8-chloro-4-oxo-chromen-2-yl)-4-methyl-phenoxy]ethoxy]cyclobutanecarboxylic acid;
cis-3-[2-[2-(8-chloro-4-oxo-chromen-2-yl)-4-ethoxy-phenoxy]ethoxy]cyclobutanecarboxylic acid;
trans-3-[2-[2-(8-chloro-4-oxo-chromen-2-yl)-4-ethoxy-phenoxy]ethoxy]cyclobutanecarboxylic acid;
cis-3-[2-[2-(8-chloro-4-oxo-chromen-2-yl)-5-(trifluoromethoxy)phenoxy]ethoxy]cyclobutanecarboxylic acid;
trans-3-[2-[4-bromo-2-(8-chloro-6-fluoro-4-oxo-chromen-2-yl)phenoxy]ethoxy]cyclobutanecarboxylic acid;
cis-3-[2-[2-(8-chloro-7-fluoro-4-oxo-chromen-2-yl)phenoxy]ethoxy]cyclobutanecarboxylic acid;
cis-3-[2-[5-chloro-2-(8-chloro-4-oxo-chromen-2-yl)-4-methyl-phenoxy]ethoxy]cyclobutanecarboxylic acid;
cis-3-[3-[5-bromo-2-(8-chloro-4-oxo-chromen-2-yl)phenoxy]propoxy]cyclobutanecarboxylic acid;
trans-3-[3-[5-bromo-2-(8-chloro-4-oxo-chromen-2-yl)phenoxy]propoxy]cyclobutanecarboxylic acid;
cis-3-[2-[5-bromo-4-chloro-2-(8-chloro-4-oxo-chromen-2-yl)phenoxy]ethoxy]cyclobutanecarboxylic acid;
cis-3-[2-[2-(8-chloro-7-cyclopropyl-4-oxo-chromen-2-yl)phenoxy]ethoxy]cyclobutanecarboxylic acid;
cis-3-[2-[2-(8-chloro-4-oxo-chromen-2-yl)-4-methoxy-phenoxy]ethoxy]cyclobutanecarboxylic acid;
3-[2-[[4-(8-chloro-4-oxo-chromen-2-yl)-3-pyridyl]oxy]ethoxy]cyclobutanecarboxylic acid
3-[2-[2-(8-chloro-4-oxo-chromen-2-yl)-5-(2-oxooxazolidin-3-yl)phenoxy]ethoxy]cyclobutanecarboxylic acid;
methyl 3-[2-[2-(8-chloro-4-oxo-chromen-2-yl)-5-(2-oxooxazolidin-3-yl)phenoxy]ethoxy]cyclobutanecarboxylate;
cis-3-[2-[2-(8-chloro-4-oxo-chromen-2-yl)-5-(2-oxopyrrolidin-1-yl)phenoxy]ethoxy]cyclobutanecarboxylic acid;
trans-3-[2-[2-(8-chloro-4-oxo-chromen-2-yl)-5-(2-oxopyrrolidin-1-yl)phenoxy]ethoxy]cyclobutanecarboxylic acid;
cis-3-[2-[2-(8-chloro-4-oxo-chromen-2-yl)-5-methylsulfanyl-phenoxy]ethoxy]cyclobutanecarboxylic acid;
trans-3-[2-[2-(8-chloro-4-oxo-chromen-2-yl)-5-methylsulfanyl-phenoxy]ethoxy]cyclobutanecarboxylic acid;
trans-methyl 3-[2-[2-(8-chloro-4-oxo-chromen-2-yl)-5-methylsulfonyl-phenoxy]ethoxy]cyclobutanecarboxylate;
cis-3-[2-[2-(8-chloro-4-oxo-chromen-2-yl)-5-thiazol-2-yl-phenoxy]ethoxy]cyclobutanecarboxylic acid;
trans-3-[2-[2-(8-chloro-4-oxo-chromen-2-yl)-5-thiazol-2-yl-phenoxy]ethoxy]cyclobutanecarboxylic acid;
trans-3-[2-[2-(8-chloro-4-oxo-chromen-2-yl)-5-morpholino-phenoxy]ethoxy]cyclobutanecarboxylic acid;
cis-3-[2-[2-(8-chloro-4-oxo-chromen-2-yl)-5-pyrrolidin-1-yl-phenoxy]ethoxy]cyclobutanecarboxylic acid;
cis-3-[2-[2-(8-chloro-4-oxo-chromen-2-yl)-5-cyclopropyl-phenoxy]ethoxy]cyclobutanecarboxylic acid;
trans-3-[2-[2-(8-chloro-4-oxo-chromen-2-yl)-5-cyclopropyl-phenoxy]ethoxy]cyclobutanecarboxylic acid;
3-[2-[2-bromo-6-(8-chloro-6-fluoro-4-oxo-chromen-2-yl)phenoxy]ethoxy]cyclobutanecarboxylic acid;
cis-3-[2-[5-bromo-2-(8-chloro-4-oxo-chromen-2-yl)-3-fluoro-phenoxy]ethoxy]cyclobutanecarboxylic acid;
cis-3-[2-[2-(8-chloro-4-oxo-chromen-2-yl)-4,5-dimethoxy-phenoxy]ethoxy]cyclobutanecarboxylic acid;
cis-3-[2-[5-bromo-2-(8-chloro-4-oxo-chromen-2-yl)-4-methoxy-phenoxy]ethoxy]cyclobutanecarboxylic acid;
3-[2-[[7-(8-chloro-4-oxo-chromen-2-yl)-2,3-dihydro-1,4-benzodioxin-6-yl]oxy]ethoxy]cyclobutanecarboxylic acid;
cis-3-[2-[2-(8-chloro-4-oxo-chromen-2-yl)-4-(difluoromethyl)-5-methyl-phenoxy]ethoxy]cyclobutanecarboxylic acid;
cis-3-[2-[2-(8-chloro-4-oxo-chromen-2-yl)-5-hydroxy-4-methoxy-phenoxy]ethoxy]cyclobutanecarboxylic acid;
cis-3-[2-[2-(8-chloro-4-oxo-chromen-2-yl)-4-methoxy-5-propoxy-phenoxy]ethoxy]cyclobutanecarboxylic acid;
cis-3-[2-[2-(8-chloro-4-oxo-chromen-2-yl)-5-ethoxy-4-methoxy-phenoxy]ethoxy]cyclobutanecarboxylic acid;
cis-3-[2-[2-(8-chloro-4-oxo-chromen-2-yl)-5-(cyclopropylmethoxy)-4-methoxy-phenoxy]ethoxy]cyclobutanecarboxylic acid;
cis-3-[2-[2-(8-chloro-4-oxo-chromen-2-yl)-4-methoxy-5-(2,2,2-trifluoroethoxy)phenoxy]ethoxy]cyclobutanecarboxylic acid;

cis-3-[2-[2-(8-chloro-4-oxo-chromen-2-yl)-5-(difluoromethoxy)-4-methoxy-phenoxy]ethoxy]cyclobutanecarboxylic acid;
cis-3-[2-[2-(8-chloro-4-oxo-chromen-2-yl)-4-(cyclopropylmethoxy)-5-methoxy-phenoxy]ethoxy]cyclobutanecarboxylic acid;
cis-3-[2-[2-(8-chloro-4-oxo-chromen-2-yl)-4-hydroxy-5-methoxy-phenoxy]ethoxy]cyclobutanecarboxylic acid;
cis-3-[2-[2-(8-chloro-4-oxo-chromen-2-yl)-4-ethoxy-5-methoxy-phenoxy]ethoxy]cyclobutanecarboxylic acid;
cis-3-[2-[2-(8-chloro-4-oxo-chromen-2-yl)-5-methoxy-4-(2,2,2-trifluoroethoxy)phenoxy]ethoxy]cyclobutanecarboxylic acid;
cis-3-[2-[2-(8-chloro-4-oxo-chromen-2-yl)-4-(difluoromethoxy)-5-methoxy-phenoxy]ethoxy]cyclobutanecarboxylic acid;
cis-3-[2-[2-(8-chloro-4-oxo-chromen-2-yl)-4,5-bis(difluoromethoxy)phenoxy]ethoxy]cyclobutanecarboxylic acid;
cis-3-[2-[2-(8-chloro-4-oxo-chromen-2-yl)-4,5-diethoxy-phenoxy]ethoxy]cyclobutanecarboxylic acid;
cis-3-[2-[2-(8-chloro-4-oxo-chromen-2-yl)-5-methoxy-4-(trifluoromethoxy)phenoxy]ethoxy]cyclobutanecarboxylic acid;
cis-3-[2-[2-(8-chloro-4-oxo-chromen-2-yl)-5-hydroxy-4-(trifluoromethoxy)phenoxy]ethoxy]cyclobutanecarboxylic acid;
cis-3-[2-[6-(8-chloro-4-oxo-chromen-2-yl)-2-oxo-indolin-5-yl]oxyethoxy]cyclobutanecarboxylic acid;
cis-3-[2-[6-(8-chloro-4-oxo-chromen-2-yl)-3,3-dimethyl-2-oxo-indolin-5-yl]oxyethoxy]cyclobutanecarboxylic acid;
cis-3-[2-[6-(8-chloro-4-oxo-chromen-2-yl)-1,3,3-trimethyl-2-oxo-indolin-5-yl]oxyethoxy]cyclobutanecarboxylic acid;
cis-3-[2-[2-[8-chloro-4-oxo-5-(trifluoromethyl)chromen-2-yl]phenoxy]ethoxy]cyclobutanecarboxylic acid;
cis-3-[2-[2-[8-chloro-4-oxo-5-(trifluoromethyl)chromen-2-yl]-5-ethoxy-phenoxy]ethoxy]cyclobutanecarboxylic acid;
cis-3-[2-[2-[8-chloro-4-oxo-5-(trifluoromethyl)chromen-2-yl]-4,5-dimethoxy-phenoxy]ethoxy]cyclobutanecarboxylic acid;
3-[2-[2-[8-chloro-4-oxo-7-(trifluoromethyl)chromen-2-yl]-5-ethoxy-phenoxy]ethoxy]cyclobutanecarboxylic acid;
cis-3-[2-[2-(8-chloro-5-hydroxy-4-oxo-chromen-2-yl)-4,5-dimethoxy-phenoxy]ethoxy]cyclobutanecarboxylic acid;
cis-3-[2-[2-(8-chloro-5-hydroxy-4-oxo-chromen-2-yl)-5-(trifluoromethyl)phenoxy]ethoxy]cyclobutanecarboxylic acid;
2-[3-[2-(8-chloro-5-hydroxy-4-oxo-chromen-2-yl)-5-(trifluoromethyl)phenoxy]propoxy]acetic acid;
cis-3-[2-[5-bromo-2-(8-chloro-3-methoxy-4-oxo-chromen-2-yl)phenoxy]ethoxy]cyclobutanecarboxylic acid;
cis-3-[2-[[6-(8-chloro-4-oxo-chromen-2-yl)-2,2-difluoro-1,3-benzodioxol-5-yl]oxy]ethoxy]cyclobutanecarboxylic acid;
3-[3-[2-(8-chloro-4-oxo-chromen-2-yl)-5-(trifluoromethyl)phenoxy]propoxy]cyclobutanecarboxylic acid;
3-[3-[2-(8-chloro-4-oxo-chromen-2-yl)-5-(trifluoromethyl)phenoxy]propoxy]cyclopentanecarboxylic acid;
3-[3-[5-bromo-2-(8-chloro-4-oxo-chromen-2-yl)phenoxy]propoxy]cyclopentanecarboxylic acid;
3-[2-[5-bromo-2-(8-chloro-4-oxo-chromen-2-yl)phenoxy]ethoxy]cyclopentanecarboxylic acid;
4-[2-[5-bromo-2-(8-chloro-4-oxo-chromen-2-yl)phenoxy]ethoxy]benzoic acid;
3-[2-[5-bromo-2-(8-chloro-4-oxo-chromen-2-yl)phenoxy]ethoxy]benzoic acid;
2-[3-[2-(8-chloro-4-oxo-chromen-2-yl)-5-(trifluoromethyl)phenoxy]propoxy]-2-methyl-propanoic acid;
cis-3-[3-[5-bromo-2-(8-chloro-4-oxo-chromen-2-yl)phenoxy]-2,2-dimethyl-propoxy]cyclobutanecarboxylic acid;
trans-3-[3-[5-bromo-2-(8-chloro-4-oxo-chromen-2-yl)phenoxy]-2,2-dimethyl-propoxy]cyclobutanecarboxylic acid;
(3R)-1-[2-[2-[5-bromo-2-(8-chloro-4-oxo-chromen-2-yl)phenoxy]ethoxy]acetyl]pyrrolidine-3-carboxylic acid;
(3S)-1-[2-[2-[5-bromo-2-(8-chloro-4-oxo-chromen-2-yl)phenoxy]ethoxy]acetyl]pyrrolidine-3-carboxylic acid;
2-[3-[5-bromo-2-(8-chloro-4-oxo-chromen-2-yl)phenoxy]-2-hydroxy-propoxy]acetic acid;
2-[3-[5-bromo-2-(8-chloro-4-oxo-chromen-2-yl)phenoxy]-2-hydroxy-propoxy]acetamide;
2-[3-[2-(8-chloro-4-oxo-chromen-2-yl)-5-(trifluoromethyl)phenoxy]-2-hydroxy-propoxy]acetic acid;
2-[2-[5-bromo-2-(8-chloro-4-oxo-chromen-2-yl)phenoxy]ethoxy]-N-cyclopropylsulfonyl-acetamide;
2-[3-[2-(8-chloro-4-oxo-chromen-2-yl)-5-(trifluoromethyl)phenoxy]propoxy]-N-cyclopropylsulfonyl-acetamide;
2-[2-[2-(8-chloro-4-oxo-chromen-2-yl)-5-(trifluoromethyl)phenoxy]ethoxy]-N-cyclopropylsulfonyl-acetamide;
cis-3-[2-[2-(8-chloro-4-oxo-chromen-2-yl)-4,5-dimethoxy-phenoxy]ethoxy]-N-cyclopropylsulfonyl-cyclobutanecarboxamide;
2-[2-[2-(8-chloro-4-oxo-chromen-2-yl)-5-(trifluoromethyl)phenoxy]ethoxy]-N-methylsulfonyl-acetamide;
cis-3-[2-[2-(8-chloro-4-oxo-chromen-2-yl)-5-(trifluoromethyl)phenoxy]ethoxy]-N-methylsulfonyl-cyclobutanecarboxamide;
cis-3-[2-[5-bromo-2-(8-chloro-4-oxo-chromen-2-yl)phenoxy]ethoxy]-N-methylsulfonyl-cyclobutanecarboxamide;
trans-3-[2-[5-bromo-2-(8-chloro-4-oxo-chromen-2-yl)phenoxy]ethoxy]-N-methylsulfonyl-cyclobutanecarboxamide;
3-[3-[2-(8-chloro-4-oxo-chromen-2-yl)-5-(trifluoromethyl)phenoxy]propoxy]-N-methylsulfonyl-cycloheptanecarboxamide;
cis-3-[2-[2-(8-chloro-4-oxo-chromen-2-yl)-4,5-dimethoxy-phenoxy]ethoxy]-N-methylsulfonyl-cyclobutanecarboxamide; and
2-[4-bromo-2-[2-[2-(3-hydroxypyrrolidin-1-yl)-2-oxo-ethoxy]ethoxy]phenyl]-8-chloro-chromen-4-one;
or a pharmaceutically acceptable salt thereof.

17. A pharmaceutical composition comprising a compound in accordance with claim 1 and a therapeutically inert carrier.

18. A compound according to claim 4, or a pharmaceutically acceptable salt thereof, wherein $R^1$ is halogen.

19. A compound according to claim 5, or a pharmaceutically acceptable salt thereof, wherein $R^8$ is selected from Cl and Br.

20. A compound according to claim 5, or a pharmaceutically acceptable salt thereof, wherein $R^6$ is selected from carboxy and $C_{1-6}$alkoxycarbonyl.

21. A compound according to claim 20, or a pharmaceutically acceptable salt thereof, wherein $R^6$ is selected from carboxy and methoxycarbonyl.

22. A compound according to claim 1, or a pharmaceutically acceptable salt thereof, wherein $A_3$ is $CR^9$, wherein $R^9$ is selected from H, $C_{1-6}$alkyl and $C_{1-6}$alkoxy.

23. A compound according to claim 22, or a pharmaceutically acceptable salt thereof, wherein $A_3$ is $CR^9$, wherein $R^9$ is selected from H, methyl and methoxy.

24. A compound according to claim 23, or a pharmaceutically acceptable salt thereof, wherein $G_1$ is $C_{1-6}$alkyl, wherein $C_{1-6}$alkyl is unsubstituted or substituted by one substituent independently selected from $C_{3-7}$cycloalkylsulfonylamino and $C_{1-6}$ alkylaminosulfonylamino.

25. A compound according to claim 24, or a pharmaceutically acceptable salt thereof, wherein $G_1$ is ethyl, wherein ethyl is unsubstituted or substituted by one substituent independently selected from cyclopropylsulfonylamino and ethylaminosulfonylamino.

26. A pharmaceutical composition comprising a compound in accordance with claim 18 and a therapeutically inert carrier.

27. A pharmaceutical composition comprising a compound in accordance with claim 8 and a therapeutically inert carrier.

28. A pharmaceutical composition comprising a compound in accordance with claim 11 and a therapeutically inert carrier.

29. A pharmaceutical composition comprising a compound in accordance with claim 16 and a therapeutically inert carrier.

* * * * *